United States Patent
Takahashi et al.

(10) Patent No.: US 10,029,983 B2
(45) Date of Patent: *Jul. 24, 2018

(54) UREA DERIVATIVE OR PHARMACOLOGICALLY ACCEPTABLE SALT THEREOF

(71) Applicant: KYORIN PHARMACEUTICAL CO. LTD., Shimotsuga-gun (JP)

(72) Inventors: Hiroyasu Takahashi, Kirihara (JP); Yoshifumi Saito, Shimotsuga-gun (JP); Kosuke Tsuda, Shimotsuga-gun (JP); Mitsuhito Shibasaki, Shimotsuga-gun (JP); Kohei Ohata, Shimotsuga-gun (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/724,002

(22) Filed: Oct. 3, 2017

(65) Prior Publication Data

US 2018/0044290 A1 Feb. 15, 2018

Related U.S. Application Data

(63) Continuation of application No. 15/039,964, filed as application No. PCT/JP2014/005933 on Nov. 27, 2014, now Pat. No. 9,822,069.

(30) Foreign Application Priority Data

Nov. 28, 2013 (JP) .................................. 2013-245502

(51) Int. Cl.
| | |
|---|---|
| C07D 207/46 | (2006.01) |
| C07D 207/50 | (2006.01) |
| C07D 207/273 | (2006.01) |
| C07D 207/22 | (2006.01) |
| C07D 413/06 | (2006.01) |
| C07D 409/14 | (2006.01) |
| C07D 403/04 | (2006.01) |
| C07D 401/06 | (2006.01) |
| C07D 413/14 | (2006.01) |
| C07D 405/14 | (2006.01) |
| C07D 209/54 | (2006.01) |
| C07D 417/12 | (2006.01) |
| C07D 413/12 | (2006.01) |
| C07D 409/12 | (2006.01) |
| C07D 409/04 | (2006.01) |
| C07D 405/12 | (2006.01) |
| C07D 405/04 | (2006.01) |
| C07D 401/12 | (2006.01) |
| C07D 401/04 | (2006.01) |
| C07D 403/12 | (2006.01) |

(52) U.S. Cl.
CPC ....... *C07D 207/273* (2013.01); *C07D 207/22* (2013.01); *C07D 209/54* (2013.01); *C07D 401/04* (2013.01); *C07D 401/06* (2013.01); *C07D 401/12* (2013.01); *C07D 403/04* (2013.01); *C07D 403/12* (2013.01); *C07D 405/04* (2013.01); *C07D 405/12* (2013.01); *C07D 405/14* (2013.01); *C07D 409/04* (2013.01); *C07D 409/12* (2013.01); *C07D 409/14* (2013.01); *C07D 413/06* (2013.01); *C07D 413/12* (2013.01); *C07D 413/14* (2013.01); *C07D 417/12* (2013.01)

(58) Field of Classification Search
None
See application file for complete search history.

(56) References Cited

U.S. PATENT DOCUMENTS

| | | |
|---|---|---|
| 2011/0178060 A1 | 7/2011 | Shirai et al. |
| 2012/0208842 A1 | 8/2012 | Beard et al. |
| 2013/0018067 A1 | 1/2013 | Garst |
| 2013/0123215 A1 | 5/2013 | Beard et al. |

FOREIGN PATENT DOCUMENTS

| | | |
|---|---|---|
| CN | 1706833 | 12/2005 |
| CN | 1894580 | 1/2007 |
| WO | 2005/047899 A2 | 5/2005 |

(Continued)

OTHER PUBLICATIONS

U.S. Appl. No. 15/039,964, filed May 2016, Takahashi, H.*
Wong et al., "Pharmacokinetic Optimization of Class-Selective Histone Deacetylase Inhibitors and Identification of Associated Candidate Predictive Biomarkers of Hepatocellular Carcinoma Tumor Response", J. Med. Chem., 2012, vol. 55, 8903-8925.

(Continued)

*Primary Examiner* — Michael Barker
(74) *Attorney, Agent, or Firm* — Baker & Hostetler LLP

(57) ABSTRACT

Provided is a compound having a formyl peptide receptor like 1 (FPRL1) agonist effect.
The present invention relates to a compound represented by the general formula (I) or a pharmacologically acceptable salt thereof. The present invention also relates to a pharmaceutical composition containing the compound represented by the general formula (I) or a pharmacologically acceptable salt thereof.

[Chemical Formula 1]

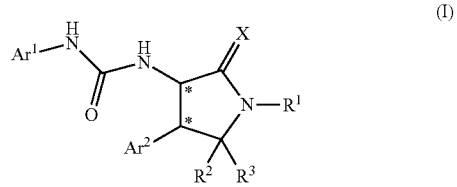

(I)

13 Claims, No Drawings

(56) References Cited

FOREIGN PATENT DOCUMENTS

| WO | 2006/127396 A1 | 11/2006 |
|---|---|---|
| WO | 2009/077954 A1 | 6/2009 |
| WO | 2009/077990 A1 | 6/2009 |
| WO | 2010/032856 A1 | 3/2010 |
| WO | 2010/094678 A1 | 8/2010 |
| WO | 2010/143158 A1 | 12/2010 |
| WO | 2011/163502 A1 | 12/2011 |
| WO | 2012/066488 A2 | 5/2012 |
| WO | 2012/074785 A1 | 6/2012 |
| WO | 2012/077049 A1 | 6/2012 |
| WO | 2012/077051 A1 | 6/2012 |
| WO | 2012/109544 A1 | 8/2012 |
| WO | 2012/125305 A1 | 9/2012 |
| WO | 2012/158413 A2 | 11/2012 |
| WO | 2013/062947 A1 | 5/2013 |
| WO | 2013/070600 A1 | 5/2013 |
| WO | 2013/071203 A1 | 5/2013 |
| WO | 2013/158597 A1 | 10/2013 |
| WO | 2014/078323 A1 | 5/2014 |
| WO | 2014/078372 A1 | 5/2014 |
| WO | 2014/078378 A1 | 5/2014 |
| WO | 2015/009545 A1 | 1/2015 |
| WO | 2015/019325 A1 | 2/2015 |
| WO | 2015/084796 A1 | 6/2015 |
| WO | 2015/175788 A1 | 11/2015 |
| WO | 2016/116900 A1 | 7/2016 |

OTHER PUBLICATIONS

Tae et al., "Airway Activation of Formyl Peptide Receptors Inhibits Th1 and Th17 Cell Responses via Inhibition of Mediator Release From Immune and Inflammatory Cells and Maturation of Dendritic Cells", Journal of Immunology, Feb. 2012, 188(4), 1799-1808.
Summers et al., "Neutrophil Kinetics in Health and Disease", Trends in Immunology, Aug. 2010, 31(8), 318-324.
Stepniewski et al., "Non-Peptide Ligand Binding to the Formyl Peptide Receptor FPR2-A Comparison to Peptide Ligand binding Modes", Bioorg. Med. Chem., 2015, vol. 23, 4072-4081.
Sogawa et al., "Inhibition of Neutrophil Migration in Mice by Mouse Formyl Peptide Receptors 1 and 2 Dual Agonist: Indication of Cross-Desentitization in Vivo", Immunology, Mar. 2011, 132(3), 441-450.
Seitzberg et al., "Discovery of Potent and Selective Small-Molecule PAR-2 Agonists", J. Med. Chem. , Sep. 2008, vol. 51, 5490-5493.
Schepetkin et al., "Gastrin-Releasing Peptide/Neuromedin B Receptor Antagonists PD176252, PD168368, and Related Analogs are Potent Agonists of Human Formyl-Peptide Receptors", Molecular Pharmacology, Jan. 2011, 79(1), 77-90.
Schepetkin et al., "3-(1H-indol-3-yl)-2-[3-(4-nitrophenyl)ureido]propanamide Enantiomers With Human Formyl-Peptide Receptor Agonist Activity: Molecular Modeling of Chiral Recognition by FPR2", Biochem. PharmacoL, 2013, vol. 85, 404-416.
Nanamori et al., "A Novel Nonpeptide Ligand for Formyl Peptide Receptor-Like 1", Molecular Pharmacology, Nov. 2004, 66(5), 1213-1222.
Murphy et al., "A Structural Homologue of the N-Formyl Peptide Receptor", The Journal of Biological Chemistry, Apr. 15, 1992, vol. 267(11), 7637-7643.
Lima et al., Bioisosterism: A useful Strategy for Molecular Modification and Drug Design, Current Medicinal Chemistry, vol. 12, No. 1, 2005, 23-49.
Li et al., "The Synthetic Peptide WKYMVm Attenuates the Function of the Chemokine Receptors CCR5 and CXCR4 Through Activation of Formyl Peptide Receptor-Like 1", Blood, May 2001, 97(10), 2941-2947.
Le et al., "Formyl-Peptide Receptors Revisited", Trends in Immunology, Nov. 2002, 23(11), 541-548.
Krishnamoorthy et al., "Resolvin D1 Binds Human Phagocytes With Evidence for Proresolving Receptors", Proc. Natl. Acad. Sci. USA, Jan. 2010, 107(4), 1660-1665.
Kirpotina et al., "Identification of Novel Small-Molecule Agonists for Human Formyl Peptide Receptors and Pharmacophore Models of Their Recognition", Molecular Pharmacology, Feb. 2010, 77(2), 159-170.
Kim et al., "The Immune-Stimulating Peptide WKYMVm Has Therapeutic Effects Against Ulcerative Colitis", Experimental & Molecular Medicine, 2013, 45, e40.
Kim et al., "The Agonists of Formyl Peptide Receptors Prevent Development of Severe Sepsis After Microbial Infection", Oct. 2010, 185(7), 4302-4310.
Kim et al., "A WKYMVm-Containing Combination Elicits Potent Anti-Tumor Activity in Heterotopic Cancer Animal Model", PLoS One, 2012, 7(1), e30522.
Khlebikov et al., "Computational Structure-Activity Relationship Analysis of Small-Molecule Agonists for Human Formyl Peptide Receptors", Eur. J. Med. Chem., 2010, vol. 45, 5406-5419.
He et al., "Characterization of Quin-C1 for It's Anti-Inflammatory Property in a Mouse Model of Bleomycin-Induced Lung Injury", Acta Pharmacol. Sin., May 2011, 32(5), 601-610.
Gavins et al., "Are Formyl Peptide Receptors Novel Targets for Therapeutic Intervention in Ischaemia-Reperfusion Injury", Trends in Pharmacological Sciences, Jun. 2010, 31(6), 266-276.
Gardell et al., "Identification and Characterization of Novel Small-Molecule Protease-Activated Receptor 2 Agonists", J. Pharmacol. Exp. Ther., 2008, vol. 327, 799-808.
Frohn et al., "New 'Chemical Probes' to Examine the Role of the hFPRL1 (or ALXR) Receptor in Inflammation", Bioorganic & Medicinal Chemistry Letters, Dec. 2007, 17(23), 6633-6637.
Duflon et al., "Anti-Inflammatory Role of the Murine Formyl-Peptide Receptor 2: Ligand-Specific Effects on Leukocyte Responses and Experimental Inflammation", Journal of Immunology, Mar. 2010, 184(5), 2611-2619.
Cilibrizzi et al., "6-Methyl-2,4-Disubstituted Pryridazin-3(2H)-Ones: A Novel Class of Small-Molecular Agonists for Formyl Peptide Receptors", Journal of Medical Chemistry, Aug. 2009, 52(16), 5044-5057.
Cattaneo et al., "Distinct Signaling Cascades Elicited by Different Formyl Peptide Receptor 2 (FPR2) Agonists", International Journal of Molecular Sciences, Apr. 2013, 14(4), 7193-7230.
Burli et al., "Potent hFPRL1 (ALXR) Agonists as Potential Anti-Inflammatory Agents", Bioorganic & Medicinal Chemistry Letters, Jul. 2006, 16(14), 3713-3718.

* cited by examiner

UREA DERIVATIVE OR PHARMACOLOGICALLY ACCEPTABLE SALT THEREOF

CROSS REFERENCE TO RELATED APPLICATIONS

This application is a continuation of U.S. patent application Ser. No. 15/039,964, filed May 27, 2016, which is a 371 application of PCT/JP2014/005933 filed Nov. 27, 2014, which is entitled to priority pursuant to 35 U.S.C. § 119(e) and 365(c) to Japanese patent application No. 2013-245502, filed Nov. 28, 2013, each of which is fully incorporated herein in its entirety.

SEQUENCE LISTING

The instant application contains a Sequence Listing which has been submitted electronically in ASCII format and is hereby incorporated by reference in its entirety. Said ASCII copy, created on Oct. 3, 2017, is named 082867_000148_SL.TXT and is 4,302 bytes in size.

TECHNICAL FIELD

The present invention relates to a urea derivative or a pharmacologically acceptable salt thereof that are useful as pharmaceuticals and have a formyl peptide receptor like 1 (hereinafter may be abbreviated as FPRL1) agonist effect, to a pharmaceutical composition containing the urea derivative or the pharmacologically acceptable salt thereof, and to a pharmaceutical use thereof.

BACKGROUND ART

FPRL1 (formyl peptide receptor like 1, also known as Lipoxin A4 Receptor, ALXR, and FPR2) is a G protein-coupled receptor cloned as a subtype of N-formyl peptide receptors (FPRs) by Murphy et al. (Non-Patent Literature 1). The FPRL1 was discovered as a receptor that mediates calcium mobilization in response to high concentration of fMLF (formyl methionine leucyl phenylalanine peptide).

Expression of FPRL1 has been found in neutrophils, monocytes, T-lymphocytes, dendritic cells, etc. (Non-Patent Literature 2), but the role of FPRL1 in a living body is complicated and has therefore not been elucidated sufficiently (Non-Patent Literature 3). However, in a paw edema model and an arthritis model using FPRL1 deficient mice, it has been recognized that the reactions become worse (Non-Patent Literature 4). Therefore, it is considered that FPRL1 contributes to the resolution of the inflammation.

Endogenous lipid mediators such as Lipoxin A4 (LXA4) and Resolvin D1 (RvD1) and peptides such as WKYMVm have been reported as agonists that bind to FPRL1 (Non-Patent Literatures 5 and 6).

Such FPRL1 agonists can reduce neutrophil chemotaxis in vitro (Non-Patent Literatures 7 and 8). Although neutrophils perform host defense, they cause vascular injury, result in an increase in vascular permeability and edema, followed by release of chemotactic factors, and thereby contribute to inflammation (Non-Patent Literature 9). Therefore, it is considered that the FPRL1 agonists exhibit an anti-inflammatory effect.

For example, it has been confirmed that peptide agonists exhibit an inhibitory effect on intestinal inflammation (Non-Patent Literature 10), an inhibitory effect on airway inflammation (Non-Patent Literature 11), an inhibitory effect on septicemia (Non-Patent Literature 12), and an inhibitory effect on a cancer model (Non-Patent Literature 13). It has also been recognized that QuinC1, a non-peptide low-molecular weight compound, inhibits bleomycin-induced lung inflammation (Non-Patent Literature 14).

Therefore, FPRL1 can be considered as a target of various diseases such as inflammatory diseases, chronic airway diseases, cancers, septicemia, allergic symptoms, HIV retrovirus infection, circulatory disorders, neuroinflammation, nervous disorders, pains, prion diseases, amyloidosis, and immune disorders. Therefore, the FPRL1 agonists can be promising therapeutic agent for these diseases.

Known examples of the non-peptide low-molecular weight compound exhibiting FPRL1 agonist activity include quinazolinones (Non-Patent Literature 15), pyrazolones (Non-Patent Literature 16), benzimidazoles (Non-Patent Literature 17), aminoazoles (Patent Literatures 1, 2, 3, 4, and 5), spiro[2,4]heptanes (Patent Literature 6), pyridazinones (Non-Patent Literature 18), cycloalkyl and cycloalkenyl-1, 2-dicarboxylic acids (Patent Literature 7), dihydronaphthalenes (Patent Literature 8), pyrrolidine-2,5-diones (Patent Literature 9), and phenyl urea derivatives (Patent Literatures 10, 11, 12, and 13) (Non-Patent Literatures 19 and 20).

However, the basic chemical structures of these compounds are different from those of the compounds of the present invention. It will be appreciated that the above compounds are not included in the claims of the present application.

CITATION LIST

Non-Patent Literature

Non-Patent Literature 1: Murphy P. M., et al., "The Journal of Biological Chemistry," 1992, vol. 267, pp. 7637-7643

Non-Patent Literature 2: Gavins F. N. E, et al., "Trends in Pharmacological Sciences," 2010, vol. 31, pp. 266-276

Non-Patent Literature 3: Cattaneo F., et al., "International Journal of Molecular Sciences," 2013, vol. 14, No. 4, pp. 7193-7230

Non-Patent Literature 4: Dufton N, et al., "The Journal of Immunology," 2010, vol. 184, pp. 2611-2619

Non-Patent Literature 5: Le Y, et al., "Trends in immunology," 2002, vol. 23, No. 11, pp. 541-548

Non-Patent Literature 6: Krishnamoorthy S, "Proceedings of the National Academy of Sciences," 2010, vol. 107, No. 4, pp. 1660-1665

Non-Patent Literature 7: Li B. Q, et al., "Blood," 2001, vol. 97, pp. 2941-2947

Non-Patent Literature 8: Sogawa Y, et al., "Immunology," 2011, 1416974161282, pp. 441-450

Non-Patent Literature 9: Summers C, et al., "Trends in Immunology," 2010, vol. 31, pp. 318-324

Non-Patent Literature 10: Kim S. D, et al., "Experimental & Molecular Medicine," 2013, vol. 13, No. 45: e40.

Non-Patent Literature 11: Tae Y. M, et al., "The Journal of Immunology," 2012, vol. 188, pp. 1799-808

Non-Patent Literature 12: Kim S. D, et al., "The Journal of Immunology," 2010, vol. 185, pp. 4302-4310

Non-Patent Literature 13: Kim S. D, et al., "PLoS ONE," vol. 7, No. 1: e30522.

Non-Patent Literature 14: Min H. E, et al., "Acta Pharmacologica Sinica" 2011, vol. 32, pp. 601-610

Non-Patent Literature 15: Nanamori M, et al., "Molecular Pharmacology," 2004, vol. 66, pp. 1213-1222

Non-Patent Literature 16: Burli R. W, et al., "Bioorganic & Medicinal Chemistry Letters," 2006, vol. 16, pp. 3713-3718

Non-Patent Literature 7: Frohn M, et al., "Bioorganic & Medicinal Chemistry Letters," 2007, vol. 17, pp. 6633-6637

Non-Patent Literature 18: Cilibrizzi A, et al., "Journal of Medicinal Chemistry," 2009, vol. 52, pp. 5044-5057

Non-Patent Literature 19: Kirpotina L. N, et al., "Molecular Pharmacology," 2010, vol. 77, pp. 159-170

Non-Patent Literature 20: Schepetkin I. A, et al., "Molecular Pharmacology," 2011, vol. 79, pp. 77-90

Patent Literature

Patent Literature 1: WO2009/077990
Patent Literature 2: WO2009/077954
Patent Literature 3: WO2010/143158
Patent Literature 4: WO2012/077049
Patent Literature 5: WO2012/077051
Patent Literature 6: WO2012/066488
Patent Literature 7: WO2011/163502
Patent Literature 8: WO2012/125305
Patent Literature 9: U.S. Ser. No. 13/001,8067
Patent Literature 10: WO2005/047899
Patent Literature 11: WO2012/074785
Patent Literature 12: WO2012/109544
Patent Literature 13: WO2013/062947

SUMMARY OF INVENTION

Technical Problem

At present, no compound has been found which has a superior FPRL1 agonist effect as a prophylactic or therapeutic agent for various disease states described above and can be used as a sufficiently satisfactory pharmaceutical.

It is an object of the present invention to provide a compound having an FPRL1 agonist effect.

Solution to Problem

The present inventors have conducted extensive studies and found that a urea compound represented by the general formula (I) below (this compound may be referred to as a compound (I)) or a pharmacologically acceptable salt thereof has a superior FPRL1 agonist effect and is sufficiently satisfactory as a pharmaceutical, and thus the present invention has been completed.

Accordingly, the present invention is as follows.

[1] A compound represented by the general formula (I) or a pharmacologically acceptable salt thereof:

[Chemical Formula 1]

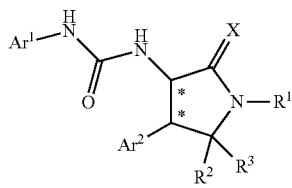

(I)

[wherein, in the formula (I), $Ar^1$ is a phenyl group optionally having substituent(s), a 5-membered aromatic heterocyclic group optionally having substituent(s), a 6-membered aromatic heterocyclic group optionally having substituent(s), or a bicyclic aromatic heterocyclic group having 8 or 9 atoms and optionally having substituent(s);

$Ar^2$ is a phenyl group optionally having substituent(s) (except for a phenyl group substituted only with halogen atom(s)), a 5-membered aromatic heterocyclic group optionally having substituent(s), a 6-membered aromatic heterocyclic group optionally having substituent(s), or a bicyclic aromatic heterocyclic group having 8 or 9 atoms and optionally having substituent(s);

X is a group selected from the group consisting of the following a), b), and c),
  a) an oxygen atom or a sulfur atom,
  b) $NR^4$, and
  c) $NOR^4$, wherein,
when X is b) or c), $R^4$ is a hydrogen atom, a phenyl group optionally having substituent(s), a heterocyclic group optionally having substituent(s), or a $C_1$ to $C_6$ alkyl group optionally having substituent(s);

$R^1$ is a hydrogen atom, a hydroxy group, a $C_1$ to $C_6$ alkoxy group optionally having substituent(s), or a $C_1$ to $C_6$ alkyl group optionally having substituent(s);

$R^2$ and $R^3$ are each independently a hydrogen atom or a $C_1$ to $C_6$ alkyl group optionally having substituent(s) or together form a $C_2$ to $C_6$ alkylene group; and each carbon atom marked with an asterisk is an asymmetric carbon atom].

[2] The compound according to [1] or a pharmacologically acceptable salt thereof, wherein
  in the formula (I), $Ar^2$ is a group selected from the group consisting of the following A1), A2), A3), A4), A5), A6), A7), A8), A9), and A10):

[Chemical Formula 2]

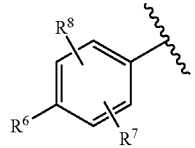

A1)

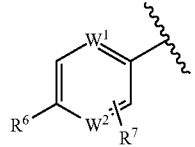

A2)

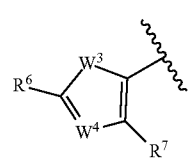

A3)

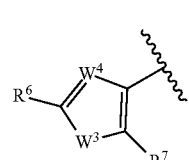

A4)

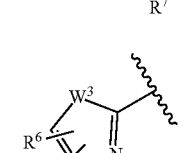

A5)

-continued

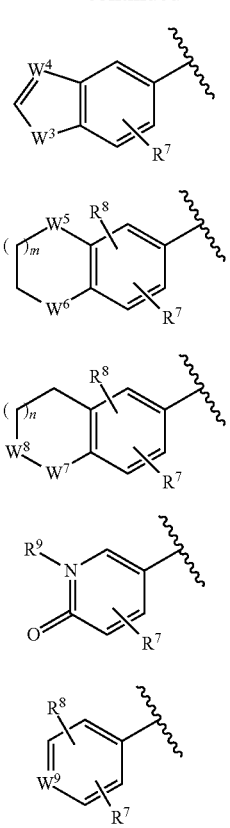

A6)

A7)

A8)

A9)

A10)

wherein, when Ar² is A2), W¹ is a nitrogen atom or CH optionally substituted with a hydrogen atom, with a halogen atom, or with a $C_1$ to $C_6$ alkyl group optionally having substituent(s);

when Ar² is A2), W² is CH or a nitrogen atom;

when Ar² is A3), A4), A5), or A6), W³ is an oxygen atom, a sulfur atom, or NH optionally substituted with a $C_1$ to $C_6$ alkyl group;

when Ar² is A3), A4), or A6), W⁴ is CH or a nitrogen atom;

when Ar² is A7), W⁵ is $CH_2$, an oxygen atom, or a sulfur atom;

when Ar² is A7), W⁶ is C=O, $CH_2$, $CF_2$, CHOH, NH optionally substituted with a $C_1$ to $C_6$ alkyl group, SO, $SO_2$, an oxygen atom, or a sulfur atom;

when Ar² is A8), W⁷ is NH optionally substituted with a $C_1$ to $C_6$ alkyl group or C=O;

when Ar² is A8), W⁸ is C=O with W⁷ being NH optionally substituted with a $C_1$ to $C_6$ alkyl group and W⁸ is NH optionally substituted with a $C_1$ to $C_6$ alkyl group with W⁷ being C=O;

when Ar² is A10), W⁹ is a nitrogen atom or N=O;

when Ar² is A1), A2), A3), A4), or A5), R⁶ is a hydrogen atom, a halogen atom, a hydroxy group, a cyano group, a $C_1$ to $C_6$ alkyl group optionally having substituent(s), a $C_1$ to $C_6$ alkoxy group optionally having substituent(s), a $C_1$ to $C_6$ acyl group optionally having substituent(s), a $C_1$ to $C_6$ alkylsulfanyl group optionally having substituent(s), a $C_1$ to $C_6$ alkylsulfinyl group optionally having substituent(s), a $C_1$ to $C_6$ alkylsulfonyl group optionally having substituent(s), a heterocyclic group optionally having substituent(s), —$CONR^{10}R^{11}$, or —$NR^{10}R^{11}$, wherein, when R⁶ is —$CONR^{10}R^{11}$ or —$NR^{10}R^{11}$, R¹⁰ is a hydrogen atom, a $C_1$ to $C_6$ alkyl group optionally having substituent(s), a $C_1$ to $C_6$ acyl group optionally having substituent(s), or a $C_1$ to $C_6$ alkylsulfonyl group optionally having substituent(s) and R¹¹ is a hydrogen atom or a $C_1$ to $C_6$ alkyl group optionally having substituent(s), or R¹⁰ and R¹¹ together form a $C_3$ to $C_{10}$ heterocycloalkyl group;

when Ar² is A1), A2), A3), A4), A5), A6), A7), A8), A9), or A10), R⁷ is a hydrogen atom, a halogen atom, a $C_1$ to $C_6$ alkyl group optionally having substituent(s), or a $C_1$ to $C_6$ alkoxy group optionally having substituent(s);

when Ar² is A1), A7), A8), or A10), R⁸ is a hydrogen atom, a halogen atom, or a $C_1$ to $C_6$ alkyl group optionally having substituent(s);

when Ar² is A9), R⁹ is a hydrogen atom or a $C_1$ to $C_6$ alkyl group;

when Ar² is A7), m is 0 or 1; and when Ar² is A8), n is 0 or 1;

provided that, when Ar² is A1), combinations of the substituents R⁶, R⁷ and R⁸ exclude a combination of a hydrogen atom and a halogen atom.

[3] The compound according to [2] or a pharmacologically acceptable salt thereof, wherein in the formula (I), Ar¹ is a group selected from the group consisting of the following B1), B2), B3), B4), B5), B6), B7), B8), B9), B10), B11), and B12):

[Chemical Formula 3]

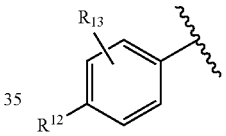

B1)

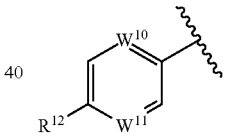

B2)

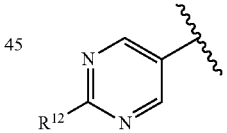

B3)

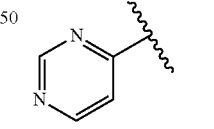

B4)

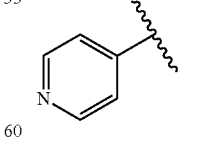

B5)

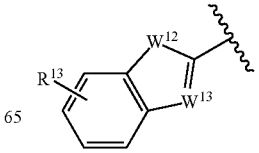

B6)

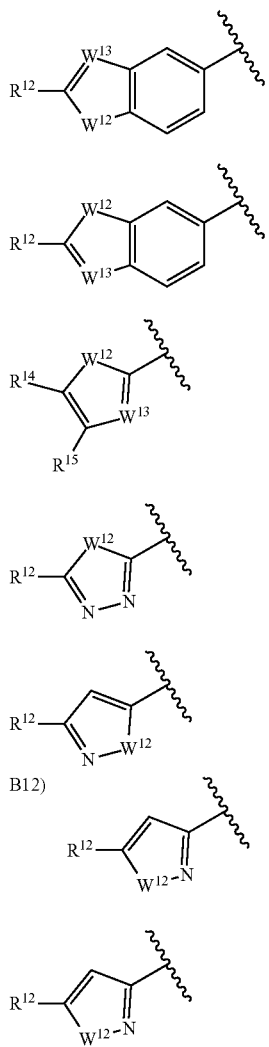

B7)

B8)

B9)

B10)

B11)

B12)

B12)

wherein, when Ar$^1$ is B2), B3), B7), B8), B10), B11), or B12), R$^{12}$ is a hydrogen atom, a halogen atom, a hydroxy group, a cyano group, a C$_1$ to C$_6$ alkyl group optionally having substituent(s), a C$_1$ to C$_6$ alkoxy group optionally having substituent(s), a C$_3$ to C$_6$ cycloalkyl group optionally having substituent(s), a C$_3$ to C$_6$ cycloalkoxy group optionally having substituent(s), a C$_1$ to C$_6$ acyl group optionally having substituent(s), a C$_2$ to C$_6$ alkenyl group optionally having substituent(s), a C$_2$ to C$_6$ alkynyl group optionally having substituent(s), a C$_1$ to C$_6$ alkoxycarbonyl group, a C$_1$ to C$_6$ alkylsulfanyl group optionally having substituent(s), a C$_1$ to C$_6$ alkylsulfinyl group optionally having substituent(s), a C$_1$ to C$_6$ alkylsulfonyl group optionally having substituent(s), —CONR$^{10}$R$^{11}$, —NR$^{10}$R$^{11}$, an aryloxy group, or a heterocyclic group optionally having substituent(s), wherein, when R$^{12}$ is —CONR$^{10}$R$^{11}$ or —NR$^{10}$R$^{11}$, R$^{10}$ is a hydrogen atom, a C$_1$ to C$_6$ alkyl group optionally having substituent(s), a C$_1$ to C$_6$ acyl group optionally having substituent(s), or a C$_1$ to C$_6$ alkylsulfonyl group optionally having substituent(s) and R$^{11}$ is a hydrogen atom or a C$_1$ to C$_6$ alkyl group optionally having substituent(s), or R$^{10}$ and R$^{11}$ together form a C$_3$ to C$_{10}$ heterocycloalkyl group;

when Ar$^1$ is B1), R$^{12}$ is a hydrogen atom, a halogen atom, a hydroxy group, a cyano group, a C$_1$ to C$_6$ alkyl group optionally having substituent(s), a C$_1$ to C$_6$ alkoxy group optionally having substituent(s), a C$_3$ to C$_6$ cycloalkyl group optionally having substituent(s), a C$_3$ to C$_6$ cycloalkoxy group optionally having substituent(s), a C$_1$ to C$_6$ acyl group optionally having substituent(s), a C$_2$ to C$_6$ alkenyl group optionally having substituent(s), a C$_2$ to C$_6$ alkynyl group optionally having substituent(s), a C$_1$ to C$_6$ alkoxycarbonyl group, a C$_1$ to C$_6$ alkylsulfanyl group optionally having substituent(s), a C$_1$ to C$_6$ alkylsulfinyl group optionally having substituent(s), a C$_1$ to C$_6$ alkylsulfonyl group optionally having substituent(s), —CONR$^{10}$R$^{11}$, —NR$^{10}$R$^{11}$, an aryloxy group, or a heterocyclic group optionally having substituent(s), wherein, when R$^{12}$ is —CONR$^{10}$R$^{11}$ or —NR$^{10}$R$^{11}$, R$^{10}$ is a hydrogen atom, a C$_1$ to C$_6$ alkyl group optionally having substituent(s), a C$_1$ to C$_6$ acyl group optionally having substituent(s), or a C$_1$ to C$_6$ alkylsulfonyl group optionally having substituent(s) and R$^{11}$ is a hydrogen atom or a C$_1$ to C$_6$ alkyl group optionally having substituent(s), or R$^{10}$ and R$^{11}$ together form a C$_3$ to C$_{10}$ heterocycloalkyl group, and R$^{13}$ is a hydrogen atom, a halogen atom, a hydroxy group, a cyano group, or a C$_1$ to C$_6$ alkyl group, or R$^{12}$ and R$^{13}$ may together form a C$_3$ to C$_5$ alkylene group or a C$_1$ to C$_2$ alkylenedioxy group;

when Ar$^1$ is B6), R$^{13}$ is a hydrogen atom, a halogen atom, a hydroxy group, a cyano group, or a C$_1$ to C$_6$ alkyl group;

when Ar$^1$ is B9), R$^{14}$ and R$^{15}$ are each independently a hydrogen atom, a halogen atom, a cyano group, a C$_1$ to C$_6$ alkyl group, or a C$_1$ to C$_6$ alkoxy group;

when Ar$^1$ is B2), one of W$^{10}$ and W$^{11}$ is a nitrogen atom, and the other thereof is CH or a nitrogen atom;

when Ar$^1$ is B6), B7), B8), B9), B10), B11), or B12), W$^{12}$ is an oxygen atom, a sulfur atom, or N—R$^{16}$, wherein, when W$^{12}$ is an N—R$^{16}$, R$^{16}$ is a hydrogen atom or a C$_1$ to C$_6$ alkyl group; and when Ar$^1$ is B6), B7), B8), or B9), W$^{13}$ is CH or a nitrogen atom.

[4] The compound according to [3] or a pharmacologically acceptable salt thereof, wherein when Ar$^2$ is A1), A2), A3), A4), or A5), R$^6$ is a hydrogen atom, a halogen atom, a hydroxy group, a cyano group, a C$_1$ to C$_6$ alkyl group, a C$_1$ to C$_6$ alkoxy group, a halo-C$_1$ to C$_6$ alkoxy group, a C$_1$ to C$_6$ acyl group, a C$_1$ to C$_6$ alkylsulfanyl group, a C$_1$ to C$_6$ alkylsulfinyl group, a C$_1$ to C$_6$ alkylsulfonyl group, a heterocyclic group optionally having substituent(s), —CONR$^{10}$R$^{11}$, or —NR$^{10}$R$^{11}$, wherein, when R$^6$ is —CONR$^{10}$R$^{11}$ or —NR$^{10}$R$^{11}$, R$^{10}$ is a hydrogen atom, a C$_1$ to C$_6$ alkyl group, a C$_1$ to C$_6$ acyl group, or a C$_1$ to C$_6$ alkylsulfonyl group and R$^{11}$ is a hydrogen atom or a C$_1$ to C$_6$ alkyl group, or R$^{10}$ and R$^{11}$ together form a C$_3$ to C$_{10}$ heterocycloalkyl group;

when Ar$^2$ is A1), A2), A3), A4), A5), A6), A7), A8), A9), or A10), R$^7$ is a hydrogen atom, a halogen atom, a C$_1$ to C$_6$ alkyl group, or a C$_1$ to C$_6$ alkoxy group;

when Ar$^2$ is A1), A7), A8), or A10), R$^8$ is a hydrogen atom, a halogen atom, or a C$_1$ to C$_6$ alkyl group; and when Ar$^2$ is A9), R$^9$ is a hydrogen atom or a C$_1$ to C$_6$ alkyl group;

provided that, when Ar$^2$ is A1), combinations of the substituents R$^6$, R$^7$ and R$^8$ exclude a combination of a hydrogen atom and a halogen atom.

[5] The compound according to [4] or a pharmacologically acceptable salt thereof, wherein R$^1$ is a hydrogen atom, a hydroxy group, a C$_1$ to C$_6$ alkyl group, a C$_1$ to C$_6$ alkoxy group, a halo-C$_1$ to C$_6$ alkyl group, a hydroxy C$_1$ to C$_6$ alkyl group, a carboxy C$_1$ to C$_6$ alkyl group, a carbamoyl C$_1$ to C$_6$ alkyl group, a mono C$_1$ to C$_6$ alkylcarbamoyl C$_1$ to C$_6$ alkyl group, a di-C$_1$ to C$_6$ alkylcarbamoyl $C_1$ to $C_6$ alkyl group, an aminosulfonyl $C_1$ to $C_6$ alkyl group, an aromatic heterocyclic $C_1$ to $C_3$ alkyl group optionally having substituent(s), or a phenyl $C_1$ to $C_3$ alkyl group optionally having substituent(s);

$R^2$ and $R^3$ are each independently a hydrogen atom or a $C_1$ to $C_3$ alkyl group or together form a $C_2$ to $C_6$ alkylene group;

when $Ar^1$ is B2), B3), B7), B8), B10), B11), or B12), $R^{12}$ is a hydrogen atom, a halogen atom, a hydroxy group, a cyano group, a $C_1$ to $C_6$ alkyl group, a halo-$C_1$ to $C_6$ alkyl group, a hydroxy $C_1$ to $C_6$ alkyl group, a $C_1$ to $C_6$ alkoxy group, a $C_3$ to $C_6$ cycloalkyl group, a $C_3$ to $C_6$ cycloalkoxy group, a $C_1$ to $C_6$ acyl group, a $C_2$ to $C_6$ alkenyl group, a $C_2$ to $C_6$ alkynyl group, a $C_1$ to $C_6$ alkoxycarbonyl group, a $C_1$ to $C_6$ alkylsulfanyl group, a $C_1$ to $C_6$ alkylsulfinyl group, a $C_1$ to $C_6$ alkylsulfonyl group, —$CONR^{10}R^{11}$, —$NR^{10}R^{11}$, an aryloxy group, or a heterocyclic group optionally having substituent(s), wherein, when $R^{12}$ is —$CONR^{10}R^{11}$ or —$NR^{10}R^{11}$, $R^{10}$ is a hydrogen atom, a $C_1$ to $C_6$ alkyl group, a $C_1$ to $C_6$ acyl group, or a $C_1$ to $C_6$ alkylsulfonyl group and $R^{11}$ is a hydrogen atom or a $C_1$ to $C_6$ alkyl group, or $R^{10}$ and $R^{11}$ together form a $C_3$ to $C_{10}$ heterocycloalkyl group;

when $Ar^1$ is B1), $R^{12}$ is a hydrogen atom, a halogen atom, a hydroxy group, a cyano group, a $C_1$ to $C_6$ alkyl group, a halo-$C_1$ to $C_6$ alkyl group, a hydroxy $C_1$ to $C_6$ alkyl group, a $C_1$ to $C_6$ alkoxy group, a $C_3$ to $C_6$ cycloalkyl group, a $C_3$ to $C_6$ cycloalkoxy group, a $C_1$ to $C_6$ acyl group, a $C_2$ to $C_6$ alkenyl group, a $C_2$ to $C_6$ alkynyl group, a $C_1$ to $C_6$ alkoxycarbonyl group, a $C_1$ to $C_6$ alkylsulfanyl group, a $C_1$ to $C_6$ alkylsulfinyl group, a $C_1$ to $C_6$ alkylsulfonyl group, —$CONR^{10}R^{11}$, —$NR^{10}R^{11}$, an aryloxy group, or a heterocyclic group optionally having substituent(s), wherein, when $R^{12}$ is —$CONR^{10}R^{11}$ or —$NR^{10}R^{11}$, $R^{10}$ is a hydrogen atom, a $C_1$ to $C_6$ alkyl group, a $C_1$ to $C_6$ acyl group, or a $C_1$ to $C_6$ alkylsulfonyl group and $R^{11}$ is a hydrogen atom or a $C_1$ to $C_6$ alkyl group, or $R^{10}$ and $R^{11}$ together form a $C_3$ to $C_{10}$ heterocycloalkyl group, and $R^{13}$ is a hydrogen atom, a halogen atom, a hydroxy group, a cyano group, or a $C_1$ to $C_6$ alkyl group, or $R^{12}$ and $R^{13}$ may together form a $C_3$ to $C_5$ alkylene group or a $C_1$ to $C_2$ alkylenedioxy group; and X is a group selected from the group consisting of the following a), b), and c), a) an oxygen atom,
b) $NR^4$, and
c) $NOR^4$, wherein, when X is b) or c), $R^4$ is a hydrogen atom, a hydroxy $C_1$ to $C_6$ alkyl group, a phenyl group, a heterocyclic group, or a $C_1$ to $C_6$ alkyl group.

[6] The compound according to [5] or a pharmacologically acceptable salt thereof, wherein
in the formula (I), $Ar^2$ is a group selected from the group consisting of A1), A2a), A3), and A7a):

[Chemical Formula 4]

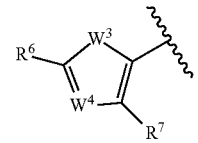

A1)

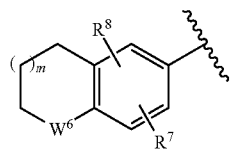

A2a)

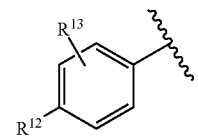

A3)

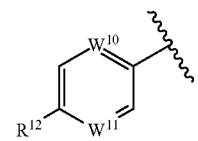

A7a)

wherein, when $Ar^2$ is A2a), $W^2$ is the same as that defined in [2] when $Ar^2$ is A2);
when $Ar^2$ is A3), $W^4$ is the same as that defined in [2] when $Ar^2$ is A3);
when $Ar^2$ is A7a), $W^6$ is the same as that defined in [2] when $Ar^2$ is A7);
when $Ar^2$ is A1), A2a), A3), or A7a), $R^7$ is the same as that defined in [4] when $Ar^2$ is A1), A2), A3), or A7);
when $Ar^2$ is A1) or A7a), $R^8$ is the same as that defined in [4] when $Ar^2$ is A1) or A7);
when $Ar^2$ is A7a), m is the same as that defined in [2] when $Ar^2$ is A7);
when $Ar^2$ is A1), A2a), or A3), $R^6$ is a hydrogen atom, a halogen atom, a cyano group, a $C_1$ to $C_6$ alkyl group, a $C_1$ to $C_6$ alkoxy group, a halo-$C_1$ to $C_6$ alkoxy group, a $C_1$ to $C_6$ acyl group, a $C_1$ to $C_6$ alkylsulfanyl group, a $C_1$ to $C_6$ alkylsulfinyl group, —$CONR^{10}R^{11}$, or —$NR^{10}R^{11}$, wherein, when $R^6$ is —$CONR^{10}R^{11}$ or —$NR^{10}R^{11}$, $R^{10}$ is a hydrogen atom, a $C_1$ to $C_6$ alkyl group, or a $C_1$ to $C_6$ acyl group and $R^{11}$ is a hydrogen atom or a $C_1$ to $C_6$ alkyl group, or $R^{10}$ and $R^{11}$ may together form a pyrrolidinyl group, a piperidinyl group, a piperazinyl group, or a morpholinyl group; and
when $Ar^2$ is A3), $W^3$ is an oxygen atom or a sulfur atom;
provided that, when $Ar^2$ is A1), combinations of the substituents $R^6$, $R^7$ and $R^8$ exclude a combination of a hydrogen atom and a halogen atom.

[7] The compound according to [6] or a pharmacologically acceptable salt thereof, wherein
in the formula (I), $Ar^1$ is a group selected from the group consisting of B1), B2), B6a), B9a), and B9b):

[Chemical Formula 5]

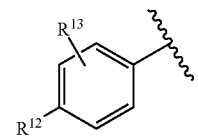

B1)

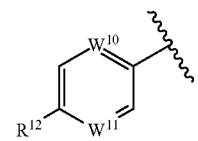

B2)

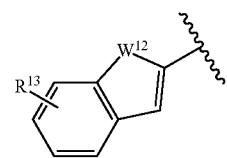

B6a)

-continued

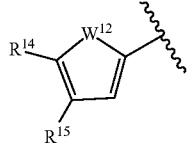
B9a)

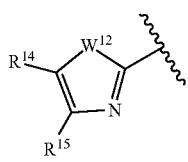
B9b)

wherein, when Ar$^1$ is B6a), R$^{13}$ is the same as that defined in [3] when Ar$^1$ is B6);

when Ar$^1$ is B9a) or B9b), R$^{14}$ and R$^{15}$ are the same as those defined in [3] when Ar$^1$ is B9);

when Ar$^1$ is B2), W$^{10}$ and W$^{11}$ are the same as those defined in [3] when Ar$^1$ is B2);

when Ar$^1$ is B2), R$^{12}$ is a hydrogen atom, a halogen atom, a hydroxy group, a cyano group, a C$_1$ to C$_6$ alkyl group, a halo-C$_1$ to C$_6$ alkyl group, a hydroxy C$_1$ to C$_6$ alkyl group, a C$_1$ to C$_6$ alkoxy group, a C$_3$ to C$_6$ cycloalkyl group, a C$_3$ to C$_6$ cycloalkoxy group, a C$_1$ to C$_6$ acyl group, a C$_2$ to C$_6$ alkenyl group, a C$_1$ to C$_6$ alkoxycarbonyl group, a C$_1$ to C$_6$ alkylsulfanyl group, a C$_1$ to C$_6$ alkylsulfinyl group, a C$_1$ to C$_6$ alkylsulfonyl group, —CONR$^{10}$R$^{11}$, —NR$^{10}$R$^{11}$, an aryloxy group, or a heterocyclic group optionally having substituent(s), wherein, when R$^{12}$ is —CONR$^{10}$R$^{11}$ or —NR$^{10}$R$^{11}$, R$^{10}$ is a hydrogen atom, a C$_1$ to C$_6$ alkyl group, or a C$_1$ to C$_6$ acyl group and R$^{11}$ is a hydrogen atom or a C$_1$ to C$_6$ alkyl group, or R$^{10}$ and R$^{11}$ may together form a pyrrolidinyl group, a piperidinyl group, a piperazinyl group, or a morpholinyl group;

when Ar$^1$ is B1), R$^{12}$ is a hydrogen atom, a halogen atom, a hydroxy group, a cyano group, a C$_1$ to C$_6$ alkyl group, a halo-C$_1$ to C$_6$ alkyl group, a hydroxy C$_1$ to C$_6$ alkyl group, a C$_1$ to C$_6$ alkoxy group, a C$_3$ to C$_6$ cycloalkyl group, a C$_3$ to C$_6$ cycloalkoxy group, a C$_1$ to C$_6$ acyl group, a C$_2$ to C$_6$ alkenyl group, a C$_1$ to C$_6$ alkoxycarbonyl group, a C$_1$ to C$_6$ alkylsulfanyl group, a C$_1$ to C$_6$ alkylsulfinyl group, a C$_1$ to C$_6$ alkylsulfonyl group, —CONR$^{10}$R$^{11}$, —NR$^{10}$R$^{11}$, an aryloxy group, or a heterocyclic group optionally having substituent(s), wherein, when R$^{12}$ is —CONR$^{10}$R$^{11}$ or —NR$^{10}$R$^{11}$, R$^{10}$ is a hydrogen atom, a C$_1$ to C$_6$ alkyl group, or a C$_1$ to C$_6$ acyl group and R$^{11}$ is a hydrogen atom or a C$_1$ to C$_6$ alkyl group, or R$^{10}$ and R$^{11}$ may together form a pyrrolidinyl group, a piperidinyl group, a piperazinyl group, or a morpholinyl group, and R$^{13}$ is a hydrogen atom, a halogen atom, a hydroxy group, a cyano group, or a C$_1$ to C$_6$ alkyl group, or R$^{12}$ and R$^{13}$ may together form a C$_3$ to C$_5$ alkylene group or a C$_1$ to C$_2$ alkylenedioxy group; and when Ar$^1$ is B6a), B9a), or B9b), W$^{12}$ is an oxygen atom or a sulfur atom.

[8] The compound according to [7] or a pharmacologically acceptable salt thereof, wherein in the formula (I), Ar$^2$ is a group selected from the group consisting of A1a), A2b), A3a), and A7b):

[Chemical Formula 6]

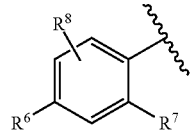
A1a)

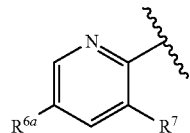
A2b)

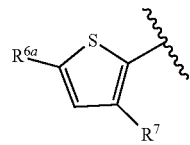
A3a)

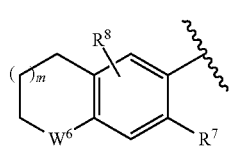
A7b)

wherein, when Ar$^2$ is A1a), R$^6$ is the same as that defined in [6] when Ar$^2$ is A1);

when Ar$^2$ is A1a) or A7b), R$^8$ is the same as that defined in [4] when Ar$^2$ is A1) or A7);

when Ar$^2$ is A7b), m is the same as that defined in [2] when Ar$^2$ is A7);

R$^1$ is a hydrogen atom, a hydroxy group, a C$_1$ to C$_3$ alkyl group, a C$_1$ to C$_3$ alkoxy group, a hydroxy C$_1$ to C$_4$ alkyl group, a carboxy C$_1$ to C$_3$ alkyl group, a carbamoyl C$_1$ to C$_3$ alkyl group, a mono-C$_1$ to C$_2$ alkylcarbamoyl C$_1$ to C$_3$ alkyl group, or a di-C$_1$ to C$_2$ alkylcarbamoyl C$_1$ to C$_3$ alkyl group;

R$^2$ and R$^3$ are each independently a hydrogen atom or a C$_1$ to C$_3$ alkyl group;

when X is b) or c), R$^4$ is a hydrogen atom, a hydroxy C$_1$ to C$_4$ alkyl group, or a C$_1$ to C$_3$ alkyl group;

when Ar$^2$ is A2b) or A3a), R$^6$ is a C$_1$ to C$_3$ alkoxy group;

when Ar$^2$ is A1a), A2b), A3a), or A7b), R$^7$ is a hydrogen atom, a fluorine atom, a chlorine atom, or a C$_1$ to C$_3$ alkyl group; and when Ar$^2$ is A7b), W$^6$ is C=O, CH$_2$, CF$_2$, CHOH, or an oxygen atom;

provided that, when Ar$^1$ is A1a), combinations of the substituents R$^6$, R$^7$ and R$^8$ exclude a combination of a hydrogen atom and a halogen atom.

[9] The compound according to [8] or a pharmacologically acceptable salt thereof, wherein in the formula (I), Ar$^2$ is a group selected from the group consisting of A1a), A2b), and A7c):

[Chemical Formula 7]

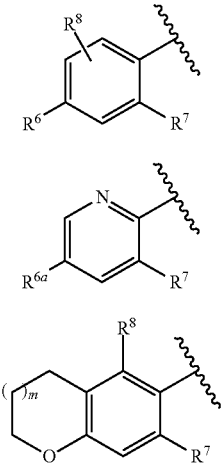

A1a)

A2b)

A7c)

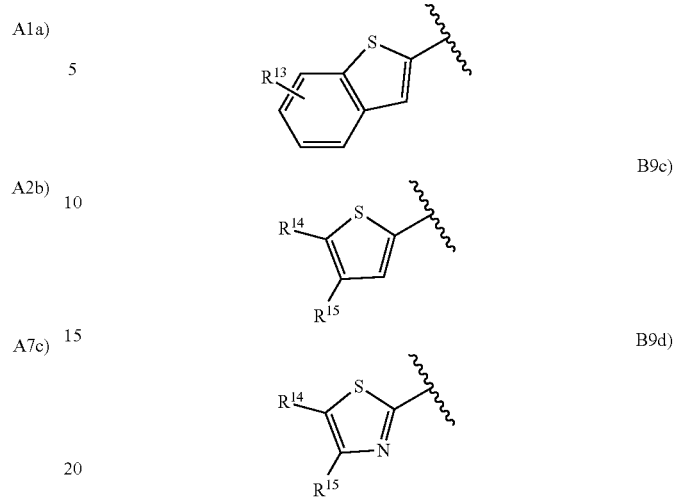

B6b)

B9c)

B9d)

wherein, when Ar² is A2b), R⁶ᵃ is the same as that defined in [8] when Ar² is A2b);

when Ar² is A1a) or A7c), R⁸ is the same as that defined in [4] when Ar² is A1) or A7);

when Ar² is A7c), m is the same as that defined in [8] when Ar² is A7b);

when Ar² is A1a), R⁶ is a hydrogen atom, a fluorine atom, a chlorine atom, a cyano group, a $C_1$ to $C_6$ alkyl group, a $C_1$ to $C_6$ alkoxy group, a halo-$C_1$ to $C_6$ alkoxy group, a $C_1$ to $C_6$ alkylsulfanyl group, a $C_1$ to $C_6$ alkylsulfinyl group, or —CONR¹⁰R¹¹, wherein, when R⁶ is —CONR¹⁰R¹¹, R¹⁰ is a hydrogen atom, a $C_1$ to $C_6$ alkyl group, or a $C_1$ to $C_6$ acyl group and R¹¹ is a hydrogen atom or a $C_1$ to $C_6$ alkyl group, or R¹⁰ and R¹¹ may together form a pyrrolidinyl group, a piperidinyl group, a piperazinyl group, or a morpholinyl group; and when Ar² is A1a), A2b), or A7c), R⁷ is a hydrogen atom, a fluorine atom, or a chlorine atom;

provided that, when Ar² is A1a), combinations of the substituents R⁶, R⁷ and R⁸ exclude a combination of a hydrogen atom and a halogen atom.

[10] The compound according to [9] or a pharmacologically acceptable salt thereof, wherein in the formula (I), Ar¹ is a group selected from the group consisting of B1), B2), B6b), B9c), and B9d):

[Chemical Formula 8]

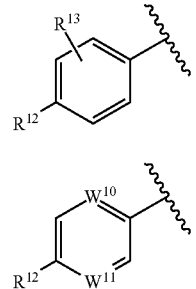

B1)

B2)

wherein R¹ is a hydrogen atom, a hydroxy group, a $C_1$ to $C_3$ alkyl group, a $C_1$ to $C_3$ alkoxy group, or a hydroxy $C_1$ to $C_4$ alkyl group;

when Ar¹ is B1) or B2), R¹² is a hydrogen atom, a fluorine atom, a chlorine atom, a cyano group, a $C_1$ to $C_3$ alkyl group, or a $C_1$ to $C_6$ alkoxy group;

when Ar¹ is B1) or B6b), R¹³ is a hydrogen atom, a hydroxy group, a fluorine atom, or a chlorine atom;

when Ar¹ is B9c) or B9d), R¹⁴ is a hydrogen atom, a fluorine atom, a chlorine atom, a $C_1$ to $C_3$ alkyl group, a methoxy group, or an ethoxy group;

when Ar¹ is B9c) or B9d), R¹⁵ is a hydrogen atom, a fluorine atom, or a chlorine atom; and when Ar¹ is B2), one of W¹⁰ and W¹¹ is N, and the other thereof is CH.

11] The compound according to [10] or a pharmacologically acceptable salt thereof, wherein in the formula (I), Ar¹ is a group selected from the group consisting of B1), B6b), and B9c1):

[Chemical Formula 9]

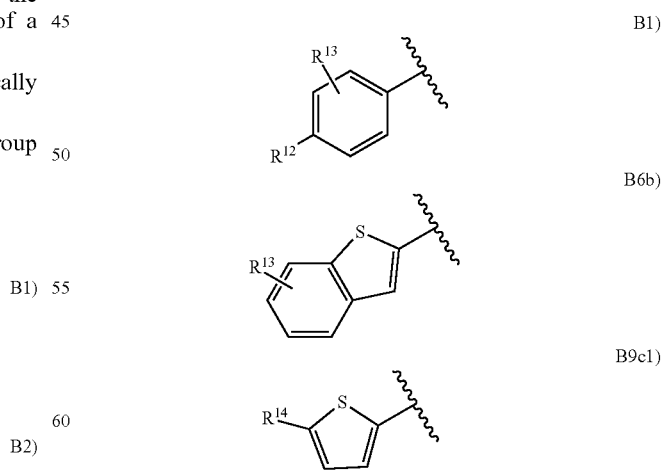

B1)

B6b)

B9c1)

wherein when Ar¹ is B1), R¹² is the same as that defined in [10] when Ar¹ is B1);

when Ar¹ is B1) or B6b), R¹³ is the same as that defined in [10] when Ar¹ is B1) or B6b); and when Ar¹ is B9c1), R¹⁴ is the same as that defined in [10] when Ar¹ is B9c).

[12] The compound according to [11] or a pharmacologically acceptable salt thereof, wherein
in the formula (I), Ar² is a group selected from the group consisting of A1b), A2b), and A7c):

[Chemical Formula 10]

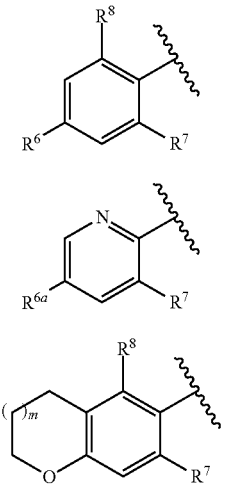

A1b)

A2b)

A7c)

wherein, when Ar² is A2b), R⁶ᵃ is the same as that defined in [8] when Ar² is A2b);
when Ar² is A7c), m is the same as that defined in [8] when Ar² is A7b);
when Ar² is A1b), R⁶ is a cyano group, an ethyl group, or a C₁ to C₃ alkoxy group;
R⁷ is a fluorine atom or a chlorine atom; and
when Ar² is A1b) or A7c), R⁸ is a hydrogen atom, a fluorine atom, a chlorine atom, or a C₁ to C₃ alkyl group.

[13] The compound according to [1] or a pharmacologically acceptable salt thereof, wherein
the compound represented by the formula (1) is
(−)-1-(4-fluorophenyl)-3-[(3S*,4R*)-4-(4-methoxyphenyl)-2-oxopyrrolidin-3-yl]urea,
(−)-1-(4-chlorophenyl)-3-[(3S*,4R*)-4-(4-methoxyphenyl)-2-oxopyrrolidin-3-yl]urea,
(−)-1-(3,4-difluorophenyl)-3-[(3S*,4R*)-4-(4-methoxyphenyl)-2-oxopyrrolidin-3-yl]urea,
(−)-1-(4-cyanophenyl)-3-[(3S*,4R*)-4-(4-methoxyphenyl)-2-oxopyrrolidin-3-yl]urea,
(−)-1-(4-chlorophenyl)-3-[(3S*,4R*)-4-(4-methoxyphenyl)-1-methyl-2-oxopyrrolidin-3-yl]urea,
(−)-1-(4-fluorophenyl)-3-[(3S*,4R*)-4-(4-methoxyphenyl)-1-methyl-2-oxopyrrolidin-3-yl]urea,
(−)-1-[(3S*,4R*)-4-(3-fluoro-4-methoxyphenyl)-2-oxopyrrolidin-3-yl]-3-(4-fluorophenyl)urea,
(−)-1-[(3S*,4R*)-4-(2-fluoro-4-methoxyphenyl)-2-oxopyrrolidin-3-yl]-3-(4-fluorophenyl)urea,
1-[(3S*,4R*)-4-(2-chloro-4-methoxyphenyl)-2-oxopyrrolidin-3-yl]-3-(4-fluorophenyl)urea,
(−)-1-(4-fluorophenyl)-3-[(3S*,4R*)-4-(4-methoxy-2-methylphenyl)-2-oxopyrrolidin-3-yl]urea,
(−)-1-[(3S*,4R*)-4-(2,6-difluoro-4-methoxyphenyl)-2-oxopyrrolidin-3-yl]-3-(4-fluorophenyl)urea,
(−)-1-[(3S*,4R*)-4-(2,5-difluoro-4-methoxyphenyl)-2-oxopyrrolidin-3-yl]-3-(4-fluorophenyl)urea,
(−)-1-[(3S*,4R*)-4-(3,5-difluoro-4-methoxyphenyl)-2-oxopyrrolidin-3-yl]-3-(4-fluorophenyl)urea,
(−)-1-[(3S*,4R*)-4-(6-fluoro-2,3-dihydrobenzofuran-5-yl)-2-oxopyrrolidin-3-yl]-3-(4-fluorophenyl)urea,
(−)-1-[(3S*,4R*)-4-(3-fluoro-5-methoxypyridin-2-yl)-2-oxopyrrolidin-3-yl]-3-(4-fluorophenyl)urea,
(−)-1-(4-fluorophenyl)-3-[(3S*,4R*)-4-(5-methoxythiophen-2-yl)-2-oxopyrrolidin-3-yl]urea,
(−)-1-(4-fluorophenyl)-3-[(3S*,4R*)-4-(4-methylthiophenyl)-2-oxopyrrolidin-3-yl]urea,
(−)-1-(4-chlorophenyl)-3-[(3S*,4R*)-4-(2,6-difluoro-4-methoxyphenyl)-2-oxopyrrolidin-3-yl]urea,
(−)-1-(4-cyanophenyl)-3-[(3S*,4R*)-4-(2,6-difluoro-4-methoxyphenyl)-2-oxopyrrolidin-3-yl]urea,
(−)-1-[(3S*,4R*)-4-(2,6-difluoro-4-methoxyphenyl)-2-oxopyrrolidin-3-yl]-3-(4-methoxyphenyl)urea,
(−)-1-(5-chlorothiazol-2-yl)-3-[(3S*,4R*)-4-(2,6-difluoro-4-methoxyphenyl)-2-oxopyrrolidin-3-yl]urea,
(−)-1-(6-chloropyridin-3-yl)-3-[(3S*,4R*)-4-(2,6-difluoro-4-methoxyphenyl)-2-oxopyrrolidin-3-yl]urea,
(−)-1-(5-chloropyridin-2-yl)-3-[(3S*,4R*)-4-(2,6-difluoro-4-methoxyphenyl)-2-oxopyrrolidin-3-yl]urea,
(−)-1-(benzo[b]thiophen-2-yl)-3-[(3S*,4R*)-4-(2,6-difluoro-4-methoxyphenyl)-2-oxopyrrolidin-3-yl]urea,
(−)-1-[(3S*,4R*)-4-(2,6-difluoro-4-methoxyphenyl)-2-oxopyrrolidin-3-yl]-3-(5-methylthiophen-2-yl)urea,
(−)-1-(4-fluorophenyl)-3-[(3S*,4R*,5S*)-4-(4-methoxyphenyl)-5-methyl-2-oxopyrrolidin-3-yl]urea,
(−)-1-(4-fluorophenyl)-3-[(3S*,4R*,5R*)-4-(4-methoxyphenyl)-5-methyl-2-oxopyrrolidin-3-yl]urea,
(+)-1-(4-chlorophenyl)-3-[(3R*,4S*)-2-oxo-4-phenylpyrrolidin-3-yl]urea,
(±)-trans-1-(4-chlorophenyl)-3-[4-(4-methoxyphenyl)-1-methyl-2-oxopyrrolidin-3-yl]urea,
(±)-trans-1-(4-fluorophenyl)-3-[4-(4-methoxyphenyl)-2-oxopyrrolidin-3-yl]urea,
(±)-trans-1-(4-chlorophenyl)-3-[4-(4-methoxyphenyl)-1-methyl-2-oxopyrrolidin-3-yl]urea,
(−)-1-[(3S*,4R*)-4-(2,6-difluoro-4-methoxyphenyl)-2-oxopyrrolidin-3-yl]-3-[4-(trifluoromethoxy)phenyl]urea,
(−)-1-[(3S*,4R*)-4-(2,6-difluoro-4-methoxyphenyl)-2-oxopyrrolidin-3-yl]-3-phenylurea,
(−)-1-[(3S*,4R*)-4-(2,6-difluoro-4-methoxyphenyl)-2-oxopyrrolidin-3-yl]-3-(4-phenoxyphenyl)urea,
(−)-1-[(3S*,4R*)-4-(2,6-difluoro-4-methoxyphenyl)-2-oxopyrrolidin-3-yl]-3-(3-fluorophenyl)urea,
(−)-1-[(3S*,4R*)-4-(2,6-difluoro-4-methoxyphenyl)-2-oxopyrrolidin-3-yl]-3-(3, 4-difluorophenyl) urea,
(−)-1-(5-chlorothiophen-2-yl)-3-[(3S*,4R*)-4-(2,6-difluoro-4-methoxyphenyl)-2-oxopyrrolidin-3-yl]urea,
(−)-1-[(3S*,4R*)-4-(2,6-difluoro-4-methoxyphenyl)-2-oxopyrrolidin-3-yl]-3-(p-tolyl)urea,
(−)-1-[(3S*,4R*)-1-ethyl-4-(4-methoxyphenyl)-2-oxopyrrolidin-3-yl]-3-(4-fluorophenyl)urea,
(−)-1-(4-fluorophenyl)-3-[(3S*,4R*)-1-(1-hydroxy-2-methylpropan-2-yl)-4-(4-methoxyphenyl)-2-oxopyrrolidin-3-yl]urea,
(±)-trans-1-(4-chlorophenyl)-3-[1-(2-hydroxyethyl)-4-(4-methoxyphenyl)-2-oxopyrrolidin-3-yl]urea,
(+)-trans-1-(4-chlorophenyl)-3-[1-(2-hydroxyethyl)-4-(4-methoxyphenyl)-2-oxopyrrolidin-3-yl]urea,
(−)-trans-1-(4-chlorophenyl)-3-[1-(2-hydroxyethyl)-4-(4-methoxyphenyl)-2-oxopyrrolidin-3-yl]urea,
(−)-2-{(3S*,4R*)-3-[3-(4-fluorophenyl)ureido]-4-(4-methoxyphenyl)-2-oxopyrrolidin-1-yl}-N-methylacetamide, (−)-2-{(3S*,4R*)-3-[3-(4-fluorophenyl)ureido]-4-(4-methoxyphenyl)-2-oxopyrrolidin-1-yl}propionic acid (isomer A),
(−)-2-{(3S*,4R*)-3-[3-(4-fluorophenyl)ureido]-4-(4-methoxyphenyl)-2-oxopyrrolidin-1-yl}-N-methylpropionamide (isomer A),
(−)-2-{(3S*,4R*)-3-[3-(4-fluorophenyl)ureido]-4-(4-methoxyphenyl)-2-oxopyrrolidin-1-yl}propionic acid (isomer B),
(−)-2-{(3S*,4R*)-3-[3-(4-fluorophenyl)ureido]-4-(4-methoxyphenyl)-2-oxopyrrolidin-1-yl}-N-methylpropionamide (isomer B),
(−)-2-{(3S*,4R*)-3-[3-(4-fluorophenyl)ureido]-4-(4-methoxyphenyl)-2-oxopyrrolidin-1-yl}-N,2-dimethylpropionamide,
(−)-1-[(3S*,4R*)-4-(2,6-difluoro-4-methoxyphenyl)-1-methyl-2-oxopyrrolidin-3-yl]-3-(4-fluorophenyl)urea,
(−)-1-[(3S*,4R*)-4-(2-fluoro-4-methoxyphenyl)-1-(2-hydroxyethyl)-2-oxopyrrolidin-3-yl]-3-(4-fluorophenyl) urea,
(−)-1-[(3S*,4R*)-4-(2,6-difluoro-4-methoxyphenyl)-1-(2-hydroxyethyl)-2-oxopyrrolidin-3-yl]-3-(4-fluorophenyl) urea,
(+)-1-(4-fluorophenyl)-3-[(3R*,4S*)-1-methoxy-4-(4-methoxyphenyl)-2-oxopyrrolidin-3-yl]urea,
(−)-3,5-difluoro-4-{(3R*,4S*)-4-[3-(4-fluorophenyl)ureido]-5-oxopyrrolidin-3-yl}benzamide,
(−)-1-(4-fluorophenyl)-3-[(3S*,4R*,Z)-2-(methoxyimino)-4-(4-methoxyphenyl) pyrrolidin-3-yl]urea,
(−)-1-[(3S*,4R*,Z)-4-(2-fluoro-4-methoxyphenyl)-2-(methoxyimino)pyrrolidin-3-yl]-3-(4-fluorophenyl)urea,
(−)-1-[(3S*,4R*,Z)-4-(2,6-difluoro-4-methoxyphenyl)-2-(methoxyimino)pyrrolidin-3-yl]-3-(4-fluorophenyl)urea,
(−)-1-(4-fluorophenyl)-3-{(3S*,4R*,Z)-2-[(2-hydroxyethoxy)imino]-4-(4-methoxyphenyl)pyrrolidin-3-yl}urea,
(−)-1-{(3S*,4R*,Z)-4-(2,6-difluoro-4-methoxyphenyl)-2-[(2-hydroxyethoxy)imino]pyrrolidin-3-yl}-3-(4-fluorophenyl)urea,
(−)-1-[(3S*,4R*,Z)-4-(2,6-difluoro-4-methoxyphenyl)-2-(methylimino)pyrrolidin-3-yl]-3-(4-fluorophenyl)urea,
(−)-1-(4-fluorophenyl)-3-[(3S*,4R*,Z)-2-(2-hydroxyimino)-4-(4-methoxyphenyl)pyrrolidin-3-yl]urea,
(−)-1-[(3S*,4R*)-4-(2,6-difluoro-4-methoxyphenyl)-2-oxopyrrolidin-3-yl]-3-(3-hydroxy-4-methylphenyl)urea,
(−)-1-[(3S*,4R*)-4-(2,6-difluoro-4-methoxyphenyl)-2-oxopyrrolidin-3-yl]-3-(4-fluoro-3-hydroxyphenyl)urea,
(−)-1-(4-chloro-3-hydroxyphenyl)-3-[(3S*,4R*)-4-(2,6-difluoro-4-methoxyphenyl)-2-oxopyrrolidin-3-yl]urea,
(−)-1-(4-cyanophenyl)-3-[(3S*,4R*)-4-(6-fluoro-2,3-dihydrobenzofuran-5-yl)-2-oxopyrrolidin-3-yl]urea,
(−)-1-{(3S*,4R*,Z)-4-(2,6-difluoro-4-methoxyphenyl)-2-[(2-hydroxyethoxy)imino]pyrrolidin-3-yl}-3-(p-tolyl) urea, or
(−)-1-[(3S*,4R*)-4-(2,6-difluoro-4-methoxyphenyl)-1-(2-hydroxyethyl)-2-oxopyrrolidin-3-yl]-3-phenylurea.
[14] A pharmaceutical containing, as an active ingredient, the compound according to any one of [1] to [13] or a pharmacologically acceptable salt thereof.
[15] An FPRL1 agonist containing, as an active ingredient, the compound according to any one of [1] to [13] or a pharmacologically acceptable salt thereof.
[16] A method of treatment or prevention of inflammatory diseases, chronic airway diseases, cancers, septicemia, allergic symptoms, HIV retrovirus infection, circulatory disorders, neuroinflammation, nervous disorders, pains, prion diseases, amyloidosis, and immune disorders, comprising administering the compound according to any one of [1] to [13] or a pharmacologically acceptable salt thereof.
[17] Use of the compound according to any one of [1] to [13] or a pharmacologically acceptable salt thereof to produce a pharmaceutical for treatment or prevention of inflammatory diseases, chronic airway diseases, cancers, septicemia, allergic symptoms, HIV retrovirus infection, circulatory disorders, neuroinflammation, nervous disorders, pains, prion diseases, amyloidosis, and immune disorders.
[18] A pharmaceutical composition containing the compound according to any one of [1] to [13] or a pharmacologically acceptable salt thereof and a pharmaceutically acceptable carrier, used for prevention or treatment of inflammatory diseases, chronic airway diseases, cancers, septicemia, allergic symptoms, HIV retrovirus infection, circulatory disorders, neuroinflammation, nervous disorders, pains, prion diseases, amyloidosis, and immune disorders.

Advantageous Effects of Invention

The compound (I) or a pharmacologically acceptable salt thereof exhibited superior agonist activity in, for example, a test of calcium influx into FPRL1-overexpressing cells. The compound (I) and salts thereof strongly suppressed lipopolysaccharide-induced neutrophilic infiltration into the lungs of mice. In addition, the compound (I) and salts thereof have low toxicity and are therefore safe. Therefore, the compound (I) according to the present invention or a pharmacologically acceptable salt thereof is useful as a therapeutic or prophylactic agent for inflammatory diseases, chronic airway diseases, cancers, septicemia, allergic symptoms, HIV retrovirus infection, circulatory disorders, neuroinflammation, nervous disorders, pains, prion diseases, amyloidosis, immune disorders and the like.

In addition, the compound (I) according to the present invention or a pharmacologically acceptable salt thereof is highly useful for treatment, prevention, or suppression of various disease states associated with the FPRL1 receptor (such as Behcet's disease, Sweet disease, systemic lupus erythematosus (SLE), Wegener's granulomatosis, virus infection, diabetes, amputations, cancers, bacterial infection, physical external injuries, physical disorders including exposure to radiation, vasoconstriction, anaphylactic reactions, allergic reactions, rhinitis, shocks (endotoxic, hemorrhagic, traumatic, splanchnic ischemia, and circulatory shocks), rheumatoid arthritis, gout, psoriasis, benign prostatic hyperplasia, myocardial ischemia, myocardial infarction, brain injuries, pulmonary diseases, COPD, COAD, COLD, acute lung injury, acute respiratory distress syndrome, chronic bronchitis, pulmonary emphysema, asthma (allergic asthma and non-allergic asthma), cystic pulmonary fibrosis, nephropathy, renal glomerular diseases, ulcerative colitis, IBD, Crohn's disease, periodontitis, pains, Alzheimer's disease, AIDS, uveitic glaucoma, conjunctivitis, Sjoegren's syndrome, and rhinitis).

DESCRIPTION OF EMBODIMENTS

Terms in the present description will be described.
The term "halogen atom" as used herein means a fluorine atom, a chlorine atom, a bromine atom, or an iodine atom. Preferably, the halogen atom is a fluorine atom or a chlorine atom.
The 5-membered aromatic heterocyclic group in the term "5-membered aromatic heterocyclic group optionally having substituent(s)" as used herein means a 5-membered aromatic heterocyclic group containing, in its ring, 1 to 4 atoms selected from sulfur, oxygen, and nitrogen atoms. Examples of the 5-membered aromatic heterocyclic group may include a furyl group, a thienyl group, a pyrrolyl group, an azepinyl group, a pyrazolyl group, an imidazolyl group, an oxazolyl group, an isoxazolyl group, a thiazolyl group, an isothiazolyl group, a 1,2,3-oxadiazolyl group, a triazolyl group, a tetrazolyl group, a thiadiazolyl group and the like.

The 6-membered aromatic heterocyclic group in the term "6-membered aromatic heterocyclic group optionally having substituent(s)" as used herein means a 6-membered aromatic heterocyclic group containing, in its ring, 1 to 4 nitrogen atoms. Examples of the 6-membered aromatic heterocyclic group may include a pyridyl group, a pyridazinyl group, a pyrimidinyl group, a pyrazinyl group and the like.

The bicyclic aromatic heterocyclic group having 8 or 9 atoms in the term "bicyclic aromatic heterocyclic group having 8 or 9 atoms and optionally having substituent(s)" as used herein means a bicyclic aromatic heterocyclic group having 8 or 9 atoms containing 1 to 4 atoms selected from sulfur, oxygen, and nitrogen atoms. Examples of the bicyclic aromatic heterocyclic group having 8 or 9 atoms may include a benzofuranyl group, an isobenzofuranyl group, a benzoxazolyl group, a benzisoxazolyl group, a benzothiazolyl group, a benzisothiazolyl group, a benzimidazolyl group, a benzothiophenyl group, an indolyl group, an isoindolyl group, an indazolyl group, a thiazolopyridyl group, an oxazolopyrazinyl group and the like.

The $C_1$ to $C_6$ alkoxy group in the terms "$C_1$ to $C_6$ alkoxy group optionally having substituent(s)" and "$C_1$ to $C_6$ alkoxy group" as used herein means a linear or branched alkoxy group having 1 to 6 carbon atoms. Examples of the $C_1$ to $C_6$ alkoxy group may include a methoxy group, an ethoxy group, a propoxy group, an isopropoxy group, an isobutoxy group, a butoxy group, a sec-butoxy group, a tert-butoxy group, a pentyloxy group, a hexyloxy group and the like. Preferred examples may include a methoxy group and an ethoxy group.

The $C_1$ to $C_6$ alkyl group in the terms "$C_1$ to $C_6$ alkyl group optionally having substituent(s)" and "$C_1$ to $C_6$ alkyl group" as used herein means a linear or branched alkyl group having 1 to 6 carbon atoms and optionally having substituent(s). Examples of the $C_1$ to $C_6$ alkyl group may include a methyl group, an ethyl group, a propyl group, an isopropyl group, a butyl group, an isobutyl group, a sec-butyl group, a tert-butyl group, a pentyl group, an isopentyl group, a neopentyl group, a 1-methylbutyl group, a 2-methylbutyl group, a 1,2-dimethylpropyl group, a hexyl group, an isohexyl group and the like.

The $C_1$ to $C_6$ acyl group in the terms "$C_1$ to $C_6$ acyl group optionally having substituent(s)" and "$C_1$ to $C_6$ acyl group" as used herein means an acyl group derived from a linear or branched aliphatic carboxylic acid having 1 to 6 carbon atoms. Examples of the $C_1$ to $C_6$ acyl group may include a formyl group, an acetyl group, a propanoyl group, a butanoyl group, a pentanoyl group, a hexanoyl group and the like.

The $C_1$ to $C_6$ alkylsulfanyl group in the terms "$C_1$ to $C_6$ alkylsulfanyl group optionally having substituent(s)" and "$C_1$ to $C_6$ alkylsulfanyl group" as used herein means a linear or branched alkylsulfanyl group having 1 to 6 carbon atoms or a cyclic alkylsulfanyl group having 3 to 6 carbon atoms. Examples of the $C_1$ to $C_6$ alkylsulfanyl group may include a methylsulfanyl group, an ethylsulfanyl group, a propylsulfanyl group, an isopropylsulfanyl group, a butylsulfanyl group, an isobutylsulfanyl group, a sec-butylsulfanyl group, a tert-butylsulfanyl group, a cyclopropylsulfanyl group, a cyclobutylsulfanyl group, a cyclopentylsulfanyl group and the like.

The $C_1$ to $C_6$ alkylsulfinyl group in the terms "$C_1$ to $C_6$ alkylsulfinyl group optionally having substituent(s)" and "$C_1$ to $C_6$ alkylsulfinyl group" as used herein means a linear or branched alkylsulfinyl group having 1 to 6 carbon atoms or a cyclic alkylsulfinyl group having 3 to 6 carbon atoms. Examples of the $C_1$ to $C_6$ alkylsulfinyl group may include a methylsulfinyl group, an ethylsulfinyl group, a propylsulfinyl group, an isopropylsulfinyl group, a butylsulfinyl group, an isobutylsulfinyl group, a sec-butylsulfinyl group, a tert-butylsulfinyl group, a cyclopropylsulfinyl group, a cyclobutylsulfinyl group, a cyclopentylsulfinyl group and the like.

The $C_1$ to $C_6$ alkylsulfonyl group in the terms "$C_1$ to $C_6$ alkylsulfonyl group optionally having substituent(s)" and "$C_1$ to $C_6$ alkylsulfonyl group" as used herein means a linear or branched alkylsulfonyl group having 1 to 6 carbon atoms or a cyclic alkylsulfonyl group having 3 to 6 carbon atoms. Examples of the $C_1$ to $C_6$ alkylsulfonyl group may include a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a cyclopropylsulfonyl group, a cyclobutylsulfonyl group, a cyclopentylsulfonyl group and the like.

The heterocyclic group in the term "heterocyclic group optionally having substituent(s)" as used herein means a 5- to 7-membered heterocyclic group containing 1 to 4 atoms selected from sulfur, oxygen, and nitrogen atoms. Examples of the heterocyclic group may include: aromatic heterocyclic groups such as a furyl group, a thienyl group, a pyrrolyl group, an azepinyl group, a pyrazolyl group, an imidazolyl group, an oxazolyl group, an isoxazolyl group, a thiazolyl group, an isothiazolyl group, a 1,2,3-oxadiazolyl group, a triazolyl group, a tetrazolyl group, a thiadiazolyl group, a pyranyl group, a pyridyl group, a pyridazinyl group, a pyrimidinyl group, and a pyrazinyl group; unsaturated heterocyclic groups such as a pyrrolinyl group, an imidazolinyl group, a pyrazolinyl group, a dihydropyranyl group, a dihydrothiopyranyl group, and a dihydropyridyl group; and saturated heterocyclic groups such as a morpholinyl group, a thiomorpholinyl group, a pyrrolidinyl group, an imidazolidinyl group, an imidazolinyl group, a pyrazolidinyl group, a pyrazolinyl group, a piperidinyl group, a piperazinyl group, a tetrahydrofuranyl group and the like.

The above "heterocyclic group" may be annelated with another cyclic group. Examples of the heterocyclic group annelated with another cyclic group may include an isobenzofuranyl group, a benzoxazolyl group, a benzisoxazolyl group, a benzothiazolyl group, a benzisothiazolyl group, a chromenyl group, a chromanonyl group, a xanthenyl group, a phenoxathiinyl group, an indolizinyl group, an isoindolizinyl group, an indolyl group, an indazolyl group, a purinyl group, a quinolizinyl group, an isoquinolyl group, a quinolyl group, a phthalazinyl group, a naphthyridinyl group, a quinoxalinyl group, a quinazolinyl group, a carbazolyl group, a carbolinyl group, an acridinyl group, an isoindolinyl group and the like.

The term "$C_3$ to $C_{10}$ heterocycloalkyl group" as used herein means a monocyclic, bicyclic, or tricyclic non-aromatic heterocycloalkyl group which has a ring structure containing at least one nitrogen atom and optionally containing an oxygen atom or a sulfur atom and in which the number of carbon atoms forming the ring(s) of the cyclic group is 4 to 10. Examples of the $C_3$ to $C_{10}$ heterocycloalkyl group may include an azetidinyl group, a pyrrolidinyl group, a piperidyl group, a piperazyl group, a morpholyl group and the like.

The $C_3$ to $C_6$ cycloalkyl group in the terms "$C_3$ to $C_6$ cycloalkyl group optionally having substituent(s)" and "$C_3$ to $C_6$ cycloalkyl group" as used herein means a monocyclic saturated alicyclic hydrocarbon group having 3 to 6 carbon atoms. Examples of the $C_3$ to $C_6$ cycloalkyl group may include a cyclopropyl group, a cyclobutyl group, a cyclopentyl group, a cyclohexyl group and the like.

The $C_3$ to $C_6$ cycloalkoxy group in the terms "$C_3$ to $C_6$ cycloalkoxy group optionally having substituent(s)" and "$C_3$ to $C_6$ cycloalkoxy group" as used herein means a cyclic alkoxy group having 3 to 6 carbon atoms. Examples of the $C_3$ to $C_6$ cycloalkoxy group may include a cyclopropyloxy group, a cyclobutyloxy group, a cyclopentyloxy group, and a cyclohexyloxy group.

The $C_2$ to $C_6$ alkenyl group in the terms "$C_2$ to $C_6$ alkenyl group optionally having substituent(s)" and "$C_2$ to $C_6$ alkenyl group" as used herein means a linear or branched unsaturated hydrocarbon group having 2 to 6 carbon atoms and having at least one double bond. Examples of the $C_2$ to $C_6$ alkenyl group may include a vinyl group, a 2-propenyl group, a 1-propenyl group, a 3-propenyl group, a 1-buten-1-yl group, a 1-buten-2-yl group, a 1-buten-3-yl group, a 1-buten-4-yl group, a 2-buten-1-yl group, a 2-buten-2-yl group, a 1-penten-1-yl group, a 1-penten-2-yl group, a 1-penten-3-yl group, a 2-penten-1-yl group, a 2-penten-2-yl group, a 2-penten-3-yl group, a 1-hexen-1-yl group, a 1-hexen-2-yl group, a 1-hexen-3-yl group, a 2-methyl-1-propen-1-yl group and the like.

The "$C_2$ to $C_6$ alkynyl group" in the term "$C_2$ to $C_6$ alkynyl group optionally having substituent(s)" as used herein means a linear or branched unsaturated hydrocarbon group having 2 to 6 carbon atoms and having at least one triple bond. Examples of the $C_2$ to $C_6$ alkynyl group may include an ethynyl group, a 1-propynyl group, a 2-propynyl group, a 1-butynyl group, a 2-butynyl group, a 3-butynyl group, a 3-methyl-1-propynyl group, a 1-ethynyl-2-propynyl group, a 2-methyl-3-propynyl group, a 1-pentynyl group, a 1-hexynyl group, a 1,3-hexanediynyl group, a 1,5-hexanediynyl group and the like.

The $C_1$ to $C_6$ alkoxycarbonyl group in the terms "$C_1$ to $C_6$ alkoxycarbonyl group optionally having substituent(s)" and "$C_1$ to $C_6$ alkoxycarbonyl group" as used herein means a linear or branched alkoxycarbonyl group having 1 to 6 carbon atoms. Examples of the $C_1$ to $C_6$ alkoxycarbonyl group may include a methoxycarbonyl group, an ethoxycarbonyl group, a propoxycarbonyl group, an isopropoxycarbonyl group, an isobutoxycarbonyl group, a butoxycarbonyl group, a sec-butoxycarbonyl group, a tert-butoxycarbonyl group, a pentyloxycarbonyl group, a hexyloxycarbonyl group and the like. Preferred examples thereof may include a methoxycarbonyl group and a tert-butoxycarbonyl group.

The term "halo-$C_1$ to $C_6$ alkoxy group" as used herein means a $C_1$ to $C_6$ alkoxy group substituted with 1 to 5 halogen atoms of the same type or different types. Examples of the halo-$C_1$ to $C_6$ alkoxy group may include a fluoromethoxy group, a difluoromethoxy group, a trifluoromethoxy group, a 2-fluoroethoxy group, a 2-chloroethoxy group, a 2,2-difluoroethoxy group, a 1,1-difluoroethoxy group, a 1,2-difluoroethoxy group, a 2,2,2-trifluoroethoxy group, a 1,1,2,2,2-pentafluoroethoxy group, a 2,2,2-trichloroethoxy group, a 3-fluoropropoxy group, a 2-fluoropropoxy group, a 1-fluoropropoxy group, a 3,3-difluoropropoxy group, a 2,2-difluoropropoxy group, a 1,1-difluoropropoxy group, a 4-fluorobutoxy group, a 5-fluoropentoxy group, a 6-fluorohexyloxy group and the like.

The term "hydroxy $C_1$ to $C_6$ alkyl group" as used herein means a $C_1$ to $C_6$ alkyl group substituted with a hydroxy group. Examples of the hydroxy $C_1$ to $C_6$ alkyl group may include a 2-hydroxyethyl group, a 1-hydroxyethyl group, a 3-hydroxypropyl group, a 2-hydroxypropyl group, a 1-hydroxypropyl group, a 4-hydroxybutyl group, a 3-hydroxybutyl group, a 2-hydroxybutyl group, a 1-hydroxybutyl group, a 5-hydroxypentyl group, a 6-hydroxyhexyl group and the like.

Examples of the "$C_1$ to $C_2$ alkylenedioxy group" as used herein may include a methylenedioxy group (—O—$CH_2$—O—) and an ethylenedioxy group (—O—$CH_2CH_2$—O—).

The term "$C_2$ to $C_6$ alkylene group" as used herein means a divalent linear or branched saturated hydrocarbon chain having 2 to 6 carbon atoms. Examples of the $C_2$ to $C_6$ alkylene group may include —$(CH_2)_2$—, —$(CH_2)_3$—, —$CH(CH_3)CH_2$—, —$CH_2CH(CH_3)$—, —$(CH_2)_4$—, —$CH(CH_3)$—$(CH_2)_2$—, —$(CH_2)_2$—$CH(CH_3)$—, —$CH(CH_2CH_3)$—$CH_2$—, —$C(CH_3)_2CH_2$—, —$CH_2$—$C(CH_3)_2$—, —$CH(CH_3)$—$CH(CH_3)$—, —$(CH_2)_5$—, —$CH(CH_3)$—$(CH_2)_3$—, —$C(CH_3)_2CH_2CH_2$—, —$(CH_2)_6$—, —$C(CH_3)_2$—$(CH_2)_3$— and the like. Preferred examples thereof may include —$(CH_2)_2$— and —$(CH_2)_3$—.

The term "$C_3$ to $C_5$ alkylene group" as used herein means a divalent linear or branched saturated hydrocarbon chain having 3 to 5 carbon atoms. Examples of the $C_3$ to $C_5$ alkylene group may include —$(CH_2)_3$—, —$CH(CH_3)CH_2$—, —$CH_2CH(CH_3)$—, —$(CH_2)_4$—, —$CH(CH_3)$—$(CH_2)_2$—, —$(CH_2)_2$—$CH(CH_3)$—, —$CH(CH_2CH_3)$—$CH_2$—, —$C(CH_3)_2CH_2$—, —$CH_2$—$C(CH_3)_2$—, —$CH(CH_3)$—$CH(CH_3)$—, —$(CH_2)_5$—, —$CH(CH_3)$—$(CH_2)_3$—, —$C(CH_3)_2CH_2CH_2$— and the like.

The term "aryloxy group" as used herein means an aromatic hydrocarbon alkoxy group having 6 to 14 carbon atoms. Examples of the aryloxy group may include a phenyloxy group, an indenyloxy group, a naphthyloxy group, a phenanthrenyloxy group, an anthracenyloxy group and the like.

The term "carboxy $C_1$ to $C_6$ alkyl group" as used herein means a $C_1$ to $C_6$ alkyl group substituted with a carboxylic acid. Examples of the carboxy $C_1$ to $C_6$ alkyl group may include a carboxymethyl group, a 2-carboxyethyl group, a 2-carboxypropyl group, a 3-carboxypropyl group, a 4-carboxybutyl group, a 5-carboxypentyl group, a 6-carboxyhexyl group and the like.

The term "carbamoyl $C_1$ to $C_6$ alkyl group" as used herein means a $C_1$ to $C_6$ alkyl group substituted with a carbamoyl group. Examples of the carbamoyl $C_1$ to $C_6$ alkyl group may include a carbamoylmethyl group, a 2-carbamoylethyl group, a 2-carbamoylpropyl group, a 3-carbamoylpropyl group, a 4-carbamoylbutyl group, a 5-carbamoylpentyl group, a 6-carbamoylhexyl group and the like.

The term "mono $C_1$ to $C_6$ alkylcarbamoyl $C_1$ to $C_6$ alkyl group" as used herein means a $C_1$ to $C_6$ alkyl group substituted with a carbamoyl group in which one hydrogen atom in the amino group is substituted with a $C_1$ to $C_6$ alkyl group. Examples of the mono $C_1$ to $C_6$ alkylcarbamoyl $C_1$ to $C_6$ alkyl group may include an N-methylcarbamoylmethyl group, an N-ethylcarbamoylmethyl group, a 2-(N-methylcarbamoyl)ethyl group, a 2-(N-ethylcarbamoyl)ethyl group, a 2-(N-propylcarbamoyl)ethyl group, a 3-(N-methylcarbamoyl)propyl group, a 4-(N-ethylcarbamoyl)butyl group, a 5-(N-ethylcarbamoyl)pentyl group, a 6-(N-propylcarbamoyl)hexyl group and the like.

The term "di-$C_1$ to $C_6$ alkylcarbamoyl $C_1$ to $C_6$ alkyl group" as used herein means a $C_1$ to $C_6$ alkyl group substituted with a carbamoyl group in which two hydrogen atoms in the amino group are substituted with $C_1$ to $C_6$ alkyl groups. Examples of the di-$C_1$ to $C_6$ alkylcarbamoyl $C_1$ to $C_6$ alkyl group may include an N,N-dimethylcarbamoylmethyl group, an N-ethyl-N-methylcarbamoylmethyl group, a 2-(N,N-dimethylcarbamoyl)ethyl group, a 2-(N-ethyl-N-methylcarbamoyl)ethyl group, a 2-(N-methyl-N-propylcarbamoyl)ethyl group, a 3-(N,N-dimethylcarbamoyl)propyl group, a 4-(N,N-diethylcarbamoyl)butyl group, a 5-(N-ethyl-N-propylcarbamoyl)pentyl group, a 6-(N,N-dipropylcarbamoyl)hexyl group and the like.

The term "$C_1$ to $C_6$ alkylamino group" as used herein means an amino group in which one or two hydrogen atoms in the amino group are substituted with linear or branched alkyl groups having 1 to 6 carbon atoms. Examples of the $C_1$ to $C_6$ alkylamino group may include a methylamino group, an ethylamino group, a propylamino group, an isopropylamino group, a butylamino group, an isobutylamino group, a sec-butylamino group, a tert-butylamino group, a pentylamino group, an isopentylamino group, a neopentylamino group, a 1-methylbutylamino group, a 2-methylbutylamino group, a 1,2-dimethylpropylamino group, a hexylamino group, an isohexylamino group, a dimethylamino group, a diethylamino group, an N-ethyl-N-methylamino group, an N-ethyl-N-propylamino group and the like.

The term "$C_1$ to $C_6$ acylamino group" as used herein means an amino group substituted with $C_1$ to $C_6$ acyl. Examples of the $C_1$ to $C_6$ acylamino group may include a formylamino group, an acetylamino group, a propanoylamino group, a butanoylamino group, a pentanoylamino group, a hexanoylamino group and the like.

The term "$C_1$ to $C_3$ alkyl group" as used herein means a linear or branched alkyl group having 1 to 3 carbon atoms. Examples of the $C_1$ to $C_3$ alkyl group may include a methyl group, an ethyl group, a propyl group, and an isopropyl group.

The term "$C_1$ to $C_3$ alkoxy group" as used herein means a linear or branched alkoxy group having 1 to 3 carbon atoms. Examples of the $C_1$ to $C_3$ alkoxy group may include a methoxy group, an ethoxy group, a propoxy group, and an isopropoxy group.

The term "hydroxy $C_1$ to $C_4$ alkyl group" as used herein means a linear or branched alkyl group having 1 to 4 carbon atoms and substituted with a hydroxy group. Examples of the hydroxy $C_1$ to $C_4$ alkyl group may include a 2-hydroxyethyl group, a 1-hydroxyethyl group, a 3-hydroxypropyl group, a 2-hydroxypropyl group, a 1-hydroxypropyl group, a 4-hydroxybutyl group, a 3-hydroxybutyl group and the like.

The term "carboxy $C_1$ to $C_3$ alkyl group" as used herein means a $C_1$ to $C_3$ alkyl group substituted with a carboxylic acid. Examples of the carboxy $C_1$ to $C_3$ alkyl group may include a carboxymethyl group, a 2-carboxyethyl group, a 2-carboxypropyl group, a 3-carboxypropyl group and the like.

The term "carbamoyl $C_1$ to $C_3$ alkyl group" as used herein means a $C_1$ to $C_3$ alkyl group substituted with a carbamoyl group. Examples of the carbamoyl $C_1$ to $C_3$ alkyl group may include a carbamoylmethyl group, a 2-carbamoylethyl group, a 2-carbamoylpropyl group, a 3-carbamoylpropyl group and the like.

The term "mono $C_1$ to $C_2$ alkylcarbamoyl $C_1$ to $C_3$ alkyl group" as used herein means a $C_1$ to $C_3$ alkyl group substituted with a carbamoyl group in which one hydrogen atom in the amino group is substituted with a $C_1$ to $C_2$ alkyl group. Examples of the mono $C_1$ to $C_2$ alkylcarbamoyl $C_1$ to $C_3$ alkyl group may include an N-methylcarbamoylmethyl group, an N-ethylcarbamoylmethyl group, a 2-(N-methylcarbamoyl)ethyl group, a 2-(N-ethylcarbamoyl)ethyl group, a 3-(N-methylcarbamoyl)propyl group and the like.

The term "di-$C_1$ to $C_2$ alkylcarbamoyl $C_1$ to $C_3$ alkyl group" as used herein means a $C_1$ to $C_3$ alkyl group substituted with a carbamoyl group in which two hydrogen atoms in the amino group are substituted with $C_1$ to $C_2$ alkyl groups. Examples of the di-$C_1$ to $C_2$ alkylcarbamoyl $C_1$ to $C_3$ alkyl group may include an N,N-dimethylcarbamoylmethyl group, an N-ethyl-N-methylcarbamoylmethyl group, a 2-(N,N-dimethylcarbamoyl)ethyl group, a 2-(N-ethyl-N-methylcarbamoyl)ethyl group, a 3-(N,N-dimethylcarbamoyl)propyl group, a 3-(N,N-diethylcarbamoyl)propyl group and the like.

Examples of an "aromatic hydrocarbon cyclic group" as used herein may include a phenyl group, an indenyl group, a 1-naphthyl group, a 2-naphthyl group, an azulenyl group, a heptalenyl group, a biphenyl group, an indacenyl group, an acenaphthyl group, a fluorenyl group, a phenalenyl group, a phenanthrenyl group, an anthracenyl group, a benzocyclooctenyl group and the like.

The term "aromatic heterocyclic group" as used herein means an aromatic cyclic structure containing a nitrogen atom, an oxygen atom, or a sulfur atom. Examples of the aromatic heterocyclic group may include a furyl group, a thienyl group, a pyrrolyl group, an azepinyl group, a pyrazolyl group, an imidazolyl group, an oxazolyl group, an isoxazolyl group, a thiazolyl group, an isothiazolyl group, a 1,2,3-oxadiazolyl group, a triazolyl group, a tetrazolyl group, a thiadiazolyl group, a pyranyl group, a pyridyl group, a pyridazinyl group, a pyrimidinyl group, a pyrazinyl group and the like. The above "heterocyclic group" may be annelated with another cyclic group. Examples of such a heterocyclic group may include an isobenzofuranyl group, a benzoxazolyl group, a benzisoxazolyl group, a benzothiazolyl group, a benzisothiazolyl group, a chromenyl group, a chromanonyl group, a xanthenyl group, a phenoxathiinyl group, an indolizinyl group, an isoindolizinyl group, an indolyl group, an indazolyl group, a purinyl group, a quinolizinyl group, an isoquinolyl group, a quinolyl group, a phthalazinyl group, a naphthyridinyl group, a quinoxalinyl group, a quinazolinyl group, a carbazolyl group, a carbolinyl group, an acridinyl group, an isoindolinyl group and the like.

The term "halo-$C_1$ to $C_6$ alkyl group" as used herein means a $C_1$ to $C_6$ alkyl group substituted with 1 to 5 halogen atoms of the same type or different types. Examples of the halo-$C_1$ to $C_6$ alkyl group may include a fluoromethyl group, a difluoromethyl group, a trifluoromethyl group, a 2-fluoroethyl group, a 2-chloroethyl group, a 2,2-difluoroethyl group, a 1,1-difluoroethyl group, a 1,2-difluoroethyl group, a 2,2,2-trifluoroethyl group, a 1,1,2,2,2-pentafluoroethyl group, a 2,2,2-trichloroethyl group, a 3-fluoropropyl group, a 2-fluoropropyl group, a 1-fluoropropyl group, a 3,3-difluoropropyl group, a 2,2-difluoropropyl group, a 1,1-difluoropropyl group, a 4-fluorobutyl group, a 5-fluoropentyl group, a 6-fluorohexyl group and the like.

No particular limitation is imposed on the groups acceptable as the "substituent(s)" in the "phenyl group optionally having substituent(s)," the "5-membered aromatic heterocyclic group optionally having substituent(s)," the "6-membered aromatic heterocyclic group optionally having substituent(s)," the "bicyclic aromatic heterocyclic group having 8 or 9 atoms and optionally having substituent(s)," and the "heterocyclic group optionally having substituent(s)," so long as the substituent(s) are generally known substituent(s). Examples of these substituent(s) may include halogen atoms, an amino group, a hydroxy group, a cyano group, a nitro group, a carboxy group, $C_1$ to $C_6$ alkoxycarbonyl groups, a formyl group, $C_1$ to $C_6$ acyl groups, $C_1$ to $C_6$ alkyl groups, $C_1$ to $C_6$ alkylamino groups, $C_1$ to $C_6$ alkoxy groups, $C_1$ to $C_6$ alkylthio groups, $C_3$ to $C_6$ cycloalkyl groups, 4- to 10-membered heterocycloalkyl groups, aromatic hydrocarbon cyclic groups optionally having a halogen atom, aromatic heterocyclic groups, $C_1$ to $C_6$ alkylcarbonylamino groups, $C_3$ to $C_6$ cycloalkylcarbonylamino groups, 4- to 10-membered heterocycloalkylcarbonylamino groups, aromatic hydrocarbon cyclic carbonylamino groups, aromatic heterocyclic carbonylamino groups and the like.

No particular limitation is imposed on the groups acceptable as the "substituent(s)" in the "$C_1$ to $C_6$ alkoxy group optionally having substituent(s)," the "$C_1$ to $C_6$ alkyl group optionally having substituent(s)," the "$C_1$ to $C_6$ acyl group optionally having substituent(s)," the "$C_1$ to $C_6$ alkylsulfanyl group optionally having substituent(s)," the "$C_1$ to $C_6$ alkylsulfinyl group optionally having substituent(s)," the "$C_1$ to $C_6$ alkylsulfonyl group optionally having substituent(s)," the "$C_3$ to $C_6$ cycloalkyl group optionally having substituent(s)," the "$C_3$ to $C_6$ cycloalkoxy group optionally having substituent(s)," the "$C_2$ to $C_6$ alkenyl group optionally having substituent(s)," the "$C_1$ to $C_6$ alkoxycarbonyl group optionally having substituent(s)," the "aromatic heterocyclic $C_1$ to $C_3$ alkyl group optionally having substituent(s)," and the "phenyl $C_1$ to $C_3$ alkyl group optionally having substituent(s)," so long as the substituent(s) are generally known substituent(s). Examples of these substituent(s) may include halogen atoms, an amino group, a hydroxy group, a cyano group, a nitro group, a carboxy group, $C_1$ to $C_6$ alkoxycarbonyl groups, a formyl group, $C_1$ to $C_6$ acyl groups, $C_1$ to $C_6$ alkyl groups, $C_1$ to $C_6$ alkylamino groups, di-$C_1$ to $C_6$ alkylamino groups, $C_1$ to $C_6$ alkoxy groups, $C_1$ to $C_6$ alkylthio groups, $C_3$ to $C_6$ cycloalkyl groups, 4- to 10-membered heterocycloalkyl groups, aromatic hydrocarbon cyclic groups optionally having a halogen atom, aromatic heterocyclic groups, $C_1$ to $C_6$ alkylcarbonylamino groups, $C_3$ to $C_6$ cycloalkylcarbonylamino groups, 4- to 10-membered heterocycloalkylcarbonylamino groups, aromatic hydrocarbon cyclic carbonylamino groups, aromatic heterocyclic carbonylamino groups and the like.

Hereinafter, the present embodiment will be described in more detail.

In the following, descriptions of the definitions of functional groups included in general formulas may be omitted, and the definitions already described may be quoted instead. The definitions quoted refer to definitions in the description of the following embodiment.

As for the definitions of functional groups included in the general formulas, the definition of a symbol is common to general formulas containing this symbol, unless otherwise mentioned.

The present embodiment relates to a urea compound represented by the following general formula (I) or a pharmacologically acceptable salt thereof.

[Chemical Formula 11]

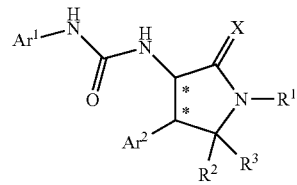

(I)

In the formula (I), $Ar^1$ is a phenyl group optionally having substituent(s), a 5-membered aromatic heterocyclic group optionally having substituent(s), a 6-membered aromatic heterocyclic group optionally having substituent(s), or a bicyclic aromatic heterocyclic group having 8 or 9 atoms and optionally having substituent(s);

$Ar^2$ is a phenyl group optionally having substituent(s) (except for a phenyl group substituted only with halogen atom(s)), a 5-membered aromatic heterocyclic group optionally having substituent(s), a 6-membered aromatic heterocyclic group optionally having substituent(s), or a bicyclic aromatic heterocyclic group having 8 or 9 atoms and optionally having substituent(s);

X is a group selected from the group consisting of the following a), b), and c), a) an oxygen atom or a sulfur atom, b) $NR^4$, and c) $NOR^4$, wherein, when X is b) or c), $R^4$ is a hydrogen atom or a $C_1$ to $C_6$ alkyl group optionally having substituent(s);

$R^1$ is a hydrogen atom, a hydroxy group, a $C_1$ to $C_6$ alkoxy group optionally having substituent(s), or a $C_1$ to $C_6$ alkyl group optionally having substituent(s);

$R^2$ and $R^3$ are each independently a hydrogen atom or a $C_1$ to $C_6$ alkyl group optionally having substituent(s) or $R^2$ and $R^3$ together form a $C_2$ to $C_6$ alkylene group; and Each carbon atom marked with an asterisk is an asymmetric carbon atom.

The term "independently" means that at least two substituents present may be the same or different.

In the compound (I) of the present embodiment or a pharmacologically acceptable salt thereof, preferred substituents are as follows.

Preferably, $Ar^1$ is a group selected from the group consisting of the following B1), B2), B3), B4), B5), B6), B7), B8), B9), B10), B11), and B12).

[Chemical Formula 12]

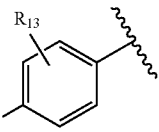

B1)

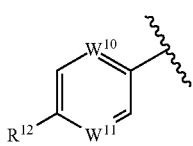

B2)

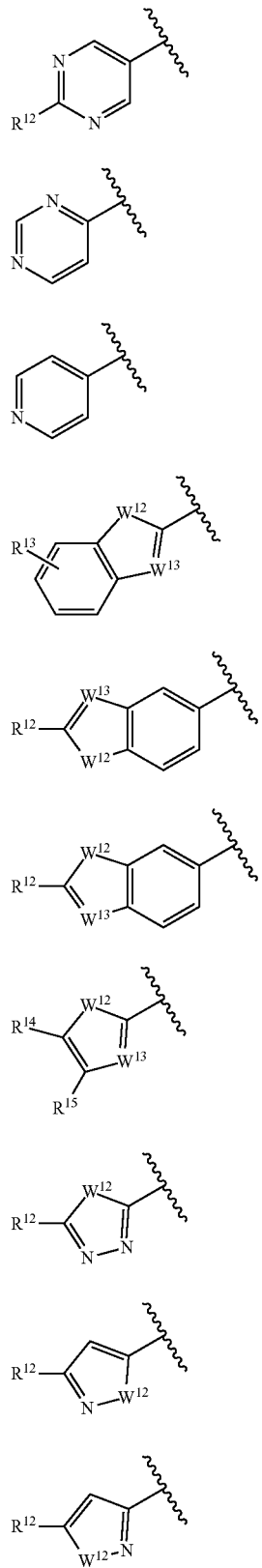
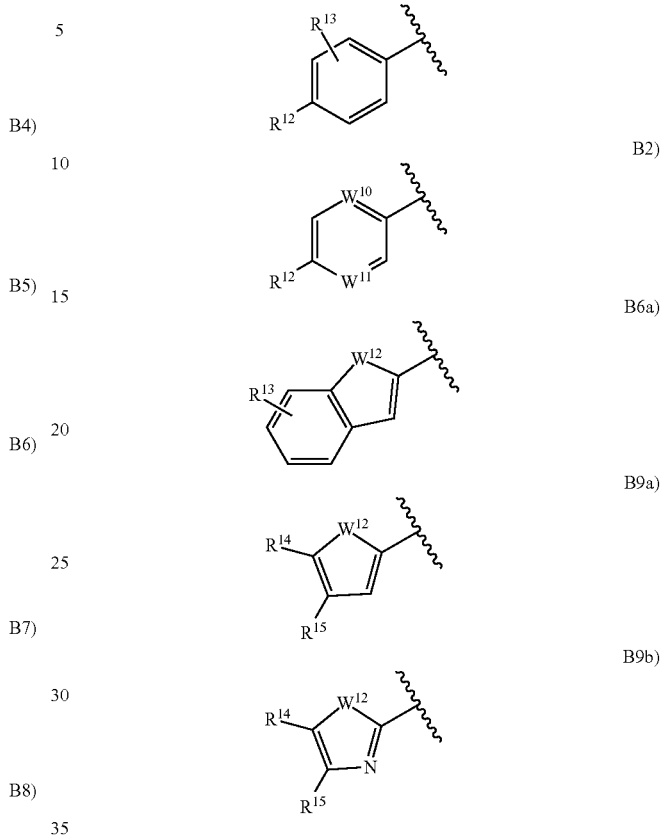

More preferably, $Ar^1$ is a group selected from the group consisting of the following B1), B2), B6a), B9a), and B9b).

$R^{12}$ is a hydrogen atom, a halogen atom, a hydroxy group, a cyano group, a $C_1$ to $C_6$ alkyl group optionally having substituent(s), a $C_1$ to $C_6$ alkoxy group optionally having substituent(s), a $C_3$ to $C_6$ cycloalkyl group optionally having substituent(s), a $C_3$ to $C_6$ cycloalkoxy group optionally having substituent(s), a $C_1$ to $C_6$ acyl group optionally having substituent(s), a $C_2$ to $C_6$ alkenyl group optionally having substituent(s), a $C_2$ to $C_6$ alkynyl group optionally having substituent(s), a $C_1$ to $C_6$ alkoxycarbonyl group, a $C_1$ to $C_6$ alkylsulfanyl group optionally having substituent(s), a $C_1$ to $C_6$ alkylsulfinyl group optionally having substituent(s), a $C_1$ to $C_6$ alkylsulfonyl group optionally having substituent(s), $—CONR^{10}R^{11}$, $—NR^{10}R^{11}$, an aryloxy group, or a heterocyclic group optionally having substituent(s). When $R^{12}$ is $—CONR^{10}R^{11}$ or $—NR^{10}R^{11}$, $R^{10}$ is a hydrogen atom, a $C_1$ to $C_6$ alkyl group optionally having substituent(s), a $C_1$ to $C_6$ acyl group optionally having substituent(s), or a $C_1$ to $C_6$ alkylsulfonyl group optionally having substituent(s) and $R^{11}$ is a hydrogen atom or a $C_1$ to $C_6$ alkyl group optionally having substituent(s), or $R^{10}$ and $R^{11}$ may together form a $C_3$ to $C_{10}$ heterocycloalkyl group.

$R^{13}$ may be a hydrogen atom, a halogen atom, a hydroxy group, a cyano group, or a $C_1$ to $C_6$ alkyl group.

When $Ar^1$ is B1), each of $R^{12}$ and $R^{13}$ is any of the above described functional groups, or $R^{12}$ and $R^{13}$ may together form a $C_3$ to $C_5$ alkylene group or a $C_1$ to $C_2$ alkylenedioxy group.

$R^{14}$ and $R^{15}$ are each independently a hydrogen atom, a halogen atom, a cyano group, a $C_1$ to $C_6$ alkyl group, or a $C_1$ to $C_6$ alkoxy group.

One of $W^{10}$ and $W^{11}$ is a nitrogen atom, and the other thereof is CH or a nitrogen atom.

$W^{12}$ is an oxygen atom, a sulfur atom, or N—$R^{16}$. When $W^{12}$ is N—$R^{16}$, $R^{16}$ is a hydrogen atom or a $C_1$ to $C_6$ alkyl group.

$W^{13}$ is CH or a nitrogen atom.

Preferably, one of $W^{10}$ and $W^{11}$ is N, and the other thereof is CH.

$W^{12}$ is preferably an oxygen atom or a sulfur atom. $W^{12}$ is more preferably a sulfur atom.

$W^{13}$ is preferably CH.

Preferably, $R^{12}$ is a hydrogen atom, a halogen atom, a cyano group, a $C_1$ to $C_6$ alkyl group optionally having substituent(s), or a $C_1$ to $C_6$ alkoxy group optionally having substituent(s). $R^{12}$ is more preferably a hydrogen atom, a fluorine atom, a chlorine atom, a cyano group, a $C_1$ to $C_3$ alkyl group, or a $C_1$ to $C_6$ alkoxy group and is particularly more preferably a hydrogen atom, a fluorine atom, a chlorine atom, a cyano group, or a $C_1$ to $C_3$ alkyl group.

Preferably, $R^{13}$ is a hydrogen atom, a hydroxy group, a halogen atom, or a $C_1$ to $C_6$ alkyl group. $R^{13}$ is more preferably a hydrogen atom, a fluorine atom, or a chlorine atom.

Preferably, $R^{14}$ is a hydrogen atom, a fluorine atom, a chlorine atom, a $C_1$ to $C_3$ alkyl group, a methoxy group, or an ethoxy group.

$R^{15}$ is preferably a hydrogen atom, a fluorine atom, or a chlorine atom and particularly preferably a hydrogen atom.

Preferably, $Ar^2$ is a group selected from the group consisting of the following A1), A2), A3), A4), A5), A6), A7), A8), A9), and A10).

[Chemical Formula 14]

A1)
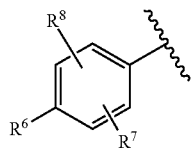

A2)
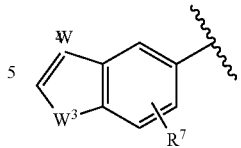

A3)
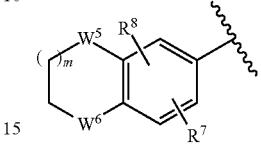

A4)
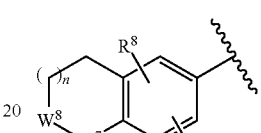

A5)
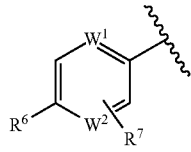

A6)
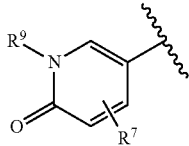

A7)
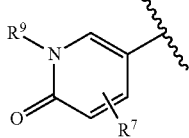

A8)
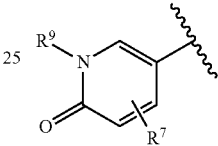

A9)
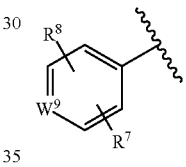

A10)
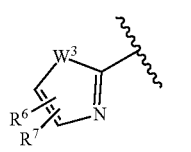

$Ar^2$ is more preferably a group selected from the group consisting of the following A1), A2a), A3), and A7a).

[Chemical Formula 15]

A1)
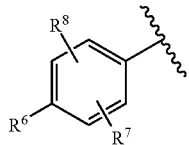

A2a)
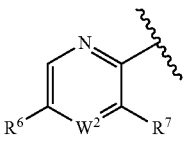

A3)
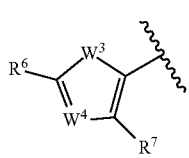

A7a)
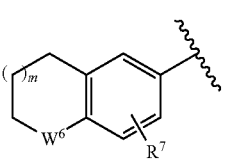

$W^1$ is a nitrogen atom or CH optionally substituted with a hydrogen atom, with a halogen atom, or with a $C_1$ to $C_6$ alkyl group optionally having substituent(s). $W^2$ is CH or a nitrogen atom.

$W^3$ is an oxygen atom, a sulfur atom, or NH optionally substituted with a $C_1$ to $C_6$ alkyl group.

$W^4$ is CH or a nitrogen atom.

$W^5$ is $CH_2$, an oxygen atom, or a sulfur atom.

$W^6$ is C=O, $CH_2$, $CF_2$, CHOH, NH optionally substituted with a $C_1$ to $C_6$ alkyl group, SO, $SO_2$, an oxygen atom, or a sulfur atom.

$W^7$ is NH optionally substituted with a $C_1$ to $C_6$ alkyl group or C=O.

$W^8$ is C=O when $W^7$ is NH optionally substituted with a $C_1$ to $C_6$ alkyl group and is NH optionally substituted with a $C_1$ to $C_6$ alkyl group when $W^7$ is C=O.

$W^9$ is a nitrogen atom or N=O.

$R^6$ is a hydrogen atom, a halogen atom, a hydroxy group, a cyano group, a $C_1$ to $C_6$ alkyl group optionally having substituent(s), a $C_1$ to $C_6$ alkoxy group optionally having substituent(s), a $C_1$ to $C_6$ acyl group optionally having substituent(s), a $C_1$ to $C_6$ alkylsulfanyl group optionally having substituent(s), a $C_1$ to $C_6$ alkylsulfinyl group optionally having substituent(s), a $C_1$ to $C_6$ alkylsulfonyl group optionally having substituent(s), a heterocyclic group optionally having substituent(s), —$CONR^{10}R^{11}$, or —$NR^{10}R^{11}$. When $R^6$ is —$CONR^{10}R^{11}$ or —$NR^{10}R^{11}$, $R^{10}$ is a hydrogen atom, a $C_1$ to $C_6$ alkyl group optionally having substituent(s), a $C_1$ to $C_6$ acyl group optionally having substituent(s), or a $C_1$ to $C_6$ alkylsulfonyl group optionally having substituent(s) and $R^{11}$ is a hydrogen atom or a $C_1$ to $C_6$ alkyl group optionally having substituent(s), or $R^{10}$ and $R^{11}$ may together form a $C_3$ to $C_{10}$ heterocycloalkyl group.

$R^7$ is a hydrogen atom, a halogen atom, a $C_1$ to $C_6$ alkyl group optionally having substituent(s), or a $C_1$ to $C_6$ alkoxy group optionally having substituent(s).

$R^8$ is a hydrogen atom, a halogen atom, or a $C_1$ to $C_6$ alkyl group optionally having substituent(s).

$R^9$ is a hydrogen atom or a $C_1$ to $C_6$ alkyl group.

m is 0 or 1.

n is 0 or 1.

When $Ar^2$ is A1), combinations of the substituents $R^6$, $R^7$ and $R^8$ exclude a combination of a hydrogen atom and a halogen atom.

Preferably, $W^1$ is CH or N. $W^1$ is more preferably N.

Preferably, $W^2$ is CH or N. $W^2$ is more preferably CH.

Preferably, $W^3$ is an oxygen atom or a sulfur atom. $W^3$ is more preferably a sulfur atom.

Preferably, $W^5$ is $CH_2$ or O.

Preferably, $W^6$ is C=O, $CH_2$, $CF_2$, CHOH, or an oxygen atom. $W^6$ is more preferably C=O, $CH_2$, CHOH, or an oxygen atom and particularly preferably an oxygen atom.

Preferably, $W^9$ is a nitrogen atom.

Preferably, m is 0.

Preferably, $R^6$ is a hydrogen atom, a halogen atom, a cyano group, a $C_1$ to $C_6$ alkyl group optionally having substituent(s), a $C_1$ to $C_6$ alkoxy group optionally having substituent(s), a halo-$C_1$ to $C_6$ alkoxy group, a $C_1$ to $C_6$ acyl group optionally having substituent(s), a $C_1$ to $C_6$ alkylsulfanyl group optionally having substituent(s), a $C_1$ to $C_6$ alkylsulfinyl group optionally having substituent(s), —$CONR^{10}R^{11}$, or —$NR^{10}R^{11}$.

Preferably, when $R^6$ is —$CONR^{10}R^{11}$ or —$NR^{10}R^{11}$, $R^{10}$ is a hydrogen atom, a $C_1$ to $C_6$ alkyl group, or a $C_1$ to $C_6$ acyl group and $R^{11}$ is a hydrogen atom or a $C_1$ to $C_6$ alkyl group, or $R^{10}$ and $R^{11}$ may together form a pyrrolidinyl group, a piperidinyl group, a piperazinyl group, or a morpholinyl group.

$R^6$ is more preferably a hydrogen atom, a fluorine atom, a chlorine atom, a cyano group, a $C_1$ to $C_6$ alkoxy group, a halo-$C_1$ to $C_6$ alkoxy group, a $C_1$ to $C_6$ alkyl group, a $C_1$ to $C_6$ alkylsulfanyl group, or a $C_1$ to $C_6$ alkylsulfinyl group and is particularly preferably a cyano group, an ethyl group, or a $C_1$ to $C_3$ alkoxy group.

Preferably, $R^7$ is a hydrogen atom, a halogen atom, a $C_1$ to $C_6$ alkyl group optionally having substituent(s), or a $C_1$ to $C_6$ alkoxy group optionally having substituent(s). $R^7$ is more preferably a hydrogen atom, a halogen atom, or a $C_1$ to $C_3$ alkyl group and is particularly preferably a hydrogen atom, a fluorine atom, or a chlorine atom.

Preferably, $R^8$ is a hydrogen atom, a halogen atom, or a $C_1$ to $C_6$ alkyl group optionally having substituent(s). $R^8$ is more preferably a hydrogen atom, a halogen atom, or a $C_1$ to $C_6$ alkyl group and is particularly preferably a hydrogen atom, a fluorine atom, a chlorine atom, or a $C_1$ to $C_3$ alkyl group.

Preferably, $R^9$ is a hydrogen atom, a methyl group, or an ethyl group.

Preferably, X is an oxygen atom, NOH, N—($C_1$ to $C_3$ alkyl group), N—O—($C_1$ to $C_3$ alkyl group), or N—O-(hydroxy $C_1$ to $C_4$ alkyl group). X is more preferably an oxygen atom, NMe, NOMe, NOH, or $NOCH_2CH_2OH$ and is particularly preferably an oxygen atom.

Preferably, $R^1$ is a hydrogen atom, a hydroxy group, a $C_1$ to $C_6$ alkyl group, a $C_1$ to $C_6$ alkoxy group, a halo-$C_1$ to $C_6$ alkyl group, a hydroxy $C_1$ to $C_6$ alkyl group, a carboxy $C_1$ to $C_6$ alkyl group, a carbamoyl $C_1$ to $C_6$ alkyl group, a monoalkylcarbamoyl $C_1$ to $C_6$ alkyl group, or a dialkylcarbamoyl $C_1$ to $C_6$ alkyl group. $R^1$ is more preferably a hydrogen atom, a hydroxy group, a $C_1$ to $C_3$ alkyl group, a $C_1$ to $C_3$ alkoxy group, or a hydroxy $C_1$ to $C_4$ alkyl group and is particularly preferably a hydrogen atom, a methyl group, an ethyl group, or a hydroxyethyl group.

Preferably, $R^2$ is a hydrogen atom or a $C_1$ to $C_3$ alkyl group. $R^2$ is more preferably a hydrogen atom or a methyl group and is particularly preferably a hydrogen atom.

Preferably, $R^3$ is a hydrogen atom or a $C_1$ to $C_3$ alkyl group. $R^3$ is more preferably a hydrogen atom or a methyl group and is particularly preferably a hydrogen atom.

Preferred examples of the compound of the present embodiment may include the following compounds:

(−)-1-(4-fluorophenyl)-3-[(3S*,4R*)-4-(4-methoxyphenyl)-2-oxopyrrolidin-3-yl]urea;

(−)-1-(4-chlorophenyl)-3-[(3S*,4R*)-4-(4-methoxyphenyl)-2-oxopyrrolidin-3-yl]urea;

(−)-1-(3,4-difluorophenyl)-3-[(3S*,4R*)-4-(4-methoxyphenyl)-2-oxopyrrolidin-3-yl]urea;

(−)-1-(2,4-difluorophenyl)-3-[(3S*,4R*)-4-(4-methoxyphenyl)-2-oxopyrrolidin-3-yl]urea;

(−)-1-(4-cyanophenyl)-3-[(3S*,4R*)-4-(4-methoxyphenyl)-2-oxopyrrolidin-3-yl]urea;

(−)-1-(4-chlorophenyl)-3-[(3S*,4R*)-4-(4-methoxyphenyl)-1-methyl-2-oxopyrrolidin-3-yl]urea;

1-(4-fluorophenyl)-3-[(3S*,4R*)-4-(4-methoxyphenyl)-1-methyl-2-oxopyrrolidin-3-yl]urea;

(−)-1-[(3S*,4R*)-4-(3-fluoro-4-methoxyphenyl)-2-oxopyrrolidin-3-yl]-3-(4-fluorophenyl)urea;

(−)-1-[(3S*,4R*)-4-(2-fluoro-4-methoxyphenyl)-2-oxopyrrolidin-3-yl]-3-(4-fluorophenyl)urea;

1-[(3S*,4R*)-4-(2-chloro-4-methoxyphenyl)-2-oxopyrrolidin-3-yl]-3-(4-fluorophenyl)urea;

(−)-1-(4-fluorophenyl)-3-[(3S*,4R*)-4-(4-methoxy-2-methylphenyl)-2-oxopyrrolidin-3-yl]urea;
(−)-1-[(3S*,4R*)-4-(2,6-difluoro-4-methoxyphenyl)-2-oxopyrrolidin-3-yl]-3-(4-fluorophenyl)urea;
(−)-1-[(3S*,4R*)-4-(2,5-difluoro-4-methoxyphenyl)-2-oxopyrrolidin-3-yl]-3-(4-fluorophenyl)urea;
(−)-1-[(3S*,4R*)-4-(3,5-difluoro-4-methoxyphenyl)-2-oxopyrrolidin-3-yl]-3-(4-fluorophenyl)urea;
(−)-1-[(3S*,4R*)-4-(2, 3-dihydrobenzofuran-5-yl)-2-oxopyrrolidin-3-yl]-3-(4-fluorophenyl)urea;
(−)-1-[(3S*,4R*)-4-(6-fluoro-2,3-dihydrobenzofuran-5-yl)-2-oxopyrrolidin-3-yl]-3-(4-fluorophenyl)urea;
(−)-1-[(3S*,4R*)-4-(7-fluorochroman-6-yl)-2-oxopyrrolidin-3-yl]-3-(4-fluorophenyl)urea;
(−)-1-[(3S*,4R*)-4-(3-fluoro-5-methoxypyridin-2-yl)-2-oxopyrrolidin-3-yl]-3-(4-fluorophenyl)urea;
(−)-1-(4-fluorophenyl)-3-[(3S*,4R*)-4-(5-methoxythiophen-2-yl)-2-oxopyrrolidin-3-yl]urea;
(−)-1-(4-fluorophenyl)-3-[(3S*,4R*)-4-(4-methylthiophenyl)-2-oxopyrrolidin-3-yl]urea;
(−)-1-[(3S*,4R*)-4-(2,6-difluoro-4-methoxyphenyl)-2-oxopyrrolidin-3-yl]-3-(4-methylsulfonylphenyl)urea;
(−)-1-(4-chlorophenyl)-3-[(3S*,4R*)-4-(2,6-difluoro-4-methoxyphenyl)-2-oxopyrrolidin-3-yl]urea;
(−)-1-(4-cyanophenyl)-3-[(3S*,4R*)-4-(2,6-difluoro-4-methoxyphenyl)-2-oxopyrrolidin-3-yl]urea;
(−)-1-[(3S*,4R*)-4-(2,6-difluoro-4-methoxyphenyl)-2-oxopyrrolidin-3-yl]-3-(4-methoxyphenyl)urea;
(−)-1-(benzo[d][1, 3]dioxole-5-yl)-3-[(3R*,4R*)-4-(2,6-difluoro-4-methoxyphenyl)-2-oxopyrrolidin-3-yl]urea;
(−)-1-(5-chlorothiazol-2-yl)-3-[(3S*,4R*)-4-(2,6-difluoro-4-methoxyphenyl)-2-oxopyrrolidin-3-yl]urea;
(−)-1-[(3S*,4R*)-4-(2,6-difluoro-4-methoxyphenyl)-2-oxopyrrolidin-3-yl]-3-(pyrimidin-4-yl)urea;
(−)-1-[(3S*,4R*)-4-(2,6-difluoro-4-methoxyphenyl)-2-oxopyrrolidin-3-yl]-3-(pyridin-2-yl)urea;
(−)-1-[(3S*,4R*)-4-(2,6-difluoro-4-methoxyphenyl)-2-oxopyrrolidin-3-yl]-3-(pyridin-3-yl)urea;
(−)-1-[(3S*,4R*)-4-(2,6-difluoro-4-methoxyphenyl)-2-oxopyrrolidin-3-yl]-3-(pyrimidin-5-yl)urea;
(−)-1-(6-chloropyridin-3-yl)-3-[(3S*,4R*)-4-(2,6-difluoro-4-methoxyphenyl)-2-oxopyrrolidin-3-yl]urea;
(−)-1-(5-chloropyridin-2-yl)-3-[(3S*,4R*)-4-(2,6-difluoro-4-methoxyphenyl)-2-oxopyrrolidin-3-yl]urea;
(−)-1-[(3S*,4R*)-4-(2,6-difluoro-4-methoxyphenyl)-2-oxopyrrolidin-3-yl]-3-(pyrazin-2-yl)urea;
(−)-1-(benzo[d]thiazol-2-yl)-3-[(3S*,4R*)-4-(2,6-difluoro-4-methoxyphenyl)-2-oxopyrrolidin-3-yl]urea;
(−)-1-(benzo[b]thiophen-2-yl)-3-[(3S*,4R*)-4-(2,6-difluoro-4-methoxyphenyl)-2-oxopyrrolidin-3-yl]urea;
(−)-1-(benzo[d]oxazol-2-yl)-3-[(3S*,4R*)-4-(2,6-difluoro-4-m
ethoxyphenyl)-2-oxopyrrolidin-3-yl]urea;
(−)-1-[(3S*,4R*)-4-(2,6-difluoro-4-methoxyphenyl)-2-oxopyrrolidin-3-yl]-3-(5-methylisoxazol-3-yl)urea;
(−)-1-[(3S*,4R*)-4-(2,6-difluoro-4-methoxyphenyl)-2-oxopyrrolidin-3-yl]-3-(2-fluorophenyl)urea;
(−)-1-[(3S*,4R*)-4-(2,6-difluoro-4-methoxyphenyl)-2-oxopyrrolidin-3-yl]-3-(5-methylthiophen-2-yl)urea;
(−)-1-(4-fluorophenyl)-3-[(3S*,4R*,5S*)-4-(4-methoxyphenyl)-5-methyl-2-oxopyrrolidin-3-yl]urea;
(−)-1-(4-fluorophenyl)-3-[(3S*,4R*,5R*)-4-(4-methoxyphenyl)-5-methyl-2-oxopyrrolidin-3-yl]urea;
1-[(3S*,4R*)-4-(4-ethyl-2,6-difluorophenyl)-2-oxopyrrolidin-3-yl]-3-(4-fluorophenyl)urea;
(+)-1-(4-chlorophenyl)-3-[(3R*,4S*)-2-oxo-4-phenylpyrrolidin-3-yl]urea;
(+)-1-(4-chlorophenyl)-3-[(3R*,4S*)-4-(4-methoxyphenyl)-2-oxopyrrolidin-3-yl]urea;
(+)-1-(4-chlorophenyl)-3-[(3R*,4S*)-4-(3-methoxyphenyl)-2-oxopyrrolidin-3-yl]urea;
(+)-1-(4-chlorophenyl)-3-[(3R*,4S*)-4-(2-methoxyphenyl)-2-oxopyrrolidin-3-yl]urea;
(+)-1-[(3R*,4S*)-4-(2,6-difluoro-4-methoxyphenyl)-2-oxopyrrolidin-3-yl]-3-(4-fluorophenyl)urea;
(+)-1-(4-chlorophenyl)-3-[(3R*,4S*)-4-(4-methoxyphenyl)-1-methyl-2-oxopyrrolidin-3-yl]urea;
(+)-1-(4-fluorophenyl)-3-[(3R*,4S*,5S*)-4-(4-methoxyphenyl)-5-methyl-2-oxopyrrolidin-3-yl]urea;
(+)-1-(4-fluorophenyl)-3-[(3R*,4S*,5R*)-4-(4-methoxyphenyl)-5-methyl-2-oxopyrrolidin-3-yl]urea;
(+)-1-(4-fluorophenyl)-3-[(3R*,4S*)-4-(5-methoxythiophen-2-yl)-2-oxopyrrolidin-3-yl]urea;
(+)-1-{(3R*,4S*)-4-[4-(difluoromethoxy)phenyl]-2-oxopyrrolidin-3-yl}-3-(4-fluorophenyl)urea;
(±)-trans-1-(4-chlorophenyl)-3-[4-(4-methoxyphenyl)-1-methyl-2-oxopyrrolidin-3-yl]urea;
(±)-trans-1-(4-fluorophenyl)-3-[4-(4-methoxyphenyl)-2-oxopyrrolidin-3-yl]urea;
(±)-trans-1-(4-chlorophenyl)-3-[4-(4-methoxyphenyl)-1-methyl-2-oxopyrrolidin-3-yl]urea;
(+)-trans-1-(4-fluorophenyl)-3-[4-(4-methoxyphenyl)-5,5-dim ethyl-2-oxopyrrolidin-3-yl]urea;
(−)-trans-1-(4-fluorophenyl)-3-[4-(4-methoxyphenyl)-5,5-dim ethyl-2-oxopyrrolidin-3-yl]urea;
(+)-trans-1-(4-fluorophenyl)-3-[4-(4-methoxyphenyl)-2-oxo-1-azaspiro[4.4]nonan-3-yl]urea;
(−)-trans-1-(4-fluorophenyl)-3-[4-(4-methoxyphenyl)-2-oxo-1-azaspiro[4.4]nonan-3-yl]urea;
(+)-trans-1-(4-fluorophenyl)-3-[4-(4-methoxyphenyl)-2-oxo-1-azaspiro[4.5]decan-3-yl]urea;
(−)-trans-1-(4-fluorophenyl)-3-[4-(4-methoxyphenyl)-2-oxo-1-azaspiro[4.5]decan-3-yl]urea;
(−)-1-(4-fluorophenyl)-3-[(3S*,4R*)-4-(4-methylsulfinylphenyl)-2-oxopyrrolidin-3-yl]urea;
(−)-1-(4-fluorophenyl)-3-[(3S*,4R*)-4-(4-methylsulfonylphenyl)-2-oxopyrrolidin-3-yl]urea;
(−)-1-[(3S*,4R*)-4-(2,6-difluoro-4-methoxyphenyl)-2-oxopyrrolidin-3-yl]-3-[4-(trifluoromethoxy)phenyl]urea;
(−)-1-[(3S*,4R*)-4-(2,6-difluoro-4-methoxyphenyl)-2-oxopyrrolidin-3-yl]-3-phenylurea;
(−)-1-[4-(tert-butyl)phenyl]-3-[(3S*,4R*)-4-(2,6-difluoro-4-methoxyphenyl)-2-oxopyrrolidin-3-yl]urea;
(−)-4-{3-[(3S*,4R*)-4-(2,6-difluoro-4-methoxyphenyl)-2-oxopyrrolidin-3-yl]ureido}benzoic acid ethyl ester;
(−)-1-[(1, 1'-biphenyl)-4-yl]-3-[(3S*,4R*)-4-(2,6-difluoro-4-methoxyphenyl)-2-oxopyrrolidin-3-yl]urea;
(−)-1-(4-acetylphenyl)-3-[(3S*,4R*)-4-(2,6-difluoro-4-methoxyphenyl)-2-oxopyrrolidin-3-yl]urea;
(−)-1-[(3S*,4R*)-4-(2,6-difluoro-4-methoxyphenyl)-2-oxopyrrolidin-3-yl]-3-(4-phenoxyphenyl)urea;
(−)-1-[(3S*,4R*)-4-(2,6-difluoro-4-methoxyphenyl)-2-oxopyrrolidin-3-yl]-3-(3-fluorophenyl)urea;
(−)-1-[(3S*,4R*)-4-(2,6-difluoro-4-methoxyphenyl)-2-oxopyrrolidin-3-yl]-3-(3,4-difluorophenyl)urea;
(−)-1-(5-chlorothiophen-2-yl)-3-[(3S*,4R*)-4-(2,6-difluoro-4-methoxyphenyl)-2-oxopyrrolidin-3-yl]urea;
(−)-1-[(3S*,4R*)-4-(2,6-difluoro-4-methoxyphenyl)-2-oxopyrrolidin-3-yl]-3-(p-tolyl)urea;
(−)-1-[(3S*,4R*)-4-(2,6-difluoro-4-methoxyphenyl)-2-oxopyrrolidin-3-yl]-3-[4-(hydroxymethyl)phenyl]urea;
(−)-4-{3-[(3S*,4R*)-4-(2,6-difluoro-4-methoxyphenyl)-2-oxopyrrolidin-3-yl]ureido}-N-methylbenzamide;

(−)-1-[(3S*,4R*)-1-ethyl-4-(4-methoxyphenyl)-2-oxopyrrolidin-3-yl]-3-(4-fluorophenyl)urea;
2-{(3S*,4R*)-3-[3-(4-fluorophenyl)ureido]-4-(4-methoxyphenyl)-2-oxopyrrolidin-1-yl}acetic acid ethyl ester;
2-{(3S*,4R*)-3-[3-(4-fluorophenyl)ureido]-4-(4-methoxyphenyl)-2-oxopyrrolidin-1-yl}-2-methylpropionic acid ethyl ester;
(−)-1-(4-fluorophenyl)-3-[(3S*,4R*)-1-(1-hydroxy-2-methylpro pan-2-yl)-4-(4-methoxyphenyl)-2-oxopyrrolidin-3-yl]urea;
(−)-2-{(3S*,4R*)-3-[3-(4-fluorophenyl)ureido]-4-(4-methoxyphenyl)-2-oxopyrrolidin-1-yl}propionic acid ethyl ester (isomer A);
(−)-2-{(3S*,4R*)-3-[3-(4-fluorophenyl)ureido]-4-(4-methoxyphenyl)-2-oxopyrrolidin-1-yl}propionic acid ethyl ester (isomer B);
(±)-trans-1-(4-chlorophenyl)-3-[1-(2-hydroxyethyl)-4-(4-methoxyphenyl)-2-oxopyrrolidin-3-yl]urea;
(+)-trans-1-(4-chlorophenyl)-3-[1-(2-hydroxyethyl)-4-(4-methoxyphenyl)-2-oxopyrrolidin-3-yl]urea;
(−)-trans-1-(4-chlorophenyl)-3-[1-(2-hydroxyethyl)-4-(4-methoxyphenyl)-2-oxopyrrolidin-3-yl]urea;
(−)-2-{(3S*,4R*)-3-[3-(4-fluorophenyl)ureido]-4-(4-methoxyphenyl)-2-oxopyrrolidin-1-yl}acetic acid;
(−)-2-{(3S*,4R*)-3-[3-(4-fluorophenyl)ureido]-4-(4-methoxyphenyl)-2-oxopyrrolidin-1-yl}-N-methylacetamide;
(−)-2-{(3S*,4R*)-3-[3-(4-fluorophenyl)ureido]-4-(4-methoxyphenyl)-2-oxopyrrolidin-1-yl}propionic acid (isomer A);
(−)-2-{(3S*,4R*)-3-[3-(4-fluorophenyl)ureido]-4-(4-methoxyphenyl)-2-oxopyrrolidin-1-yl}-N-methylpropionamide (isomer A);
(−)-2-{(3S*,4R*)-3-[3-(4-fluorophenyl)ureido]-4-(4-methoxyphenyl)-2-oxopyrrolidin-1-yl}propionic acid (isomer B);
(−)-2-{(3S*,4R*)-3-[3-(4-fluorophenyl)ureido]-4-(4-methoxyphenyl)-2-oxopyrrolidin-1-yl}-N-methylpropionamide (isomer B);
2-{(3S*,4R*)-3-[3-(4-fluorophenyl)ureido]-4-(4-methoxyphenyl)-2-oxopyrrolidin-1-yl}-2-methylpropionic acid;
(−)-2-{(3S*,4R*)-3-[3-(4-fluorophenyl)ureido]-4-(4-methoxyphenyl)-2-oxopyrrolidin-1-yl}-N,2-dimethylpropionamide;
(−)-1-[(3S*,4R*)-4-(2,6-difluoro-4-methoxyphenyl)-1-methyl-2-oxopyrrolidin-3-yl]-3-(4-fluorophenyl)urea;
(−)-1-[(3S*,4R*)-4-(2-fluoro-4-methoxyphenyl)-1-(2-hydroxyethyl)-2-oxopyrrolidin-3-yl]-3-(4-fluorophenyl)urea;
(−)-1-[(3S*,4R*)-4-(2,6-difluoro-4-methoxyphenyl)-1-(2-hydroxyethyl)-2-oxopyrrolidin-3-yl]-3-(4-fluorophenyl)urea;
(+)-1-(4-fluorophenyl)-3-[(3R*,4S*)-1-methoxy-4-(4-methoxyphenyl)-2-oxopyrrolidin-3-yl]urea;
(−)-1-[(3S*,4R*)-4-(2,6-difluoro-4-hydroxyphenyl)-2-oxopyrrolidin-3-yl]-3-(4-fluorophenyl)urea;
(−)-3,5-difluoro-4-{(3R*,4S*)-4-[3-(4-fluorophenyl)ureido]-5-oxopyrrolidin-3-yl}-N,N-dimethylbenzamide;
(−)-3,5-difluoro-4-{(3R*,4S*)-4-[3-(4-fluorophenyl)ureido]-5-oxopyrrolidin-3-yl}-N-methylbenzamide;
(−)-1-[(3S*,4R*)-4-(4-cyano-2,6-difluorophenyl)-2-oxopyrrolidin-3-yl]-3-(4-fluorophenyl)urea;
(−)-3,5-difluoro-4-{(3R*,4S*)-4-[3-(4-fluorophenyl)ureido]-5-oxopyrrolidin-3-yl}benzamide;
(−)-1-(4-fluorophenyl)-3-[(3S*,4R*,Z)-2-(methoxyimino)-4-(4-methoxyphenyl) pyrrolidin-3-yl]urea;
(−)-1-[(3S*,4R*,Z)-4-(2-fluoro-4-methoxyphenyl)-2-(methoxyimino)pyrrolidin-3-yl]-3-(4-fluorophenyl)urea;
(−)-1-[(3S*,4R*,Z)-4-(2,6-difluoro-4-methoxyphenyl)-2-(methoxyimino)pyrrolidin-3-yl]-3-(4-fluorophenyl)urea;
(−)-1-(4-fluorophenyl)-3-{(3S*,4R*,Z)-2-[(2-hydroxyethoxy)imino]-4-(4-methoxyphenyl)pyrrolidin-3-yl}urea;
(−)-1-{(3S*,4R*,Z)-4-(2,6-difluoro-4-methoxyphenyl)-2-[(2-hydroxyethoxy)imino]pyrrolidin-3-yl}-3-(4-fluorophenyl)urea;
(−)-1-[(3S*,4R*,Z)-4-(2,6-difluoro-4-methoxyphenyl)-2-(methylimino)pyrrolidin-3-yl]-3-(4-fluorophenyl) urea;
(+)-1-(4-fluorophenyl)-3-[(3R*,4S*,Z)-2-(methoxyimino)-4-(4-methoxyphenyl) pyrrolidin-3-yl]urea;
(−)-1-(4-fluorophenyl)-3-[(3S*,4R*,Z)-2-(2-hydroxyimino)-4-4-methoxyphenyl)pyrrolidin-3-yl]urea;
1-[(3S*,4R*)-4-(2,6-difluoro-4-methoxyphenyl)-2-oxopyrrolidin-3-yl]-3-(3-hydroxyphenyl)urea;
(−)-1-[(3S*,4R*)-4-(2,6-difluoro-4-methoxyphenyl)-2-oxopyrrolidin-3-yl]-3-(3-methylisothiazol-5-yl)urea;
(−)-1-(4-cyclopropylphenyl)-3-[(3S*,4R*)-4-(2,6-difluoro-4-methoxyphenyl)-2-oxopyrrolidin-3-yl]urea;
(−)-1-[(3S*,4R*)-4-(2,6-difluoro-4-methoxyphenyl)-2-oxopyrrolidin-3-yl]-3-[4-(trifluoromethyl)phenyl]urea;
(−)-1-[(3S*,4R*)-4-(2,6-difluoro-4-methoxyphenyl)-2-oxopyrrolidin-3-yl]-3-(3-hydroxy-4-methylphenyl)urea;
(−)-1-[(3S*,4R*)-4-(2,6-difluoro-4-methoxyphenyl)-2-oxopyrrolidin-3-yl]-3-(4-fluoro-3-hydroxyphenyl)urea;
(−)-1-(4-chloro-3-hydroxyphenyl)-3-[(3S*,4R*)-4-(2,6-difluoro-4-methoxyphenyl)-2-oxopyrrolidin-3-yl]urea;
1-(4-cyano-3-hydroxyphenyl)-3-[(3S*,4R*)-4-(2,6-difluoro-4-methoxyphenyl)-2-oxopyrrolidin-3-yl]urea;
1-{(3S*,4R*)-4-[4-(difluoromethoxy)-2,6-difluorophenyl]-2-oxopyrrolidin-3-yl}-3-(4-fluorophenyl)urea;
(−)-1-[(3S*,4R*)-4-(6-fluorobenzofuran-5-yl)-2-oxopyrrolidin-3-yl]-3-(4-fluorophenyl)urea;
1-[(3S*,4R*)-4-(4, 6-difluoro-2,3-dihydrobenzofuran-5-yl)-2-oxopyrrolidin-3-yl]-3-(4-fluorophenyl)urea;
(−)-1-(4-cyanophenyl)-3-[(3S*,4R*)-4-(6-fluoro-2,3-dihydrobenzofuran-5-yl)-2-oxopyrrolidin-3-yl]urea;
(−)-1-(benzo[b]thiophene-2-yl)-3-[(3S*,4R*)-4-(6-fluoro-2,3-dihydrobenzofuran-5-yl)-2-oxopyrrolidin-3-yl]urea;
(−)-1-[(3S*,4R*)-4-(2,6-difluoro-4-methoxyphenyl)-2-oxopyrrolidin-3-yl]-3-(4-ethylphenyl)urea;
(−)-1-(3-cyanophenyl)-3-[(3S*,4R*)-4-(2,6-difluoro-4-methoxyphenyl)-2-oxopyrrolidin-3-yl]urea;
(−)-1-(5-chlorothiophen-2-yl)-3-[(3S*,4R*)-4-(3-fluoro-5-methoxypyridine-2-yl)-2-oxopyrrolidin-3-yl]urea;
(−)-1-(4-chlorophenyl)-3-[4-(4-methoxyphenyl)-2-oxopyrrolidin-3-yl]urea;
(+)-1-(4-chlorophenyl)-3-[4-(4-methoxyphenyl)-2-oxopyrrolidin-3-yl]urea;
(+)-1-(4-fluorophenyl)-3-[4-(4-methoxyphenyl)-2-oxopyrrolidin-3-yl]urea;
(+)-1-(4-fluorophenyl)-3-[1-(2-hydroxyethyl)-4-(4-methoxyphenyl)-2-oxopyrrolidin-3-yl]urea;
(−)-2-{(3S*,4R*)-4-(2,6-difluoro-4-methoxyphenyl)-3-[3-(4-fluorophenyl)ureido]-2-oxopyrrolidin-1-yl}acetic acid;
(−)-2-{(3S*,4R*)-4-(6-fluoro-2,3-dihydrobenzofuran-5-yl)-3-[3-(4-fluorophenyl)ureido]-2-oxopyrrolidin-1-yl}acetic acid;
(−)-2-{(3S*,4R*)-4-(2,6-difluoro-4-methoxyphenyl)-3-[3-(4-fluorophenyl)ureido]-2-oxopyrrolidin-1-yl}-N-methylacetamide;

(−)-2-{(3S*,4R*)-4-(6-fluoro-2,3-dihydrobenzofuran-5-yl)-3-[3-(4-fluorophenyl)ureido]-2-oxopyrrolidin-1-yl}acetamide;

(−)-2-{(3S*,4R*)-4-(6-fluoro-2,3-dihydrobenzofuran-5-yl)-3-[3-(4-fluorophenyl)ureido]-2-oxopyrrolidin-1-yl}-2-methylpropanoic acid;

(−)-1-(4-cyanophenyl)-3-[(3S*,4R*)-4-(2,6-difluoro-4-methoxyphenyl)-1-methyl-2-oxopyrrolidin-3-yl]urea;

(−)-1-(6-chloropyridin-3-yl)-3-[(3S*,4R*)-4-(2,6-difluoro-4-methoxyphenyl)-1-methyl-2-oxopyrrolidin-3-yl]urea;

(−)-1-(benzo[b]thiophene-2-yl)-3-[(3S*,4R*)-4-(2,6-difluoro-4-methoxyphenyl)-1-methyl-2-oxopyrrolidin-3-yl]urea;

(−)-1-[(3S*,4R*)-4-(2,6-difluoro-4-methoxyphenyl)-1-(2-hydroxyethyl)-2-oxopyrrolidin-3-yl]-3-phenylurea;

(−)-1-[(3S*,4R*)-4-(2,6-difluoro-4-methoxyphenyl)-1-(2-hydroxyethyl)-2-oxopyrrolidin-3-yl]-3-(p-tolyl)urea;

(−)-1-(4-cyanophenyl)-3-[(3S*,4R*)-4-(2,6-difluoro-4-methoxyphenyl)-1-(2-hydroxyethyl)-2-oxopyrrolidin-3-yl]urea;

(−)-1-(6-chloropyridin-3-yl)-3-[(3S*,4R*)-4-(2,6-difluoro-4-methoxyphenyl)-1-(2-hydroxyethyl)-2-oxopyrrolidin-3-yl]urea;

(−)-1-(benzo[b]thiophene-2-yl)-3-[(3S*,4R*)-4-(2,6-difluoro-4-methoxyphenyl)-1-(2-hydroxyethyl)-2-oxopyrrolidin-3-yl]urea;

(−)-1-[(3S*,4R*)-4-(2,6-difluoro-4-methoxyphenyl)-2-oxo-1-propylpyrrolidin-3-yl]-3-(4-fluorophenyl)urea;

(−)-1-[(3S*,4R*)-1-benzyl-4-(2,6-difluoro-4-methoxyphenyl)-2-oxopyrrolidin-3-yl]-3-(4-fluorophenyl)urea;

(−)-1-[(3S*,4R*)-4-(2,6-difluoro-4-methoxyphenyl)-2-oxo-1-(pyridin-3-ylmethyl)pyrrolidin-3-yl]-3-(4-fluorophenyl)urea;

(−)-1-{(3S*,4R*)-4-(2,6-difluoro-4-methoxyphenyl)-1-[(methyl sulfonyl)methyl]-2-oxopyrrolidin-3-yl}-3-(4-fluorophenyl)urea;

(−)-{(3S*,4R*)-4-(2,6-difluoro-4-methoxyphenyl)-3-[3-(4-fluorophenyl)ureido]-2-oxopyrrolidin-1-yl}methanesulfonamide;

(−)-2-{(3S*,4R*)-4-(2,6-difluoro-4-methoxyphenyl)-3-[3-(4-fluorophenyl)ureido]-2-oxopyrrolidin-1-yl}acetic acid ethyl ester;

(−)-1-{(3S*,4R*)-4-(2,6-difluoro-4-methoxyphenyl)-1-[(5-methyloxazol-2-yl)methyl]-2-oxopyrrolidin-3-yl}-3-(4-fluorophenyl)urea;

(−)-1-{(3S*,4R*)-4-(2,6-difluoro-4-methoxyphenyl)-1-[(5-methyl-1,3,4-oxadiazol-2-yl)methyl]-2-oxopyrrolidin-3-yl}-3-(4-fluoro phenyl) urea;

(−)-1-[(3S*,4R*)-4-(6-fluoro-2,3-dihydrobenzofuran-5-yl)-1-(2-hydroxyethyl)-2-oxopyrrolidin-3-yl]-3-(4-fluorophenyl)urea;

(−)-2-{(3S*,4R*)-4-(6-fluoro-2,3-dihydrobenzofuran-5-yl)-3-[3-(4-fluorophenyl)ureido]-2-oxopyrrolidin-1-yl}acetic acid ethyl ester;

(−)-2-{(3S*,4R*)-4-(6-fluoro-2,3-dihydrobenzofuran-5-yl)-3-[3-(4-fluorophenyl)ureido]-2-oxopyrrolidin-1-yl}-2-methylpropanoic acid ethyl ester;

(−)-1-[(3S*,4R*)-1-(cyclopropylmethyl)-4-(6-fluoro-2,3-dihydrobenzofuran-5-yl)-2-oxopyrrolidin-3-yl]-3-(4-fluorophenyl)urea;

(−)-1-[(3S*,4R*)-1-(cyanomethyl)-4-(6-fluoro-2,3-dihydrobenzofuran-5-yl)-2-oxopyrrolidin-3-yl]-3-(4-fluorophenyl)urea;

(−)-1-{(3S*,4R*)-4-(6-fluoro-2,3-dihydrobenzofuran-5-yl)-1-[(5-methyl-1,3,4-oxadiazol-2-yl)methyl]-2-oxopyrrolidin-3-yl}-3-(4-fluorophenyl) urea;

(−)-1-[(3S*,4R*)-4-(2,6-difluoro-4-methoxyphenyl)-1-methoxy-2-oxopyrrolidin-3-yl]-3-(4-fluorophenyl)urea;

1-[(3S*,4R*)-4-(2,6-difluoro-4-hydroxyphenyl)-2-oxopyrrolidin-3-yl]-3-(4-fluorophenyl)urea;

(−)-1-[(3S*,4R*,Z)-4-(2,6-difluoro-4-methoxyphenyl)-2-(methoxyimino)pyrrolidin-3-yl]-3-(p-tolyl)urea;

(−)-1-(4-cyanophenyl)-3-[(3S*,4R*,Z)-4-(2,6-difluoro-4-methoxyphenyl)-2-(methoxyimino)pyrrolidin-3-yl]urea;

(−)-1-(6-chloropyridin-3-yl)-3-[(3S*,4R*,Z)-4-(2,6-difluoro-4-methoxyphenyl)-2-(methoxyimino)pyrrolidin-3-yl]urea;

(−)-1-(benzo[b]thiophen-2-yl)-3-[(3S*,4R*,Z)-4-(2,6-difluoro-4-methoxyphenyl)-2-(methoxyimino)pyrrolidin-3-yl]urea;

(−)-1-{(3S*,4R*,Z)-4-(2,6-difluoro-4-methoxyphenyl)-2-[(2-hydroxyethoxy)imino]pyrrolidin-3-yl}-3-(p-tolyl)urea;

(−)-1-(4-cyanophenyl)-3-{(3S*,4R*,Z)-4-(2,6-difluoro-4-methoxyphenyl)-2-[(2-hydroxyethoxy)imino]pyrrolidin-3-yl}urea;

(−)-1-(6-chloropyridin-3-yl)-3-{(3S*,4R*,Z)-4-(2,6-difluoro-4-methoxyphenyl)-2-[(2-hydroxyethoxy)imino]pyrrolidin-3-yl}urea;

(−)-1-(benzo[b]thiophen-2-yl)-3-{(3S*,4R*,Z)-4-(2,6-difluoro-4-methoxyphenyl)-2-[(2-hydroxyethoxy)imino]pyrrolidin-3-yl}urea;

(−)-1-{(3R*,4S*)-3-(2,6-difluoro-4-methoxyphenyl)-5-[(1-methyl-1H-pyrazol-3-yl)amino]-3,4-dihydro-2H-pyrrole-4-yl}-3-(4-fluorophenyl)urea;

(−)-1-[(3S*,4R*,Z)-4-(2,6-difluoro-4-methoxyphenyl)-2-(morpholinoimino)pyrrolidin-3-yl]-3-(4-fluorophenyl)urea;

1-[(3R*,4S*)-3-(2,6-difluoro-4-methoxyphenyl)-5-(phenylamino)-3,4-dihydro-2H-pyrrole-4-yl]-3-(4-fluorophenyl)urea;

(−)-1-((3S*,4R*,Z)-4-(6-fluoro-2,3-dihydrobenzofuran-5-yl)-2-[(2-hydroxyethoxy)imino]pyrrolidin-3-yl)-3-(4-fluorophenyl)urea;

3-((Z)-{(3S*,4R)-4-(2,6-difluoro-4-methoxyphenyl)-3-[3-(4-fluorophenyl)ureido]pyrrolidin-2-ylidene}amino)propanoic acid ethyl ester;

(−)-1-((3S*,4R*,Z)-4-(2,6-difluoro-4-methoxyphenyl)-2-(hydroxyimino)pyrrolidin-3-yl)-3-(4-fluorophenyl)urea;

(−)-1-[(3S*,4R*)-4-(2,6-difluoro-4-methoxyphenyl)-2-oxopyrrolidin-3-yl]-3-(4-ethynylphenyl)urea;

(−)-1-{(3S*,4R*)-4-[2,6-difluoro-4-(methylamino)phenyl]-2-oxopyrrolidin-3-yl}-3-(4-fluorophenyl)urea; and (−)-1-(4-fluorophenyl)-3-[(3S*,4R*,Z)-2-(methoxyimino)-4-(4-methoxyphenyl)pyrrolidin-3-yl]urea.

More preferred examples of the compound of the present embodiment may include the following compounds:

(−)-1-(4-fluorophenyl)-3-[(3S*,4R*)-4-(4-methoxyphenyl)-2-oxopyrrolidin-3-yl]urea;

(−)-1-(4-chlorophenyl)-3-[(3S*,4R*)-4-(4-methoxyphenyl)-2-oxopyrrolidin-3-yl]urea;

(−)-1-(3,4-difluorophenyl)-3-[(3S*,4R*)-4-(4-methoxyphenyl)-2-oxopyrrolidin-3-yl]urea;

(−)-1-(4-cyanophenyl)-3-[(3S*,4R*)-4-(4-methoxyphenyl)-2-oxopyrrolidin-3-yl]urea;

(−)-1-(4-chlorophenyl)-3-[(3S*,4R*)-4-(4-methoxyphenyl)-1-methyl-2-oxopyrrolidin-3-yl]urea;

(−)-1-(4-fluorophenyl)-3-[(3S*,4R*)-4-(4-methoxyphenyl)-1-methyl-2-oxopyrrolidin-3-yl]urea;

(−)-1-[(3S*,4R*)-4-(3-fluoro-4-methoxyphenyl)-2-oxopyrrolidin-3-yl]-3-(4-fluorophenyl)urea;

(−)-1-[(3S*,4R*)-4-(2-fluoro-4-methoxyphenyl)-2-oxopyrrolidin-3-yl]-3-(4-fluorophenyl)urea;

1-[(3S*,4R*)-4-(2-chloro-4-methoxyphenyl)-2-oxopyrrolidin-3-yl]-3-(4-fluorophenyl)urea;
(−)-1-(4-fluorophenyl)-3-[(3S*,4R*)-4-(4-methoxy-2-methylphenyl)-2-oxopyrrolidin-3-yl]urea;
(−)-1-[(3S*,4R*)-4-(2,6-difluoro-4-methoxyphenyl)-2-oxopyrrolidin-3-yl]-3-(4-fluorophenyl)urea;
(−)-1-[(3S*,4R*)-4-(2,5-difluoro-4-methoxyphenyl)-2-oxopyrrolidin-3-yl]-3-(4-fluorophenyl)urea;
(−)-1-[(3S*,4R*)-4-(3,5-difluoro-4-methoxyphenyl)-2-oxopyrrolidin-3-yl]-3-(4-fluorophenyl)urea;
(−)-1-[(3S*,4R*)-4-(6-fluoro-2,3-dihydrobenzofuran-5-yl)-2-oxopyrrolidin-3-yl]-3-(4-fluorophenyl)urea;
(−)-1-[(3S*,4R*)-4-(3-fluoro-5-methoxypyridin-2-yl)-2-oxopyrrolidin-3-yl]-3-(4-fluorophenyl)urea;
(−)-1-(4-fluorophenyl)-3-[(3S*,4R*)-4-(5-methoxythiophen-2-yl)-2-oxopyrrolidin-3-yl]urea;
(−)-1-(4-fluorophenyl)-3-[(3S*,4R*)-4-(4-methylthiophenyl)-2-oxopyrrolidin-3-yl]urea;
(−)-1-(4-chlorophenyl)-3-[(3S*,4R*)-4-(2,6-difluoro-4-methoxyphenyl)-2-oxopyrrolidin-3-yl]urea;
(−)-1-(4-cyanophenyl)-3-[(3S*,4R*)-4-(2,6-difluoro-4-methoxyphenyl)-2-oxopyrrolidin-3-yl]urea;
(−)-1-[(3S*,4R*)-4-(2,6-difluoro-4-methoxyphenyl)-2-oxopyrrolidin-3-yl]-3-(4-methoxyphenyl)urea;
(−)-1-(5-chlorothiazol-2-yl)-3-[(3S*,4R*)-4-(2,6-difluoro-4-methoxyphenyl)-2-oxopyrrolidin-3-yl]urea;
(−)-1-(6-chloropyridin-3-yl)-3-[(3S*,4R*)-4-(2,6-difluoro-4-methoxyphenyl)-2-oxopyrrolidin-3-yl]urea;
(−)-1-(5-chloropyridin-2-yl)-3-[(3S*,4R*)-4-(2,6-difluoro-4-methoxyphenyl)-2-oxopyrrolidin-3-yl]urea;
(−)-1-(benzo[b]thiophen-2-yl)-3-[(3S*,4R*)-4-(2,6-difluoro-4-methoxyphenyl)-2-oxopyrrolidin-3-yl]urea;
(−)-1-[(3S*,4R*)-4-(2,6-difluoro-4-methoxyphenyl)-2-oxopyrrolidin-3-yl]-3-(5-methylthiophen-2-yl)urea;
(−)-1-(4-fluorophenyl)-3-[(3S*,4R*,5S*)-4-(4-methoxyphenyl)-5-methyl-2-oxopyrrolidin-3-yl]urea;
(−)-1-(4-fluorophenyl)-3-[(3S*,4R*,5R*)-4-(4-methoxyphenyl)-5-methyl-2-oxopyrrolidin-3-yl]urea;
(+)-1-(4-chlorophenyl)-3-[(3R*,4S*)-2-oxo-4-phenylpyrrolidin-3-yl]urea;
(±)-trans-1-(4-chlorophenyl)-3-[4-(4-methoxyphenyl)-1-methyl-2-oxopyrrolidin-3-yl]urea;
(±)-trans-1-(4-fluorophenyl)-3-[4-(4-methoxyphenyl)-2-oxopyrrolidin-3-yl]urea;
(±)-trans-1-(4-chlorophenyl)-3-[4-(4-methoxyphenyl)-1-methyl-2-oxopyrrolidin-3-yl]urea;
(−)-1-[(3S*,4R*)-4-(2,6-difluoro-4-methoxyphenyl)-2-oxopyrrolidin-3-yl]-3-[4-(trifluoromethoxy)phenyl]urea;
(−)-1-[(3S*,4R*)-4-(2,6-difluoro-4-methoxyphenyl)-2-oxopyrrolidin-3-yl]-3-phenylurea;
(−)-1-[(3S*,4R*)-4-(2,6-difluoro-4-methoxyphenyl)-2-oxopyrrolidin-3-yl]-3-(4-phenoxyphenyl)urea;
(−)-1-[(3S*,4R*)-4-(2,6-difluoro-4-methoxyphenyl)-2-oxopyrrolidin-3-yl]-3-(3-fluorophenyl)urea;
(−)-1-[(3S*,4R*)-4-(2,6-difluoro-4-methoxyphenyl)-2-oxopyrrolidin-3-yl]-3-(3,4-difluorophenyl)urea;
(−)-1-(5-chlorothiophen-2-yl)-3-[(3S*,4R*)-4-(2,6-difluoro-4-methoxyphenyl)-2-oxopyrrolidin-3-yl]urea;
(−)-1-[(3S*,4R*)-4-(2,6-difluoro-4-methoxyphenyl)-2-oxopyrrolidin-3-yl]-3-(p-tolyl)urea;
(−)-1-[(3S*,4R*)-1-ethyl-4-(4-methoxyphenyl)-2-oxopyrrolidin-3-yl]-3-(4-fluorophenyl)urea;
(−)-1-(4-fluorophenyl)-3-[(3S*,4R*)-1-(1-hydroxy-2-methylpropan-2-yl)-4-(4-methoxyphenyl)-2-oxopyrrolidin-3-yl]urea;
(±)-trans-1-(4-chlorophenyl)-3-[1-(2-hydroxyethyl)-4-(4-methoxyphenyl)-2-oxopyrrolidin-3-yl]urea;
(+)-trans-1-(4-chlorophenyl)-3-[1-(2-hydroxyethyl)-4-(4-methoxyphenyl)-2-oxopyrrolidin-3-yl]urea;
(−)-trans-1-(4-chlorophenyl)-3-[1-(2-hydroxyethyl)-4-(4-methoxyphenyl)-2-oxopyrrolidin-3-yl]urea;
(−)-2-{(3S*,4R*)-3-[3-(4-fluorophenyl)ureido]-4-(4-methoxyphenyl)-2-oxopyrrolidin-1-yl}-N-methylacetamide;
(−)-2-{(3S*,4R*)-3-[3-(4-fluorophenyl)ureido]-4-(4-methoxyphenyl)-2-oxopyrrolidin-1-yl}propionic acid (isomer A);
(−)-2-{(3S*,4R*)-3-[3-(4-fluorophenyl)ureido]-4-(4-methoxyphenyl)-2-oxopyrrolidin-1-yl}-N-methylpropionamide (isomer A);
(−)-2-{(3S*,4R*)-3-[3-(4-fluorophenyl)ureido]-4-(4-methoxyphenyl)-2-oxopyrrolidin-1-yl}propionic acid (isomer B);
(−)-2-{(3S*,4R*)-3-[3-(4-fluorophenyl)ureido]-4-(4-methoxyphenyl)-2-oxopyrrolidin-1-yl}-N-methylpropionamide (isomer B);
(−)-2-{(3S*,4R*)-3-[3-(4-fluorophenyl)ureido]-4-(4-methoxyphenyl)-2-oxopyrrolidin-1-yl}-N,2-dimethylpropionamide;
(−)-1-[(3S*,4R*)-4-(2,6-difluoro-4-methoxyphenyl)-1-methyl-2-oxopyrrolidin-3-yl]-3-(4-fluorophenyl)urea;
(−)-1-[(3S*,4R*)-4-(2-fluoro-4-methoxyphenyl)-1-(2-hydroxyethyl)-2-oxopyrrolidin-3-yl]-3-(4-fluorophenyl)urea;
(−)-1-[(3S*,4R*)-4-(2,6-difluoro-4-methoxyphenyl)-1-(2-hydroxyethyl)-2-oxopyrrolidin-3-yl]-3-(4-fluorophenyl)urea;
(+)-1-(4-fluorophenyl)-3-[(3R*,4S*)-1-methoxy-4-(4-methoxyphenyl)-2-oxopyrrolidin-3-yl]urea;
(−)-3,5-difluoro-4-{(3R*,4S*)-4-[3-(4-fluorophenyl)ureido]-5-oxopyrrolidin-3-yl}benzamide;
(−)-1-(4-fluorophenyl)-3-[(3S*,4R*,Z)-2-(methoxyimino)-4-(4-methoxyphenyl) pyrrolidin-3-yl]urea;
(−)-1-[(3S*,4R*,Z)-4-(2-fluoro-4-methoxyphenyl)-2-(methoxyimino)pyrrolidin-3-yl]-3-(4-fluorophenyl)urea;
(−)-1-[(3S*,4R*,Z)-4-(2,6-difluoro-4-methoxyphenyl)-2-(methoxyimino)pyrrolidin-3-yl]-3-(4-fluorophenyl)urea;
(−)-1-(4-fluorophenyl)-3-{(3S*,4R*,Z)-2-[(2-hydroxyethoxy)imino]-4-(4-methoxyphenyl)pyrrolidin-3-yl}urea;
(−)-1-{(3S*,4R*,Z)-4-(2,6-difluoro-4-methoxyphenyl)-2-[(2-hydroxyethoxy)imino]pyrrolidin-3-yl}-3-(4-fluorophenyl)urea;
(−)-1-[(3S*,4R*,Z)-4-(2,6-difluoro-4-methoxyphenyl)-2-(methylimino)pyrrolidin-3-yl]-3-(4-fluorophenyl)urea;
(−)-1-(4-fluorophenyl)-3-[(3S*,4R*,Z)-2-(2-hydroxyimino)-4-(4-methoxyphenyl)pyrrolidin-3-yl]urea;
(−)-1-[(3S*,4R*)-4-(2,6-difluoro-4-methoxyphenyl)-2-oxopyrrolidin-3-yl]-3-(3-hydroxy-4-methylphenyl)urea;
(−)-1-[(3S*,4R*)-4-(2,6-difluoro-4-methoxyphenyl)-2-oxopyrrolidin-3-yl]-3-(4-fluoro-3-hydroxyphenyl)urea;
(−)-1-(4-chloro-3-hydroxyphenyl)-3-[(3S*,4R*)-4-(2,6-difluoro-4-methoxyphenyl)-2-oxopyrrolidin-3-yl]urea;
(−)-1-(4-cyanophenyl)-3-[(3S*,4R*)-4-(6-fluoro-2,3-dihydrobenzofuran-5-yl)-2-oxopyrrolidin-3-yl]urea;
(−)-1-{(3S*,4R*,Z)-4-(2,6-difluoro-4-methoxyphenyl)-2-[(2-hydroxyethoxy)imino]pyrrolidin-3-yl}-3-(p-tolyl)urea; and
(−)-1-[(3S*,4R*)-4-(2,6-difluoro-4-methoxyphenyl)-1-(2-hydroxyethyl)-2-oxopyrrolidin-3-yl]-3-phenylurea.

If necessary, the compound (I) of the present embodiment can be converted to a pharmacologically acceptable salt according to a usual method. The pharmacologically acceptable salt means a salt with a pharmacologically acceptable nontoxic base or acid (for example, an inorganic or organic base or an inorganic or organic acid).

Examples of the salt derived from a pharmacologically acceptable nontoxic base may include: salts with inorganic bases such as sodium salts, potassium salts, calcium salts, magnesium salts and the like; and salts with organic bases such as piperidine, morpholine, pyrrolidine, arginine, lysine and the like.

Examples of the salt derived from a pharmacologically acceptable nontoxic acid may include: acid addition salts with mineral acids such as hydrochloric acid, hydrobromic acid, sulfuric acid, nitric acid and the like; and acid addition salts with organic acids such as formic acid, acetic acid, maleic acid, fumaric acid, succinic acid, lactic acid, malic acid, tartaric acid, citric acid, methanesulfonic acid, p-toluenesulfonic acid, salicylic acid, stearic acid, palmitic acid and the like.

The compound (I) of the present embodiment or a pharmacologically acceptable salt thereof may be present as a hydrate or a solvate. Any hydrate and solvate formed from the urea derivative represented by the general formula (I) above, including any of the preferred compounds specifically described above, or a salt thereof are included in the scope of the present invention. Examples of the solvent that can form the solvate may include methanol, ethanol, 2-propanol, acetone, ethyl acetate, dichloromethane, diisopropyl ether and the like.

The compound (I) of the present embodiment or a pharmacologically acceptable salt thereof may be a racemate and also includes their optically active substances, stereoisomers, and rotational isomers.

When the compound (I) of the present embodiment is one of its optical isomers having one or more asymmetric carbon atom, the configuration of each asymmetric carbon atoms in the compound (I) of the present embodiment is any of the R configuration and the S configuration. Any of the optical isomers is included in the present invention, and a mixture of these optical isomers is also included in the present invention. A mixture of optically active substances may be a racemate formed of equal amounts of the optical isomers, and this racemate is also included in the scope of the present invention. When the compound (I) of the present embodiment is a solid or crystalline racemate, the racemate, a racemic mixture, a racemic solid solution are included in the scope of the present invention.

When the compound (I) of the present embodiment includes geometrical isomers, all the geometrical isomers are included in the present invention.

When the compound (I) of the present embodiment includes tautomers, all the tautomers are included in the present invention.

Pharmacologically acceptable salts of the compound (I) include proton tautomers.

The compound (I) of the present embodiment or a pharmacologically acceptable salt thereof may be a compound labeled with an isotope (for example, $^3$H, $^{14}$C, $^{35}$S and the like). Such a compound is also included in the present invention.

The compound (I) of the present embodiment or a pharmacologically acceptable salt thereof may be a deuterium-substituted compound in which $^1$H is substituted with $^2$H(D). Such a compound is also included in the present invention.

The term "FPRL1 agonist effect" in the present embodiment means agonist activity obtained by the action on formyl peptide receptor like 1 (FPRL1). The compound (I) of the present embodiment or a pharmacologically acceptable salt thereof exhibits superior agonist activity in, for example, a test of calcium influx into FPRL1-overexpressing cells. Therefore, it can be understood that the compound (I) of the present embodiment or a pharmacologically acceptable salt thereof is useful as a therapeutic or prophylactic agent for inflammatory diseases, chronic airway diseases, cancers, septicemia, allergic symptoms, HIV retrovirus infection, circulatory disorders, neuroinflammation, nervous disorders, pains, prion diseases, amyloidosis, immune disorders and the like.

Method of Producing the Compound (I) of the Present Embodiment

The compound (I) of the present embodiment or a pharmacologically acceptable salt thereof can be produced, for example, in accordance with any of methods described in the following schemes 1 to 17, methods similar thereto, methods described in other literatures, and methods similar thereto.

Synthesis of Compound (Ia)

The compound (I) of the present embodiment when X is O (this compound is hereinafter referred to as the compound (Ia)) can be produced in accordance with any of methods described in scheme 1, methods similar thereto, methods described in other literatures, and methods similar thereto.

Scheme 1

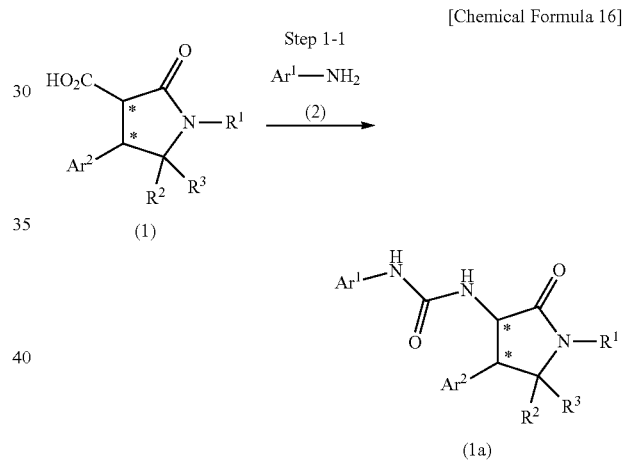

[Chemical Formula 16]

In the above formulas, $Ar^1$, $Ar^2$, $R^1$, $R^2$, and $R^3$ are as described above, and each carbon atom marked with an asterisk is an asymmetric carbon atom.

Step 1-1

This step is a step of reacting the compound (1) with the compound (2) to produce the compound (Ia). The compound (Ia) can be produced by, for example, allowing diphenylphosphoryl azide (DPPA) and the like to act on the compound (1) in a solvent in the presence or absence of a base and then reacting the compound (2) with the obtained product.

The above reaction is usually performed in a solvent that does not adversely affect the reaction, and examples of the solvent used may include benzene, toluene, tetrahydrofuran, acetonitrile, dioxane, mixed solvents of them and the like. Examples of the base used may include trimethylamine, triethylamine, N-methylmorpholine and the like. The amount of the base used is usually about 0.5 to about 100 molar equivalents with respect to 1 mole of the compound and preferably about 1 to about 5 molar equivalents. The reaction temperature can usually be performed at −10° C. to the reflux temperature of the solvent and is performed preferably at 20° C. to 120° C. The reaction time varies depending on the starting materials used, the solvent used, the reaction temperature, or the like, but is usually 10 minutes to 3 days.

The compound (1) used in this step can be produced in accordance with any of methods described below in detail, methods similar thereto, methods described in other literatures, and methods similar thereto.

Further, the compound (2) used in this step may be a commercially available, or can be produced in accordance with any of methods described in other literatures, and methods similar thereto.

Step 1-2

This step is a step of reacting the compound (3) with the compound (4) to produce the compound (Ia). The compound (Ia) can be produced by, for example, reacting the compound (3) with the compound (4) in a solvent in the presence or absence of a base. The amount of the compound (4) used is about 0.5 to about 10 molar equivalents with respect to 1 mole of the compound (3) and is preferably about 1 to about 2 molar equivalents.

The above reaction is usually performed in a solvent that does not adversely affect the reaction, and examples of the solvent used may include dichloromethane, 1,2-dichloroethane, benzene, toluene, tetrahydrofuran, ethyl acetate, methanol, water, mixed solvents of them and the like. Examples of the base used may include alkali metal hydrides such as lithium hydride, sodium hydride, potassium hydride and the like, alkali metal hydroxides such as sodium hydroxide, potassium hydroxide and the like, hydrogen carbonates such as sodium hydrogen carbonate, potassium hydrogen carbonate and the like, carbonates such as sodium carbonate, potassium carbonate and the like, organic acid salts such as sodium acetate and the like, tertiary amines such as trimethylamine, triethylamine, N-methylmorpholine and the like, and aromatic amines such as pyridine, picoline, N,N-dimethyl aniline and the like. The amount of the base used is usually about 1 to about 100 molar equivalents with respect to 1 mole of the compound and preferably about 1 to about 5 molar equivalents. The reaction temperature can usually be performed at −20° C. to the reflux temperature of the solvent and is performed preferably at 0° C. to 50° C. The reaction time varies depending on the starting materials used, the solvent used, the reaction temperature or the like, but is usually 10 minutes to 48 hours.

The compound (3) used in this step can be produced in accordance with any of methods described below in detail, methods similar thereto, methods described in other literatures, and methods similar thereto.

Further, the compound (4) used in this step may be a commercially available, or can be produced in accordance with any of methods described in other literatures, and methods similar thereto.

Synthesis of Compound (Ib)

The compound (I) of the present embodiment when X is O and $R^1$ is H (this compound may hereinafter be referred to as the compound (Ib)) can be produced in accordance with any of methods described in scheme 2, methods similar thereto, methods described in other literatures, and methods similar thereto.

[Chemical Formula 17]

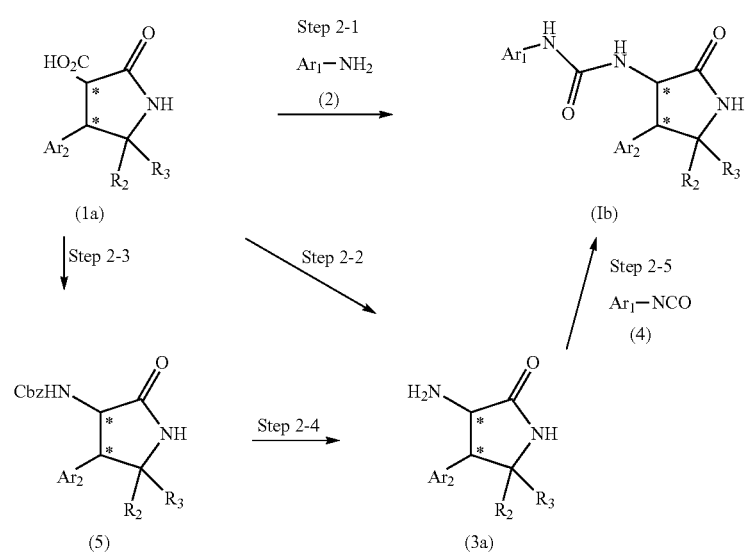

In the above formulas, $Ar^1$, $Ar^2$, $R^2$, and $R^3$ are as described above, and each carbon atom marked with an asterisk is an asymmetric carbon atom.

Step 2-1

This step is a step of producing the compound (Ib) from the compound (Ia). The compound (Ib) by the step 2-1 can be produced in accordance with any of the method described in step 1-1 of scheme 1, methods similar thereto, methods described in other literatures, and methods similar thereto.

Step 2-2

This step is a step of converting the carboxy group in the compound (Ia) to a primary amine to produce the compound (3a). The compound (3a) can be produced by, for example, allowing diphenylphosphoryl azide (DPPA) and the like to act on the compound (Ia) in a solvent A in the presence or absence of a base and then reacting the product obtained with an acid in a solvent B. Examples of the solvent A may include benzene, toluene, tetrahydrofuran, acetonitrile, dioxane, mixed solvents of them and the like. Examples of the solvent B may include dioxane, water and the like.

Examples of the base used may include trimethylamine, triethylamine, N-methylmorpholine and the like. Examples of the acid used may include conc. hydrochloric acid, conc. sulfuric acid and the like. The reaction temperature can usually be performed at −10° C. to the reflux temperature of the solvent and is performed preferably at 0° C. to 100° C. The reaction time varies depending on the starting materials used, the solvent used, the reaction temperature or the like, but is usually 30 minutes to 3 days.

Step 2-3

This step is a step of producing the compound (5) from the compound (1a). The compound (5) can be produced by, for example, allowing diphenylphosphoryl azide (DPPA) and the like to act on the compound (1a) in a solvent in the presence or absence of a base and then reacting the obtained product with benzyl alcohol in a solvent or without any solvent. Examples of the solvent used may include benzene, toluene, tetrahydrofuran, acetonitrile, dioxane, mixed solvents of them and the like. Examples of the base used may include trimethylamine, triethylamine, N-methylmorpholine and the like. The reaction temperature can usually be performed at 0° C. to the reflux temperature of the solvent and is performed preferably at 10° C. to 120° C. The reaction time varies depending on the starting materials used, the solvent used, the reaction temperature or the like, but is usually 30 minutes to 3 days.

Step 2-4

This step is a step of deprotecting the Cbz (benzyloxycarbonyl) group in the compound (5) to produce the compound (3a). The compound (3a) can be produced by, for example, hydrogenating the compound (5) in a solvent in the presence of a catalyst such as 10% palladium on carbon (10% Pd—C). Examples of the solvent used may include methanol, ethanol, dichloromethane, tetrahydrofuran, ethyl acetate, mixed solvents of them and the like. The reaction temperature can usually be performed at 0° C. to the reflux temperature of the solvent and is performed preferably at 10° C. to 40° C. The reaction time varies depending on the starting materials used, the solvent used, the reaction temperature or the like, but is usually 30 minutes to 3 days.

Step 2-5

This step is a step of producing the compound (Ib) from the compound (3a). The compound (Ib) by the step 2-5 can be produced in accordance with any of the method described in step 1-2 of scheme 1, methods similar thereto, methods described in other literatures, and methods similar thereto.

Synthesis of Compound (1b)

The compound (1b) among the compound (1) when $R^3$ is H can be produced from the compound (6) in accordance with any of methods described in scheme 3, methods similar thereto, methods described in other literatures, and methods similar thereto.

Scheme 3

[Chemical Formula 18]

Step 3-1

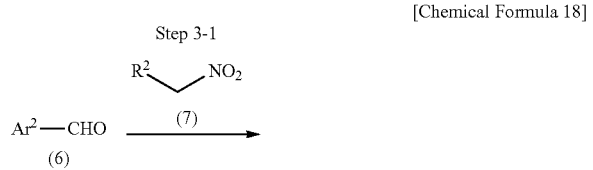

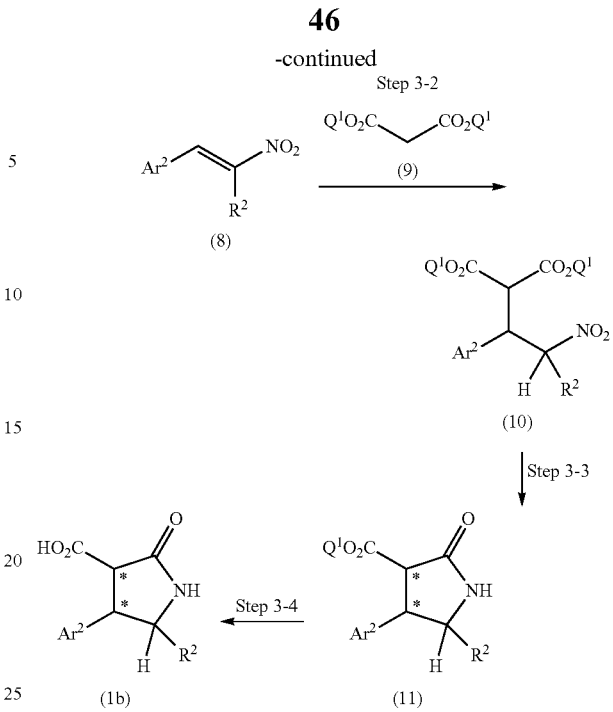

In the above formulas, $Ar^2$ and $R^2$ are as described above; $Q^1$ is a $C_{1-6}$ alkyl group and the like, and each carbon atom marked with an asterisk is an asymmetric carbon atom.

Step 3-1

This step is a step of reacting the compound (6) with the compound (7) to produce the compound (8). The compound (8) can be produced by, for example, reacting the compound (6) with the compound (7) in acetic acid in the presence of ammonium acetate. The reaction temperature can usually be performed at 20° C. to the reflux temperature of the solvent and is performed preferably at 80° C. to 110° C. Alternatively, the compound (8) can be produced by reacting the compound (6) with the compound (7) in 2-hydroxyethylammonium formate (2-HEAF). The reaction temperature can usually be performed at 0° C. to 80° C. and is performed preferably at 10° C. to 50° C. The reaction time varies depending on the starting materials used, the solvent used, the reaction temperature or the like, but is usually 30 minutes to 3 days.

The compound (6) and the compound (7) used in this step may be a commercially available, or can also be produced in accordance with any of methods described in other literatures, and methods similar thereto.

Step 3-2

This step is a step of reacting the compound (8) with a malonic ester (9) to produce the compound (10). The compound (10) can be produced by, for example, reacting the compound (8) with the compound (9) in a solvent in the presence of a catalyst. Examples of the solvent used may include benzene, toluene, tetrahydrofuran, methyl t-butyl ether, acetonitrile, methanol, ethanol, ethyl acetate and the like. Examples of the catalyst used may include nickel(II) bis[(S,S)—N,N'-dibenzylcyclohexane-1,2-diamine]bromide, nickel(II) bis[(R,R)—N,N'-dibenzylcyclohexane-1,2-diamine]bromide, 1-(3,5-bis(trifluoromethyl)phenyl)-3-((1S,2S)-2-(dimethylamino)cyclohexyl)thiourea, and 1-(3,5-bis(trifluoromethyl)phenyl)-3-((1R,2R)-2-(dimethylamino)cyclohexyl)thiourea that can be obtained according to methods described in Non Patent Literature.

The amount of the catalyst used is usually 0.001 to 0.2 moles with respect to 1 mole of the compound (8). The reaction temperature can usually be performed at −0° C. to the reflux temperature of the solvent and is performed preferably at 10° C. to 50° C. The reaction time varies depending on the starting materials used, the solvent used, the reaction temperature or the like, but is usually 30 minutes to 7 days.

Further, the compound (9) used in this step may be a commercially available, or can be produced in accordance with any of methods described in other literatures, and methods similar thereto. Also, the compound (8) may be a commercially available in addition to that obtained in step 3-1, or can be produced in accordance with any of methods described in other literatures, and methods similar thereto.

Step 3-3

This step is a step of producing the compound (11) from the compound (10). The compound (11) can be produced by, for example, allowing sodium borohydride ($NaBH_4$) to act on the compound (10) in a solvent in the presence of nickel(II) chloride hexahydrate ($NiCl_2 \cdot 6H_2O$). Examples of the solvent used may include methanol, ethanol, tetrahydrofuran, methyl t-butyl ether and the like. The reaction temperature can usually be performed at −30° C. to the reflux temperature of the solvent and is performed preferably at 0° C. to 80° C. The reaction time varies depending on the starting materials used, the solvent used, the reaction temperature or the like, but is usually 30 minutes to 3 days.

Step 3-4

This step is a step of hydrolyzing the ester moiety of the compound (11) to produce the compound (1b). The compound (1b) can be produced by, for example, treating the compound (11) with a base in a solvent. Examples of the solvent used may include water, methanol, ethanol, propanol, 2-propanol, butanol, tetrahydrofuran, mixed solvents of them and the like. Examples of the base used may include lithium hydroxide, sodium hydroxide, potassium hydroxide and the like. The reaction temperature can usually be performed at 0° C. to the reflux temperature of the solvent and is performed preferably at 10° C. to 70° C. The reaction time varies depending on the starting materials used, the solvent used, the reaction temperature or the like, but is usually 30 minutes to 3 days.

Synthesis of Compound (1c)

The compound (1) when $R^2$ and $R^3$ are not H (this compound may hereinafter be referred to as the compound (1c)) can be produced from the compound (6) in accordance with any of methods described in scheme 4, methods similar thereto, methods described in other literatures, and methods similar thereto.

[Chemical Formula 19]

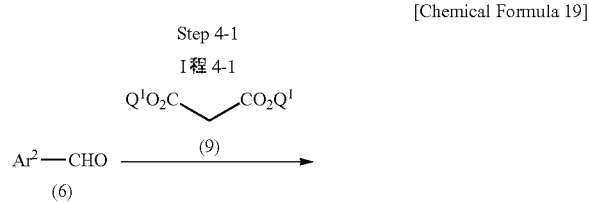

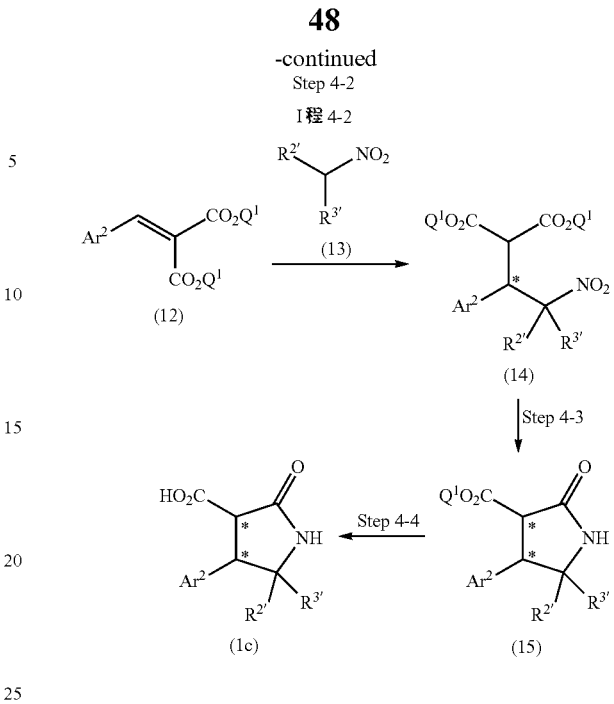

In the above formulas, $Ar^2$ and $Q^1$ are as described above, $R^{2'}$ and $R^{3'}$ are each independently a $C_{1-6}$ alkyl group optionally having substituent(s) or together form a $C_2$ to $C_6$ alkylene group, and each carbon atom marked with an asterisk is an asymmetric carbon atom.

Step 4-1

This step is a step of reacting the compound (6) with the compound (9) to produce the compound (12). The compound (12) can be produced by, for example, reacting the compound (6) with the compound (9) in a solvent in the presence of a base. Examples of the solvent used may include benzene, toluene, dimethyl sulfoxide, N,N-dimethylformamide, mixed solvents of them and the like. Examples of the base used may include aliphatic amines such as piperidine, pyrrolidine, triethylamine, N-methylmorpholine and the like, aromatic amines such as pyridine, picoline, N,N-dimethyl aniline and the like, and organic acid salts such as piperidinium acetate, ammonium acetate and the like. The reaction temperature can usually be performed at 0° C. to the reflux temperature of the solvent and is performed preferably at 70° C. to 110° C. The reaction time varies depending on the starting materials used, the solvent used, the reaction temperature or the like, and is usually 30 minutes to 3 days.

Further, the compound (6) and the compound (9) used in this step may be a commercially available, or can be produced in accordance with any of methods described in other literatures, and methods similar thereto.

Step 4-2

This step is a step of reacting the compound (12) with the compound (13) to produce the compound (14). The compound (14) can be produced by, for example, reacting the compound (12) with the compound (13) in a solvent in the presence of a base. Examples of the solvent used may include toluene, benzene, tetrahydrofuran, acetonitrile, dimethyl sulfoxide, N,N-dimethylformamide, mixed solvents of them and the like. Examples of the base used may include alumina-treated potassium fluoride (KF—$Al_2O_3$) and the like. The reaction temperature can usually be performed at 0° C. to the reflux temperature of the solvent and is performed preferably at 10° C. to 40° C. The reaction time varies depending on the starting materials used, the solvent used, the reaction temperature or the like, but is usually 30 minutes to 3 days.

Step 4-3

This step is a step of producing the compound (15) from the compound (14). The compound (15) can be produced in accordance with any of the method described in step 3-3 of scheme 3, methods similar thereto, methods described in other literatures, and methods similar thereto.

Step 4-4

This step is a step of hydrolyzing the ester moiety of the compound (15) to produce the compound (1c). The compound (1c) can be produced in accordance with any of the method described in step 3-4 of scheme 3, methods similar thereto, methods described in other literatures, and methods similar thereto.

Synthesis of Compound (3b)

The compound (3) when $R^3$ is H (this compound may hereinafter be referred to as the compound (3b)) can be produced from the compound (8) in accordance with any of methods described in scheme 5, methods similar thereto, methods described in other literatures, and methods similar thereto.

[Chemical Formula 20]

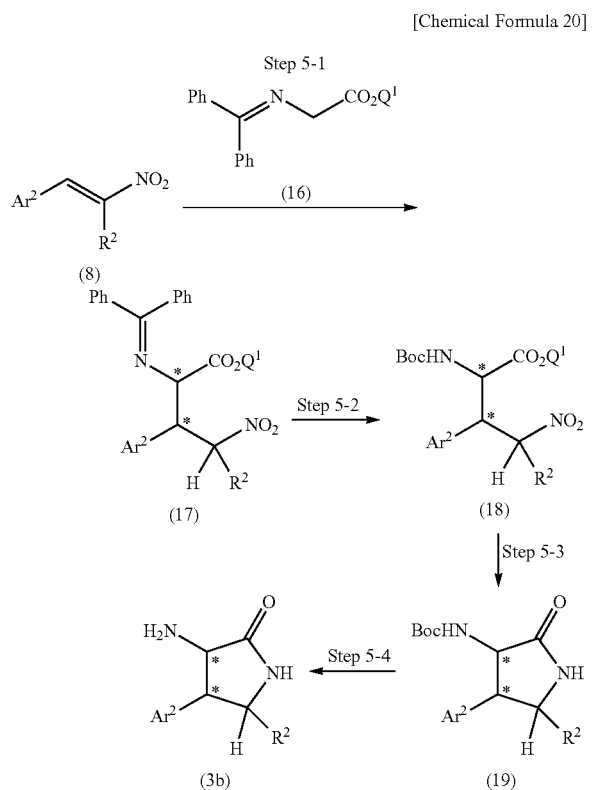

In the above formulas, $Ar^2$, $R^2$ and $Q^1$ are as described above, and each carbon atom marked with an asterisk is an asymmetric carbon atom.

Step 5-1

This step is a step of reacting the compound (8) with the compound (16) to produce the compound (17). The compound (17) can be produced by, for example, reacting the compound (16) with the compound (8) in a solvent in the presence of a base. Examples of the solvent used may include tetrahydrofuran, hexane, mixed solvents of them and the like. Examples of the base used may include organolithiums such as lithium diisopropylamide (LDA) lithium hexamethyl disilazide (LHMDS) and the like. The reaction temperature can usually be performed at −78° C. to the reflux temperature of the solvent and is performed preferably at −78° C. to 30° C. The reaction time varies depending on the starting materials used, the solvent used, the reaction temperature or the like, but is usually 30 minutes to 3 days.

Further, the compound (8) and the compound (16) used in this step may be a commercially available, or can be produced in accordance with any of methods described in other literatures, and methods similar thereto.

Step 5-2

This step is a step of converting the imine moiety of the compound (17) to produce the compound (18). The compound (18) can be produced by, for example, reacting the compound (17) with water in acetic acid and then reacting the obtained product with di-tert-butyl dicarbonate ((Boc)$_2$O) in a solvent in the presence of a base. Examples of the solvent used may include water, methanol, ethanol, tetrahydrofuran, ethyl acetate, N,N-dimethylformamide, 1,4-dioxane, acetonitrile, mixed solvents of them and the like. Examples of the base used may include triethylamine, sodium hydrogen carbonate, sodium carbonate and the like. The reaction temperature can usually be performed at 0° C. to the reflux temperature of the solvent and is performed preferably at 10° C. to 70° C. The reaction time varies depending on the starting materials used, the solvent used, the reaction temperature or the like, but is usually 30 minutes to 3 days.

Step 5-3

This step is a step of producing the compound (19) from the compound (18). The compound (19) can be produced in accordance with any of the method described in step 3-3 of scheme 3, methods similar thereto, methods described in other literatures, and methods similar thereto.

Step 5-4

This step is a step of deprotecting the tert-butoxycarbonyl (Boc) group in the compound (19) to produce the compound (3b). The compound (3b) can be produced by, for example, reacting the compound (19) with an acid such as trifluoroacetic acid (TFA) or hydrogen chloride in a solvent. Examples of the solvent used may include dichloromethane, dioxane, ethyl acetate, methanol, water, mixed solvents of them and the like. The reaction temperature can usually be performed at 0° C. to the reflux temperature of the solvent and is performed preferably at 0° C. to 60° C. The reaction time varies depending on the starting materials used, the solvent used, the reaction temperature or the like, but is usually 30 minutes to 3 days.

Synthesis of Compound (1d)

The compound (1) when $R^1$ is a $C_1$ to $C_6$ alkyl group (this compound may hereinafter be referred to as the compound (1d)) can be produced from the compound (20) in accordance with any of methods described in scheme 6, methods similar thereto, methods described in other literatures, and methods similar thereto.

Scheme 6

[Chemical Formula 21]

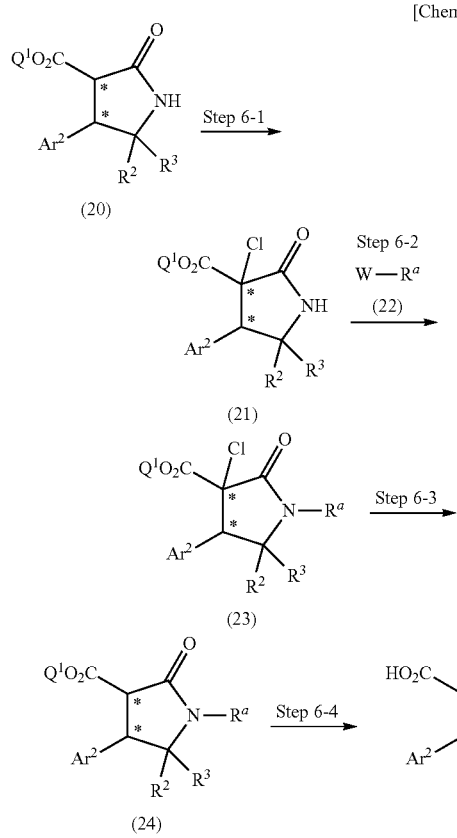

In the above formulas, $Ar^2$, $R^2$, $R^3$, and $Q^1$ are as described above, $R^a$ is a $C_{1-6}$ alkyl group, W is an leaving group such as a chlorine atom, a bromine atom, an iodine atom, a methane sulfonyloxy group, a trifluoromethane sulfonyloxy group and the like, and each carbon atom marked with an asterisk is an asymmetric carbon atom.

Step 6-1

This step is a step of chlorinating the compound (20) to produce the compound (21). The compound (21) can be produced by, for example, reacting the compound (20) with sulfuryl chloride ($SO_2Cl_2$) in a solvent. Examples of the solvent used may include tetrahydrofuran and the like. The reaction temperature can usually be performed at 0° C. to the reflux temperature of the solvent and is performed preferably at 20° C. to 70° C. The reaction time varies depending on the starting materials used, the solvent used, the reaction temperature or the like, but is usually 30 minutes to 3 days.

The compound (20) used in this step can be produced in accordance with any of methods described in scheme 3 or 4, methods similar thereto, methods described in other literatures, and methods similar thereto.

Step 6-2

This step is a step of reacting the compound (21) with the compound (22) to produce the compound (23). The compound (23) can be produced by, for example, reacting the compound (21) with the compound (22) in a solvent in the presence of a base. Examples of the solvent used may include tetrahydrofuran, N,N-dimethylformamide, mixed solvents of them and the like. Examples of the base used may include alkali metal hydrides such as lithium hydride, sodium hydride and the like, alkali metal hydroxides such as sodium hydroxide, potassium hydroxide and the like, and carbonates such as potassium carbonate, cesium carbonate and the like. The reaction temperature can usually be performed at −10° C. to the reflux temperature of the solvent and is performed preferably at 0° C. to 60° C. The reaction time varies depending on the starting materials used, the solvent used, the reaction temperature or the like, but is usually 30 minutes to 3 days.

The compound (22) used in this step may be a commercially available, or can also be produced in accordance with any of methods described in other literatures, and methods similar thereto.

Step 6-3

This step is a step of dechlorinating the compound (23) to produce the compound (24). The compound (24) can be produced by, for example, reacting the compound (23) with zinc powder (Zn powder) in a solvent in the presence of acetic acid. Examples of the solvent used may include methanol, ethanol, water, tetrahydrofuran, mixed solvents of them and the like. The reaction temperature can usually be performed at 0° C. to the reflux temperature of the solvent and is performed preferably at 10° C. to 40° C. The reaction time varies depending on the starting materials used, the solvent used, the reaction temperature or the like, but is usually 30 minutes to 3 days.

Step 6-4

This step is a step of hydrolyzing the ester moiety of the compound (24) to produce the compound (1d). The compound (1d) can be produced in accordance with any of the method described in step 3-4 of scheme 3, methods similar thereto, methods described in other literatures, and methods similar thereto.

Synthesis of Compound (1e)

The compound (1) when $R^1$ is a —O—$C_1$ to $C_6$ alkyl group (this compound may hereinafter be referred to as the compound (1e)) can be produced from the compound (14) in accordance with any of methods described in scheme 7, methods similar thereto, methods described in other literatures, and methods similar thereto.

Scheme 7

[Chemical Formula 22]

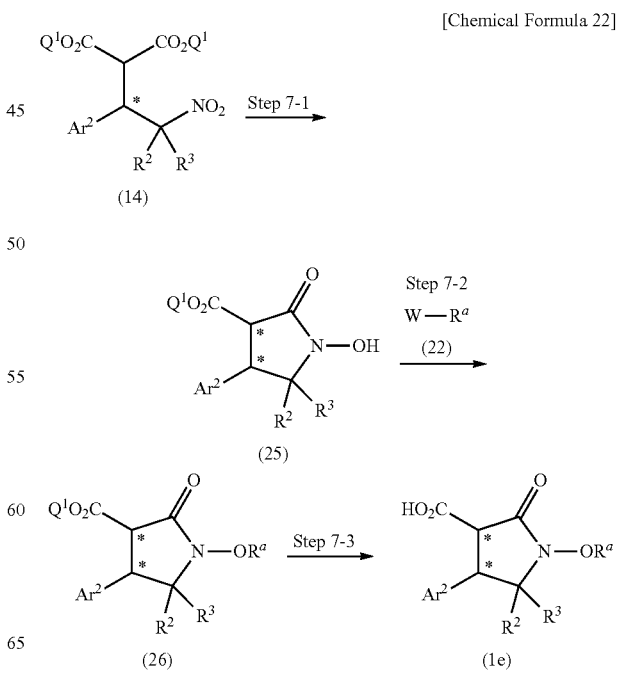

In the above formulas, $Ar^2$, $R^2$, $R^3$, $R^a$, $Q^1$, and W are as described above, and each carbon atom marked with an asterisk is an asymmetric carbon atom.

Step 7-1

This step is a step of producing the compound (25) from the compound (14). The compound (25) can be produced by, for example, reacting the compound (14) with zinc powder in a solvent in the presence of ammonium chloride. Examples of the solvent used may include methanol, ethanol, water, tetrahydrofuran, mixed solvents of them and the like. The reaction temperature can usually be performed at 0° C. to the reflux temperature of the solvent and is performed preferably at 10° C. to 40° C. The reaction time varies depending on the starting materials used, the solvent used, the reaction temperature or the like, but is usually 10 minutes to 3 days.

Step 7-2

This step is a step of reacting the compound (25) with the compound (22) to produce the compound (26). The compound (26) can be produced in accordance with any of the method described in step 6-2 of scheme 6, methods similar thereto, methods described in other literatures, and methods similar thereto.

Step 7-3

This step is a step of hydrolyzing the ester moiety of the compound (26) to produce the compound (1e). The compound (1e) can be produced in accordance with any of the method described in step 3-4 of scheme 3, methods similar thereto, methods described in other literatures, and methods similar thereto.

Synthesis of Compound (1f)

The compound (1) when $R^1$ is a hydrogen atom and $Ar^2$ is a group represented by A7) (this compound may hereinafter be referred to as the compound (1f)) can be produced from the compound (27) in accordance with any of methods described in scheme 8, methods similar thereto, methods described in other literatures, and methods similar thereto.

Scheme 8

[Chemical Formula 23]

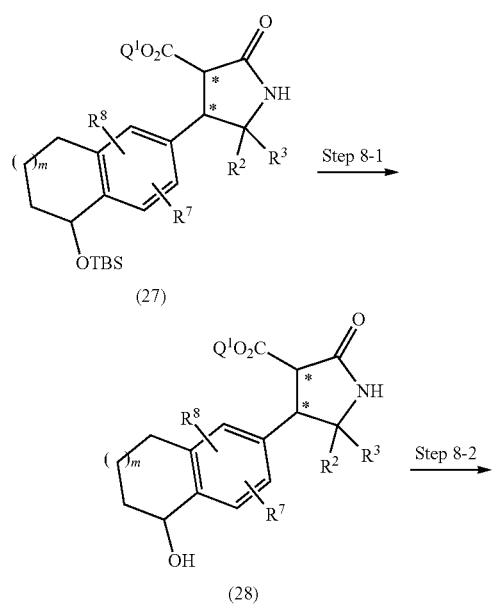

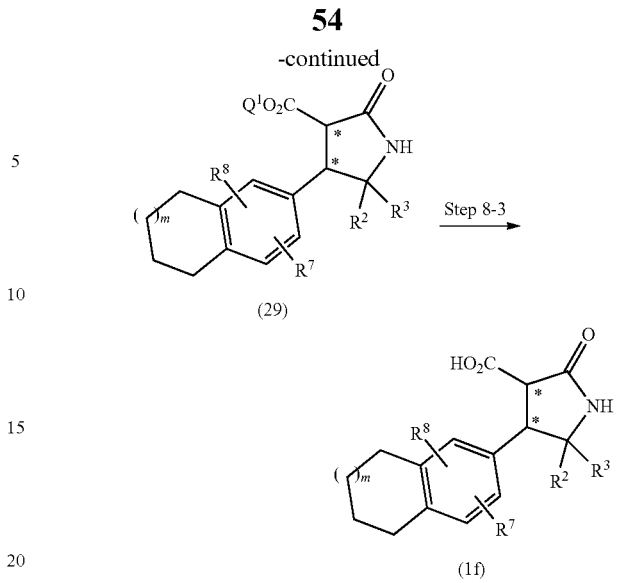

In the above formulas, $R^2$, $R^3$, $R^7$, $R^8$, $Q^1$, and m are as described above, and each carbon atom marked with an asterisk is an asymmetric carbon atom.

Step 8-1

This step is a step of deprotecting the tert-butyldimethylsilyl (TBS) group in the compound (27) to produce the compound (28). The compound (28) can be produced by, for example, reacting the compound (27) with an aqueous hydrogen chloride solution in a solvent. Examples of the solvent used may include tetrahydrofuran, water, mixed solvents of them and the like. The reaction temperature can usually be performed at 0° C. to the reflux temperature of the solvent and is performed preferably at 20° C. to 40° C. The reaction time varies depending on the starting materials used, the solvent used, the reaction temperature or the like, but is usually 30 minutes to 3 days.

The compound (27) used in this step can be produced in accordance with any of methods described in scheme 3 or 4, methods similar thereto, methods described in other literatures, and methods similar thereto.

Step 8-2

This step is a step of reducing the hydroxy group in the compound (28) to produce the compound (29). The compound (29) can be produced by, for example, hydrogenating the compound (28) in a solvent in the presence of a catalyst such as 10% palladium on carbon (10% Pd—C). Examples of the solvent used may include methanol, ethanol, dichloromethane, tetrahydrofuran, ethyl acetate, acetic acid, mixed solvents of them and the like. The reaction temperature can usually be performed at 0° C. to the reflux temperature of the solvent and is performed preferably at 20° C. to 40° C. The reaction time varies depending on the starting materials used, the solvent used, the reaction temperature or the like, but is usually 30 minutes to 3 days.

Step 8-3

This step is a step of hydrolyzing the ester moiety of the compound (29) to produce the compound (1f). The compound (1f) can be produced in accordance with any of the method described in step 3-4 of scheme 3, methods similar thereto, methods described in other literatures, and methods similar thereto.

Synthesis of Compounds (3c) to (3e)

The compound (3) when $R^1$ is a $C_1$ to $C_6$ alkyl group optionally having substituent(s) (these compounds may hereinafter be referred to as the compound (3c), the compound (3d), and the compound (3e)) can be produced from the compound (3a) in accordance with any of methods described in scheme 9, methods similar thereto, methods described in other literatures, and methods similar thereto.

Step 9-2

This step is a step of reacting the compound (30) with the compound (22) to produce the compound (31). The compound (31) can be produced by, for example, reacting the

[Chemical Formula 24]

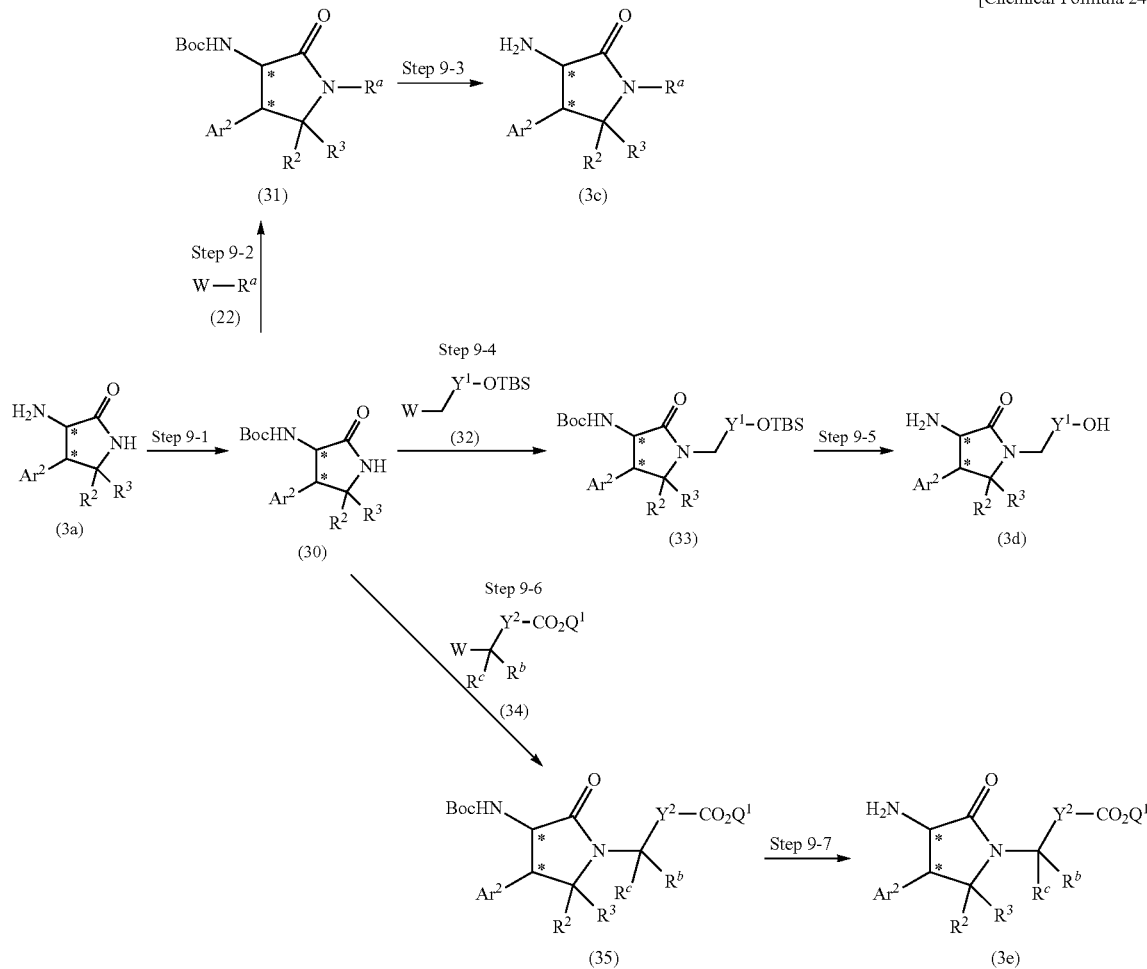

In the above formulas, $Ar^2$, $R^2$, $R^3$, $R^a$, $Q^1$, and W are as described above, $R^b$ and $R^c$ are each independently a hydrogen atom or a $C_{1-6}$ alkyl group, $Y^1$ is a $C_{1-3}$ alkylene, $Y^2$ is a single bond or a $C_{1-3}$ alkylene group, and each carbon atom marked with an asterisk is an asymmetric carbon atom.

Step 9-1

This step is a step of protecting the amino group in the compound (3a) with a tert-butoxycarbonyl (Boc) group to produce the compound (30). The compound (30) can be produced by, for example, reacting the compound (3a) with di-tert-butyl dicarbonate ((Boc)$_2$O) in a solvent in the presence or absence of a base. Examples of the solvent used may include water, methanol, ethanol, tetrahydrofuran, N,N-dimethylformamide, 1,4-dioxane, acetonitrile, mixed solvents of them and the like. Examples of the base used may include trimethylamine, triethylamine, N-methylmorpholine and the like. The reaction temperature can usually be performed at 0° C. to the reflux temperature of the solvent and is performed preferably at 10° C. to 60° C. The reaction time varies depending on the starting materials used, the solvent used, the reaction temperature or the like, but is usually 30 minutes to 3 days.

compound (30) with the compound (22) in a solvent in the presence of a base. Examples of the solvent used may include tetrahydrofuran, N,N-dimethylformamide, mixed solvents of them and the like. Examples of the base used may include lithium hydride, sodium hydride, potassium tert-butoxide and the like. The reaction temperature can usually be performed at −10° C. to the reflux temperature of the solvent and is performed preferably at 0° C. to 60° C. The reaction time varies depending on the starting materials used, the solvent used, the reaction temperature or the like, but is usually 30 minutes to 3 days.

Further, the compound (22) used in this step may be a commercially available, or can be produced in accordance with any of methods described in other literatures, and methods similar thereto.

Step 9-3

This step is a step of deprotecting the tert-butoxycarbonyl (Boc) group in the compound (31) to produce the compound (3c). The compound (3c) can be produced in accordance with any of the method described in step 5-4 of scheme 5, methods similar thereto, methods described in other literatures, and methods similar thereto.

Step 9-4

This step is a step of reacting the compound (30) with the compound (32) to produce the compound (33). The compound (33) can be produced in accordance with any of the method described in step 9-2 of scheme 9, methods similar thereto, methods described in other literatures, and methods similar thereto.

Further, the compound (32) used in this step may be a commercially available, or can be produced in accordance with any of methods described in other literatures, and methods similar thereto.

pound (3e) can be produced in accordance with any of the method described in step 5-4 of scheme 5, methods similar thereto, methods described in other literatures, and methods similar thereto.

Alternative Synthesis of Compounds (3c) and (3d)

The compounds (3c) and (3d) can be produced from the compound (5) in accordance with any of methods described in scheme 10, methods similar thereto, methods described in other literatures, and methods similar thereto.

Scheme 10

[Chemical Formula 25]

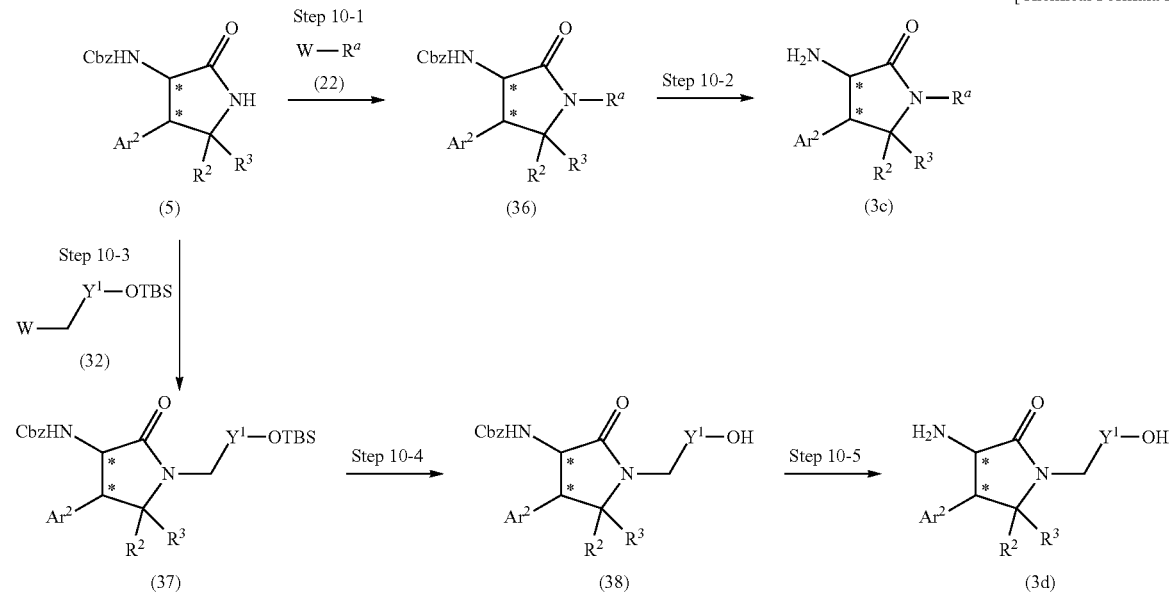

Step 9-5

This step is a step of deprotecting the TBS and Boc groups in the compound (33) to produce the compound (3d). The compound (3d) can be produced by, for example, reacting the compound (33) with an acid such as trifluoroacetic acid (TFA) or hydrogen chloride in a water-containing solvent. Examples of the solvent used may include mixtures of water with methanol, ethanol, dioxane, and so on. The reaction temperature can usually be performed at −10° C. to the reflux temperature of the solvent and is performed preferably at 0° C. to 60° C. The reaction time varies depending on the starting materials used, the solvent used, the reaction temperature or the like, but is usually 30 minutes to 3 days.

Step 9-6

This step is a step of reacting the compound (30) with the compound (34) to produce the compound (35). The compound (35) can be produced in accordance with any of the method described in step 9-2 of scheme 9, methods similar thereto, methods described in other literatures, and methods similar thereto.

Further, the compound (34) used in this step may be a commercially available, or can be produced in accordance with any of methods described in other literatures, and methods similar thereto.

Step 9-7

This step is a step of deprotecting the Boc group in the compound (35) to produce the compound (3e). The com- In the above formulas, $Ar^2$, $R^2$, $R^3$, $R^a$, W, and $Y^1$ are as described above, and each carbon atom marked with an asterisk is an asymmetric carbon atom.

Step 10-1

This step is a step of reacting the compound (5) with the compound (22) to produce the compound (36). The compound (36) can be produced in accordance with any of the method described in step 9-2 of scheme 9, methods similar thereto, methods described in other literatures, and methods similar thereto.

The compound (22) used in this step may be a commercially available, or can also be produced in accordance with any of methods described in other literatures, and methods similar thereto.

Step 10-2

This step is a step of deprotecting the benzyloxycarbonyl (Cbz) group in the compound (36) to produce the compound (3c). The compound (3c) can be produced in accordance with any of the method described in step 2-4 of scheme 2, methods similar thereto, methods described in other literatures, and methods similar thereto.

Step 10-3

This step is a step of reacting the compound (5) with the compound (32) to produce the compound (37). The compound (37) can be produced in accordance with any of the method described in step 9-2 of scheme 9, methods similar thereto, methods described in other literatures, and methods similar thereto.

The compound (32) used in this step may be a commercially available, or can also be produced in accordance with any of methods described in other literatures, and methods similar thereto.

Step 10-4

This step is a step of deprotecting the TBS group in the compound (37) to produce the compound (38). The compound (38) can be produced by, for example, reacting the compound (37) with tetrabutylammonium fluoride (TBAF) in a solvent. Examples of the solvent used may include tetrahydrofuran, N,N-dimethylformamide, mixed solvents of them and the like. The reaction temperature can usually be performed at 0° C. to the reflux temperature of the solvent and is performed preferably at 10° C. to 40° C. The reaction time varies depending on the starting materials used, the solvent used, the reaction temperature or the like, but is usually 30 minutes to 3 days.

Step 10-5

This step is a step of deprotecting the Cbz group in the compound (38) to produce the compound (3d). The compound (3d) can be produced in accordance with any of the method described in step 2-4 of scheme 2, methods similar thereto, methods described in other literatures, and methods similar thereto.

Synthesis of Compounds (3f) to (3g)

The compounds represented by the following formula (3f) (the compound may hereinafter be referred to as the compound (3f)) and represented by the following formula (3g) (the compound may hereinafter be referred to as the compound (3g)) among the compound (3) can be produced from the compound (39) in accordance with any of methods described in scheme 11, methods similar thereto, methods described in other literatures, and methods similar thereto.

Scheme 11

[Chemical Formula 26]

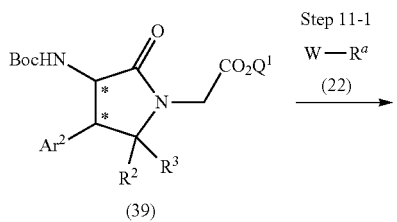

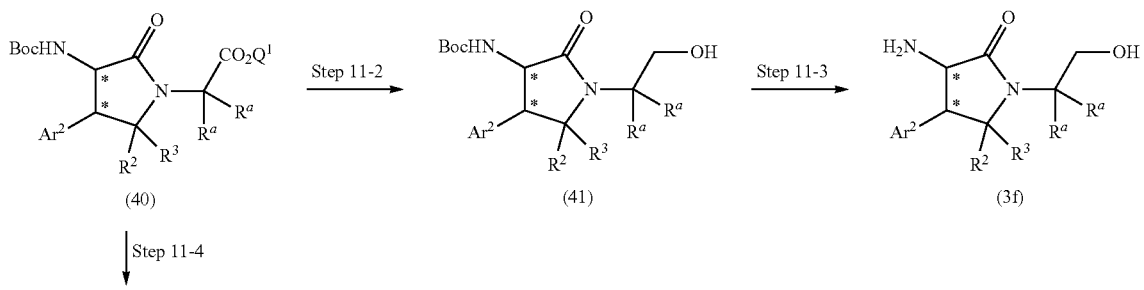

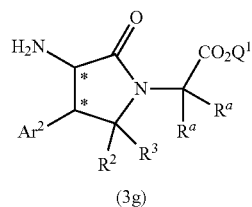

(3g)

In the above formulas, $Ar^2$, $R^2$, $R^3$, $R^a$, $Q^1$, and W are as described above, and each carbon atom marked with an asterisk is an asymmetric carbon atom.

Step 11-1

This step is a step of reacting the compound (39) with the compound (22) to produce the compound (40). The compound (40) can be produced by, for example, reacting the compound (39) with the compound (22) in a solvent in the presence of a base. Examples of the solvent used may include tetrahydrofuran and the like. Examples of the base used may include organolithiums such as lithium diisopropylamide (LDA), lithium hexamethyl disilazide (LHMDS) and the like. The reaction temperature can usually be performed at −78° C. to the reflux temperature of the solvent and is performed preferably at −78° C. to 30° C. The reaction time varies depending on the starting materials used, the solvent used, the reaction temperature or the like, but is usually 30 minutes to 3 days.

The compound (39) used in this step can be produced in accordance with any of the method described in step 9-2 of scheme 9, methods similar thereto, methods described in other literatures, and methods similar thereto.

Further, the compound (22) used in this step may be a commercially available, or can be produced in accordance with any of methods described in other literatures, and methods similar thereto.

Step 11-2

This step is a step of reducing the ester moiety of the compound (40) to produce the compound (41). The compound (41) can be produced by, for example, reacting the compound (40) with a reducing agent such as lithium borohydride ($LiBH_4$), lithium aluminum hydride ($LiAlH_4$), diisobutylaluminium hydride (DIBAL) and the like in a solvent. Examples of the solvent used may include tetrahydrofuran and the like. The reaction temperature can usually be performed at −20° C. to the reflux temperature of the solvent and is performed preferably at 0° C. to 30° C. The reaction time varies depending on the starting materials used, the solvent used, the reaction temperature or the like, but is usually 30 minutes to 3 days.

Step 11-3

This step is a step of deprotecting the Boc group in the compound (41) to produce the compound (3f). The compound (3f) can be produced in accordance with any of the method described in step 5-4 of scheme 5, methods similar thereto, methods described in other literatures, and methods similar thereto.

Step 11-4

This step is a step of deprotecting the Boc group in the compound (40) to produce the compound (3g). The compound (3g) can be produced in accordance with any of the method described in step 5-4 of scheme 5, methods similar thereto, methods described in other literatures, and methods similar thereto.

The compound (3g) can be produced from the compound (42) in accordance with any of methods described in scheme 12, methods similar thereto, methods described in other literatures, and methods similar thereto.

Scheme 12

[Chemical Formula 27]

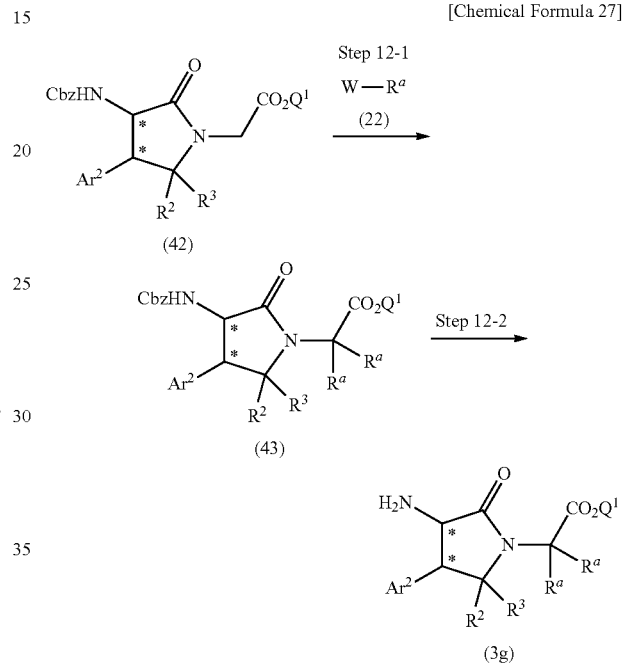

In the above formulas, $Ar^2$, $R^2$, $R^3$, $R^a$, and $Q^1$ are as described above, and each carbon atom marked with an asterisk is an asymmetric carbon atom.

Step 12-1

This step is a step of reacting the compound (22) with the compound (42) to produce the compound (43). The compound (43) can be produced in accordance with any of the method described in step 11-1 of scheme 11, methods similar thereto, methods described in other literatures, and methods similar thereto.

The compound (42) used in this step can be produced in accordance with any of the method described in step 10-1 of scheme 10, methods similar thereto, methods described in other literatures, and methods similar thereto.

Step 12-2

This step is a step of deprotecting the Cbz group in the compound (43) to produce the compound (3g). The compound (3g) can be produced in accordance with any of the method described in step 2-4 of scheme 2, methods similar thereto, methods described in other literatures, and methods similar thereto.

Synthesis of Compounds (3h) and (3i)

The compounds represented by the following formula (3h) (the compound may hereinafter be referred to as the compound (3h)) and represented by the following formula (3i) (the compound may hereinafter be referred to as the compound (3i)) among the compound (3) can be produced from the compound (5) in accordance with any of methods described in scheme 13, methods similar thereto, methods described in other literatures, and methods similar thereto.

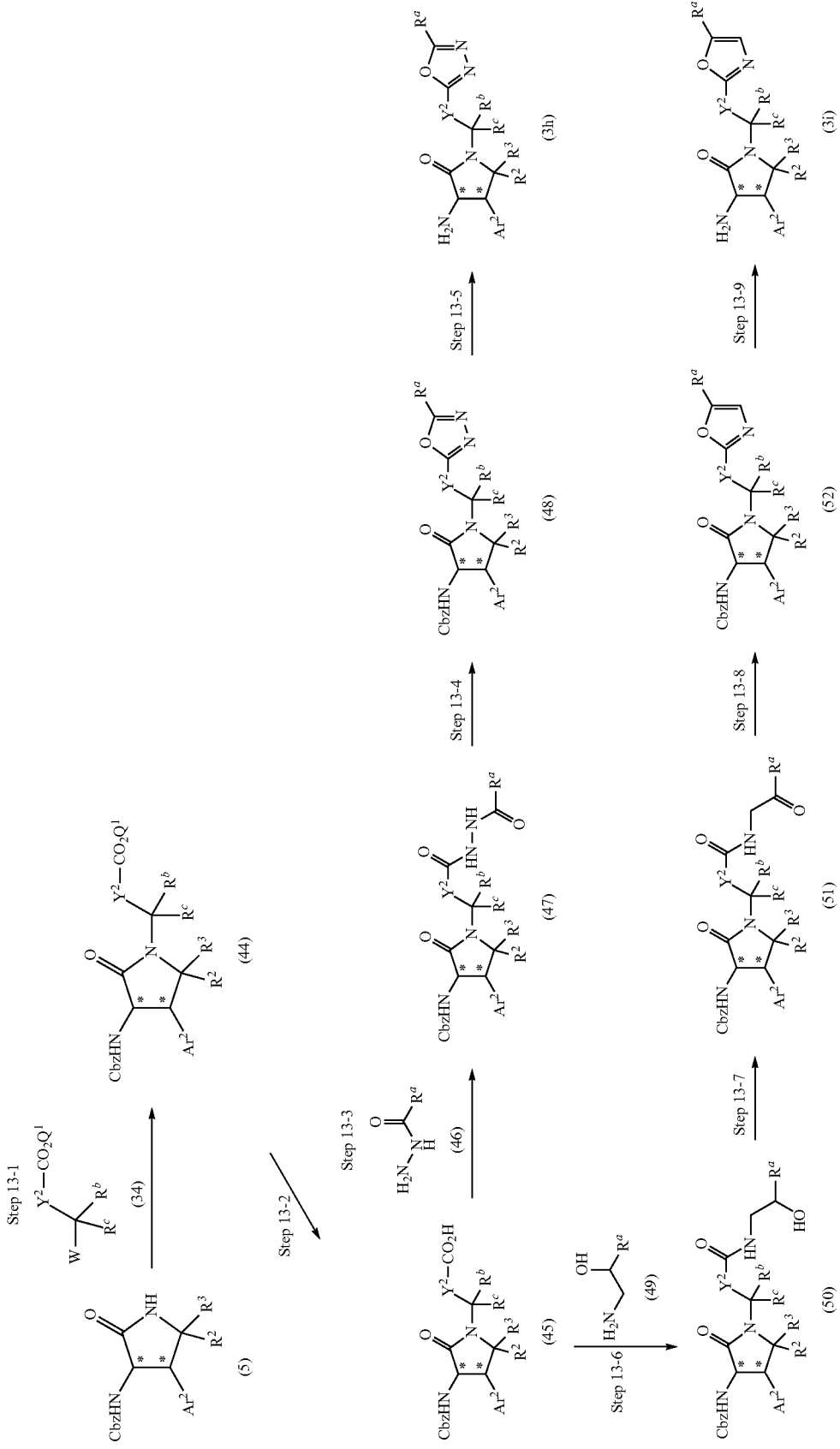

In the above formulas, $Ar^2$, $R^2$, $R^3$, $R^a$, $R^b$, $R^c$, $Q^1$, W, and $Y^2$ are as described above, and each carbon atom marked with an asterisk is an asymmetric carbon atom.

Step 13-1

This step is a step of reacting the compound (5) with the compound (34) to produce the compound (44). The compound (44) can be produced in accordance with any of the method described in step 9-2 of scheme 9, methods similar thereto, methods described in other literatures, and methods similar thereto.

The compound (34) used in this step may be a commercially available, or can also be produced in accordance with any of methods described in other literatures, and methods similar thereto.

Step 13-2

This step is a step of hydrolyzing the ester moiety of the compound (44) to produce the compound (45). The compound (45) can be produced in accordance with any of the method described in step 3-4 of scheme 3, methods similar thereto, methods described in other literatures, and methods similar thereto.

Step 13-3

This step is a step of reacting the compound (45) with the compound (46) to produce the compound (47). The compound (47) can be produced by, for example, reacting the compound (45) with the compound (46) in a solvent in the presence or absence of a base and in the presence of a condensing agent. Examples of the solvent used may include N,N-dimethylformamide, dichloromethane, 1,4-dioxane, tetrahydrofuran, mixed solvents of them and the like. Examples of the condensing agent used may include 1-ethyl-3-(3-dimethylaminopropyl)carbodiimide (EDCI), dicyclohexylcarbodiimide (DCC), 2-(1H-7-azabenzotriazol-1-yl)-1,1,3,3-tetramethyluronium hexafluorophosphatemethanaminium (HATU) and the like. If required, N,N-dimethylamino pyridine, pyridine, 1-hydroxybenzotriazole (HOBT) and the like can be used as a reaction promotor. The reaction temperature can usually be performed at 0° C. to the reflux temperature of the solvent and is performed preferably at 0° C. to 30° C. Examples of the usable base may include potassium carbonate, sodium carbonate, triethylamine, N,N-diisopropylethylamine and the like. The reaction time varies depending on the starting materials used, the solvent used, the reaction temperature or the like, but is usually 30 minutes to 3 days.

The compound (46) used in this step may be a commercially available, or can also be produced in accordance with any of methods described in other literatures, and methods similar thereto.

Step 13-4

This step is a step of producing the compound (48) from the compound (47). The compound (48) can be produced by, for example, reacting the compound (47) with triphenylphosphine, triethylamine, and 1,1,1,2,2,2-hexachloroethane in a solvent. Examples of the solvent used may include dichloromethane and the like. The reaction temperature can usually be performed at −78° C. to the reflux temperature of the solvent and is performed preferably at 0° C. to 30° C. The reaction time varies depending on the starting materials used, the solvent used, the reaction temperature or the like, but is usually 30 minutes to 3 days.

Step 13-5

This step is a step of deprotecting the Cbz group in the compound (48) to produce the compound (3h). The compound (3h) can be produced in accordance with any of the method described in step 2-4 of scheme 2, methods similar thereto, methods described in other literatures, and methods similar thereto.

Step 13-6

This step is a step of reacting the compound (45) with the compound (49) to produce the compound (50). The compound (50) can be produced in accordance with any of the method described in step 13-3 of scheme 13, methods similar thereto, methods described in other literatures, and methods similar thereto.

The compound (49) used in this step may be a commercially available, or can also be produced in accordance with any of methods described in other literatures, and methods similar thereto.

Step 13-7

This step is a step of oxidizing the alcohol moiety of the compound (50) to a ketone to produce the compound (51). The compound (51) can be produced by, for example, reacting the compound (50) with an oxidizer such as 2-iodoxybenzoic acid in a solvent. Examples of the solvent used may include dimethyl sulfoxide and the like. The reaction temperature can usually be performed at 0° C. to the reflux temperature of the solvent and is performed preferably at 10° C. to 30° C. The reaction time varies depending on the starting materials used, the solvent used, the reaction temperature or the like, but is usually 30 minutes to 3 days.

Step 13-8

This step is a step of producing the compound (52) from the compound (51). The compound (52) can be produced by, for example, reacting the compound (51) with triphenylphosphine and triethylamine in a solvent. Examples of the solvent used may include carbon tetrachloride and the like. The reaction temperature can usually be performed at 0° C. to the reflux temperature of the solvent and is performed preferably at 50° C. to 90° C. The reaction time varies depending on the starting materials used, the solvent used, the reaction temperature or the like, but is usually 30 minutes to 3 days.

Step 13-9

This step is a step of deprotecting the Cbz group in the compound (52) to produce the compound (3i). The compound (3i) can be produced in accordance with any of the method described in step 2-4 of scheme 2, methods similar thereto, methods described in other literatures, and methods similar thereto.

Synthesis of Compound (3j)

The compound represented by the following formula (3j) (the compound may hereinafter be referred to as the compound (3j)) among the compound (3) can be produced from the compound (53) in accordance with any of methods described in scheme 14, methods similar thereto, methods described in other literatures, and methods similar thereto.

Scheme 14

[Chemical Formula 29]

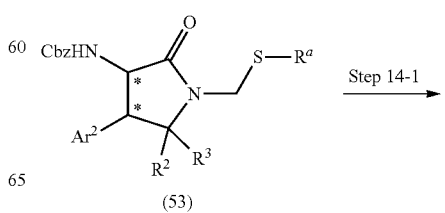

(53)

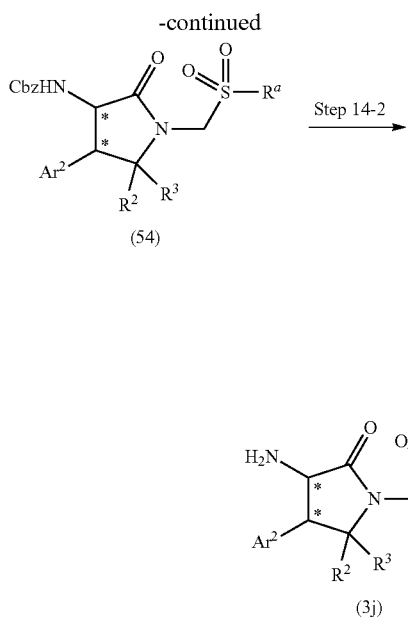

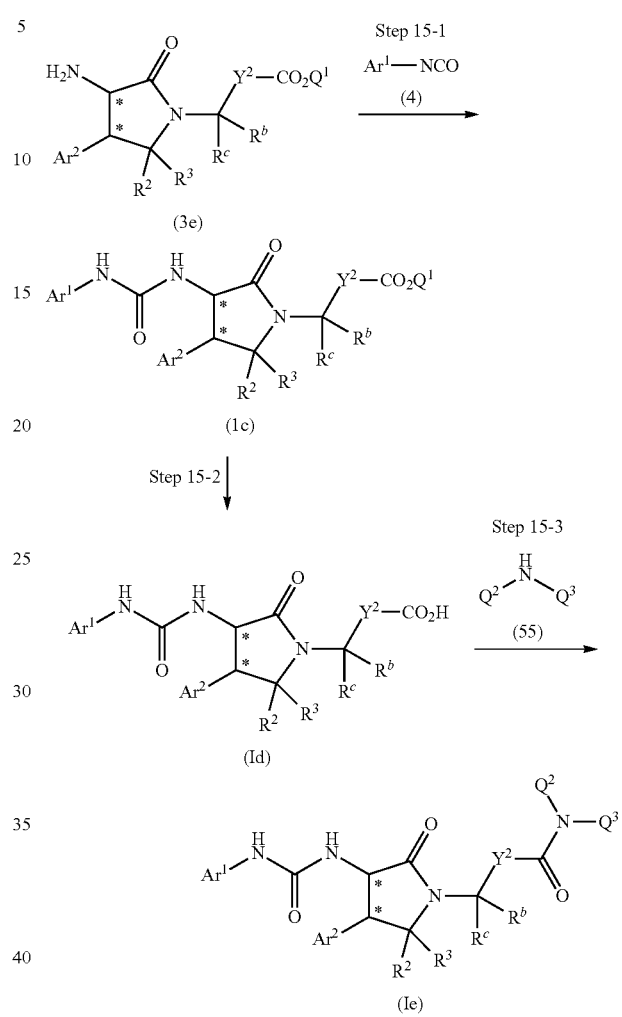

Scheme 15

[Chemical Formula 30]

In the above formulas, $Ar^2$, $R^2$, $R^3$, and $R^a$ are as described above, and each carbon atom marked with an asterisk is an asymmetric carbon atom.

Step 14-1

This step is a step of converting the sulfanyl group in the compound (53) to a sulfonyl group to produce the compound (54). The compound (54) can be produced by, for example, treating the compound (53) with an oxidizer such as meta-chloroperoxybenzoic acid (m-CPBA) in a solvent. Examples of the solvent used may include dichloromethane, acetonitrile, tetrahydrofuran, mixed solvents of them and the like. The amount of the oxidizer used is usually about 2 to 5 molar equivalents with respect to 1 mole of the compound (53). The reaction temperature can usually be performed at 0° C. to the reflux temperature of the solvent and is performed preferably at 0° C. to 30° C. The reaction time varies depending on the starting materials used, the solvent used, the reaction temperature or the like, but is usually 30 minutes to 3 days.

The compound (53) used in this step can be produced in accordance with any of the method described in step 10-1 of scheme 10, methods similar thereto, methods described in other literatures, and methods similar thereto.

Step 14-2

This step is a step of deprotecting the Cbz group in the compound (54) to produce the compound (3j). The compound (3j) can be produced in accordance with any of the method described in step 2-4 of scheme 2, methods similar thereto, methods described in other literatures, and methods similar thereto.

Synthesis of Compounds (Ic), (Id), and (Ie)

The compounds represented by the following formulas (Ic), (Id), and (Ie) (the compounds may hereinafter be referred to as the compounds (Ic), (Id), and (Ie)) among the compound (I) can be produced from the compound (3e) in accordance with any of methods described in scheme 15, methods similar thereto, methods described in other literatures, and methods similar thereto.

In the above formulas, $Ar^1$, $Ar^2$, $R^2$, $R^3$, $R^b$, $R^c$, $Y^2$, and $Q^1$ are as described above, $Q^2$ and $Q^3$ are each independently a hydrogen atom or a $C_{1-6}$ alkyl group optionally having substituent(s) or $Q^2$ and $Q^3$ together form an alkylene group, and each carbon atom marked with an asterisk is an asymmetric carbon atom.

Step 15-1

This step is a step of reacting the compound (3e) with the compound (4) to produce the compound (1c). The compound (1c) can be produced in accordance with any of the method described in step 1-2 of scheme 1, methods similar thereto, methods described in other literatures, and methods similar thereto.

Step 15-2

This step is a step of hydrolyzing the ester moiety of the compound (Ic) to produce the compound (Id). The compound (Id) can be produced in accordance with any of the method described in step 3-4 of scheme 3, methods similar thereto, methods described in other literatures, and methods similar thereto.

Step 15-3

This step is a step of reacting the compound (Id) with the compound (55) to produce the compound (Ie). The compound (Ie) can be produced in accordance with any of the method described in step 13-3 of scheme 13, methods similar thereto, methods described in other literatures, and methods similar thereto.

Further, the compound (55) used in this step may be a commercially available, or can be produced in accordance with any of methods described in other literatures, and methods similar thereto.

Synthesis of Compounds (If), (Ig), (Ih), and (Ii)

The compounds represented by the following formulas (If), (Ig), (Ih), and (Ii) (the compounds may hereinafter be referred to as the compounds (If), (Ig), (Ih), and (Ii)) among the compound (I) of the embodiment can be produced from the compound (56) in accordance with any of methods described in scheme 16, methods similar thereto, methods described in other literatures, and methods similar thereto.

[Chemical Formula 31]

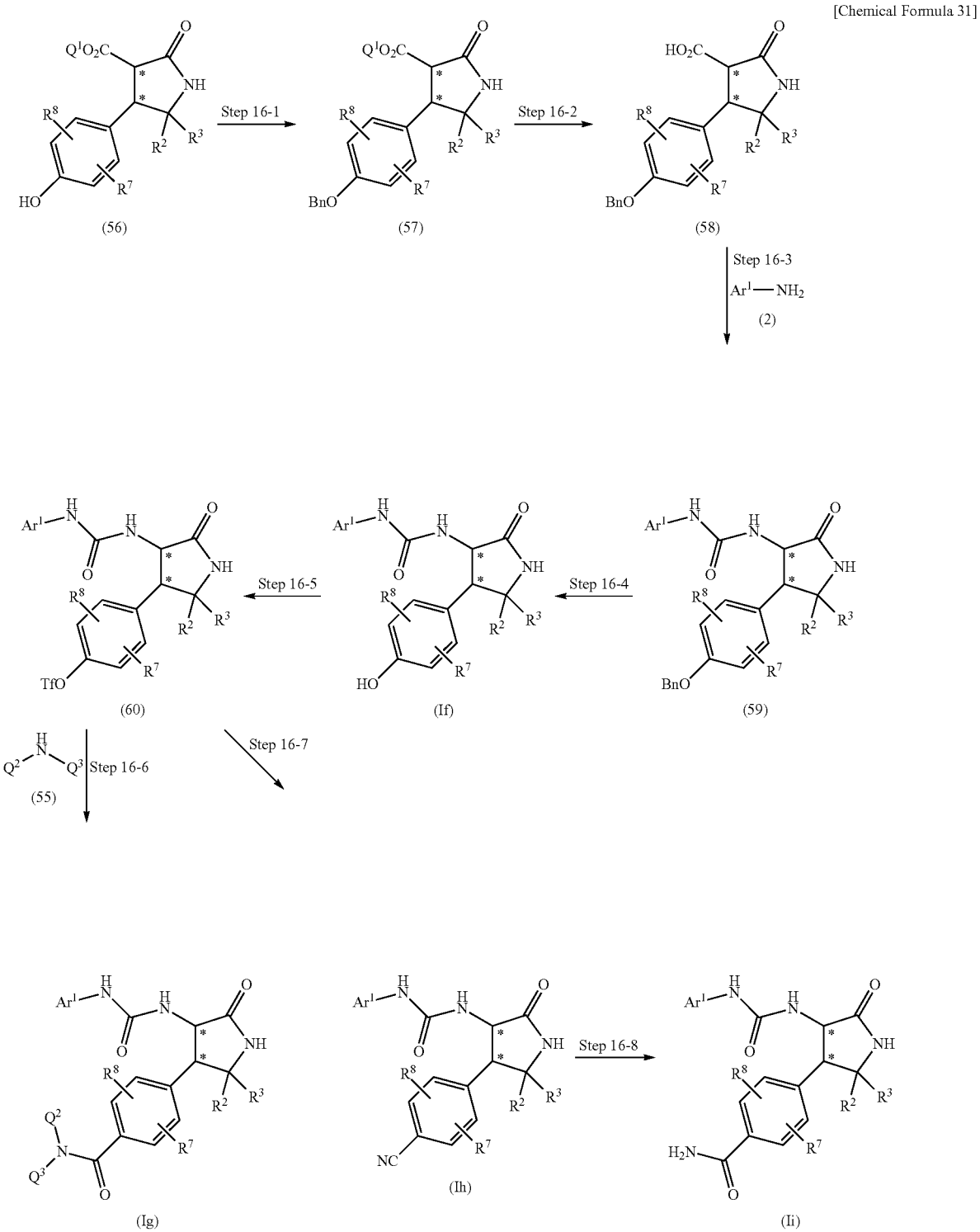

In the above formulas, $Ar^1$, $R^2$, $R^3$, $R^7$, $R^8$, $Q^1$, $Q^2$, and $Q^3$ are as described above, and each carbon atom marked with an asterisk is an asymmetric carbon atom.

Step 16-1

This step is a step of protecting the phenolic hydroxy group in the compound (56) with a benzyl (Bn) group to produce the compound (57). The compound (57) can be produced by, for example, reacting the compound (56) with benzyl bromide in a solvent in the presence of a base. Examples of the solvent used may include tetrahydrofuran, N,N-dimethylformamide, mixed solvents of them and the like. Examples of the base used may include sodium carbonate, potassium carbonate, cesium carbonate and the like. The reaction temperature can usually be performed at 0° C. to the reflux temperature of the solvent and is performed preferably at 10° C. to 40° C. The reaction time varies depending on the starting materials used, the solvent used, the reaction temperature or the like, but is usually 30 minutes to 3 days.

The compound (56) used in this step can be produced in accordance with any of methods described in scheme 3 or 4, methods similar thereto, methods described in other literatures, and methods similar thereto.

Step 16-2

This step is a step of hydrolyzing the ester moiety of the compound (57) to produce the compound (58). The compound (58) can be produced in accordance with any of the method described in step 3-4 of scheme 3, methods similar thereto, methods described in other literatures, and methods similar thereto.

Step 16-3

This step is a step of producing the compound (59) from the compound (58). The compound (59) can be produced in accordance with any of the method described in step 1-1 of scheme 1, methods similar thereto, methods described in other literatures, and methods similar thereto.

Step 16-4

This step is a step of deprotecting the Bn group in the compound (59) to produce the compound (If). The compound (If) can be produced by, for example, hydrogenating the compound (59) in a solvent in the presence of a catalyst such as 10% palladium on carbon (10% Pd—C) and the like. Examples of the solvent used may include methanol, ethanol, dichloromethane, tetrahydrofuran, ethyl acetate, mixed solvents of them and the like. The reaction temperature can usually be performed at 0° C. to the reflux temperature of the solvent and is performed preferably at 10° C. to 40° C. The reaction time varies depending on the starting materials used, the solvent used, the reaction temperature or the like, but is usually 30 minutes to 3 days.

Step 16-5

This step is a step of trifluoromethane-sulfonylating the hydroxy group in the compound (If) to produce the compound (60). The compound (60) can be produced by, for example, reacting the compound (If) with a trifluoromethane-sulfonylation agent in a solvent in the presence of a base. Examples of the solvent used may include dichloromethane, 1,2-dichloroethane, pyridine, tetrahydrofuran, N,N-dimethylformamide, 1,4-dioxane, acetonitrile, diethyl ether, mixed solvents of them and the like. Examples of the trifluoromethane-sulfonylation agent may include N-phenyl bis(trifluoromethanesulfonimide), trifluoromethanesulfonic anhydride and the like. Examples of the base used may include potassium carbonate, sodium carbonate, sodium hydride, potassium phosphate, N,N-diisopropylethylamine, triethylamine, 2,6-lutidine and the like. The reaction temperature can usually be performed at −78° C. to the reflux temperature of the solvent and is performed preferably at −20° C. to 30° C. The reaction time varies depending on the starting materials used, the solvent used, the reaction temperature or the like, but is usually 30 minutes to 3 days.

Step 16-6

This step is a step of producing the compound (Ig) from the compound (60). The compound (Ig) can be produced by, for example, reacting the compound (60) with the compound (55) in a solvent in the presence of acetonitrile, cesium carbonate, 2,2'-bis(diphenylphosphino)-1,1'-binaphthyl (BINAP), palladium acetate(II), and molybdenum hexacarbonyl ($Mo(CO)_6$). Examples of the solvent used may include toluene and the like. The reaction temperature can usually be performed at 0° C. to the reflux temperature of the solvent and is performed preferably at 50° C. to 80° C. The reaction time varies depending on the starting materials used, the solvent used, the reaction temperature or the like, but is usually 30 minutes to 3 days.

Step 16-7

This step is a step of producing the compound (Ih) from the compound (60). The compound (Ih) can be produced by, for example, reacting the compound (60) with zinc cyanide ($Zn(CN)_2$) in a solvent using a palladium reagent as a catalyst. Examples of the solvent used may include 1,4-dioxane, toluene, N,N-dimethylformamide, mixed solvents of them and the like. Examples of the palladium reagent used may include tetrakis(triphenylphosphine) palladium (0) ($Pd(PPh_3)_4$) and the like. The reaction temperature can usually be performed at 20° C. to the reflux temperature of the solvent and is performed preferably at 60° C. to 100° C. The reaction time varies depending on the starting materials used, the solvent used, the reaction temperature or the like, but is usually 30 minutes to 3 days.

Step 16-8

This step is a step of hydrolyzing the cyano group in the compound (Ih) to an amido group to produce the compound (Ii). The compound (Ii) can be produced by, for example, reacting the compound (Ih) in a solvent in the presence of a base. Examples of the solvent used may include water, methanol, ethanol, propanol, 2-propanol, butanol, tetrahydrofuran, mixed solvents of them and the like. Examples of the base used may include lithium hydroxide, sodium hydroxide, potassium hydroxide and the like. The reaction temperature can usually be performed at 0° C. to the reflux temperature of the solvent and is performed preferably at 60° C. to 100° C. The reaction time varies depending on the starting materials used, the solvent used, the reaction temperature or the like, but is usually 30 minutes to 3 days.

Synthesis of Compounds (Ij), (Ik), and Compound (Il)

The compound represented by the following formula (Ij) (the compound may hereinafter be referred to as the compound (Ij)) among the compound (I) of the embodiment can be produced in accordance with any of methods described in scheme 1, methods similar thereto, methods described in other literatures, and methods similar thereto.

Furthermore, the compounds represented by the following formulas (Ik) and (Il) (the compounds may hereinafter be referred to as the compounds (Ik) and (Il)) among the compound (I) of the embodiment can be produced from the compound (Ij) in accordance with any of methods described in scheme 17, methods similar thereto, methods described in other literatures, and methods similar thereto.

Scheme 17

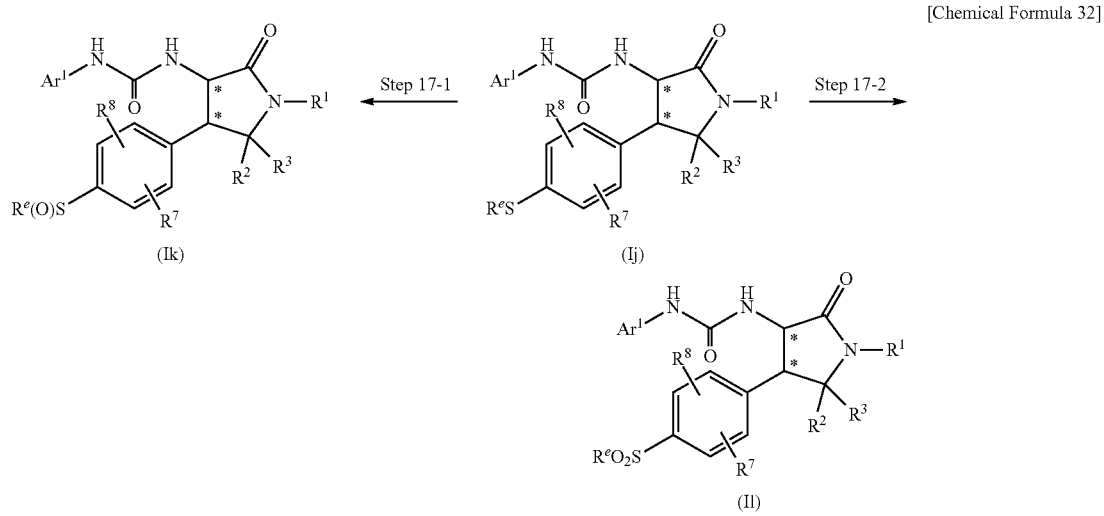

[Chemical Formula 32]

In the above formulas, $Ar^1$, $R^1$, $R^2$, $R^3$, $R^7$, and $R^8$ are as described above, $R^e$ is a $C_{1-6}$ alkyl group, and each carbon atom marked with an asterisk is an asymmetric carbon atom.

Step 17-1

This step is a step of converting the sulfanyl group in the compound (Ij) to a sulfinyl group to produce the compound (Ik). The compound (Ik) can be produced by, for example, treating the compound (Ij) with an oxidizer such as meta-chloroperoxybenzoic acid (m-CPBA) in a solvent. Examples of the solvent used may include dichloromethane, acetonitrile, tetrahydrofuran, mixed solvents of them and the like. The amount of the oxidizer used is usually about 1 to 2 molar equivalents with respect to 1 mole of the compound (Ij). The reaction temperature can usually be performed at 0° C. to the reflux temperature of the solvent and is performed preferably at 0° C. to 30° C. The reaction time varies depending on the starting materials used, the solvent used, the reaction temperature or the like, but is usually 30 minutes to 3 days.

Step 17-2

This step is a step of converting the sulfanyl group in the compound (Ij) to a sulfonyl group to produce the compound (Il). The compound (Il) can be produced by, for example, treating the compound (Ij) with an oxidizer such as meta-chloroperoxybenzoic acid (m-CPBA) in a solvent. Examples of the solvent used may include dichloromethane, acetonitrile, tetrahydrofuran, mixed solvents of them and the like. The amount of the oxidizer used is usually about 2 to 5 molar equivalents with respect to 1 mole of the compound (Ij). The reaction temperature can usually be performed at 0° C. to the reflux temperature of the solvent and is performed preferably at 0° C. to 30° C. The reaction time varies depending on the starting materials used, the solvent used, the reaction temperature or the like, but is usually 30 minutes to 3 days.

Synthesis of Compounds (Im), (In), Compound (Io), and Compound (Ip)

The compound represented by the following formula (Im) (the compound may hereinafter be referred to as the compound (Im)) among the compound (I) of the embodiment can be produced in accordance with any of methods described in scheme 1, methods similar thereto, methods described in other literatures, and methods similar thereto.

Furthermore, the compounds represented by the following formulas (In), (Io) and (Ip) (the compounds may hereinafter be referred to as the compounds (In), (Io) and (Ip)) among the compound (I) of the embodiment can be produced from the compound (Im) in accordance with any of methods described in scheme 18, methods similar thereto, methods described in other literatures, and methods similar thereto.

Scheme 18

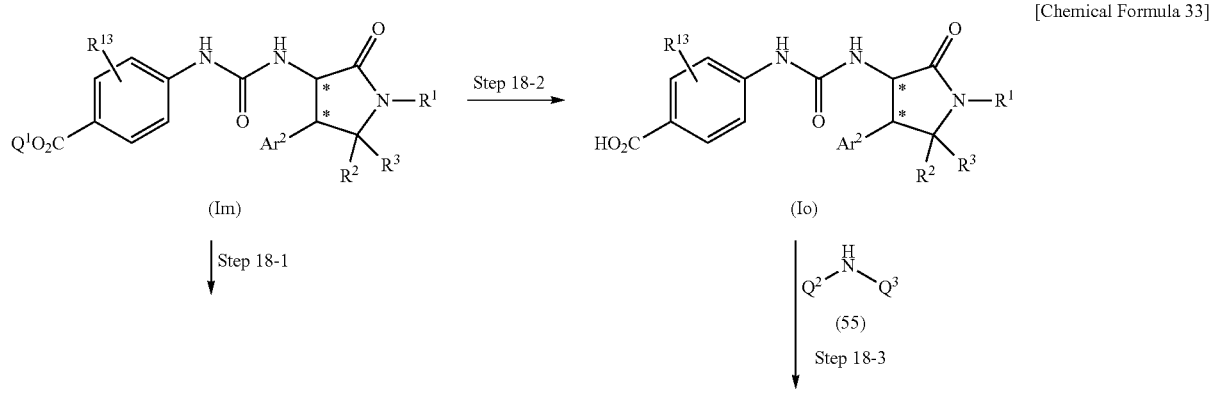

[Chemical Formula 33]

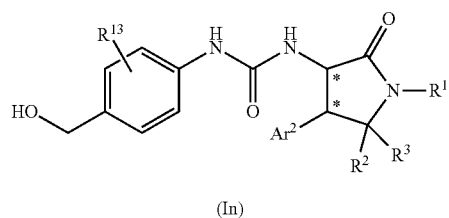 (In)

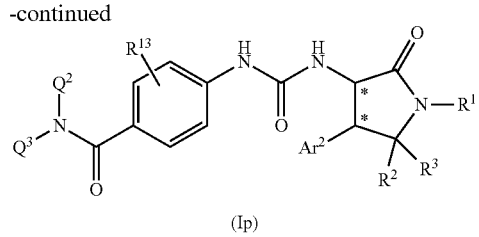 (Ip)

In the above formulas, $Ar^2$, $R^1$, $R^2$, $R^3$, $R^{13}$, $Q^1$, $Q^2$, and $Q^3$ are as described above, and each carbon atom marked with an asterisk is an asymmetric carbon atom.

Step 18-1

This step is a step of reducing the ester moiety of the compound (Im) to produce the compound (In). The compound (In) can be produced by, for example, treating the compound (Im) with a reducing agent such as diisobutylaluminum hydride in a solvent. Examples of the solvent used may include dichloromethane, tetrahydrofuran, toluene, mixed solvents of them and the like. The reaction temperature can usually be performed at 0° C. to the reflux temperature of the solvent and is performed preferably at 0° C. to 30° C. The reaction time varies depending on the starting materials used, the solvent used, the reaction temperature or the like, but is usually 30 minutes to 3 days.

Step 18-2

This step is a step of hydrolyzing the ester moiety of the compound (Im) to produce the compound (Io). The compound (Io) can be produced in accordance with any of the method described in step 3-4 of scheme 3, methods similar thereto, methods described in other literatures, and methods similar thereto.

Step 18-3

This step is a step of reacting the compound (Io) with the compound (55) to produce the compound (Ip). The compound (Ip) can be produced in accordance with any of the method described in step 13-3 of scheme 13, methods similar thereto, methods described in other literatures, and methods similar thereto.

Synthesis of Compound (Iq)

The compound represented by the following formula (Iq) (the compound may hereinafter be referred to as the compound (Iq)) among the compound (I) of the embodiment can be produced from the compound (61) in accordance with any of method described in scheme 19, methods similar thereto, methods described in other literatures, and methods similar thereto.

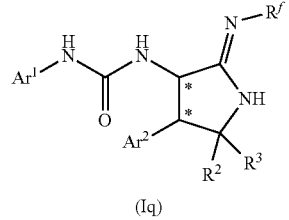 (Iq)

In the above formulas, $Ar^1$, $Ar^2$, $R^2$, and $R^3$ are as described above, $R^f$ is a $C_{1-6}$ alkyl group, a $C_{1-6}$ alkoxy group, or a TBSO group, and each carbon atom marked with an asterisk is an asymmetric carbon atom.

Step 19-1

This step is a step of producing the compound (Iq) from the compound (61). The compound (Iq) can be produced in accordance with any of the method described in step 1-2 of scheme 1, methods similar thereto, methods described in other literatures, and methods similar thereto.

The compound (61) can be produced from the compound (5) in accordance with any of methods described in scheme 20, methods similar thereto, methods described in other literatures, and methods similar thereto.

Scheme 20

[Chemical Formula 35]

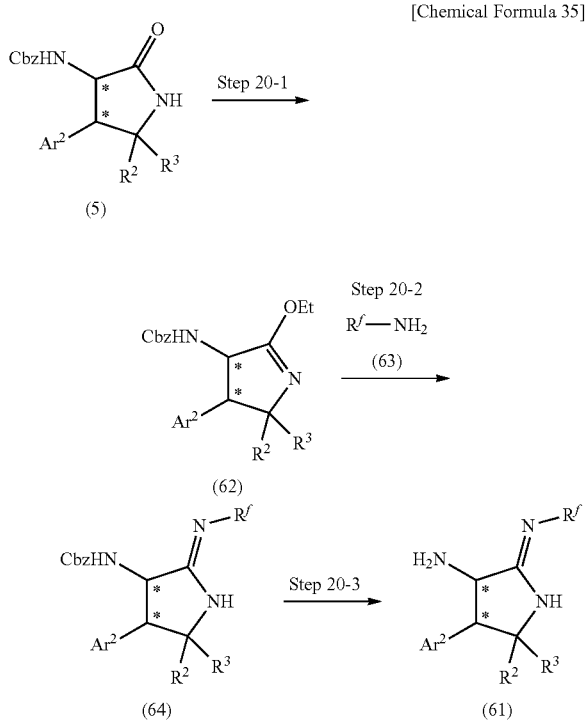

Scheme 19

[Chemical Formula 34]

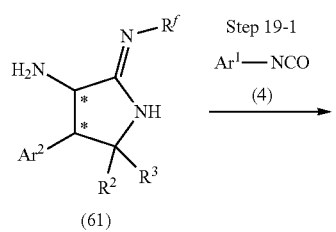

In the above formulas, $Ar^2$, $R^2$, $R^3$, and $R^f$ are as described above, and each carbon atom marked with an asterisk is an asymmetric carbon atom.

Step 20-1

This step is a step of producing the compound (62) from the compound (5). The compound (62) can be produced by, for example, reacting the compound (5) with triethyloxonium hexafluorophosphate ($Et_3OPF_6$) in a solvent. Examples of the solvent used may include dichloromethane and the like. The reaction temperature can usually be performed at 0° C. to the reflux temperature of the solvent and is performed preferably at 10° C. to 40° C. The reaction time varies depending on the starting materials used, the solvent used, the reaction temperature or the like, but is usually 30 minutes to 3 days.

Step 20-2

This step is a step of reacting the compound (62) with the compound (63) to produce the compound (64). The compound (64) can be produced by, for example, reacting the compound (62) with the compound (63) in a solvent in the presence or absence of an acid or a base. Examples of the solvent used may include methanol, ethanol, toluene, tetrahydrofuran, acetonitrile, dioxane, mixed solvents of them and the like. Examples of the acid that may be used may include hydrogen chloride, ammonium chloride and the like. Examples of the base that may be used may include trimethylamine, triethylamine, N-methylmorpholine and the like. The reaction temperature can usually be performed at 0° C. to the reflux temperature of the solvent and is performed preferably at 0° C. to 50° C. The reaction time varies depending on the starting materials used, the solvent used, the reaction temperature or the like, but is usually 10 minutes to 3 days.

Further, the compound (63) may be a commercially available, or can be produced in accordance with any of methods described in other literatures, and methods similar thereto.

Step 20-3

This step is a step of deprotecting the Cbz group in the compound (64) to produce the compound (61). The compound (61) can be produced in accordance with any of the method described in step 2-4 of scheme 2, methods similar thereto, methods described in other literatures, and methods similar thereto.

Synthesis of Compound (Ir)

The compound (Ir) can be produced from the compound (65) in accordance with any of methods described in scheme 21, methods similar thereto, methods described in other literatures, and methods similar thereto.

Scheme 21

[Chemical Formula 36]

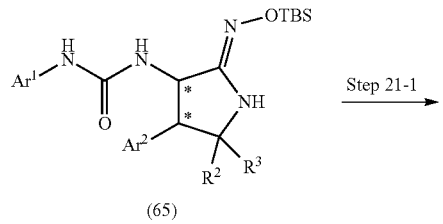

(65)

Step 21-1 →

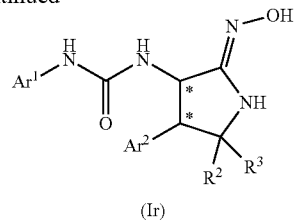

(Ir)

In the above formulas, $Ar^1$, $Ar^2$, $R^2$, and $R^3$ are as described above, and each carbon atom marked with an asterisk is an asymmetric carbon atom.

Step 21-1

This step is a step of deprotecting the TBS group in the compound (65) to produce the compound (Ir). The compound (Ir) can be produced by, for example, reacting the compound (65) with an acid such as trifluoroacetic acid (TFA) or hydrogen chloride in a solvent mixture of water-dioxane.

The reaction temperature can usually be performed at −20° C. to the reflux temperature of the solvent and is performed preferably at 0° C. to 30° C. The reaction time varies depending on the starting materials used, the solvent used, the reaction temperature or the like, but is usually 30 minutes to 3 days.

The compound (65) used in this step can be produced in accordance with any of methods described in scheme 19, methods similar thereto, methods described in other literatures, and methods similar thereto.

Step 22

Synthesis of Compounds (Is) and (It)

The compound represented by the following formula (Is) (the compound may hereinafter be referred to as the compound (Is)) among the compound (I) of the embodiment can be produced in accordance with any of methods described in scheme 1, methods similar thereto, methods described in other literatures, and methods similar thereto.

Furthermore, the compound represented by the following formula (It) (the compound may hereinafter be referred to as the compound (It)) among the compound (I) of the embodiment can be produced, for example, from the compound (Is) in accordance with any of methods described in scheme 22, methods similar thereto, methods described in other literatures, and methods similar thereto.

Scheme 22

[Chemical Formula 37]

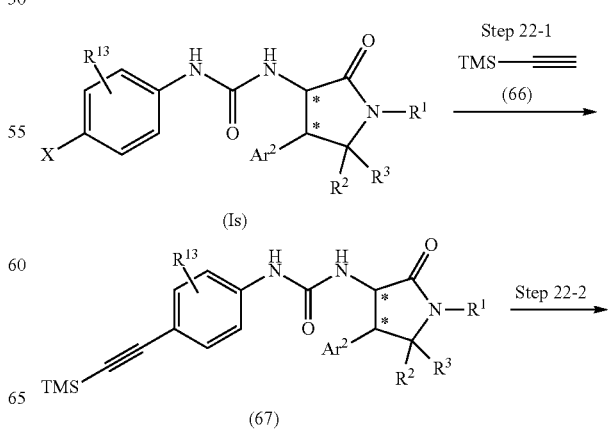

-continued

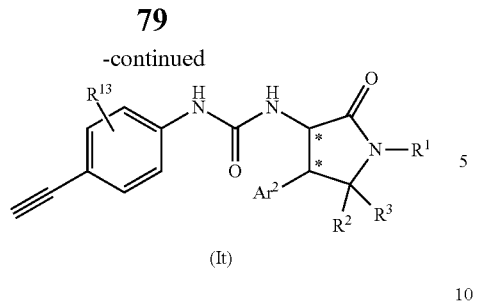

(It)

In the above formulas, Ar², R¹, R², R³, and R¹³ are as described above, X is a halogen atom, and each carbon atom marked with an asterisk is an asymmetric carbon atom.

Step 22-1

This step is a step of reacting the compound (Is) with trimethylsilylacetylene (66) to produce the compound (67). The compound (67) can be produced by, for example, reacting the compound (Is) with trimethylsilylacetylene (66) in a solvent in the presence of dichlorobis(triphenylphosphine)palladium(II), copper(I) iodide, and triethylamine. Examples of the solvent used may include N,N-dimethylformamide and the like. The reaction temperature can usually be performed at 0° C. to the reflux temperature of the solvent and is performed preferably at 40° C. to 60° C. The reaction time varies depending on the starting materials used, the solvent used, the reaction temperature or the like, but is usually 30 minutes to 3 days.

Step 22-2

This step is a step of deprotecting the TMS group in the compound (67) to produce the compound (It). The compound (It) can be produced by, for example, reacting the compound (67) with potassium carbonate in a solvent. Examples of the solvent used may include methanol and the like. The reaction temperature can usually be performed at 0° C. to the reflux temperature of the solvent and is performed preferably at 20° C. to 40° C. The reaction time varies depending on the starting materials used, the solvent used, the reaction temperature or the like, but is usually 30 minutes to 3 days.

Synthesis of Compound (Iu)

The compound represented by the following formula (Iu) (the compound may hereinafter be referred to as the compound (Iu)) among the compound (I) of the embodiment can be produced, for example, from the compound (68) in accordance with any of method described in scheme 23, methods similar thereto, methods described in other literatures, and methods similar thereto.

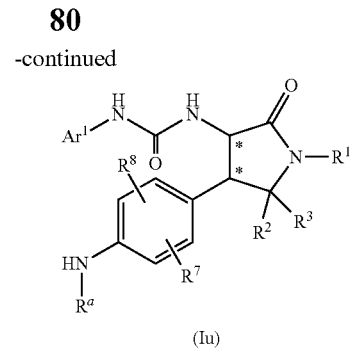

(Iu)

In the above formulas, Ar¹, R¹, R², R³, R⁷, R⁸, and Rᵃ are as described above, and each carbon atom marked with an asterisk is an asymmetric carbon atom.

Step 23-1

This step is a step of deprotecting the Boc group in the compound (68) to produce the compound (Iu). The compound (Iu) can be produced in accordance with any of the method described in step 5-4 of scheme 5, methods similar thereto, methods described in other literatures, and methods similar thereto.

The compound (68) used in this step can be produced in accordance with any of methods described in scheme 1, methods similar thereto, methods described in other literatures, and methods similar thereto.

Synthesis of Compounds (Iv) and (Iw)

The compound represented by the following formula (Iv) (the compound may hereinafter be referred to as the compound (Iv)) among the compound (I) of the embodiment can be produced in accordance with any of methods described in scheme 1, methods similar thereto, methods described in other literatures, and methods similar thereto.

Furthermore, the compound represented by the following formula (Iw) (the compound may hereinafter be referred to as the compound (Iw)) among the compound (I) of the embodiment can be produced, for example, from the compound (Iv) in accordance with any of methods described in scheme 24, methods similar thereto, methods described in other literatures, and methods similar thereto.

Scheme 23

[Chemical Formula 38]

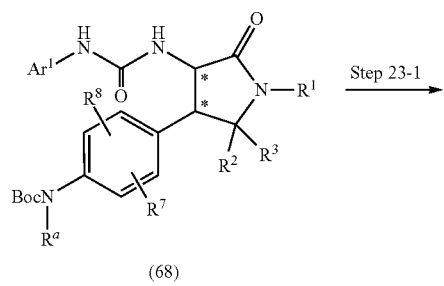 Step 23-1 →

(68)

Scheme 24

[Chemical Formula 39]

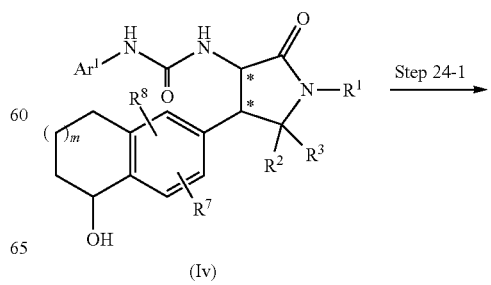 Step 24-1 →

(Iv)

-continued

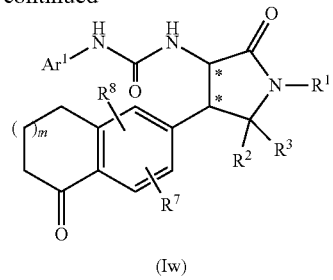

(Iw)

In the above formulas, Ar¹, R¹, R², R³, R⁷, R⁸, and m are as described above, and each carbon atom marked with an asterisk is an asymmetric carbon atom.

Step 24-1

This step is a step of converting the hydroxy group in the compound (Iv) to a ketone to produce the compound (Iw). The compound (Iw) can be produced by, for example, treating the compound (Iv) with an oxidizer such as Dess-Martin periodinane in a solvent. Examples of the solvent used may include dichloromethane, acetonitrile, mixed solvents of them and the like. The amount of the oxidizer used is usually about 1 to 2 molar equivalents with respect to 1 mole of the compound. The reaction temperature can usually be performed at 0° C. to the reflux temperature of the solvent and is performed preferably at 20° C. to 30° C. The reaction time varies depending on the starting materials used, the solvent used, the reaction temperature or the like, but is usually 30 minutes to 3 days.

Step 25

Synthesis of Compound (Ix)

The compound represented by the following formula (Ix) (the compound may hereinafter be referred to as the compound (Ix)) among the compound (I) of the embodiment can be produced, for example, from the compound (69) in accordance with any of method described in scheme 25, methods similar thereto, methods described in other literatures, and methods similar thereto.

In the above formulas, Ar¹, R¹, R², R³, R⁷, R⁸, and m are as described above, and each carbon atom marked with an asterisk is an asymmetric carbon atom.

Step 25-1

This step is a step of deprotecting the Bn group in the compound (69) to produce the compound (Ix). The compound (Ix) can be produced by, for example, hydrogenating the compound (69) in a solvent in the presence of a catalyst such as 10% palladium on carbon (10% Pd—C). Examples of the solvent used may include methanol, ethanol, dichloromethane, tetrahydrofuran, ethyl acetate, N,N-dimethylformamide, mixed solvents of them and the like. Examples of the base used may include triethylamine acetate and the like. The reaction temperature can usually be performed at 0° C. to the reflux temperature of the solvent and is performed preferably at 20° C. to 40° C. The reaction time varies depending on the starting materials used, the solvent used, the reaction temperature or the like, but is usually 30 minutes to 3 days.

The compound (69) used in this step can be produced in accordance with any of methods described in scheme 1, methods similar thereto, methods described in other literatures, and methods similar thereto.

Synthesis of Compound (Iz)

The compound represented by the following formula (Iy) (the compound may hereinafter be referred to as the compound (Iy)) among the compound (I) of the embodiment can be produced in accordance with any of methods described in scheme 1, methods similar thereto, methods described in other literatures, and methods similar thereto.

The compound represented by the following formula (Iz) (the compound may hereinafter be referred to as the compound (Iz)) among the compound (I) of the embodiment can be produced, for example, from the compound (Iy) in accordance with any of methods described in scheme 26, methods similar thereto, methods described in other literatures, and methods similar thereto.

Scheme 25

[Chemical Formula 40]

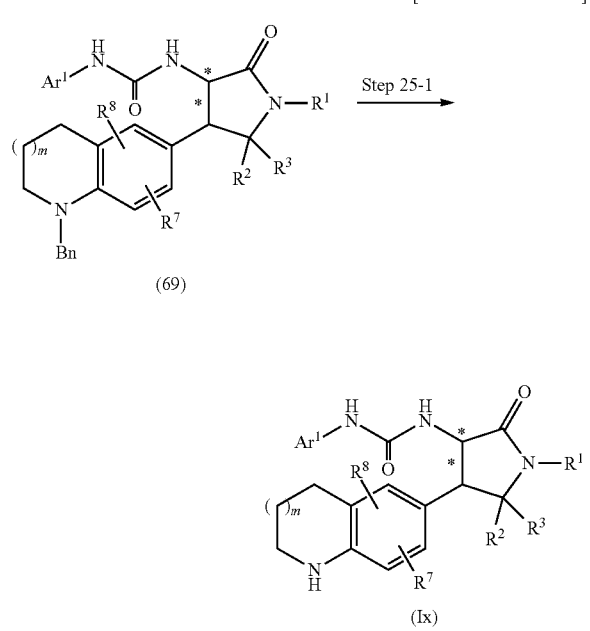

[Chemical Formula 41]

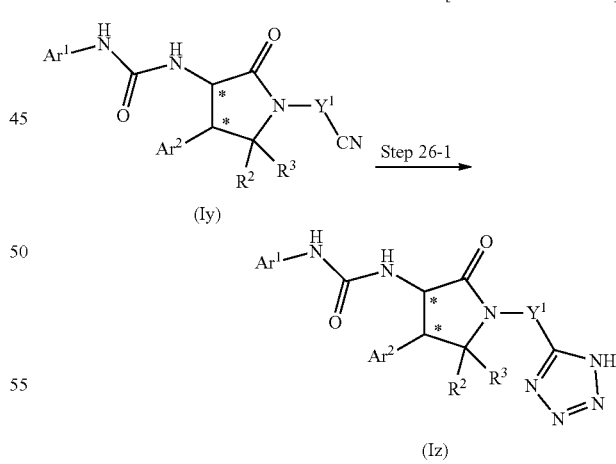

In the above formulas, Ar¹, Ar², R², R³, and Y¹ are as described above, and each carbon atom marked with an asterisk is an asymmetric carbon atom.

Step 26-1

This step is a step of producing the compound (Iz) from the compound (Iy). The compound (Iz) can be produced by, for example, reacting the compound (Iy) with sodium azide in a solvent in the presence of triethylamine and acetic acid.

Examples of the solvent used may include toluene, N,N-dimethylformamide, isopropanol, water, mixed solvents of them and the like. The reaction temperature can usually be performed at 0° C. to the reflux temperature of the solvent and is performed preferably at 100° C. to 130° C. The reaction time varies depending on the starting materials used, the solvent used, the reaction temperature or the like, but is usually 30 minutes to 3 days.

A pharmacologically acceptable salt of the compound (I) of the present embodiment can be produced using the compound (I) of the present embodiment according to a usual method.

The schemes described above are examples of the method of producing the compound (I) of the present embodiment or a production intermediate thereof. These schemes can be modified to various schemes that can be readily understood by a person skilled in the art.

Also, in the case that there is a need of a protective group according to the kind of the functional group, an appropriate combination of introduction and removal procedures may be performed according to a usual method. For the types of protective groups and introduction and removal of the protective groups, see, for example, methods described in "Greene's Protective Groups in Organic Synthesis," Theodra W. Green & Peter G. M. Wuts, ed., fourth edition, Wiley-Interscience, 2006.

The intermediates used for preparation of the compound (I) of the present embodiment or a pharmacologically acceptable salt thereof can be isolated/purified, as necessary, by solvent extraction, crystallization, recrystallization, chromatography, or preparative high-performance liquid chromatography or the like, that is an isolation/purification means well-known to a skilled person in the art.

The term "FPRL1 agonist effect" used in the present embodiment means that agonist activity exhibits through the action on formyl peptide receptor like 1 (FPRL1).

As described above, it is known that LXA4 and peptides reported as endogenous agonists of FPRL1 contribute to resolution of inflammation.

The compound (I) of the present embodiment or a pharmacologically acceptable salt thereof exhibits superior agonist activity in, for example, a test of calcium influx into FPRL1-overexpressing cells. Therefore, the compound (I) of the present embodiment or a pharmacologically acceptable salt thereof is useful as a therapeutic or prophylactic agent for inflammatory diseases, chronic airway diseases, cancers, septicemia, allergic symptoms, HIV retrovirus infection, circulatory disorders, neuroinflammation, nervous disorders, pains, prion diseases, amyloidosis, immune disorders and the like.

The compound (I) of the present embodiment or a pharmacologically acceptable salt thereof can also be used to produce pharmaceuticals for treatment or prevention of inflammatory diseases, chronic airway diseases, cancers, septicemia, allergic symptoms, HIV retrovirus infection, circulatory disorders, neuroinflammation, nervous disorders, pains, prion diseases, amyloidosis, immune disorders and the like.

In addition, pharmaceuticals containing, as an active ingredient, the compound (I) of the present embodiment or a pharmacologically acceptable salt thereof can be used as, for example, prophylactic or therapeutic agents for various disease states associated with the FPRL1 receptor (such as Behcet's disease, Sweet disease, systemic lupus erythematosus (SLE), Wegener's granulomatosis, virus infection, diabetes, amputations, cancers, bacterial infection, physical external injuries, physical disorders including exposure to radiation, vasoconstriction, anaphylactic reactions, allergic reactions, rhinitis, shocks (endotoxic, hemorrhagic, traumatic, splanchnic ischemia, and circulatory shocks), rheumatoid arthritis, gout, psoriasis, benign prostatic hyperplasia, myocardial ischemia, myocardial infarction, brain injuries, pulmonary diseases, COPD, COAD, COLD, acute lung injury, acute respiratory distress syndrome, chronic bronchitis, pulmonary emphysema, asthma (allergic asthma and non-allergic asthma), cystic pulmonary fibrosis, nephropathy, renal glomerular diseases, ulcerative colitis, IBD, Crohn's disease, periodontitis, pains, Alzheimer's disease, AIDS, uveitic glaucoma, conjunctivitis, Sjoegren's syndrome, rhinitis and the like).

Pharmaceutical Containing the Compound (I) of the Present Embodiment or Pharmacologically Acceptable Salt Thereof A pharmaceutical containing, as an active ingredient, the compound (I) of the present embodiment or a pharmacologically acceptable salt thereof can have various forms according to the usages. Examples of the forms may include powders, granules, fine granules, dry syrups, tablets, capsules, injections, liquids, ointments, suppositories, patches, sublingual tablets and the like, which are administered orally or parenterally.

Such a pharmaceutical can be formed as a pharmaceutical composition containing, as an active ingredient, the compound (I) of the present embodiment or a pharmacologically acceptable salt thereof and a pharmacologically acceptable additive using a well-known method according to the form of the pharmaceutical. Examples of the additive contained in the pharmaceutical composition may include an excipient, a disintegrant, a binder, a lubricant, a diluent, a buffering agent, an isotonizing agent, an antiseptic, a humectant, an emulsifier, a dispersant, a stabilizer, a solubilizing agent and the like. The pharmaceutical composition can be prepared by appropriately mixing the compound (I) of the present embodiment or a pharmacologically acceptable salt thereof with an additive or by diluting the compound (I) or a pharmacologically acceptable salt thereof with an additive and dissolving it in the additive. When the compound (I) of the present embodiment or a pharmacologically acceptable salt thereof is used in combination with agents other than the FPRL1 receptor agonist, a pharmaceutical composition can be produced by forming active ingredients of these components into a formulation simultaneously or separately in the manner described above.

The pharmaceutical according to the present embodiment can be systemically or locally administered orally or parenterally (transnasally, pulmonary, intravenously, intrarectally, hypodermically, intramuscularly, percutaneously and the like).

When a pharmaceutical composition containing, as an active ingredient, the compound (I) of the present embodiment or a pharmacologically acceptable salt thereof is used for practical treatment, the dose of the compound (I) of the present embodiment or the pharmacologically acceptable salt thereof used as the active ingredient is appropriately determined according to the age, sex, and body weight of the patient, the disease of the patient, the degree of the treatment and the like. For example, in the case of oral administration, it may be appropriately administered to an adult (the body weight is assumed to be 60 kg) at a daily dose within the range of about 0.03 to about 1,000 mg/body in one portion or several divided portions. The dose per day as an oral administration is preferably 0.06 to 540 mg/body and more preferably 0.18 to 180 mg/body. In the case of parenteral administration, it may be appropriately administered to an adult at a daily dose within the range of about 0.01 to about 300 mg/body in one portion or several divided portions. The dose per day as a parenteral administration is preferably 0.01 to 100 mg/body and more preferably 0.06 to 60 mg/body. The dose of the compound (I) of the present embodiment or a pharmacologically acceptable salt thereof may be reduced according to the dose of agents other than the FPRL1 receptor agonist.

EXAMPLES

Hereinafter, the present invention will be described in more detail on the basis of Test Examples, Examples, and Reference Examples. Starting materials used in production of the compound (I) include a novel compound, and therefore Production examples for the starting materials will be also described as Reference Examples. The present invention is not limited to compounds described in the following Examples, and may be modified without departing from the scope of the present invention.

Among symbols used in each Reference Example, each Example, and each Table, Ref.No. represents Reference Example Number, Ex.No. represents Example Number, P.D. represents physical chemical data, Str. represents a structural formula, and $^1$H-NMR represents a proton nuclear magnetic resonance spectrum. CDCl$_3$ represents chloroform-d, and DMSO-d$_6$ represents dimethyl sulfoxide-d$_6$. MS(ESI$^+$) represents mass spectral data measured by electron-spray ionization. An optical rotation represents a specific optical rotation, which measured in described solvent at described concentration and temperature using sodium D-line as light source.

Wedge-shaped solid line and dashed line in a structural formula represent relative configuration in an optically active substance, but do not represent absolute configuration. Thick solid line and dashed line represent relative configuration in a racemate and an optically active substance obtained by resolution of a racemate. A carbon atom marked with "*" represents an asymmetric carbon. A wavy line bond of carbon atom marked with "*" represents the presence of a racemate.

Both R* and S* in the name of a compound represent relative steric configuration about an asymmetric carbon atom.

When both a substituent and a hydrogen atom are bonded to each of two positions of a pyrrolidine ring in a structural formula, the relative configuration of the substituents is expressed as cis or trans, and cis or trans is sometimes followed by a hyphen and the name of a compound.

When the pyrrolidine ring is considered as a face, cis means that the two adjacent substituents are on the same side, and trans means that the two adjacent substituents are on the respective opposite sides.

In order to represent isomers about a double bond and a double bond of imine in the name of a compound, a cis-isomer is expressed as "Z," and a trans-isomer is expressed as "E."

Reference Example 1-1

[Chemical Formula 42]

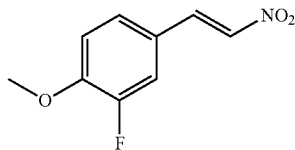

(E)-2-Fluoro-1-methoxy-4-(2-nitrovinyl)benzene

3-Fluoro-4-methoxybenzaldehyde (500 mg) was dissolved in 2-hydroxyethylammonium formate (1.7 g) under an argon atmosphere, and nitromethane (175 μL) was added to produce a reaction solution. The reaction solution was stirred at room temperature for 9 hours. Water was added to the reaction solution, and the precipitated solid was collected by filtration, and washed with water. The resulting solid was dried to obtain the title compound as a yellow solid (607 mg).

$^1$H-NMR (400 MHz, CDCl$_3$) δ 3.96 (3H, s), 7.01 (1H, t, J=8.5 Hz), 7.27-7.32 (2H, m), 7.48 (1H, d, J=13.3 Hz), 7.92 (1H, d, J=13.3 Hz).

The following Reference Examples 1-2 to 1-27 were obtained using each corresponding aromatic aldehyde in the same method as in Reference Example 1-1.

The structures and spectral data thereof are shown in Tables 1 to 5.

TABLE 1

| Ref. No | Str. | Chemical name | P.D. |
|---|---|---|---|
| 1-2 | MeO—[benzene ring]—Me with CH=CH—NO$_2$ | (E)-4-methoxy-2-methyl-1-(2-nitrovinyl)benzene | $^1$H-NMR (400 MHz, CDCl$_3$) δ 2.47 (3H, s), 3.85 (3H, s), 6.77-6.81 (2H, m), 7.46-7.51 (2H, m), 8.27 (1H, d, J = 13.4 Hz). |
| 1-3 | MeO—[benzene ring]—F with CH=CH—NO$_2$ | (E)-2-fluoro-4-methoxy-1-(2-nitrovinyl)benzene | $^1$H-NMR (400 MHz, CDCl$_3$) δ 3.87 (3H, s), 6.71 (1H, dd, J = 12.1, 2.4 Hz), 6.78 (1H, dd, J = 8.5, 2.4 Hz), 7.43 (1H, t, J = 8.5 Hz), 7.66 (1H, d, J = 13.9 Hz), 8.02 (1H, d, J = 13.9 Hz). |
| 1-4 | MeO—[benzene ring]—Cl with CH=CH—NO$_2$ | (E)-2-chloro-4-methoxy-1-(2-nitrovinyl)benzene | $^1$H-NMR (400 MHz, CDCl$_3$) δ 3.87 (3H, s), 6.87 (1H, dd, J = 8.5, 2.4 Hz), 7.02 (1H, d, J = 2.4 Hz), 7.53 (1H, d, J = 8.5 Hz), 7.56 (1H, d, J = 13.9 Hz), 8.38 (1H, d, J = 13.9 Hz). |

TABLE 1-continued

| Ref. No | Str. | Chemical name | P.D. |
|---|---|---|---|
| 1-5 | (structure) | (E)-1,3-difluoro-5-methoxy-2-(2-nitrovinyl)benzene | ¹H-NMR (400 MHz, CDCl₃) δ 3.87 (3H, s), 6.54-6.59 (2H, m), 7.77 (1H, d, J = 13.4 Hz), 8.11 (1H, d, J = 13.4 Hz). |

TABLE 2

| Ref. No | Str. | Chemical name | P.D. |
|---|---|---|---|
| 1-6 | (structure) | (E)-1,4-difluoro-2-methoxy-5-(2-nitrovinyl)benzene | ¹H-NMR (400 MHz, CDCl₃) δ 3.95 (3H, s), 6.79 (1H, dd, J = 11.0, 6.7 Hz), 7.21 (1H, dd, J = 11.0, 6.7 Hz), 7.61 (1H, d, J = 13.4 Hz), 7.98 (1H, d, J = 13.4 Hz). |
| 1-7 | (structure) | (E)-1,3-difluoro-2-methoxy-5-(2-nitrovinyl)benzene | ¹H-NMR (400 MHz, CDCl₃) δ 4.10 (3H, t, J = 1.8 Hz), 7.07-7.15 (2H, m), 7.46 (1H, d, J = 13.4 Hz), 7.84 (1H, d, J = 13.4 Hz). |
| 1-8 | (structure) | (E)-5-(2-nitrovinyl)-2,3-dihydrobenzofuran | ¹H-NMR (400 MHz, CDCl₃) δ 3.26 (2H, t, J = 8.8 Hz), 4.67 (2H, t, J = 8.8 Hz), 6.84 (1H, d, J = 8.3 Hz) 7.35 (1H, d, J = 8.3 Hz), 7.41 (1H, s), 7.51 (1H, d, J = 13.4 Hz), 7.97 (1H, d, J = 13.4 Hz). |
| 1-9 | (structure) | (E)-6-fluoro-5-(2-nitrovinyl)-2,3-dihydrobenzofuran | ¹H-NMR (400 MHz, CDCl₃) δ 3.23 (2H, t, J = 8.9 Hz), 4.72 (2H, t, J = 8.9 Hz), 6.60 (1H, d, J = 11.6 Hz) 7.30 (1H, d, J = 6.7 Hz), 7.62 (1H, d, J = 13.4 Hz), 8.03 (1H, d, J = 13.4 Hz). |
| 1-10 | (structure) | (E)-6-fluoro-5-(2-nitrovinyl)chromane | ¹H-NMR (400 MHz, CDCl₃) δ 2.00-2.05 (2H, m), 2.77 (2H, t, J = 6.4 Hz), 4.24 (2H, t, J = 5.5 Hz), 6.59 (1H, d, J = 11.6 Hz) 7.17 (1H, d, J = 8.6 Hz), 7.64 (1H, d, J = 13.4 Hz), 7.97 (1H, d, J = 13.4 Hz). |
| 1-11 | (structure) | (E)-3-fluoro-5-methoxy-2-(2-nitrovinyl)pyridine | ¹H-NMR (400 MHz, CDCl₃) δ 3.93 (3H, s), 6.98 (1H, dd, J = 11.0, 2.4 Hz) 7.93 (1H, d, J = 13.4 Hz), 8.13 (1H, d, J = 13.4 Hz), 8.22 (1H, d, J = 2.4 Hz). |

TABLE 3

| Ref. No | Str. | Chemical name | P.D. |
|---|---|---|---|
| 1-12 | (structure) | (E)-3,5-difluoro-4-(2-nitrovinyl)phenol | ¹H-NMR (400 MHz, CDCl₃) δ 6.49-6.55 (2H, m), 7.76 (1H, d, J = 14.1 Hz), 8.10 (1H, d, J = 14.1 Hz). |

TABLE 3-continued

| Ref. No | Str. | Chemical name | P.D. |
|---|---|---|---|
| 1-13 | (structure: 4-MeS-C6H4-CH=CH-NO2) | (E)-methyl (4-(2-nitrovinyl) phenyl) sulfane | $^1$H-NMR (400 MHz, CDCl$_3$) δ 2.53 (3H, s), 7.27 (2H, d, J = 8.5 Hz), 7.45 (2H, d, J = 8.5 Hz), 7.57 (1H, d, J = 13.3 Hz), 7.97 (1H, d, J = 13.3 Hz). |
| 1-14 | (structure: 5-MeO-thiophen-2-yl-CH=CH-NO2) | (E)-2-methoxy-5-(2-nitrovinyl) thiophene | $^1$H-NMR (400 MHz, CDCl$_3$) δ 3.98 (3H, s), 6.27 (1H, d, J = 4.2 Hz), 7.19 (1H, d, J = 4.2 Hz), 7.26 (1H, d, J = 13.3 Hz), 8.03 (1H, d, J = 13.3 Hz). |
| 1-15 | (structure: 4-F2HCO-C6H4-CH=CH-NO2) | (E)-1-(difluoro-methoxy)-4-(2-nitrovinyl) benzene | $^1$H-NMR (400 MHz, CDCl$_3$) δ 6.59 (1H, t, J = 73.0 Hz), 7.20 (2H, d, J = 8.5 Hz), 7.53-7.59 (3H, m), 7.99 (1H, d, J = 13.3 Hz). |
| 1-16 | (structure: 5-ethyl-2,6-difluorophenyl-CH=CH-NO2) | (E)-5-ethyl-1,3-difluoro-2-(2-nitrovinyl) benzene | $^1$H-NMR (400 MHz, CDCl$_3$) δ 1.26 (3H, t, J = 7.6 Hz), 2.69 (2H, q, J = 7.6 Hz), 6.86 (2H, d, J = 9.8 Hz), 7.82 (1H, d, J = 13.4 Hz), 8.13 (1H, d, J = 13.4 Hz). |

TABLE 4

| Ref. No. | Str. | Chemical name | P.D |
|---|---|---|---|
| 1-17 | (structure: 5-(difluoromethoxy)-2,6-difluorophenyl-CH=CH-NO2) | (E)-5-(difluoro-methoxy)-1,3-difluoro-2-(2-nitrovinyl) benzene | $^1$H-NMR (400 MHz, CDCl$_3$) δ 6.60 (1H, t, J = 71.5 Hz), 6.82-6.87 (2H, m), 7.81 (1H, d, J = 13.9 Hz), 8.09 (1H, d, J = 13.9 Hz). |
| 1-18 | (structure: 5-ethoxy-2,6-difluorophenyl-CH=CH-NO2) | (E)-5-ethoxy-1,3-difluoro-2-(2-nitrovinyl) benzene | $^1$H-NMR (400 MHz, CDCl$_3$) δ 1.45 (3H, t, J = 7.1 Hz), 4.07 (2H, q, J = 7.1 Hz), 6.54 (2H, d, J = 10.4 Hz), 7.76 (1H, d, J = 13.8 Hz), 8.11 (1H, d, J = 13.8 Hz). |
| 1-19 | (structure: 4-NMe2-2,6-difluorophenyl-CH=CH-NO2) | (E)-3,5-difluoro-N,N-dimethyl-4-(2-nitrovinyl) aniline | $^1$H-NMR (400 MHz, CDCl$_3$) δ 3.06 (6H, s), 6.22 (2H, d, J = 12.8 Hz), 7.71 (1H, d, J = 13.4 Hz), 8.13 (1H, d, J = 13.4 Hz). |
| 1-20 | (structure: 6-fluorobenzofuran-5-yl-CH=CH-NO2) | (E)-6-fluoro-5-(2-nitrovinyl) benzofuran | $^1$H-NMR (400 MHz, CDCl$_3$) δ 6.81-6.82 (1H, m), 7.35 (1H, d, J = 11.0 Hz), 7.69-7.79 (3H, m), 8.17 (1H, d, J = 14.1 Hz). |
| 1-21 | (structure: 6-MeO-pyridin-3-yl-CH=CH-NO2) | (E)-2-methoxy-5-(2-nitrovinyl) pyridine | $^1$H-NMR (400 MHz, CDCl$_3$) δ 4.00 (3H, s), 6.83 (1H, d, J = 8.9 Hz), 7.53 (1H, d, J = 14.1 Hz), 7.76 (1H, dd, J = 8.9, 2.4 Hz), 7.98 (1H, d, J = 14.1 Hz), 8.35 (1H, d, J = 2.4 Hz). |

TABLE 4-continued

| Ref. No. | Str. | Chemical name | P.D |
|---|---|---|---|
| 1-22 | | (E)-N-(3,5-difluoro-4-(2-nitrovinyl)phenyl)acetamide | ¹H-NMR (400 MHz, CDCl₃) δ 2.22 (3H, s), 7.30 (2H, d, J = 10.4 Hz), 7.42 (1H, brs), 7.79 (1H, d, J = 13.8 Hz), 8.10 (1H, d, J = 13.8 Hz), |
| 1-23 | | (E)-[3,5-difluoro-4-(2-nitrovinyl)phenyl](methyl)carbamic acid t-butyl | ¹H-NMR (400 MHz, CDCl₃) δ 1.53 (9H, s), 3.31 (3H, s), 7.09 (2H, d, J = 11.0 Hz), 7.81 (1H, d, J = 14.1 Hz), 8.11 (1H, d, J = 14.1 Hz). |

TABLE 5

| Ref. No. | Str. | Chemical name | P.D |
|---|---|---|---|
| 1-24 | | (E)-4,6-difluoro-5-(2-nitrovinyl)-2,3-dihydrobenzofuran | ¹H-NMR (400 MHz, CDCl₃) δ 3.29 (2H, t, J = 8.9 Hz), 4.76 (2H, t, J = 8.9 Hz), 6.48 (1H, d, J = 10.4 Hz), 7.75 (1H, d, J = 14.1 Hz), 8.12 (1H, d, J = 14.1 Hz). |
| 1-25 | | (E)-tert-butyl {[6-fluoro-5-(2-nitrovinyl)-2,3-dihydro-1H-inden-1-yl]oxy}dimethylsilane | ¹H-NMR (400 MHz, CDCl₃) δ 0.16 (3H, s), 0.19 (3H, s), 0.95 (9H, s), 1.92-2.05 (1H, m), 2.45-2.52 (1H, m), 2.72-2.80 (1H, m), 2.96 (1H, dd, J = 15.6, 6.4 Hz), 5.22 (1H, t, J = 7.6 Hz), 7.07 (1H, d, J = 10.4 Hz), 7.32 (1H, d, J = 6.1 Hz), 7.70 (1H, d, J = 14.1 Hz), 8.05 (1H, d, J = 14.1 Hz). |
| 1-26 | | (E)-1-benzyl-6-fluoro-5-(2-nitrovinyl)indoline | ¹H-NMR (400 MHz, CDCl₃) δ 3.04 (2H, t, J = 8.5 Hz), 3.61 (2H, t, J = 8.5 Hz), 4.38 (2H, s), 6.16 (1H, d, J = 12.1 Hz), 7.09 (1H, d, J = 6.7 Hz), 7.25-7.38 (5H, m), 7.55 (1H, d, J = 13.9 Hz), 8.05 (1H, d, J = 13.9 Hz). |
| 1-27 | | (E)-3,5-difluoro-4-(2-nitrovinyl)pyridine | ¹H-NMR (400 MHz, CDCl₃) δ 7.90 (1H, d, J = 14.1 Hz), 8.06 (1H, d, J = 14.1 Hz), 8.52 (2H, s). |

Reference Example 2-1

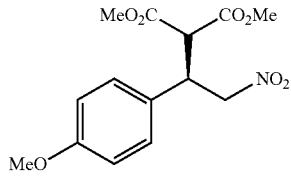 [SMILES: COC(=O)C(C(=O)OC)[C@@H](C[N+](=O)[O-])c1ccc(OC)nc1]

(−)-(R*)-2-[1-(4-Methoxyphenyl)-2-nitroethyl]malonic acid dimethyl ester

Malonic acid dimethyl ester (0.36 mL) and nickel(II) bis[(S,S)—N,N'-dibenzylcyclohexane-1,2-diamine]bromide (68 mg) were added to a solution of (E)-1-methoxy-4-(2-nitrovinyl)benzene (500 mg) in toluene (2.8 mL) under an argon atmosphere, and the mixture was stirred at room temperature for 6 hours. The solvent was removed under reduced pressure, and the residue was then purified by silica gel column chromatography (ethyl acetate:hexane=4:1), to obtain the title compound as a colorless liquid (865 mg).

$^1$H-NMR (400 MHz, CDCl$_3$) δ 3.57 (3H, s), 3.76 (3H, s), 3.78 (3H, s), 3.83 (1H, d, J=9.1 Hz), 4.16-4.22 (1H, m), 4.83 (1H, dd, J=12.7, 9.1 Hz), 4.89 (1H, dd, J=12.7, 5.1 Hz), 6.84 (2H, d, J=9.1 Hz), 7.14 (2H, d, J=9.1 Hz).

$[α]_D^{25}$=−20 (c 0.26, EtOH)

The following Reference Examples 2-2 to 2-28 were obtained using a corresponding nitrostyrene in the same method as in Reference Example 2-1.

The structures and spectral data thereof are shown in Tables 6 to 12.

TABLE 6

| Ref. No | Str. | Chemical name | P.D. |
|---|---|---|---|
| 2-2 | (structure) | (R*)-2-[1-(4-methoxy-2-methylphenyl)-2-nitroethyl] malonic acid dimethyl ester | $^1$H-NMR (400 MHz, DMSO-d$_6$) δ 2.40 (3H, s), 3.55 (3H, s), 3.76 (3H, s), 3.77 (3H, s), 3.80 (1H, J = 9.1 Hz), 4.47-4.53 (1H, m), 4.78-4.89 (2H, m), 6.69-6.72 (2H, m), 7.02-7.05 (1H, m). |
| 2-3 | (structure) | (R*)-2-[1-(2-chloro-4-methoxy-phenyl)-2-nitroethyl]malonic acid dimethyl ester | ($^1$H-NMR (400 MHz, CDCl$_3$) δ 3.64 (3H, s), 3.74 (3H, s), 3.78 (3H, s), 4.08 (1H, d, J = 9.7 Hz), 4.64-4.70 (1H, m), 4.92 (1H, dd, J = 13.4, 4.3 Hz), 5.07 (1H, dd, J = 13.4, 8.6 Hz), 6.77 (1H, dd, J = 8.6, 3.1 Hz), 6.94 (1H, d, J = 3.1 Hz), 7.14 (1H, d, J = 8.6 Hz). |
| 2-4 | (structure) | (R*)-2-[1-(2-fluoro-4-methoxyphenyl)-2-nitroethyl]malonic acid dimethyl ester | $^1$H-NMR (400 MHz, CDCl$_3$) δ 3.57 (3H, s), 3.77 (6H, s), 3.96 (1H, d, J = 9.7 Hz), 4.36 (1H, q, J = 9.7 Hz), 4.89 (2H, d, J = 6.7 Hz), 6.59-6.64 (2H, m), 7.11 (1H, t, J = 8.8 Hz). |
| 2-5 | (structure) | (R*)-2-[1-(3-fluoro-4-methoxyphenyl)-2-nitroethyl]malonic acid dimethyl ester | $^1$H-NMR (400 MHz, CDCl$_3$) δ 3.61 (3H, s), 3.77 (3H, s), 3.80 (1H, d, J = 9.2 Hz), 3.86 (3H, s), 4.14-4.20 (1H, m), 4.79-4.91 (2H, m), 6.87-6.99 (3H, m). |

TABLE 7

| Ref. No | Str. | Chemical name | P.D. |
|---|---|---|---|
| 2-6 | MeO₂C structure with 3,5-difluoro-4-methoxyphenyl, NO₂ | (R*)-2-[1-(3,5-difluoro-4-methoxyphenyl)-2-nitroethyl] malonic acid dimethyl ester | $^1$H-NMR (400 MHz, CDCl$_3$) δ 3.65 (3H, s), 3.76-3.79 (1H, m), 3.77 (3H, s), 3.98 (3H, s), 4.14-4.19 (1H, m), 4.79-4.91 (2H, m), 6.77-6.84 (2H, m). |
| 2-7 | MeO₂C structure with 2,5-difluoro-4-methoxyphenyl, NO₂ | (R*)-2-[1-(2,5-difluoro-4-methoxyphenyl)-2-nitroethyl] malonic acid dimethyl ester | $^1$H-NMR (400 MHz, CDCl$_3$) δ 3.61 (3H, s), 3.78 (3H, s), 3.86 (3H, s), 3.92 (1H, d, J = 9.8 Hz), 4.30-4.37 (1H, m), 4.83-4.91 (2H, m), 6.69 (1H, dd, J = 11.0, 7.3 Hz), 6.96 (1H, dd, J = 11.0, 7.3 Hz). |
| 2-8 | MeO₂C structure with 2,6-difluoro-4-methoxyphenyl, NO₂ | (-)-(R*)-2-[1-(2,6-difluoro-4-methoxyphenyl)-2-nitroethyl] malonic acid dimethyl ester | $^1$H-NMR (400 MHz, CDCl$_3$) δ 3.57 (3H, s), 3.77 (3H, s), 3.80 (3H, s), 3.93 (1H, d, J = 10.4 Hz), 4.63-4.70 (1H, m), 4.81 (1H, dd, J = 13.1, 10.1 Hz), 4.91 (1H, dd, J = 13.1, 4.7 Hz), 6.41-6.47 (2H, m). $[α]_D^{24}$ = -25 (c 0.11, EtOH) |
| 2-9 | MeO₂C structure with 2,3-dihydrobenzofuran-5-yl, NO₂ | (R*)-2-[1-(2,3-dihydrobenzofuran-5-yl)-2-nitroethyl] malonic acid dimethyl ester | $^1$H-NMR (400 MHz, CDCl$_3$) δ 3.17 (2H, t, J = 8.8 Hz), 3.59 (3H, s), 3.76 (3H, s), 3.81 (1H, d, J = 9.2 Hz), 4.14-4.20 (1H, m), 4.55 (2H, t, J 8.8 Hz), 4.78-4.90 (2H, m), 6.70 (1H, d, J = 7.9 Hz), 6.94 (1H, d, J = 7.9 Hz ), 7.05 (1H, s). |
| 2-10 | MeO₂C structure with 6-fluoro-2,3-dihydrobenzofuran-5-yl, NO₂ | (-)-(R*)-2-[1-(6-fluoro-2,3-dihydrobenzofuran-5-yl)-2-nitroethyl] malonic acid dimethyl ester | $^1$H-NMR (400 MHz, CDCl$_3$) δ 3.13 (2H, t, J = 8.9 Hz), 3.58 (3H, s), 3.77 (3H, s), 3.96 (1H, d, J = 9.8 Hz), 4.29-4.35 (1H, m), 4.59 (2H, t, J = 8.9 Hz), 4.87 (2H, d, J = 7.3 Hz), 6.48 (1H, d, J = 11.6 Hz), 6.99 (1H, d, J = 7.3 Hz). $[α]_D^{24}$ = -20 (c 0.31, EtOH) |

TABLE 8

| Ref. No | Str. | Chemical name | P.D. |
|---|---|---|---|
| 2-11 | MeO₂C structure with 7-fluorochroman-6-yl, NO₂ | (R*)-2-[1-(7-fluorochroman-6-yl)-2-nitroethyl]malonic acid dimethyl ester | $^1$H-NMR (400 MHz, CDCl$_3$) δ 1.92-1.98 (2H, m), 2.68 (2H, t, J = 6.4 Hz), 3.58 (3H, s), 3.77 (3H, s), 3.94 (1H, d, J = 9.8 Hz), 4.14 (2H, t, J = 4.9 Hz), 4.30 (1H, q, J = 7.3 Hz), 4.87 (2H, d, J = 7.3 Hz), 6.48 (1H, d, J = 12.2 Hz), 6.84 |

TABLE 8-continued

| Ref. No | Str. | Chemical name | P.D. |
|---|---|---|---|
| | | | (1H, d, J = 8.6 Hz). |
| 2-12 | MeO₂C, CO₂Me, N, NO₂, MeO, F | (S*)-2-[1-(3-fluoro-5-methoxypridin-2-yl)-2-nitroethyl] malonic acid dimethyl ester | ¹H-NMR (400 MHz, CDCl₃) δ 3.66 (3H, s), 3.76 (3H, s), 3.84 (3H, s), 3.98 (1H, d, J = 7.9 Hz), 4.62-4.67 (1H, m), 4.89 (1H, dd, J = 14.1, 4.3 Hz), 5.09 (1H, dd, J = 14.1, 9.5 Hz), 6.94 (1H, dd, J = 11.0, 2.4 Hz), 8.05 (1H, d, J = 2.4 Hz). |
| 2-13 | MeO₂C, CO₂Me, S, NO₂, MeO | (S*)-2-[1-(5-methoxythiophen-2-yl)-2-nitroethyl] malonic acid dimethyl ester | ¹H-NMR (400 MHz, CDCl₃) δ 3.70 (3H, s), 3.77 (3H, s), 3.84 (3H, s), 3.86 (1H, d, J = 7.9 Hz), 4.31-4.36 (1H, m), 4.81-4.89 (2H, m), 5.98 (1H, d, J = 4.2 Hz), 6.55 (1H, d, J = 4.2 Hz). |
| 2-14 | MeO₂C, CO₂Me, F, NO₂, HO, F | (R*)-2-[1-(2,6-difluoro-4-hydroxyphenyl)-2-nitroethyl] malonic acid dimethyl ester | ¹H-NMR (400 MHz, CDCl₃) δ 3.58 (3H, s), 3.80 (3H, s), 3.92 (1H, d, J = 10.4 Hz), 4.62-4.69 (1H, m), 4.80 (1H, dd, J = 12.8, 10.4 Hz), 4.91 (1H, dd, J = 12.8, 4.9 Hz), 5.79 (1H, brs), 6.35-6.41 (2H, m). |
| 2-15 | MeO₂C, CO₂Me, NO₂, MeS | (R*)-2-[1-(4-(methylthio)phenyl)-2-nitroethyl]malonic acid dimethyl ester | ¹H-NMR (400 MHz, CDCl₃) δ 2.45 (3H, s), 3.59 (3H, s), 3.76 (3H, s), 3.83 (1H, d, J = 9.1 Hz), 4.17-4.23 (1H, m), 4.81-4.92 (2H, m), 7.14 (2H, d, J = 8.5 Hz), 7.18 (2H, d, J = 8.5 Hz). |

TABLE 9

| Ref. No | Str. | Chemical name | P.D. |
|---|---|---|---|
| 2-16 | MeO₂C, CO₂Me, NO₂, Me, MeO | 2-[(1R*)-1-(4-methoxyphenyl)-2-nitropropyl] malonic acid dimethyl ester | ¹H-NMR (400 MHz, CDCl₃) δ 1.35 (0.6H, d, J = 6.7 Hz), 1.42 (2.4H, d, J = 6.7 Hz), 3.40-3.52 (6H, m), 3.72-4.41 (5H, m), 5.01-5.15 (1H, m), 6.80-7.40 (4H, m). |
| 2-17 | MeO₂C, CO₂Me, F, NO₂, H₃C, F | (R*)-2-[1-(4-ethyl-2,6-difluorophenyl)-2-nitroethyl]malonic acid dimethyl ester | ¹H-NMR (400 MHz, CDCl₃) δ 1.20 (3H, t, J = 7.6 Hz), 2.60 (2H, q, J = 7.6 Hz), 3.55 (3H, s), 3.80 (3H, s), 3.95 (1H, d, J = 10.4 Hz), 4.68-4.75 (1H, m), 4.84 (1H, dd, J = 13.4, 9.8 Hz), 4.93 (1H, dd, J = 13.4, 4.9 Hz), 6.73 (2H, dd, J = 14.1, 4.3 Hz). |

TABLE 10

| Ref. No. | Str. | Chemical name | P.D |
|---|---|---|---|
| 2-18 | (structure: 4-(difluoromethoxy)-2,6-difluorophenyl with MeO₂C, CO₂Me, NO₂ substituents) | (R*)-2-{1-[4-(difluoromethoxy)-2,6-difluorophenyl]-2-nitroethyl}malonic acid dimethyl ester | $^1$H-NMR (400 MHz, CDCl$_3$) δ 3.58 (3H, s), 3.81 (3H, s), 3.93 (1H, d, J = 10.3 Hz), 4.71 (1H, dt, J = 10.3, 4.2 Hz), 4.82 (1H, dd, J = 13.3, 10.3 Hz), 4.93 (1H, dd, J = 13.3, 4.2 Hz), 6.50 (1H, t, J = 72.6 Hz), 6.69-6.74 (2H, m). |
| 2-19 | (structure: 4-ethoxy-2,6-difluorophenyl) | (R*)-2-[1-(4-ethoxy-2,6-difluorophenyl)-2-nitroethyl]malonic acid dimethyl ester | $^1$H-NMR (400 MHz, CDCl$_3$) δ 1.40 (3H, t, J = 7.1 Hz), 3.57 (3H, s), 3.80 (3H, s), 3.92 (1H, d, J = 10.2 Hz), 3.96 (2H, q, J = 7.1 Hz), 4.66 (1H, td, J = 10.2, 4.8 Hz), 4.81 (1H, dd, J = 13.0, 10.2 Hz), 4.91 (1H, dd, J = 13.0, 4.8 Hz), 6.39-6.45 (2H, m). |
| 2-20 | (structure: 4-(dimethylamino)-2,6-difluorophenyl) | (R*)-2-{1-[4-(dimethylamino)-2,6-difluorophenyl]-2-nitroethyl}malonic acid dimethyl ester | $^1$H-NMR (400 MHz, CDCl$_3$) δ 2.92 (6H, s), 3.57 (3H, s), 3.79 (3H, s), 3.92 (1H, d, J = 10.4 Hz), 4.62 (1H, td, J = 10.4, 5.1 Hz), 4.80 (1H, t, J = 11.3 Hz), 4.89 (1H, dd, J = 12.8, 4.9 Hz), 6.13 (2H, d, J = 12.8 Hz). |
| 2-21 | (structure: 6-fluorobenzofuran-5-yl) | (R*)-2-[1-(6-fluorobenzofuran-5-yl)-2-nitroethyl]malonic acid dimethyl ester | $^1$H-NMR (400 MHz, CDCl$_3$) δ 3.54 (3H, s), 3.78 (3H, s), 4.06 (1H, d, J = 9.8 Hz), 4.49-4.55 (1H, m), 4.95 (1H, dd, J = 13.2, 5.2 Hz), 4.99 (1H, dd, J = 13.2, 8.9 Hz), 6.71-6.72 (1H, m), 7.25 (1H, d, J = 12.8 Hz), 7.44 (1H, d, J = 7.3 Hz), 7.61 (1H, d, J = 2.4 Hz) |

TABLE 11

| Ref. No. | Str. | Chemical name | P.D |
|---|---|---|---|
| 2-22 | (structure: 6-methoxypyridin-3-yl) | (R*)-2-[1-(6-methoxypyridin-3-yl)-2-nitroethyl]malonic acid dimethyl ester | $^1$H-NMR (400 MHz, CDCl$_3$) δ 3.62 (3H, s), 3.78 (3H, s), 3.83 (1H, d, J = 9.2 Hz), 3.91 (3H, s), 4.17-4.23 (1H, m), 4.80-4.93 (2H, m), 6.71 (1H, d, J = 8.6 Hz), 7.47 (1H, dd, J = 8.6, 2.4 Hz), 8.05 (1H, d, J = 2.4 Hz). |
| 2-23 | (structure: 4-acetamide-2,6-difluorophenyl) | (R*)-2-[1-(4-acetamide-2,6-difluorophenyl)-2-nitroethyl]malonic acid dimethyl ester | $^1$H-NMR (400 MHz, CDCl$_3$) δ 2.18 (3H, s), 3.57 (3H, s), 3.80 (3H, s), 3.94 (1H, d, J = 10.4 Hz), 4.66-4.73 (1H, m), 4.82 (1H, dd, J = 13.1, 10.1 Hz), 4.92 (1H, dd, J = 13.1, 4.9 Hz), 7.16 (2H, d, J = 10.2 Hz), 7.25 (1H, brs), |

TABLE 11-continued

| Ref. No. | Str. | Chemical name | P.D |
|---|---|---|---|
| 2-24 | | (R*)-2-(1-{4-[(tert-butoxy-carbonyl)(methyl)amino]-2,6-difluoro-phenyl}-2-nitro-ethyl)malonic acid dimethyl ester | ¹H-NMR (400 MHz, CDCl₃) δ 1.48 (9H, s), 3.23 (3H, s), 3.58 (3H, s), 3.80 (3H, s), 3.94 (1H, d, J = 10.4 Hz), 4.67-4.75 (1H, m), 4.83 (1H, dd, J = 13.4, 9.8 Hz), 4.93 (1H, dd, J = 13.4, 4.9 Hz), 6.92 (2H, d, J = 10.4 Hz). |
| 2-25 | | (R*)-2-[1-(4,6-difluoro-2,3-dihydrobenzo-furan-5-yl)-2-nitroethyl] malonic acid dimethyl ester | ¹H-NMR (400 MHz, CDCl₃) δ 3.20 (2H, t, J = 8.6 Hz), 3.58 (3H, s), 3.80 (3H, s), 3.92 (1H, d, J = 11.0 Hz), 4.62-4.69 (3H, m), 4.80 (1H, dd, J = 12.8, 9.8 Hz), 4.90 (1H, dd, J = 12.8, 4.9 Hz), 6.34 (1H, d, J = 9.8 Hz). |

TABLE 12

| Ref. No. | Str. | Chemical name | P.D |
|---|---|---|---|
| 2-26 | | 2-((1R*)-1-{1-[(tert-butyldi-methylsilyl)oxy]-6-fluoro-2,3-dihydro-1H-inden-5-yl}-2-nitroethyl) malonic acid dimethyl ester | ¹H-NMR (400 MHz, CDCl₃) δ 0.14 (3H, s), 0.16 (3H, s), 0.94 (9H, d, J = 1.2 Hz), 1.85-1.95 (1H, m), 2.39-2.46 (1H, m), 2.64-2.72 (1H, m), 2.84-2.90 (1H, m), 3.50 (1.5H, s), 3.60 (1.5H, s), 3.76 (1.5H, s), 3.77 (1.5H, s), 3.98 (1H, dd, J = 9.8, 4.9 Hz), 4.36-4.45 (1H, m), 4.87-4.97 (2H, m), 5.15-5.19 (1H, m), 6.93-6.97 (1H, m), 7.01-7.04 (1H, m). |
| 2-27 | | (R*)-2-[1-(1-benzyl-6-fluoro-indolin-5-yl)-2-nitroethyl] malonic acid dimethyl ester | ¹H-NMR (400 MHz, CDCl₃) δ 2.89 (2H, t, J = 8.5 Hz), 3.37 (2H, t, J = 8.5 Hz), 3.60 (3H, s), 3.76 (3H, s), 3.93 (1H, d, J = 9.7 Hz), 4.20 (2H, s), 4.28 (1H, dt, J = 9.7, 7.3 Hz), 4.85 (2H, d, J = 7.3 Hz), 6.11 (1H, d, J = 12.1 Hz), 6.82 (1H, d, J = 7.2 Hz), 7.28-7.36 (5H, m). |
| 2-28 | | (R*)-2-[1-(3,5-difluoropyridin-4-yl)-2-nitroethyl]malonic acid dimethyl ester | ¹H-NMR (400 MHz, CDCl₃) δ 3.60 (3H, s), 3.83 (3H, s), 3.96 (1H, d, J = 9.8 Hz), 4.76 (1H, td, J = 9.9, 4.5 Hz), 4.88 (1H, dd, J = 13.8, 10.1 Hz), 4.97 (1H, dd, J = 13.8, 4.6 Hz), 8.36 (2H, s). |

Reference Example 3-1

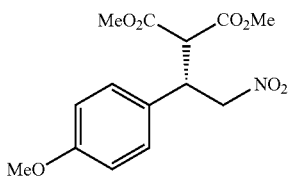

(+)-(S*)-2-[1-(4-Methoxyphenyl)-2-nitroethyl]malonic acid dimethyl ester

Nickel (II) bis[(R,R)—N,N'-dibenzylcyclohexane-1,2-diamine]bromide was used as a catalyst in place of nickel(II) bis[(S,S)—N,N'-dibenzylcyclohexane-1,2-diamine]bromide, and the same method as in Reference Example 2-1 was performed to obtain the title compound.

$^1$H-NMR (400 MHz, CDCl$_3$) δ 3.57 (3H, s), 3.76 (3H, s), 3.78 (3H, s), 3.83 (1H, d, J=9.1 Hz), 4.16-4.22 (1H, m), 4.83 (1H, dd, J=12.7, 9.1 Hz), 4.89 (1H, dd, J=12.7, 5.1 Hz), 6.84 (2H, d, J=9.1 Hz), 7.14 (2H, d, J=9.1 Hz).

$[α]_D^{25}$=+14 (c 0.26, EtOH)

The same method as in Reference Example 3-1 was performed using a corresponding nitrostyrene to obtain the following Reference Examples 3-2 to 3-8.

The structures and spectral data thereof are shown in Tables 13 to 14.

TABLE 13

| Ref. No | Str. | Chemical name | P.D. |
|---|---|---|---|
| 3-2 | MeO$_2$C, CO$_2$Me, phenyl, NO$_2$ | (S*)-2-(2-nitro-1-phenylethyl]malonic acid dimethyl ester | $^1$H-NMR (400 MHz, CDCl$_3$) δ 3.57 (3H, s), 3.76 (3H, s), 3.87 (1H, d, J = 8.5 Hz), 4.22-4.28 (1H, m), 4.85-4.95 (2H, m), 7.22-7.35 (5H, m). |
| 3-3 | MeO$_2$C, CO$_2$Me, 3-OMe-phenyl, NO$_2$ | (S*)-2-[1-(3-methoxyphenyl)-2-nitroethyl]malonic acid dimethyl ester | $^1$H-NMR (400 MHz, CDCl$_3$) δ 3.60 (3H, s), 3.76 (3H, s), 3.78 (3H, s), 3.86 (1H, d, J = 9.1 Hz), 4.18-4.25 (1H, m), 4.84-4.94 (2H, m), 6.75-6.83 (3H, m), 7.23 (1H, t, J = 7.9 Hz). |
| 3-4 | MeO$_2$C, CO$_2$Me, 2-OMe-phenyl, NO$_2$ | (S*)-2-[1-(2-methoxyphenyl)-2-nitroethyl]malonic acid dimethyl ester | $^1$H-NMR (400 MHz, CDCl$_3$) δ 3.49 (3H, s), 3.73 (3H, s), 3.85 (3H, s), 4.16 (1H, d, J = 9.6 Hz), 4.34-4.41 (1H, m), 4.86 (1H, dd, J = 13.0, 4.8 Hz), 5.01 (1H, dd, J = 13.0, 9.6 Hz), 6.84-6.88 (2H, m), 7.12 (1H, dd, J = 7.6, 1.8 Hz), 7.21-7.26 (1H, m). |
| 3-5 | MeO$_2$C, CO$_2$Me, 2,6-difluoro-4-methoxyphenyl, NO$_2$ | (+)-(S*)-2-[1-(2,6-difluoro-4-methoxyphenyl)-2-nitroethyl]malonic acid dimethyl ester | $^1$H-NMR (400 MHz, CDCl$_3$) δ 3.57 (3H, s), 3.77 (3H, s), 3.80 (3H, s), 3.93 (1H, d, J = 10.4 Hz), 4.63-4.70 (1H, m), 4.81 (1H, dd, J = 13.1, 10.1 Hz), 4.91 (1H, dd, J = 13.1, 4.7 Hz), 6.41-6.47 (2H, m). $[α]_D^{24}$ = +15 (c 0.07, EtOH) |
| 3-6 | MeO$_2$C, CO$_2$Me, 5-methoxythiophen-2-yl, NO$_2$ | (R*)-2-[1-(5-methoxythiophen-2-yl)-2-nitroethyl]malonic acid dimethyl ester | $^1$H-NMR (400 MHz, CDCl$_3$) δ 3.70 (3H, s), 3.77 (3H, s), 3.84 (3H, s), 3.86 (1H, d, J = 7.9 Hz), 4.31-4.36 (1H, m), 4.81-4.89 (2H, m), 5.98 (1H, d, J = 4.2 Hz), 6.55 (1H, d, J = 4-2 Hz). |

TABLE 14

| Ref. No | Str. | Chemical name | P.D. |
|---|---|---|---|
| 3-7 | (structure: MeO-phenyl with CH(CH(CO2Me)2)-CH(Me)-NO2) | 2-[(1S*)-1-(4-methoxyphenyl)-2-nitropropyl] malonic acid dimethyl ester | $^1$H-NMR (400 MHz, CDCl$_3$) δ 1.35 (0.6H, d, J = 6.7 Hz), 1.42 (2.4H, d, J = 6.7 Hz), 3.40-3.52 (6H, m), 3.72-4.41 (5H, m), 5.01-5.15 (1H, m), 6.80-7.40 (4H, m). |
| 3-8 | (structure: F2HCO-phenyl with CH(CH(CO2Me)2)-CH2-NO2) | (S*)-2-[1-(4-difluoromethoxy)phenyl)-2-nitroethyl]malonic acid dimethyl ester | $^1$H-NMR (400 MHz, CDCl$_3$) δ 3.59 (3H, s), 3.77 (3H, s), 3.83 (1H, d, J = 9.1 Hz), 4.22-4.28 (1H, m), 4.82-4.94 (2H, m), 6.49 (1H, t, J = 73.6 Hz), 7.08 (2H, d, J = 8.5 Hz), 7.24 (2H, d, J = 8.5 Hz). |

Reference Example 4-1

[Chemical Formula 45]

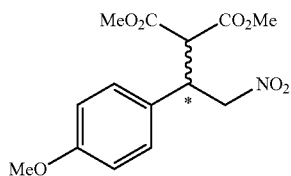

(±)-2-[1-(4-Methoxyphenyl)-2-nitroethyl]malonic acid dimethyl ester

The same method as in Reference Example 2-1 was performed using (±)-Nickel(II) bis[N,N'-dibenzylcyclohexane-1,2-diamine]bromide as a catalyst in place of nickel (II) bis[(S,S)—N,N'-dibenzylcyclohexane-1,2-diamine]bromide to obtain the title compound.

$^1$H-NMR (400 MHz, CDCl$_3$) δ 3.57 (3H, s), 3.76 (3H, s), 3.78 (3H, s), 3.83 (1H, d, J=9.1 Hz), 4.16-4.22 (1H, m), 4.83 (1H, dd, J=12.7, 9.1 Hz), 4.89 (1H, dd, J=12.7, 5.1 Hz), 6.84 (2H, d, J=9.1 Hz), 7.14 (2H, d, J=9.1 Hz).

Reference Example 5-1

[Chemical Formula 46]

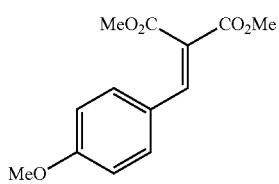

2-(4-Methoxybenzylidene)malonic acid dimethyl ester

Piperidine (0.4 mL) and acetic acid (0.47 mL) were added to a solution of p-anisaldehyde (5.0 mL) and malonic acid dimethyl ester (4.7 mL) in benzene (0.9 mL) under an argon atmosphere, to produce a reaction solution. The reaction solution was heated to reflux with a Dean-Stark apparatus for 3 hours. Ethyl acetate was added to the reaction solution, and the mixture was washed with a 1 mol/L hydrochloric acid, a saturated aqueous sodium hydrogen carbonate solution, and a brine successively, and dried over anhydrous sodium sulfate. The solvent was removed under reduced pressure, and the residue was then purified by silica gel column chromatography (ethyl acetate:hexane=4:1), to obtain the title compound as a white solid (9.5 g).

$^1$H-NMR (400 MHz, CDCl$_3$) δ 3.83 (3H, s), 3.84 (3H, s), 3.87 (3H, s), 6.90 (2H, d, J=8.6 Hz), 7.39 (2H, d, J=8.6 Hz), 7.71 (s, 1H).

Reference Example 6-1

[Chemical Formula 47]

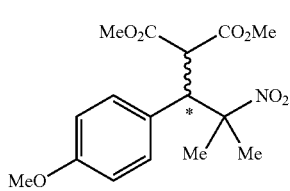

(±)-2-[1-(4-Methoxyphenyl)-2-methyl-2-nitropropyl] malonic acid dimethyl ester

2-Nitropropane (0.14 mL) and potassium fluoride supported on alumina (KF/Al$_2$O$_3$) (400 mg) were added to a solution of 2-(4-methoxybenzylidene)malonic acid dimethyl ester (250 mg) in dimethyl sulfoxide (0.8 mL) under an argon atmosphere, to produce a reaction solution. The reaction solution was stirred at room temperature for 1 hour and a half. Diethyl ether was added to the reaction solution, the insoluble was removed by filtration, and the solution was washed with water and a brine successively, and dried over anhydrous sodium sulfate. The solvent was removed under reduced pressure, and the residue was then purified by silica gel column chromatography (ethyl acetate:hexane=4:1), to obtain the title compound as a white solid (298 mg).

$^1$H-NMR (400 MHz, CDCl$_3$) δ 1.43 (3H, s), 1.64 (3H, s), 3.35 (3H, s), 3.75 (3H, s), 3.78 (3H, s), 4.22 (2H, s), 6.81 (2H, d, J=9.1 Hz), 7.10 (2H, d, J=9.1 Hz).

Reference Example 6-2

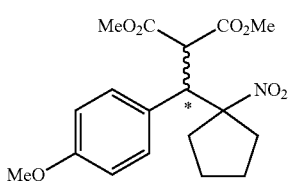

(±)-2-[(4-Methoxyphenyl)-(1-nitrocyclopentyl)methyl]malonic acid dimethyl ester

The same method as in Reference Example 6-1 was performed using nitrocyclopentane in place of 2-nitropropane to obtain the title compound.

1H-NMR (400 MHz, CDCl3) δ1.43-1.86 (6H, m), 2.33-2.42 (1H, m), 2.45-2.53 (1H, m), 3.35 (3H, s), 3.77 (3H, s), 3.80 (3H, s), 4.14 (1H, d, J=11.5 Hz), 4.31 (1H, d, J=11.5 Hz), 6.80 (2H, d, J=8.5 Hz), 7.04 (2H, d, J=9.1 Hz).

Reference Example 6-3

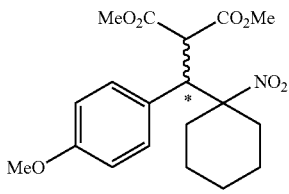

(±)-2-[(4-Methoxyphenyl)-(1-nitrocyclohexyl)methyl]malonic acid dimethyl ester

The same method as in Reference Example 6-1 was performed using nitrocyclohexane in place of 2-nitropropane to obtain the title compound.

$^1$H-NMR (400 MHz, CDCl$_3$) δ1.10-1.17 (2H, m), 1.22-1.68 (6H, m), 2.35-2.44 (2H, m), 3.28 (3H, s), 3.78 (3H, s), 3.79 (3H, s), 3.94 (1H, d, J=10.9 Hz), 4.32 (1H, d, J=10.9 Hz), 6.79 (2H, d, J=7.9 Hz), 7.02 (2H, brd, J=7.9 Hz).

Reference Example 7-1

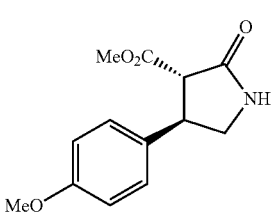

(−)-(3S*,4R*)-4-(4-Methoxyphenyl)-2-oxopyrrolidine-3-carboxylic acid methyl ester Nickel(II) chloride hexahydrate (1.3 g) was added to a solution of (R*)-2-[1-(4-methoxyphenyl)-2-nitroethyl]malonic acid dimethyl ester (1.7 g) in methanol (110 mL) under an argon atmosphere, to produce a reaction solution. To the reaction solution, sodium borohydride (1.03 g) was added in several doses under ice-cooling, and the reaction solution was warmed to room temperature, and stirred for 2 hours. A saturated aqueous ammonium chloride solution and ethyl acetate were added to the reaction solution, and the mixture was stirred at room temperature for 1 hour. The mixture was extracted with ethyl acetate, and the extract was washed with water and a brine successively, and dried over anhydrous sodium sulfate. The solvent was removed under reduced pressure, and the crude product was washed with ethanol-diisopropyl ether, to obtain the title compound as a white solid (840 mg).

$^1$H-NMR (400 MHz, CDCl$_3$) δ 3.40 (1H, t, J=9.1 Hz), 3.53 (1H, d, J=9.7 Hz), 3.76-3.81 (1H, m), 3.78 (3H, s), 3.80 (3H, s), 4.08 (1H, q, J=8.9 Hz), 5.85 (1H, brs), 6.88 (2H, d, J=8.5 Hz), 7.18 (2H, d, J=8.5 Hz).

$[α]_D^{25}$=−96 (c 0.19, EtOH)

The same method as in Reference Example 7-1 was performed using a corresponding nitro substance to obtain the following Reference Examples 7-2 to 7-42. The structures and spectral data thereof are shown in Tables 15 to 25.

TABLE 15

| Ref. No | Str. | Chemical name | P.D. |
| --- | --- | --- | --- |
| 7-2 | | (3S*,4R-)-4-(3-fluoro-4-methoxyphenyl)-2-oxopyrrolidine-3-carboxylic acid methyl ester | $^1$H-NMR (400 MHz, CDCl$_3$) δ 3.38 (1H, t, J = 8.9 Hz), 3.50 (1H, d, J = 9.8 Hz), 3.76-3.81 (1H, m), 3.79 (3H, s), 3.88 (3H, s), 4.06 (1H, q, J = 8.8 Hz), 5.94 (1H, brs), 6.90-7.01 (3H, m). |

TABLE 16

| Ref. No | Str. | Chemical name | P.D. |
|---|---|---|---|
| 7-3 | | (3S*,4R*)-4-(2-fluoro-4-methoxyphenyl)-2-oxopyrrolidine-3-carboxylic acid methyl ester | $^1$H-NMR (400 MHz, CDCl$_3$) δ 3.44 (1H, dd, J = 9.7, 7.9 Hz), 3.68 (1H, d, J = 9.7 Hz), 3.75-3.79 (1H, m), 3.78 (3H, s), 3.79 (3H, s) 4.22 (1H, q, J = 8.9 Hz), 6.15 (1H, s), 6.62-6.68 (2H, m), 7.15 (1H, t, J = 8.5 Hz). |
| 7-4 | | (3S*,4R*)-4-(2-chloro-4-methoxyphenyl)-2-oxopyrrolidine-3-carboxylic acid methyl ester | $^1$H-NMR (400 MHz, CDCl$_3$) δ 3.35-3.41 (1H, m), 3.67 (1H, d, J = 8.6 Hz), 3.79 (3H, s), 3.80 (3H, s), 3.89 (1H, t, J = 8.6 Hz), 4.47 (1H, q, J = 7.9 Hz), 5.70 (1H, brs), 6.82 (1H, dd, J = 8.6, 2.4 Hz), 6.95 (1H, d, J = 2.4Hz), 7.20 (2H, t, J = 8.6 Hz). |
| 7-5 | | (3S',4R*)-4-(4-methoxy-2-methylphenyl)-2-oxopyrrolidine-3-carboxylic acid methyl ester | $^1$H-NMR (400 MHz, DMSO-d$_6$) δ 2.36 (3H, s), 3.29-3.36 (1H, m), 3.57 (1H, d, J = 9.1 Hz), 3.76-3.81 (1H, m), 3.77 (3H, s), 3.78 (3H, s), 4.31 (1H, q, J = 8.4 Hz), 6.09 (1H, brs), 6.73 (1H, d, J = 3.0 Hz), 6.76 (1H, dd, J = 8.5, 3.0 Hz), 7.17 (1H, d, J = 8.5 Hz). |
| 7-6 | | (3S*,4R*)-4-(3,5-difluoro-4-methoxyphenyl)-2-oxopyrrolidine-3-carboxylic acid methyl ester | $^1$H-NMR (400 MHz, CDCl$_3$) δ 3.37 (1H, t, J = 8.6 Hz), 3.47 (1H, d, J = 9.8 Hz), 3.77-3.81 (1H, m), 3.81 (3H, s), 3.98 (3H, s) 4.05 (1H, q, J = 8.8 Hz), 5.69 (1H, brs), 6.78-6.85 (2H, m). |
| 7-7 | | (3S*,4R*)-4-(2,5-difluoro-4-methoxyphenyl)-2-oxopyrrolidine-3-carboxylic acid methyl ester | $^1$H-NMR (400 MHz, CDCl$_3$) δ 3.42 (1H, t, J = 8.9 Hz), 3.62 (1H, d, J = 9.8 Hz), 3.75-3.81 (1H, m), 3.79 (3H, s), 3.87 (3H, s) 4.20 (1H, q, J = 8.9 Hz], 6.14 (1H, brs) 6.71 (1H, dd, J = 11.0, 7.3 Hz), 6.98 (1H, dd, J = 11.0, 7.3 Hz). |

TABLE 17

| Ref. No | Str. | Chemical name | P.D. |
|---|---|---|---|
| 7-8 | | (-)-(3S*,4R*)-4-(2,6-difluoro-4-methoxyphenyl)-2-oxopyrrolidine-3-carboxylic acid methyl ester | $^1$H-NMR (400 MHz, CDCl$_3$) δ 3.51 (1H, t, J = 9.2 Hz), 3.64-3.70 (1H, m), 3.78 (6H, s), 3.78-3.81 (1H, m), 4.46 (1H, q, J = 9.4 Hz), 6.24 (1H, brs), 6.43-6.50 (2H, m). [α]$_D^{23}$ = -120 (c 0.11, EtOH) |

TABLE 17-continued

| Ref. No | Str. | Chemical name | P.D. |
|---|---|---|---|
| 7-9 | | (3S*,4R*)-4-(2,3-dihydrobenzofuran-5-yl)-2-oxopyrrolidine-3-carboxylic acid methyl ester | $^1$H-NMR (400 MHz, CDCl$_3$) δ 3.20 (2H, t, J = 8.8 Hz), 3.38 (1H, t, J = 8.9 Hz), 3.53 (1H, d, J = 9.8 Hz), 3.77 (1H, t, J = 9.0 Hz), 3.78 (3H, s) 4.06 (1H, q, J = 9.0 Hz), 4.57 (2H, t, J = 8.8 Hz), 5.94 (1H, brs), 6.74 (1H, d, J = 7.9 Hz), 6.99 (1H, d, J = 7.9 Hz), 7.09 (1H, s). |
| 7-10 | | (−)-(3S*,4R*)-4-(6-fluoro-2,3-dihydrobenzofuran-5-yl)-2-oxopyrrolidine-3-carboxylic acid methyl ester | $^1$H-NMR (400 MHz, CDCl$_3$) δ 3.15 (2H, t, J = 8.9 Hz), 3.41 (1H, t, J = 8.6 Hz), 3.66 (1H, d, J = 9.8 Hz), 3.74-3.79 (1H, m), 3.79 (3H, s), 4.19 (1H, q, J = 8.6 Hz), 4.61 (2H, t, J = 8.9 Hz), 5.68 (1H, brs), 6.52 (1H, d, J = 11.6 Hz), 7.03 (1H, d, J = 7.9 Hz). $[α]_D^{26}$ = −121 (c 0.20, EtOH) |
| 7-11 | | (3S*,4R*)-4-(7-fluorochroman-6-yl)-2-oxopyrrolidine-3-carboxylic acid methyl ester | $^1$H-NMR (400 MHz, CDCl$_3$) δ 1.94-2.01 (2H, m), 2.71 (2H, t, J = 6.1 Hz), 3.42 (1H, t, J = 8.9 Hz), 3.67 (1H, d, J = 9.8 Hz), 3.73-3.78 (1H, m), 3.78 (3H, s), 4.11-4.17 (3H, m), 5.68 (1H, brs), 6.52 (1H, d, J = 11.6 Hz), 6.87 (1H, d, J = 7.9 Hz). |

TABLE 18

| Ref. No | Str. | Chemical name | P.D. |
|---|---|---|---|
| 7-12 | | (3S*,4R*)-4-(3-fluoro-5-methoxypyridin-2-yl)-2-oxopyrrolidine-3-carboxylic acid methyl ester | $^1$H-NMR (400 MHz, CDCl$_3$) δ 3.53 (1H, t, J = 8.6 Hz), 3.77-3.81 (1H, m), 3.79 (3H, s), 3.86 (3H, s), 4.04 (1H, d, J = 9.2 Hz), 4.52 (1H, q, J = 8.8 Hz), 5.72 (1H, brs), 6.94 (1H, dd, J = 11.0, 2.4 Hz), 8.11 (1H, d, J = 2.4 Hz). |
| 7-13 | | (3S*,4R*)-4-(5-methoxythiophen-2-yl)-2-oxopyrrolidine-3-carboxylic acid methyl ester | $^1$H-NMR (400 MHz, CDCl$_3$) δ 3.41 (1H, t, J = 9.1 Hz), 3.49 (1H, d, J = 10.3 Hz), 3.75-3.79 (1H, m), 3.81 (3H, s), 3.86 (3H, s), 4.22 (1H, q, J = 9.1 Hz), 5.78 (1H, brs), 6.01 (1H, d, J = 4.2 Hz), 6.54 (1H, d, J = 4.2 Hz). |
| 7-14 | | (3S*,4R*)-4-(7,6-difluoro-4-hydroxyphenyl)-2-oxopyrrolidine-3-carboxylic acid methyl ester | $^1$H-NMR (400 MHz, CDCl$_3$) δ 3.25 (1H, t, J = 9.2 Hz), 3.52-3.59 (2H, m), 3.63 (3H, s), 4.12 (1H, q, J = 9.6 Hz), 6.43-6.49 (2H, m), 8.27 (1H, s), 10.41 (1H, brs). |

TABLE 18-continued

| Ref. No | Str. | Chemical name | P.D. |
|---|---|---|---|
| 7-15 | | (3S*,4R*)-4-(4-methylthiophenyl)-2-oxopyrrolidine-3-carboxylic acid methyl ester | $^1$H-NMR (400 MHz, CDCl$_3$) δ 2.48 (3H, s), 3.41 (1H, t, J = 8.9 Hz), 3.54 (1H, d, J = 9.7 Hz), 3.78 (3H, s), 3.80 (1H, t, J = 8.9 Hz), 4.10 (1H, q, J = 8.9 Hz), 5.92 (1H, brs), 7.18 (2H, d, J = 8.5 Hz), 7.24 (2H, d, J = 8.5 Hz). |
| 7-16 | | (3S*,4R*,5S*)-4-(4-methoxyphenyl)-5-methyl-2-oxopyrrolidine-3-carboxylic acid methyl ester | $^1$H-NMR (400 MHz, DMSO-d$_6$) δ 0.67 (3H, d, J = 6.7 Hz), 3.60 (3H, s), 3.72 (3H, s), 3.80-3.90 (1H, m), 3.95-4.05 (2H, m), 6.88 (2H, d, J = 9.1 Hz), 7.21 (2H, d, J = 9.1 Hz), 8.21 (1H, s). |

TABLE 19

| Ref. No | Str. | Chemical name | P.D. |
|---|---|---|---|
| 7-17 | | (3S*,4R*,5R*)-4-(4-methoxyphenyl)-5-methyl-2-oxopyrrolidine-3-carboxylic acid methyl ester | $^1$H-NMR (400 MHz, CDCl$_3$) δ 1.27 (3H, d, J = 6.1 Hz), 3.49 (1H, dd, J = 10.9, 8.5 Hz), 3.63 (1H, d, J = 10.9 Hz), 3.68-3.73 (1H, m), 3.74 (3H, s), 3.80 (3H, s), 5.65 (1H, s), 6.89 (2H, d, J = 9.1 Hz), 7.19 (2H, d, J = 9.1 Hz). |
| 7-18 | | (3S*,4R*)-4-(4-ethyl-2,6-difluorophenyl)-2-oxopyrrolidine-3-carboxylic acid methyl ester | $^1$H-NMR (400 MHz, CDCl$_3$) δ 1.22 (3H, t, J = 7.6 Hz), 2.62 (2H, q, J = 7.6 Hz), 3.53 (1H, t, J = 9.2 Hz), 3.68 (1H, t, J = 9.2 Hz), 3.78 (3H, s), 3.83 (1H, d, J = 9.8 Hz), 4.52 (1H, q, J = 9.8 Hz), 6.03 (1H, brs), 6.75 (2H, dd, J = 12.2, 3.1 Hz). |
| 7-19 | | (3S*,4S*)-2-oxo-4-phenylpyrrolidine-3-carboxylic acid methyl ester | $^1$H-NMR (400 MHz, CDCl$_3$) δ 3.44 (1H, dd, J = 9.7, 8.5 Hz), 3.59 (1H, d, J = 9.7 Hz), 3.79 (3H, s), 3.80-3.85 (1H, m), 4.14 (1H, q, J = 8.9 Hz), 5.82 (1H, brs), 7.25-7.38 (5H, m). |
| 7-20 | | (+) - (3R*,4S*)-4-(4-methoxyphenyl)-2-oxopyrrolidine-3-carboxylic acid methyl ester | $^1$H-NMR (400 MHz, CDCl$_3$) δ 3.40 (1H, t, J = 9.1 Hz), 3.53 (1H, d, J = 9.7 Hz), 3.76-3.81 (1H, m), 3.78 (3H, s), 3.80 (3H, s), 4.08 (1H, q, J = 8.9 Hz), 5.85 (1H, brs), 6.88 (2H, d, J = 8.5 Hz), 7.18 (2H, d, J = 8.5 Hz). $[\alpha]_D^{25}$ = +89 (c 0.16, EtOH) |

TABLE 20

| Ref. No | Str. | Chemical name | P.D. |
|---|---|---|---|
| 7-21 | | (3R*,4S*)-4-(3-methoxyphenyl)-2-oxopyrrolidine-3-carboxylic acid methyl ester | 1H-NMR (400 MHz, CDCl$_3$) δ 3.43 (1H, t, J = 8.6 Hz), 3.59 (1H, d, J = 9.7 Hz), 3.79 (3H, s), 3.79-3.84 (1H, m), 3.81 (3H, s), 4.05-4.15 (1H, m), 6.05-6.25 (1H, br), 6.76-6.86 (3H, m), 7.27 (1H, t, J = 8.0 Hz). |
| 7-22 | | (3R*,4S*)-4-(2-methoxyphenyl)-2-oxopyrrolidine-3-carboxylic acid methyl ester | 1H-NMR (400 MHz, CDCl$_3$) δ 3.49 (1H, t, J = 8.5 Hz), 3,73 (1H, d, J = 9.2 Hz), 3.77 (3H, s), 3.83 (3H, s), 3.84 (1H, d, J = 9.2 Hz), 4.26 (1H, q, J = 8.5, Hz), 5.85 (1H, brs), 6.89-6.95 (2H, m), 7.20 (1H, dd, J = 7.3, 1.8 Hz), 7.27-7.30 (1H, m). |
| 7-23 | | (+)-(3R*,4S*)-4-(2,6-difluoro-4-methoxyphenyl)-2-oxopyrrolidine-3-carboxylic acid methyl ester | 1H-NMR (400 MHz, CDCl$_3$) δ 3.51 (1H, t, J = 9.2 Hz), 3.64-3.70 (1H, m), 3.78 (6H, s), 3.78-3.81 (1H, m), 4.46 (1H, q, J = 9.4 Hz), 6.24 (1H, brs), 6.43-6.50 (2H, m). [α]$_D^{24}$= +105 (c 0.09, EtOH) |
| 7-24 | | (3R*,4S*,5R*)-4-(4-methoxyphenyl)-5-methyl-2-oxopyrrolidine-3-carboxylic acid methyl ester | 1H-NMR (400 MHz, DMSO-d$_6$) δ 0.67 (3H, d, J = 6.7 Hz), 3.60 (3H, s), 3.72 (3H, s), 3.80-3.90 (1H, m), 3.95-4.05 (2H, m), 6.88 (2H, d, J = 9.1 Hz), 7.21 (2H, d, J = 9.1 Hz), 8.21 (1H, s). |
| 7-25 | | (3R*,4S*,5S*)-4-(4-methoxyphenyl)-5-methyl-2-oxopyrrolidine-3-carboxylic acid methyl ester | 1H-NMR (400 MHz, CDCl$_3$) δ 1.27 (3H, d, J = 6.1 Hz), 3.49 (1H, dd, J = 10.9, 8.5 Hz), 3.63 (1H, d, J = 10.9 Hz), 3.68-3.73 (1H, m), 3.74 (3H, s), 3.80 (3H, s), 5.65 (1H, s), 6.89 (2H, d, J = 9.1 Hz), 7.19 (2H, d, J = 9.1 Hz). |

TABLE 21

| Ref. No | Str. | Chemical name | P.D. |
| --- | --- | --- | --- |
| 7-26 | (structure: MeO₂C, thiophene with OMe, pyrrolidinone NH) | (3R*,4R*)-4-(5-methoxythiophen-2-yl)-2-oxo-pyrrolidine-3-carboxylic acid methyl ester | $^1$H-NMR (400 MHZ, CDCl$_3$) δ 3.41 (1H, t, J = 9.1 Hz), 3.49 (1H, d, J = 10.3 Hz), 3.75-3.79 (1H, m), 3.81 (3H, s), 3.86 (3H, s), 4.22 (1H, q, J = 9.1 Hz), 5.78 (1H, s), 6.01 (1H, d, J = 4.2 Hz), 6.54 (1H, d, J = 4.2 Hz). |
| 7-27 | (structure: MeO₂C, 4-OCHF₂ phenyl, pyrrolidinone NH) | (3R*,4S*)-4-[4-(difluoromethoxy)phenyl]-2-oxo-pyrrolidine-3-carboxylic acid methyl ester | $^1$H-NMR (400 MHz, CDCl$_3$) δ 3.39-3.44 (1H, m), 3.54 (1H, d, J = 9.7 Hz), 3.80 (3H, s), 3.80 (1H, t, J = 9.2 Hz), 4.12 (1H, q, J = 8.8 Hz), 5.98 (1H, brs), 6.50 (1H, t, J = 73.6 Hz), 7.12 (2H, d, J = 9.2 Hz), 7.22-7.26 (2H, m). |
| 7-28 | (structure: MeO₂C, 4-MeO-phenyl, pyrrolidinone NH, (±)-trans) | (±)-trans-4-[4-methoxyphenyl]-2-oxopyrrolidine-3-carboxylic acid methyl ester | $^1$H-NMR (400 MHz, CDCl$_3$) δ 3.40 (1H, t, J = 9.1 Hz), 3.53 (1H, d, J = 9.7 Hz), 3.76-3.81 (1H, m), 3.78 (3H, s), 3.80 (3H, s), 4.08 (1H, q, J = 8.9 Hz), 5.85 (1H, brs), 6.88 (2H, d, J = 8.5 Hz), 7.18 (2H, d, J = 8.5 Hz). |
| 7-29 | (structure: MeO₂C, 4-MeO-phenyl, 5,5-dimethyl pyrrolidinone NH, (±)-trans) | (±)-trans-4-(4-methoxyphenyl)-5,5-dimethyl-2-oxopyrrolidine-3-carboxylic acid methyl ester | $^1$H-NMR (400 MHz, CDCl$_3$) δ 0.92 (3H, s), 1.39 (3H, s), 3.72 (3H, s), 3.80 (1H, d, J = 12.1 Hz), 3.81 (3H, s), 3.93 (1H, d, J = 12.1 Hz), 5.90 (1H, s), 6.89 (2H, d, J = 8.6 Hz), 7.18 (2H, d, J = 8.6 Hz). |

TABLE 22

| Ref. No | Str. | Chemical name | P.D. |
| --- | --- | --- | --- |
| 7-30 | (structure: MeO₂C, 4-MeO-phenyl, spiro[4.4]nonane lactam, (±)-trans) | (±)-trans-4-(4-methoxyphenyl)-2-oxo-1-azaspiro[4,4]nonane-3-carboxylic acid methyl ester | $^1$H-NMR (400 MHz, CDCl$_3$) δ 1.21-1.67 (6H, m), 1.77-1.85 (1H, m), 1.88-1.95 (1H, m), 3.72 (3H, s), 3.80 (3H, s), 3.85 (1H, d, J = 11.0 Hz), 3.97 (1H, d, J = 11.0 Hz), 6.01 (1H, brs), 6.88 (2H, d, J = 8.6 Hz), 7.17 (2H, d, J = 8.6 Hz). |
| 7-31 | (structure: MeO₂C, 4-MeO-phenyl, spiro[4.5]decane lactam, (±)-trans) | (±)-trans-4-(4-methoxyphenyl)-2-oxo-1-azaspiro[4,5]decane-3-carboxylic acid methyl ester | $^1$H-NMR (400 MHz, CDCl$_3$) δ 0.78-0.89 (1H, m), 0.92-1.07 (1H, m), 1.16-1.34 (2H, m), 1.41-1.51 (2H, m), 1.52-1.80 (4H, m), 3.69 (1H, d, J = 12.1 Hz), 3.72 (3H, s), 3.81 (3H, s), 3.93 (1H, d, J = 12.1 Hz), 6.22 (1H, brs), 6.88 (2H, d, J = 9.1 Hz), 7.15 (2H, d, J = 9.1 Hz). |

TABLE 23

| Ref. No. | Str. | Chemical name | P.D. |
|---|---|---|---|
| 7-32 | | (3S*,4R*)-4-[4-(difluoromethoxy)-2,6-difluorophenyl]-2-oxopyrrolidine-3-carboxylic acid methyl ester | $^1$H-NMR (400 MHz, CDCl$_3$) δ 3.52 (1H, t, J = 9.1 Hz), 3.68-3.73 (1H, m), 3.79-3.82 (4H, m), 4.49-4.56 (1H, m), 6.27 (1H, br), 6.51 (1H, t, J = 72.1 Hz), 6.72-6.78 (2H, m). |
| 7-33 | | (3S*,4R*)-4-(4-ethoxy-2,6-difluorophenyl)-2-oxopyrrolidine-3-carboxylic acid methyl ester | $^1$H-NMR (400 MHz, CDCl$_3$) δ 1.40 (3H, t, J = 7.1 Hz), 3.51 (1H, t, J = 8.9 Hz), 3.67 (1H, t, J = 9.5 Hz), 3.78 (3H, s), 3.79 (1H, d, J = 11.0 Hz), 3.98 (2H, q, J = 7.1 Hz), 4.42-4.49 (1H, m), 6.33 (1H, s), 6.42-6.48 (2H, m). |
| 7-34 | | (3S*,4R*)-4-[4-(dimethylamino)-2,6-difluorophenyl]-2-oxopyrrolidine-3-carboxylic acid methyl ester | $^1$H-NMR (400 MHz, CDCl$_3$) δ 2.93 (6H, s), 3.50 (1H, t, J = 9.2 Hz), 3.64 (1H, t, J = 9.5 Hz), 3.77-3.80 (4H, m), 4.42 (1H, q, J = 9.6 Hz), 5.83 (1H, s), 6.18 (2H, d, J = 12.2 Hz). |
| 7-35 | | (3S*,4R*)-4-(6-fluorobenzofuran-5-yl)-2-oxo-pyrrolidine-3-carboxylic acid methyl ester | $^1$H-NMR (400 MHz, CDCl$_3$) δ 3.50 (1H, t, J = 8.9 Hz), 3.78 (1H, d, J = 10.4 Hz), 3.79 (3H, s), 3.86 (1H, t, J = 8.9 Hz), 4.34-4.40 (1H, m), 6.04 (1H, s), 6.74 (1H, d, J = 1.5 Hz), 7.25-7.28 (1H, m), 7.47 (1H, d, J = 7.3 Hz), 7.63 (1H, d, J = 1.5 Hz). |

TABLE 24

| Ref. No. | Str. | Chemical name | P.D. |
|---|---|---|---|
| 7-36 | | (3S*,4R*)-4-(6-methoxypyridin-3-yl)-2-oxo-pyrrolidine-3-carboxylic acid methyl ester | ¹H-NMR (400 MHz, CDCl₃) δ 3.39 (1H, t, J = 9.2 Hz), 3.51 (1H, d, J = 9.8 Hz), 3.80 (3H, s), 3.78-3.83 (1H, m), 3.93 (3H, s), 4.05-4.11 (1H, m), 6.23 (1H, brs), 6.76 (1H, d, J = 8.6 Hz), 7.49 (1H, dd, J = 8.6, 2.4 Hz), 8.08 (1H, d, J = 2.4 Hz). |
| 7-37 | | (3S*,4R*)-4-(4-acetamide-2,6-difluorophenyl)-2-oxopyrrolidine-3-carboxylic acid methyl ester | ¹H-NMR (400 MHz, CDCl₃) δ 2.19 (3H, s), 3.52 (1H, t, J = 9.2 Hz), 3.66-3.72 (1H, m), 3.78 (3H, s), 3.78-3.81 (1H, m), 4.50 (1H, q, J = 9.4 Hz), 5.88 (1H, s), 7.17 (2H, d, J = 0.4 Hz), 7.32 (1H, s). |
| 7-38 | | (3S*,4R*)-4-{4-[(tert-butoxy-carbonyl)(methyl)amino]-2,6-difluorophenyl}-2-oxopyrrolidine-3-carboxylic acid methyl ester | ¹H-NMR (400 MHz, CDCl₃) δ 1.49 (9H, s), 3.25 (3H, s), 3.53 (1H, t, J = 8.9 Hz), 3.66-3.72 (1H, m), 3.79 (3H, s), 3.82 (1H, d, J = 9.8 Hz), 4.52 (1H, q, J = 9.4 Hz), 5.99 (1H, brs), 6.92 (2H, d, J = 10.4 Hz). |
| 7-39 | | (3S*,4R*)-4-(4,6-difluoro-2,3-dihydrobenzofuran-5-yl)-2-oxo-pyrrolidine-3-carboxylic acid methyl ester | ¹H-NMR (400 MHz, CDCl₃) δ 3.21 (2H, t, J = 8.6 Hz), 3.50 (1H, dd, J = 11.6, 6.7 Hz), 3.66 (1H, t, J = 8.9 Hz), 3.77-3.80 (4H, m), 4.46 (1H, q, J = 9.4 Hz), 4.65 (2H, t, J = 8.6 Hz), 6.16 (1H, s), 6.37 (1H, d, J = 10.4 Hz). |

TABLE 25

| Ref. No. | Str. | Chemical name | P.D. |
|---|---|---|---|
| 7-40 | | (3S*,4R*)-4-{1-[(tert-butyl-dimethylsilyl)oxy]-6-fluoro-2,3-dihydro-1H-inden-5-yl}-2-oxopyrrolidine-3-carboxylic acid methyl ester | ¹H-NMR (400 MHz, CDCl₃) δ 0.14 (3H, s), 0.17 (3H, s), 0.94 (9H, s), 1.87-1.97 (1H, m), 2.41-2.49 (1H, m), 2.67-2.75 (1H, m), 2.91 (1H, dd, J = 15.9, 6.7 Hz), 3.41-3.46 (1H, m), 3.68-3.72 (1H, m), 3.75-3.81 (4H, m), 4.22-4.29 (1H, m), 5.20 (1H, t, J = 7.0 Hz), 5.82 (1H, s), 6.98 (1H, d, J = 10.4 Hz), 7.07 (1H, d, J = 6.7 Hz). |
| 7-41 | | (3S*,4R*)-4-(1-benzyl-6-fluoroindolin-5-yl)-2-oxo-pyrrolidine-3-carboxylic acid methyl ester | ¹H-NMR (400 MHz, CDCl₃) δ 2.93 (2H, t, J = 8.6 Hz), 3.37-3.43 (3H, m), 3.65 (1H, d, J = 9.8 Hz), 3.70-3.75 (1H, m), 3.78 (3H, s, 4.11-4.19 (1H, m), 4.22 (2H, s), 5.81 (1H, br), 6.16 (1H, d, J = 11.6 Hz), 6.89 (1H, d, J = 7.9 Hz), 7.28-7.36 (5H, m). |

TABLE 25-continued

| Ref. No. | Str. | Chemical name | P.D. |
|---|---|---|---|
| 7-42 | (structure) | (3S*,4R*)-4-(3,5-difluoropyridin-4-yl)-2-oxo-pyrrolidine-3-carboxylic acid methyl ester | 1H-NMR (400 MHz, CDCl3) δ 3.56 (1H, t, J = 9.2 Hz), 3.76-3.85 (5H, m), 4.60 (1H, q, J = 9.2 Hz), 5.91 (1H, s), 8.37 (2H, s). |

Reference Example 7-43

[Chemical Formula 51]

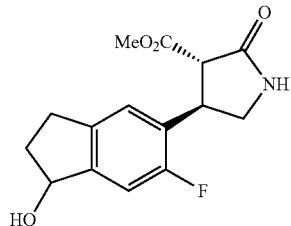

(3S*,4R*)-4-(6-Fluoro-1-hydroxy-2,3-dihydro-1H-inden-5-yl)-2-oxo pyrrolidine-3-carboxylic acid methyl ester A 1 mol/L hydrochloric acid (15 mL) was added to a solution of (3S*,4R*)-4-{1-[(tert-butyldimethylsilyl)oxy]-6-fluoro-2,3-dihydro-1H-inden-5-yl}-2-oxopyrrolidine-3-carboxylic acid methyl ester (2.0 g) in tetrahydrofuran (25 mL) under an argon atmosphere to produce a reaction solution. The reaction solution was stirred at room temperature for 8 hours. The reaction solution was extracted with ethyl acetate, and the extract was washed with water and a brine successively, and dried over anhydrous sodium sulfate. The solvent was removed under reduced pressure, and the residue was then purified by silica gel column chromatography (hexane:ethyl acetate=4:1 followed by 1:4), to obtain the title compound as a colorless amorphous (1.37 g).

$^1$H-NMR (400 MHz, CDCl$_3$) δ 1.80 (1H, dd, J=7.3. 4.3 Hz), 1.92-2.01 (1H, m), 2.49-2.57 (1H, m), 2.73-2.81 (1H, m), 2.96-3.03 (1H, m), 3.44 (1H, t, J=8.9 Hz), 3.70 (1H, dd, J=9.5, 2.1 Hz), 3.78-3.83 (4H, m), 4.27 (1H, q, J=8.8 Hz), 5.21 (1H, q, J=6.3 Hz), 5.87 (1H, s), 7.11 (1H, d, J=4.3 Hz), 7.13 (1H, s).

Reference Example 7-44

[Chemical Formula 52]

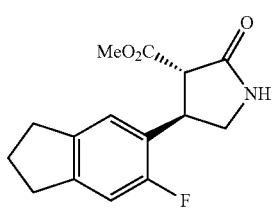 [SMILES: COC(=O)[C@@H]1C(=O)NC[C@H]1c1cc2c(cc1F)OCC2]

(3S*,4R*)-4-(6-Fluoro-2,3-dihydro-1H-inden-5-yl)-2-oxopyrrolidine-3-carboxylic acid methyl ester 10% Palladium on carbon (100 mg) was added to a solution of (3S*,4R*)-4-(6-fluoro-1-hydroxy-2,3-dihydro-1H-inden-5-yl)-2-oxo pyrrolidine-3-carboxylic acid methyl ester (200 mg) in methanol (5 mL) under an argon atmosphere to produce a reaction solution. The reaction solution was stirred at room temperature under a hydrogen atmosphere for 4 hours. The reaction solution was filtered over Celite and washed with ethyl acetate. The solvent was removed under reduced pressure to obtain the title compound as a colorless amorphous (170 mg).

$^1$H-NMR (400 MHz, CDCl$_3$) δ 2.05-2.13 (2H, m), 2.83-2.89 (4H, m), 3.44 (1H, t, J=8.9 Hz), 3.70 (1H, d, J=9.8 Hz), 3.76-3.81 (4H, m), 4.25 (1H, q, J=8.8 Hz), 5.67 (1H, s), 6.92 (1H, d, J=10.4 Hz), 7.08 (1H, d, J=6.7 Hz).

Reference Example 8-1

[Chemical Formula 53]

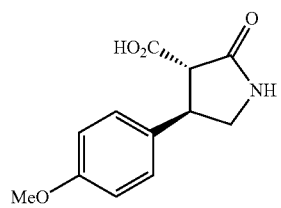

(−)-(3S*,4R*)-4-(4-Methoxyphenyl)-2-oxopyrrolidine-3-carboxylic acid

A 2 mol/L sodium hydroxide aqueous solution (0.52 mL) was added to a solution of (−)-(3S*,4R*)-4-(4-methoxyphenyl)-2-oxopyrrolidine-3-carboxylic acid methyl ester (130 mg) in methanol (2.6 mL) to produce a reaction solution. The reaction solution was stirred at 60° C. for 1 hour. A 1 mol/L hydrochloric acid was added to the reaction solution to make the reaction solution acidic (pH: 1), and the mixture was extracted with ethyl acetate. The organic layer was washed with water and a s brine successively, and dried over anhydrous sodium sulfate. The solvent was removed under reduced pressure, and the crude product was washed with ethyl acetate-diisopropyl ether, to obtain the title compound as a white solid (112 mg).

$^1$H-NMR (400 MHz, DMSO-d$_6$) δ 3.16 (1H, t, J=9.4 Hz), 3.42 (1H, d, J=10.9 Hz), 3.55 (1H, t, J=8.2 Hz), 3.72 (3H, s), 3.79 (1H, q, J=9.5 Hz), 6.88 (2H, d, J=8.5 Hz), 7.24 (2H, d, J=8.5 Hz), 8.03 (1H, s), 12.54 (1H, brs).

$[\alpha]_D^{27}$=−68 (c 0.15, EtOH)

The same method as in Reference Example 8-1 was performed using a corresponding ester substance to obtain the following Reference Examples 8-2 to 8-41. The structures and spectral data thereof are shown in Tables 26 to 35.

TABLE 26

| Ref. No | Str. | Chemical name | P.D. |
|---|---|---|---|
| 8-2 | | (3S*,4R*)-4-(3-fluoro-4-methoxyphenyl)-2-oxopyrrolidine-3-carboxylic acid | $^1$H-NMR (400 MHz, DMSO-$d_6$) δ 3.16 (1H, t, J = 9.4 Hz), 3.47 (1H, d, J = 10.9 Hz), 3.54 (1H, t, J = 8.2 Hz), 3.75-3.84 (1H, m), 3.80 (3H, s), 7.06-7.12 (2H. m), 7.24-7.28 (1H, m), 8.05 (1H, s), 12.65 (1H, brs). |
| 8-3 | | (3S*,4R*)-4-(2-fluoro-4-methoxyphenyl)-2-oxopyrrolidine-3-carboxylic acid | $^1$H-NMR (400 MHz, DMSO-$d_6$) δ 3.18 (1H, t, J = 9.1 Hz), 3.48 (1H, d, J = 10.3 Hz), 3.55 (1H, t, J = 9.1 Hz), 3.74 (3H, s), 4.00 (1H, q, J = 10.3), 6.75-6.83 (2H, m), 7.37 (1H. t, J = 8.8 Hz), 8.09 (1H, s), 12.66 (1H, brs). |
| 8-4 | | (3S*,4*R)-4-(2-chloro-4-methoxyphenyl)-2-oxopyrrolidine-3-carboxylic acid | $^1$H-NMR (4 00 MHz, DMSO-$d_6$) δ 3.11 (1H, t, J = 9.2 Hz), 3.54-3.61 (2H, m), 3.75 (3H, s), 4.20 (1H, q, J = 9.0 Hz), 6.93 (1H, dd, J = 8.9, 2.8 Hz), 7.02 (1H, d, J = 2.8 Hz), 7.49 (1H, d, J = 8.9 Hz), 8.10 (1H, s), 12.67 (1H, brs). |
| 8-5 | | (3S*,4R*)-4-(4-methoxy-2-methylphenyl)-2-oxopyrrolidine-3-carboxylic acid | $^1$H-NMR (400 MHz, DMSO-$d_6$) δ 2.28 (3H, s), 3.08 (1H, t, J = 9.1 Hz), 3.44 (1H, d, J = 10.3 Hz), 3.55 (1H, t, J = 9.1 Hz), 3.70 (3H, s), 3.97-4.04 (1H, m), 6.72-6.76 (2H, m), 7.33 (1H, d, J = 7.9 Hz), 8.04 (1H, s), 12.61 (1H, brs). |
| 8-6 | | (3S*,4R*)-4-(3,5-difluoro-4-methoxyphenyl)-2-oxopyrrolidine-3-carboxylic acid | $^1$H-NMR (400 MHz, DMSO-$d_6$) δ 3.15 (1H, t, J = 9.5 Hz), 3.52-3.57 (2H, m), 3.83 (1H, q, J = 9.6 Hz), 3.88 (3H, s), 7.15-7.22 (2H, m), 8.08 (1H, s), 12.68 (1H, brs). |

TABLE 27

| Ref. No | Str. | Chemical name | P.D. |
| --- | --- | --- | --- |
| 8-7 | | (3S*,4R*)-4-(2,5-difluoro-4-methoxyphenyl)-2-oxopyrrolidine-3-carboxylic acid | $^1$H-NMR (400 MHz, DMSO-$d_6$) δ 3.18 (1H, t, J = 9.5 Hz), 3.49-3.55 (2H, m), 3.82 (3H, s), 4.02 (1H, q, J = 9.5 Hz), 7.10 (1H, dd, J = 12.2, 7.3 Hz), 7.44 (1H, dd, J = 12.2, 7.3 Hz), 8.11 (1H, s), 12.67 (1H, brs). |
| 8-8 | | (-)-(3S*,4R*)-4-(2,6-difluoro-4-methoxyphenyl)-2-oxopyrrolidine-3-carboxylic acid | $^1$H-NMR (400 MHz, DMSO-$d_6$) δ 3.25 (1H, t, J = 9.2 Hz), 3.43 (1H, d, J = 10.4 Hz), 3.56 (1H, t, J = 9.2 Hz), 3.76 (3H, s), 4.14 (1H, q, J = 9.4 Hz), 6.73-6.80 (2H, m), 8.20 (1H, s), 12.77 (1H, brs). $[α]_D^{23}$ = -121 (c 0.10, EtOH) |
| 8-9 | | (3S*,4R*)-4-(6-fluoro-2,3-dihydrobenzofuran-5-yl)-2-oxo-pyrrolidine-3-carboxylic acid | $^1$H-NMR (400 MHz, DMSO-$d_6$) δ 3.10-3.17 (3H, m), 3.41(1H, d. J = 11.0 Hz), 3.53 (1H, t, J = 8.9 Hz), 3.77 (1H, q, J = 9.6 Hz), 4.48 (2H, t, J = 8.6 Hz), 6.68 (1H, d, J = 8.6 Hz), 7.02 (1H, d, J = 8.6 Hz), 7.20 (1H, s), 8.03 (1H, s), 12.62 (1H, brs). |
| 8-10 | | (-)-(3S*,4R*)-4-(6-fluoro-2,3-dihydrobenzofuran-5-yl)-2-oxo-pyrrolidine-3-carboxylic acid | $^1$H-NMR (400 MHz, DMSO-$d_6$) δ 3.09-3.19 (3H, m), 3.46 (1H, d. J = 10.4 Hz), 3.52 (1H, t, J = 8.9 Hz), 3.94-4.03 (1H, m), 4.55 (2H, t, J = 8.6 Hz), 6.65 (1H, d, J = 11.0 Hz), 7.31 (1H, d, J = 7.9 Hz), 8.09 (1H, s), 12.65 (1H, brs). $[α]_D^{27}$ = -114 (c 0.30, EtOH) |

TABLE 28

| Ref. No | Str. | Chemical name | P.D. |
|---|---|---|---|
| 8-11 | | (3S*,4R*)-4-(7-fluorochroman-6-yl)-2-oxopyrrolidine-3-carboxylic acid | $^1$H-NMR (400 MHz, DMSO-d$_6$) δ 1.84-1.90 (2H, m), 2.67 (2H, t, J = 6.1 Hz), 3.16 (1H, t, J = 9.2 Hz), 3.45 (1H, d, J = 10.4 Hz), 3.52 (1H, t, J = 8.9 Hz), 3.94 (1H, q, J = 9.4 Hz), 4.10 (2H, t, J = 5.2 Hz), 6.56 (1H, d, J = 12.2 Hz), 7.13 (1H, d, J = 8.6 Hz), 8.08 (1H, s), 12.67 (1H, brs). |
| 8-12 | | (3S*,4S*)-4-(3-fluoro-5-methoxypyridin-2-yl)-2-oxopyrrolidine-3-carboxylic acid | $^1$H-NMR (400 MHz, DMSO-d$_6$) δ 3.28 (1H, t, J = 8.9 Hz), 3.60-3.66 (2H, m), 3.83 (3H, s), 4.21 (1H, q, J = 9.0 Hz), 7.44 (1H, dd, J = 11.6, 2.4 Hz), 8.06 (1H, s), 8.17 (1H, d, J = 2.4 Hz), 12.70 (1H, brs). |
| 8-13 | | (3S*,4S*)-4-(5-methoxythiophen-2-yl)-2-oxopyrrolidine-3-carboxylic acid | $^1$H-NMR (400 MHz, DMSO-d$_6$) δ 3.18 (1H, t, J = 9.4 Hz), 3.30 (1H, d, J = 10.3 Hz), 3.55-3.59 (1H, m), 3.79 (3H, s), 3.91 (1H, q, J = 10.3), 6.12 (1H, d, J = 4.2 Hz), 6.59 (1H, d, J = 4.2 Hz), 8.08 (1H, s), 12.78 (1H, brs). |
| 8-14 | | (3S*,4R*,5R*)-4-(4-methoxyphenyl)-5-methyl-2-oxo-pyrrolidine-3-carboxylic acid | $^1$H-NMR (400 MHz, DMSO-d$_6$) δ 1.05 (3H, d, J = 6.1 Hz), 3.16 (1H, dd, J = 11.5, 9.1 Hz), 3.49-3.58 (2H, m), 3.72 (3H, s), 6.88 (2H, d, J = 8.5 Hz), 7.27 (2H, d, J = 8.5 Hz), 8.11 (1H, s), 12.54 (1H, s). |

TABLE 29

| Ref. No | Str. | Chemical name | P.D. |
|---|---|---|---|
| 8-15 | | (3S*,4R*,5S*)-4-(4-methoxyphenyl)-5-methyl-2-oxo-pyrrolidine-3-carboxylic acid | $^1$H-NMR (400 MHz, DMSO-d$_6$) δ 0.66 (3H, s), J = 6.7 Hz), 3.72 (3H, s), 3.77 (1H, d, J = 10.9 Hz), 3.81-3.89 (1H, m), 3.94 (1H, dd, J = 10.9, 7.3 Hz), 6.88 (2H, d, J = 8.5 Hz), 7.20 (2H, d, J = 8.5 Hz), 8.12 (1H, s), 12.61 (1H, s). |
| 8-16 | | (3S*,4R*)-4-(4-methylthiophenyl)-2-oxopyrrolidine-3-carboxylic acid | $^1$H-NMR (400 MHz, DMSO-d$_6$) δ 2.49 (3H, s), 3.22 (1H, t, J = 9.4 Hz), 3.50 (1H, d, J = 9.7 Hz), 3.62 (1H, t, J = 8.8 Hz), 3.86 (1H, q, J = 9.5 Hz), 7.26 (2H, d, J = 8.5 Hz), 7.32 (2H, d, J = 8.5 Hz), 8.10 (1H, brs). |

TABLE 29-continued

| Ref. No | Str. | Chemical name | P.D. |
|---|---|---|---|
| 8-17 | | (3S*,4R*)-4-(4-ethyl-2,6-difluorophenyl)-2-oxopyrrolidine-3-carboxylic acid | $^1$H-NMR (400 MHz, DMSO-$d_6$) δ 1.15 (3H, t, J = 7.6 Hz), 2.59 (2H, q, J = 7.6 Hz), 3.27 (1H, t, J = 9.2 Hz), 3.46 (1H, d, J = 10.4 Hz), 3.58 (1H, t, J = 9.2 Hz), 4.20 (1H, q, J = 9.4 Hz), 6.99 (2H, dd, J = 12.8, 3.1 Hz), 8.22 (1H, s), 12.81 (1H, brs). |
| 8-18 | | (3R',4S*)-4-phenyl-2-oxo-pyrrolidine-3-carboxylic acid | $^1$H-NMR (400 MHz, CDCl$_3$) δ 3.47 (1H, t, J = 9.1 Hz), 3.57 (1H, d, J = 10.3 Hz), 3.82 (1H, t, J = 9.1 Hz), 4.05 (1H, q, J = 9.4 Hz), 6.71 (1H, s), 7.24-7.37 (5H, m). |
| 8-19 | | (+)-(3R*,4S*)-4-(4-methoxyphenyl)-2-oxopyrrolidine-3-carboxylic acid | $^1$H-NMR (400 MHz, DMSO-$d_6$) δ 3.16 (1H, t, J = 9.4 Hz), 3.42 (1H, d, J = 10.9 Hz), 3.55 (1H, t, J = 8.2 Hz), 3.72 (3H, s), 3.79 (1H, q, J = 9.5 Hz), 6.88 (2H, d, J = 8.5 Hz), 7.24 (2H, d, J = 8.5 Hz), 8.03 (1H, s), 12.54 (1H, brs). $[α]_D^{25}$ = +99 (c 0.19, EtOH) |

TABLE 30

| Ref. No | Str. | Chemical name | P.D. |
|---|---|---|---|
| 8-20 | | (3R*,4S*)-methyl-4-(3-methoxy-phenyl)-2-oxo-pyrrolidine-3-carboxylic acid | $^1$H-NMR (400 MHz, CDCl$_3$) δ 3.46 (1H, t, J = 9.4 Hz), 3.56 (1H, d, J = 9.7 Hz), 3.75-3.83 (1H, m), 3.79 (3H, s), 4.01 (1H, q, J = 9.4 Hz), 6.58 (1H, s), 6.79-6.89 (3H, m), 7.26 (1H, t, J = 8.0 Hz). |
| 8-21 | | (3R*,4S*)-methyl-4-(2-methoxy-phenyl)-2-oxo-pyrrolidine-3-carboxylic acid | $^1$H-NMR (400 MHz, CDCl$_3$) δ 3.58 (1H, t, J = 9.1 Hz), 3.71 (1H, t, J = 9.1 Hz), 3.86 (3H, s), 3.98 (1H, d, J = 10.3 Hz), 4.06 (1H, t, J = 9.4 Hz), 6.31 (1H, brs), 6.91 (1H, d, J = 8.6 Hz), 6.93-6.98 (1H, m), 7.26-7.32 (2H, m). |
| 8-22 | | (+)-(3R*,4S*)-4-(2,6-difluoro-4-methoxyphenyl)-2-oxopyrrolidine-3-carboxylic acid | $^1$H-NMR (400 MHz, DMSO-$d_6$) δ 3.25 (1H, t, J = 9.2 Hz), 3.43 (1H, d, J = 10.4 Hz), 3.56 (1H, t, J = 9.2 Hz), 3.76 (3H, s), 4.14 (1H, q, J = 9.4 Hz), 6.73-6.80 (2H, m), 8.20 (1H, s), 12.77 (1H, brs). $[α]_D^{23}$ = +120 (c 0.10, EtOH) |

TABLE 30-continued

| Ref. No | Str. | Chemical name | P.D. |
|---|---|---|---|
| 8-23 | (structure) | (3R*,4S*,5S*)-4-(4-methoxyphenyl)-5-methyl-2-oxo-pyrrolidine-3-carboxylic acid | $^1$H-NMR (400 MHz, DMSO-$d_6$) δ 1.05 (3H, d, J = 6.1 Hz), 3.16 (1H, dd, J = 11.5, 9.1 Hz), 3.49-3.58 (2H, m), 3.72 (3H, s), 6.88 (2H, d, J = 8.5 Hz), 7.27 (2H, d, J = 8.5 Hz), 8.11 (1H, s), 12.54 (1H, s). |
| 8-24 | (structure) | (3R*,4S*,5R*)-4-(4-methoxyphenyl)-5-methyl-2-oxo-pyrrolidine-3-carboxylic acid | $^1$H-NMR (400 MHz, DMSO-$d_6$) δ 0.66 (3H, d, J = 6.7 Hz), 3.72 (3H, s), 3.77 (1H, d, J = 10.9 Hz), 3.81-3.89 (1H, m), 3.94 (1H, dd, J = 10.9, 7.3 Hz), 6.88 (2H, d, J = 8.5 Hz), 7.20 (2H, d, J = 8.5 Hz), 8.12 (1H, s), 12.61 (1H, s). |

TABLE 31

| Ref. No | Str. | Chemical name | P.D. |
|---|---|---|---|
| 8-25 | (structure) | (3R*,4R*)-4-(5-methoxythiophen-2-yl)-2-oxo-pyrrolidine-3-carboxylic acid | $^1$H-NMR (400 MHz, DMSO-$d_6$) δ 3.18 (1H, t, J = 9.4 Hz), 3.30 (1H, d, J = 10.3 Hz), 3.55-3.59 (1H, m), 3.79 (3H, s), 3.91 (1H, q, J = 10.3), 6.12 (1H, d, J = 4.2 Hz), 6.59 (1H, d, J = 4.2 Hz), 8.08 (1H, s), 12.78 (1H, brs). |
| 8-26 | (structure) | (3R*,4S*)-4-(4-(difluoromethoxy)phenyl)-2-oxo-pyrrolidine-3-carboxylic acid | $^1$H-NMR (400 MHz, CDCl$_3$) δ 3.46 (1H, t, J = 9.7 Hz), 3.54 (1H, d, J = 9.7 Hz), 3.83 (1H, t, J = 9.4 Hz), 4.05 (1H, q, J = 9.4 Hz), 6.50 (1H, t, J = 73.9 Hz), 6.80 (1H, s), 7.13 (2H, d, J = 9.1 Hz), 7.31 (2H, d, J = 9.1 Hz). |
| 8-27 | (structure) (±)-trans | (±)-trans-4-(4-methoxyphenyl)-2-oxopyrrolidine-3-carboxylic acid | $^1$H-NMR (400 MHz, DMSO-$d_6$) δ 3.16 (1H, t, J = 9.4 Hz), 3.42 (1H, d, J = 10.9 Hz), 3.55 (1H, t, J = 8.2 Hz), 3.72 (3H, s), 3.79 (1H, q, J = 9.5 Hz), 6.88 (2H, d, J = 8.5 Hz), 7.24 (2H, d, J = 8.5 Hz), 8.03 (1H, s), 12.54 (1H, brs). |
| 8-28 | (structure) (±)-trans | (±)-trans-4-(4-methoxyphenyl)-5,5-dimethyl-2-oxopyrrolidine-3-carboxylic acid | $^1$H-NMR (400 MHz, DMSO-$d_6$) δ 0.78 (3H, s), 1.21 (3H, s), 3.50 (1H, d, J = 12.1 Hz), 3.73 (3H, s), 3.98 (1H, d, J = 12.1 Hz), 6.88 (2H, d, J = 8.5 Hz), 7.27 (2H, d, J = 8.5 Hz), 8.09 (1H, s), 12.50 (1H, brs). |

TABLE 32

| Ref. No | Str. | Chemical name | P.D. |
|---|---|---|---|
| 8-29 | | (±)-trans-4-(4-methoxyphenyl)-2-oxo-1-azaspiro[4.4]nonane-3-carboxylic acid | $^1$H-NMR (400 MHz, DMSO-$d_6$) δ 1.00-1.81 (8H, m), 3.69 (1H, d, J = 11.6 Hz), 3.72 (3H, s), 3.88 (1H, d, J = 1.6 Hz), 6.88 (2H, d, J = 8.6 Hz), 7.28 (2H, d, J = 8.6 Hz), 8.37 (1H, s), 12.48 (1H, brs). |
| 8-30 | | (±)-trans-4-(4-methoxyphenyl)-2-oxo-1-azaspiro[4.5]decane-3-carboxylic acid | $^1$H-NMR (400 MHz, CDCl$_3$) δ 0.80-0.89 (1H, m), 0.94-1.09 (1H, m), 1.16-1.37 (2H, m), 1.41-1.49 (2H, m), 1.56-1.82 (4H, m), 3.55 (1H, d, J = 11.5 Hz), 3.81 (3H, s), 3.86 (1H, d, J = 11.5 Hz), 6.72 (1H, brs), 6.90 (2H, d, J = 9.1 Hz), 7.15 (2H, d, J = 9.1 Hz). |

TABLE 33

| Ref. No | Str. | Chemical name | P. D. |
|---|---|---|---|
| 8-31 | | (3S*,4R*)-4-[4-(difluoromethoxy)-2,6-difluorophenyl]-2-oxopyrrolidine-3-carboxylic acid | $^1$H-NMR (400 MHz, CDCl$_3$) δ 3.58 (1H, t, J = 9.7 Hz), 3.69-3.74 (1H, m), 3.82 (1H, d, J = 10.9 Hz), 4.35 (1H, dt, J = 10.3, 9.7 Hz), 6.26 (1H, br), 6.51 (1H, t, J = 72.1 Hz), 6.74-6.80 (2H, m). |
| 8-32 | | (3S*,4R*)-4-(4-ethoxy-2,6-difluorophenyl)-2-oxopyrrolidine-3-carboxylic acid | $^1$H-NMR (400 MHz, DMSO-$d_6$) δ 1.29 (3H, t, J = 6.3 Hz), 3.24 (1H, t, J = 9.2 Hz), 3.42 (1H, d, J = 9.8 Hz), 3.56 (1H, t, J = 9.2 Hz), 4.03 (2H, q, J = 6.3 Hz), 4.14 (1H, ddd, J = 9.8, 9.2, 9.2 Hz), 6.74 (2H, d, J = 10.4 Hz), 8.19 (1H, s), 12.81 (1H, s). |
| 8-33 | | (3S*,4R*)-4-[4-(dimethylamino)-2,6-difluorophenyl]-2-oxopyrrolidine-3-carboxylic acid | $^1$H-NMR (400 MHz, DMSO-$d_6$) δ 2.88 (6H, s), 3.21 (1H, t, J = 9.2 Hz), 3.37 (1H, d, J = 10.4 Hz), 3.50 (1H, t, J = 9.2 Hz), 4.08 (1H, q, J = 9.4 Hz), 6.36 (2H, d, J = 12.8 Hz), 8.11 (1H, s), 12.75 (1H, s). |
| 8-34 | | (3S*,4R*)-4-{6-fluorobenzofuran-5-yl)-2-oxopyrrolidine-3-carboxylic acid | $^1$H-NMR (400 MHz, DMSO-$d_6$) δ 2.32 (1H, t, J = 9.1 Hz), 3.52 (1H, d, J = 9.2 Hz), 3.63 (1H, t, J = 9.1 Hz), 4.09-4.16 (1H, m), 6.95 (1H, d, J = 2.1 Hz), 7.56 (1H, d, J = 11.0 Hz), 7.71 (1H, d, J = 7.9 Hz), 8.00 (1H, d, J = 2.1 Hz), 8.06 (1H, s), 12.78 (1H, brs) |

TABLE 33-continued

| Ref. No | Str. | Chemical name | P. D. |
|---|---|---|---|
| 8-35 |  | (3S*,4R*)-4-(6-methoxypyridin-3-yl)-2-oxopyrrolidine-3-carboxylic acid | ¹H-NMR (400 MHz, CDCl₃) δ 3.43-3.51 (2H, m), 3.82 (1H, t, J = 9.2 Hz) 3.93 (3H, s), 4.01 (1H, q, J = 9.4 Hz), 6.37 (1H, brs), 6.77 (1H, d, J = 8.6 Hz), 7.56 (1H, dd, J = 8.6, 2.4 Hz), 8.15 (1H, d, J = 2.4 Hz). |

TABLE 34

| Ref. No | Str. | Chemical name | P. D. |
|---|---|---|---|
| 8-36 |  | (3S*,4R*)-4-(4-acetamide-2,6-difluorophenyl)-2-oxopyrrolidine-3-carboxylic acid | ¹H-NMR (400 MHz, DMSO-d₆) δ 2.05 (3H, s) , 3.26 (1H, t, J = 9.5 Hz), 3.44 (1H, d, J = 9.8 Hz), 3.57 (1H, t, J = 9.5 Hz), 4.16 (1H, q, J = 9.5 Hz), 7.30 (2H, d, J = 11.0 Hz), 8.21 (1H, s), 10.30 (1H, s), 12.80 (1H, brs). |
| 8-37 |  | (3S*,4R*)-4-{4-[(tert-butoxycarbonyl)(methyl)amino]-2,6-difluorophenyl}-2-oxopyrrolidine-3-carboxylic acid | ¹H-NMR (400 MHz, CDCl₃) δ 1.49 (9H, s), 3.25 (3H, s), 3.58 (1H, t, J = 9.5 Hz), 3.70 (1H, t, J = 9.2 Hz), 3.84 (1H, d, J = 11.0 Hz), 4.34 (1H, q, J = 9.8 Hz), 6.16 (1H, brs), 6.94 (2H, d, J = 10.4 Hz). |
| 8-38 |  | (3S*,4R*)-4-(4,6-difluoro-2,3-dihydrobenzofuran-5-yl)-2-oxopyrrolidine-3-carboxylic acid | ¹H-NMR (400 MHz, DMSO-d₆) δ 3.17-3.26 (3H, m), 3.42 (1H, d, J = 10.4 Hz), 3.54 (1H, t, J = 9.2 Hz), 4.14 (1H, q, J = 9.6 Hz), 4.63 (2H, t, J = 8.6 Hz), 6.64 (1H, d, J = 11.0 Hz), 8.19 (1H, s), 12.53 (1H, brs). |
| 8-39 |  | (3S*,4R*)-4-(6-fluoro-2,3-dihydro-1H-inden-5-yl)-2-oxopyrrolidine-3-carboxylic acid | ¹H-NMR (400 MHz, DMSO-d₆) δ 1.97-2.04 (2H, m), 2.76-2.84 (4H, m), 3.18 (1H, t, J = 9.2 Hz), 3.47 (1H, d, J = 9.8 Hz), 3.55 (1H, t, J = 8.6 Hz), 3.98-4.05 (1H, m), 7.03 (1H, d, J = 11.0 Hz), 7.28 (1H, d, J = 7.3 Hz), 8.08 (1H, s), 12.71 (1H, brs). |
| 8-40 |  | (3S*,4R*)-4-(1-benzyl-6-fluoroindolin-5-yl)-2-oxopyrrolidine-3-carboxylic acid | ¹H-NMR (400 MHz, CDCl₃) δ 2.93-2.97 (2H, m), 3.43-3.51 (3H, m), 3.68-3.78 (2H, m), 3.97 (1H, q, J = 9.2 Hz), 4.26 (2H, s), 6.15 (1H, br), 6.28 (1H, d, J = 12.2 Hz), 7.01 (1H, d, J = 6.7 Hz), 7.30-7.38 (5H, m). |

TABLE 35

| Ref. No | Str. | Chemical name | P.D |
|---|---|---|---|
| 8-41 | (structure) | (3S*,4R*)-4-(3,5-difluoropyridin-4-yl)-2-oxopyrrolidine-3-carboxylic acid | $^1$H-NMR (400 MHz, DMSO-d$_6$) δ 3.28 (1H, t, J = 9.2 Hz), 3.43 (1H, d, J = 9.2 Hz), 3.64 (1H, t, J = 9.5 Hz), 4.30 (1H, q, J = 8.8 Hz), 8.18 (1H, s), 8.51 (2H, s), 13.00 (1H, brs). |

Reference Example 8-42

[Chemical Formula 54]

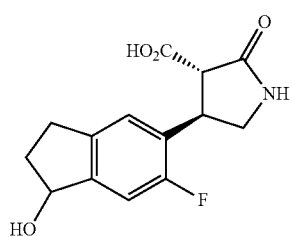

(3S*,4R*)-4-(6-Fluoro-1-hydroxy-2,3-dihydro-1H-inden-5-yl)-2-oxo pyrrolidine-3-carboxylic acid A 2 mol/L sodium hydroxide aqueous solution (0.44 mL) was added to a solution of (3S*,4R*)-4-{1-[(tert-butyldimethylsilyl)oxy]-6-fluoro-2,3-dihydro-1H-inden-5-yl}-2-oxopyrrolidine-3-carboxylic acid methyl ester (180 mg) in methanol (0.88 mL) to produce a reaction solution. The reaction solution was stirred at 60° C. for 2 hours. A 1 mol/L hydrochloric acid was added to the reaction solution to make the reaction solution acidic (pH: 1), and the reaction solution was stirred at room temperature for 1 hour, and extracted with ethyl acetate. The organic layer was washed with water and a brine successively, and dried over anhydrous sodium sulfate. The solvent was removed, and the crude product was washed with a mixed solution of ethyl acetate and methanol at a ratio of 6:1, to obtain the title compound as a white solid (110 mg).

$^1$H-NMR (400 MHz, DMSO-d$_6$) δ 1.74-1.81 (1H, m), 2.29-2.36 (1H, m), 2.61-2.69 (1H, m), 2.81-2.87 (1H, m), 3.19 (1H, t, J=9.2 Hz), 3.49 (1H, d, J=10.4 Hz), 3.56 (1H, t, J=9.2 Hz), 4.04 (1H, q, J=9.2 Hz), 4.99 (1H, q, J=6.7 Hz), 5.32 (1H, d, J=5.5 Hz), 7.06 (1H, d, J=10.4 Hz), 7.30 (1H, d, J=7.3 Hz), 8.11 (1H, s), 12.69 (1H, brs).

(4R*)-3-Chloro-4-(4-methoxyphenyl)-1-methyl-2-oxopyrrolidine-3-carboxylic acid methyl ester Sulfuryl chloride (200 μL) was added to a solution of (−)-(3S*,4R*)-4-(4-methoxyphenyl)-2-oxopyrrolidine-3-carboxylic acid methyl ester (250 mg) in tetrahydrofuran (5 mL) under an argon atmosphere to produce a reaction solution. The reaction solution was stirred at room temperature for 2 hours. A saturated aqueous sodium hydrogen carbonate solution was added to the reaction solution under ice-cooling, and the reaction solution was extracted with ethyl acetate. The organic layer was washed with water and a brine, and dried over anhydrous sodium sulfate. The solvent was removed under reduced pressure, and the residue was then purified by silica gel column chromatography (ethyl acetate:hexane=9:1 followed by ethyl acetate), to obtain (4R*)-3-chloro-4-(4-methoxyphenyl)2-oxopyrrolidine-3-carboxylic acid methyl ester as an intermediate compound.

To a solution of the obtained (4R*)-3-chloro-4-(4-methoxyphenyl)2-oxopyrrolidine-3-carboxylic acid methyl ester (222 mg) in N,N-dimethylformamide (3.4 mL), sodium hydride (56 mg, 60% in oil) was added under ice-cooling to produce a reaction solution. The reaction solution was stirred for 5 minutes, then iodomethane (97 μL) was added, and the reaction solution was stirred at room temperature for 1 hour. A 1 mol/L hydrochloric acid was added to the reaction solution, and the mixture was extracted with ethyl acetate. The organic layer was washed with water and a brine successively, and dried over anhydrous sodium sulfate. The solvent was removed under reduced pressure, and the residue was then purified by silica gel column chromatography (ethyl acetate:hexane=9:1 followed by ethyl acetate), to obtain the title compound as a white solid (184 mg).

$^1$H-NMR (400 MHz, CDCl$_3$) δ 3.07 (3H, s), 3.50 (3H, s), 3.61-3.65 (1H, m), 3.80 (3H, s), 3.88-3.99 (2H, m), 6.88 (2H, d, J=8.5 Hz), 7.23 (2H, d, J=8.5 Hz).

Reference Example 9-1

[Chemical Formula 55]

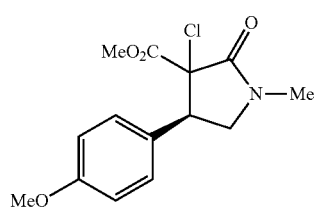

Reference Example 9-2

[Chemical Formula 56]

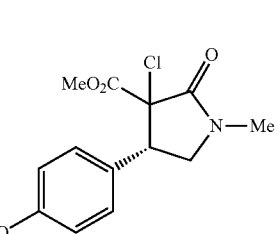

(4S*)-3-Chloro-4-(4-methoxyphenyl)-1-methyl-2-oxopyrrolidine-3-carboxylic acid methyl ester The same method as in Reference Example 9-1 was performed using (+)-(3R*,4S*)-4-(4-methoxyphenyl)-2-oxopyrrolidine-3-carboxylic acid methyl ester in place of (−)-(3S*,4R*)-4-(4-methoxyphenyl)-2-oxopyrrolidine-3-carboxylic acid methyl ester to obtain the title compound.

$^1$H-NMR (400 MHz, CDCl$_3$) δ 3.07 (3H, s), 3.50 (3H, s), 3.61-3.65 (1H, m), 3.80 (3H, s), 3.88-3.99 (2H, m), 6.88 (2H, d, J=8.5 Hz), 7.23 (2H, d, J=8.5 Hz).

Reference Example 9-3

[Chemical Formula 57]

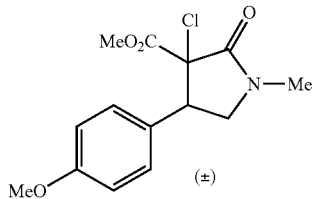

(±)-3-Chloro-4-(4-methoxyphenyl)-1-methyl-2-oxopyrrolidine-3-carboxylic acid methyl ester The same method as in Reference Example 9-1 was performed using (±)-trans-4-(4-methoxyphenyl)-2-oxopyrrolidine-3-carboxylic acid methyl ester in place of (−)-(3S*,4R*)-4-(4-methoxyphenyl)-2-oxopyrrolidine-3-carboxylic acid methyl ester to obtain the title compound.

$^1$H-NMR (400 MHz, CDCl$_3$) δ 3.07 (3H, s), 3.50 (3H, s), 3.61-3.65 (1H, m), 3.80 (3H, s), 3.88-3.99 (2H, m), 6.88 (2H, d, J=8.5 Hz), 7.23 (2H, d, J=8.5 Hz).

Reference Example 10-1

[Chemical Formula 58]

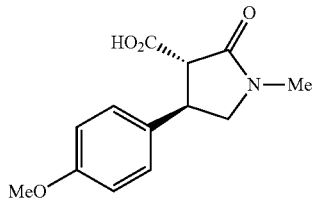

(3S*,4R*)-4-(4-Methoxyphenyl)-1-methyl-2-oxopyrrolidine-3-carboxylic acid

Metal zinc (595 mg) and acetic acid (0.3 mL) were added to a solution of (4R*)-3-chloro-4-(4-methoxyphenyl)-1-methyl-2-oxopyrrolidine-3-carboxylic acid methyl ester (184 mg) in methanol (11 mL) to produce a reaction solution. The reaction solution was stirred at room temperature for 1 hour. The reaction solution was filtered over Celite to remove the insoluble, and the solvent was removed under reduced pressure. A saturated aqueous sodium hydrogen carbonate solution was added to the residue, and the mixture was extracted with ethyl acetate. The organic layer was washed with a 1 mol/L hydrochloric acid and a brine, and dried over anhydrous sodium sulfate. The solvent was removed under reduced pressure, and the residue was then purified by silica gel column chromatography (hexane followed by ethyl acetate:hexane=1:1), to obtain (3S*,4R*)-4-(4-methoxyphenyl)-1-methyl-2-oxopyrrolidine-3-carboxylic acid methyl ester as an intermediate compound.

A 2 mol/L sodium hydroxide aqueous solution (0.57 mL) was added to a solution of the obtained (3S*,4R*)-4-(4-methoxyphenyl)-1-methyl-2-oxopyrrolidine-3-carboxylic acid methyl ester (130 mg) in methanol (2.8 mL) to produce a reaction solution. The reaction solution was stirred at 70° C. for 1 hour. A 1 mol/L hydrochloric acid was added to the reaction solution to make the reaction solution acidic (pH: 1), and the mixture was extracted with ethyl acetate. The organic layer was washed with water and a brine successively, and dried over anhydrous sodium sulfate. The solvent was removed under reduced pressure, and the crude product was washed with ethyl acetate-diisopropyl ether, to obtain the title compound as a white solid (133 mg).

$^1$H-NMR (400 MHz, DMSO-d$_6$) δ 2.78 (3H, s), 3.27-3.34 (1H, m), 3.45 (1H, d, J=10.3 Hz), 3.65 (1H, t, J=8.8 Hz), 3.70-3.77 (1H, m), 3.72 (3H, s), 6.89 (2H, d, J=8.5 Hz), 7.24 (2H, d, J=8.5 Hz), 12.70 (1H, brs).

Reference Example 10-2

[Chemical Formula 59]

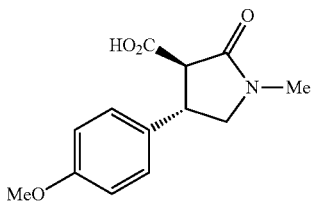

(3R*,4S*)-4-(4-Methoxyphenyl)-1-methyl-2-oxopyrrolidine-3-carboxylic acid

The same method as in Reference Example 10-1 was performed using (4S*)-3-chloro-4-(4-methoxyphenyl)-1-methyl-2-oxopyrrolidine-3-carboxylic acid methyl ester in place of (4R*)-3-chloro-4-(4-methoxyphenyl)-1-methyl-2-oxopyrrolidine-3-carboxylic acid methyl ester to obtain the title compound.

$^1$H-NMR (400 MHz, DMSO-d$_6$) δ 2.78 (3H, s), 3.27-3.34 (1H, m), 3.45 (1H, d, J=10.3 Hz), 3.65 (1H, t, J=8.8 Hz), 3.70-3.77 (1H, m), 3.72 (3H, s), 6.89 (2H, d, J=8.5 Hz), 7.24 (2H, d, J=8.5 Hz), 12.70 (1H, brs).

Reference Example 10-3

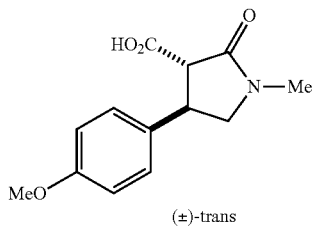

(±)-trans (±)-trans-4-(4-Methoxyphenyl)-1-methyl-2-oxopyrrolidine-3-carboxylic acid The same method as in Reference Example 10-1 was performed using (±)-3-Chloro-4-(4-methoxyphenyl)-1-methyl-2-oxopyrrolidine-3-carboxylic acid methyl ester in place of (4R*)-3-chloro-4-(4-methoxyphenyl)-1-methyl-2-oxopyrrolidine-3-carboxylic acid methyl ester to obtain the title compound.

$^1$H-NMR (400 MHz, DMSO-$d_6$) δ 2.78 (3H, s), 3.27-3.34 (1H, m), 3.45 (1H, d, J=10.3 Hz), 3.65 (1H, t, J=8.8 Hz), 3.70-3.77 (1H, m), 3.72 (3H, s), 6.89 (2H, d, J=8.5 Hz), 7.24 (2H, d, J=8.5 Hz), 12.70 (1H, brs).

Reference Example 11-1

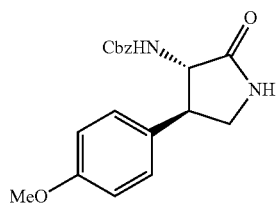 [SMILES: COC(=O)[C@@H]1C(=O)NC[C@H]1c1ccc(SC)cc1]

(−)-[(3S*,4R*)-4-(4-Methoxyphenyl)-2-oxopyrrolidin-3-yl]carbamic acid benzyl ester Triethylamine (3.95 mL) and diphenylphosphoryl azide (6.2 mL) were added to a solution of (−)-(3S*,4R*)-4-(4-methoxyphenyl)-2-oxopyrrolidine-3-carboxylic acid (6.04 g) in toluene (128 mL) to produce a reaction solution. The reaction solution was stirred at room temperature for 4.5 hours. The reaction temperature of the reaction solution was heated up to 80° C., and the reaction solution was then stirred for 30 minutes. To the reaction solution, benzyl alcohol (13.3 mL) was added, and the reaction solution was stirred at 120° C. for 5 hours. The reaction solution was concentrated under reduced pressure, and the residue was then purified by silica gel column chromatography (ethyl acetate followed by ethyl acetate:methanol=10:1), to obtain the title compound as a white solid (6.3 g).

$^1$H-NMR (400 MHz, CDCl$_3$) δ 3.36 (1H, t, J=9.1 Hz), 3.49-3.70 (2H, m), 3.80 (3H, s), 4.42 (1H, dd, J=11.5, 8.5 Hz), 5.07 (2H, s), 5.16 (1H, brs), 5.98 (1H, brs), 6.89 (2H, d, J=7.9 Hz), 7.22 (2H, d, J=7.9 Hz), 7.20-7.40 (5H, m). [α]$_D^{27}$=−79 (c 0.17, EtOH)

Reference Example 11-2

(±)-[(3R*,4S*)-4-(4-Methoxyphenyl)-2-oxopyrrolidin-3-yl]carbamic acid benzyl ester The same method as in Reference Example 11-1 was performed using (+)-(3R*,4S*)-4-(4-methoxyphenyl)-2-oxopyrrolidine-3-carboxylic acid in place of (−)-(3S*,4R*)-4-(4-methoxyphenyl)-2-oxopyrrolidine-3-carboxylic acid to obtain the title compound.

$^1$H-NMR (400 MHz, CDCl$_3$) δ 3.36 (1H, t, J=9.1 Hz), 3.49-3.70 (2H, m), 3.80 (3H, s), 4.42 (1H, dd, J=11.5, 8.5 Hz), 5.07 (2H, s), 5.16 (1H, brs), 5.98 (1H, brs), 6.89 (2H, d, J=7.9 Hz), 7.22 (2H, d, J=7.9 Hz), 7.20-7.40 (5H, m). [α]$_D^{27}$=+81 (c 0.16, EtOH).

Reference Example 12-1

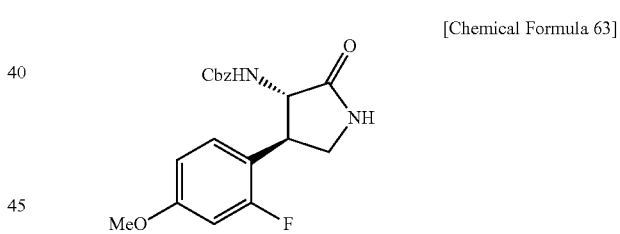

(−)-[(3S*,4R*)-4-(2-Fluoro-4-methoxyphenyl)-2-oxopyrrolidin-3-yl]carbamic acid benzyl ester Triethylamine (1.0 mL) and diphenylphosphoryl azide (1.5 mL) were added to a solution of (3S*,4R*)-4-(2-fluoro-4-methoxyphenyl)-2-oxopyrrolidine-3-carboxylic acid (1.6 g) in a mixture of toluene (63 mL) and acetonitrile (10 mL) to produce a reaction solution. The reaction solution was stirred at room temperature for 3 hours. The reaction temperature of the reaction solution was heated up to 80° C., and the reaction solution was then stirred for 30 minutes. To the reaction solution, benzyl alcohol (3.3 mL) was added, and the reaction solution was stirred at 110° C. for 3.5 hours. Ethyl acetate was added to the reaction solution, and the mixture was washed with a 1 mol/L hydrochloric acid, water, and a brine successively, and dried over anhydrous sodium sulfate. The solvent was removed under reduced pressure, and the residue was then purified by silica gel column chromatography (hexane:ethyl acetate=4:1 followed by ethyl acetate:methanol=10:1), to obtain the title compound as a white solid (767 mg) $^1$H-NMR (400 MHz, CDCl$_3$) δ 3.40 (1H, t, J=8.6 Hz), 3.63-3.82 (2H, m), 3.79 (3H, s), 4.62 (1H, dd, J=11.0, 8.6 Hz), 5.07 (2H, brs), 5.16 (1H, brs), 6.01 (1H, brs), 6.58-6.73 (2H, m), 7.25-7.33 (6H, m).

$[α]_D^{24}$=−134 (c 0.16, EtOH)

The same method as in Reference Example 12-1 was performed using a corresponding carboxylic acid substance to obtain the following Reference Examples 12-2 to 12-4. The structures and spectral data thereof are shown in Table 36.

solution was stirred under a hydrogen atmosphere for 2 hours. The reaction solution was filtered over Celite, and the solvent was removed under reduced pressure. The residue was purified by silica gel column chromatography (hexane: ethyl acetate=1:1 followed by ethyl acetate:methanol=9:1), to obtain the title compound as a white solid (520 mg).

$^1$H-NMR (400 MHz, DMSO-d$_6$) δ 3.22 (1H, t, J=8.0 Hz), 3.34-3.43 (2H, m), 3.47 (1H, d, J=9.8 Hz), 3.76 (3H, s), 6.74 (2H, d, J=11.0 Hz), 7.88 (1H, s).

$[α]_D^{24}$=−90 (c 0.11, EtOH)

TABLE 36

| Ref. No | Str. | Chemical name | P. D. |
|---|---|---|---|
| 12-2 | | (−)-[(3S*,4R*)-4-(2,6-difluoro-4-methoxyphenyl)-2-oxopyrrolidin-3-yl]carbamic acid benzyl ester | $^1$H-NMR (400 MHz, CDCl$_3$) δ 3.48-3.62 (2H, m), 3.79 (3H, s), 3.80-3.96 (1H, m), 4.67-4.75 (1H, m), 5.05 (2H, s), 5.38 (1H, brd, J = 8.0 Hz), 6.42-6.53 (2H, m), 6.60 (1H, s), 7.26-7.36 (5H, m). $[α]_D^{24}$ = −107 (c 0.10, EtOH) |
| 12-3 | | (−)-[(3S*,4R*)-4-(6-fluoro-2,3-dihydrobenzofuran-5-yl)-2-oxopyrrolidin-3-yl]carbamic acid benzyl ester | $^1$H-NMR (400 MHz, CDCl$_3$) δ 3.05-3.25 (2H, m), 3.37 (1H, t, J = 9.2 Hz), 3.55-3.80 (2H, m), 4.50-4.65 (3H, m), 5.04-5.14 (3H, m), 5.83 (1H, s), 6.50 (1H, d, J = 10.4 Hz), 7.10-7.22 (1H, m), 7.26-40 (5H, m). $[α]_D^{29}$ = −185 (c 0.16, EtOH) |
| 12-4 | | (−)-[(3S*,4R*)-4-(3-fluoro-5-methoxypyridin-2-yl)-2-oxopyrrolidin-3-yl]carbamic acid benzyl ester | $^1$H-NMR (400 MHz, DMSO-d$_6$) δ 3.29-3.36 (1H, m), 3.45 (1H, t, J = 8.9 Hz), 3.83 (3H, s), 3.91-3.98 (1H, m), 4.38 (1H, t, J = 9.8 Hz), 4.93 (1H, d, J = 12.8 Hz), 4.98 (1H, d, J = 12.8 Hz), 7.27-7.35 (5H, m), 7.40 (1H, dd, J = 11.6, 1.8 Hz), 7.61 (1H, d, J = 8.6 Hz), 7.94 (1H, s), 8.20 (1H, d, J = 1.8 Hz). $[α]_D^{29}$ = −126 (c 0.12, EtOH) |

Reference Example 13-1

[Chemical Formula 64]

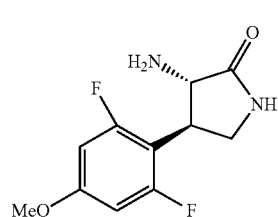

(−)-(3S*,4R*)-3-Amino-4-(2,6-difluoro-4-methoxyphenyl) pyrrolidin-2-one

10% Palladium on carbon (81 mg) was added to a solution of (−)-[(3S*,4R*)-4-(2,6-difluoro-4-methoxyphenyl)-2-oxopyrrolidin-3-yl]carbamic acid benzyl ester (811 mg) in ethanol (30 mL) to produce a reaction solution. The reaction Reference Example 13-2

[Chemical Formula 65]

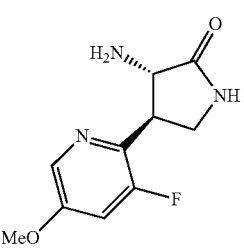

(3S*,4R*)-3-Amino-4-(3-fluoro-5-methoxypyridin-2-yl)pyrrolidin-2-one

The same method as in Reference Example 13-1 was performed using (−)-[(3S*,4R*)-4-(3-fluoro-5-methoxypyridin-2-yl)-2-oxopyrrolidin-3-yl]carbamic acid benzyl ester in place of (−)-[(3S*,4R*)-4-(2,6-difluoro-4-methoxyphenyl)-2-oxopyrrolidin-3-yl]carbamic acid benzyl ester to obtain the title compound.

$^1$H-NMR (400 MHz, DMSO-d$_6$) δ 1.84 (2H, s), 3.22 (1H, t, J=9.2 Hz), 3.40 (1H, t, J=8.6 Hz), 3.51-3.58 (1H, m), 3.61 (1H, d, J=9.8 Hz), 3.83 (3H, s), 7.41 (1H, dd, J=11.9, 1.4 Hz), 7.77 (1H, s), 8.19 (1H, d, J=1.4 Hz).

Reference Example 14-1

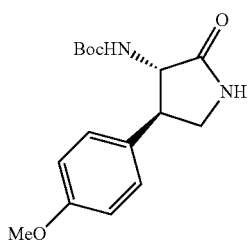 [SMILES: COC(=O)[C@@H]1C(=O)NC[C@H]1c1ccc(OC)nc1]

[Chemical Formula 66]

(−)-[(3S*,4R*)-4-(4-Methoxyphenyl)-2-oxopyrrolidin-3-yl]carbamic acid tert-butyl ester Triethylamine (2.64 mL) and diphenylphosphoryl azide (4.07 mL) were added to a solution of (−)-(3S*,4R*)-4-(4-methoxyphenyl)-2-oxopyrrolidine-3-carboxylic acid (4.05 g) in toluene (80 mL) to produce a first reaction solution. The first reaction solution was stirred at room temperature for 5 hours. The reaction temperature of the first reaction solution was heated up to 80° C., and the first reaction solution was then stirred for 20 minutes. After that, the first reaction solution was concentrated under reduced pressure. To the residue, dioxane (50 mL) and a 1 mol/L hydrochloric acid (50 mL) were added to produce a second reaction solution. The second reaction solution was stirred at room temperature for 30 minutes. The second reaction solution was concentrated under reduced pressure, water (40 mL) was added, and the mixture was washed with diethyl ether. The aqueous layer was concentrated under reduced pressure, and methanol (77 mL), triethylamine (10 mL), and di-tert-butyl dicarbonate (4.28 g) were added to the residue to produce a third reaction solution. The third reaction solution was stirred at room temperature for 3 hours. The third reaction solution was concentrated under reduced pressure, water was added to the residue, and the mixture was extracted with ethyl acetate. The organic layer was washed with a brine, and dried over anhydrous sodium sulfate. The solvent was removed under reduced pressure, and the crude product was washed with chloroform, to obtain the title compound as a white solid (2.97 g).

$^1$H-NMR (400 MHz, CDCl$_3$) δ 1.33 (9H, s), 3.10-3.17 (1H, m), 3.37-3.45 (2H, m), 3.71 (3H, s), 4.12 (1H, t, J=7.0 Hz), 6.87 (2H, d, J=8.6 Hz), 7.07 (1H, d, J=9.2 Hz), 7.23 (2H, d, J=8.6 Hz), 7.83 (1H, brs).

[α]$_D^{27}$=−64 (c 0.14, EtOH)

Reference Example 14-2

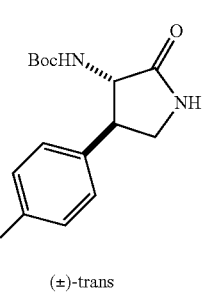

[Chemical Formula 67]

(±)-trans (±)-trans-[4-(4-Methoxyphenyl)-2-oxopyrrolidin-3-yl]carbamic acid tert-butyl ester The same method as in Reference Example 14-1 was performed using (±)-trans-4-(4-methoxyphenyl)-2-oxopyrrolidine-3-carboxylic acid in place of (−)-(3S*,4R*)-4-(4-methoxyphenyl)-2-oxopyrrolidine-3-carboxylic acid to obtain the title compound.

$^1$H-NMR (400 MHz, CDCl$_3$) δ 1.33 (9H, s), 3.10-3.17 (1H, m), 3.37-3.45 (2H, m), 3.71 (3H, s), 4.12 (1H, t, J=7.0 Hz), 6.87 (2H, d, J=8.6 Hz), 7.07 (1H, d, J=9.2 Hz), 7.23 (2H, d, J=8.6 Hz), 7.83 (1H, brs).

Reference Example 15-1

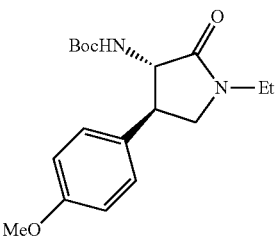

[Chemical Formula 68]

[(3S*,4R*)-1-Ethyl-4-(4-methoxyphenyl)-2-oxopyrrolidin-3-yl]carbamic acid tert-butyl ester A solution of (−)-[(3S*,4R*)-4-(4-methoxyphenyl)-2-oxopyrrolidin-3-yl]carbamic acid tert-butyl ester (181 mg) in N,N-dimethylformamide (0.9 mL) and a solution of ethyl iodide (50 μL) in tetrahydrofuran (1.2 mL) were added to a solution of sodium hydride (42 mg, 60% in oil) in tetrahydrofuran (2.3 mL) under cooling, and the mixture was stirred at room temperature for 4 hours. Water was added to the reaction mixture, and the mixture was extracted with ethyl acetate. The organic layer was washed with a brine, and dried over anhydrous sodium sulfate. The solvent was removed under reduced pressure, and the residue was then purified by silica gel column chromatography (ethyl acetate:hexane=4:1), to obtain the title compound as a white solid (65 mg).

$^1$H-NMR (400 MHz, CDCl$_3$) δ1.17 (3H, t, J=7.4 Hz), 1.38 (9H, s), 3.31-3.60 (5H, m), 3.80 (3H, s), 4.30 (1H, t, J=9.2 Hz), 4.84 (1H, brs), 6.89 (2H, d, J=8.6 Hz), 7.25 (2H, d, J=8.6 Hz).

Reference Example 15-2

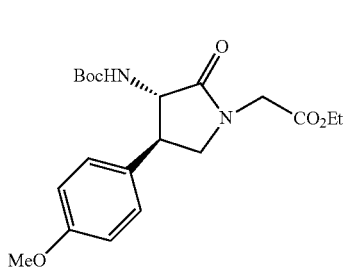

[Chemical Formula 69]

2-{(3S*,4R*)-3-[(tert-Butoxycarbonyl)amino]-4-(4-methoxyphenyl)-2-oxopyrrolidin-1-yl}acetic acid ethyl ester The same method as in Reference Example 15-1 was performed using bromoacetic acid ethyl ester in place of ethyl iodide as an alkylating agent to obtain the title compound.

$^1$H-NMR (400 MHz, CDCl$_3$) δ1.30 (3H, t, J=7.3 Hz), 1.39 (9H, s), 3.50-3.65 (3H, m), 3.80 (3H, s), 3.96 (1H, d, J=17.8 Hz), 4.21 (2H, q, J=7.3 Hz), 4.31 (1H, d, J=17.8 Hz), 4.34 (1H, t, J=8.6 Hz), 4.87 (1H, brs), 6.89 (2H, d, J=8.6 Hz), 7.25 (2H, d, J=8.6 Hz).

Reference Example 15-3

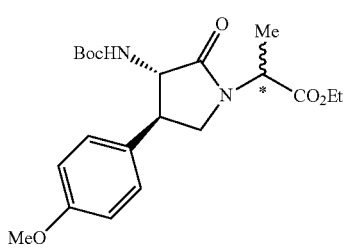

[Chemical Formula 70]

2-{(3S*,4R*)-3-[(tert-Butoxycarbonyl)amino]-4-(4-methoxyphenyl)-2-oxopyrrolidin-1-yl}propionic acid ethyl ester The same method as in Reference Example 15-1 was performed using 2-bromopropionic acid ethyl ester in place of ethyl iodide as an alkylating agent to obtain the title compound.

$^1$H-NMR (400 MHz, CDCl$_3$) δ 1.27-1.48 (15H, m), 3.29-3.80 (3H, m), 3.80 (3H, s), 4.15-4.31 (3H, m), 4.57 (0.5H, brs), 4.80 (0.5H, brs), 4.88-4.99 (1H, m), 6.88 (2H, d, J=8.6 Hz), 7.25 (2H, d, J=9.2 Hz).

Reference Example 16-1

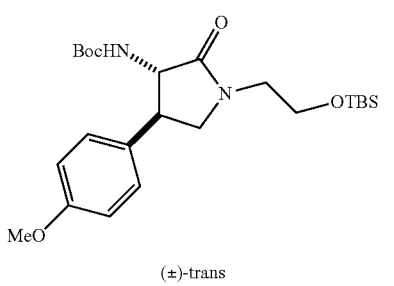

[Chemical Formula 71]

(±)-trans (±)-trans-({1-{2-[(tert-Butyldimethylsilyl)oxy]ethyl}-4-(4-meth oxyphenyl)-2-oxopyrrolidin-3-yl)carbamic acid tert-butyl ester To a solution of (±)-trans-(4-(4-methoxyphenyl)-2-oxopyrrolidin-3-yl)carbamic acid tert-butyl ester (1.03 g) and (2-bromoethoxy) (tert-butyl)dimethylsilane (1.44 mL) in N,N-dimethylformamide (10 mL), sodium hydride (141 mg, 60% in oil) was added in several portions under cooling to produce a reaction solution. The reaction solution was stirred at room temperature for 2 hours. A saturated aqueous ammonium chloride solution was added to the reaction solution, and the mixture was extracted with ethyl acetate. The organic layer was washed with water and a brine successively, and dried over anhydrous sodium sulfate. The solvent was removed under reduced pressure, and the residue was then purified by silica gel column chromatography (hexane:ethyl acetate=3:1), to obtain the title compound as a colorless oil (1.1 g).

$^1$H-NMR (400 MHz, CDCl$_3$) δ 0.06 (6H, s), 0.89 (9H, s), 1.37 (9H, s), 3.30-3.47 (2H, m), 3.52 (1H, t, J=9.7 Hz), 3.57-3.64 (1H, m), 3.71 (1H, t, J=9.1 Hz), 3.76-3.80 (2H, m), 3.80 (3H, s), 4.33 (1H, t, J=9.4 Hz), 4.81 (1H, brs), 6.89 (2H, d, J=8.8 Hz), 7.22 (2H, d, J=8.8 Hz).

Reference Example 17-1

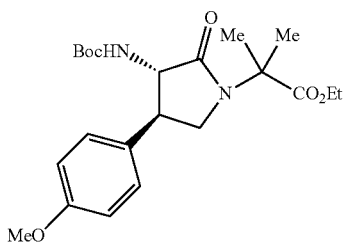

[Chemical Formula 72]

2-{(3S*,4R*)-3-[(tert-Butoxycarbonyl)amino]-4-(4-methoxyphenyl)-2-oxopyrrolidin-1-yl}-2-methylpropionic acid ethyl ester Lithium hexamethyldisilazide (3.8 mL, 1.3 mol/L tetrahydrofuran solution) was added to a solution of 2-{(3S*,4R*)-3-[(tert-butoxycarbonyl)amino]-4-(4-methoxyphenyl)-2-oxopyrrolidin-1-yl}acetic acid ethyl ester (384 mg) in tetrahydrofran (10 mL) at −78° C., to produce a reaction solution. The reaction solution was stirred for 30 minutes. Methyl iodide (0.31 mL) was added to the reaction solution, the temperature was heated up to room temperature, and the reaction solution was stirred for 24 hours. A 10% citric acid aqueous solution was added to the reaction solution, and the mixture was extracted with ethyl acetate. The organic layer was washed with water and a brine successively, and dried over anhydrous sodium sulfate. The solvent was removed under reduced pressure, and the residue was then purified by silica gel column chromatography (ethyl acetate:hexane=4:1 followed by ethyl acetate), to obtain the title compound as a white solid (222 mg).

$^1$H-NMR (400 MHz, CDCl$_3$) δ 1.29 (3H, t, J=7.4 Hz), 1.36 (9H, s), 1.50 (3H, s), 1.57 (3H, s), 3.34-3.42 (2H, m), 3.70-3.77 (1H, m), 3.80 (3H, s), 4.20 (2H, q, J=7.4 Hz), 4.36 (1H, t, J=10.4 Hz), 4.83 (1H, brs), 6.89 (2H, d, J=8.6 Hz), 7.25 (2H, d, J=8.6 Hz).

Reference Example 17-2

[Chemical Formula 73]

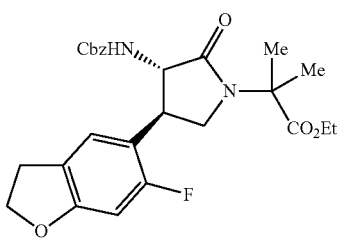

2-((3S*,4R*)-3-{[(Benzyloxy)carbonyl]amino}-4-(6-fluoro-2,3-dihydrobenzofuran-5-yl)-2-oxopyrrolidin-1-yl)-2-methylpropanoic acid ethyl ester The same method as in Reference Example 17-1 was performed using 2-((3S*,4R*)-3-{[(benzyloxy)carbonyl]amino}-4-(6-fluoro-2,3-dihydrobenzofuran-5-yl)-2-oxopyrrolidin-1-yl)acetic acid ethyl ester in place of (−)-[(3S*,4R*)-4-(4-methoxyphenyl)-2-oxopyrrolidin-3-yl]carbamic acid tert-butyl ester to obtain the title compound.

$^1$H-NMR (400 MHz, CDCl$_3$) δ 1.28 (3H, t, J=7.0 Hz), 1.50 (3H, s), 1.56 (3H, s), 3.10-3.22 (2H, m), 3.37 (1H, t, J=9.2 Hz), 3.52-3.66 (1H, m), 3.69-3.80 (1H, m), 4.20 (2H, q, J=7.0 Hz), 4.57-4.65 (1H, m), 4.60 (2H, t, J=8.6 Hz), 5.00-5.13 (3H, m), 6.51 (1H, d, J=10.4 Hz), 7.17-7.23 (1H, m), 7.28-7.36 (5H, m).

Reference Example 18-1

[Chemical Formula 74]

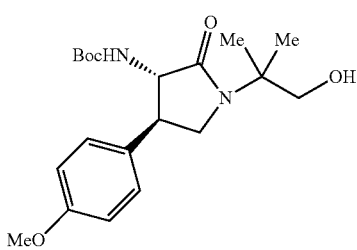

[(3S*,4R*)-1-(1-Hydroxy-2-methylpropan-2-yl)-4-(4-methoxyphenyl)-2-oxopyrrolidin-3-yl]carbamic acid tert-butyl ester Lithiumborohydride (1.5 mL, 3 mol/L tetrahydrofuran solution) was added to a solution of 2-{(3S*,4R*)-3-[(tert-butoxycarbonyl)amino]-4-(4-methoxyphenyl)-2-oxopyrrolidin-1-yl}-2-methylpropionic acid ethyl ester (421 mg) in tetrahydrofran (10 mL) under ice-cooling, to produce a reaction solution. The reaction solution was stirred at room temperature for 2 hours. A 10% citric acid aqueous solution was added to the reaction solution, and the mixture was extracted with ethyl acetate. The organic layer was washed with water and a brine successively, and dried over anhydrous sodium sulfate. The solvent was removed under reduced pressure, and the residue was then purified by silica gel column chromatography (ethyl acetate:hexane=4:1), to obtain the title compound as a white solid (88 mg).

$^1$H-NMR (400 MHz, CDCl$_3$) δ 1.30 (3H, s), 1.31 (3H, s), 1.40 (9H, s), 3.28-3.39 (2H, m), 3.65-3.75 (2H, m), 3.81 (3H, s), 3.92 (1H, brs), 4.32 (1H, t, J=9.2 Hz), 4.57 (1H, brs), 4.86 (1H, brs), 6.89 (2H, d, J=8.6 Hz), 7.22 (2H, d, J=8.6 Hz).

Reference Example 19-1

[Chemical Formula 75]

[(3S*,4R*)-4-(2,6-Difluoro-4-methoxyphenyl)-1-methyl-2-oxopyrrolidin-3-yl]carbamic acid benzyl ester Potassium tert-butoxide (60 mg) and iodomethane (33 μL) were added to a solution of (−)-[(3S*,4R*)-4-(2,6-difluoro-4-methoxyphenyl)-2-oxopyrrolidin-3-yl]carbamic acid benzyl ester (200 mg) in N,N-dimethylformamide (5.3 mL) under ice-cooling, to produce a reaction solution. The reaction solution was stirred for 2 hours. A saturated aqueous ammonium chloride solution was added to the reaction solution, and the mixture was extracted with ethyl acetate. The organic layer was washed with a brine, and dried over anhydrous sodium sulfate. The solvent was removed under reduced pressure, and the residue was then purified by silica gel column chromatography (hexane:ethyl acetate=4:1 followed by ethyl acetate), to obtain the title compound as a white solid (100 mg).

$^1$H-NMR (400 MHz, CDCl$_3$) δ 2.95 (3H, s), 3.40-3.62 (2H, m), 3.77 (3H, s), 3.80-3.84 (1H, m), 4.57-4.67 (1H, m), 5.04 (2H s), 5.20 (1H, brs), 6.40-6.51 (2H, m), 7.26-7.33 (5H, m).

The same method as in Reference Example 19-1 was performed using a corresponding alkylating agent to obtain the following Reference Examples 19-2 to 19-9. The structures and spectral data thereof are shown in Tables 37 to 39.

TABLE 37

| Ref. No | Str. | Chemical name | P. D. |
|---|---|---|---|
| 19-2 | | [(3S*,4R*)-4-(2,6-difluoro-4-methoxyphenyl)-2-oxo-1-propylpyrrolidin-3-yl]carbamic acid benzyl ester | $^1$H-NMR (400 MHz, CDCl$_3$) δ 0.94 (3H, t, J = 7.3 Hz), 1.52-1.65 (2H, m), 3.20-3.35 (1H, m), 3.36-3.63 (3H, m), 3.65-3.85 (1H, m), 3.77 (3H, s), 4.63-4.70 (1H, m), 5.03 (2H, s), 5.21 (1H, brs), 6.42-6.52 (2H, m), 7.25-7.35 (5H, m). |
| 19-3 | | [(3S*,4R*)-1-benzyl-4-(2,6-difluoro-4-methoxyphenyl)-2-oxopyrrolidin-3-yl]carbamic acid benzyl ester | $^1$H-NMR (400 MHz, CDCl$_3$) δ 3.30-3.47 (2H, m), 3.73-3.82 (1H, m), 3.75 (3H, s), 4.50 (1H, d, J = 14.7 Hz), 4.61 (1H, d, J = 15.3 Hz), 4.70 (1H, t, J = 9.8 Hz), 5.04 (2H, d, J = 11.2 Hz), 5.27 (1H, brs), 6.42 (2H, d, J = 10.4 Hz), 7.26-7.37 (10H, m). |
| 19-4 | | [(3S*,4R*)-4-(2,6-difluoro-4-methoxyphenyl)-2-oxo-1-(pyridin-3-ylmethyl)pyrrolidin-3-yl]carbamic acid benzyl ester | $^1$H-NMR (400 MHz, CDCl$_3$) δ 3.56 (2H, t, J = 8.0 Hz), 3.76-3.95 (4H, m), 4.61-4.79 (3H, m), 5.03-5.08 (2H, m), 5.26 (1H, brs), 6.42 (2H, d, J = 9.8 Hz), 7.20-7.31 (7H, m), 7.71 (1H, brs), 8.54 (1H, d, J = 4.9 Hz). |

TABLE 38

| Ref. No | Str. | Chemical name | P. D. |
|---|---|---|---|
| 19-5 | | 2-((3S*,4R*)-3-{[(benzyloxy)carbonyl]amino}-4-(2,6-difluoro-4-methoxyphenyl)-2-oxopyrrolidin-1-yl) acetic acid ethyl ester | $^1$H-NMR (400 MHz, DMSO-d$_6$) δ 1.30 (3H, t, J = 7.3 Hz), 3.47-3.60 (1H, m), 3.70-3.95 (2H, m), 3.78 (3H, s), 4.06 (1H, d, J = 17.8 Hz) 4.22 (2H, q, J = 7.3 Hz), 4.22-4.27 (1H, d, J = 17.8 Hz) 4.76 (1H, t, J = 9.2 Hz), 4.98-5.10 (2H, m), 5.19 (1H, brs), 6.40-6.55 (2H, m), 7.26-2.36 (5H, m). |
| 19-6 | | 2-((3S*,4R*)-3-{[(benzyloxy)carbonyl]amino}-4-(6-fluoro-2,3-dihydrobenzofuran-5-yl)-2-oxopyrrolidin-1-yl) acetic acid ethyl ester | $^1$H-NMR (400 MHz, CDCl$_3$) δ 1.29 (3H, t, J = 7.1 Hz), 3.09-3.23 (2H, m), 3.49-3.59 (1H, m), 3.70-3.76 (2H, m), 3.98 (1H, d, J = 17.7 Hz), 4.11-4.31 (1H, m), 4.21 (2H, q, J = 7.1 Hz), 4.58-4.66 (3H, m), 5.00-5.20 (1H, m), 5.08 (2H, s), 6.51 (1H, d, J = 11.0 Hz), 7.10-7.20 (1H, m), 7.26-7.36 (5H, m). |

TABLE 38-continued

| Ref. No | Str. | Chemical name | P. D. |
|---|---|---|---|
| 19-7 | | [(3S*,4R*)-1-(cyclopropylmethyl)-4-(6-fluoro-2,3-dihydrobenzofuran-5-yl)-2-oxopyrrolidin-3-yl] carbamic acid benzyl ester | $^1$H-NMR (400 MHz, CDCl$_3$) δ 0.22-0.26 (2H, m), 0.52-0.57 (2H, m), 0.85-0.99 (1H, m), 3.09 (1H, dd, J = 13.9, 7.3 Hz), 3.10-3.22 (2H, m), 3.37 (1H, dd, J = 13.9, 7.0 Hz), 3.43 (1H, t, J = 9.2 Hz), 3.55-3.77 (2H, m), 4.58-4.64 (3H, m), 5.02-5.17 (3H, m), 6.52 (1H, d, J = 11.0 Hz), 7.10-7.22 (1H, m), 7.28-7.36 (5H, m). |

TABLE 39

| Ref. No | Str. | Chemical name | P. D. |
|---|---|---|---|
| 19-8 | | [(3S*,4R*)-1-(cyanomethyl)-4-(6-fluoro-2,3-dihydrobenzofuran-5-yl)-2-oxopyrrolidin-3-yl] carbamic acid benzyl ester | $^1$H-NMR (400 MHz, CDCl$_3$) δ 3.14-3.19 (2H, m), 3.48-3.54 (1H, m), 3.70-3.80 (2H, m), 4.23-4.27 (1H, m), 4.44-4.52 (2H, m), 4.62 (2H, t, J = 9.1 Hz), 5.06-5.13 (3H, m), 6.52-6.54 (1H, m), 7.09-7.12 (1H, m,), 7.32-7.34 (5H, m). |
| 19-9 | | {(3S*,4R*)-4-(6-fluoro-2,3-dihydrobenzofuran-5-yl)-1-[(5-methyl-1,3,4-oxadiazol-2-yl)methyl]-2-oxopyrrolidin-3-yl} carbamic acid benzyl ester | $^1$H-NMR (400 MHz, CDCl$_3$) δ 2.53 (3H, s), 3.12-3.16 (2H, m), 3.43-3.47 (1H, m), 3.67-3.73 (2H, m), 4.57-4.66 (4H, m), 4.80-4.84 (1H, m), 5.07 (2H, s), 5.42 (1H, br), 6.59 (1H, d, J = 10.9 Hz), 7.13-7.14 (1H, m), 7.27-7.32 (5H, m). |

Reference Example 19-10

[Chemical Formula 76]

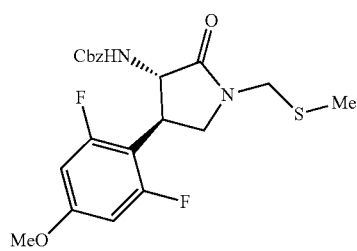

{(3S*,4R*)-4-(2,6-Difluoro-4-methoxyphenyl)-1-[(methylthio)methyl]-2-oxopyrrolidin-3-yl}carbamic acid benzyl ester Chloromethylmethyl sulfide (73 μL), tetrabutylammonium iodide (12 mg), and potassium tert-butoxide (86 mg) were added to a solution of [(3S*,4R*)-4-(2,6-difluoro-4-methoxyphenyl)-2-oxopyrrolidin-3-yl]carbamic acid benzyl ester (120 mg) in N,N-dimethylformamide (3.2 mL) under ice-cooling, to produce a reaction solution. The reaction solution was stirred at room temperature for 4 hours. A saturated aqueous ammonium chloride solution was added to the reaction solution, and the mixture was extracted with ethyl acetate. The organic layer was washed with water and a brine successively, and dried over anhydrous sodium sulfate. The solvent was removed under reduced pressure, and the residue was then purified by silica gel column chromatography (hexane:ethyl acetate=9:1 followed by 1:1), to obtain the title compound (56 mg).

$^1$H-NMR (400 MHz, CDCl$_3$) δ 2.14 (3H, brs), 3.60-3.69 (2H, m), 3.78 (3H, s), 3.85-3.93 (1H, m), 4.49 (2H, s), 4.58-4.66 (1H, m), 5.03 (1H, d, J=12.2 Hz), 5.09 (1H, d, J=12.2 Hz), 5.20 (1H, brs), 6.48 (2H, d, J=9.8 Hz), 7.28-7.34 (5H, m).

Reference Example 19-11

[Chemical Formula 77]

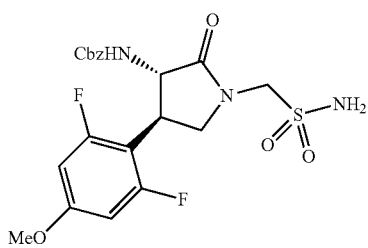

[(3S*,4R*)-4-(2,6-Difluoro-4-methoxyphenyl)-2-oxo-1-(sulfamoylmethyl)pyrrolidin-3-yl]carbamic acid benzyl ester The same method as in Reference Example 19-10 was performed using 1-chloromethanesulfonamide in place of chloromethyl methysulfide to obtain the title compound.

¹H-NMR (400 MHz, CDCl₃) δ 3.60-3.70 (1H, m), 3.78 (3H, s), 4.21-4.24 (4H, m), 5.05 (1H, d, J=12.2 Hz), 5.11-5.17 (2H, m), 5.29 (2H, brs), 5.63 (1H, brs), 6.48 (2H, d, J=10.4 Hz), 7.29-7.38 (5H, m).

Reference Example 19-12

[Chemical Formula 78]

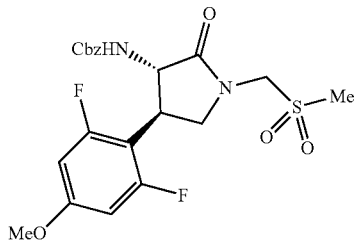

{(3S*,4R*)-4-(2,6-Difluoro-4-methoxyphenyl)-1-[(methylsulfonyl)methyl]-2-oxopyrrolidin-3-yl}carbamic acid benzyl ester Meta-chloroperoxybenzoic acid (79 mg) was added to a solution of {(3S*,4R*)-4-(2,6-difluoro-4-methoxyphenyl)-1-[(methylthio)methyl]-2-oxopyrrolidin-3-yl}carbamic acid benzyl ester (56 mg) in dichloromethane (2.2 mL) under ice-cooling to produce a reaction solution. The reaction solution was stirred at room temperature for 4 hours. A saturated aqueous sodium sulfite solution was added to the reaction solution, and the mixture was extracted with dichloromethane. The organic layer was washed with a saturated sodium hydrogen carbonate solution and a brine successively, and dried over anhydrous sodium sulfate. The solvent was removed under reduced pressure, and the residue was then purified by silica gel column chromatography (hexane:ethyl acetate=9:1 followed by ethyl acetate), to obtain the title compound (57 mg).

¹H-NMR (400 MHz, CDCl₃) δ 3.01 (3H, brs), 3.75-3.81 (4H, m), 4.06-4.22 (2H, m), 4.30-4.41 (2H, m), 4.86 (1H, d, J=14.7 Hz), 5.04 (1H, d, J=12.2 Hz), 5.12 (1H, d, J=12.2 Hz), 5.29 (1H, d, J=4.2 Hz), 6.48 (2H, d, J=10.4 Hz), 7.28-7.37 (5H, m).

Reference Example 20-1

[Chemical Formula 79]

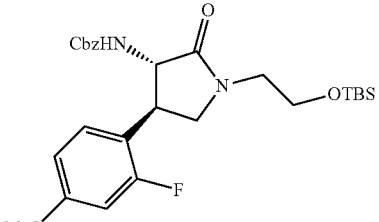

((3S*,4R*)-1-{2-[(tert-Butyldimethylsilyl)oxy]ethyl}-4-(2-fluoro-4-methoxyphenyl)-2-oxopyrrolidin-3-yl) carbamic acid benzyl ester To a solution of (−)-[(3S*,4R*)-4-(2-fluoro-4-methoxyphenyl)-2-oxopyrrolidin-3-yl)carbamic acid benzyl ester (346 mg) and (2-bromoethoxy) (tert-butyl)dimethylsilane (2.0 mL) in N,N-dimethylformamide (9.7 mL), potassium tert-butoxide (216 mg) was added in several portions to produce a reaction solution. The reaction solution was stirred at room temperature for 15 hours. A saturated aqueous ammonium chloride solution was added to the reaction solution, and the mixture was extracted with ethyl acetate. The organic layer was washed with water and a brine successively, and dried over anhydrous sodium sulfate. The solvent was removed under reduced pressure, and the residue was then purified by silica gel column chromatography (hexane:ethyl acetate=9:1 followed by ethyl acetate), to obtain the title compound as a colorless oil (204 mg).

¹H-NMR (400 MHz, CDCl₃) δ 0.06 (6H, s), 0.88 (9H, s), 3.32-3.41 (1H, m), 3.48-3.63 (3H, m), 3.75-3.81 (6H, m), 4.64 (1H, dd, J=11.0, 8.0 Hz), 5.00-5.15 (3H, m), 6.58-6.73 (2H, m), 7.24-7.32 (6H, m).

The same method as in Reference Example 20-1 was performed using a corresponding 2-oxopyrrolidine substance to obtain the following Reference Examples 20-2 to 20-4.

The structures and spectral data thereof are shown in Table 40.

TABLE 40

| Ref. No | Str. | Chemical name | P. D. |
| --- | --- | --- | --- |
| 20-2 | ![structure] | ((3S*,4R*)-1-{2-[(tert-butyldimethylsilyl)oxy]ethyl}-4-(2,6-difluoro-4-methoxyphenyl)-2-oxopyrrolidin-3-yl) carbamic acid benzyl ester | ¹H-NMR (400 MHz, CDCl₃) δ 0.00 (6H, s), 0.82 (9H, s), 3.24-3.33 (1H, m), 3.48-3.62 (3H, m), 3.66-3.75 (6H, m), 4.64-4.70 (1H, m), 4.97 (2H, s), 5.16 (1H, brs), 6.35-6.45 (2H, m), 7.21-7.27 (5H, m). |

TABLE 40-continued

| Ref. No | Str. | Chemical name | P. D. |
|---|---|---|---|
| 20-3 | ![structure] BocHN, 4-methoxyphenyl pyrrolidinone with OTBS, cis | (1-{2-[(tert-butyldimethylsilyl)oxy]ethyl}-4-(4-methoxyphenyl)-2-oxopyrrolidin-3-yl) carbamic acid tert-butyl ester | $^1$H-NMR (400 MHz, CDCl$_3$) δ 0.08 (6H, s), 0.89 (9H, s), 1.36 (9H, s), 3.48 (1H, dt, J = 14.0, 4.9 Hz), 3.89 (1H, dt, J = 14.0, 4.9 Hz), 3.66 (1H, d, J = 10.4 Hz), 3.79 (3H, s), 3.84 (2H, t, J = 4.9 Hz), 3.92 (1H, dd, J = 10.4, 6.1 Hz), 4.57-4.61 (2H, m), 6.80 (2H, d, J = 8.6 Hz), 7.05 (2H, d, J = 8.6 Hz). |
| 20-4 | ![structure] CbzHN, 6-fluoro-2,3-dihydrobenzofuran-5-yl pyrrolidinone with OTBS | ((3S*,4R*)-1-{2-[(tert-butyldimethylsilyl)oxy]ethyl}-4-(6-fluoro-2,3-dihydrobenzofuran-5-yl)-2-oxopyrrolidin-3-yl) carbamic acid benzyl ester | $^1$H-NMR (400 MHz, CDCl$_3$) δ 0.06 (6H, s), 0.88 (9H, s), 3.10-3.20 (2H, m), 3.32-3.39 (1H, m), 3.47-3.61 (3H, m), 3.70-3.79 (3H, m), 4.58-4.64 (3H, m), 5.00-5.15 (3H, m), 6.51 (1H, d, J = 11.0 Hz), 7.10-7.20 (1H, m), 7.26-7.40 (5H, m). |

Reference Example 21-1

[Chemical Formula 80]

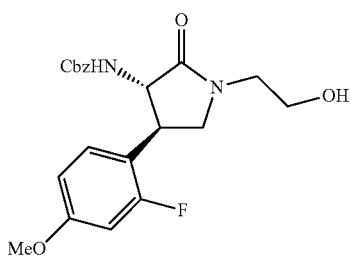

[(3S*,4R*)-4-(2-Fluoro-4-methoxyphenyl)-1-(2-hydroxyethyl)-2-oxopyrrolidin-3-yl]carbamic acid benzyl ester To a solution of ((3S*,4R*)-1-{2-[(tert-butyldimethylsilyl)oxy]ethyl}-4-(2-fluoro-4-methoxyphenyl)-2-oxopyrrolidin-3-yl) carbamic acid benzyl ester (219 mg) in tetrahydrofuran (4.2 mL), tetrabutylammonium fluoride (465 µL, 1.0 M tetrahydrofuran solution) was added to produce a reaction solution. The reaction solution was stirred at room temperature for 30 minutes. Water was added to the reaction solution, and the mixture was extracted with ethyl acetate. The organic layer was washed with water and a brine successively, and dried over anhydrous sodium sulfate. The solvent was removed under reduced pressure, and the residue was then purified by silica gel column chromatography (hexane:ethyl acetate=4:1, ethyl acetate, and ethyl acetate:methanol=10:1 in turn), to obtain the title compound as a white solid (150 mg).

$^1$H-NMR (400 MHz, CDCl$_3$) δ 2.73 (1H, brs), 3.40-3.64 (3H, m), 3.65-3.89 (7H, m), 4.53 (1H, t, J=9.2 Hz), 5.00-5.12 (2H, brs), 5.25 (1H, brs), 6.57-6.73 (2H, m), 7.23-7.35 (6H, m).

The same method as in Reference Example 21-1 was performed using a corresponding [(tert-butyldimethylsilyl)oxy]ethyl substance to obtain the following Reference Examples 21-2 to 21-4. The structures and spectral data thereof are shown in Table 41.

TABLE 41

| Ref. No | Str. | Chemical name | P. D. |
|---|---|---|---|
| 21-2 | ![structure] CbzHN, 2,6-difluoro-4-methoxyphenyl pyrrolidinone with OH | [(3S*,4R*)-4-(2,6-difluoro-4-methoxyphenyl)-1-(2-hydroxyethyl)-2-oxopyrrolidin-3-yl] carbamic acid benzyl ester | $^1$H-NMR (400 MHz, CDCl$_3$) δ 2.70 (1H, brs), 3.40-3.48 (1H, m), 3.59-3.70 (3H, m), 3.78 (3H, s), 3.80-3.94 (3H, m), 4.50-4.61 (1H, m), 5.01-5.09 (2H, m), 5.29 (1H, brs), 6.41-6.52 (2H, m), 7.27-7.36 (5H, m). |

TABLE 41-continued

| Ref. No | Str. | Chemical name | P. D. |
|---|---|---|---|
| 21-3 | (structure: BocHN, cis, 4-methoxyphenyl pyrrolidinone with N-CH2CH2OH) | [1-(2-hydroxyethyl)-4-(4-methoxyphenyl)-2-oxopyrrolidin-3-yl] carbamic acid tert-butyl ester | $^1$H-NMR (400 MHz, CDCl$_3$) δ 1.36 (9H, s), 2.71 (1H, brs), 3.50 (1H, dt, J = 14.0, 4.9 Hz), 3.62-3.68 (2H, m), 3.79-3.92 (7H, m), 4.57 (1H, t, J = 7.3 Hz), 4.64 (1H, d, J = 6.8 Hz), 6.83 (2H, d, J = 8.6 Hz), 7.07 (2H, d, J = 8.6 Hz). |
| 21-4 | (structure: CbzHN, dihydrobenzofuran-F, pyrrolidinone with N-CH2CH2OH) | [(3S*,4R*)-4-(6-fluoro-2,3-dihydrobenzofuran-5-yl)-1-(2-hydroxyethyl)-2-oxopyrrolidin-3-yl] carbamic acid benzyl ester | $^1$H-NMR (400 MHz, DMSO-d$_6$) δ 3.10-3.18 (3H, m), 3.30-3.63 (6H, m), 4.42 (1H, t, J = 9.8 Hz), 4.56 (2H, t, J = 8.6 Hz), 4.74 (1H, t, J = 4.0 Hz), 4.99 (2H, s), 6.65 (1H, d, J = 11.0 Hz), 7.28-7.35 (6H, m), 7.62 (1H, d, J = 9.8 Hz). |

Reference Example 22-1

Reference Example 22-2

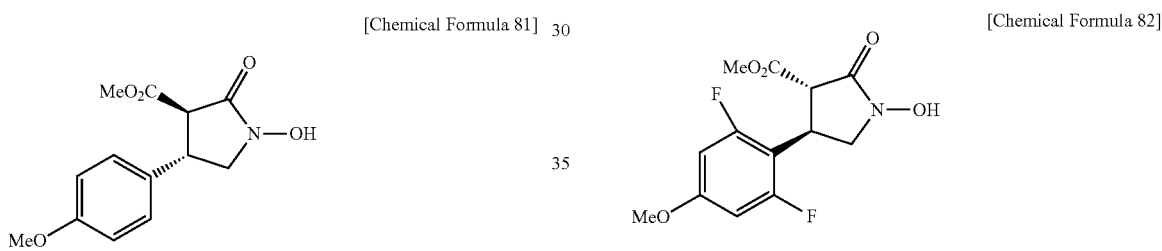

[Chemical Formula 81]

(3R*,4S*)-1-Hydroxy-4-(4-methoxyphenyl)-2-oxopyrrolidine-3-carboxylic acid methyl ester

[Chemical Formula 82]

(3S*,4R*)-4-(2,6-Difluoro-4-methoxyphenyl)-1-hydroxy-2-oxopyrrolidine-3-carboxylic acid methyl ester Zinc powder (2.0 g) and an aqueous solution (5 mL) of ammonium chloride (0.9 g) was added to a solution of (+)-(S*)-2-[1-(4-methoxyphenyl)-2-nitroethyl]malonic acid dimethyl ester (1.04 g) in methanol (30 mL) to produce a reaction solution. The reaction solution was stirred for 1 hour. Ethyl acetate was added to the reaction solution, and the reaction solution was filtered over Celite. The filtrate was washed with a 1 mol/L hydrochloric acid, water, and a brine successively, and dried over anhydrous sodium sulfate. The solvent was removed under reduced pressure, and the residue was then purified by silica gel column chromatography (ethyl acetate), to obtain the title compound as a colorless oil (760 mg).

$^1$H-NMR (400 MHz, CDCl$_3$) δ 3.57 (1H, d, J=8.5 Hz), 3.68 (1H, t, J=8.1 Hz), 3.78 (3H, s), 3.79 (3H, s), 3.95 (1H, q, J=8.1 Hz), 4.03 (1H, t, J=8.5 Hz), 6.88 (2H, d, J=8.8 Hz), 7.18 (2H, d, J=8.8 Hz).

The same method as in Reference Example 22-1 was performed using (−)-(R)-2-[1-(2,6-difluoro-4-methoxyphenyl)-2-nitroethyl]malonic acid dimethyl ester in place of (+)-(S*)-2-[1-(4-methoxyphenyl)-2-nitroethyl]malonic acid dimethyl ester to obtain the title compound.

$^1$H-NMR (400 MHz, CDCl$_3$) δ 3.72-3.82 (8H, m), 3.93 (1H, t, J=8.8 Hz), 4.33 (1H, q, J=8.8 Hz), 6.48 (2H, d, J=8.6 Hz).

Reference Example 23-1

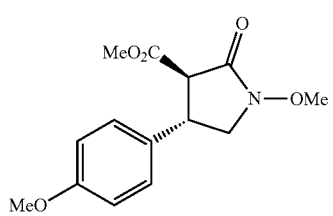

[Chemical Formula 83]

(3R*,4S*)-1-Methoxy-4-(4-methoxyphenyl)-2-oxopyrrolidine-3-carboxylic acid methyl ester Potassium carbonate (276 mg) and iodomethane (0.12 mL) were added to a solution of (3R*,4S*)-1-hydroxy-4-(4-methoxyphenyl)-2-oxopyrrolidine-3-carboxylic acid methyl ester (265 mg) in N,N-dimethylformamide (2 mL), to produce a reaction solution. The reaction solution was stirred at room temperature for 12 hours. Ethyl acetate was added to the reaction solution, and the mixture was washed with water and a brine successively, and dried over anhydrous sodium sulfate. The solvent was removed under reduced pressure, and the residue was then purified by silica gel column chromatography (ethyl acetate:hexane=1:1), to obtain the title compound as a colorless oil (220 mg).

$^1$H-NMR (400 MHz, CDCl$_3$) δ 3.48 (1H, d, J=9.1 Hz), 3.51 (1H, t, J=8.5 Hz), 3.78 (3H, s), 3.80 (3H, s), 3.85 (3H, s), 3.90 (1H, dd, J=8.5, 8.2 Hz), 3.98 (1H, t, J=8.2 Hz), 6.89 (2H, d, J=9.1 Hz), 7.16 (2H, d, J=9.1 Hz).

Reference Example 23-2

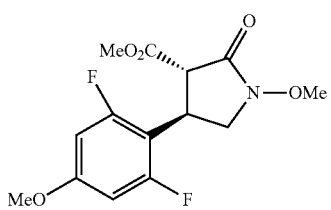

[Chemical Formula 84]

(3S*,4R*)-4-(2,6-Difluoro-4-methoxyphenyl)-1-methoxy-2-oxopyrrolidine-3-carboxylic acid methyl ester The same method as in Reference Example 23-1 was performed using (3S*,4R*)-4-(2,6-difluoro-4-methoxyphenyl)-1-hydroxy-2-oxopyrrolidine-3-carboxylic acid methyl ester in place of (3R*,4S*)-1-hydroxy-4-(4-methoxyphenyl)-2-oxopyrrolidine-3-carboxylic acid methyl ester to obtain the title compound.

$^1$H-NMR (400 MHz, CDCl$_3$) δ 3.62 (3H, s), 3.62-3.91 (10H, m), 6.43-6.50 (2H, m).

Reference Example 24-1

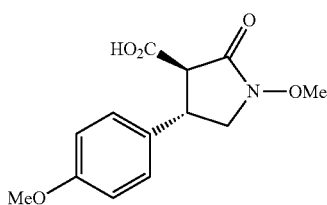

[Chemical Formula 85]

(3R*,4S*)-1-Methoxy-4-(4-methoxyphenyl)-2-oxopyrrolidine-3-carboxylic acid

The same method as in Reference Example 8-1 was performed using (3R*,4S*)-1-methoxy-4-(4-methoxyphenyl)-2-oxopyrrolidine-3-carboxylic acid methyl ester in place of (−)-(3S*,4R*)-4-(4-methoxyphenyl)-2-oxopyrrolidine-3-carboxylic acid methyl ester to obtain the title compound.

$^1$H-NMR (400 MHz, CDCl$_3$) δ 3.47 (1H, d, J=9.1 Hz), 3.60 (1H, t, J=8.5 Hz), 3.80 (3H, s), 3.88 (3H, s), 3.85-3.93 (1H, m), 3.99 (1H, t, J=8.8 Hz), 6.90 (2H, d, J=9.1 Hz), 7.23 (2H, d, J=9.1 Hz).

Reference Example 24-2

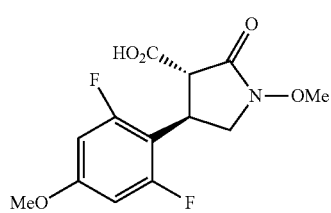

[Chemical Formula 86]

(3S*,4R*)-4-(2,6-Difluoro-4-methoxyphenyl)-1-methoxy-2-oxopyrrolidine-3-carboxylic acid The same method as in Reference Example 8-1 was performed using (3S*,4R*)-4-(2,6-difluoro-4-methoxyphenyl)-1-methoxy-2-oxopyrrolidine-3-carboxylic acid methyl ester in place of (−)-(3S*,4R*)-4-(4-methoxyphenyl)-2-oxopyrrolidine-3-carboxylic acid methyl ester to obtain the title compound.

$^1$H-NMR (400 MHz, CDCl$_3$) δ3.68-3.91 (9H, m), 4.18-4.26 (1H, m), 6.46-6.52 (2H, m).

Reference Example 25-1

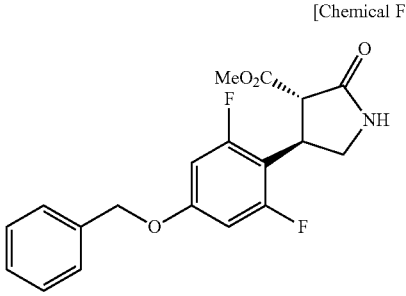

[Chemical Formula 87]

(3S*,4R*)-4-[4-(Benzyloxy)-2,6-difluorophenyl]-2-oxopyrrolidine-3-carboxylic acid methyl ester Potassium carbonate (268 mg) and benzyl bromide (0.23 mL) were added to a solution of (3S*,4R*)-4-(2,6-difluoro-4-hydroxyphenyl)-2-oxopyrrolidine-3-carboxylic acid methyl ester (500 mg) in N,N-dimethylformamide (4 mL), to produce a reaction solution. The reaction solution was stirred at room temperature for 25 hours. A saturated aqueous ammonium chloride solution was added to the reaction solution, and the mixture was extracted with ethyl acetate. The organic layer was washed with water and a brine successively, and dried over anhydrous sodium sulfate. The solvent was removed under reduced pressure, and the residue was then purified by silica gel column chromatography (hexane:ethyl acetate=4:1), to obtain the title compound as a colorless oil (643 mg).

$^1$H-NMR (400 MHz, CDCl$_3$) δ 3.50 (1H, t, J=8.5 Hz), 3.66 (1H, t, J=8.5 Hz), 3.76-3.80 (1H, m), 3.78 (3H, s), 4.46 (1H, q, J=9.5 Hz), 5.02 (2H, s), 5.89 (1H, brs), 6.54 (2H, d, J=10.3 Hz), 7.36-7.40 (5H, m).

Reference Example 26-1

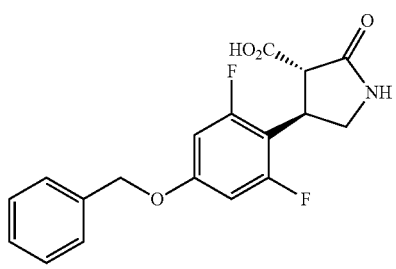

[Chemical Formula 88]

(3S*,4R*)-4-[4-(Benzyloxy)-2,6-difluorophenyl]-2-oxopyrrolidine-3-carboxylic acid The same method as in Reference Example 8-1 was performed using (3S*,4R*)-4-[4-(benzyloxy)-2,6-difluorophenyl]-2-oxopyrrolidine-3-carboxylic acid methyl ester to obtain the title compound.

$^1$H-NMR (400 MHz, DMSO-d$_6$) δ 3.25 (1H, t, J=9.4 Hz), 3.43 (1H, d, J=10.3 Hz), 3.56 (1H, d, J=9.1 Hz), 4.15 (1H, q, J=9.4 Hz), 5.11 (2H, s), 6.85 (2H, d, J=10.9 Hz), 7.32-7.44 (5H, m), 8.18 (1H, s), 12.76 (1H, brs).

Reference Example 27-1

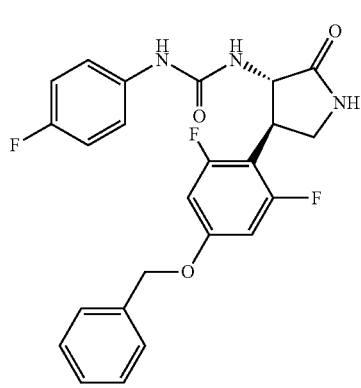

[Chemical Formula 89]

1-{(3S*,4R*)-4-[4-(Benzyloxy)-2,6-difluorophenyl]-2-oxopyrrolidin-3-yl}-3-(4-fluorophenyl)urea The same method as in Example 1-1 was performed using (3S*,4R*)-4-[4-(benzyloxy)-2,6-difluorophenyl]-2-oxopyrrolidine-3-carboxylic acid in place of (−)-(3S*,4R*)-4-(4-methoxyphenyl)-2-oxopyrrolidine-3-carboxylic acid to obtain the title compound.

$^1$H-NMR (400 MHz, DMSO-d$_6$) δ 3.27-3.32 (1H, m), 3.44 (1H, t, J=8.9 Hz), 3.79 (1H, q, J=9.8 Hz), 4.56 (1H, dd, J=11.0, 8.6 Hz), 5.10 (2H, s), 6.46 (1H, d, J=8.6 Hz), 6.82 (2H, d, J=10.4 Hz), 6.99-7.05 (2H, m), 7.30-7.44 (7H, m), 8.05 (1H, s), 8.66 (1H, s).

The same method as in Reference Example 27-1 was performed using a corresponding carboxylic acid substance to obtain the following Reference Examples 27-2 to 27-4. The structures and spectral data thereof are shown in Table 42.

TABLE 42

| Ref. No | Str. | Chemical name | P. D. |
|---|---|---|---|
| 27-2 | | 1-[(3S*,4R*)-4-(4-benzyloxy-2,6-difluorophenyl)-2-oxopyrrolidin-3-yl]-3-phenylurea | $^1$H-NMR (400 MHz, CDCl$_3$) δ 3.56-3.61 (2H, m), 4.05-4.11 (1H, m), 4.67 (1H, t, J = 8.9 Hz), 4.99 (2H, s), 5.88 (1H, brs), 6.34 (1H, brs), 6.51 (2H, d, J = 10.4 Hz), 6.92 (1H, t, J = 7.6 Hz), 7.13 (1H, t, J = 7.6 Hz), 7.23 (2H, d, J = 7.6 Hz), 7.30-7.40 (5H, m), 7.46 (1H, brs). |

TABLE 42-continued

| Ref. No | Str. | Chemical name | P. D. |
|---|---|---|---|
| 27-3 | | (3,5-difluoro-4-{(3R*,4S*)-4-[3-(4-fluorophenyl)ureido]-5-oxopyrrolidin-3-yl}phenyl)(methyl)carbamic acid tert-butyl ester | $^1$H-NMR (400 MHz, CDCl$_3$) δ 1.49 (9H, s), 3.25 (3H, s), 3.59-3.71 (2H, m), 4.18-4.26 (1H, m), 4.54-4.59 (1H, m), 5.75 (1H, brs), 6.03 (1H, brs), 6.80-6.85 (2H, m), 6.92 (2H, d, J = 10.4 Hz), 7.13-7.18 (2H, m), 7.29 (1H, brs). |
| 27-4 | | (−)-1-[(3S*,4R*)-4-(1-benzyl-6-fluoroindolin-5-yl)-2-oxopyrrolidin-3-yl]-3-(4-fluorophenyl)urea | $^1$H-NMR (400 MHz, DMSO-d$_6$) δ 2.84 (2H, t, J = 8.5 Hz), 3.13 (1H, t, J = 9.7 Hz), 3.27-3.29 (2H, m), 3.38 (1H, t, J = 8.5 Hz), 3.56-3.64 (1H, m), 4.25 (2H, s), 4.48 (1H, dd, J = 11.5, 9.1 Hz), 6.36-6.40 (2H, m), 7.03 (2H, t, J = 9.1 Hz), 7.14 (1H, d, J = 7.9 Hz), 7.25-7.37 (7H, m), 7.88 (1H, s), 8.55 (1H, s). MS (ESI$^+$) m/z: 463 (MH$^+$). [α]$_D^{22}$ = −155 (c 0.10, EtOH) |

Reference Example 28-1

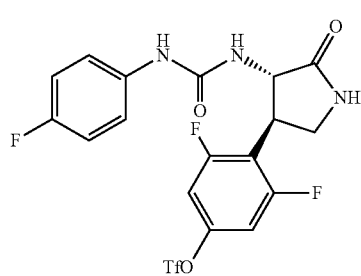

[Chemical Formula 90]

Trifluoromethanesulfonoc acid 3,5-difluoro-4-{(3R*,4S*)-4-[3-(4-fluorophenyl)ureido]-5-oxopyrrolidin-3-yl}phenyl ester To a solution of 1-[(3S*,4R*)-4-(2,6-difluoro-4-hydroxyphenyl)-2-oxopyrrolidin-3-yl]-3-(4-fluorophenyl)urea (365 mg) in dichloromethane (5 mL), pyridine (0.4 mL) and trifluoromethanesulfonic anhydride (0.25 mL) were added under an argon atmosphere under ice-cooling to produce a reaction solution. The reaction solution was stirred at room temperature for 3 hours. Water was added to the reaction solution, the mixture was extracted with ethyl acetate, and the extract was washed with water and a brine, and dried over anhydrous sodium sulfate. The solvent was removed under reduced pressure, and the residue was then purified by silica gel column chromatography (hexane:ethyl acetate=4:1 followed by ethyl acetate), to obtain the title compound as a brown oil (388 mg).

$^1$H-NMR (400 MHz, DMSO-d$_6$) δ 3.36 (1H, t, J=9.5 Hz), 3.52 (1H, t, J=9.2 Hz), 3.93 (1H, q, J=9.6 Hz), 4.55 (1H, dd, J=10.4, 7.9 Hz), 6.51 (1H, d, J=7.9 Hz), 6.98-7.04 (2H, m), 7.27-7.33 (2H, m), 7.58 (2H, d, J=8.6 Hz), 8.13 (1H, s), 8.74 (1H, s).

MS (ESI$^+$) m/z: 498 (MH$^+$).

Reference Example 29-1

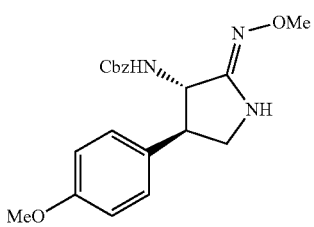

[Chemical Formula 91]

[(3S*,4R*,Z)-2-(Methoxyimino)-4-(4-methoxyphenyl)pyrrolidin-3-yl]carbamic acid benzyl ester Triethyloxonium hexafluoro phosphate (446 mg) was added to a suspension of (−)-[(3S*,4R*)-4-(4-methoxyphenyl)-2-oxopyrrolidin-3-yl]carbamic acid benzyl ester (500 mg) in dichloromethane (3.7 mL) to produce a reaction solution. The reaction solution was stirred at room temperature for 20 hours. After that, a saturated aqueous sodium hydrogen carbonate solution was added, and the reaction solution was stirred at room temperature for 30 minutes, and extracted with dichloromethane. The organic layer was dried over anhydrous sodium sulfate, and the solvent was removed under reduced pressure to obtain [(3R*,4S*)-5-ethoxy-3-(4-methoxyphenyl)-3,4-dihydro-2H-pyrrol-4-yl]carbamic acid benzyl ester that was an intermediate as a yellow oil.

O-methylhydroxylamine hydrochloride (91 mg) was added to a solution of [(3R*,4S*)-5-ethoxy-3-(4-methoxyphenyl)-3,4-dihydro-2H-pyrrolo-4-yl]carbamic acid benzyl ester (325 mg) in methanol (2 mL) to produce a reaction solution. The reaction solution was stirred at room temperature for 3.5 hours. After that, a saturated aqueous sodium hydrogen carbonate solution was added to the reaction solution under ice-cooling, and the mixture was extracted with ethyl acetate. The organic layer was washed with a brine, and dried over anhydrous sodium sulfate. The solvent was removed under reduced pressure, and the residue was then purified by silica gel column chromatography (ethyl acetate:hexane=2:1), to obtain the title compound as a colorless oil (228 mg).

$^1$H-NMR (400 MHz, DMSO-d$_6$) δ 3.15 (1H, t, J=9.1 Hz), 3.22-3.30 (1H, m), 3.45 (1H, t, J=8.2 Hz), 3.59 (3H, s), 3.72 (3H, s), 4.60 (1H, t, J=9.7 Hz), 4.96 (2H, s), 6.63 (1H, s), 6.86 (2H, d, J=8.5 Hz), 7.20-7.34 (7H, m), 7.59 (1H, d, J=9.1 Hz).

The same method as in Reference Example 29-1 was performed using a corresponding Cbz substance and amine to obtain the following Reference Examples 29-2 to 29-7.

The structures and spectral data thereof are shown in Tables 43 to 44.

TABLE 43

| Ref. No | Str. | Chemical name | P. D. |
|---|---|---|---|
| 29-2 | | [(3S*,4R*,Z)-4-(2-fluoro-4-methoxyphenyl)-2-(methoxyimino)pyrrolidin-3-yl] carbamic acid benzyl ester | $^1$H-NMR (400 MHz, CDCl$_3$) δ 3.35 (1H, t, J = 9.2 Hz), 3.48-3.69 (2H, m), 3.70-3.81 (6H, m), 4.92-5.11 (5H, m), 6.51-6.72 (2H, m), 7.24-7.34 (6H, m). |
| 29-3 | | [(3S*,4R*,Z)-4-(2,6-difluoro-4-methoxyphenyl)-2-(methoxyimino)pyrrolidin-3-yl] carbamic acid benzyl ester | $^1$H-NMR (400 MHz, CDCl$_3$) δ 3.52-3.58 (2H, m), 3.60-3.81 (7H, m), 4.94-5.18 (5H, m), 6.40-6.48 (2H, m), 7.26-7.31 (5H, m). |
| 29-4 | | {(3S*,4R*,Z)-2-[(2-hydroxyethoxy)imino]-4-(4-methoxyphenyl)pyrrolidin-3-yl} carbamic acid benzyl ester | $^1$H-NMR (400 MHz, DMSO-d$_6$) δ 3.16 (1H, t, J = 9.1 Hz), 3.24-3.30 (1H, m), 3.47 (1H, t, J = 8.2 Hz), 3.53-3.59 (2H, m), 3.72 (3H, s), 3.80 (2H, t, J = 5.1 Hz), 4.44 (1H, t, J = 5.8 Hz), 4.60 (1H, t, J = 9.7 Hz), 4.96 (2H, s), 6.63 (1H, s), 6.86 (2H, d, J = 8.5 Hz), 7.20-7.34 (7H, m), 7.61 (1H, d, J = 9.1 Hz). |
| 29-5 | | {(3S*,4R*,Z)-4-(2,6-difluoro-4-methoxyphenyl)-2-[(2-hydroxyethoxy)imino]pyrrolidin-3-yl} carbamic acid benzyl ester | $^1$H-NMR (400 MHz, CDCl$_3$) δ 2.87 (1H, brs), 3.50-3.64 (2H, m), 3.65-3.80 (4H, m), 3.83-3.90 (2H, m), 4.08 (1H, dd, J = 4.3, 4.3 Hz), 4.80-5.15 (3H, m), 5.13 (1H, dd, J = 9.8, 8.0 Hz), 5.25 (1H, s), 6.40-6.50 (2H, m), 7.26-7.32 (5H, m). |

TABLE 44

| Ref. No | Str. | Chemical name | P. D. |
|---|---|---|---|
| 29-6 | (structure) | [(3R*,4S*)-3-(2,6-difluoro-4-methoxyphenyl)-5-(methylamino)-3,4-dihydro-2H-pyrrolo-4-yl] carbamic acid benzyl ester | $^1$H-NMR (400 MHz, DMSO-$d_6$) δ 2.66 (3H, d, J = 4.9 Hz), 3.34-3.43 (1H, m), 3.45-3.56 (1H, m), 3.63-3.73 (1H, m), 3.75 (3H, s), 4.86 (1H, t, J = 9.5 Hz), 4.92 (1H, d, J = 12.8 Hz), 4.99 (1H, d, J = 12.8 Hz), 5.99-6.06 (1H, m), 6.70 (2H, d, J = 10.4 Hz), 7.22-7.36 (5H, m), 7.69 (1H, d, J = 9.2 Hz). |
| 29-7 | (structure) | ((3S*,4R*,Z)-2-{[(tert-butyldimethylsilyl)oxy]imino}-4-(4-methoxyphenyl)pyrrolidin-3-yl) carbamic acid benzyl ester | $^1$H-NMR (400 MHz, DMSO-$d_6$) δ 0.05 (6H, s), 0.90 (9H, s), 3.18 (1H, t, J = 9.1 Hz), 3.22-3.40 (1H, m), 3.49 (1H, t, J = 8.2 Hz), 3.72 (3H, s), 4.55 (1H, t, J = 9.7 Hz), 4.91 (1H, d, J = 13.3 Hz), 5.03 (1H, d, J = 13.3 Hz), 6.49 (1H, s), 6.86 (2H, d, J = 8.5 Hz), 7.20-7.33 (7H, m), 7.58 (1H, d, J = 9.1 Hz). |

The same method as in Reference Example 29-1 was performed using a corresponding Cbz substance and amine to obtain the following Reference Examples 29-8 to 29-13. The structures and spectral data thereof are shown in Tables 45 to 46.

TABLE 45

| Ref. No | Str. | Chemical name | Spectrum data |
|---|---|---|---|
| 29-8 | (structure) | ((3S*,4R*,Z)-2-{[(tert-butyldimethylsilyl)oxy]imino}-4-(2,6-difluoro-4-methoxyphenyl)pyrrolidin-3-yl) carbamic acid benzyl ester | $^1$H-NMR (400 MHz, CDCl$_3$) δ 0.15 (6H, s), 0.94 (9H, s), 3.50-3.62 (2H, m), 3.65-3.80 (4H, m), 5.01 (2H, brs), 5.06-5.13 (1H, m), 5.31 (1H, s), 6.45 (2H, d, J = 10.4 Hz), 7.25-7.35 (5H, m). |
| 29-9 | (structure) | [(3S*,4R*,Z)-4-(2,6-difluoro-4-methoxyphenyl)-2-(morpholinoimino)pyrrolidin-3-yl] carbamic acid benzyl ester | $^1$H-NMR (400 MHz, CDCl$_3$) δ 2.66-2.72 (4H, m), 3.52-3.82 (10H, m), 4.90-5.07 (3H, m), 5.27 (1H, brs), 5.70 (1H, brs), 6.40-6.50 (2H, m), 7.25-7.35 (5H, m). |
| 29-10 | (structure) | {(3R*,4S*)-3-(2,6-difluoro-4-methoxyphenyl)-5-[(1-methyl-1H-pyrazol-3-yl)amino]-3,4-dihydro-2H-pyrrol-4-yl} carbamic acid benzyl ester | $^1$H-NMR (400 MHz, CDCl$_3$) δ 3.50-3.80 (6H, m), 3.82 (3H, s), 4.95-5.15 (3H, m), 6.06 (1H, s), 6.42-6.52 (2H, m), 7.21 (1H, s), 7.25-7.40 (5H, m), 8.50 (1H, brs). |

TABLE 45-continued

| Ref. No | Str. | Chemical name | Spectrum data |
|---|---|---|---|
| 29-11 | | [(3R*,4S*)-3-(2,6-difluoro-4-methoxyphenyl)-5-(phenylamino)-3,4-dihydro-2H-pyrrol-4-yl] carbamic acid benzyl ester | $^1$H-NMR (400 MHz, CDCl$_3$) δ 3.50-3.90 (5H, m), 4.18-4.32 (1H, m), 4.90-5.20 (3H, m), 6.40-6.50 (2H, m), 7.10-7.40 (10H, m), 7.55 (1H, brs). |

TABLE 46

| Ref. No | Str. | Chemical name | Spectrum data |
|---|---|---|---|
| 29-12 | | {(3S*,4R*,Z)-4-(6-fluoro-2,3-dihydrobenzofuran-5-yl)-2-[(2-hydroxyethoxy)imino]pyrrolidin-3-yl carbamic acid benzyl ester | $^1$H-NMR (400 MHz, CDCl$_3$) δ 3.00 (1H, brs), 3.10-3.20 (2H, m), 3.32-3.36 (1H, m), 3.50-3.65 (2H, m), 3.86 (2H, s), 4.07-4.09 (1H, m), 4.93-5.11 (4H, m), 5.23 (1H, s), 6.50 (1H, d, J = 10.4 Hz), 7.15 (1H, d, J = 6.12 Hz), 7.26-7.40 (5H, m) |
| 29-13 | | 3-((Z)-{(3S,4R)-3-[(benzyloxycarbonyl)amino]-4-(2,6-difluoro-4-methoxyphenyl)pyrrolidin-2-ylidene} amino) propanoic acid ethyl ester | $^1$H-NMR (CDCl$_3$) δ: 1.28 (3H, t, J = 7.3 Hz), 2.64-2.78 (1H, m), 3.50-4.20 (9H, m), 4.02-4.09 (1H, m), 4.65-4.75 (1H, m), 4.95-5.20 (3H, m), 5.75 (1H, brs), 6.42-6.52 (2H, m), 7.27-7.37 (5H, m). |

Reference Example 30-1

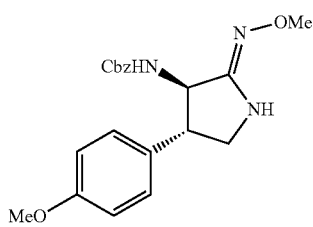

[Chemical Formula 92]

[(3R*,4S*,Z)-2-(Methoxyimino)-4-(4-methoxyphenyl)pyrrolidin-3-yl]carbamic acid benzyl ester The same method as in Reference Example 29-1 was performed using (+)-[(3R*,4S*)-4-(4-methoxyphenyl)-2-oxopyrrolidin-3-yl]carbamic acid benzyl ester in place of (−)-[(3S*,4R*)-4-(4-methoxyphenyl)-2-oxopyrrolidin-3-yl]carbamic acid benzyl ester to obtain the title compound.

$^1$H-NMR (400 MHz, DMSO-d$_6$) δ 3.15 (1H, t, J=9.1 Hz), 3.22-3.30 (1H, m), 3.45 (1H, t, J=8.2 Hz), 3.59 (3H, s), 3.72 (3H, s), 4.60 (1H, t, J=9.7 Hz), 4.96 (2H, s), 6.63 (1H, s), 6.86 (2H, d, J=8.5 Hz), 7.20-7.34 (7H, m), 7.59 (1H, d, J=9.1 Hz).

Reference Example 31-1

[Chemical Formula 93]

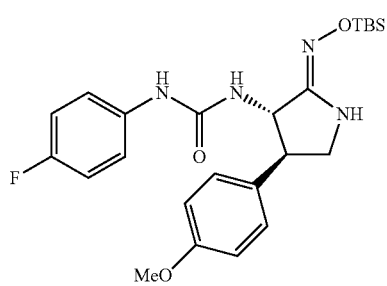

1-((3S*,4R*,Z)-2-{[(tert-Butyldimethylsilyl)oxy]imino}-4-(4-methoxyphenyl)pyrrolidin-3-yl)-3-(4-fluorophenyl)urea The same method as in Example 32-1 was followed using ((3S*,4R*,Z)-2-{[(tert-butyldimethylsilyl)oxy]imino}-4-(4-methoxyphenyl)pyrrolidin-3-yl)carbamic acid benzyl ester in place of [(3S*,4R*,Z)-2-(methoxyimino)-4-(4-methoxyphenyl)pyrrolidin-3-yl)carbamic acid benzyl ester to obtain the title compound.

$^1$H-NMR (400 MHz, DMSO-$d_6$) δ 0.04 (3H, s), 0.05 (3H, s), 0.89 (9H, s), 3.17 (1H, t, J=8.8 Hz), 3.28-3.37 (1H, m), 3.53 (1H, t, J=8.5 Hz), 3.71 (3H, s), 4.74 (1H, t, J=9.1 Hz), 6.34 (1H, d, J=9.1 Hz), 6.56 (1H, s), 6.86 (2H, d, J=8.5 Hz), 7.00-7.04 (2H, m), 7.27 (2H, d, J=8.5 Hz), 7.30-7.34 (2H, m), 8.45 (1H, s).

MS (FD$^+$) m/z: 472 (M$^+$).

Reference Example 31-2

[Chemical Formula 94]

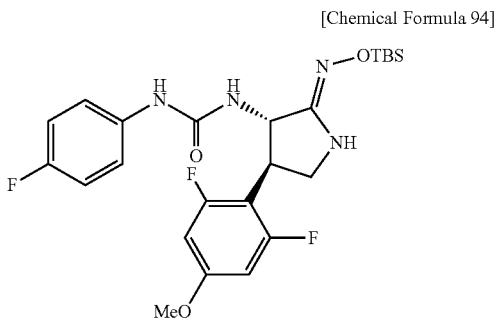 [SMILES: COc1cc(F)c([C@@H]2CN/C(=N\O[Si](C)(C)C(C)(C)C)[C@H]2NC(=O)Nc2ccc(F)cc2)c(F)c1]

1-((3S*,4R*,Z)-2-{[(tert-Butyldimethylsilyl)oxy]imino}-4-(2,6-difluoro-4-methoxyphenyl)pyrrolidin-3-yl)-3-(4-fluorophenyl)urea The same method as in Example 32-1 was followed using ((3S*,4R*,Z)-2-{[(tert-butyldimethylsilyl)oxy]imino}-4-(2,6-difluoro-4-methoxyphenyl)pyrrolidin-3-yl)carbamic acid benzyl ester in place of [(3S*,4R*,Z)-2-(methoxyimino)-4-(4-methoxyphenyl)pyrrolidin-3-yl]carbamic acid benzyl ester to obtain the title compound.

$^1$H-NMR (400 MHz, CDCl$_3$) δ 0.12 (6H, s), 0.93 (9H, s), 3.57-3.64 (2H, m), 3.73-3.82 (1H, m), 3.76 (3H, s), 5.12-5.21 (1H, m), 5.38 (1H, brs), 5.47 (1H, s), 6.46 (2H, d, J=10.8 Hz), 6.86-6.93 (2H, m), 7.17-7.22 (2H, m), 7.39 (1H, brs).

Reference Example 32-1

[Chemical Formula 95]

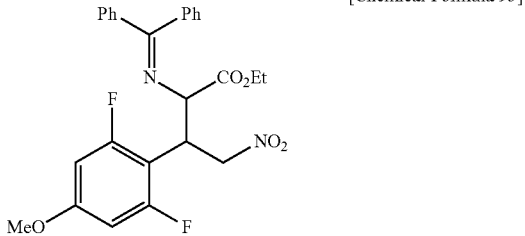

3-(2,6-Difluoro-4-methoxyphenyl)-2-[(diphenylmethylene)amino]-4-nitrobutanoic acid ethyl ester Lithium diisopropylamide (1.1 mL, 1.05 M in tetrahydrofuran/hexane) was added to a solution of 2-[(diphenylmethylene)amino]acetic acid ethyl ester (300 mg) in tetrahydrofuran (2.3 mL) at −78° C. to produce a reaction solution. The reaction solution was stirred for 1 hour, a solution of (E)-1,3-difluoro-5-methoxy-2-(2-nitrovinyl)benzene (241 mg) in tetrahydrofuran was added, and the reaction solution was stirred at the same temperature for 15 minutes. The temperature of the reaction solution was gradually heated up to room temperature, and the reaction solution was stirred for 30 minutes. Water was added to the reaction solution, and the mixture was extracted with ethyl acetate. The organic layer was washed with a brine, and dried over sodium sulfate. The solvent was removed, and the residue was purified by silica gel column chromatography (hexane:ethyl acetate=2:1), to obtain the title compound as a yellow oil (543 mg).

$^1$H-NMR (400 MHz, CDCl$_3$) δ 1.12 (3H, t, J=7.3 Hz), 3.73 (3H, s), 4.00-4.06 (2H, m), 4.43 (1H, d, J=7.8 Hz), 4.73-4.95 (3H, m), 6.36 (2H, d, J=10.4 Hz), 7.00-7.05 (2H, m), 7.31-7.38 (6H, m), 7.81-7.85 (2H, m).

Reference Example 32-2

[Chemical Formula 96]

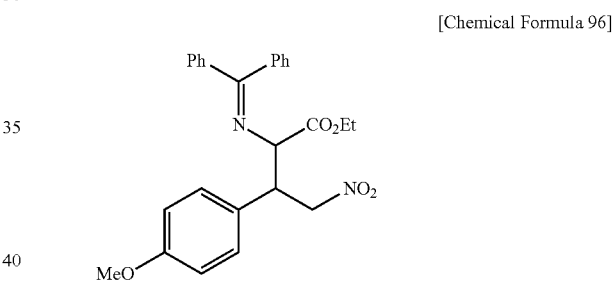

2-[(Diphenylmethylene)amino]-3-(4-methoxyphenyl)-4-nitrobutanoic acid ethyl ester The same method as in Reference Example 32-1 was performed using (E)-1-methoxy-4-(2-nitrovinyl)benzene in place of (E)-1,3-difluoro-5-methoxy-2-(2-nitrovinyl)benzene to obtain the title compound.

$^1$H-NMR (400 MHz, CDCl$_3$) δ 1.19 (3H, t, J=6.7 Hz), 3.76 (3H, s), 3.90-4.36 (6H, m), 7.05 (2H, d, J=8.6 Hz), 7.24-7.47 (10H, m), 7.63 (2H, d, J=8.6 Hz).

Reference Example 33-1

[Chemical Formula 97]

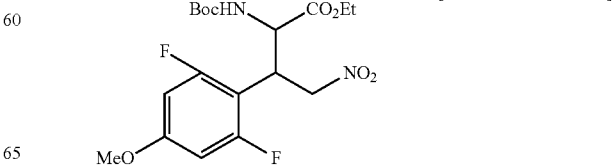

2-[(tert-Butoxycarbonyl)amino]-3-(2,6-difluoro-4-methoxyphenyl)-4-nitrobutanoic acid ethyl ester Acetic acid (4.2 mL) and water (0.8 mL) were added to 3-(2,6-difluoro-4-methoxyphenyl)-2-[(diphenylmethylene)amino]-4-nitrobutyricacidethyl ester (530 mg) at room temperature to produce a first reaction solution. The first reaction solution was stirred at 60° C. for 7 hours. The reaction solution was concentrated under reduced pressure, a saturated aqueous sodium hydrogen carbonate solution was added to the residue until the pH was 8, to produce a second reaction solution. After that, tetrahydrofuran (5.0 mL) was added to the second reaction solution, di-tert-butyl dicarbonate (290 mg) was then added, and the mixture was stirred at room temperature for 16 hours. The second reaction solution was extracted with ethyl acetate, and the organic layer was washed with a brine, and dried over anhydrous sodium sulfate. The solvent was removed, and the residue was purified by silica gel column chromatography (toluene:ethyl acetate=2:1), to obtain the title compound as a white solid (315 mg).

$^1$H-NMR (400 MHz, CDCl$_3$) δ 1.08 (3H, brt), 1.46 (9H, s), 3.78 (3H, s), 4.00-4.10 (2H, m), 4.22-4.33 (1H, m), 4.71 (1H, brt), 4.88 (2H, d, J=7.9 Hz), 5.22 (1H, brd), 6.45 (2H, d, J=10.4 Hz).

Reference Example 33-2

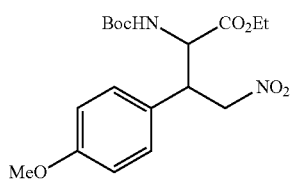

[Chemical Formula 98]

2-[(tert-Butoxycarbonyl)amino]-3-(4-methoxyphenyl)-4-nitrobutanoic acid ethyl ester The same method as in Reference Example 33-1 was performed using 2-[(Diphenylmethylene)amino]-3-(4-methoxyphenyl)-4-nitrobutanoic acid ethyl ester in place of 3-(2,6-difluoro-4-methoxyphenyl)-2-[(diphenylmethylene)amino]-4-nitrobutanoic acid ethyl ester to obtain the title compound.

$^1$H-NMR (400 MHz, CDCl$_3$) δ 1.08 (3H, brt), 1.46 (9H, s), 3.78 (3H, s), 3.82 (1H, q, J=8.6 Hz), 4.02 (2H, d, J=6.7 Hz), 4.55 (1H, t, J=6.7 Hz), 4.77 (1H, dd, J=13.4, 9.2 Hz), 4.85 (1H, dd, J=13.4, 5.5 Hz), 5.12 (1H, brs), 6.85 (2H, d, J=8.6 Hz), 7.09 (2H, d, J=8.6 Hz).

Reference Example 34-1

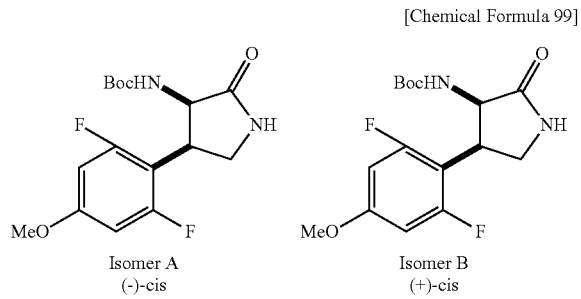

[Chemical Formula 99]

Isomer A  
(−)-cis

Isomer B  
(+)-cis (−)-[4-(2,6-Difluoro-4-methoxyphenyl)-2-oxopyrrolidin-3-yl]carbamic acid tert-butyl ester (+)-[4-(2,6-Difluoro-4-methoxyphenyl)-2-oxopyrrolidin-3-yl]carbamic acid tert-butyl ester 2-[(tert-Butoxycarbonyl)amino]-3-(2,6-difluoro-4-methoxyphenyl)-4-nitrobutanoic acid ethyl ester was used in place of (R*)-2-[1-(4-methoxyphenyl)-2-nitroethyl]malonic acid dimethyl ester, and (±)-[4-(2,6-difluoro-4-methoxyphenyl)-2-oxopyrrolidin-3-yl]carbamic acid tert-butyl ester was obtained in the same method as in Reference Example 7-1. The obtained compound was subjected to optical resolution by high performance liquid chromatography (hexane:methyl tert-butyl ether:ethanol=45:25:30, flow rate: 15.0 mL) using a column for separation of enantiomers (CHIRALPAK ID). An isomer A(−) with a retention time of 13.4 minutes and an isomer B(+) with a retention time of 22.5 minutes that were the title compounds were each obtained as a white solid by the optical resolution.

Isomer A(−):  
$^1$H-NMR (400 MHz, CDCl$_3$) δ 1.26 (9H, s), 3.40 (1H, d, J=10.4 Hz), 3.78 (3H, s), 3.85 (1H, d, J=10.4, 8.6 Hz), 4.46 (1H, t, J=6.6 Hz), 4.60 (1H, dd, J=9.8, 6.1 Hz), 4.94 (1H, d, J=5.5 Hz), 5.75 (1H, s) 6.44 (2H, d, J=10.0 Hz).  
$[α]_D^{25}$=−131 (c 0.10, EtOH)

Isomer B(+):  
$^1$H-NMR (400 MHz, CDCl$_3$) δ 1.26 (9H, s), 3.40 (1H, d, J=10.4 Hz), 3.78 (3H, s), 3.85 (1H, d, J=10.4, 8.6 Hz), 4.46 (1H, t, J=6.6 Hz), 4.60 (1H, dd, J=9.8, 6.1 Hz), 4.94 (1H, d, J=5.5 Hz), 5.90 (1H, s) 6.44 (2H, d, J=10.0 Hz).  
$[α]_D^{25}$=+144 (c 0.10, EtOH)

Reference Example 34-2

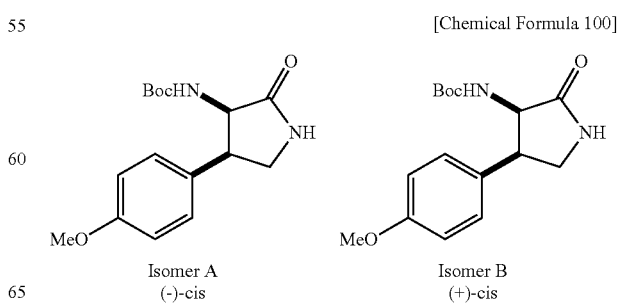

[Chemical Formula 100]

Isomer A  
(−)-cis

Isomer B  
(+)-cis (−)-[4-(4-Methoxyphenyl)-2-oxopyrrolidin-3-yl]
carbamic acid tert-butyl ester (+)-[4-(4-Methoxyphenyl)-2-oxopyrrolidin-3-yl]
carbamic acid tert-butyl ester 2-[(tert-Butoxycarbonyl)amino]-3-(4-methoxyphenyl)-4-nitrobutanoic acid ethyl ester was used in place of (R*)-2-[1-(4-methoxyphenyl)-2-nitroethyl]malonic acid dimethyl ester, and (±)-[4-(4-methoxyphenyl)-2-oxopyrrolidin-3-yl] carbamic acid tert-butyl ester was obtained in the same method as in Reference Example 7-1. The obtained compound was subjected to optical resolution by high performance liquid chromatography (hexane:methyl tert-butyl ether:ethanol=45:25:30, flow rate: 15.0 mL) using a column for separation of enantiomers (CHIRALPAK ID). An isomer A(−) with a retention time of 7.5 minutes and an isomer B(+) with a retention time of 10.2 minutes that were the title compounds were each obtained as a white solid by the optical resolution.
Isomer A(−):
$^1$H-NMR (400 MHz, CDCl$_3$) δ 1.37 (9H, s), 3.56 (1H, d, J=9.8 Hz), 3.80 (3H, s), 3.84 (1H, dd, J=10.4, 6.1 Hz), 3.92 (1H, brs), 4.56 (2H, s), 5.75 (1H, s), 6.83 (2H, d, J=8.6 Hz), 7.10 (2H, d, J=8.6 Hz).
[α]$_D^{22}$=−88 (c 0.10, EtOH)
Isomer B(+):
$^1$H-NMR (400 MHz, CDCl$_3$) δ 1.37 (9H, s), 3.56 (1H, d, J=9.8 Hz), 3.80 (3H, s), 3.84 (1H, dd, J=10.4, 6.1 Hz), 3.92 (1H, brs), 4.56 (2H, s), 5.75 (1H, s), 6.83 (2H, d, J=8.6 Hz), 7.10 (2H, d, J=8.6 Hz).
[α]$_D^{22}$=+98 (c 0.10, EtOH)

Reference Example 35-1

[Chemical Formula 101]

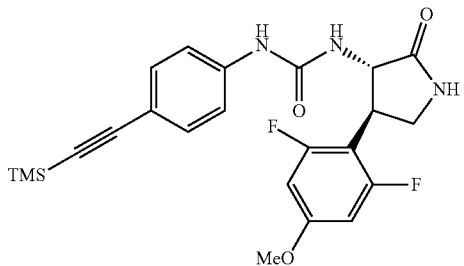

1-[(3S*,4R*)-4-(2,6-Difluoro-4-methoxyphenyl)-2-oxopyrrolidin-3-yl]-3-{4-[(trimethylsilyl)ethynyl]phenyl}urea Trimethylsilylacetylene (115 µL) and triethylamine (115 µL) were added to a solution of 1-[(3S*,4R*)-4-(2,6-difluoro-4-methoxyphenyl)-2-oxopyrrolidin-3-yl]-3-(4-iodophenyl)urea (80 mg), bis(triphenylphosphine)palladium(II) dichloride (11.5 mg), and copper(I) iodide (15.6 mg) in N,N-dimethylformamide (2 mL) to produce a reaction solution. The reaction solution was stirred at 50° C. for 9 hours. The reaction solution was concentrated under reduced pressure, and the residue was then purified by silica gel column chromatography (hexane:ethyl acetate=1:1, ethyl acetate, and ethyl acetate:methanol=4:1 in turn), to obtain the title compound as a colorless solid (67 mg).

$^1$H-NMR (400 MHz, CDCl$_3$) δ 0.22 (9H, s), 3.52-3.63 (2H, m), 3.75 (3H, s), 4.09 (1H, q, J=9.2 Hz), 4.65 (1H, dd, J=10.4, 7.4 Hz), 6.08 (1H, brs), 6.36-6.45 (3H, m), 7.16 (2H, d, J=8.6 Hz), 7.21 (2H, d, J=8.6 Hz), 7.81 (1H, brs).

Reference Example 36-1

[Chemical Formula 102]

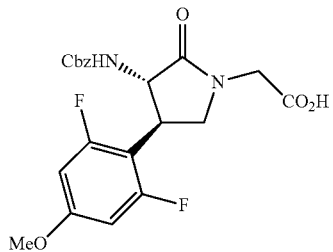

2-((3S*,4R*)-3-{[(Benzyloxy)carbonyl]amino}-4-(2,6-difluoro-4-methoxyphenyl)-2-oxopyrrolidin-1-yl)acetic acid A 2 mol/L sodium hydroxide aqueous solution (1.26 mL) was added to a solution of 2-((3S*,4R*)-3-{[(benzyloxy)carbonyl]amino}-4-(2,6-difluoro-4-methoxyphenyl)-2-oxopyrrolidin-1-yl)acetic acid ethyl ester (521 mg) in methanol (25 mL) to produce a reaction solution. The reaction solution was stirred at room temperature for 5 hours. A 1 mol/L Hydrochloric acid was added to the reaction solution to make the reaction solution acidic (pH: 1), and the mixture was extracted with ethyl acetate. The organic layer was washed with a brine, and dried over anhydrous sodium sulfate. The solvent was removed to obtain the title compound as a white solid (465 mg).
$^1$H-NMR (400 MHz, DMSO-d$_6$) δ 3.50-3.58 (2H, m), 3.72-3.79 (4H, m), 3.87 (1H, d, J=17.7 Hz), 4.11 (1H, d, J=17.7 Hz), 4.48 (1H, t, J=10.0 Hz), 4.94 (1H, d, J=12.2 Hz), 4.99 (1H, d, J=12.2 Hz), 6.78 (2H, d, J=10.4 Hz), 7.25-7.35 (5H, m), 7.74 (1H, d, J=9.2 Hz), 12.9 (1H, s).

Reference Example 37-1

[Chemical Formula 103]

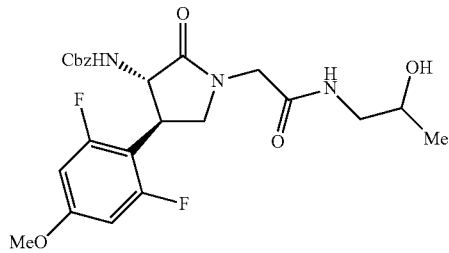

((3S*,4R*)-4-(2,6-Difluoro-4-methoxyphenyl)-1-{2-[(2-hydroxypropyl)amino]-2-oxoethyl}-2-oxopyrrolidin-3-yl)carbamic acid benzyl ester 1-Hydroxybenzotriazole (35 mg), 1-amino-2-propanol (20 µL), and 1-ethyl-3-(3-dimethylaminopropyl)carbodiimide (57 mg) were added to a solution of 2-((3S*,4R*)-3-{[(benzyloxy) carbonyl]amino}-4-(2,6-difluoro-4-methoxyphenyl)-2-oxopyrrolidin-1-yl)acetic acid (100 mg) in dichloromethane (1.0 mL) to produce a reaction solution. The reaction solution was stirred at room temperature for 4 hours. Water was added to the reaction solution, and the mixture was extracted with dichloromethane. The organic layer was washed with a brine, and dried over anhydrous sodium sulfate. The solvent was removed under reduced pressure, and the residue was then purified by silica gel column chromatography (ethyl acetate followed by ethyl acetate:methanol=4:1), to obtain the title compound (96 mg).

$^1$H-NMR (400 MHz, DMSO-d$_6$) δ 1.00 (3H, d, J=6.1 Hz), 2.98-3.05 (2H, m), 3.54 (2H, t, J=9.2 Hz), 3.60-3.66 (1H, m), 3.77-3.81 (4H, m), 4.04 (1H, d, J=16.5 Hz), 4.47 (1H, t, J=9.8 Hz), 4.68 (1H, q, J=2.0 Hz), 4.97 (2H, dd, J=17.4, 12.5 Hz), 6.76 (2H, d, J=11.0 Hz), 7.26-7.33 (5H, m), 7.73 (1H, d, J=9.2 Hz), 7.94 (1H, t, J=5.5 Hz).

Reference Example 37-2

[Chemical Formula 104]

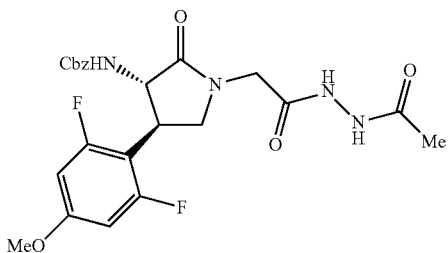

((3S*,4R*)-1-[2-(2-[(Acetyl hydrazinyl)-2-oxo-ethyl]-4-(2,6-difluoro-4-methoxyphenyl)-2-oxopyrrolidin-3-yl)carbamic acid benzyl ester The same method as in Reference Example 37-1 was performed using acetylhydrazine in place of 1-amino-2-propanol as amine to obtain the title compound.

$^1$H-NMR (400 MHz, DMSO-d$_6$) δ 1.84 (3H, s), 3.55 (2H, d, J=10.4 Hz), 3.76 (4H, s), 3.85 (1H, d, J=16.5 Hz), 4.12 (1H, d, J=16.5 Hz), 4.50 (1H, t, J=9.2 Hz), 4.97 (2H, dd, J=16.5, 12.2 Hz), 6.75 (2H, d, J=11.0 Hz), 7.25-7.33 (5H, m), 7.70 (1H, d, J=9.2 Hz), 7.94 (2H, s).

Reference Example 38-1

[Chemical Formula 105]

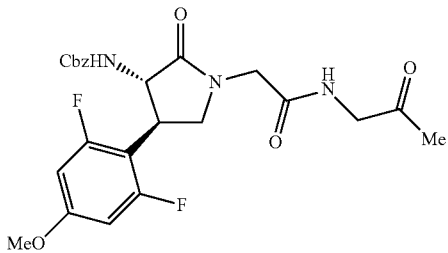

((3S*,4R*)-4-(2,6-Difluoro-4-methoxyphenyl)-2-oxo-1-{2-oxo-2-[(2-oxopropyl)amino]ethyl}pyrrolidin-3-yl)carbamic acid benzyl ester 2-Iodoxybenzoic acid (131 mg) was added to a solution of ((3S*,4R*)-4-(2,6-difluoro-4-methoxyphenyl)-1-{2-[(2-hydroxypropyl)amino]-2-oxoethyl}-2-oxopyrrolidin-3-yl)carbamic acid benzyl ester (96 mg) in dimethyl sulfoxide (2.0 mL), to produce a reaction solution. The reaction solution was stirred at room temperature for 18 hours. A saturated aqueous sodium hydrogen carbonate solution was added to the reaction solution, and the mixture was extracted with ethyl acetate. The organic layer was washed with a brine successively, and dried over anhydrous sodium sulfate. The solvent was removed to obtain the title compound (84 mg).

$^1$H-NMR (400 MHz, DMSO-d$_6$) δ 2.02 (3H, s), 3.46-3.54 (2H, m), 3.69 (1H, d, J=9.8 Hz), 3.73 (3H, s), 3.82 (1H, d, J=16.5 Hz), 3.91 (2H, d, J=5.5 Hz), 4.07 (1H, d, J=16.5 Hz), 4.45 (1H, t, J=11.0 Hz), 4.92 (2H, dd, J=16.5, 12.2 Hz), 6.72 (2H, d, J=10.4 Hz), 7.22-7.31 (5H, m), 7.67 (1H, d, J=9.2 Hz), 8.23 (1H, t, J=5.5 Hz).

Reference Example 39-1

[Chemical Formula 106]

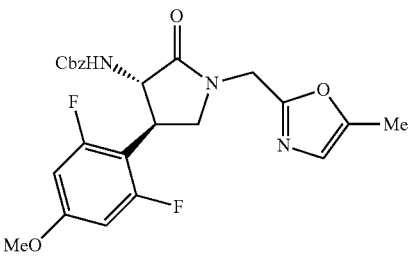

{(3S*,4R*)-4-(2,6-Difluoro-4-methoxyphenyl)-1-[(5-methyloxazol-2-yl)methyl]-2-oxopyrrolidin-3-yl}carbamic acid benzyl ester Triphenylphosphine (325 mg) and triethylamine (860 μL) were added to a solution of ((3S*,4R*)-4-(2,6-difluoro-4-methoxyphenyl)-2-oxo-1-{2-oxo-2-[(2-oxopropyl)amino]ethyl}pyrrolidin-3-yl) carbamic acid benzyl ester (76 mg) in carbon tetrachloride (7.8 mL) to produce a reaction solution. The reaction solution was stirred at 80° C. for 30 minutes, dichloromethane (2 mL) was added, and the reaction solution was stirred at 80° C. for 4 hours. A saturated aqueous sodium hydrogen carbonate solution was added to the reaction solution, and the mixture was extracted with dichloromethane. The organic layer was washed with water and a brine successively, and dried over anhydrous sodium sulfate. The solvent was removed under reduced pressure, and the residue was then purified by silica gel column chromatography (chloroform:methanol=9:1), to obtain the title compound (15 mg).

$^1$H-NMR (400 MHz, CDCl$_3$) δ 2.30 (3H, s), 3.58 (2H, brs), 3.77 (4H, s), 4.64 (2H, s), 4.75 (1H, dd, J=10.4, 7.3 Hz), 5.02 (2H, d, J=12.2 Hz), 5.22 (1H, brs), 6.45 (2H, d, J=9.8 Hz), 6.67 (1H, s), 7.27-7.35 (5H, m).

Reference Example 39-2

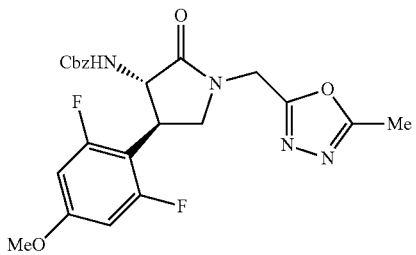

{(3S*,4R*)-4-(2,6-Difluoro-4-methoxyphenyl)-1-[(5-methyl-1,3, 4-oxadiazol-2-yl)methyl]-2-oxopyrrolidin-3-yl}carbamic acid benzyl ester Triphenylphosphine (151 mg), triethylamine (160 μL), and 1,1,1,2,2,2-hexachloroethane (136 mg) were added to a solution of {(3S*,4R*)-1-[2-(2-acetyl hydrazinyl)-2-oxoethyl]-4-(2,6-difluoro-4-methoxyphenyl)-2-oxopyrrolidin-3-yl}carbamic acid benzyl ester (113 mg) in dichloromethane (11.5 mL) to produce a reaction solution. The reaction solution was stirred at room temperature for 3 hours. A saturated aqueous sodium hydrogen carbonate solution was added to the reaction solution, and the mixture was extracted with dichloromethane. The organic layer was washed with water and a brine successively, and dried over anhydrous sodium sulfate. The solvent was removed under reduced pressure, and the residue was then purified by silica gel column chromatography (hexane:ethyl acetate=4:1 followed by ethyl acetate), to obtain the title compound (69 mg).

$^1$H-NMR (400 MHz, CDCl$_3$) δ 2.54 (3H, s), 3.61 (2H, d, J=8.6 Hz), 3.77 (3H, s), 3.82-3.92 (1H, m), 4.70 (1H, t, J=9.8 Hz), 4.76 (2H, s), 5.01-5.10 (2H, m), 5.29 (1H, brs), 6.45 (2H, d, J=9.8 Hz), 7.26-7.35 (5H, m).

Reference Example 40-1

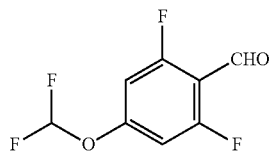

4-(Difluoromethoxy)-2,6-difluorobenzaldehyde

A solution (reaction solution) of 2,6-difluoro-4-hydroxybenzaldehyde (1.41 g), potassium carbonate (1.48 g), and sodium chlorodifluoroacetate (2.73 g) in a mixture of N,N-dimethylformamide (15.8 mL) and water (1.84 mL) was stirred at 100° C. for 1 hour and a half.

The reaction solution was ice-cooled, water (4.1 mL) and concentrated hydrochloric acid (2.8 mL) were added, and the reaction solution was stirred at room temperature overnight. A 2 mol/L sodium hydroxide aqueous solution was added to the reaction solution under ice-cooling to adjust the pH to 10, and the mixture was extracted with ethyl acetate. The organic layer was washed with a brine, and dried over anhydrous sodium sulfate. The solvent was removed under reduced pressure, and the residue was then purified by silica gel column chromatography (hexane:ethyl acetate=95:5 followed by 3:1), to obtain the title compound as a light brown oil (1.61 g).

$^1$H-NMR (400 MHz, CDCl$_3$) δ 6.63 (1H, t, J=71.5 Hz), 6.78 (2H, d, J=9.1 Hz), 10.26 (1H, s).

Reference Example 41-1

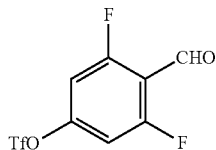

3,5-Difluoro-4-formylphenyl trifluoromethanesulfonate

Pyridine (0.8 mL) and trifluoromethanesulfonic anhydride (1.18 mL) were added to a solution of 2,6-difluoro-4-hydroxybenzaldehyde (1.03 g) in dichloromethane (30 mL) under an argon atmosphere under ice-cooling to produce a reaction solution. The reaction solution was stirred at room temperature for 3 hours. Water was added to the reaction solution, the mixture was extracted with ethyl acetate. The extract was washed with water and a brine, and dried over anhydrous sodium sulfate. The solvent was removed under reduced pressure, and the residue was then purified by silica gel column chromatography (hexane:ethyl acetate=4:1), to obtain the title compound as a colorless oil (1.5 g).

$^1$H-NMR (400 MHz, CDCl$_3$) δ 6.99-7.04 (2H, m), 10.32 (1H, s).

Reference Example 42-1

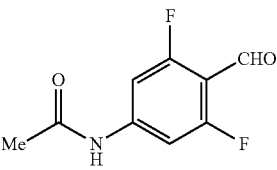

N-(3,5-Difluoro-4-formylphenyl)acetamide

Acetamide (225 mg), tris(dibenzylideneacetone)dipalladium(0) (116 mg), xantphos (145 mg), and cesium carbonate (1.24 g) were added to a solution of 3,5-difluoro-4-formylphenyl trifluoromethanesulfonate (737 mg) in toluene (15 mL) to produce a reaction solution. The reaction solution was stirred at 100° C. under an argon atmosphere for 5 hours. The reaction solution was filtered over Celite and washed with ethyl acetate. The solvent was removed under reduced pressure, and the residue was then purified by silica gel column chromatography (hexane:ethyl acetate=4:1 followed by ethyl acetate), to obtain the title compound as a pale yellow solid (255 mg).

¹H-NMR (400 MHz, CDCl₃) δ 2.22 (3H, s), 7.24 (2H, d, J=10.4 Hz), 7.44 (1H, brs), 10.23 (1H, s).

Reference Example 42-2

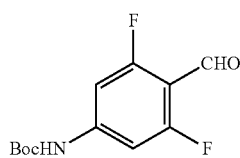

[Chemical Formula 111]

(3,5-Difluoro-4-formylphenyl)carbamic acid tert-butyl ester

The same method as in Reference Example 42-1 was performed using tert-butyl carbamate in place of acetamide as a reagent to obtain the title compound.

¹H-NMR (400 MHz, CDCl₃) δ 1.53 (9H, s), 6.77 (1H, brs), 7.07 (2H, d, J=11.0 Hz), 10.20 (1H, s).

Reference Example 43-1

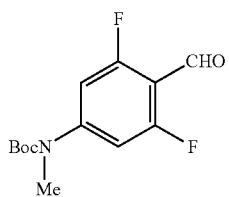

[Chemical Formula 112]

(3,5-Difluoro-4-formylphenyl)(methyl)carbamic acid tert-butyl ester

Iodomethane (110 μL) and sodium hydride (51 mg, 60% in oil) were added to a solution of (3,5-difluoro-4-formylphenyl)carbamic acid tert-butyl ester (220 mg) in N,N-dimethylformamide (4 mL) under cooling to produce a reaction solution. The reaction solution was stirred at room temperature for 3 hours. A saturated aqueous ammonium chloride solution was added to the reaction solution, and the mixture was extracted with ethyl acetate. The organic layer was washed with water and a brine successively, and dried over anhydrous sodium sulfate. The solvent was removed under reduced pressure, and the residue was then purified by silica gel column chromatography (ethyl acetate:hexane=4:1), to obtain the title compound as a colorless oil (150 mg).

¹H-NMR (400 MHz, CDCl₃) δ 1.53 (9H, s), 3.32 (3H, s), 7.05 (2H, d, J=11.0 Hz), 10.25 (1H, s).

Reference Example 44-1

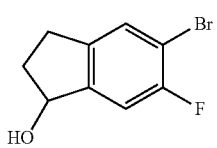

[Chemical Formula 113]

5-Bromo-6-fluoro-2,3-dihydro-1H-inden-1-ol

Sodium borohydride (56 mg) was added to a solution of 5-bromo-6-fluoro-2,3-dihydro-1H-inden-1-one (310 mg) in a mixture of tetrahydrofuran (7 mL) and ethanol (7 mL) under an argon atmosphere under ice-cooling to produce a reaction solution. The reaction solution was stirred at room temperature for 1 hour. Water was added to the reaction solution, and the mixture was extracted with ethyl acetate. The organic layer was washed with water and a brine, and dried over anhydrous sodium sulfate. The solvent was removed under reduced pressure, and the residue was then purified by silica gel column chromatography (hexane:ethyl acetate=4:1), to obtain the title compound as a colorless solid (290 mg).

¹H-NMR (400 MHz, CDCl₃) δ 1.78 (1H, d, J=7.3 Hz), 1.92-2.01 (1H, m), 2.50-2.58 (1H, m), 2.74-2.82 (1H, m), 2.96-3.03 (1H, m), 5.19 (1H, q, J=6.7 Hz), 7.15 (1H, d, J=7.9 Hz), 7.41 (1H, d, J=6.7 Hz).

Reference Example 45-1

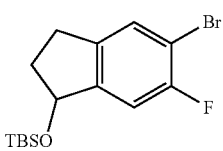

[Chemical Formula 114]

[(5-Bromo-6-fluoro-2,3-dihydro-1H-inden-1-yl)oxy](tert-butyl)dimethylsilane

Triethylamine (0.34 mL), N,N-dimethyl-4-aminopyridine (7.4 mg), and tert-butyl dimethyl chlorosilane (274 mg) were added to a solution of 5-bromo-6-fluoro-2,3-dihydro-1H-inden-1-ol (280 mg) in N,N-dimethylformamide (2.4 mL) under an argon atmosphere, to produce a reaction solution. The reaction solution was stirred at room temperature for 3 hours. Water was added to the reaction solution, and the mixture was extracted with ethyl acetate. The organic layer was washed with water and a brine, and dried over anhydrous sodium sulfate. The solvent was removed under reduced pressure, and the residue was then purified by silica gel column chromatography (hexane:ethyl acetate=9:1), to obtain the title compound as a colorless solid (410 mg).

¹H-NMR (400 MHz, CDCl₃) δ 0.14 (3H, s), 0.17 (3H, s), 0.94 (9H, s), 1.89-1.98 (1H, m), 2.40-2.48 (1H, m), 2.68-2.76 (1H, m), 2.88-2.94 (1H, m), 5.16 (1H, t, J=7.0 Hz), 7.01 (1H, d, J=7.9 Hz), 7.36 (1H, d, J=6.1 Hz).

Reference Example 46-1

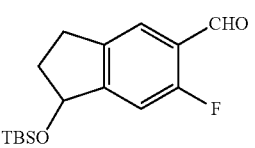

[Chemical Formula 115]

1-[(tert-Butyldimethylsilyl)oxy]-6-fluoro-2,3-dihydro-1H-indene-5-carbaldehyde n-Butyllithium (4.15 mL, 2.65 mol/L hexane solution) was slowly added to a solution of [(5-bromo-6-fluoro-2,3-dihydro-1H-inden-1-yl)oxy](tert-butyl)dimethyl silane (3.45 g) in tetrahydrofuran (50 mL) at −78° C. under an argon atmosphere to produce a reaction solution. The reaction solution was stirred for 40 minutes. After that, N,N-dimethylformamide (1.26 mL) was added to the reaction solution, and the reaction solution was stirred at −78° C. for 1 hour. A saturated aqueous sodium chloride solution was added to the reaction solution, and the mixture was stirred at 0° C. for 1 hour and extracted with ethyl acetate. The organic layer was washed with water and a brine, and dried over anhydrous sodium sulfate. The solvent was removed under reduced pressure, and the residue was then purified by silica gel column chromatography (hexane:ethyl acetate=4:1), to obtain the title compound as a yellow oil (2.63 g).

$^1$H-NMR (400 MHz, CDCl$_3$) δ 0.16 (3H, s), 0.19 (3H, s), 0.95 (9H, s), 1.91-2.01 (1H, m), 2.44-2.52 (1H, m), 2.71-2.79 (1H, m), 2.96 (1H, dd, J=14.7, 7.9 Hz), 5.22 (1H, t, J=7.6 Hz), 7.05 (1H, d, J=10.4 Hz), 7.67 (1H, d, J=6.7 Hz), 10.32 (1H, s).

Reference Example 47-1

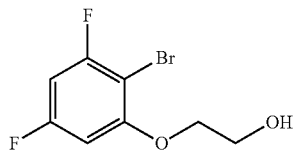

[Chemical Formula 116]

2-(2-Bromo-3, 5-difluorophenoxy)ethanol

Ethylene glycol (2.65 mL) and N-methyl-2-pyrrolidone (2 mL) were added to 2-bromo-1,3,5-trifluorobenzene (2.0 g) under an argon atmosphere, and potassium tert-butoxide (1.28 g) was added under ice-cooling to produce a reaction solution. The reaction solution was stirred under heating at 90° C. for 2 hours. The reaction solution was cooled to room temperature, water was added, and the mixture was extracted with ethyl acetate. The organic layer was washed with water and a brine, and dried over anhydrous sodium sulfate. The solvent was removed under reduced pressure, and the residue was then purified by silica gel column chromatography (hexane:ethyl acetate=9:1 followed by 1:1), to obtain the title compound as a colorless oil (1.43 g).

$^1$H-NMR (400 MHz, CDCl$_3$) δ 2.10 (1H, t, J=6.4 Hz), 4.00-4.04 (2H, m), 4.13 (2H, t, J=4.6 Hz), 6.48-6.52 (1H, m), 6.55-6.61 (1H, m).

Reference Example 48-1

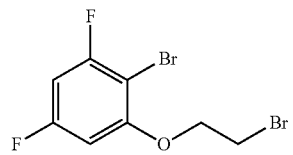

[Chemical Formula 117]

2-Bromo-1-(2-bromoethoxy)-3,5-difluorobenzene

Carbon tetrabromide (606 mg) and triphenyl phosphine (575 mg) were added to a solution of 2-(2-bromo-3, 5-difluorophenoxy) ethanol (370 mg) in dichloromethane (3.7 mL) under an argon atmosphere under ice-cooling to produce a reaction solution. The reaction solution was stirred at room temperature for 3 hours. The reaction solution was concentrated under reduced pressure, ethyl acetate was added, and the precipitated solid was removed by filtration. The filtrate was concentrated under reduced pressure, and the residue was then purified by silica gel column chromatography (hexane followed by hexane:ethyl acetate=9:1), to obtain the title compound as a colorless solid (453 mg).

$^1$H-NMR (400 MHz, CDCl$_3$) δ 3.69 (2H, t, J=6.4 Hz), 4.32 (2H, t, J=6.4 Hz), 6.47 (1H, dt, J=10.0, 2.3 Hz), 6.59 (1H, td, J=8.4, 2.3 Hz).

Reference Example 49-1

[Chemical Formula 118]

4,6-Difluoro-2,3-dihydrobenzofuran n-Butyllithium (0.55 mL, 2.65 mol/L hexane solution) was added to a solution of 2-bromo-1-(2-bromoethoxy)-3, 5-difluorobenzene (440 mg) in tetrahydrofuran (5 mL) at −78° C. under an argon atmosphere to produce a reaction solution. The reaction solution was stirred for 2 hours, and stirred at room temperature for 1 hour. A saturated aqueous ammonium chloride solution was added to the reaction solution, and the mixture was extracted with ethyl acetate. The organic layer was washed with water and a brine, and dried over anhydrous sodium sulfate. The solvent was removed under reduced pressure to obtain the title compound (205 mg).

$^1$H-NMR (400 MHz, CDCl$_3$) δ 3.20 (2H, t, J=8.9 Hz), 4.65 (2H, t, J=8.9 Hz), 6.28-6.34 (2H, m).

Reference Example 50-1

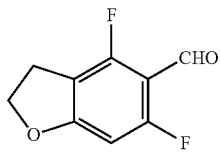

[Chemical Formula 119]

4,6-Difluoro-2,3-dihydrobenzofuran-5-carbaldehyde

Phosphorus oxychloride (778 µL) was added to a solution of 4,6-difluoro-2,3-dihydrobenzofuran (650 mg) in N,N-dimethylformamide (710 µL) under an argon atmosphere, to produce a reaction solution. The reaction solution was stirred at 100° C. for 20 hours. The reaction solution was allowed to cool to room temperature, and added to iced water, and the mixture was extracted with ethyl acetate. The organic layer was washed with a saturated sodium hydrogen carbonate aqueous solution and a brine, and dried over anhydrous sodium sulfate. The solvent was removed under reduced pressure, and the residue was then purified by silica gel column chromatography (hexane:ethyl acetate=4:1), to obtain the title compound as a pale yellow oil (121 mg).

$^1$H-NMR (400 MHz, CDCl$_3$) δ 3.27 (2H, t, J=8.9 Hz), 4.77 (2H, t, J=8.9 Hz), 6.41 (1H, d, J=11.0 Hz), 10.16 (1H, s).

Reference Example 51-1

[Chemical Formula 120]

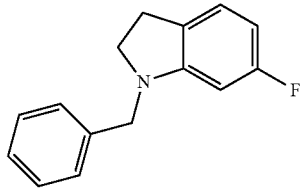

1-Benzyl-6-fluoroindoline

Potassium carbonate (4.45 g) and benzyl bromide (3.83 mL) were added to a solution of 6-fluoroindoline (4.2 g) in methanol (38 mL), to produce a reaction solution. The reaction solution was heated to reflux for 3 hours. The reaction solution was allowed to cool to room temperature, and the insoluble was removed by filtration. The filtrate was concentrated under reduced pressure, and the residue was then purified by silica gel column chromatography (hexane:ethyl acetate=1:1), to obtain the title compound as a pale brown oil (6.14 g).

$^1$H-NMR (400 MHz, CDCl$_3$) δ 2.92 (2H, t, J=8.5 Hz), 3.38 (2H, t, J=8.5 Hz), 4.23 (2H, s), 6.18 (1H, dd, J=10.9, 2.4 Hz), 6.27-6.32 (1H, m), 6.93-6.97 (1H, m), 7.25-7.34 (5H, m).

Reference Example 52-1

[Chemical Formula 121]

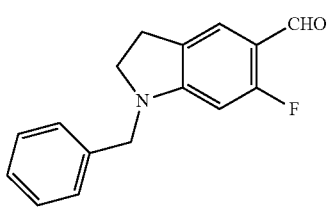

1-Benzyl-6-fluoroindoline-5-carbaldehyde

Phosphorus oxychloride (518 μL) was added to a solution of 1-benzyl-6-fluoroindoline (1.0 g) in N,N-dimethylformamide (4.9 mL) under ice-cooling, to produce a reaction solution. The reaction solution was stirred at 100° C. for 2 hours. The reaction solution was allowed to cool to room temperature, and added to iced water. A 2 mol/L sodium hydroxide aqueous solution was added to the iced water to adjust the pH to 10, and the mixture was extracted with chloroform. The organic layer was washed with a brine, and dried over anhydrous sodium sulfate. The solvent was removed under reduced pressure, and the residue was then purified by silica gel column chromatography (hexane:ethyl acetate=8:1 followed by 2:1), to obtain the title compound as a pale yellow oil (1.07 g).

$^1$H-NMR (400 MHz, CDCl$_3$) δ 3.02 (2H, t, J=8.5 Hz), 3.61 (2H, t, J=8.5 Hz), 4.39 (2H, s), 6.05 (1H, d, J=12.1 Hz), 7.25-7.38 (5H, m), 7.48-7.49 (1H, m), 10.02 (1H, s).

Example 1-1

[Chemical Formula 122]

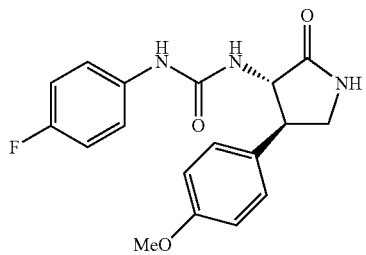

(−)-1-(4-Fluorophenyl)-3-[(3S*,4R*)-4-(4-methoxyphenyl)-2-oxopyrrolidin-3-yl]urea Triethylamine (131 μL) and diphenylphosphoryl azide (171 μL) were added to a solution of (−)-(3S*,4R*)-4-(4-methoxyphenyl)-2-oxopyrrolidine-3-carboxylic acid (170 mg) in toluene (3.6 mL) under an argon atmosphere to produce a reaction solution. The reaction solution was stirred at room temperature for 1 hour. The temperature was heated up to 90° C. and the reaction solution was stirred for 1 hour. After that, 4-fluoroaniline (140 μL) was added to the reaction solution, and the reaction solution was stirred at 120° C. for 3 hours. The reaction solution was cooled to room temperature, a 1 mol/L hydrochloric acid was added, and the mixture was extracted with ethyl acetate. The organic layer was washed with water and a brine successively, and dried over anhydrous sodium sulfate. The solvent was removed under reduced pressure, and the residue was then purified by silica gel column chromatography (ethyl acetate:hexane=4:1, ethyl acetate, and ethyl acetate:methanol=10:1 in turn), to obtain the title compound as a white solid (44 mg).

$^1$H-NMR (400 MHz, DMSO-d$_6$) δ 3.11-3.17 (1H, m), 3.38-3.48 (2H, m), 3.69 (3H, s), 4.45 (1H, dd, J=10.9, 9.1 Hz), 6.38 (1H, d, J=9.1 Hz), 6.86 (2H, d, J=8.5 Hz), 7.01 (2H, t, J=9.1 Hz), 7.28 (2H, d, J=8.5 Hz), 7.32-7.35 (2H, m), 7.88 (1H, s), 8.53 (1H, s).

MS (ESI$^+$) m/z: 344 (MH$^+$).

$[\alpha]_D^{28}$=−156 (c 0.10, EtOH)

The same method as in Example 1-1 was performed using a corresponding carboxylic acid and aromatic amine to obtain the following Examples 1-2 to 1-87.

The structures and spectral data thereof are shown in Tables 47 to 75.

TABLE 47

| Ex. No | Str. | Chemical name | P. D. |
|---|---|---|---|
| 1-2 | | (−)-1-(4-chlorophenyl)-3-[(3S*,4R*)-4-(4-methoxyphenyl)-2-oxopyrrolidin-3-yl] urea | $^1$H-NMR (400 MHz, DMSO-d$_6$) δ 3.11-3.21 (1H, m), 3.41-3.50 (2H, m), 3.71 (3H, s), 4.46 (1H, dd, J = 10.9, 9.1 Hz), 6.47 (1H, d, J = 9.1 Hz), 6.87 (2H, d, J = 8.5 Hz), 7.23 (2H, d, J = 9.1 Hz), 7.29 (2H, d, J = 9.1 Hz), 7.38 (2H, d, J = 8.5 Hz), 7.90 (1H, s), 8.67 (1H, s). MS (ESI$^+$) m/z: 360 (MH$^+$). $[α]_D^{28}$ = −130 (c 0.10, EtOH) |
| 1-3 | | (−)-1-(3,4-difluorophenyl)-3-[(3S*,4R*)-4-(4-methoxyphenyl)-2-oxopyrrolidin-3-yl] urea | $^1$H-NMR (400 MHz, DMSO-d$_6$) δ 3.13-3.20 (1H, m), 3.42-3.51 (2H, m), 3.71 (3H, s), 4.45 (1H, t, J = 9.7 Hz), 6.52 (1H, d, J = 8.5 Hz), 6.87 (2H, d, J = 8.5 Hz), 6.98-7.03 (1H, m), 7.21-7.28 (1H, m), 7.29 (2H, d, J = 8.5 Hz), 7.53-7.60 (1H, m), 7.91 (1H, s), 8.76 (1H, s). MS (ESI$^+$) m/z: 362 (MH$^+$). $[α]_D^{28}$ = −149 (c 0.10, EtOH) |
| 1-4 | | (−)-1-(2,4-difluorophenyl)-3-[(3S*,4R*)-4-(4-methoxyphenyl)-2-oxopyrrolidin-3-yl] urea | $^1$H-NMR (400 MHz, DMSO-d$_6$) δ 3.17 (1H, t, J = 9.1 Hz), 3.36-3.49 (2H, m), 3.71 (3H, s), 4.47 (1H, dd, J = 11.2, 8.8 Hz), 6.80 (1H, d, J = 8.5 Hz), 6.88 (2H, d, J = 8.5 Hz), 6.93-6.98 (1H, m), 7.19-7.25 (1H, m), 7.30 (2H, d, J = 8.5 Hz), 7.93 (1H, s), 7.94-8.01 (1H, m), 8.28 (1H, s). MS (ESI$^+$) m/z: 362 (MH$^+$). $[α]_D^{28}$ = −126 (c 0.10, EtOH) |

TABLE 48

| Ex. No | Str. | Chemical name | P.D. |
|---|---|---|---|
| 1-5 | | (−)-1-(4-cyanophenyl)-3-[(3S*,4R*)-4-(4-methoxyphenyl)-2-oxopyrrolidin-3-yl]urea | $^1$H-NMR (400 MHz, DMSO-d$_6$) δ 3.14-3.21 (1H, m), 3.43-3.52 (2H, m), 3.71 (3H, s), 4.48 (1H, t, J = 9.7 Hz), 6.67 (1H, d, J = 9.1 Hz), 6.87 (2H, d, J = 9.1 Hz), 7.29 (2H, d, J = 9.1 Hz), 7.53 (2H, dd, J = 7.0, 2.1 Hz), 7.64 (2H, dd, J = 7.0, 2.1 Hz), 7.93 (1H, s), 9.09 (1H, s). MS (ESI$^+$) m/z: 351 (MH$^+$). $[α]_D^{28}$ = −166 (c 0.10, EtOH) |
| 1-6 | | (−)-1-(4-chlorophenyl)-3-[(3S*,4R*)-4-(4-methoxyphenyl)-1-methyl-2-oxopyrrolidin-3-yl]urea | $^1$H-NMR (400 MHz, DMSO-d$_6$) δ 2.79 (3H, s), 3.29 (1H, t, J = 9.7 Hz), 3.43 (1H, q, J = 9.5 Hz), 3.54 (1H, t, J = 8.5 Hz), 3.71 (3H, s), 4.46 (1H, t, J = 10.0 Hz), 6.53 (1H, d, J = 9.1 Hz), 6.88 (2H, d, J = 8.5 Hz), 7.23 (2H, d, J = 9.1 Hz), 7.29 (2H, d, J = 9.1 Hz), 7.38 (2H, d, J = 8.5 Hz), 8.71 (1H, s). MS (ESI$^+$) m/z: 374 (MH$^+$). $[α]_D^{26}$ = −170 (c 0.10, EtOH) |

TABLE 48-continued

| Ex. No | Str. | Chemical name | P.D. |
|---|---|---|---|
| 1-7 | | 1-(4-fluorophenyl)-3-[(3S*,4R*)-4-(4-methoxyphenyl)-1-methyl-2-oxopyrrolidin-3-yl]urea | $^1$H-NMR (400 MHz, DMSO-d$_6$) δ 2.79 (3H, s), 3.28 (1H, t, J = 10.0 Hz), 3.43 (1H, q, J = 9.5 Hz), 3.54 (1H, t, J = 8.8 Hz), 3.71 (3H, s), 4.47 (1H, t, J = 10.0 Hz), 6.46 (1H, d, J = 9.1 Hz), 6.88 (2H, d, J = 8.5 Hz), 7.02 (2H, t, J = 8.8 Hz), 7.29 (2H, d, J = 8.5 Hz), 7.35 (2H, dd, J = 8.8, 4.8 Hz), 8.58 (1H, s). MS (ESI$^+$) m/z: 358 (MH$^+$). |

TABLE 49

| Ex. No | Str. | Chemical name | P.D. |
|---|---|---|---|
| 1-8 | | (−)-1-[(3S*,4R*)-4-(3-fluoro-4-methoxyphenyl)-2-oxopyrrolidin-3-yl]-3-(4-fluorophenyl)urea | $^1$H-NMR (400 MHz, DMSO-d$_6$) δ 3.13-3.20 (1H, m), 3.43-3.50 (2H, m), 3.79 (3H, s), 4.47 (1H, t, J = 9.7 Hz), 6.42 (1H, d, J = 8.5 Hz), 7.00-7.14 (4H, m), 7.29-7.37 (3H, m), 7.91 (1H, s), 8.58 (1H, s). MS (ESI$^+$) m/z: 362 (MH$^+$). $[\alpha]_D^{28}$ = −130 (c 0.10, EtOH) |
| 1-9 | | (−)-1-[(3S*,4R*)-4-(2-fluoro-4-methoxyphenyl)-2-oxopyrrolidin-3-yl]-3-(4-fluorophenyl)urea | $^1$H-NMR (400 MHz, DMSO-d$_6$) δ 3.17 (1H, t, J = 9.8 Hz), 3.45 (1H, t, J = 8.9 Hz), 3.68 (1H, q, J = 9.8 Hz), 3.73 (3H, s), 4.56 (1H, dd, J = 11.3, 8.9 Hz), 6.41 (1H, d, J = 8.6 Hz), 6.74-6.80 (2H, m), 7.00-7.05 (2H, m), 7.32-7.37 (2H, m), 7.45 (1H, t, J = 8.9 Hz), 7.94 (1H, s), 8.59 (1H, s). MS (ESI$^+$) m/z: 362 (MH$^+$). $[\alpha]_D^{28}$ = −99 (c 0.10, EtOH) |
| 1-10 | | 1-[(3S*,4R*)-4-(2-chloro-4-methoxyphenyl)-2-oxopyrrolidin-3-yl]-3-(4-fluorophenyl)urea | $^1$H-NMR (400 MHz, DMSO-d$_6$) δ 3.07 (1H, t, J = 9.8 Hz), 3.50 (1H, t, J = 8.5 Hz), 3.74 (3H, s), 3.91 (1H, q, J = 9.8 Hz), 4.66 (1H, dd, J = 11.3, 8.9 Hz), 6.42 (1H, d, J = 8.6 Hz), 6.93 (1H, dd, J = 8.6, 2.4 Hz), 7.00-7.06 (3H, m), 7.33-7.37 (2H, m), 7.59 (1H, d, J = 8.6 Hz), 7.94 (1H, s), 8.57 (1H, s). MS (ESI$^+$) m/z: 378 (MH$^+$). |

TABLE 50

| Ex. No | Str. | Chemical name | P.D. |
| --- | --- | --- | --- |
| 1-11 | | (−)-1-(4-fluorophenyl)-3-[(3S*,4R*)-4-(4-methoxy-2-methylphenyl)-2-oxopyrrolidin-3-yl]urea | $^1$H-NMR (400 MHz, DMSO-d$_6$) δ 2.27 (3H, s), 3.05 (1H, t, J = 9.7 Hz), 3.46 (1H, t, J = 8.4 Hz), 3.69 (3H, s), 3.74 (1H, dd, J = 9.8, 8.4 Hz), 4.51 (1H, dd, J = 11.5, 9.1 Hz), 6.37 (1H, d, J = 9.1 Hz), 6.71 (1H, d, J = 3.0 Hz), 6.75 (1H, dd, J = 8.5, 3.0 Hz), 7.00-7.04 (2H, m), 7.32-7.36 (2H, m), 7.40 (1H, d, J = 8.5 Hz), 7.89 (1H, s), 8.51 (1H, s). MS (ESI$^+$) m/z: 358 (MH$^+$). [α]$_D$$^{23}$ = −187 (c 0.35, EtOH) |
| 1-12 | | (−)-1-[(3S*,4R*)-4-(2,6-difluoro-4-methoxyphenyl)-2-oxopyrrolidin-3-yl]-3-(4-fluorophenyl)urea | $^1$H-NMR (400 MHz, DMSO-d$_6$) δ 3.27-3.33 (1H, m), 3.44 (1H, t, J = 9.5 Hz), 3.75 (3H, s), 3.79 (1H, q, J = 9.8 Hz), 4.56 (1H, dd, J = 11.0, 8.6 Hz), 6.46 (1H, d, J = 8.6 Hz), 6.73 (2H, d, J = 10.4 Hz), 6.98-7.04 (2H, m), 7.30-7.34 (2H, m), 8.05 (1H, s), 8.66 (1H, s). MS (ESI$^+$) m/z: 380 (MH$^+$). [α]$_D$$^{28}$ = −156 (c 0.10, EtOH) |
| 1-13 | | (−)-1-[(3S*,4R*)-4-(2,5-difluoro-4-methoxyphenyl)-2-oxopyrrolidin-3-yl]-3-(4-fluorophenyl)urea | $^1$H-NMR (400 MHz, DMSO-d$_6$) δ 3.18 (1H, t, J = 9.8 Hz), 3.43 (1H, t, J = 8.9 Hz), 3.72 (1H, q, J = 9.8 Hz), 3.80 (3H, s), 4.53 (1H, dd, J = 11.6, 8.6 Hz), 6.42 (1H, d, J = 8.6 Hz), 7.00-7.10 (3H, m), 7.32-7.36 (2H, m), 7.52 (1H, dd, J = 11.6, 8.6 Hz), 7.96 (1H, s), 8.62 (1H, s). MS (ESI$^+$) m/z: 380 (MH$^+$). [α]$_D$$^{28}$ = −123 (c 0.10, EtOH) |

TABLE 51

| Ex. No | Str. | Chemical name | P.D. |
| --- | --- | --- | --- |
| 1-14 | | (−)-1-[(3S*,4R*)-4-(3,5-difluoro-4-methoxyphenyl)-2-oxopyrrolidin-3-yl]-3-(4-fluorophenyl)urea | $^1$H-NMR (400 MHz, DMSO-d$_6$) δ 3.13-3.19 (1H, m), 3.45-3.56 (2H, m), 3.87 (3H, s), 4.49 (1H, dd, J = 11.3, 8.9 Hz), 6.44 (1H, d, J = 9.2 Hz), 7.01-7.07 (2H, m), 7.19-7.26 (2H, m), 7.33-7.38 (2H, m), 7.95 (1H, s), 8.61 (1H, s). MS (ESI$^+$) m/z: 380 (MH$^+$). [α]$_D$$^{28}$ = −111 (c 0.10, EtOH) |

TABLE 51-continued

| Ex. No | Str. | Chemical name | P.D. |
|---|---|---|---|
| 1-15 | | (−)-1-[(3S*,4R*)-4-(2,3-di-hydrobenzofuran-5-yl)-2-oxo-pyrrolidin-3-yl]-3-(4-fluoro-phenyl)urea | $^1$H-NMR(400 MHz, DMSO-d$_6$) δ 3.10-3.18 (3H, m), 3.39-3.47 (2H, m), 4.40-4.49 (3H, m), 6.40 (1H, d, J = 8.6 Hz), 6.68 (1H, d, J = 8.6 Hz), 7.00-7.08 (3H, m), 7.24 (1H, s), 7.33-7.37 (2H, m), 7.88 (1H, s), 8.55 (1H, s). MS (ESI$^+$) m/z: 356 (MH$^+$). [α]$_D^{28}$ = −130 (c 0.10, EtOH) |
| 1-16 | | (−)-1-[(3S*,4R*)-4-(6-fluoro-2,3-dihydro-benzofuran-5-yl)-2-oxopyrrolidin-3-yl]-3-(4-fluorophenyl)urea | $^1$H-NMR(400 MHz, DMSO-d$_6$) δ 3.09-3.18 (3H, m), 3.39-3.46 (1H, m), 3.67 (1H, q, J = 10.0 Hz), 4.50-4.57 (3H, m), 6.41 (1H, d, J = 9.2 Hz), 6.62 (1H, d, J = 11.0 Hz), 7.02 (2H, t, J = 8.9 Hz), 7.33-7.38 (3H, m), 7.93 (1H, s), 8.60 (1H, s). MS (ESI$^+$) m/z: 374 (MH$^+$). [α]$_D^{28}$ = −152 (c 0.10, EtOH) |

TABLE 52

| Ex. No | Str. | Chemical name | P.D. |
|---|---|---|---|
| 1-17 | | (−)-1-[(3S*,4R*)-4-(7-fluoro-chroman-6-yl)-2-oxopyrrolidin-3-yl]-3-(4-fluoro-phenyl)urea | $^1$H-NMR (400 MHz, DMSO-d$_6$) δ 1.84-1.90 (2H, m), 2.60-2.73 (2H, m), 3.16 (1H, t, J = 9.8 Hz), 3.42 (1H, t, J = 8.9 Hz), 3.64 (1H, q, J = 9.8 Hz), 4.09 (2H, t, J = 4.9 Hz), 4.51 (1H, dd, J = 11.3, 8.9 Hz), 6.40 (1H, d, J = 8.6 Hz), 6.54 (1H, d, J = 11.6 Hz), 7.00-7.06 (2H, m), 7.20 (1H, d, J = 8.6 Hz), 7.33-7.37 (2H, m), 7.92 (1H, s), 8.58 (1H, s). MS (ESI$^+$) m/z: 388 (MH$^+$). [α]$_D^{28}$ = −220 (c 0.10, EtOH) |
| 1-18 | | (−)-1-[(3S*,4R*)-4-(3-fluoro-5-methoxypyridin-2-yl)-2-oxo pyrrolidin-3-yl]-3-(4-fluorophenyl)urea | $^1$H-NMR (400 MHz, DMSO-d$_6$) δ 3.38 (1H, t, J = 9.2 Hz), 3.47 (1H, t, J = 8.9 Hz), 3.83 (3H, s), 3.96 (1H, q, J = 9.5 Hz), 4.51 (1H, dd, J = 10.4, 7.9 Hz), 6.48 (1H, d, J = 7.9 Hz), 7.01 (2H, t, J = 8.9 Hz), 7.29-7.35 (2H, m), 7.38 (1H, dd, J = 11.6, 2.4 Hz), 7.95 (1H, s), 8.20 (1H, d, J = 2.4 Hz), 8.62 (1H, s). MS (ESI$^+$) m/z: 363 (MH$^+$). [α]$_D^{28}$ = −142 (c 0.10, EtOH) |

TABLE 52-continued

| Ex. No | Str. | Chemical name | P.D. |
|---|---|---|---|
| 1-19 |  | (−)-1-(4-fluoro-phenyl)-3-[(3S*,4R*)-4-(5-methoxy-thiophen-2-yl)-2-oxopyrrolidin-3-yl]urea | $^1$H-NMR (400 MHz, DMSO-d$_6$) δ 3.18 (1H, t, J = 9.7 Hz), 3.49 (1H, t, J = 9.5 Hz), 3.60 (1H, q, J = 9.5 Hz), 3.78 (3H, s), 4.28 (1H, dd, J = 10.9, 9.1 Hz), 6.11 (1H, d, J = 3.6 Hz), 6.47 (1H, d, J = 9.1 Hz), 6.62 (1H, d, J = 3.6 Hz), 7.01-7.08 (2H, m), 7.36-7.41 (2H, m), 7.93 (1H, s), 8.64 (1H, s). MS (ESI$^+$) m/z: 350 (MH$^+$). [α]$_D^{28}$ = −129 (c 0.10, EtOH) |

TABLE 53

| Ex. No | Str. | Chemical name | P.D. |
|---|---|---|---|
| 1-20 |  | (−)-1-(4-fluoro-phenyl)-3-[(3S*,4R*)-4-(4-methylthiophenyl)-2-oxopyrrolidin-3-yl]urea | $^1$H-NMR (400 MHz, DMSO-d$_6$) δ 2.49 (3H, s), 3.20-3.27 (1H, m), 3.50-3.58 (2H, m), 4.54 (1H, t, J = 9.7 Hz), 6.47 (1H, d, J = 9.1 Hz), 7.05-7.11 (2H, m), 7.26 (2H, d, J = 8.5 Hz), 7.35-7.42 (4H, m), 7.97 (1H, s), 8.61 (1H, s). MS (ESI$^+$) m/z: 360 (MH$^+$). [α]$_D^{27}$ = −544 (c 0.26, DMSO) |
| 1-21 |  | (−)-1-[(3S*,4R*)-4-(2,6-difluoro-4-methoxy-phenyl)-2-oxo-pyrrolidin-3-yl]-3-(4-methyl-sulfonylphenyl)urea | $^1$H-NMR (400 MHz, DMSO-d$_6$) δ 3.10 (3H, s), 3.29-3.31 (1H, m), 3.46 (1H, t, J = 9.2 Hz), 3.75 (3H, s), 3.79-3.87 (1H, m), 4.58 (1H, dd, J = 11.0, 8.0 Hz), 6.70-6.78 (3H, m), 7.57 (2H, d, J = 9.2 Hz), 7.72 (2H, d, J = 9.2 Hz), 8.09 (1H, s), 9.25 (1H, s). MS (ESI$^+$) m/z: 440 (MH$^+$). [α]$_D^{27}$ = −138 (c 0.10, EtOH) |
| 1-22 |  | (−)-1-(4-chloro-phenyl)-3-[(3S*,4R*)-4-(2,6-difluoro-4-methoxyphenyl)-2-oxopyrrolidin-3-yl]urea | $^1$H-NMR (400 MHz, DMSO-d$_6$) δ 3.27-3.31 (1H, m), 3.44 (1H, t, J = 9.8 Hz), 3.75 (3H, s), 3.75-3.83 (1H, m), 4.56 (1H, t, J = 9.6 Hz), 6.51 (1H, d, J = 8.0 Hz), 6.73 (2H, d, J = 12.0 Hz), 7.22 (2H, d, J = 9.2 Hz), 7.35 (2H, d, J = 9.2 Hz), 8.06 (1H, s), 8.79 (1H, s). MS (ESI$^+$) m/z: 396 (MH$^+$). [α]$_D^{27}$ = −195 (c 0.10, EtOH) |

TABLE 54

| Ex. No | Str. | Chemical name | P.D. |
|---|---|---|---|
| 1-23 | (structure) | (−)-1-(4-cyano-phenyl)-3-[(3S*,4R*)-4-(2,6-difluoro-4-methoxyphenyl)-2-oxopyrrolidin-3-yl]urea | $^1$H-NMR (400 MHz, DMSO-d$_6$) δ 3.26-3.33 (1H, m), 3.45 (1H, t, J = 9.8 Hz), 3.75 (3H, s). 3.78-3.86 (1H, m), 4.58 (1H, dd, J = 11.0, 8.0 Hz), 6.70-6.77 (3H, m), 7.51 (2H, d, J = 9.2 Hz), 7.63 (2H, d, J = 9.2 Hz), 8.09 (1H, s), 9.24 (1H, s). MS (ESI$^+$) m/z: 387 (MH$^+$). [α]$_D^{26}$ = −163 (c 0.10, EtOH) |
| 1-24 | (structure) | (−)-1-[(3S*,4R*)-4-(2,6-difluoro-4-methoxyphenyl)-2-oxo-pyrrolidin-3-yl]-3-(4-methoxyphenyl)urea | $^1$H-NMR (400 MHz, DMSO-d$_6$) δ 3.29 (1H, t, J = 8.6 Hz), 3.43 (1H, t, J = 8.9 Hz), 3.66 (s, 3H), 3.70-3.82 (1H, m), 3.75 (3H, s), 4.55 (1H, dd, J = 10.4, 8.6 Hz), 6.34 (1H, d, J = 8.6 Hz), 6.71-6.79 (4H, m), 7.22 (2H, d, J = 8.6 Hz), 8.03 (1H, s), 8.40 (1H, s). MS (ESI$^+$) m/z: 392 (MH$^+$). [α]$_D^{28}$ = −168 (c 0.29, EtOH) |
| 1-25 | (structure) | (−)-1-(benzo[d][1,3]dioxol-5-yl)-3-[(3S*,4R*)-4-(2,6-difluoro-4-methoxyphenyl)-2-oxo-pyrrolidin-3-yl]urea | $^1$H-NMR (400 MHz, DMSO-d$_6$) δ 3.29 (1H, t, J = 8.6 Hz), 3.43 (1H, t, J = 8.9 Hz), 3.72-3.82 (1H, m), 3.75 (3H, s), 4.55 (1H, dd, J = 11.0, 8.6 Hz), 5.90 (2H, s), 6.37 (1H, d, J = 7.9 Hz), 6.64 (1H, dd, J = 8.3, 2.1 Hz), 6.70-6.76 (3H, m), 7.06 (1H, d, J = 2.1 Hz), 8.04 (1H, s), 8.50 (1H, s). MS (ESI$^+$) m/z: 406 (MH$^+$). [α]$_D^{28}$ = −150 (c 0.30, EtOH) |

TABLE 55

| Ex. No | Str. | Chemical name | P.D. |
|---|---|---|---|
| 1-26 | (structure) | (−)-1-(5-chloro-thiazol-2-yl)-3-[(3S*,4R*)-4-(2,6-difluoro-4-methoxyphenyl)-2-oxo-pyrrolidin-3-yl]urea | $^1$H-NMR (400 MHz, DMSO-d$_6$) δ 3.28-3.31 (1H, m), 3.46 (1H, t, J = 9.8 Hz), 3.75 (3H, s), 3.82-3.91 (1H, m), 4.55 (1H, dd, J = 9.8, 6.8 Hz), 6.75 (2H, d, J = 11.0 Hz), 6.88 (1H, d, J = 6.8 Hz), 7.31 (1H, s), 8.11 (1H, s), 10.9 (1H, s). MS (ESI$^+$) m/z: 403 (MH$^+$). [α]$_D^{27}$ = −88 (c 0.10, EtOH) |

TABLE 55-continued

| Ex. No | Str. | Chemical name | P.D. |
|---|---|---|---|
| 1-27 | | (−)-1-[(3S*,4R*)-4-(2,6-difluoro-4-methoxyphenyl)-2-oxopyrrolidin-3-yl]-3-(pyrimidin-4-yl) urea | $^1$H-NMR (400 MHz, DMSO-d$_6$) δ 3.27-3.31 (1H, m), 3.46 (1H, t, J = 8.6 Hz), 3.75 (3H, s), 3.80-3.88 (1H, m), 4.60 (1H, dd, J = 10.4, 8.0 Hz), 6.75 (2H, d, J = 11.0 Hz), 7.46 (1H, d, J = 6.1 Hz), 7.86 (1H, brs), 8.14 (1H, s), 8.44 (1H, d, J = 5.5 Hz), 8.70 (1H, s), 9.68 (1H, brs). MS (ESI$^+$) m/z: 364 (MH$^+$). [α]$_D^{29}$ = −180 (c 0.10, DMSO) |
| 1-28 | | (−)-1-[(3S*,4R*)-4-(2,6-difluoro-4-methoxyphenyl)-2-oxopyrrolidin-3-yl]-3-(pyridin-2-yl) urea | $^1$H-NMR (400 MHz, DMSO-d$_6$) δ 3.27-3.30 (1H, m), 3.40-3.47 (1H, m), 3.75 (3H, s), 3.79-3.88 (1H, m), 4.58-4.63 (1H, m), 6.73 (2H, d, J = 10.4 Hz), 6.90-6.93 (1H, m), 7.28 (1H, d, J = 8.0 Hz), 7.62-7.67 (1H, m), 8.10 (1H, m), 8.14-8.16 (1H, m), 8.37-8.43 (1H, m), 9.22 (1H, s). MS (ESI$^+$) m/z: 363 (MH$^+$). [α]$_D^{27}$ = −188 (c 0.10, EtOH) |

TABLE 56

| Ex. No | Str. | Chemical name | P.D. |
|---|---|---|---|
| 1-29 | | (−)-1-[(3S*,4R*)-4-(2,6-difluoro-4-methoxyphenyl)-2-oxopyrrolidin-3-yl]-3-(pyridin-3-yl)urea | $^1$H-NMR (400 MHz, DMSO-d$_6$) δ 3.28-3.31 (1H, m), 3.45 (1H, t, J = 9.2 Hz), 3.75 (3H, s), 3.82 (1H, q, J = 9.5 Hz), 4.57 (1H, dd, J = 11.0, 8.6 Hz), 6.66 (1H, d, J = 8.6 Hz), 6.74 (2H, d, J = 10.4 Hz), 7.21 (1H, dd, J = 8.6, 4.9 Hz) 7.78-7.82 (1H, m), 8.07 (1H, s), 8.08-8.10 (1H, m), 8.47 (1H, d, J = 2.4 Hz), 8.87 (1H, s). MS (ESI$^+$) m/z: 363 (MH$^+$). [α]$_D^{27}$ = −168 (c 0.10, EtOH) |
| 1-30 | | (−)-1-[(3S*,4R*)-4-(2,6-difluoro-4-methoxyphenyl)-2-oxopyrrolidin-3-yl]-3-(pyrimidin-5-yl)urea | 1H-NMR (400 MHz, DMSO-d$_6$) δ 3.28-3.50 (2H, m), 3.74 (3H, s), 3.75-3.90 (1H, m), 4.58 (1H, dd, J = 9.8, 8.6 Hz), 6.74 (2H, d, J = 10.4 Hz), 6.92 (1H, d, J = 8.6 Hz), 8.08 (1H, s), 8.71 (1H, s), 8.78 (2H, s), 9.11 (1H, s). MS (ESI$^+$) m/z: 364 (MH$^+$). [α]$_D^{28}$ = −139 (c 0.10, DMSO) |

TABLE 56-continued

| Ex. No | Str. | Chemical name | P.D. |
|---|---|---|---|
| 1-31 | | (−)-1-(6-chloro-pyridin-3-yl)-3-[(3S*,4R*)-4-(2,6-difluoro-4-methoxy-phenyl)-2-oxo-pyrrolidin-3-yl]urea | ¹H-NMR (400 MHz, DMSO-d₆) δ 3.28-3.31 (1H, m), 3.45 (1H, t, J = 9.2 Hz), 3.75 (3H, s), 3.83 (1H, q, J = 9.2 Hz), 4.57 (1H, dd, J = 11.0, 8.6 Hz), 6.70-6.79 (3H, m), 7.32 (1H, d, J = 8.6 Hz), 7.86 (1H, dd, J = 8.6, 3.0 Hz) 8.07 (1H, s), 8.34 (1H, d, J = 3.0 Hz), 9.07 (1H, s). MS (ESI⁺) m/z: 397 (MH⁺). [α]$_D^{27}$ = −152 (c 0.10, EtOH) |

TABLE 57

| Ex. No | Str. | Chemical name | P.D. |
|---|---|---|---|
| 1-32 | | (−)-1-(5-chloro-pyridin-2-yl)-3-[(3S*,4R*)-4-(2,6-difluoro-4-methoxy-phenyl)-2-oxo-pyrrolidin-3-yl]urea | ¹H-NMR (400 MHz, DMSO-d₆) δ 3.29-3.35 (1H, m), 3.47 (1H, t, J = 9.2 Hz), 3.75 (3H, s), 3.81 (1H, q, J = 9.2 Hz), 4.59 (1H, dd, J = 11.0, 8.6 Hz), 6.74 (2H, d, J = 11.0 Hz), 7.49 (1H, d, J = 8.6 Hz), 7.73-7.79 (2H, m), 8.11 (1H, s), 8.20 (1H, d, J = 3.0 Hz), 9.35 (1H, s). MS (ESI⁺) m/z: 397 (MH⁺). [α]$_D^{27}$ = −180 (c 0.10, EtOH) |
| 1-33 | | (−)-1-[(3S*,4R*)-4-(2,6-di-fluoro-4-methoxy-phenyl)-2-oxo-pyrrolidin-3-yl]-3-(pyrazin-2-yl)urea | ¹H-NMR (400 MHz, DMSO-d₆) δ 3.36-3.30 (1H, m), 3.48 (1H, t, J = 9.2 Hz), 3.75 (3H, s), 3.85 (1H, q, J = 9.5 Hz), 4.60 (1H, dd, J = 10.4, 8.6 Hz), 6.74 (2H, d, J = 11.0 Hz), 7.70 (1H, d, J = 8.6 Hz), 8.12 (1H, s), 8.16-8.22 (2H, m), 8.79 (1H, s), 9.51 (1H, s). MS (ESI⁺) m/z: 364 (MH⁺). [α]$_D^{28}$ = −178 (c 0.10, DMSO) |
| 1-34 | | (−)-1-(benzo[d]thiazol-2-yl)-3-[(3S*,4R*)-4-(2,6-difluoro-4-methoxy-phenyl)-2-oxo-pyrrolidin-3-yl]urea | ¹H-NMR (400 MHz, DMSO-d₆) δ 3.29-3.36 (1H, m), 3.48 (1H, t, J = 8.6 Hz), 3.75 (3H, s), 3.89 (1H, q, J = 9.2 Hz), 4.60 (1H, dd, J = 10.4, 9.2 Hz), 6.75 (2H, d, J = 11.0 Hz), 7.06-7.23 (2H, m), 7.30-7.37 (1H, m), 7.54-7.62 (1H, m), 7.83 (1H, d, J = 6.7 Hz), 8.14 (1H, s), 11.0 (1H, brs). MS (ESI⁺) m/z: 419 (MH⁺). [α]$_D^{28}$ = −164 (c 0.10, DMSO) |

TABLE 58

| Ex. No | Str. | Chemical name | P.D. |
|---|---|---|---|
| 1-35 | | (−)-1-(benzo[b]thiophen-2-yl)-3-[(3S*,4R*)-4-(2,6-difluoro-4-methoxyphenyl)-2-oxopyrrolidin-3-yl]urea | $^1$H-NMR (400 MHz, DMSO-d$_6$) δ 3.27-3.31 (1H, m), 3.46 (1H, t, J = 8.6 Hz), 3.75 (3H, s), 3.86 (1H, q, J = 9.2 Hz), 4.59 (1H, dd, J = 11.0, 8.6 Hz), 6.66 (1H, s), 6.75 (2H, d, J = 11.0 Hz), 6.82 (1H, d, J = 8.6 Hz), 7.09 (1H, t, J = 8.0 Hz), 7.21 (1H, t, J = 8.0 Hz), 7.52 (1H, d, J = 8.0 Hz), 7.69 (1H, d, J = 8.0 Hz), 8.09 (1H, s), 10.1 (1H, s). MS (ESI$^+$) m/z: 418 (MH$^+$). $[α]_D^{27}$ = −74 (c 0.10, EtOH) |
| 1-36 | | (−)-1-(benzo[d]oxazol-2-yl)-3-[(3S*,4R*)-4-(2,6-difluoro-4-methoxyphenyl)-2-oxopyrrolidin-3-yl]urea | $^1$H-NMR (400 MHz, DMSO-d$_6$) δ 3.32-3.38 (1H, m), 3.51 (1H, t, J = 9.2 Hz), 3.75 (3H, s), 3.97 (1H, q, J = 9.5 Hz), 4.67 (1H, dd, J = 9.8, 8.0 Hz), 6.74 (2H, d, J = 11.0 Hz), 7.17-7.30 (2H, m), 7.46-7.57 (2H, m), 8.16 (1H, s), 8.57 (1H, d, J = 7.3 Hz), 11.14 (1H, brs). MS (ESI$^+$) m/z: 403 (MH$^+$). $[α]_D^{28}$ = −158 (c 0.10, EtOH) |
| 1-37 | | (−)-1-[(3S*,4R*)-4-(2,6-difluoro-4-methoxyphenyl)-2-oxopyrrolidin-3-yl]-3-(5-methylisoxazol-3-yl)urea | $^1$H-NMR(400 MHz, DMSO-d$_6$) δ 2.29(3H, s), 3.27-3.32 (1H, m), 3.45 (1H, t, J = 9.2 Hz), 3.75 (3H, s), 3.76-3.84 (1H, m), 4.55 (1H, t, J = 9.8 Hz), 6.31 (1H, s), 6.70-6.81 (3H, m), 8.09 (1H, s), 9.44 (1H, s). MS (ESI$^+$) m/z: 367 (MH$^+$). $[α]_D^{27}$ = −154 (c 0.10, EtOH) |

TABLE 59

| Ex. No | Str. | Chemical name | P.D. |
|---|---|---|---|
| 1-38 | | (−)-1-[(3S*,4R*)-4-(2,6-difluoro-4-methoxyphenyl)-2-oxopyrrolidin-3-yl]-3-(2-fluorophenyl)urea | $^1$H-NMR (400 MHz, DMSO-d$_6$) δ 3.29-3.35 (1H, m), 3.46 (1H, t, J = 9.2 Hz), 3.67-3.74 (1H, m), 3.75 (3H, s), 4.57 (1H, dd, J = 11.0, 8.6 Hz), 6.75 (2H, d, J = 10.4 Hz), 6.88-6.96 (2H, m), 7.03 (1H, t, J = 7.2 Hz), 7.12-7.18 (1H, m), 7.93-7.98 (1H, m), 8.11 (1H, s), 8.41 (1H, d, J = 2.4 Hz). MS (ESI$^+$) m/z: 380 (MH$^+$). $[α]_D^{27}$ = −152 (c 0.10, EtOH) |

TABLE 59-continued

| Ex. No | Str. | Chemical name | P.D. |
|---|---|---|---|
| 1-39 | 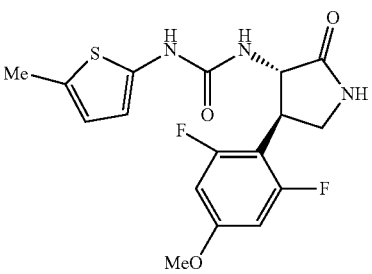 [SMILES: COc1cc(F)c([C@@H]2CNC(=O)[C@H]2NC(=O)Nc2ccc(C)s2)c(F)c1] | (−)-1-[(3S*,4R*)-4-(2,6-di-fluoro-4-methoxy-phenyl)-2-oxo-pyrrolidin-3-yl]-3-(5-methyl-thiophen-2-yl)urea | $^1$H-NMR (400 MHz, DMSO-d$_6$) δ 2.25 (3H, s), 3.26-3.32 (1H, m), 3.43 (1H, t, J = 9.2 Hz), 3.75 (3H, s), 3.76-3.84 (1H, m), 4.53 (1H, dd, J = 9.2, 8.0 Hz), 6.17 (1H, d, J = 3.2 Hz), 6.38 (1H, br s), 6.52 (1H, d, J = 8.0 Hz), 6.73 (2H, d, J = 10.3 Hz), 8.03 (1H, s), 9.42 (1H, s). MS (ESI$^+$) m/z: 382 (MH$^+$). [α]$_D^{27}$ = −162 (c 0.10, EtOH) |
| 1-40 | 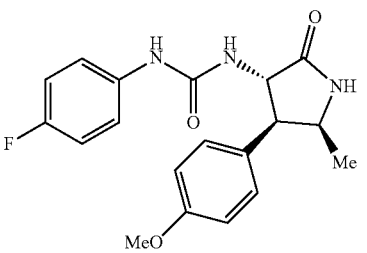 [SMILES: COc1ccc([C@@H]2[C@H](C)NC(=O)[C@H]2NC(=O)Nc2ccc(F)cc2)cc1] | (−)-1-(4-fluoro-phenyl)-3-[(3S*,4R*,5S*)-4-(4-methoxyphenyl)-5-methyl-2-oxopyrrolidin-3-yl]urea | $^1$H-NMR (400 MHz, DMSO-d$_6$) δ 0.68 (3H, d, J = 6.7 Hz), 3.64-3.71 (1H, m), 3.71 (3H, s), 3.74-3.80 (1H, m), 4.79 (1H, dd, J = 12.1, 9.1 Hz), 6.37 (1H, d, J = 9.1 Hz), 6.89 (2H, d, J = 9.1 Hz), 7.01-7.06 (2H, m), 7.25 (2H, d, J = 8.5 Hz), 7.35-7.39 (2H, m), 8.05 (1H, s), 8.51 (1H, s). MS (ESI$^+$) m/z: 358 (MH$^+$). [α]$_D^{25}$ = −149 (c 0.22, EtOH). |

TABLE 60

| Ex. No | Str. | Chemical name | P.D. |
|---|---|---|---|
| 1-41 | 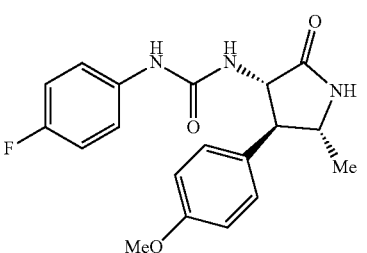 [SMILES: COc1ccc([C@H]2[C@H](NC(=O)Nc3ccc(F)cc3)C(=O)N[C@@H]2C)cc1] | (−)-1-(4-fluoro-phenyl)-3-[(3S*,4R*,5R*)-4-(4-methoxyphenyl)-5-methyl-2-oxopyrrolidin-3-yl]urea | $^1$H-NMR (400 MHz, DMSO-d$_6$) δ 1.04 (3H, d, J = 6.1 Hz), 2.86 (1H, dd, J = 11.5, 9.1 Hz), 3.45-3.54 (1H, m), 3.71 (3H, s), 4.53 (1H, dd, J = 11.5, 8.5 Hz), 6.34 (1H, d, J = 8.5 Hz), 6.87 (2H, d, J = 8.5 Hz), 6.99-7.03 (2H, m), 7.27 (2H, d, J = 8.5 Hz), 7.31-7.34 (2H, m), 7.98 (1H, s), 8.50 (1H, s). MS (ESI$^+$) m/z: 358 (MH$^+$). [α]$_D^{25}$ = −108 (c 0.39, EtOH). |
| 1-42 | 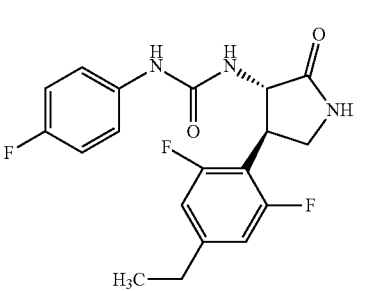 [SMILES: CCc1cc(F)c([C@@H]2CNC(=O)[C@H]2NC(=O)Nc2ccc(F)cc2)c(F)c1] | 1-[(3S*,4R*)-4-(4-ethyl-2,6-difluorophenyl)-2-oxopyrrolidin-3-yl]-3-(4-fluorophenyl)urea | $^1$H-NMR (400 MHz, DMSO-d$_6$) δ 1.15 (3H, t, J = 7.6 Hz), 2.58 (2H, q, J =7.6 Hz), 3.29-3.36 (1H, m), 3.41-3.48 (1H, m), 3.86 (1H, q, J = 9.8 Hz), 4.59 (1H, dd, J = 10.4, 8.6 Hz), 6.48 (1H, d, J = 8.6 Hz), 6.96 (2H, d, J = 9.8 Hz), 7.01 (2H, t, J = 8.9 Hz), 7.30-7.34 (2H, m), 8.06 (1H, s), 8.68 (1H, s). MS (ESI$^+$) m/z: 378 (MH$^+$). |

TABLE 60-continued

| Ex. No | Str. | Chemical name | P.D. |
|---|---|---|---|
| 1-43 | | (+)-1-(4-chloro-phenyl)-3-[(3R*,4S*)-2-oxo-4-phenylpyrrolidin-3-yl]urea | $^1$H-NMR (400 MHz, DMSO-d$_6$) δ 3.17-3.23 (1H, m), 3.49-3.58 (2H, m), 4.51 (1H, dd, J = 11.2, 8.5 Hz), 6.51 (1H, d, J = 8.5 Hz), 7.21-7.25 (3H, m), 7.29-7.33 (2H, m), 7.36-7.39 (4H, m), 7.94 (1H, s), 8.70 (1H, s). MS (ESI$^+$) m/z: 330 (MH$^+$). [α]$_D^{25}$ = +122 (c 0.35, DMSO) |

TABLE 61

| Ex. No | Str. | Chemical name | P.D. |
|---|---|---|---|
| 1-44 | | (+)-1-(4-chloro-phenyl)-3-[(3R*,4S*)-4-(4-methoxyphenyl)-2-oxopyrrolidin-3-yl]urea | $^1$H-NMR (400 MHz, DMSO-d$_6$) δ 3.11-3.21 (1H, m), 3.41-3.50 (2H, m), 3.71 (3H, s), 4.46 (1H, dd, J = 10.9, 9.1 Hz), 6.47 (1H, d, J = 9.1 Hz), 6.87 (2H, d, J = 8.5 Hz), 7.23 (2H, d, J = 9.1 Hz), 7.29 (2H, d, J = 9.1 Hz), 7.38 (2H, d, J = 8.5 Hz), 7.90 (1H, s), 8.67 (1H, s). MS (ESI$^+$) m/z: 360 (MH$^+$). [α]$_D^{25}$ = +146 (c 0.30, EtOH) |
| 1-45 | | (+)-1-(4-chloro-phenyl)-3-[(3R*,4S*)-4-(3-methoxyphenyl)-2-oxopyrrolidin-3-yl]urea | $^1$H-NMR (400 MHz, DMSO-d$_6$) δ 3.16-3.23 (1H, m), 3.47-3.56 (2H, m), 3.72 (3H, s), 4.52 (1H, t, J = 9.7 Hz), 6.49 (1H, d, J = 9.1 Hz), 6.80 (1H, dd, J = 8.5, 2.1 Hz), 6.93 (1H, d, J = 7.4 Hz), 6.97 (1H, s), 7.20-7.24 (3H, m), 7.38 (2H, d, J = 8.5 Hz), 7.92 (1H, s), 8.68 (1H, s). MS (ESI$^+$) m/z: 360 (MH$^+$). [α]$_D^{25}$ = +115 (c 0.35, DMSO) |
| 1-46 | | (+)-1-(4-chloro-phenyl)-3-[(3R*,4S*)-4-(2-methoxyphenyl)-2-oxopyrrolidin-3-yl]urea | $^1$H-NMR (400 MHz, DMSO-d$_6$) δ 3.09 (1H, t, J = 9.4 Hz), 3.40-3.50 (1H, m), 3.69-3.75 (1H, m), 3.78 (3H, s), 4.72 (1H, dd, J = 11.2, 8.8 Hz), 6.45 (1H, d, J = 9.1 Hz), 6.88-6.93 (1H, m), 6.98 (1H, d, J = 7.3 Hz), 7.20-7.24 (3H, m), 7.34-7.39 (3H, m), 7.88 (1H, s), 8.66 (1H, s). MS (ESI$^+$) m/z: 360 (MH$^+$). [α]$_D^{25}$ = +110 (c 0.35, EtOH) |

TABLE 62

| Ex. No | Str. | Chemical name | P.D. |
|---|---|---|---|
| 1-47 | | (+)-1-[(3R*,4S*)-4-(2,6-di-fluoro-4-methoxy-phenyl)-2-oxo-pyrrolidin-3-yl]-3-(4-fluoro-phenyl)urea | $^1$H-NMR (400 MHz, DMSO-d$_6$) δ 3.27-3.33 (1H, m), 3.44 (1H, t, J = 9.5 Hz), 3.75 (3H, s), 3.79 (1H, q, J = 9.8 Hz), 4.56 (1H, dd, J = 11.0, 8.6 Hz), 6.46 (1H, d, J = 8.6 Hz), 6.73 (2H, d, J = 10.4 Hz), 6.98-7.04 (2H, m), 7.30-7.34 (2H, m), 8.05 (1H, s), 8.66 (1H, s). MS (ESI$^+$) m/z: 380 (MH$^+$). [α]$_D^{28}$ +175 (c0.10, EtOH) |
| 1-48 | | (+)-1-(4-chloro-phenyl)-3-[(3R*,4S*)-4-(4-methoxyphenyl)-1-methyl-2-oxo-pyrrolidin-3-yl]urea | $^1$H-NMR (400 MHz, DMSO-d$_6$) δ 2.79 (3H, s), 3.29 (1H, t, J = 9.7 Hz), 3.43 (1H, q, J = 9.5 Hz), 3.54 (1H, t, J = 8.5 Hz), 3.71 (3H, s), 4.46 (1H, t, J = 10.0 Hz), 6.53 (1H, d, J = 9.1 Hz), 6.88 (2H, d, J = 8.5 Hz), 7.23 (2H, d, J = 9.1 Hz), 7.29 (2H, d, J = 9.1 Hz), 7.38 (2H, d, J = 8.5 Hz), 8.71 (1H, s). MS (ESI$^+$) m/z: 374 (MH$^+$). [α]$_D^{25}$ = +162 (c 0.31, EtOH) |
| 1-49 | | (+)-1-(4-fluoro-phenyl)-3-[(3R*,4S*,5S*)-4-(4-methoxyphenyl)-5-methyl-2-oxopyrrolidin-3-yl]urea | $^1$H-NMR (400 MHz, DMSO-d$_6$) δ 1.04 (3H, d, J = 6.1 Hz), 2.86 (1H, dd, J = 11.5, 9.1 Hz), 3.45-3.54 (1H, m), 3.71 (3H, s), 4.53 (1H, dd, J = 11.5, 8.5 Hz), 6.34 (1H, d, J = 8.5 Hz), 6.87 (2H, d, J = 8.5 Hz), 6.99-7.03 (2H, m), 7.27 (2H, d, J = 8.5 Hz), 7.31-7.34 (2H, m), 7.98 (1H, s), 8.50 (1H, s). MS (ESI$^+$) m/z: 358 (MH$^+$). [α]$_D^{25}$ +116 (c 0.38, EtOH). |

TABLE 63

| Ex. No | Str. | Chemical name | P.D. |
|---|---|---|---|
| 1-50 | | (+)-1-(4-fluorophenyl)-3-[(3R*,4S*,5R*)-4-(4-methoxyphenyl)-5-methyl-2-oxo-pyrrolidin-3-yl]urea | $^1$H-NMR (400 MHz, DMSO-d$_6$) δ 0.68 (3H, d, J = 6.7 Hz), 3.64-3.71 (1H, m), 3.71 (3H, s), 3.74-3.80 (1H, m), 4.79 (1H, dd, J = 12.1, 9.1 Hz), 6.37 (1H, d, J = 9.1 Hz), 6.89 (2H, d, J = 9.1 Hz), 7.01-7.06 (2H, m), 7.25 (2H, d, J = 8.5 Hz), 7.35-7.39 (2H, m), 8.05 (1H, s), 8.51 (1H, s). MS (ES$^+$) m/z: 358 (MH$^+$). [α]$_D^{25}$ +167 (c 0.45, EtOH). |
| 1-51 | | (+)-1-(4-fluorophenyl)-3-[(3R*,4S*)-4-(5-methoxythiophen-2-yl)-2-oxopyrrolidin-3-yl]urea | $^1$H-NMR (400 MHz, DMSO-d$_6$) δ 3.18 (1H, t, J = 9.7 Hz), 3.49 (1H, t, J = 9.5 Hz), 3.60 (1H, q, J = 9.5 Hz), 3.78 (3H, s), 4.28 (1H, dd, J = 10.9, 9.1 Hz), 6.11 (1H, d, J = 3.6 Hz), 6.47 (1H, d, J = 9.1 Hz), 6.62 (1H, d, J = 3.6 Hz), 7.04 (2H, m), 7.37-7.40 (2H, m), 7.93 (1H, s), 8.64 (1H, s). MS (ESI$^+$) m/z: 350 (MH$^+$). [α]$_D^{25}$ = +122 (c 0.10, EtOH) |

TABLE 63-continued

| Ex. No | Str. | Chemical name | P.D. |
|---|---|---|---|
| 1-52 | | (+)-1-{(3R*,4S*)-4-[4-(difluoromethoxy)phenyl]-2-oxo-pyrrolidin-3-yl}-3-(4-fluorophenyl)urea | $^1$H-NMR (400 MHz, DMSO-d$_6$) δ 3.17-3.22 (1H, m), 3.47-3.57 (2H, m), 4.50 (1H, dd, J = 10.9, 9.1 Hz), 6.44 (1H, d, J = 9.1 Hz), 7.00-7.05 (2H, m), 7.00-7.37 (1H, m), 7.12 (2H, d, J = 8.5 Hz), 7.33-7.37 (2H, m), 7.44 (2H, d, J = 8.5 Hz), 7.94 (1H, s), 8.57 (1H, s).<br>MS (ESI$^+$) m/z: 380 (MH$^+$).<br>[α]$_D$$^{23}$ = +107 (c 0.35, EtOH) |

TABLE 64

| Ex. No | Str. | Chemical Name | P.D. |
|---|---|---|---|
| 1-53 | (±)-trans | (±)-trans-1-(4-chlorophenyl)-3-[4-(4-methoxy-phenyl)-2-oxopyrrolidin-3-yl]urea | $^1$H-NMR (400 MHz, DMSO-d$_6$) δ 3.11-3.21 (1H, m), 3.41-3.50 (2H, m), 3.71 (3H, s), 4.46 (1H, dd, J = 10.9, 9.1 Hz), 6.47 (1H, d, J = 9.1 Hz), 6.87 (2H, d, J = 8.5 Hz), 7.23 (2H, d, J = 9.1 Hz), 7.29 (2H, d, J = 9.1 Hz), 7.38 (2H, d, J = 8.5 Hz), 7.90 (1H, s), 8.67 (1H, s).<br>MS (ESI$^+$) m/z: 360 (MH$^+$). |
| 1-54 | (±)-trans | (±)-trans-1-(4-fluorophenyl)-3-[4-(4-methoxy-phenyl)-2-oxopyrrolidin-3-yl]urea | $^1$H-NMR (400 MHz, DMSO-d$_6$) δ 3.11-3.17 (1H, m), 3.38-3.48 (2H, m), 3.69 (3H, s), 4.45 (1H, dd, J = 10.9, 9.1 Hz), 6.38 (1H, d, J = 9.1 Hz), 6.86 (2H, d, J = 8.5 Hz), 7.01 (2H, t, J = 9.1 Hz), 7.28 (2H, d, J = 8.5 Hz), 7.32-7.35 (2H, m), 7.88 (1H, s), 8.53 (1H, s).<br>MS (ESI$^+$) m/z: 344 (MH$^+$). |
| 1-55 | (±)-trans | (±)-trans-1-(4-chlorophenyl)-3-[4-(4-methoxyphenyl)-1-methyl-2-oxopyrrolidin-3-yl]urea | $^1$H-NMR (400 MHz, DMSO-d$_6$) δ 2.79 (3H, s), 3.29 (1H, t, J = 9.7 Hz), 3.43 (1H, q, J = 9.5 Hz), 3.54 (1H, t, J = 8.5 Hz), 3.71 (3H, s), 4.46 (1H, t, J = 10.0 Hz), 6.53 (1H, d, J = 9.1 Hz), 6.88 (2H, d, J = 8.5 Hz), 7.23 (2H, d, J = 9.1 Hz), 7.29 (2H, d, J = 9.1 Hz), 7.38 (2H, d, J = 8.5 Hz), 8.71 (1H, s).<br>MS (ESI$^+$) m/z: 374 (MH$^+$). |

TABLE 65

| Ex. No. | Str. | Chemical name | P.D. |
|---|---|---|---|
| 1-56 | | 1-[(3S*,4R*)-4-(2,6-difluoro-4-methoxyphenyl)-2-oxopyrrolidin-3-yl]-3-(4-hydroxyphenyl)urea | $^1$H-NMR (400 MHz, DMSO-d$_6$) δ 3.26-3.31 (1H, m), 3.43 (1H, t, J = 9.7 Hz), 3.72-3.79 (4H, m), 4.64 (1H, dd, J = 10.3, 7.8 Hz), 6.29 (1H, d, J = 8.5 Hz), 6.57-6.60 (2H, m), 6.73 (2H, d, J = 10.9 Hz), 7.06-7.09 (2H, m), 8.02 (1H, s), 8.25 (1H, s), 8.92 (1H, s).<br>MS (ESI$^+$) m/z: 378 (MH$^+$). |

TABLE 65-continued

| Ex. No. | Str. | Chemical name | P.D. |
|---|---|---|---|
| 1-57 | | 1-[(3S*,4R*)-4-(2,6-difluoro-4-methoxyphenyl)-2-oxopyrrolidin-3-yl]-3-(3-hydroxyphenyl)urea | $^{1}$H-NMR (400 MHz, DMSO-d$_6$) δ 3.27-3.32 (1H, m), 3.44 (1H, t, J = 9.7 Hz), 3.72-3.80 (4H, m), 4.56 (1H, dd, J = 10 9, 8.5 Hz), 6.27 (1H, dd, J = 7.3, 1.8 Hz), 6.37 (1H, d, J = 8.5 Hz), 6.65 (1H, dd, J = 7.2, 1.8 Hz), 6.73 (2H, d, J = 10.9 Hz), 6.91-6.96 (2H, m), 8.05 (1H, s), 8.49 (1H, s), 9.16 (1H, s). MS (ESI$^+$) m/z: 378 (MH$^+$). |
| 1-58 | | (−)-1-[(3S*,4R*)-4-(2,6-difluoro-4-methoxyphenyl)-2-oxopyrrolidin-3-yl]-3-(3-methylisothiazol-5-yl)urea | $^{1}$H-NMR (400 MHz, DMSO-d$_6$) δ 2.21 (3H, s), 3.27-3.32 (1H, m), 3.45 (1H, t, J = 9.6 Hz), 3.75 (3H, s), 3.87 (1H, q, J = 9.6 Hz), 4.54 (1H, dd, J = 9.6, 8.6 Hz), 6.46 (1H, s), 6.75 (2H, d, J = 10.4 Hz), 7.16 (1H, d, J = 8.6 Hz), 8.09 (1H, s), 10.5 (1H, s). MS (ESI$^+$) m/z: 383 (MH$^+$). $[α]_D^{26}$ = −264 (c 0.03, EtOH) |

TABLE 66

| Ex. No. | Str. | Chemical name | P.D. |
|---|---|---|---|
| 1-59 | | (−)-1-[(3S*,4R*)-4-(2,6-difluoro-4-methoxyphenyl)-2-oxopyrrolidin-3-yl]-3-(1H-indol-5-yl)urea | $^{1}$H-NMR (400 MHz, DMSO-d$_6$) δ 3.30 (1H, t, J = 9.2 Hz), 3.44 (1H, t, J = 9.2 Hz), 3.75 (3H, s), 3.77 (1H, q, J = 9.2 Hz), 4.58 (1H, dd, J = 10.4, 8.6 Hz), 6.27 (1H, brs) 6.32 (1H, d, J = 8.6 Hz), 6.71-6.77 (2H, d, J = 10.4 Hz), 6.94 (1H, dd, J = 8.6, 1.8 Hz), 7.20 (1H, d, J = 8.6 Hz), 7.23 (1H, t, J = 3.0 Hz), 7.52 (1H, d, J = 1.8 Hz), 8.04 (1H, s), 8.31 (1H, s), 10.9 (1H, s). MS (ESI$^+$) m/z: 401 (MH$^+$). $[α]_D^{27}$ = −156 (c 0.11, EtOH) |
| 1-60 | | 1-[(3S*,4R*)-4-(2,6-difluoro-4-methoxyphenyl)-2-oxopyrrolidin-3-yl]-3-(4-iodophenyl)urea | $^{1}$H-NMR (400 MHz, DMSO-d$_6$) δ 3.25-3.34 (1H, m), 3.44 (1H, t, J = 9.2 Hz), 3.75 (3H, s), 3.79 (1H, q, J = 9.2 Hz), 4.55 (1H, dd, J = 11, 8.6 Hz), 6.53-6.65 (1H, m), 6.79-6.77 (2H, m), 7.18 (2H, d, J = 8.6 Hz), 7.49 (2H, d, J = 8.6 Hz), 8.05 (1H, s), 8.79-8.88 (1H, m). MS (ESI$^+$) m/z: 488 (MH$^+$). |
| 1-61 | | (−)-1-[(3S*,4R*)-4-(2,6-difluoro-4-methoxyphenyl)-2-oxopyrrolidin-3-yl]-3-[4-(oxazol-2-yl)phenyl]urea | $^{1}$H-NMR (400 MHz, DMSO-d$_6$) δ 3.26-3.33 (1H, m), 3.46 (1H, t, J = 9.2 Hz), 3.75 (3H, s), 3.82 (1H, q, J = 9.2 Hz), 4.58 (1H, dd, J = 10.4, 8.0 Hz), 6.64 (1H, brd), 6.71-6.78 (2H, m), 7.29 (1H, s), 7.49 (2H, d, J = 8.6 Hz), 7.80 (2H, d, J = 8.6 Hz), 8.08 (1H, s), 8.11 (1H, s), 9.02 (1H, brs). MS (ESI$^+$) m/z: 429 (MH$^+$). $[α]_D^{29}$ = −166 (c 0.15, EtOH) |

TABLE 67

| Ex. No. | Str. | Chemical name | P.D. |
|---|---|---|---|
| 1-62 | | (−)-1-(4-cyclopropyl-phenyl)-3-[(3S*,4R*)-4-(2,6-difluoro-4-methoxyphenyl)-2-oxopyrrolidin-3-yl]urea | $^1$H-NMR (400 MHz, DMSO-d$_6$) δ 0.52-0.56 (2H, m), 0.81-0.87 (2H, m), 1.76-1.82 (1H, m), 3.29 (1H, t, J = 9.2 Hz), 3.44 (1H, t, J = 9.2 Hz), 3.75 (3H, s), 3.77 (1H, q, J = 9.2 Hz), 4.55 (1H, dd, J = 10.4, 8.6 Hz), 6.39 (1H, d, J = 8.6 Hz), 6.70-6.76 (2H, m), 6.89 (2H, d, J = 8.6 Hz), 7.18 (2H, d, J = 8.6 Hz), 8.04 (1H, s), 8.50 (1H, s).<br>MS (ESI$^+$) m/z: 401 (MH$^+$).<br>$[α]_D^{25}$ = −157 (c 0.14, EtOH) |
| 1-63 | | (−)-1-[3S*,4R*)-4-(2,6-difluoro-4-methoxyphenyl)-2-oxopyrrolidin-3-yl]-3-[4-(trifluoro-methyl)phenyl]urea | $^1$H-NMR (400 MHz, DMSO-d$_6$) δ 3.29-3.35 (1H, m), 3.47 (1H, t, J = 9.2 Hz), 3.76 (3H, s), 3.80-3.88 (1H, m), 4.60 (1H, dd, J = 11.0, 8.6 Hz), 6.65 (1H, d, J = 7.9 Hz), 6.75 (2H, d, J = 11.0 Hz), 7.50-7.55 (4H, m), 8.09 (1H, s), 9.11 (1H, s).<br>MS (ESI$^+$) m/z: 430 (MH$^+$).<br>$[α]_D^{26}$ = −95 (c 0.13, EtOH) |
| 1-64 | | (−)-1-[(3S*,4R*)-4-(2,6-difluoro-4-methoxyphenyl)-2-oxopyrrolidin-3-yl]-3-(3-fluoro-4-methyl-phenyl)urea | $^1$H-NMR (400 MHz, DMSO-d$_6$) δ 2.10 (3H, s), 3.25-3.35 (1H, m), 3.41-3.47 (1H, m), 3.75 (3H, s), 3.77-3.83 (1H, m), 4.55 (1H, dd, J = 11.0, 8.6 Hz), 6.52 (1H, d, J = 8.6 Hz), 6.73 (2H, d, J = 11.0 Hz), 6.91 (1H, dd, J = 8.3, 2.1 Hz), 7.06 (1H, t, J = 8.9 Hz), 7.28 (1H, dd, J = 12.5, 2.1 Hz), 8.05 (1H, s), 8.77 (1H, s).<br>MS (ESI$^+$) m/z: 394 (MH$^+$).<br>$[α]_D^{25}$ = −125 (c 0.13, EtOH) |

TABLE 68

| Ex. No. | Str. | Chemical name | P.D. |
|---|---|---|---|
| 1-65 | | (−)-1-[(3S*,4R*)-4-(2,6-difluoro-4-methoxyphenyl)-2-oxopyrrolidin-3-yl]-3-(4-fluoro-3-methylphenyl)urea | $^1$H-NMR (400 MHz, DMSO-d$_6$) δ 2.14 (3H, s), 3.26-3.33 (1H, m), 3.44 (1H, t, J = 8.9 Hz), 3.75 (3H, s), 3.77-3.83 (1H, m), 4.55 (1H, dd, J = 11.0, 8.6 Hz), 6.44 (1H, d, J = 8.6 Hz), 6.73 (2H, d, J = 11.0 Hz), 6.94 (1H, t, J = 9.2 Hz), 7.07-7.12 (1H, m), 7.23-7.26 (1H, m), 8.04 (1H, s), 8.57 (1H, s).<br>MS (ESI$^+$) m/z: 394 (MH$^+$).<br>$[α]_D^{26}$ = −151 (c 0.14, EtOH) |
| 1-66 | | (−)-1-[(3S*,4R*)-4-(2,6-difluoro-4-methoxyphenyl)-2-oxopyrrolidin-3-yl]-3-(6-methylpyridin-3-yl)urea | $^1$H-NMR (400 MHz, DMSO-d$_6$) δ 2.34 (3H, s), 3.25-3.34 (1H, m), 3.44 (1H, t, J = 9.8 Hz), 3.75 (3H, s), 3.77-3.85 (1H, m), 4.56 (1H, dd, J = 10.7, 8.3 Hz), 6.57 (1H, d, J = 8.6 Hz), 6.74 (2H, d, J = 11.0 Hz), 7.06 (1H, d, J = 8.6 Hz), 7.68 (1H, dd, J = 8.6, 2.4 Hz), 8.05 (1H, s), 8.34 (1H, d, J = 2.4 Hz), 8.72 (1H, s).<br>MS (ESI$^+$) m/z: 377 (MH$^+$).<br>$[α]_D^{24}$ = −168 (c 0.22, EtOH) |

TABLE 68-continued

| Ex. No. | Str. | Chemical name | P.D. |
| --- | --- | --- | --- |
| 1-67 | | (−)-1-[(3S*,4R*)-4-(2,6-difluoro-4-methoxyphenyl)-2-oxopyrrolidin-3-yl]-3-[6-(trifluoromethyl)pyridin-3-yl]urea | 1H-NMR (400 MHz, DMSO-d$_6$) δ 3.25-3.35 (1H, m), 3.40-3.50 (1H, m), 3.75 (3H, s), 3.81-3.90 (1H, m), 4.59 (1H, dd, J = 10.7, 8.3 Hz), 6.74 (2H, d, J = 11.0 Hz), 6.84 (1H, d, J = 8.6 Hz), 7.71 (1H, d, J = 9.2 Hz), 8.06-8.11 (2H, m), 8.62 (1H, d, J = 2.4 Hz), 9.36 (1H, s). MS (ESI+) m/z: 431 (MH+). [α]$_D^{24}$ = −236 (c 0.20, EtOH) |

TABLE 69

| Ex. No. | Str. | Chemical name | P.D. |
| --- | --- | --- | --- |
| 1-68 | | (−)-1-[(3S*,4R*)-4-(2,6-difluoro-4-methoxyphenyl)-2-oxopyrrolidin-3-yl]-3-(3-hydroxy-4-methylphenyl)urea | 1H-NMR (400 MHz, DMSO-d$_6$) δ 1.98 (3H, s), 3.26-3.33 (1H, m), 3.50-3.47 (1H, m), 3.70-3.79 (1H, m), 3.75 (3H, s), 4.56 (1H, dd, J = 10.7, 8.3 Hz), 6.31 (1H, d, J = 7.9 Hz), 6.54 (1H, dd, J = 8.6, 2.4 Hz), 6.73 (2H, d, J = 11.0 Hz), 6.81 (1H, d, J = 8.6 Hz), 6.97 (1H, d, J = 2.4 Hz), 8.05 (1H, s), 8.39 (1H, s), 9.08 (1H, s). MS (ESI+) m/z: 392 (MH+). [α]$_D^{25}$ = −198 (c 0.15, EtOH) |
| 1-69 | | (−)-1-[(3S*,4R*)-4-(2,6-difluoro-4-methoxyphenyl)-2-oxopyrrolidin-3-yl]-3-(2-fluoro-4-methylphenyl)urea | 1H-NMR (400 MHz, DMSO-d$_6$) δ 2.21 (3H, s), 3.26-3.33 (1H, m), 3.46 (1H, t, J = 9.5 Hz), 3.66-3.74 (1H, m), 3.75 (3H, s), 4.56 (1H, dd, J = 10.7, 8.3 Hz), 6.74 (2H, d, J = 11.0 Hz), 6.82-6.86 (2H, m), 6.97 (1H, d, J = 12.8 Hz), 7.78 (1H, t, J = 8.3 Hz), 8.10 (1H, s), 8.27 (1H, s). MS (ESI+) m/z: 394 (MH+). [α]$_D^{26}$ = −188 (c 0.12, EtOH) |
| 1-70 | | (−)-1-[(3S*,4R*)-4-(2,6-difluoro-4-methoxyphenyl)-2-oxopyrrolidin-3-yl]-3-(2,3-dihydro-1H-inden-5-yl)urea | 1H-NMR (400 MHz, DMSO-d$_6$) δ 1.90-1.99 (2H, m), 2.74 (4H, q, J = 7.7 Hz), 3.26-3.33 (1H, m), 3.44 (1H, t, J = 9.2 Hz), 3.72-3.80 (1H, m), 3.75 (3H, s), 4.56 (1H, dd, J = 11.0, 8.6 Hz), 6.37 (1H, td J = 8.6 Hz), 6.73 (2H, d, J = 11.0 Hz), 6.97-7.03 (2H, m), 7.25 (1H, s), 8.04 (1H, s), 8.45 (1H, s). MS (ESI+) m/z: 402 (MH+). [α]$_D^{26}$ = −186 (c 0.26, EtOH) |

TABLE 70

| Ex. No. | Str. | Chemical name | P.D. |
|---|---|---|---|
| 1-71 | | (−)-1-[(3S*,4R*)-4-(2,6-difluoro-4-methoxyphenyl)-2-oxopyrrolidin-3-yl]-3-(4-fluoro-3-hydroxyphenyl)urea | $^1$H-NMR (400 MHz, DMSO-$d_6$) δ 3.26-3.33 (1H, m), 3.43 (1H, t, J = 9.5 Hz), 3.73-3.81 (1H, m), 3.75 (3H, s), 4.56 (1H, dd, J = 10.7, 8.3 Hz), 6.36 (1H, d, J = 8.6 Hz), 6.58-6.62 (1H, m), 6.73 (2H, d, J = 11.0 Hz), 6.90 (1H, dd, J = 11.0, 9.2 Hz), 7.12 (1H, dd, J = 7.9, 2.4 Hz), 8.05 (1H, s), 8.54 (1H, s), 9.65 (1H, s). MS (ESI$^+$) m/z: 396 (MH$^+$). [α]$_D^{26}$ = −188 (c 0.12, EtOH) |
| 1-72 | | (−)-1-(4-chloro-3-hydroxyphenyl)-3-[(3S*,4R*)-4-(2,6-difluoro-4-methoxyphenyl)-2-oxopyrrolidin-3-yl]urea | $^1$H-NMR (400 MHz, DMSO-$d_6$) δ 3.26-3.33 (1H, m), 3.44 (1H, t, J = 9.2 Hz), 3.75 (3H, s), 3.76-3.82 (1H, m), 4.56 (1H, dd, J = 10.7, 8.3 Hz), 6.42 (1H, d, J = 8.6 Hz), 6.66 (1H, dd, J = 8.6, 2.4 Hz), 6.73 (2H, d, J = 11.0 Hz), 7.07 (1H, d, J = 8.6 Hz), 7.21 (1H, d, J = 2.4 Hz), 8.07 (1H, s), 8.67 (1H, s), 9.95 (1H, s). MS (ESI$^+$) m/z: 412 (MH$^+$). [α]$_D^{26}$ = −189 (c 0.18, EtOH) |
| 1-73 | | 1-(4-cyano-3-hydroxyphenyl)-3-[(3S*,4R*)-4-(2,6-difluoro-4-methoxyphenyl)-2-oxopyrrolidin-3-yl]urea | $^1$H-NMR (400 MHz, DMSO-$d_6$) δ 3.26-3.33 (1H, m), 3.44 (1H, t, J = 9.2 Hz), 3.75 (3H, s), 3.76-3.84 (1H, m), 4.57 (1H, dd, J = 11.0, 8.6 Hz), 6.61 (1H, d, J = 7.9 Hz), 6.71-6.76 (3H, m), 7.29 (1H, s), 7.35 (1H, d, J = 8.6 Hz), 8.09 (1H, s), 9.08 (1H, s), 10.81 (1H, brs). MS (ESI$^+$) m/z: 403 (MH$^+$). |

TABLE 71

| Ex. No. | Str. | Chemical name | P.D. |
|---|---|---|---|
| 1-74 | | 1-{(3S*,4R*)-4-[4-(difluoromethoxy)-2,6-difluorophenyl]-2-oxopyrrolidin-3-yl}-3-(4-fluorophenyl)urea | $^1$H-NMR (400 MHz, DMSO-$d_6$) δ 3.28-3.34 (1H, m), 3.46-3.50 (1H, m), 3.86 (1H, q, J = 9.7 Hz), 4.57 (1H, dd, J = 10.9, 7.9 Hz), 6.48 (1H, d, J = 8.5 Hz), 6.99-7.08 (4H, m), 7.30-7.33 (2H, m), 7.32 (1H, t, J = 73.3 Hz), 8.09 (1H, br), 8.70 (1H, s). MS (ESI$^+$) m/z: 416 (MH$^+$). |
| 1-75 | | (−)-1-[(3S*,4R*)-4-(4-ethoxy-2,6-difluorophenyl)-2-oxopyrrolidin-3-yl]-3-(4-fluorophenyl)urea | $^1$H-NMR (400 MHz, CDCl$_3$) δ 1.29 (3H, t, J = 7.0 Hz), 3.25-3.34 (1H, m), 3.44 (1H, t, J = 9.2 Hz), 3.75-3.82 (1H, m), 4.02 (2H, q, J = 7.0 Hz), 4.54 (1H, dd, J = 10.4, 8.3 Hz), 6.68-6.75 (1H, m), 6.71 (2H, d, J = 11.0 Hz), 7.01 (2H, t, J = 9.0 Hz), 7.34 (2H, dd, J = 9.0, 4.9 Hz), 8.03 (1H, s), 8.89 (1H, s) MS (ESI$^+$) m/z: 394 (MH$^+$). [α]$_D^{26}$ = −149 (c 0.13, EtOH) |

TABLE 71-continued

| Ex. No. | Str. | Chemical name | P.D. |
|---|---|---|---|
| 1-76 | | 1-{(3S*,4R*)-4-[4-(dimethylamino)-2,6-difluorophenyl]-2-oxopyrrolidin-3-yl}-3-(4-fluorophenyl)urea | $^1$H-NMR (400 MHz, DMSO-$d_6$) δ 2.87 (6H, s), 3.27 (1H, t, J = 9.8 Hz), 3.39 (1H, t, J = 8.9 Hz), 3.71 (1H, q, J = 10.0 Hz), 4.54 (1H, dd, J = 11.0, 8.6 Hz), 6.34 (2H, d, J = 12.2 Hz), 6.52 (1H, d, J = 9.2 Hz), 6.98-7.04 (2H, m), 7.31-7.37 (2H, m), 7.99 (1H, s), 8.71 (1H, s). MS (ESI$^+$) m/z: 393 (MH$^+$). |

TABLE 72

| Ex. No. | Str. | Chemical name | P.D. |
|---|---|---|---|
| 1-77 | | (−)-1-[(3S*,4R*)-4-(6-fluorobenzofuran-5-yl)-2-oxopyrrolidin-3-yl]-3-(4-fluorophenyl)urea | $^1$H-NMR (400 MHz, DMSO-$d_6$) δ 3.21-3.26 (1H, m), 3.51-3.55 (1H, m), 3.80-3.87 (1H, m), 4.65 (1H, dd, J = 11.3, 8.8 Hz), 6.77 (1H, d, J = 8.8 Hz), 6.94 (1H, d, J = 2.4 Hz), 7.00 (2H, t, J = 9.0 Hz), 7.34 (2H, dd, J = 9.0, 4.9 Hz), 7.54 (1H, d, J = 11.0 Hz), 7.80 (1H, d, J = 7.3 Hz), 7.97 (1H, s), 7.99 (1H, d, J = 2.4 Hz), 8.87 (1H, s). MS (ESI$^+$) m/z: 372 (MH$^+$). $[α]_D^{25}$ = −201 (c 0.10, EtOH) |
| 1-78 | | (−)-1-(4-fluorophenyl)-3-[(3S*,4R*)-4-(6-methoxypyridin-3-yl)-2-oxopyrrolidin-3-yl]urea | $^1$H-NMR (400 MHz, DMSO-$d_6$) δ 3.17-3.24 (1H, m), 3.42-3.52 (2H, m), 3.80 (3H, s), 4.47-4.52 (1H, m), 6.60 (1H, brs), 6.79 (1H, d, J = 8.6 Hz), 7.02 (2H, dd, J = 9.2, 8.6 Hz), 7.35 (2H, dd, J = 9.2, 4.9 Hz), 7.80 (1H, dd, J = 8.6, 2.4 Hz), 7.95 (1H, s), 8.10 (1H, d, J = 2.4 Hz), 8.75 (1H, brs). MS (ESI$^+$) m/z: 345 (MH$^+$). $[α]_D^{26}$ = −103 (c 0.12, EtOH) |
| 1-79 | | (−)-N-(3,5-difluoro-4-{(3R*,4S*)-4-[3-(4-fluorophenyl)ureido]-5-oxopyrrolidin-3-yl}phenyl)acetamide | $^1$H-NMR (400 MHz, DMSO-$d_6$) δ 2.03 (3H, s), 3.28-3.35 (1H, m), 3.42-3.48 (1H, m), 3.81 (1H, q, J = 9.8 Hz), 4.56 (1H, dd, J = 10.7, 8.3 Hz), 6.46 (1H, d, J = 8.6 Hz), 6.97-7.04 (2H, m), 7.25-7.34 (4H, m), 8.06 (1H, s), 8.67 (1H, s), 10.26 (1H, s). MS (ESI$^+$) m/z: 407 (MH$^+$). $[α]_D^{24}$ = −31 (c 0.12, EtOH) |

TABLE 73

| Ex. No. | Str. | Chemical name | P.D. |
|---|---|---|---|
| 1-80 | | 1-[(3S*,4R*)-4-(4,6-difluoro-2,3-dihydrobenzofuran-5-yl)-2-oxopyrrolidin-3-yl]-3-(4-fluorophenyl)urea | $^1$H-NMR (400 MHz, DMSO-d$_6$) δ 3.18 (2H, t, J = 8.6 Hz), 3.28 (1H, t, J = 9.5 Hz), 3.42 (1H, t, J = 9.2 Hz), 3.79 (1H, q, J = 9.8 Hz), 4.55 (1H, dd, J = 10.4, 8.6 Hz), 4.62 (2H, t, J = 8.6 Hz), 6.48 (1H, d, J = 8.6 Hz), 6.62 (1H, d, J = 11.0 Hz), 6.99-7.05 (2H, m), 7.31-7.37 (2H, m), 8.03 (1H, s), 8.68 (1H, s). MS (ESI$^+$) m/z: 392 (MH$^+$). |
| 1-81 | | 1-[(3S*,4R*)-4-(6-fluoro-1-hydroxy-2,3-dihydro-1H-inden-5-yl)-2-oxopyrrolidin-3-yl]-3-(4-fluorophenyl)urea | $^1$H-NMR (400 MHz, DMSO-d$_6$) δ 1.74-1.81 (1H, m), 2.28-2.36 (1H, m), 2.62-2.69 (1H, m), 2.79-2.86 (1H, m), 3.18 (1H, t, J = 9.5 Hz), 3.46 (1H, t, J = 8.9 Hz), 3.74 (1H, q, J = 10.0 Hz), 4.57 (1H, dd, J = 11.3, 8.9 Hz), 4.98 (1H, q, J = 6.3 Hz), 5.28 (1H, t, J = 5.2 Hz), 6.66 (1H, d, J = 8.6 Hz), 6.99-7.05 (3H, m), 7.33-7.38 (3H, m), 7.95 (1H, s), 8.79 (1H, s). MS (ESI$^+$) m/z: 388 (MH$^+$). |
| 1-82 | | 1-[(3S*,4R*)-4-(6-fluoro-2,3-dihydro-1H-inden-5-yl)-2-oxopyrrolidin-3-yl]-3-(4-fluorophenyl)urea | $^1$H-NMR (400 MHz, DMSO-d$_6$) δ 1.96-2.04 (2H, m), 2.80 (4H, q, J = 8.2 Hz), 3.18 (1H, t, J = 9.8 Hz), 3.45 (1H, d, J = 8.9 Hz), 3.72 (1H, q, J = 9.8 Hz), 4.56 (1H, dd, J = 11.3, 8.9 Hz), 6.54 (1H, d, J = 7.9 Hz), 6.99-7.05 (3H, m), 7.32-7.37 (3H, m), 7.94 (1H, s), 8.69 (1H, s). MS (ESI$^+$) m/z: 372 (MH$^+$). |

TABLE 74

| Ex. No. | Str. | Chemical name | P.D. |
|---|---|---|---|
| 1-83 | | (−)-1-[(3S*,4R*)-4-(6-fluoro-2,3-dihydrobenzofuran-5-yl)-2-oxopyrrolidin-3-yl]-3-(p-tolyl)urea | $^1$H-NMR (400 MHz, DMSO-d$_6$) δ 2.19 (3H, s), 3.11 (2H, t, J = 8.6 Hz), 3.15 (1H, t, J = 9.5 Hz), 3.42 (1H, t, J = 8.9 Hz), 3.61-3.68 (1H, m), 4.50-4.56 (3H, m), 6.46 (1H, brs), 6.62 (1H, d, J = 11.0 Hz), 6.99 (2H, d, J = 8.6 Hz), 7.22 (2H, d, J = 8.6 Hz), 7.37 (1H, d, J = 7.3 Hz), 7.92 (1H, s), 8.52 (1H, brs). MS (ESI$^+$) m/z: 370 (MH$^+$). [α]$_D^{28}$ = −158 (c 0.20, EtOH) |
| 1-84 | | (−)-1-(4-cyanophenyl)-3-[(3S*,4R*)-4-(6-fluoro-2,3-dihydrobenzofuran-5-yl)-2-oxopyrrolidin-3-yl]urea | $^1$H-NMR (400 MHz, DMSO-d$_6$) δ 3.04-3.21 (3H, m), 3.43 (1H, t, J = 8.9 Hz), 3.66-3.73 (1H, m), 4.51-4.56 (3H, m), 6.63 (1H, d, J = 11.6 Hz), 7.29 (1H, brs), 7.36 (1H, d, J = 7.9 Hz), 7.55 (2H, d, J = 8.6 Hz), 7.62 (2H, d, J = 8.6 Hz), 7.94 (1H, s), 9.70 (1H, brs). MS (ESI$^+$) m/z: 381 (MH$^+$). [α]$_D^{27}$ = −138 (c 0.12, EtOH) |

TABLE 74-continued

| Ex. No. | Str. | Chemical name | P.D. |
| --- | --- | --- | --- |
| 1-85 | | (−)-1-(benzo[b]thiophen-2-yl)-3-[(3S*,4R*)-4-(6-fluoro-2,3-dihydrobenzofuran-5-yl)-2-oxopyrrolidin-3-yl]urea | $^1$H-NMR (400 MHz, DMSO-d$_6$) δ 3.12 (2H, t, J = 8.6 Hz), 3.18 (1H, t, J = 9.8 Hz), 3.44 (1H, t, J = 9.8 Hz), 3.69-3.76 (1H, m), 4.52-4.56 (3H, m), 6.62-6.64 (2H, m), 7.01 (1H, brs), 7.07 (1H, dd, J = 7.9, 7.4 Hz), 7.20 (1H, dd, J = 7.9, 7.4 Hz), 7.39 (1H, d, J = 7.9 Hz), 7.50 (1H, d, J = 7.9 Hz), 7.68 (1H, d, J = 7.9 Hz), 7.95 (1H, s), 10.21 (1H, brs). MS (ESI$^+$) m/z: 412 (MH$^+$). [α]$_D^{29}$ = −128 (c 0.14, EtOH) |

TABLE 75

| Ex. No. | Str. | Chemical name | P.D. |
| --- | --- | --- | --- |
| 1-86 | | (+)-1-[(3R*,4S*)-4-(2,6-difluoro-4-methoxyphenyl)-2-oxopyrrolidin-3-yl]-3-(p-tolyl)urea | $^1$H-NMR (400 MHz, DMSO-d$_6$) δ 2.18 (3H, s), 3.29-3.49 (2H, m), 3.71-3.78 (1H, m), 3.75 (3H, s), 4.56 (1H, dd, J = 11.0, 8.6 Hz), 6.41 (1H, brd, J = 8.6 Hz), 6.73 (2H, d, J = 11.0 Hz), 6.98 (2H, d, J = 8.6 Hz), 7.20 (2H, d, J = 8.6 Hz), 8.04 (1H, s), 8.51 (1H, s). MS (ESI$^+$) m/z: 376 (MH$^+$). [α]$_D^{25}$ +108 (c 0.13, EtOH) |
| 1-87 | | (+)-1-[(3R*,4S*)-4-(2,6-difluoro-4-methoxyphenyl)-2-oxopyrrolidin-3-yl]-3-phenylurea | $^1$H-NMR (400 MHz, DMSO-d$_6$) δ 3.30 (1H, t, J = 9.8 Hz), 3.45 (1H, t, J = 9.8 Hz), 3.75 (3H, s), 3.76-3.82 (m, 1H), 4.57 (1H, dd, J = 11.0, 8.6 Hz), 6.46 (1H, d, J = 8.6 Hz), 6.74 (2H, d, J = 11.0 Hz), 6.86 (1H, t, J = 7.3 Hz), 7.18 (2H, dd, J = 8.6, 7.3 Hz), 7.32 (2H, d, J = 8.6 Hz), 8.06 (1H, s), 8.62 (1H, s). MS (ESI$^+$) m/z: 362 (MH$^+$). [α]$_D^{24}$ = +153 (c 0.10, EtOH) |

Example 2-1

[Chemical Formula 123]

Isomer A

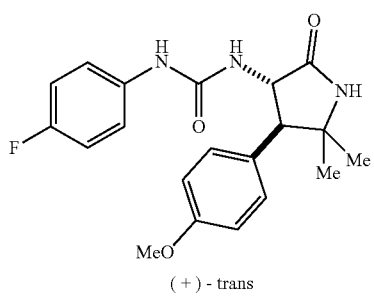

(+)-trans

Isomer B

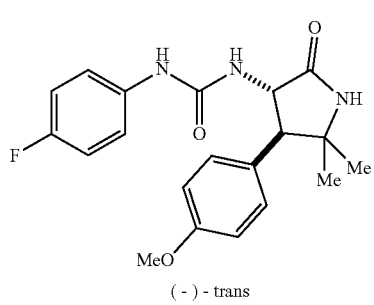

(−)-trans (+)-trans-1-(4-Fluorophenyl)-3-[4-(4-methoxyphenyl)-5,5-dimethyl-2-oxopyrrolidin-3-yl]urea (−)-trans-1-(4-Fluorophenyl)-3-[4-(4-methoxyphenyl)-5,5-dimethyl-2-oxopyrrolidin-3-yl]urea The same method as in Example 1-1 was performed using (±)-trans-4-(4-methoxyphenyl)-5,5-dimethyl-2-oxopyrrolidine-3-carboxylic acid in place of (−)-(3S*,4R*)-4-(4-methoxyphenyl)-2-oxopyrrolidine-3-carboxylic acid to obtain (±)-trans-1-(4-fluorophenyl)-3-[4-(4-methoxyphenyl)-5,5-dimethyl-2-oxopyrrolidin-3-yl]urea.

The obtained (±)-trans-1-(4-fluorophenyl)-3-[4-(4-methoxyphenyl)-5,5-dimethyl-2-oxopyrrolidin-3-yl]urea was subjected to optical resolution by high performance liquid chromatography (methyl tert-butyl ether:ethanol=4:1, flow rate: 15.0 mL) using a column for separation of enantiomers (Daicel Corporation, CHIRALPAK ID). An isomer A(+) with a retention time of 6.94 minutes and an isomer B(−) with a retention time of 16.14 minutes that were the title compounds were each obtained as a white solid.

Isomer A(+):
$^1$H-NMR (400 MHz, DMSO-d$_6$) δ 0.78 (3H, s), 1.22 (3H, s), 3.26 (1H, d, J=12.1 Hz), 3.72 (3H, s), 4.88 (1H, dd, J=12.1, 9.1 Hz), 6.31 (1H, d, J=9.1 Hz), 6.89 (2H, d, J=8.5 Hz), 7.02 (2H, t, J=9.1 Hz), 7.25 (2H, d, J=8.5 Hz), 7.34 (2H, dd, J=9.1, 4.8 Hz), 8.01 (1H, s), 8.48 (1H, s).
MS (ESI$^+$) m/z: 372 (MH$^+$).
[α]$_D^{25}$=+133 (c 0.21, CHCl$_3$)

Isomer B(−):
$^1$H-NMR (400 MHz, DMSO-d$_6$) δ 0.78 (3H, s), 1.22 (3H, s), 3.26 (1H, d, J=12.1 Hz), 3.72 (3H, s), 4.88 (1H, dd, J=12.1, 9.1 Hz), 6.31 (1H, d, J=9.1 Hz), 6.89 (2H, d, J=8.5 Hz), 7.02 (2H, t, J=9.1 Hz), 7.25 (2H, d, J=8.5 Hz), 7.34 (2H, dd, J=9.1, 4.8 Hz), 8.01 (1H, s), 8.48 (1H, s).
MS (ESI$^+$) m/z: 372 (MH$^+$).
[α]$_D^{25}$=−147 (c 0.21, CHCl$_3$)

Example 3-1

[Chemical Formula 124]

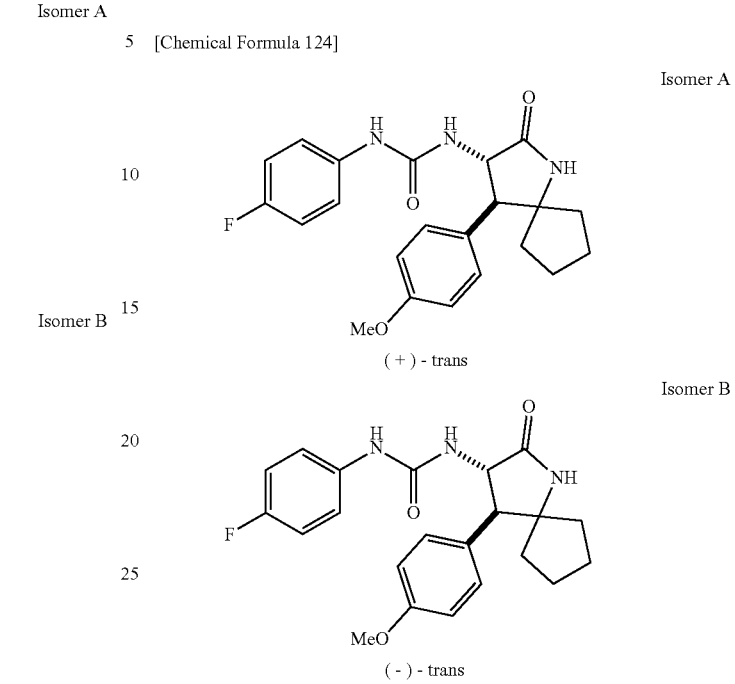

(+)-trans-1-(4-Fluorophenyl)-3-[4-(4-methoxyphenyl)-2-oxo-1-azaspiro[4.4]nonan-3-yl]urea (−)-trans-1-(4-Fluorophenyl)-3-[4-(4-methoxyphenyl)-2-oxo-1-azaspiro[4.4]nonan-3-yl]urea The same method as in Example 1-1 was performed using (±)-trans-4-(4-methoxyphenyl)-2-oxo-1-azaspiro[4.4]nonane-3-carboxylic acid in place of (−)-(3S*,4R*)-4-(4-methoxyphenyl)-2-oxopyrrolidine-3-carboxylic acid to obtain (±)-trans-1-(4-fluorophenyl)-3-[4-(4-methoxyphenyl)-2-oxo-1-azaspiro[4.4]nonan-3-yl]urea. The obtained (±)-trans-1-(4-fluorophenyl)-3-[4-(4-methoxyphenyl)-2-oxo-1-azaspiro[4.4]nonan-3-yl]urea was subjected to optical resolution by high performance liquid chromatography (methyl tert-butyl ether:ethanol=4:1, flow rate: 20.0 mL) using a column for separation of enantiomers (CHIRALPAK ID). An isomer A(+) with a retention time of 9.02 minutes and an isomer B(−) with a retention time of 14.27 minutes that were the title compounds were each obtained as a white solid.

Isomer A(+):
$^1$H-NMR (400 MHz, DMSO-d6) δ 1.05-1.81 (8H, m), 3.45 (1H, d, J=12.1 Hz), 3.71 (3H, s), 4.82 (1H, dd, J=12.1, 9.1 Hz), 6.31 (1H, d, J=9.1 Hz), 6.88 (2H, d, J=9.1 Hz), 7.02 (2H, t, J=9.1 Hz), 7.25 (2H, d, J=9.1 Hz), 7.34 (2H, dd, J=9.1, 4.8 Hz), 8.28 (1H, s), 8.47 (1H, s).
MS (ESI$^+$) m/z: 398 (MH$^+$).
HRMS (ESI$^+$) for $C_{22}H_{25}FN_3O_3$(MH$^+$): calcd, 398.18799. found, 398.18738.
[α]$_D^{24}$=+124 (c 0.31, CHCl$_3$).

Isomer B(−):
$^1$H-NMR (400 MHz, DMSO-d$_6$) δ 1.05-1.81 (8H, m), 3.45 (1H, d, J=12.1 Hz), 3.71 (3H, s), 4.82 (1H, dd, J=12.1, 9.1 Hz), 6.31 (1H, d, J=9.1 Hz), 6.88 (2H, d, J=9.1 Hz), 7.02

(2H, t, J=9.1 Hz), 7.25 (2H, d, J=9.1 Hz), 7.34 (2H, dd, J=9.1, 4.8 Hz), 8.28 (1H, s), 8.47 (1H, s).

MS (ESI⁺) m/z: 398 (MH⁺).

HRMS (ESI⁺) for C₂₂H₂₅FN₃O₃(MH⁺): calcd, 398.18799. found, 398.18880.

[α]_D^24=−125 (c 0.31, CHCl₃).

Example 4-1

[Chemical Formula 125]

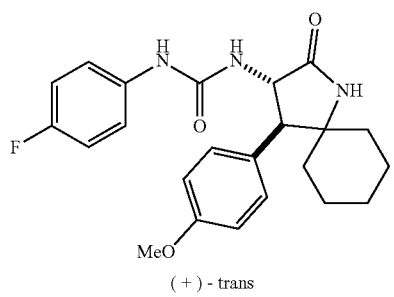

(+)-trans

Isomer A

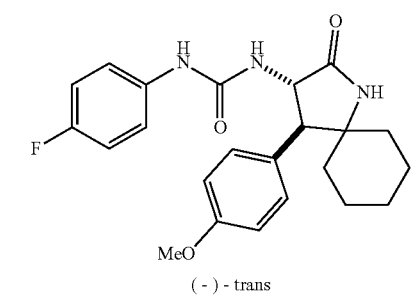

(−)-trans

Isomer B (+)-trans-1-(4-Fluorophenyl)-3-[4-(4-methoxyphenyl)-2-oxo-1-azaspiro[4.5]decan-3-yl]urea (−)-trans-1-(4-Fluorophenyl)-3-[4-(4-methoxyphenyl)-2-oxo-1-azaspiro[4.5]decan-3-yl]urea The same method as in Example 1-1 was performed using (±)-trans-4-(4-methoxyphenyl)-2-oxo-1-azaspiro[4.5]decane-3-carboxylic acid in place of (−)-(3S*,4R*)-4-(4-methoxyphenyl)-2-oxopyrrolidine-3-carboxylic acid to obtain (±)-trans-1-(4-fluorophenyl)-3-[4-(4-methoxyphenyl)-2-oxo-1-azaspiro[4.5]decan-3-yl]urea. The obtained (±)-trans-1-(4-fluorophenyl)-3-[4-(4-methoxyphenyl)-2-oxo-1-azaspiro[4.5]decan-3-yl]urea was subjected to optical resolution by high performance liquid chromatography (methyl tert-butyl ether:ethanol=85:15, flow rate: 15.0 mL) using a column for separation of enantiomers (CHIRALPAK ID). An isomer A(+) with a retention time of 12.16 minutes and an isomer B(−) with a retention time of 17.07 minutes that were the title compounds were each obtained as a white solid.

Isomer A(+):

¹H-NMR (400 MHz, DMSO-d₆) δ 0.55-0.67 (1H, m), 0.76-0.92 (1H, m), 1.29-1.71 (8H, m), 3.14 (1H, d, J=12.2 Hz), 3.72 (3H, s), 4.89 (1H, dd, J=12.2, 8.6 HzH), 6.31 (1H, d, J=8.6 Hz), 6.88 (2H, d, J=8.6 Hz), 7.02 (2H, t, J=8.8 Hz), 7.25 (2H, d, J=8.5 Hz), 7.34 (2H, dd, J=9.1, 4.8 Hz), 8.01 (1H, s), 8.48 (1H, s).

MS (ESI⁺) m/z: 412 (MH⁺).

HRMS (ESI⁺) for C₂₃H₂₇FN₃O₃(MH⁺): calcd, 412.20364. found, 412.20364.

[α]_D^25=+133 (c 0.32, CHCl₃).

Isomer B(−):

¹H-NMR (400 MHz, DMSO-d₆) δ 0.55-0.67 (1H, m), 0.76-0.92 (1H, m), 1.29-1.71 (8H, m), 3.14 (1H, d, J=12.2 Hz), 3.72 (3H, s), 4.89 (1H, dd, J=12.2, 8.6 Hz), 6.31 (1H, d, J=8.6 Hz), 6.88 (2H, d, J=8.6 Hz), 7.02 (2H, t, J=8.8 Hz), 7.25 (2H, d, J=8.5 Hz), 7.34 (2H, dd, J=9.1, 4.8 Hz), 8.01 (1H, s), 8.48 (1H, s).

MS (ESI⁺) m/z: 412 (MH⁺).

HRMS (ESI⁺) for C₂₃H₂₇FN₃O₃(MH⁺): calcd, 412.20364. found, 412.20416.

[α]_D^25=−137 (c 0.31, CHCl₃).

Example 5-1

[Chemical Formula 126]

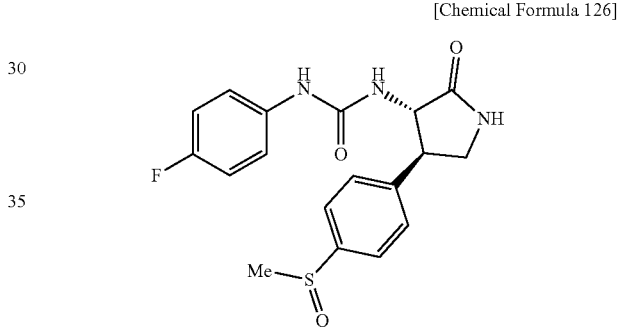

(−)-1-(4-Fluorophenyl)-3-[(3S*,4R*)-4-(4-methylsulfinylphenyl)-2-oxopyrrolidin-3-yl]urea Meta-chloroperoxybenzoic acid (mCPBA) (70 mg) was added to a solution of 1-(4-fluorophenyl)-3-[(3S*,4R*)-4-(4-methylthiophenyl)-2-oxopyrrolidin-3-yl]urea (100 mg) in dichloromethane (5 mL) to produce a reaction solution. The reaction solution was stirred at room temperature for 1 hour. A saturated sodium hydrogen carbonate solution was added to the reaction solution, and the mixture was extracted with a dichloromethane-methanol mixed solution. The extract was washed with water and a brine successively, and dried over anhydrous sodium sulfate. The solvent was removed under reduced pressure, and the residue was then purified by silica gel column chromatography (ethyl acetate:methanol=5:1), to obtain the title compound as a white solid (85 mg).

¹H-NMR (400 MHz, DMSO-d₆) δ 2.71 (3H, s), 3.23 (1H, t, J=9.4 Hz), 3.50-3.68 (2H, m), 4.55 (1H, dd, J=11.5, 8.5 Hz), 6.47 (1H, d, J=8.5 Hz), 7.00-7.05 (2H, m), 7.32-7.37 (2H, m), 7.58-7.64 (4H, m), 7.97 (1H, s), 8.59 (1H, s).

MS (ESI⁺) m/z: 376 (MH⁺).

[α]_D^26=−168 (c 0.14, EtOH).

Example 6-1

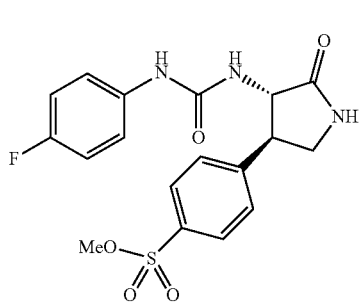

(−)-1-(4-Fluorophenyl)-3-[(3S*,4R*)-4-(4-methylsulfonylphenyl)-2-oxopyrrolidin-3-yl]urea Meta-chloroperoxybenzoic acid (mCPBA) (140 mg) was added to a solution of 1-(4-fluorophenyl)-3-[(3S*,4R*)-4-(4-methylthiophenyl)-2-oxopyrrolidin-3-yl]urea (84 mg) in dichloromethane (5 mL) to produce a reaction solution. The reaction solution was stirred at room temperature for 1 hour. A saturated sodium hydrogen carbonate solution was added to the reaction solution, and the mixture was extracted with a dichloromethane-methanol mixed solution. The extract was washed with water and a brine successively, and dried over anhydrous sodium sulfate. The solvent was removed under reduced pressure, and the residue was then purified by silica gel column chromatography (ethyl acetate:methanol=5:1), to obtain the title compound as a white solid (67 mg).
$^1$H-NMR (400 MHz, DMSO-$d_6$) δ 3.19 (3H, s), 3.25 (1H, t, J=9.7 Hz), 3.55 (1H, t, J=8.5 Hz), 3.64-3.72 (1H, m), 4.57 (1H, dd, J=10.9, 8.5 Hz), 6.49 (1H, d, J=8.5 Hz), 7.00-7.05 (2H, m), 7.32-7.36 (2H, m), 7.68 (2H, d, J=8.5 Hz), 7.87 (2H, d, J=8.5 Hz), 8.00 (1H, s), 8.61 (1H, s).
MS (ESI$^+$) m/z: 392 (MH$^+$).
$[α]_D^{26}$=−189 (c 0.14, EtOH).

Example 7-1

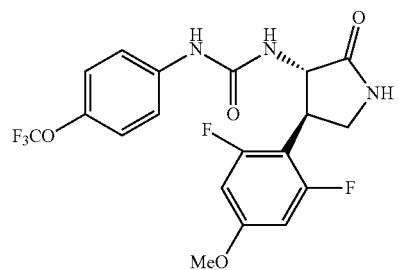

(−)-1-[(3S*,4R*)-4-(2,6-Difluoro-4-methoxyphenyl)-2-oxopyrrolidin-3-yl]-3-[4-(trifluoromethoxy)phenyl]urea 4-(Trifluoromethoxy)phenyl isocyanate (36 μL) was added to a solution of (−)-(3S*,4R*)-3-amino-4-(2,6-difluoro-4-methoxyphenyl)pyrrolidin-2-one (58 mg) in tetrahydrofuran (2.4 mL) to produce a reaction solution. The reaction solution was stirred at room temperature for 30 minutes. The reaction solution was concentrated, and the residue was then purified by silica gel column chromatography (hexane:ethyl acetate=9:1 followed by ethyl acetate), to obtain the title compound as a white solid (94 mg).
$^1$H-NMR (400 MHz, DMSO-$d_6$) δ 3.27-3.31 (1H, m), 3.44 (1H, t, J=9.2 Hz), 3.74 (3H, s), 3.76-3.84 (1H, m), 4.57 (1H, dd, J=10.4, 8.6 Hz), 6.56 (1H, d, J=8.6 Hz), 6.74 (2H, d, J=10.4 Hz), 7.18 (2H, d, J=8.6 Hz), 7.14 (2H, d, J=8.6 Hz), 8.06 (1H, s), 8.89 (1H, s).
MS (ESI$^+$) m/z: 446 (MH$^+$).
$[α]_D^{27}$=−150 (c 0.10, EtOH).

The same method as in Example 7-1 was performed using a corresponding isocyanate to obtain the following Examples 7-2 to 7-14.

The structures and spectral data thereof are shown in Tables 76 to 80.

TABLE 76

| Ex. No | Str. | Chemical name | P.D. |
|---|---|---|---|
| 7-2 | ![structure] | (−)-1-[(3S*,4R*)-4-(2,6-difluoro-4-methoxyphenyl)-2-oxopyrrolidin-3-yl]-3-phenylurea | $^1$H-NMR (400 MHz, DMSO-$d_6$) δ 3.30 (1H, t, J = 9.8 Hz), 3.45 (1H, t, J = 9.8 Hz), 3.75 (3H, s), 3.76-3.82 (m, 1H), 4.57 (1H, dd, J = 11.0, 8.6 Hz), 6.46 (1H, d, J = 8.6 Hz), 6.74 (2H, d, J = 11.0 Hz), 6.86 (1H, t, J = 7.3 Hz), 7.18 (2H, dd, J = 8.6, 7.3 Hz), 7.32 (2H, d, J = 8.6 Hz), 8.06 (1H, s), 8.62 (1H, s). MS (ESI$^+$) m/z: 362 (MH$^+$). $[α]_D^{27}$ = −162 (c 0.10, EtOH) |

TABLE 76-continued

| Ex. No | Str. | Chemical name | P.D. |
|---|---|---|---|
| 7-3 | | (−)-1-[4-(tert-butyl)phenyl]-3-[(3S*,4R*)-4-(2,6-difluoro-4-methoxyphenyl)-2-oxopyrrolidin-3-yl]urea | $^1$H-NMR (400 MHz, DMSO-d$_6$) δ 1.21 (9H, s), 3.27-3.48 (2H, m), 3.71-3.80 (1H, m), 3.74 (3H, s), 4.56 (1H, dd, J = 11.0, 8.0 Hz), 6.39 (1H, d, J = 8.0 Hz), 6.73 (2H, d, J = 11.0 Hz), 7.17-7.23 (4H, m), 8.04 (1H, s), 8.51 (1H, s). MS (ESI$^+$) m/z: 418 (MH$^+$). [α]$_D^{27}$ = −117 (c 0.11, EtOH) |
| 7-4 | | (−)-4-{(3S*,4R*)-3-[4-(2,6-difluoro-4-methoxyphenyl)-2-oxopyrrolidin-3-yl]ureido}benzoic acid ethyl ester | $^1$H-NMR (400 MHz, DMSO-d$_6$) δ 1.28 (3H, t, J = 6.8 Hz), 3.28-3.39 (1H, m), 3.45 (1H, t, J = 9.2 Hz), 3.75 (3H, s), 3.78-3.86 (1H, m), 4.23 (2H, q, J = 6.8 Hz), 4.57 (1H, dd, J = 10.4, 8.6 Hz), 6.66 (1H, d, J = 8.6 Hz), 6.74 (2H, d, J = 10.4 Hz), 7.46 (2H, d, J = 8.6 Hz), 7.79 (2H, d, J = 8.6 Hz), 8.08 (1H, s), 9.13 (1H, s). MS (ESI$^+$) m/z: 434 (MH$^+$). [α]$_D^{27}$ = −161 (c 0.10, EtOH) |

TABLE 77

| Ex. No | Str. | Chemical name | P.D. |
|---|---|---|---|
| 7-5 | | (−)-1-[(1,1'-biphenyl)-4-yl]-3-[(3S*,4R*)-4-(2,6-difluoro-4-methoxyphenyl)-2-oxopyrrolidin-3-yl]urea | $^1$H-NMR (400 MHz, DMSO-d$_6$) δ 3.29-3.34 (1H, m), 3.46 (1H, t, J = 8.6 Hz), 3.75 (3H, s), 3.81 (1H, q, J = 8.6 Hz), 4.59 (1H, dd, J = 8.6, 8.6 Hz), 6.51 (1H, d, J = 8.6 Hz), 6.74 (2H, d, J = 10.4 Hz), 7.28 (1H, t, J = 7.3 Hz), 7.38-7.43 (4H, m), 7.50 (2H, d, J = 9.2 Hz), 7.58 (2H, d, J = 8.0 Hz), 8.07 (1H, s), 8.75 (1H, s). MS (ESI$^+$) m/z: 438 (MH$^+$). [α]$_D^{27}$ = −168 (c 0.10, EtOH) |
| 7-6 | | (−)-1-(4-acetylphenyl)-3-[(3S*,4R*)-4-(2,6-difluoro-4-methoxyphenyl)-2-oxopyrrolidin-3-yl]urea | $^1$H-NMR (400 MHz, DMSO-d$_6$) δ 2.45 (3H, s), 3.26-3.31 (1H, m), 3.44 (1H, t, J = 9.2 Hz), 3.74 (3H, s), 3.81 (1H, q, J = 9.2 Hz), 4.57 (1H, dd, J = 9.2, 8.6 Hz), 6.65 (1H, d, J = 8.6 Hz), 6.73 (2H, d, J = 10.4 Hz), 7.45 (2H, d, J = 8.6 Hz), 7.80 (2H, d, J = 8.6 Hz), 8.07 (1H, s), 9.11 (1H, s). MS (ESI$^+$) m/z: 404 (MH$^+$). [α]$_D^{27}$ = −153 (c 0.10, EtOH) |

TABLE 77-continued

| Ex. No | Str. | Chemical name | P.D. |
|---|---|---|---|
| 7-7 |  | (−)-1-[(3S*,4R*)-4-(2,6-difluoro-4-methoxyphenyl)-2-oxopyrrolidin-3-yl]-3-(4-phenoxyphenyl)urea | $^1$H-NMR (400 MHz, DMSO-d$_6$) δ 3.30 (1H, t, J = 9.2 Hz), 3.44 (1H, t, J = 9.2 Hz), 3.75 (3H, s), 3.79 (1H, q, J = 9.2 Hz), 4.57 (1H, t, J = 8.6 Hz), 6.47 (1H, d, J = 8.6 Hz), 6.74 (2H, d, J = 11.0 Hz), 6.88-6.91 (4H, m), 7.05 (1H, t, J = 7.3 Hz), 7.30-7.35 (4H, m), 8.05 (1H, s), 8.67 (1H, s). MS (ESI$^+$) m/z: 454 (MH$^+$). [α]$_D^{27}$ = −163 (c 0.10, EtOH) |

TABLE 78

| Ex. No | Str. | Chemical name | P.D. |
|---|---|---|---|
| 7-8 |  | (−)-1-[(3S*,4R*)-4-(2,6-difluoro-4-methoxyphenyl)-2-oxopyrrolidin-3-yl]-3-(3-fluorophenyl)urea | $^1$H-NMR (400 MHz, DMSO-d$_6$) δ 3.28-3.33 (1H, m), 3.40-3.49 (1H, m), 3.75 (3H, s), 3.81 (1H, q, J = 9.5 Hz), 4.56 (1H, dd, J = 11.0, 8.0 Hz), 6.57 (1H, d, J = 8.0 Hz), 6.64-6.70 (1H, m), 6.74 (2H, d, J = 10.4 Hz), 7.00 (1H, d, J = 8.6 Hz), 7.17-7.23 (1H, m), 7.32-7.37 (1H, m), 8.07 (1H, s), 8.90 (1H, s). MS (ESI$^+$) m/z: 380 (MH$^+$). [α]$_D^{27}$ = −152 (c 0.10, EtOH) |
| 7-9 |  | (−)-1-[(3S*,4R*)-4-(2,6-difluoro-4-methoxyphenyl)-2-oxopyrrolidin-3-yl]-3-(3,4-difluorophenyl)urea | $^1$H-NMR (400 MHz, DMSO-d$_6$) δ 3.27-3.36 (1H, m), 3.40-3.48 (1H, m), 3.75 (3H, s), 3.81 (1H, q, J = 9.2 Hz), 4.56 (1H, dd, J = 9.2, 8.6 Hz), 6.60 (1H, d, J = 8.6 Hz), 6.74 (2H, d, J = 11.0 Hz), 6.97-7.03 (1H, m), 7.20-7.27 (1H, m), 7.49-7.56 (1H, m), 8.06 (1H, s), 8.91 (1H, s). MS (ESI$^+$) m/z: 398 (MH$^+$). [α]$_D^{27}$ = −138 (c 0.10, EtOH) |

TABLE 79

| Ex. No | Str. | Chemical name | P.D. |
|---|---|---|---|
| 7-10 |  | (−)-1-[(3S*,4R*)-4-(2,6-difluoro-4-methoxyphenyl)-2-oxopyrrolidin-3-yl]-3-(4-ethylphenyl)urea | $^1$H-NMR (400 MHz, DMSO-d$_6$) δ 1.11 (3H, t, J = 7.4 Hz), 2.49 (2H, q, J = 7.4 Hz), 3.30 (1H, t, J = 9.2 Hz), 3.44 (1H, t, J = 9.2 Hz), 3.75 (3H, s), 3.77 (1H, q, J = 9.2 Hz), 4.56 (1H, dd, J = 10.4, 8.6 Hz), 6.42 (1H, d, J = 8.6 Hz), 6.73 (2H, d, J = 10.4 Hz), 7.01 (2H, d, J = 8.6 Hz), 7.22 (2H, d, J = 8.6 Hz), 8.05 (1H, s), 8.53 (1H, s). MS (ESI$^+$) m/z: 390 (MH$^+$). [α]$_D^{27}$ = −134 (c 0.10, EtOH) |

TABLE 79-continued

| Ex. No | Str. | Chemical name | P.D. |
|---|---|---|---|
| 7-11 | | (−)-1-[(3S*,4R*)-4-(2,6-difluoro-4-methoxyphenyl)-2-oxopyrrolidin-3-yl]-3-(m-tolyl)urea | $^1$H-NMR (400 MHz, DMSO-$d_6$) δ 2.20 (3H, s), 3.27-3.33 (1H, m), 3.44 (1H, t, J = 9.5 Hz), 3.75 (3H, s), 3.76-3.82 (1H, m), 4.56 (1H, dd, J = 10.7, 8.3 Hz), 6.43 (1H, d, J = 7.9 Hz), 6.69 (1H, d, J = 6.7 Hz), 6.73 (2H, d, J = 11.0 Hz), 7.02-7.10 (2H, m), 7.18 (1H, s), 8.05 (1H, s), 8.53 (1H, s). MS (ESI$^+$) m/z: 376 (MH$^+$). $[α]_D^{25} = -135$ (c 0.22, EtOH) |
| 7-12 | | (−)-1-(3-cyanophenyl)-3-[(3S*,4R*)-4-(2,6-difluoro-4-methoxyphenyl)-2-oxopyrrolidin-3-yl]urea | $^1$H-NMR (400 MHz, DMSO-$d_6$) δ 3.25-3.35 (1H, m), 3.40-3.50 (1H, m), 3.75 (3H, s), 3.78-3.87 (1H, m), 4.57 (1H, dd, J = 10.7, 8.3 Hz), 6.74 (2H, d, J = 11.0 Hz), 7.30-7.33 (1H, m), 7.40 (1H, t, J = 7.9 Hz), 7.52-7.57 (1H, m), 7.85 (1H, s), 8.07 (1H, s), 9.08 (1H, s). MS (ESI$^+$) m/z: 387 (MH$^+$). $[α]_D^{25} = -86$ (c 0.13, EtOH) |

TABLE 80

| Ex. No | Str. | Chemical name | P.D. |
|---|---|---|---|
| 7-13 | | (−)-1-[(3S*,4R*)-4-(2,6-difluoro-4-methoxyphenyl)-2-oxopyrrolidin-3-yl]-3-(3-methoxyphenyl)urea | $^1$H-NMR (400 MHz, DMSO-$d_6$) δ 3.27-3.33 (1H, m), 3.44 (1H, t, J = 9.5 Hz), 3.67 (3H, s), 3.75 (3H, s), 3.80 (1H, t, J = 9.8 Hz), 4.56 (1H, dd, J = 11.0, 8.6 Hz), 6.43-6.47 (2H, m), 6.74 (2H, d, J = 11.0 Hz), 6.80-6.83 (1H, m), 7.04-7.10 (2H, m), 8.05 (1H, s), 8.63 (1H, s). MS (ESI$^+$) m/z: 392 (MH$^+$). $[α]_D^{26} = -173$ (c 0.14, EtOH) |
| 7-14 | | (−)-1-[(3S*,4R*)-4-(3-fluoro-5-methoxypyridin-2-yl)-2-oxopyrrolidin-3-yl]-3-(p-tolyl)urea | $^1$H-NMR (400 MHz, DMSO-$d_6$) δ 2.18 (3H, s), 3.38 (1H, t, J = 9.5 Hz), 3.47 (1H, t, J = 9.2 Hz), 3.83 (3H, s), 3.90-4.01 (1H, m), 4.50 (1H, dd, J = 10.1, 8.3 Hz), 6.51 (1H, d, J = 7.3 Hz), 6.98 (2H, d, J = 8.3 Hz), 7.20 (2H, d, J = 8.3 Hz), 7.38 (1H, dd, J = 12.2, 2.4 Hz), 7.93 (1H, s), 8.20 (1H, d, J = 2.4 Hz), 8.53 (1H, s). MS (ESI$^+$) m/z: 359 (MH$^+$). $[α]_D^{26} = -177$ (c 0.10, EtOH) |

Example 8-1

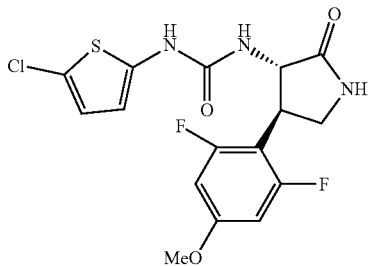

(−)-1-(5-Chlorothiophen-2-yl)-3-[(3S*,4R*)-4-(2,6-difluoro-4-methoxyphenyl)-2-oxopyrrolidin-3-yl]urea Triethylamine (51 μL) and diphenylphosphoryl azide (83 μL) were added to a solution of 5-chlorothiophene-2-carboxylic acid (60 mg) in toluene (3.7 mL) to produce a reaction solution. The reaction solution was stirred at room temperature for 3 hours. The reaction temperature was heated up to 100° C., and the reaction solution was then stirred for 1 hour.

(−)-(3S*,4R*)-3-amino-4-(2,6-difluoro-4-methoxyphenyl)pyrrolidin-2-one (71 mg) was added and the reaction solution was stirred at 100° C. for 1 hour. The reaction solution was concentrated, and the residue was then purified by silica gel column chromatography (hexane:ethyl acetate=4:1 followed by ethyl acetate), to obtain the title compound as a white solid (45 mg).

$^1$H-NMR (400 MHz, DMSO-d$_6$) δ 3.27-3.31 (1H, m), 3.44 (1H, t, J=9.2 Hz), 3.75 (3H, s), 3.80-3.88 (1H, m), 4.52 (1H, dd, J=11.0, 9.2 Hz), 6.20 (1H, d, J=4.3 Hz), 6.71-6.81 (4H, m), 8.06 (1H, s), 9.94 (1H, s).

MS (ESI$^+$) m/z: 402 (MH$^+$).

$[α]_D^{27}$=−135 (c 0.11, EtOH)

The same method as in Example 8-1 was performed using a corresponding carboxylic acid substance and amine to obtain the following Examples 8-2 to 8-3. The structures and spectral data thereof are shown in Table 81.

TABLE 81

| Ex. No | Str. | Chemical name | P.D. |
|---|---|---|---|
| 8-2 | | (−)-1-(5-chlorothiophen-2-yl)-3-[(3S*,4R*)-4-(3-fluoro-5-methoxypyridin-2-yl)-2-oxopyrrolidin-3-yl]urea | $^1$H-NMR (400 MHz, DMSO-d$_6$) δ 3.30-3.37 (1H, m), 3.46 (1H, t, J = 8.9 Hz), 3.83 (3H, s), 3.96-4.03 (1H, m), 4.48 (1H, d, J = 10.4 Hz), 6.05-6.15 (1H, m), 6.66 (1H, d, J = 4.3 Hz), 7.00-7.30 (1H, m), 7.38 (1H, dd, J = 11.6, 2.4 Hz), 7.89 (1H, s), 8.20 (1H, d, J = 2.4 Hz), 10.3-10.6 (1H, m). MS (ESI$^+$) m/z: 385 (MH$^+$). $[α]_D^{26}$ = −166 (c 0.10, EtOH) |
| 8-3 | | (−)-1-(benzo[b]thiophen-2-yl)-3-[(3S*,4R*)-4-(3-fluoro-5-methoxypyridin-2-yl)-2-oxopyrrolidin-3-yl]urea | 1H-NMR (400 MHz, DMSO-d$_6$) δ 3.39 (1H, t, J = 9.2 Hz), 3.49 (1H, t, J = 9.2 Hz), 3.83 (3H, s), 4.00-4.07 (1H, m), 4.57 (1H, t, J = 9.2 Hz), 6.65 (1H, s), 6.98-7.06 (1H, m), 7.08 (1H, t, J = 7.6 Hz), 7.21 (1H, t, J = 7.6 Hz), 7.38-7.42 (1H, m), 7.52 (1H, d, J = 7.9 Hz), 7.69 (1H, d, J = 7.9 Hz), 7.98 (1H, s), 8.20-8.23 (1H, m), 10.19 (1H, s). MS (ESI$^+$) m/z: 401 (MH$^+$). $[α]_D^{27}$ = −157 (c 0.11, EtOH) |

Example 9-1

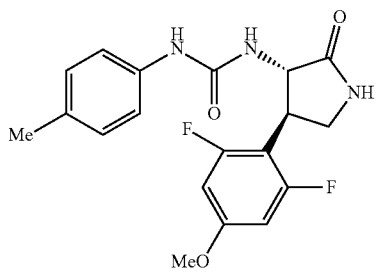

[Chemical Formula 130]

(−)-1-[(3S*,4R*)-4-(2,6-Difluoro-4-methoxyphenyl)-2-oxopyrrolidin-3-yl]-3-(p-tolyl)urea The same method as in Example 8-1 was performed using 4-methyl benzoic acid in place of 5-chlorothiophene-2-carboxylic acid to obtain the title compound.

$^1$H-NMR (400 MHz, DMSO-$d_6$) δ 2.18 (3H, s), 3.29-3.49 (2H, m), 3.71-3.78 (1H, m), 3.75 (3H, s), 4.56 (1H, dd, J=11.0, 8.6 Hz), 6.41 (1H, brd, J=8.6 Hz), 6.73 (2H, d, J=11.0 Hz), 6.98 (2H, d, J=8.6 Hz), 7.20 (2H, d, J=8.6 Hz), 8.04 (1H, s), 8.51 (1H, s).
MS (ESI$^+$) m/z: 376 (MH$^+$).
$[α]_D^{27}$=−144 (c 0.10, EtOH)

Example 10-1

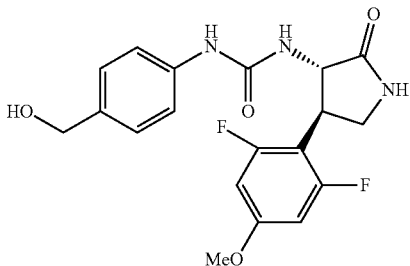

[Chemical Formula 131]

(−)-1-[(3S*,4R*)-4-(2,6-Difluoro-4-methoxyphenyl)-2-oxopyrrolidin-3-yl]-3-[4-(hydroxymethyl)phenyl]urea Diisobutylaluminum hydride (1.0 mL, 1.04 mol/L hexane solution) was added to a solution of (−)-4-{3-[(3S*,4R*)-4-(2,6-difluoro-4-methoxyphenyl)-2-oxopyrrolidin-3-yl]ureido}benzoic acid ethyl ester (87 mg) in dichloromethane (2.5 mL) under ice-cooling to produce a reaction solution. The reaction solution was stirred at room temperature for 2.5 hours. A 10% potassium sodium tartrate aqueous solution and ethyl acetate were added to the reaction solution, and the mixture was stirred for 30 minutes and extracted with ethyl acetate. The organic layer was washed with a brine, and dried over anhydrous sodium sulfate. The solvent was removed under reduced pressure, and the residue was then purified by silica gel column chromatography (ethyl acetate:methanol=50:1 followed by ethyl acetate:methanol=4:1), to obtain the title compound as a white solid (66 mg).

$^1$H-NMR (400 MHz, DMSO-$d_6$) δ 3.30 (1H, dd, J=9.8, 9.2 Hz), 3.44 (1H, t, J=9.2 Hz), 3.75 (3H, s), 3.75-3.81 (1H, m), 4.36 (2H, d, J=5.5 Hz), 4.56 (1H, dd, J=11.0, 8.6 Hz), 4.99 (1H, t, J=5.5 Hz), 6.43 (1H, d, J=7.9 Hz), 6.73 (2H, d, J=11.0 Hz), 7.12 (2H, d, J=8.6 Hz), 7.27 (2H, d, J=8.6 Hz), 8.05 (1H, s), 8.58 (1H, s).
MS (ESI$^+$) m/z: 392 (MH$^+$).
$[α]_D^{27}$=−159 (c 0.10, EtOH)

Example 11-1

[Chemical Formula 132]

(−)-4-{3-[(3S*,4R*)-4-(2,6-Difluoro-4-methoxyphenyl)-2-oxopyrrolidin-3-yl]ureido}-N-methylbenzamide A 2 mol/L sodium hydroxide aqueous solution (0.28 mL) was added to a solution of (−)-4-{3-[(3S*,4R*)-4-(2,6-difluoro-4-methoxyphenyl)-2-oxopyrrolidin-3-yl]ureido}benzoic acid ethyl ester (100 mg) in methanol (2.4 mL) to produce a reaction solution. The reaction solution was stirred at 60° C. for 9 hours. The reaction solution was concentrated under reduced pressure, a 1 mol/L hydrochloric acid was added to the residue under ice-cooling to make the mixture acidic (pH: 1), and the mixture was extracted with ethyl acetate. The organic layer was washed with a brine, and dried over anhydrous sodium sulfate. The solvent was removed under reduced pressure to obtain 4-{3-[(3S*,4R*)-4-(2,6-difluoro-4-methoxyphenyl)-2-oxopyrrolidin-3-yl]ureido}benzoic acid as an intermediate compound.

2-(1H-7-azabenzotriazol-1-yl)-1,1,3,3-tetramethyluronium hexafluorophosphate methanaminium (HATU) (92 mg) was added to a solution of the obtained 4-{3-[(3S*,4R*)-4-(2,6-difluoro-4-methoxyphenyl)-2-oxopyrrolidin-3-yl]ureido}benzoic acid (45 mg), methylamine (45 μL, 12 M/L aqueous solution), and diisopropyl ethyl amine (DIEA) (40 μL) in N,N-dimethylformamide (1.1 mL) to produce a reaction solution. The reaction solution was stirred at room temperature for 1 hour. Water was added to the reaction solution, and the mixture was extracted with ethyl acetate. The organic layer was washed with a brine, and dried over anhydrous sodium sulfate. The solvent was removed under reduced pressure to obtain the title compound as a white solid (17 mg).

$^1$H-NMR (400 MHz, DMSO-$d_6$) δ 2.72 (3H, s), 3.55-3.25 (2H, m), 3.75 (3H, s), 3.76-3.86 (1H, m), 4.52-4.61 (1H, m), 6.61 (1H, brs), 6.70-6.79 (2H, m), 7.34-7.41 (2H, m), 7.63-7.71 (2H, m), 8.07 (1H, s), 8.16-8.23 (1H, brs), 8.93 (1H, brs).

MS (ESI$^-$) m/z: 417 (M-H)$^-$.

$[α]_D^{28}$=−159 (c 0.10, DMSO)

Example 12-1

[Chemical Formula 133]

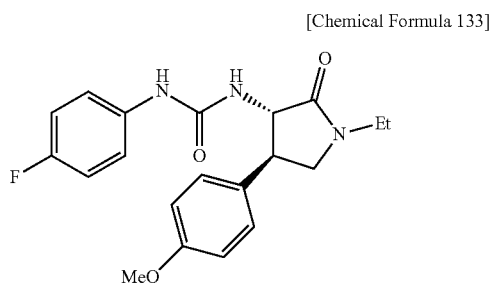 [SMILES: CCN1C[C@@H](c2ccc(OC)cc2)[C@H](NC(=O)Nc2ccc(F)cc2)C1=O]

(−)-1-[(3S*,4R*)-1-Ethyl-4-(4-methoxyphenyl)-2-oxopyrrolidin-3-yl]-3-(4-fluorophenyl)urea Trifluoroacetic acid (0.4 mL) was added to a solution of [(3S*,4R*)-1-ethyl-4-(4-methoxyphenyl)-2-oxopyrrolidin-3-yl]carbamic acid tert-butyl ester (63 mg) in dichloromethane (2 mL) to produce a reaction solution. The reaction solution was stirred at room temperature for 1 hour. The reaction solution was concentrated under reduced pressure, ethyl acetate and a saturated aqueous sodium hydrogen carbonate solution were added to the residue to adjust the pH of the aqueous layer to 9. 4-Fluorophenyl isocyanate (20 μL) was added to the solution of two layers, and the mixture was stirred at room temperature for 15 minutes and extracted with ethyl acetate. The organic layer was washed with water and a brine successively, and dried over anhydrous sodium sulfate. The solvent was removed under reduced pressure, and the residue was then purified by silica gel column chromatography (ethyl acetate:hexane=4:1 followed by ethyl acetate), to obtain the title compound as a white solid (48 mg).

$^1$H-NMR (400 MHz, CDCl$_3$) δ 1.21 (3H, t, J=7.3 Hz), 3.31-3.45 (2H, m), 3.52-3.61 (1H, m), 3.71-3.77 (2H, m), 3.80 (3H, s), 4.24 (1H, dd, J=9.8, 6.7 Hz), 6.13 (1H, brs), 6.76 (2H, t, J=8.6 Hz), 6.89 (2H, d, J=8.6 Hz), 7.06-7.10 (2H, m), 7.24 (2H, d, J=8.6 Hz), 7.84 (1H, brs).

MS (ESI$^+$) m/z: 372 (MH$^+$).

$[α]_D^{24}$=−135 (c 0.30, EtOH).

The same method as in Example 12-1 was performed using a corresponding Boc substance to obtain the following Examples 12-2 to 12-15.

The structures and spectral data thereof are shown in Tables 82 to 87.

TABLE 82

| Ex. No | Str. | Chemical name | P.D. |
|---|---|---|---|
| 12-2 | | 2-{(3S*,4R*)-3-[3-(4-fluorophenyl)ureido]-4-(4-methoxyphenyl)-2-oxopyrrolidin-1-yl} acetic acid ethyl ester | $^1$H-NMR (400 MHz, CDCl$_3$) δ 1.29 (3H, t, J = 7.4 Hz), 3.61 (1H, t, J = 9.2 Hz), 3.72 (1H, t, J = 9.2 Hz), 3.79 (3H, s), 3.81-3.89 (1H, m), 3.95 (1H, d, J = 17.8 Hz), 4.17-4.25 (2H, m), 4.37 (1H, d, J = 17.8 Hz), 4.39-4.43 (1H, m), 6.12 (1H, brs), 6.73 (2H, t, J = 8.6 Hz), 6.88 (2H, d, J = 8.6 Hz), 7.05-7.09 (2H, m), 7.27 (2H, d, J = 8.6 Hz), 7.80 (1H, brs). MS (ESI$^+$) m/z: 430 (MH$^+$). |

TABLE 83

| Ex. No | Str. | Chemical name | P.D. |
|---|---|---|---|
| 12-3 | | 2-{(3S*,4R*)-3-[3-(4-fluoro-phenyl)ureido]-4-(4-methoxy-phenyl)-2-oxo-pyrrolidin-1-yl}-2-methylpropionic acid ethyl ester | $^1$H-NMR (400 MHz, CDCl$_3$) δ 1.18 (3H, t, J = 7.4 Hz), 1.52 (3H, s), 1.57 (3H, s) 3.38 (1H, t, J = 9.2 Hz), 3.68 (1H, q, J = 9.2 Hz), 3.79 (3H, s), 3.83 (1H, t, J = 8.6 Hz), 4.10 (2H, q, J = 7.4 Hz), 4.80 (1H, dd, J = 11.6, 9.2 Hz), 5.87 (1H, brd, J = 8.6 Hz), 6.73 (2H, t, J = 9.2 Hz), 6.89 (2H, d, J = 8.6 Hz), 7.10 (2H, dd, J = 9.2, 4.9 Hz), 7.30 (2H, d, J = 8.6 Hz), 7.88 (1H, brs). MS (ESI$^+$) m/z: 458 (MH$^+$). |
| 12-4 | | (−)-1-(4-fluoro-phenyl)-3-[(3S*,4R*)-1-(1-hydroxy-2-methylpropan-2-yl)-4-(4-methoxy-phenyl)-2-oxo-pyrrolidin-3-yl] urea | $^1$H-NMR (400 MHz, CDCl$_3$) δ 1.39 (3H, s), 1.41 (3H, s), 3.42-3.53 (2H, m), 3.71 (1H, q, J = 9.6 Hz), 3.80 (3H, s), 3.98-4.06 (2H, m), 4.17-4.24 (2H, m), 6.49 (1H, brs), 6.70-6.75 (2H, m), 6.89 (2H, d, J = 8.6 Hz), 7.03-7.08 (2H, m), 7.21 (2H, d, J = 8.6 Hz), 7.56 (1H, s). MS (ESI$^+$) m/z: 416 (MH$^+$). $[α]_D^{27}$ = −113 (c 0.31, EtOH). |

TABLE 84

| Ex. No | Str. | Chemical name | P.D. |
|---|---|---|---|
| 12-5 | (−)-cis | (−)-1-[4-(2,6-difluoro-4-methoxyphenyl)-2-oxopyrrolidin-3-yl]-3-(4-fluoro-phenyl)urea | $^1$H-NMR (400 MHz, DMSO-d$_6$) δ 3.13 (1H, d, J = 10.4 Hz), 3.31 (3H, s), 3.72-3.76 (1H, m), 4.18-4.23 (1H, m), 4.61 (1H, dd, J = 9.8, 6.7 Hz), 6.04 (1H, d, J = 6.7 Hz), 6.66 (2H, d, J = 11.0 Hz), 6.97-7.05 (2H, m), 7.22-7.26 (2H, m), 8.06 (1H, s), 8.65 (1H, s). MS (ESI$^+$) m/z: 380 (MH$^+$). $[α]_D^{25}$ −239 (c 0.10, EtOH) |
| 12-6 | (+)-cis | (+)-1-[4-(2,6-difluoro-4-methoxyphenyl)-2-oxopyrrolidin-3-yl]-3-(4-fluoro-phenyl)urea | $^1$H-NMR (400 MHz, DMSO-d$_6$) δ 3.13 (1H, d, J = 10.4 Hz), 3.31 (3H, s), 3.72-3.76 (1H, m), 4.18-4.23 (1H, m), 4.61 (1H, dd, J = 9.8, 6.7 Hz), 6.04 (1H, d, J = 6.7 Hz), 6.66 (2H, d, J = 11.0 Hz), 6.97-7.05 (2H, m), 7.22-7.26 (2H, m), 8.06 (1H, s), 8.65 (1H, s). MS (ESI$^+$) m/z: 380 (MH$^+$). $[α]_D^{25}$ +188 (c 0.10, EtOH) |

TABLE 84-continued

| Ex. No | Str. | Chemical name | P.D. |
|---|---|---|---|
| 12-7 | (-)-cis | (−)-1-[4-(2,6-difluoro-4-methoxyphenyl)-2-oxopyrrolidin-3-yl]-3-(p-tolyl)urea | ¹H-NMR (400 MHz, DMSO-d₆) δ 2.17 (3H, s), 3.12 (1H, d, J = 10.4 Hz), 3.71 (3H, s), 3.72-3.76 (1H, m), 4.17-4.23 (1H, m), 4.61 (1H, dd, J = 9.8, 6.7 Hz), 6.01 (1H, d, J = 6.7 Hz), 6.66 (2H, d, J = 11.0 Hz), 6.97 (2H, d, J = 8.6 Hz), 7.11 (2H, d, J = 8.6 Hz), 8.04 (1H, s), 8.49 (1H, s).<br><br>MS (ESI⁺) m/z: 376 (MH⁺).<br><br>$[α]_D^{26}$ −142 (c 0.12, EtOH) |

TABLE 85

| Ex. No | Str. | Chemical name | P.D. |
|---|---|---|---|
| 12-8 | (+)-cis | (+)-1-[4-(2,6-difluoro-4-methoxyphenyl)-2-oxopyrrolidin-3-yl]-3-(p-tolyl)urea | ¹H-NMR (400 MHz, DMSO-d₆) δ 2.17 (3H, s), 3.12 (1H, d, J = 10.4 Hz), 3.71 (3H, s), 3.72-3.76 (1H, m), 4.17-4.23 (1H, m), 4.61 (1H, dd, J = 9.8, 6.7 Hz), 6.01 (1H, d, J = 6.7 Hz), 6.66 (2H, d, J = 11.0 Hz), 6.97 (2H, d, J = 8.6 Hz), 7.11 (2H, d, J = 8.6 Hz), 8.04 (1H, s), 8.49 (1H, s).<br><br>MS (ESI⁺) m/z: 376 (MH⁺).<br><br>$[α]_D^{26}$ +125 (c 0.11, EtOH) |
| 12-9 | (-)-cis | (−)-1-[4-(2,6-difluoro-4-methoxyphenyl)-2-oxopyrrolidin-3-yl]-3-phenylurea | ¹H-NMR (400 MHz, DMSO-d₆) δ 3.13 (1H, d, J = 10.4 Hz), 3.71 (3H, s), 3.74 (1H, dd, J = 10.4, 8.6 Hz), 4.21 (1H, t, J = 8.0 Hz), 4.62 (1H, dd, J = 9.8, 6.7 Hz), 6.08 (1H, d, J = 6.7 Hz), 6.66 (2H, d, J = 13.8 Hz), 6.85 (1H, t, J = 7.4 Hz), 7.17 (2H, t, J = 7.3 Hz), 7.23 (2H, t, J = 7.3 Hz), 8.06 (1H, s), 8.62 (1H, s).<br><br>MS (ESI⁺) m/z: 362 (MH⁺).<br><br>$[α]_D^{26}$ −201 (c 0.10, EtOH) |

TABLE 86

| Ex. No | Str. | Chemical name | P.D. |
|---|---|---|---|
| 12-10 | (+)-cis structure with 2,6-difluoro-4-methoxyphenyl and phenylurea | (+)-1-[4-(2,6-difluoro-4-methoxyphenyl)-2-oxopyrrolidin-3-yl]-3-phenylurea | $^1$H-NMR (400 MHz, DMSO-$d_6$) δ 3.13 (1H, d, J = 10.4 Hz), 3.71 (3H, s), 3.74 (1H, dd, J = 10.4, 8.6 Hz), 4.21 (1H, t, J = 8.0 Hz), 4.62 (1H, dd, J = 9.8, 7.3 Hz), 6.08 (1H, d, J = 7.3 Hz), 6.66 (2H, d, J = 13.8 Hz), 6.85 (1H, t, J = 7.4 Hz), 7.17 (2H, t, J = 7.3 Hz), 7.23 (2H, t, J = 7.3 Hz), 8.05 (1H, s), 8.62 (1H, s). MS (ESI$^+$) m/z: 362 (MH$^+$). $[α]_D^{26}$ +242 (c 0.10, EtOH) |
| 12-11 | (−)-cis structure with 4-chlorophenyl and 4-methoxyphenyl | (−)-1-(4-chlorophenyl)-3-[4-(4-methoxyphenyl)-2-oxopyrrolidin-3-yl]urea | $^1$H-NMR (400 MHz, DMSO-$d_6$) δ 3.29 (1H, t, J = 7.4 Hz), 3.67-3.72 (5H, m), 4.59 (1H, t, J = 6.7 Hz), 5.80 (1H, d, J = 6.7 Hz), 6.85 (2H, d, J = 8.6 Hz), 7.05 (2H, d, J = 8.6 Hz), 7.23 (2H, d, J = 8.6 Hz), 7.32 (2H, d, J = 8.6 Hz), 8.10 (1H, s), 8.74 (1H, s). MS (ESI$^+$) m/z: 360 (MH$^+$). $[α]_D^{25}$ −260 (c 0.10, EtOH) |
| 12-12 | (+)-cis structure with 4-chlorophenyl and 4-methoxyphenyl | (+)-1-(4-chlorophenyl)-3-[4-(4-methoxyphenyl)-2-oxopyrrolidin-3-yl]urea | $^1$H-NMR (400 MHz, DMSO-$d_6$) δ 3.29 (1H, t, J = 7.4 Hz), 3.67-3.72 (5H, m), 4.59 (1H, t, J = 6.7 Hz), 5.80 (1H, d, J = 6.7 Hz), 6.85 (2H, d, J = 8.6 Hz), 7.05 (2H, d, J = 8.6 Hz), 7.23 (2H, d, J = 8.6 Hz), 7.32 (2H, d, J = 8.6 Hz), 8.10 (1H, s), 8.74 (1H, s). MS (ESI$^+$) m/z: 360 (MH$^+$). $[α]_D^{25}$ +235 (c 0.10, EtOH) |

TABLE 87

| Ex. No | Str. | Chemical name | P.D. |
|---|---|---|---|
| 12-13 | (+)-cis structure with 4-fluorophenyl and 4-methoxyphenyl | (+)-1-(4-fluorophenyl)-3-[4-(4-methoxyphenyl)-2-oxopyrrolidin-3-yl]urea | $^1$H-NMR (400 MHz, DMSO-$d_6$) δ 3.25-3.29 (1H, m), 3.68-3.72 (5H, m), 4.59 (1H, t, J = 6.7 Hz), 5.69 (1H, d, J = 6.7 Hz), 6.85 (2H, d, J = 8.6 Hz), 7.00-7.06 (4H, m), 7.28-7.31 (2H, m), 8.09 (1H, s), 8.59 (1H, s). MS (ESI$^+$) m/z: 344 (MH$^+$). $[α]_D^{25}$ +288 (c 0.10, EtOH) |
| 12-14 | (+)-cis structure with p-tolyl and 4-methoxyphenyl | (+)-1-[4-(4-methoxyphenyl)-2-oxopyrrolidin-3-yl]-3-(p-tolyl)urea | $^1$H-NMR (400 MHz, DMSO-$d_6$) δ 2.19 (3H, s), 3.26-3.29 (1H, m), 3.69-3.71 (5H, m), 4.59 (1H, t, J = 6.7 Hz), 5.67 (1H, d, J = 6.7 Hz), 6.85 (2H, d, J = 8.6 Hz), 6.99 (2H, d, J = 8.6 Hz), 7.04 (2H, d, J = 8.6 Hz), 7.17 (2H, m), 8.08 (1H, s), 8.44 (1H, s). MS (ESI$^+$) m/z: 340 (MH$^+$). $[α]_D^{25}$ +177 (c 0.12, EtOH) |

TABLE 87-continued

| Ex. No | Str. | Chemical name | P.D. |
|---|---|---|---|
| 12-15 | (structure shown; (+)-cis) | (+)-1-(4-fluorophenyl)-3-[1-(2-hydroxyethyl)-4-(4-methoxyphenyl)-2-oxopyrrolidin-3-yl]urea | $^1$H-NMR (400 MHz, DMSO-$d_6$) δ 3.29-3.39 (2H, m), 3.46 (1H, d, J = 9.8 Hz), 3.57 (2H, q, J = 5.5 Hz), 3.66 (1H, t, J = 8.0 Hz), 3.69 (3H, s), 3.86 (1H, dd, J = 10.4, 6.7 Hz), 4.69 (1H, t, J = 8.0 Hz), 4.86 (1H, brs), 5.76 (1H, brs), 6.84 (2H, d, J = 8.6 Hz), 7.00-7.06 (4H, m), 7.29 (2H, dd, J = 9.2, 5.5 Hz), 8.65 (1H, s). MS (ESI$^+$) m/z: 388 (MH$^+$). $[\alpha]_D^{25}$ +155 (c 0.11, EtOH) |

Example 13-1

[Chemical Formula 134]

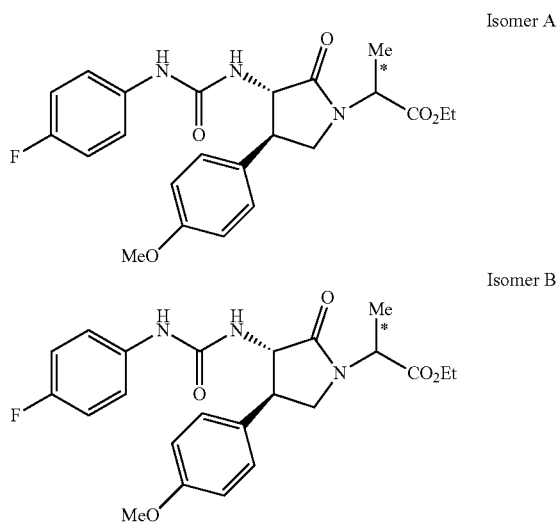

2-{(3S*,4R*)-3-[3-(4-Fluorophenyl) ureido]-4-(4-methoxyphenyl)-2-oxopyrrolidin-1-yl}propionic acid ethyl ester Trifluoroacetic acid (3 mL) was added to a solution of 2-{(3S*,4R*)-3-[(tert-butoxycarbonyl)amino]-4-(4-methoxyphenyl)-2-oxopyrrolidin-1-yl}propionic acid ethyl ester (651 mg) in dichloromethane (12 mL) to produce a reaction solution. The reaction solution was stirred at room temperature for 1 hour. The reaction solution was concentrated under reduced pressure, and ethyl acetate and a saturated aqueous sodium hydrogen carbonate solution were added to the residue to adjust the pH of the aqueous layer to 9. 4-Fluorophenyl isocyanate (180 μL) was added to the solution of two layers, and the mixture was stirred at room temperature for 15 minutes and extracted with ethyl acetate. The organic layer was washed with water and a brine successively, and dried over anhydrous sodium sulfate. The solvent was removed under reduced pressure, and the residue was then purified by silica gel column chromatography (ethyl acetate:hexane=1:1 followed by 1:3), to obtain an isomer A (298 mg) as a low polar fraction and an isomer B (276 mg) as a high polar fraction that were the title compounds as white solids.

Isomer A:

$^1$H-NMR (400 MHz, CDCl$_3$) δ 1.26 (3H, t, J=7.3 Hz), 1.48 (3H, d, J=7.4 Hz), 3.35 (1H, t, J=11.0 Hz), 3.56-3.64 (1H, m), 3.75 (1H, d, J=9.2 Hz), 3.79 (3H, s), 4.13-4.21 (2H, m), 4.84 (1H, q, J=7.4 Hz), 5.02 (1H, dd, J=11.6, 9.2 Hz), 5.65 (1H, d, J=9.2 Hz), 6.78 (2H, d, J=9.2 Hz), 6.88 (2H, d, J=9.2 Hz), 7.14 (2H, dd, J=4.9, 9.2 Hz), 7.28 (2H, d, J=9.2 Hz), 7.87 (1H, brs).

MS (ESI$^+$) m/z: 444 (MH$^+$).

$[\alpha]_D^{25}$=−102 (c 0.21, EtOH).

Isomer B:

$^1$H-NMR (400 MHz, CDCl$_3$) δ 1.28 (3H, t, J=6.7 Hz), 1.52 (3H, d, J=7.9 Hz), 3.52 (1H, t, J=8.6 Hz), 3.80 (3H, s), 3.77-3.88 (2H, m), 4.16-4.22 (3H, m), 4.90 (1H, q, J=7.9 Hz), 6.13 (1H, brd, J=6.7 Hz), 6.72-6.77 (2H, m), 6.89 (2H, d, J=8.6 Hz), 7.04-7.08 (2H, m), 7.26 (2H, d, J=8.6 Hz), 7.72 (1H, brs).

MS (ESI$^+$) m/z: 444 (MH$^+$).

$[α]_D^{25}$=−94 (c 0.21, EtOH).

Example 14-1

[Chemical Formula 135]

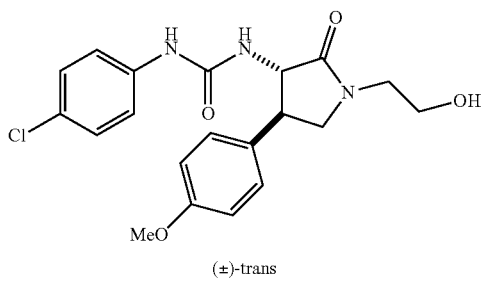

(±)-trans (±)-trans-1-(4-Chlorophenyl)-3-[1-(2-hydroxyethyl)-4-(4-methoxyphenyl)-2-oxopyrrolidin-3-yl]urea Trifluoroacetic acid (1.5 mL) and water (0.5 mL) were added to a solution of (±)-trans-1-{2-[(tert-butyldimethylsilyl)oxy]ethyl}-4-(4-methoxyphenyl)-2-oxopyrrolidin-3-yl]carbamic acid tert-butyl ester (1.2 g) in dichloromethane (2 mL) to produce a reaction solution. The reaction solution was stirred at room temperature for 3 hours. The reaction solution was concentrated under reduced pressure, a saturated aqueous sodium hydrogen carbonate solution was added to the residue to adjust the pH of the aqueous layer to 9, and an ethyl acetate-methanol (5:1) mixed liquid (10 mL) was added. 4-Chlorophenyl isocyanate (396 mg) was added to the solution of two layers, and the mixture was stirred at room temperature for 1 hour and extracted with ethyl acetate. The organic layer was washed with water and a brine, and dried over anhydrous sodium sulfate. The solvent was removed under reduced pressure, and the residue was then purified by silica gel column chromatography (ethyl acetate followed by ethyl acetate:methanol=4:1), to obtain the title compound as a white solid (500 mg).

$^1$H-NMR (400 MHz, DMSO-d$_6$) δ 3.13-3.20 (1H, m), 3.35-3.45 (3H, m), 3.52 (2H, q, J=5.7 Hz), 3.61 (1H, t, J=6.7 Hz), 3.71 (3H, s), 4.57 (1H, t, J=10.0 Hz), 4.75 (1H, t, J=5.8 Hz), 6.52 (1H, d, J=9.1 Hz), 6.88 (2H, d, J=8.5 Hz), 7.23 (2H, d, J=9.1 Hz), 7.29 (2H, d, J=9.1 Hz), 7.38 (2H, d, J=8.5 Hz), 8.71 (1H, s).

MS (ESI$^+$) m/z: 404 (MH$^+$).

Example 15-1

[Chemical Formula 136]

Isomer A

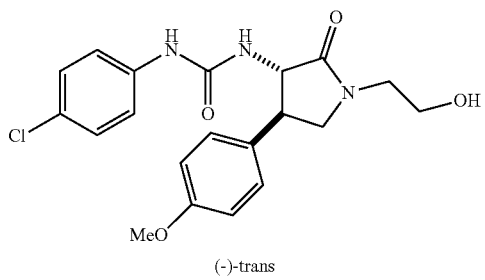

(−)-trans

Isomer B

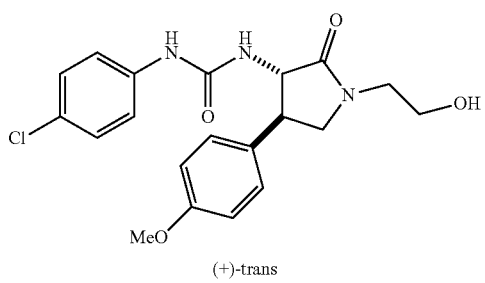

(+)-trans (+)-trans-1-(4-Chlorophenyl)-3-[1-(2-hydroxyethyl)-4-(4-methoxyphenyl)-2-oxopyrrolidin-3-yl]urea (−)-trans-1-(4-Chlorophenyl)-3-[1-(2-hydroxyethyl)-4-(4-methoxyphenyl)-2-oxopyrrolidin-3-yl]urea (±)-trans-1-(4-Chlorophenyl)-3-[1-(2-hydroxyethyl)-4-(4-methoxyphenyl)-2-oxopyrrolidin-3-yl]urea was subjected to optical resolution by high performance liquid chromatography (hexane:ethanol=1:1, flow rate: 15.0 mL) using a column for separation of enantiomers (CHIRALPAK ID). An isomer A(−) with a retention time of 7.91 minutes and an isomer B(+) with a retention time of 17.78 minutes that were the title compounds were each obtained as a white solid.

Isomer A(−):

$^1$H-NMR (400 MHz, DMSO-d$_6$) δ 3.13-3.20 (1H, m), 3.35-3.45 (3H, m), 3.52 (2H, q, J=5.7 Hz), 3.61 (1H, t, J=6.7 Hz), 3.71 (3H, s), 4.57 (1H, t, J=10.0 Hz), 4.75 (1H, t, J=5.8 Hz), 6.52 (1H, d, J=9.1 Hz), 6.88 (2H, d, J=8.5 Hz), 7.23 (2H, d, J=9.1 Hz), 7.29 (2H, d, J=9.1 Hz), 7.38 (2H, d, J=8.5 Hz), 8.71 (1H, s).

MS (ESI$^+$) m/z: 404 (MH$^+$).

$[α]_D^{25}$=−140 (c 0.1, EtOH)

Isomer B(+):

$^1$H-NMR (400 MHz, DMSO-d$_6$) δ 3.13-3.20 (1H, m), 3.35-3.45 (3H, m), 3.52 (2H, q, J=5.7 Hz), 3.61 (1H, t, J=6.7 Hz), 3.71 (3H, s), 4.57 (1H, t, J=10.0 Hz), 4.75 (1H, t, J=5.8 Hz), 6.52 (1H, d, J=9.1 Hz), 6.88 (2H, d, J=8.5 Hz), 7.23 (2H, d, J=9.1 Hz), 7.29 (2H, d, J=9.1 Hz), 7.38 (2H, d, J=8.5 Hz), 8.71 (1H, s).

MS (ESI$^+$) m/z: 404 (MH$^+$).

$[α]_D^{26}$=+140 (c 0.1, EtOH)

Example 16-1

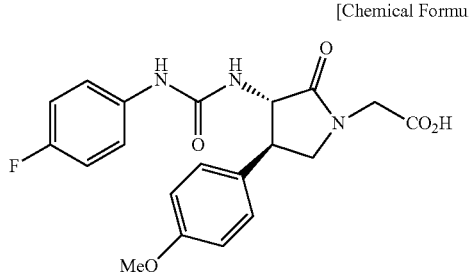

(−)-2-{(3S*,4R*)-3-[3-(4-Fluorophenyl)ureido]-4-(4-methoxyphenyl)-2-oxopyrrolidin-1-yl}acetic acid A 2 mol/L sodium hydroxide aqueous solution (0.6 mL) was added to a solution of 2-{(3S*,4R*)-3-[3-(4-fluorophenyl)ureido]-4-(4-methoxyphenyl)-2-oxopyrrolidin-1-yl}acetic acid ethyl ester (258 mg) in methanol (3.0 mL) to produce a reaction solution. The reaction solution was stirred at room temperature for 30 minutes. A 1 mol/L hydrochloric acid was added to the reaction solution to make the reaction solution acidic (pH: 1), and the mixture was extracted with ethyl acetate. The organic layer was washed with a brine, and dried over anhydrous sodium sulfate. The solvent was removed under reduced pressure, and the crude product was washed with diisopropyl ether, to obtain the title compound as a white solid (228 mg).

$^1$H-NMR (400 MHz, DMSO-$d_6$) δ 3.34 (1H, t, J=9.8 Hz), 3.44-3.51 (1H, m), 3.63 (1H, t, J=8.6 Hz), 3.71 (3H, s), 3.93 (1H, d, J=17.7 Hz), 4.05 (1H, d, J=17.7 Hz), 4.51-4.56 (1H, m), 6.56 (1H, d, J=9.2 Hz), 6.89 (2H, d, J=8.6 Hz), 7.03 (2H, t, J=8.6 Hz), 7.28 (2H, d, J=8.6 Hz), 7.33-7.37 (2H, m), 8.58 (1H, s), 12.9 (1H, brs).

MS (ESI$^+$) m/z: 402 (MH$^+$).

[α]$_D^{24}$=−90 (c 0.31, EtOH).

The same method as in Example 16-1 was performed using a corresponding ester substance to obtain the following Examples 16-2 to 16-3. The structures and spectral data thereof are shown in Table 88.

TABLE 88

| Ref. No | Str. | Chemical name | P.D. |
|---|---|---|---|
| 16-2 | | (−)-2-{(3S*,4R*)-4-(2,6-difluoro-4-methoxyphenyl)-3-[3-(4-fluorophenyl)ureido]-2-oxopyrrolidin-1-yl}acetic acid | $^1$H-NMR (400 MHz, DMSO-$d_6$) δ 3.51-3.60 (2H, m), 3.72-3.82 (1H, m), 3.75 (3H, s), 3.87 (1H, d, J = 17.0 Hz), 4.12 (1H, d, J = 17.0 Hz), 4.70 (1H, dd, J = 10.4, 8.6 Hz), 6.61 (1H, brs), 6.71-6.6.78 (2H, m), 7.01 (2H, t, J = 9.2 Hz), 7.33 (2H, dd, J = 9.2, 4.9 Hz), 8.68 (1H, s), 12.9 (1H, brs). MS (ESI$^+$) m/z: 438 (MH$^+$). [α]$_D^{28}$ = −115 (c 0.08, EtOH) |
| 16-3 | | (−)-2-{(3S*,4R*)-4-(6-fluoro-2,3-dihydrobenzofuran-5-yl)-3-[3-(4-fluorophenyl)ureido]-2-oxopyrrolidin-1-yl}acetic acid | 1H-NMR (400 MHz, DMSO-$d_6$) δ 3.12 (2H, t, J = 8.6 Hz), 3.40-3.52 (1H, m), 3.59 (1H, t, J = 8.6 Hz), 3.66 (1H, t, J = 9.8 Hz), 3.90 (1H, d, J = 17.7 Hz), 4.03 (1H, d, J = 17.7 Hz), 4.55 (2H, t, J = 8.6 Hz), 4.61-4.65 (1H, m), 6.60-6.70 (1H, m), 6.65 (1H, d, J = 11.0 Hz), 7.03 (2H, t, J = 8.6 Hz), 7.32-7.37 (3H, m), 8.67 (1H, s), 12.99 (1H, brs). MS (ESI$^+$) m/z: 432 (MH$^+$). [α]$_D^{26}$ = −120 (c 0.13, DMSO) |

Example 17-1

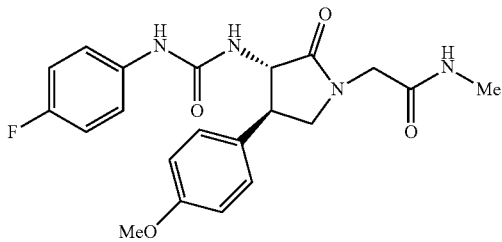

(−)-2-{(3S*,4R*)-3-[3-(4-Fluorophenyl)ureido]-4-(4-methoxyphenyl)-2-oxopyrrolidin-1-yl}-N-methylacetamide 1-Hydroxybenzotriazole (46 mg), methylamine (0.5 mL, 2 mol/L, tetrahydrofuran solution), and 1-ethyl-3-(3-dimethylaminopropyl)carbodiimide (53 mg) were added to a solution of (−)-2-{(3S*,4R*)-3-[3-(4-fluorophenyl)ureido]-4-(4-methoxyphenyl)-2-oxopyrrolidin-1-yl}acetic acid (103 mg) in tetrahydrofuran (1.3 mL) under cooling to produce a reaction solution. The reaction solution was stirred at room temperature for 3 hours. Water was added to the reaction solution, and the mixture was extracted with ethyl acetate. The organic layer was washed with a brine, and dried over anhydrous sodium sulfate. The solvent was removed under reduced pressure, the residue was purified by preparative TLC (chloroform:methanol=9:1), and the crude product was washed with diisopropyl ether, to obtain the title compound as a white solid (81 mg).

$^1$H-NMR (400 MHz, CDCl$_3$) δ 2.83 (3H, d, J=4.9 Hz), 3.50 (1H, dd, J=9.8, 6.7 Hz), 3.57 (1H, d, J=17.1 Hz), 3.77 (1H, t, J=7.4 Hz), 3.80 (3H, s), 3.88-3.94 (1H, m), 4.00 (1H, t, J=9.8 Hz), 4.64 (1H, d, J=17.1 Hz), 6.67 (2H, t, J=8.6 Hz), 6.89 (2H, d, J=8.6 Hz), 6.92-6.96 (2H, m), 7.04 (1H, d, J=6.7 Hz), 7.15 (2H, d, J=8.6 Hz), 7.80 (1H, brs), 7.87 (1H, d, J=4.9 Hz).

MS (ESI$^+$) m/z: 415 (MH$^+$).

$[α]_D^{25}$=−152 (c 0.31, EtOH).

The same method as in Example 17-1 was performed using a corresponding carboxylic acid substance and amine to obtain the following Examples 17-2 to 17-3. The structures and spectral data thereof are shown in Table 89.

TABLE 89

| Ref. No | Str. | Chemical name | P.D. |
|---|---|---|---|
| 17-2 | (structure) | (−)-2-{(3S*,4R*)-4-(2,6-difluoro-4-methoxyphenyl)-3-[3-(4-fluorophenyl)ureido]-2-oxopyrrolidin-1-yl}-N-methylacetamide | $^1$H-NMR (400 MHz, DMSO-d$_6$) δ 2.61 (3H, d, J = 4.9 Hz), 3.49-3.58 (2H, m), 3.76 (3H, s), 3.82 (1H, q, J = 10.4 Hz), 3.88 (2H, s), 4.60 (1H, dd, J = 10.4, 8.6 Hz), 6.68 (1H, brs), 6.71-6.79 (2H, m), 7.01 (2H, t, J = 9.2 Hz), 7.33 (2H, dd, J = 9.2, 4.9 Hz), 7.92 (1H, q, J = 4.9 Hz), 8.85 (1H, s). MS (ESI$^+$) m/z: 451 (MH$^+$). $[α]_D^{27}$ = −156 (c 0.11, EtOH) |
| 17-3 | (structure) | (−)-2-{(3S*,4R*)-4-(6-fluoro-2,3-dihydrobenzofuran-5-yl)-3-[3-(4-fluorophenyl)ureido]-2-oxopyrrolidin-1-yl}acetamide | $^1$H-NMR (400 MHz, DMSO-d$_6$) δ 3.13 (2H, t, J = 8.6 Hz), 3.27-3.39 (1H, m), 3.56 (1H, t, J = 8.6 Hz), 3.68-3.75 (1H, m), 3.78 (1H, d, J = 16.5 Hz), 3.86 (1H, d, J = 16.5 Hz), 4.55 (2H, t, J = 8.6 Hz), 4.65 (1H, dd, J = 10.7, 8.9 Hz), 6.59-6.64 |

| Ref. No | Str. | Chemical name | P.D. |
|---|---|---|---|
| | | | (1H, m), 6.64 (1H, d, J = 11.0 Hz), 7.01-7.05 (2H, m), 7.19 (1H, s), 7.34-7.43 (4H, m), 8.77 (1H, s). MS (ESI$^+$) m/z: 431 (MH$^+$). $[\alpha]_D^{27} = -145$ (c 0.11, EtOH) |

Example 18-1

[Chemical Formula 139]

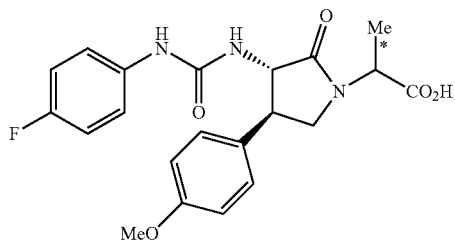

Isomer A (−)-2-{(3S*,4R*)-3-[3-(4-Fluorophenyl) ureido]-4-(4-methoxyphenyl)-2-oxopyrrolidin-1-yl}propionic acid (isomer A)

The same method as in Example 16-1 was performed using (−)-2-{(3S*,4R*)-3-[3-(4-fluorophenyl)ureido]-4-(4-methoxyphenyl)-2-oxopyrrolidin-1-yl}propionic acid ethyl ester (isomer A) in place of 2-{(3S*,4R*)-3-[3-(4-fluorophenyl)ureido]-4-(4-methoxyphenyl)-2-oxopyrrolidin-1-yl}acetic acid ethyl ester to obtain the title compound as a white solid.

$^1$H-NMR (400 MHz, DMSO-d$_6$) δ 1.35 (3H, d, J=7.4 Hz), 3.27-3.41 (2H, m), 3.61 (1H, t, J=9.1 Hz), 3.71 (3H, s), 4.58 (1H, q, J=7.4 Hz), 4.66 (1H, dd, J=11.6, 9.2 Hz), 6.55 (1H, d, J=9.2 Hz), 6.88 (2H, d, J=8.6 Hz), 7.03 (2H, t, J=8.6 Hz), 7.31-7.36 (4H, m), 8.46 (1H, s), 12.8 (1H, brs).

MS (ESI$^+$) m/z: 416 (MH$^+$).

$[\alpha]_D^{25} = -103$ (c 0.33, EtOH).

Example 19-1

[Chemical Formula 140]

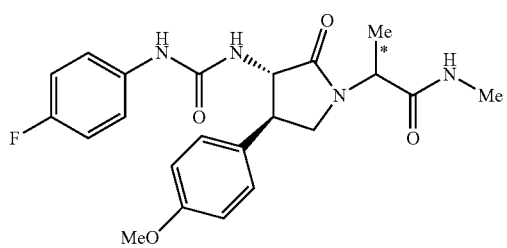

Isomer A (−)-2-{(3S*,4R*)-3-[3-(4-Fluorophenyl)ureido]-4-(4-methoxyphenyl)-2-oxopyrrolidin-1-yl}-N-methyl-propionamide (isomer A)

The same method as in Example 17-1 was performed using (−)-2-{(3S*,4R*)-3-[3-(4-fluorophenyl)ureido]-4-(4-methoxyphenyl)-2-oxopyrrolidin-1-yl}propionic acid (isomer A) in place of (−)-2-{(3S*,4R*)-3-[3-(4-fluorophenyl)ureido]-4-(4-methoxyphenyl)-2-oxopyrrolidin-1-yl}acetic acid to obtain the title compound as a white solid.

$^1$H-NMR (400 MHz, DMSO-d$_6$) δ 1.29 (3H, d, J=7.3 Hz), 2.62 (3H, d, J=4.9 Hz), 3.28 (1H, t, J=9.8 Hz), 3.43-3.51 (1H, m), 3.68 (1H, t, J=8.6 Hz), 3.71 (3H, s), 4.48-4.55 (2H, m), 6.54 (1H, d, J=9.2 Hz), 6.87 (2H, d, J=8.6 Hz), 7.04 (2H, t, J=8.6 Hz), 7.31-7.38 (4H, m), 7.83 (1H, d, J=4.9 Hz), 8.67 (1H, brs).

MS (ESI$^+$) m/z: 429(MH$^+$).

$[\alpha]_D^{25} = -199$ (c 0.34, EtOH).

Example 20-1

[Chemical Formula 141]

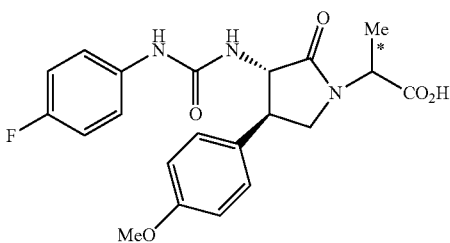

Isomer B

(−)-2-{(3S*,4R*)-3-[3-(4-Fluorophenyl)ureido]-4-(4-methoxyphenyl)-2-oxopyrrolidin-1-yl}propionic acid (isomer B)

The same method as in Example 16-1 was performed using (−)-2-{(3S*,4R*)-3-[3-(4-fluorophenyl)ureido]-4-(4-methoxyphenyl)-2-oxopyrrolidin-1-yl}propionic acid ethyl ester (isomer B) in place of 2-{(3S*,4R*)-3-[3-(4-fluorophenyl)ureido]-4-(4-methoxyphenyl)-2-oxopyrrolidin-1-yl}acetic acid ethyl ester to obtain the title compound.

$^1$H-NMR (400 MHz, DMSO-$d_6$) δ 1.36 (3H, d, J=7.4 Hz), 3.20 (1H, t, J=9.2 Hz), 3.43-3.50 (1H, m), 3.68-3.74 (1H, m), 3.72 (3H, s), 4.49 (1H, dd, J=11.0, 8.6 Hz), 4.62 (1H, q, J=7.4 Hz), 6.53 (1H, d, J=8.6 Hz), 6.90 (2H, d, J=8.6 Hz), 7.03 (2H, t, J=9.2 Hz), 7.27 (2H, d, J=8.6 Hz), 7.32-7.38 (2H, m), 8.61 (1H, s), 12.9 (1H, brs).

MS (ESI$^+$) m/z: 416 (MH$^+$).

$[α]_D^{25}$=−111 (c 0.32, EtOH).

Example 21-1

[Chemical Formula 142]

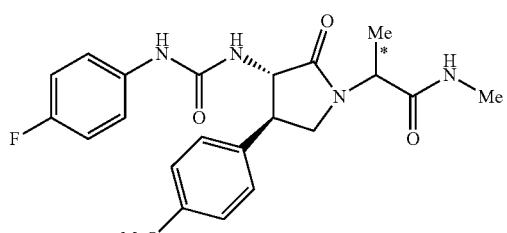

Isomer B (−)-2-{(3S*,4R*)-3-[3-(4-Fluorophenyl)ureido]-4-(4-methoxyphenyl)-2-oxopyrrolidin-1-yl}-N-methylpropionamide (isomer B)

The same method as in Example 17-1 was performed using (−)-2-{(3S*,4R*)-3-[3-(4-fluorophenyl) ureido]-4-(4-methoxyphenyl)-2-oxopyrrolidin-1-yl}propionic acid (isomer B) in place of (−)-2-{(3S*,4R*)-3-[3-(4-fluorophenyl)ureido]-4-(4-methoxyphenyl)-2-oxopyrrolidin-1-yl}acetic acid to obtain the title compound.

$^1$H-NMR (400 MHz, DMSO-$d_6$) δ 1.29 (3H, d, J=7.3 Hz), 2.57 (3H, d, J=4.9 Hz), 3.24 (1H, t, J=9.8 Hz), 3.34-3.44 (1H, m), 3.66 (1H, t, J=8.6 Hz), 3.72 (3H, s), 4.56 (1H, q, J=7.3 Hz), 4.69 (1H, dd, J=11.6, 9.2 Hz), 6.50 (1H, d, J=9.2 Hz), 6.89 (2H, d, J=8.6 Hz), 7.03 (2H, t, J=9.2 Hz), 7.30 (2H, d, J=8.6 Hz), 7.34-7.38 (2H, m), 7.87 (1H, d, J=4.9 Hz), 8.60 (1H, s).

MS (ESI$^+$) m/z: 429 (MH$^+$).

$[α]_D^{25}$=−94 (c 0.30, EtOH).

Example 22-1

[Chemical Formula 143]

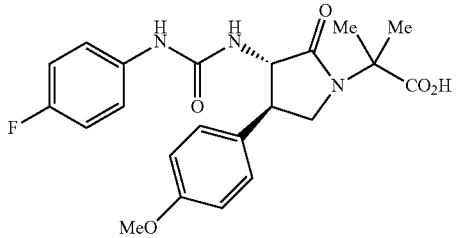

2-{(3S*,4R*)-3-[3-(4-Fluorophenyl)ureido]-4-(4-methoxyphenyl)-2-oxopyrrolidin-1-yl}-2-methylpropionic acid The same method as in Example 16-1 was performed using 2-{(3S*,4R*)-3-[3-(4-fluorophenyl) ureido]-4-(4-methoxyphenyl)-2-oxopyrrolidin-1-yl}-2-methylpropionic acid ethyl ester in place of 2-{(3S*,4R*)-3-[3-(4-fluorophenyl)ureido]-4-(4-methoxyphenyl)-2-oxopyrrolidin-1-yl}propionic acid ethyl ester to obtain the title compound.

$^1$H-NMR (400 MHz, CDCl$_3$) δ 1.52 (3H, s), 1.53 (3H, s), 3.36 (1H, t, J=9.2 Hz), 3.60-3.80 (1H, m), 3.76 (3H, s), 3.78-3.86 (1H, m), 4.60-4.68 (1H, m), 6.06 (1H, brs), 6.72-6.78 (2H, m), 6.84 (2H, d, J=8.6 Hz), 7.07-7.13 (2H, m), 7.23 (2H, d, J=8.6 Hz), 7.61 (1H, brs).

MS (ESI$^+$) m/z: 430 (MH$^+$).

Example 22-2

[Chemical Formula 144]

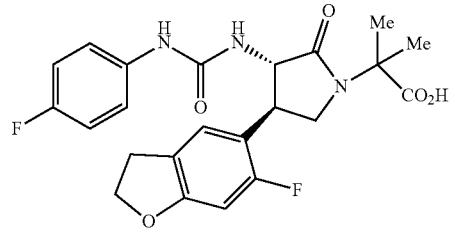

(−)-2-{(3S*,4R*)-4-(6-Fluoro-2,3-dihydrobenzofuran-5-yl)-3-[3-(4-fluorophenyl)ureido]-2-oxopyrrolidin-1-yl}-2-methylpropanoic acid A 2 mol/L sodium hydroxide aqueous solution (0.2 mL) was added to a solution of 2-{(3S*,4R*)-4-(6-fluoro-2,3-dihydrobenzofuran-5-yl)-3-[3-(4-fluorophenyl)ureido]-2-oxopyrrolidin-1-yl}-2-methylpropanoic acid ethyl ester (18 mg) in methanol (0.2 mL) to produce a reaction solution. The reaction solution was stirred at room temperature for 18 hours. A 1 mol/L hydrochloric acid was added to the reaction solution to adjust the pH of the reaction solution to 1, and the reaction solution was concentrated under reduced pressure. Water was added to the resulting residue, and the precipitate was collected by filtration and purified by preparative TLC (chloroform:methanol=10:1) to obtain the title compound as a colorless solid (4.4 mg).

¹H-NMR (400 MHz, DMSO-d₆) δ 1.40 (3H, s), 1.42 (3H, s), 3.12 (2H, t, J=8.6 Hz), 3.28-3.37 (1H, m), 3.47-3.59 (1H, m), 3.70 (1H, t, J=8.3 Hz), 4.53-4.62 (3H, m), 6.64 (1H, d, J=11.6 Hz), 6.70 (1H, brs), 7.02 (2H, t, J=8.9 Hz), 7.31-7.40 (3H, m), 8.73 (1H, brs), 12.47 (1H, brs).

MS (ESI⁺) m/z: 460 (MH⁺).

$[\alpha]_D^{27}$=−163 (c 0.09, DMSO)

Example 23-1

[Chemical Formula 145]

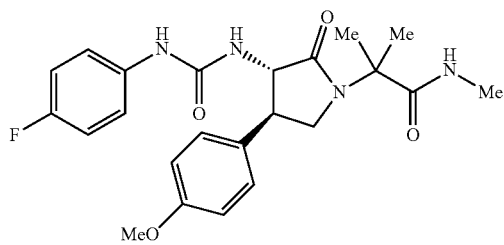

(−)-2-{(3S*,4R*)-3-[3-(4-Fluorophenyl)ureido]-4-(4-methoxyphenyl)-2-oxopyrrolidin-1-yl}-N,2-dimethylpropionamide The same method as in Example 17-1 was performed using 2-{(3S*,4R*)-3-[3-(4-fluorophenyl) ureido]-4-(4-methoxyphenyl)-2-oxopyrrolidin-1-yl}-2-methylpropionic acid in place of (−)-2-{(3S*,4R*)-3-[3-(4-fluorophenyl) ureido]-4-(4-methoxyphenyl)-2-oxopyrrolidin-1-yl}acetic acid to obtain the title compound.

¹H-NMR (400 MHz, CDCl₃) δ 1.53 (3H, s), 1.72 (3H, s), 2.69 (3H, d, J=4.9 Hz), 3.45-3.49 (1H, m), 3.80 (3H, s), 3.85 (2H, dd, J=7.3, 4.3 Hz), 3.93-3.98 (1H, m), 6.73 (1H, brs), 6.78 (2H, t, J=9.2 Hz), 6.89 (2H, t, J=8.6 Hz), 7.08 (2H, dd, J=9.2, 4.9 Hz), 7.17 (2H, d, J=8.6 Hz), 7.36 (1H, d, J=4.3 Hz), 7.88 (1H, brs).

MS (ESI⁺) m/z: 443 (MH⁺).

$[\alpha]_D^{29}$=−109 (c 0.31, EtOH).

Example 24-1

[Chemical Formula 146]

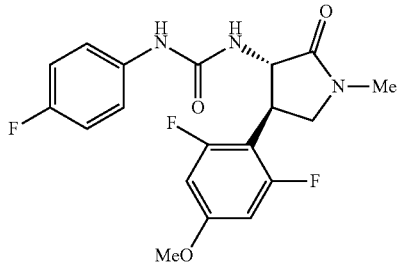

(−)-1-[(3S*,4R*)-4-(2,6-Difluoro-4-methoxyphenyl)-1-methyl-2-oxopyrrolidin-3-yl]-3-(4-fluorophenyl)urea 10% Palladium on carbon (10 mg) was added to a solution of [(3S*,4R*)-4-(2,6-difluoro-4-methoxyphenyl)-1-methyl-2-oxopyrrolidin-3-yl]carbamic acid benzyl ester (100 mg) in ethanol (5 mL) to produce a reaction solution. The reaction solution was stirred under a hydrogen atmosphere for 1 hour. The reaction solution was filtered over Celite, and the solvent was removed under reduced pressure to obtain (3S*,4R*)-3-amino-4-(2,6-difluoro-4-methoxyphenyl)-1-methylpyrrolidin-2-one as a colorless oily intermediate compound. 4-Fluorophenyl isocyanate (28 μL) was added to a solution of the resulting (3S*,4R*)-3-amino-4-(2,6-difluoro-4-methoxyphenyl)-1-methylpyrrolidin-2-one (66 mg) in tetrahydrofuran (2.6 mL) to produce a reaction solution. The reaction solution was stirred at room temperature for 20 minutes. The reaction solution was concentrated under reduced pressure, and the residue was then purified by silica gel column chromatography (hexane:ethyl acetate=4:1 followed by ethyl acetate), to obtain the title compound as a white solid (91 mg).

¹H-NMR (400 MHz, DMSO-d₆) δ 2.81 (3H, s), 3.40 (1H, dd, J=9.8, 9.2 Hz), 3.53 (1H, t, J=9.2 Hz), 3.73-3.81 (1H, m), 3.75 (3H, s), 4.57 (1H, dd, J=9.8, 8.6 Hz), 6.52 (1H, d, J=8.6 Hz), 6.74 (2H, d, J=11.0 Hz), 6.97-7.05 (2H, m), 7.30-7.36 (2H, m), 8.72 (1H, s).

MS (ESI⁺) m/z: 394 (MH⁺).

$[\alpha]_D^{27}$=−143 (c 0.10, EtOH)

The same method as in Example 24-1 was performed using a corresponding Cbz substance and isocyanate to obtain the following Examples 24-2 to 24-24.

The structures and spectral data thereof are shown in Tables 90 to 100.

TABLE 90

| Ex. No | Structure | Chemical name | P.D. |
|---|---|---|---|
| 24-2 | 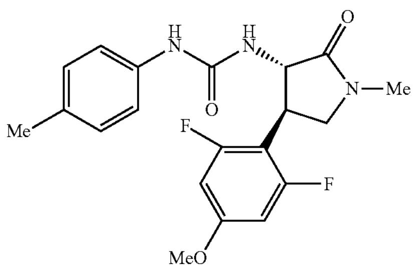 | (−)-1-[(3S*,4R*)-4-(2,6-difluoro-4-methoxyphenyl)-1-methyl-2-oxopyrrolidin-3-yl]-3-(p-tolyl)urea | $^1$H-NMR (400 MHz, DMSO-d$_6$) δ 2.18 (3H, s), 2.81 (3H, s), 3.40 (1H, t, J = 9.2 Hz), 3.52 (1H, t, J = 7.8 Hz), 3.71-3.80 (1H, m), 3.75 (3H, s), 4.56 (1H, dd, J = 10.4, 8.6 Hz), 6.51 (1H, d, J = 8.6 Hz), 6.70-6.78 (2H, m), 6.98 (2H, d, J = 8.0 Hz), 7.21 (2H, d, J = 8.0 Hz), 8.59 (1H, s). MS (ESI$^+$) m/z: 390 (MH$^+$). [α]$_D^{27}$ = −120 (c 0.14, EtOH) |
| 24-3 | 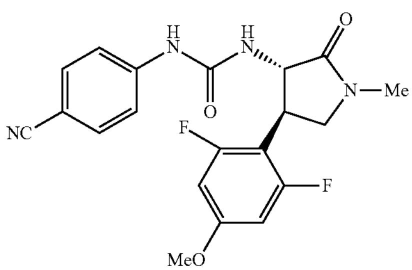 [SMILES: COc1cc(F)c([C@@H]2CN(C)C(=O)[C@H]2NC(=O)Nc2ccc(C#N)cc2)c(F)c1] | (−)-1-(4-cyanophenyl)-3-[(3S*,4R*)-4-(2,6-difluoro-4-methoxyphenyl)-1-methyl-2-oxopyrrolidin-3-yl]urea | $^1$H-NMR (400 MHz, DMSO-d$_6$) δ 2.81 (3H, s), 3.41 (1H, t, J = 9.8 Hz), 3.54 (1H, t, J = 9.8 Hz), 3.75 (3H, s), 3.80 (1H, q, J = 9.8 Hz), 4.58 (1H, t, J = 9.8 Hz), 6.71-6.78 (2H, m), 6.85 (1H, brd, J = 7.9 Hz), 7.51 (2H, d, J = 8.0 Hz), 7.62 (2H, d, J = 8.0 Hz), 9.34 (1H, s). MS (ESI$^+$) m/z: 401 (MH$^+$). [α]$_D^{27}$ = −176 (c 0.11, EtOH) |
| 24-4 | 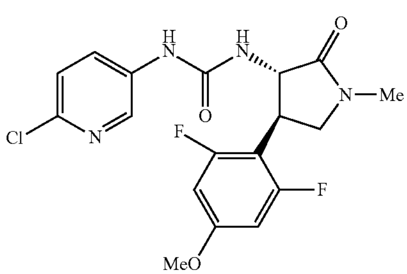 [SMILES: COc1cc(F)c([C@@H]2CN(C)C(=O)[C@H]2NC(=O)Nc2ccc(Cl)nc2)c(F)c1] | (−)-1-(6-chloropyridin-3-yl)-3-[(3S*,4R*)-4-(2,6-difluoro-4-methoxyphenyl)-1-methyl-2-oxopyrrolidin-3-yl]urea | $^1$H-NMR (400 MHz, DMSO-d$_6$) δ 2.81 (3H, s), 3.41 (1H, t, J = 9.8 Hz), 3.53 (1H, t, J = 9.8 Hz), 3.75 (3H, s), 3.80 (1H, q, J = 9.8 Hz), 4.57 (1H, t, J = 9.8 Hz), 6.70-6.79 (2H, m), 6.94 (1H, brs), 7.32 (1H, d, J = 8.6 Hz), 7.87 (1H, dd, J = 8.6, 3.1 Hz), 8.35 (1H, d, J = 3.1 Hz), 9.24 (1H, brs). MS (ESI$^+$) m/z: 411 (MH$^+$). [α]$_D^{27}$ = −197 (c 0.11, EtOH) |

TABLE 91

| Ex. No | Structure | Chemical name | P.D. |
|---|---|---|---|
| 24-5 | 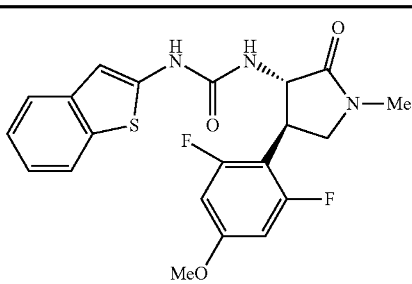 | (−)-1-(benzo[b]thiophen-2-yl)-3-[(3S*,4R*)-4-(2,6-difluoro-4-methoxyphenyl)-1-methyl-2-oxopyrrolidin-3-yl]urea | $^1$H-NMR (400 MHz, DMSO-d$_6$) δ 2.83 (3H, s), 3.43 (1H, t, J = 9.8 Hz), 3.55 (1H, t, J = 9.8 Hz), 3.75 (3H, s), 3.83 (1H, q, J = 9.8 Hz), 4.60 (1H, t, J = 9.8 Hz), 6.67 (1H, s), 6.72-6.79 (2H, m), 6.84 (1H, brd, J = 8.0 Hz), 7.09 (1H, td, J = 7.9, 1.2 Hz), 7.21 (1H, td, J = 7.9, 1.2 Hz), 7.52 (1H, d, J = 7.9 Hz), 7.69 (1H, d, J = 7.9 Hz), 10.1 (1H, s). MS (ESI$^+$) m/z: 432 (MH$^+$). [α]$_D^{29}$ = −189 (c 0.10, EtOH) |

TABLE 91-continued

| Ex. No | Structure | Chemical name | P.D. |
|---|---|---|---|
| 24-6 | 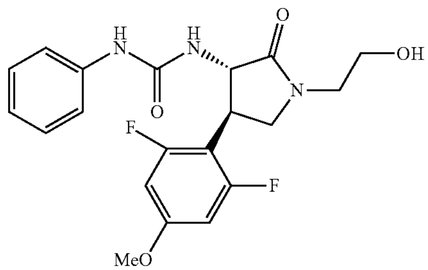 [SMILES: COc1cc(F)c([C@@H]2CN(CCO)C(=O)[C@H]2NC(=O)Nc2ccccc2)c(F)c1] | (−)-1-[(3S*,4R*)-4-(2,6-difluoro-4-methoxyphenyl)-1-(2-hydroxyethyl)-2-oxopyrrolidin-3-yl]-3-phenylurea | $^1$H-NMR (400 MHz, CDCl$_3$) δ 3.21-3.28 (1H, m), 3.35-3.44 (1H, m), 3.47-3.63 (4H, m), 3.68-3.75 (1H, m), 3.75 (3H, s), 4.64-4.68 (1H, m), 4.77 (1H, t, J = 5.5 Hz), 6.51 (1H, d, J = 8.6 Hz), 6.74 (2H, d, J = 10.4 Hz), 6.87 (1H, t, J = 7.3 Hz), 7.18 (2H, t, J = 7.9 Hz), 7.32 (2H, d, J = 7.3 Hz), 8.64 (1H, s). MS (ESI$^+$) m/z: 406 (MH$^+$). [α]$_D^{24}$ = −88 (c 0.13, EtOH) |

TABLE 92

| Ex. No | Structure | Chemical name | P.D. |
|---|---|---|---|
| 24-7 | 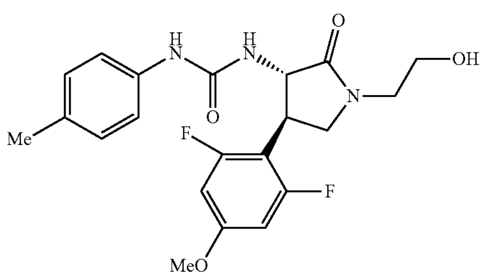 [SMILES: COc1cc(F)c([C@@H]2CN(CCO)C(=O)[C@H]2NC(=O)Nc2ccc(C#N)cc2)c(F)c1] | (−)-1-[(3S*,4R*)-4-(2,6-difluoro-4-methoxyphenyl)-1-(2-hydroxyethyl)-2-oxopyrrolidin-3-yl]-3-(p-tolyl)urea | $^1$H-NMR (400 MHz, DMSO-d$_6$) δ 2.18 (3H, s), 3.20-3.30 (1H, m), 3.33-3.43 (1H, m), 3.45-3.62 (4H, m), 3.67-3.75 (1H, m), 3.75 (3H, s), 4.65 (1H, dd, J = 9.2, 8.6 Hz), 4.77 (1H, t, J = 5.5 Hz), 6.46 (1H, d, J = 8.6 Hz), 6.70-6.77 (2H, m), 6.98 (2H, d, J = 8.6 Hz), 7.20 (2H, d, J = 8.6 Hz), 8.53 (1H, s). MS (ESI$^+$) m/z: 420 (MH$^+$). [α]$_D^{27}$ = −199 (c 0.12, EtOH) |
| 24-8 | 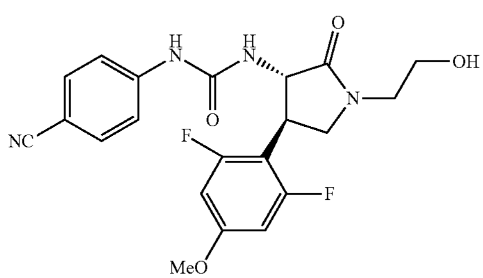 | (−)-1-(4-cyanophenyl)-3-[(3S*,4R*)-4-(2,6-difluoro-4-methoxyphenyl)-1-(2-hydroxyethyl)-2-oxopyrrolidin-3-yl]urea | $^1$H-NMR (400 MHz, DMSO-d$_6$) δ 3.20-3.28 (1H, m), 3.37-3.46 (1H, m), 3.48-3.63 (4H, m), 3.72-3.82 (1H, m), 3.75 (3H, s), 4.66 (1H, dd, J = 10.4, 8.6 Hz), 4.78 (1H, t, J = 4.9 Hz), 6.70-6.78 (2H, m), 6.83 (1H, d, J = 8.6 Hz), 7.49 (2H, d, J = 8.6 Hz), 7.62 (2H, d, J = 8.6 Hz), 9.29 (1H, s). MS (ESI$^+$) m/z: 431 (MH$^+$). [α]$_D^{28}$ = −148 (c 0.11, EtOH) |

TABLE 93

| Ex. No | Structure | Chemical name | P.D. |
|---|---|---|---|
| 24-9 | 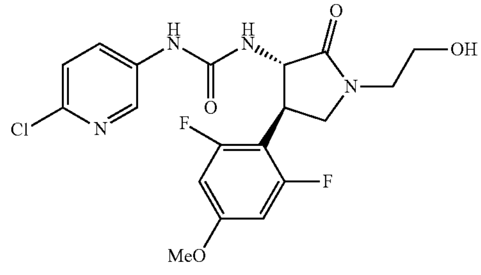 [SMILES: COc1cc(F)c([C@@H]2CN(CCO)C(=O)[C@H]2NC(=O)Nc2ccc(Cl)nc2)c(F)c1] | (−)-1-(6-chloropyridin-3-yl)-3-[(3S*,4R*)-4-(2,6-difluoro-4-methoxyphenyl)-1-(2-hydroxyethyl)-2-oxopyrrolidin-3-yl]urea | $^1$H-NMR (400 MHz, DMSO-d$_6$) δ 3.18-3.28 (1H, m), 3.38-3.46 (1H, m), 3.47-3.63 (4H, m), 3.73-3.81 (1H, m), 3.75 (3H, s), 4.66 (1H, dd, J = 11.0, 8.6 Hz), 4.77 (1H, t, J = 5.5 Hz), 6.71-6.78 (2H, m), 6.83 (1H, d, J = 8.6 Hz), 7.32 (1H, d, J = 8.6 Hz), 7.87 (1H, dd, J = 8.6, 3.0 Hz), 8.34 (1H, d, J = 3.0 Hz), 9.09 (1H, s). MS (ESI$^+$) m/z: 441 (MH$^+$). [α]$_D^{26}$ = −153 (c 0.10, EtOH) |

TABLE 93-continued

| Ex. No | Structure | Chemical name | P.D. |
|---|---|---|---|
| 24-10 | 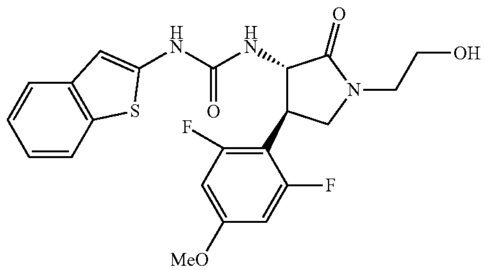 [SMILES: COc1cc(F)c([C@@H]2CN(CCO)C(=O)[C@H]2NC(=O)Nc2cc3ccccc3s2)c(F)c1] | (−)-1-(benzo[b]thiophen-2-yl)-3-[(3S*,4R*)-4-(2,6-difluoro-4-methoxyphenyl)-1-(2-hydroxyethyl)-2-oxopyrrolidin-3-yl]urea | $^1$H-NMR (400 MHz, DMSO-$d_6$) δ 3.20-3.27 (1H, m), 3.40-3.48 (1H, m), 3.50-3.64 (4H, m), 3.76 (3H, s), 3.80 (1H, q, J = 9.8 Hz), 4.68 (1H, dd, J = 9.8, 8.6 Hz), 4.78 (1H, t, J = 5.5 Hz), 6.67 (1H, s), 6.72-6.79 (2H, m), 6.87 (1H, brd, J = 8.0 Hz), 7.09 (1H, td, J = 7.9, 1.2 Hz), 7.21 (1H, td, J = 7.9, 1.2 Hz), 7.52 (1H, d, J = 7.9 Hz), 7.69 (1H, d, J = 7.9 Hz), 10.1 (1H, s). MS (ESI$^+$) m/z: 462 (MH$^+$). $[\alpha]_D^{28}$ = −170 (c 0.11, EtOH) |

TABLE 94

| Ex. No | Structure | Chemical name | P.D. |
|---|---|---|---|
| 24-11 | 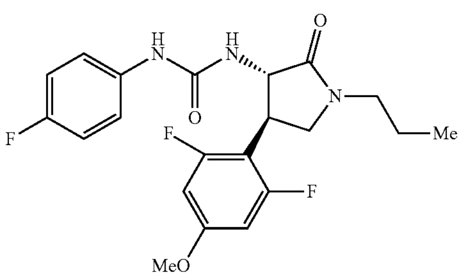 [SMILES: CCCN1C[C@@H](c2c(F)cc(OC)cc2F)[C@H](NC(=O)Nc2ccc(F)cc2)C1=O] | (−)-1-[(3S*,4R*)-4-(2,6-difluoro-4-methoxyphenyl)-2-oxo-1-propylpyrrolidin-3-yl]-3-(4-fluorophenyl)urea | $^1$H-NMR (400 MHz, CDCl$_3$) δ 0.96 (3H, t, J = 7.3 Hz), 1.57-1.67 (2H, m), 3.25-3.33 (1H, m), 3.42-3.50 (1H, m), 3.57 (1H, t, J = 9.2 Hz), 3.62-3.70 (1H, m), 3.78 (3H, s), 4.14-4.23 (1H, m), 4.39-4.46 (1H, m), 6.20 (1H, brs), 6.47 (2H, d, J = 10.4 Hz), 6.70-6.77 (2H, m), 7.03-7.10 (2H, m), 7.68 (1H, brs). MS (ESI$^+$) m/z: 422 (MH$^+$). $[\alpha]_D^{24}$ = −126 (c 0.19, EtOH) |
| 24-12 | 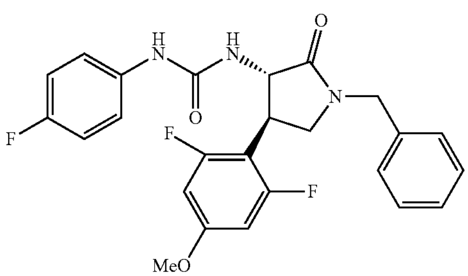 [SMILES: COc1cc(F)c([C@@H]2CN(Cc3ccccc3)C(=O)[C@H]2NC(=O)Nc2ccc(F)cc2)c(F)c1] | (−)-1-[(3S*,4R*)-1-benzyl-4-(2,6-difluoro-4-methoxyphenyl)-2-oxopyrrolidin-3-yl]-3-(4-fluorophenyl)urea | $^1$H-NMR (400 MHz, CD$_3$CN) δ 3.35-3.45 (2H, m), 3.72 (3H, s), 3.88 (1H, q, J = 9.2 Hz), 4.47 (2H, s), 4.65 (1H, dd, J = 10.4, 8.0 Hz), 5.66 (1H, d, J = 8.0 Hz), 6.53 (2H, d, J = 11.0 Hz), 6.91 (2H, t, J = 9.2 Hz), 7.23-7.36 (7H, m), 7.48 (1H, s). MS (ESI$^+$) m/z: 470 (MH$^+$). $[\alpha]_D^{29}$ = −109 (c 0.17, EtOH) |
| 24-13 | 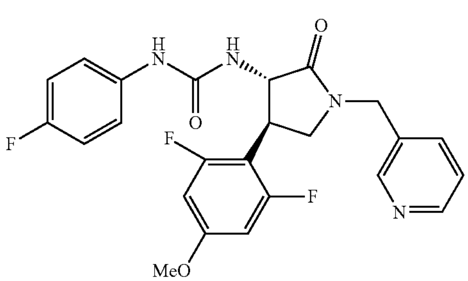 [SMILES: COc1cc(F)c([C@@H]2CN(Cc3cccnc3)C(=O)[C@H]2NC(=O)Nc2ccc(F)cc2)c(F)c1] | (−)-1-[(3S*,4R*)-4-(2,6-difluoro-4-methoxyphenyl)-2-oxo-1-(pyridin-3-ylmethyl)pyrrolidin-3-yl]-3-(4-fluorophenyl)urea | $^1$H-NMR (400 MHz, DMSO-$d_6$) δ 3.46 (1H, t, J = 9.8 Hz), 3.55 (1H, s), J = 9.8 Hz), 3.74 (3H, ), 3.88 (1H, q, J = 9.6 Hz), 4.51 (1H, d, J = 15.9 Hz), 4.61-4.69 (2H, m), 64 (1H, d, J = 9.5 Hz), 6.74 (2H, d, J = 9.5 Hz), 7.03 (2H, td, J = 7.6, 2.2 Hz), 7.29-7.37 (4H, m), 7.81 (1H, td, J = 7.6, 1.8 Hz), 8.54 (1H, q, J = 2.2 Hz), 8.74 (1H, s). MS (ESI$^+$) m/z: 470 (MH$^+$). $[\alpha]_D^{3?}$ = −142 (c 0.10, EtOH) |

TABLE 95

| Ex. No | Structure | Chemical name | P.D. |
|---|---|---|---|
| 24-14 | 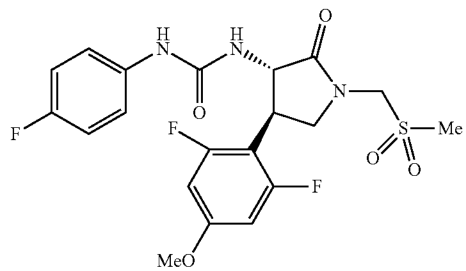 [SMILES: COc1cc(F)c([C@@H]2CN(CS(C)(=O)=O)C(=O)[C@H]2NC(=O)Nc2ccc(F)cc2)c(F)c1] | (−)-1-{(3S*,4R*)-4-(2,6-difluoro-4-methoxyphenyl)-1-[(methylsulfonyl)methyl]-2-oxopyrrolidin-3-yl}-3-(4-fluorophenyl)urea | $^1$H-NMR (400 MHz, DMSO-d$_6$) δ 3.31 (3H, s), 3.67 (1H, t, J = 9.5 Hz), 3.76 (3H, s), 3.85 (1H, t, J = 8.9 Hz), 4.02 (1H, q, J = 9.8 Hz), 4.55 (1H, dd, J = 11.0, 7.9 Hz), 4.71 (1H, d, J = 14.7 Hz), 4.82 (1H, d, J = 14.7 Hz), 6.72 (1H, d, J = 10.0 Hz), 6.77 (2H, d, J = 10.0 Hz), 7.03 (2H, dt, J = 14.5, 3.7 Hz), 7.33-7.36 (2H, m), 8.89 (1H, s). MS (ESI$^+$) m/z: 472 (MH$^+$). [α]$_D^{28}$ = −203 (c 0.10, EtOH) |
| 24-15 | 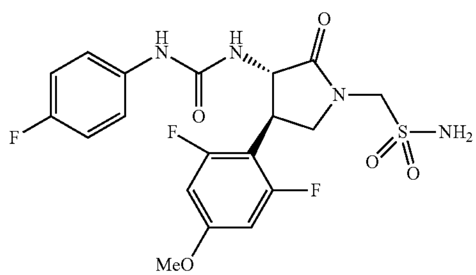 [SMILES: COc1cc(F)c([C@@H]2CN(CS(N)(=O)=O)C(=O)[C@H]2NC(=O)Nc2ccc(F)cc2)c(F)c1] | (−)-{(3S*,4R*)-4-(2,6-difluoro-4-methoxyphenyl)-3-[3-(4-fluorophenyl)ureido]-2-oxopyrrolidin-1-yl}methanesulfonamide | $^1$H-NMR (400 MHz, DMSO-d$_6$) δ 3.68-3.90 (6H, m), 4.53 (1H, d, J = 13.5 Hz), 4.69 (1H, d, J = 13.5 Hz), 4.77 (1H, t, J = 10.0 Hz), 6.51 (1H, d, J = 8.6 Hz), 6.76 (2H, d, J = 10.4 Hz), 7.03 (2H, t, J = 8.6 Hz), 7.09 (2H, s), 7.31-7.35 (2H, m), 8.81 (1H, s). MS (ESI$^+$) m/z: 473 (MH$^+$). [α]$_D^{25}$ = −120 (c 0.10, EtOH) |

TABLE 96

| Ex. No | Structure | Chemical name | P.D. |
|---|---|---|---|
| 24-16 | 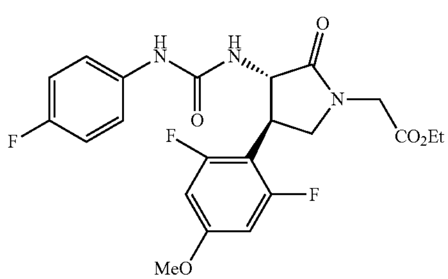 [SMILES: CCOC(=O)CN1C[C@@H](c2c(F)cc(OC)cc2F)[C@H](NC(=O)Nc2ccc(F)cc2)C1=O] | (−)-2-{(3S*,4R*)-4-(2,6-difluoro-4-methoxyphenyl)-3-[3-(4-fluorophenyl)ureido]-2-oxopyrrolidin-1-yl}acetic acid ethyl ester | $^1$H-NMR (400 MHz, DMSO-d$_6$) δ 1.21 (3H, t, J = 6.7 Hz), 3.51-3.61 (2H, m), 3.76 (3H, s), 3.82 (1H, q, J = 10.4 Hz), 3.97 (1H, d, J = 17.0 Hz), 4.13 (2H, q, J = 6.7 Hz), 4.27 (1H, d, J = 17.0 Hz), 4.67 (1H, dd, J = 10.4, 8.6 Hz), 6.68-6.80 (3H, m), 7.01 (2H, t, J = 9.2 Hz), 7.33 (2H, dd, J = 9.2, 4.9 Hz), 8.79 (1H, s). MS (ESI$^+$) m/z: 466 (MH$^+$). [α]$_D^{26}$ = −128 (c 0.11, EtOH) |
| 24-17 | 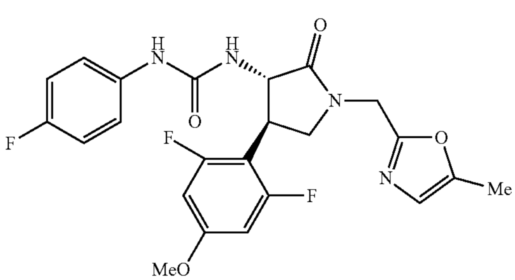 [SMILES: COc1cc(F)c([C@@H]2CN(Cc3ncc(C)o3)C(=O)[C@H]2NC(=O)Nc2ccc(F)cc2)c(F)c1] | (−)-1-{(3S*,4R*)-4-(2,6-difluoro-4-methoxyphenyl)-1-[(5-methyloxazol-2-yl)methyl]-2-oxopyrrolidin-3-yl}-3-(4-fluorophenyl)urea | $^1$H-NMR (400 MHz, DMSO-d$_6$) δ 2.27 (3H, s), 3.49 (1H, t, J = 9.2 Hz), 3.59 (1H, t, J = 9.2 Hz), 3.75 (3H, s), 3.82 (1H, q, J = 9.8 Hz), 4.44 (1H, d, J = 16.5 Hz), 4.64-4.71 (2H, m), 6.61 (1H, d, J = 8.6 Hz), 6.75 (2H, d, J = 10.4 Hz), 6.80 (1H, s), 7.02 (2H, t, J = 9.2 Hz), 7.33 (2H, dd, J = 8.6, 4.9 Hz), 8.71 (1H, s). MS (ESI$^+$) m/z: 475 (MH$^+$). [α]$_D^{25}$ = −108 (c 0.12, EtOH) |

TABLE 97

| Ex. No | Structure | Chemical name | P.D. |
|---|---|---|---|
| 24-18 | 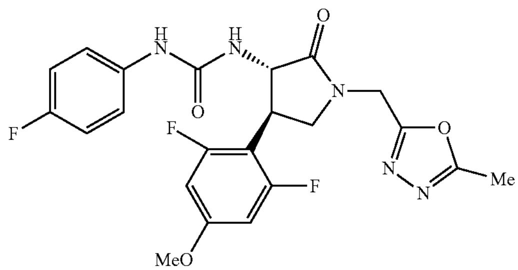 [SMILES: COc1cc(F)c([C@@H]2CN(Cc3nnc(C)o3)C(=O)[C@H]2NC(=O)Nc2ccc(F)cc2)c(F)c1] | (−)-1-{(3S*,4R*)-4-(2,6-difluoro-4-methoxyphenyl)-1-[(5-methyl-1,3,4-oxadiazol-2-yl)methyl]-2-oxopyrrolidin-3-yl}-3-(4-fluorophenyl)urea | $^1$H-NMR (400 MHz, DMSO-d$_6$) δ 2.49 (3H, s), 3.51 (1H, t, J = 9.2 Hz), 3.62 (1H, t, J = 9.2 Hz), 3.75 (3H, s), 3.84 (1H, q, J = 9.2 Hz), 4.64-4.68 (2H, m), 4.81 (1H, d, J = 16.5 Hz), 6.61 (1H, d, J = 8.6 Hz), 6.76 (2H, d, J = 11.0 Hz), 7.02 (2H, t, J = 9.2 Hz), 7.33 (2H, dd, J = 8.6, 4.9 Hz), 8.71 (1H, s). MS (ESI$^+$) m/z: 476 (MH$^+$). $[α]_D^{29}$ = −106 (c 0.11, EtOH) |
| 24-19 | 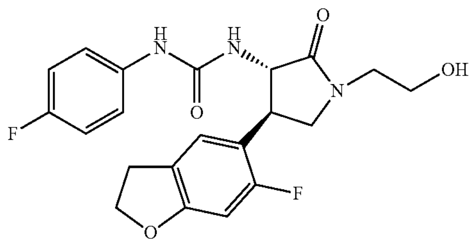 [SMILES: O=C(Nc1ccc(F)cc1)N[C@@H]1C(=O)N(CCO)C[C@H]1c1cc2c(cc1F)OCC2] | (−)-1-[(3S*,4R*)-4-(6-fluoro-2,3-dihydrobenzofuran-5-yl)-1-(2-hydroxyethyl)-2-oxopyrrolidin-3-yl]-3-(4-fluorophenyl)urea | $^1$H-NMR (400 MHz, DMSO-d$_6$) δ 3.12 (2H, t, J = 8.6 Hz), 3.16-3.21 (1H, m), 3.29-3.3.44 (2H, m), 3.49-3.53 (2H, m), 3.56-3.66 (2H, m), 4.55 (2H, t, J = 8.6 Hz), 4.62 (1H, t, J = 9.5 Hz), 4.76 (1H, t, 5.5 Hz), 6.53-6.66 (1H, m), 6.64 (1H, d, J = 11.0 Hz), 7.03 (2H, t, J = 8.6 Hz), 7.34-7.39 (3H, m), 8.67-8.76 (1H, m). MS (ESI$^+$) m/z: 418 (MH$^+$). $[α]_D^{26}$ = −164 (c 0.12, EtOH) |

TABLE 98

| Ex. No | Structure | Chemical name | P.D. |
|---|---|---|---|
| 24-20 | 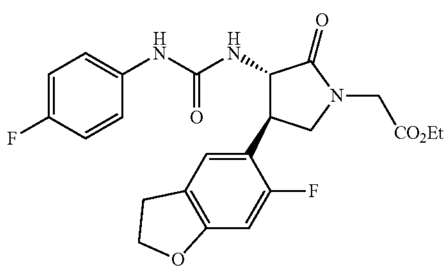 [SMILES: CCOC(=O)CN1C[C@@H](c2cc3c(cc2F)OCC3)[C@H](NC(=O)Nc2ccc(F)cc2)C1=O] | (−)-2-{(3S*,4R*)-4-(6-fluoro-2,3-dihydrobenzofuran-5-yl)-3-[3-(4-fluorophenyl)ureido]-2-oxopyrrolidin-1-yl}acetic acid ethyl ester | $^1$H-NMR (400 MHz, DMSO-d$_6$) δ 1.21 (3H, t, J = 6.7 Hz), 3.10-3.16 (2H, m), 3.27-3.38 (1H, m), 3.60 (1H, t, J = 8.6 Hz), 3.65-3.70 (1H, m), 4.02 (1H, d, J = 17.7 Hz), 4.11-4.19 (3H, m), 4.55 (2H, t, J = 8.3 Hz), 4.62 (1H, t, J = 9.8 Hz), 6.66 (1H, d, J = 11.0 Hz), 6.81 (1H, brs), 7.03 (2H, t, J = 8.6 Hz), 7.31-7.38 (3H, m), 8.81-8.84 (1H, m). MS (ESI$^+$) m/z: 460 (MH$^+$). $[α]_D^{27}$ = −109 (c 0.11, EtOH) |
| 24-21 | 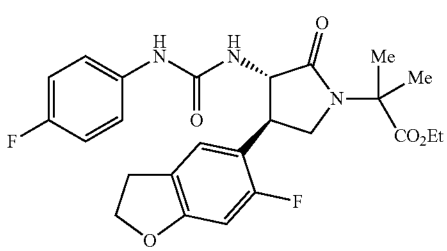 [SMILES: CCOC(=O)C(C)(C)N1C[C@@H](c2cc3c(cc2F)OCC3)[C@H](NC(=O)Nc2ccc(F)cc2)C1=O] | (−)-2-{(3S*,4R*)-4-(6-fluoro-2,3-dihydrobenzofuran-5-yl)-3-[3-(4-fluorophenyl)ureido]-2-oxopyrrolidin-1-yl}-2-methylpropanoic acid ethyl ester | $^1$H-NMR (400 MHz, DMSO-d$_6$) δ 1.18 (3H, t, J = 7.0 Hz), 1.39 (3H, s), 1.44 (3H, s), 3.12 (2H, t, J = 8.9 Hz), 3.28-3.38 (1H, m), 3.60 (1H, t, J = 10.1 Hz), 3.74 (1H, t, J = 8.9 Hz), 4.03-4.09 (2H, m), 4.53-4.57 (3H, m), 6.62-6.67 (1H, m), 6.66 (1H, d, J = 11.0 Hz), 7.02 (2H, t, J = 8.9 Hz), 7.33-7.36 (3H, m), 8.70 (1H, s). MS (ESI$^+$) m/z: 488 (MH$^+$). $[α]_D^{27}$ = −140 (c 0.12, EtOH) |

TABLE 99

| Ex. No | Structure | Chemical name | P.D. |
|---|---|---|---|
| 24-22 | 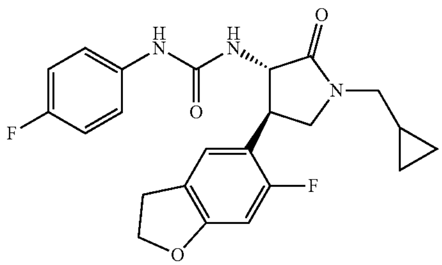 [SMILES: O=C(Nc1ccc(F)cc1)N[C@@H]1C(=O)N(CC2CC2)C[C@H]1c1cc2c(cc1F)OCC2] | (−)-1-[(3S*,4R*)-1-(cyclopropylmethyl)-4-(6-fluoro-2,3-dihydrobenzofuran-5-yl)-2-oxopyrrolidin-3-yl]-3-(4-fluorophenyl)urea | $^1$H-NMR (400 MHz, DMSO-d$_6$) δ 0.21-0.29 (2H, m), 0.49-0.55 (2H, m), 0.92-1.02 (1H, m), 3.03 (1H, dd, J = 13.9, 7.3), 3.17 (2H, t, J = 8.8 Hz), 3.28 (1H, dd, J = 13.9, 7.0 Hz), 3.33-3.43 (1H, m), 3.64-3.73 (2H, m), 4.58-4.67 (1H, m), 4.60 (2H, t, J = 8.8 Hz), 6.64-6.71 (1H, m), 6.70 (1H, J = 11.0 Hz), 7.07 (2H, t, J = 8.9 Hz), 7.38-7.46 (3H, m), 8.77 (1H, s). MS (ESI$^+$) m/z: 428 (MH$^+$). $[α]_D^{27}$ = −159 (c 0.11, EtOH) |
| 24-23 | 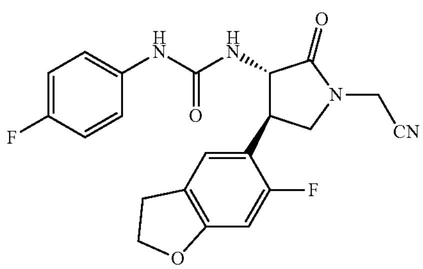 [SMILES: N#CCN1C[C@@H](c2cc3c(cc2F)OCC3)[C@H](NC(=O)Nc2ccc(F)cc2)C1=O] | (−)-1-[(3S*,4R*)-1-(cyanomethyl)-4-(6-fluoro-2,3-dihydrobenzofuran-5-yl)-2-oxopyrrolidin-3-yl]-3-(4-fluorophenyl)urea | $^1$H-NMR (400 MHz, DMSO-d$_6$) δ 3.12 (2H, t, J = 9.1 Hz), 3.29-3.34 (1H, m), 3.65 (1H, t, J = 9.1 Hz), 3.73-3.81 (1H, m), 4.44 (2H, s), 4.53-4.60 (3H, m), 6.65 (2H, d, J = 10.9 Hz), 7.25-7.32 (1H, m), 7.37-7.40 (3H, m), 9.32 (1H, brs). MS (ESI$^+$) m/z: 413 (MH$^+$). $[α]_D^{26}$ = −136 (c 0.11, EtOH) |

TABLE 100

| Ex. No | Structure | Chemical name | P.D. |
|---|---|---|---|
| 24-24 | 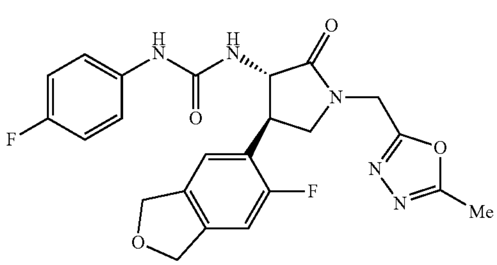 [SMILES: Cc1nnc(CN2C[C@@H](c3cc4c(cc3F)COC4)[C@H](NC(=O)Nc3ccc(F)cc3)C2=O)o1] | (−)-1-{(3S*,4R*)-4-(6-fluoro-2,3-dihydrobenzofuran-5-yl)-1-([5-methyl-1,3,4-oxadiazol-2-yl)methyl]-2-oxopyrrolidin-3-yl}-3-(4-fluorophenyl)urea | $^1$H-NMR (400 MHz, DMSO-d$_6$) δ 2.49 (3H, s), 3.12 (2H, t, J = 9.1 Hz), 3.29-3.37 (1H, m), 3.63 (1H, t, J = 9.1 Hz), 3.69-3.77 (1H, m), 4.55 (2H, t, J = 8.5 Hz), 4.62-4.76 (3H, m), 6.57 (1H, d, J = 9.1 Hz), 6.65 (1H, d, J = 10.9 Hz), 7.01-7.06 (2H, m), 7.34-7.38 (3H, m), 8.64 (1H, s). MS (ESI$^+$) m/z: 470 (MH$^+$). $[α]_D^{27}$ = −126 (c 0.10, EtOH) |

Example 25-1

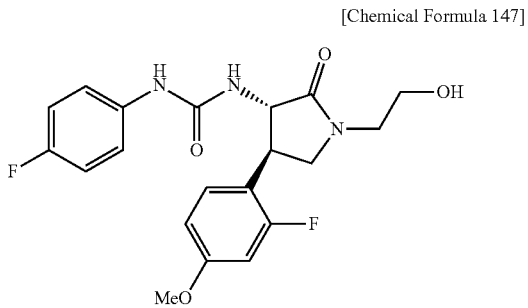 [SMILES: COc1ccc([C@@H]2CN(CCO)C(=O)[C@H]2NC(=O)Nc2ccc(F)cc2)c(F)c1]

(−)-1-[(3S*,4R*)-4-(2-Fluoro-4-methoxyphenyl)-1-(2-hydroxyethyl)-2-oxopyrrolidin-3-yl]-3-(4-fluorophenyl)urea The same method as in Example 24-1 was performed using [(3S*,4R*)-4-(2-fluoro-4-methoxyphenyl)-1-(2-hydroxyethyl)-2-oxopyrrolidin-3-yl]carbamic acid benzyl ester in place of [(3S*,4R*)-4-(2,6-difluoro-4-methoxyphenyl)-1-methyl-2-oxopyrrolidin-3-yl]carbamic acid benzyl ester to obtain the title compound.

$^1$H-NMR (400 MHz, DMSO-d$_6$) δ 3.14-3.20 (1H, m), 3.28-3.42 (2H, m), 3.48-3.52 (2H, m), 3.57-3.66 (2H, m), 3.72 (3H, s), 4.66 (1H, dd, J=11.0, 8.6 Hz), 4.73 (1H, t, J=5.5 Hz), 6.45 (1H, d, J=8.6 Hz), 6.75-6.80 (2H, m), 6.98-7.04 (2H, m), 7.30-7.36 (2H, m), 7.44 (1H, dd, J=9.2, 9.2 Hz), 8.60 (1H, s).

MS (ESI$^+$) m/z: 406 (MH$^+$).

[α]$_D^{27}$=−118 (c 0.10, EtOH)

Example 26-1

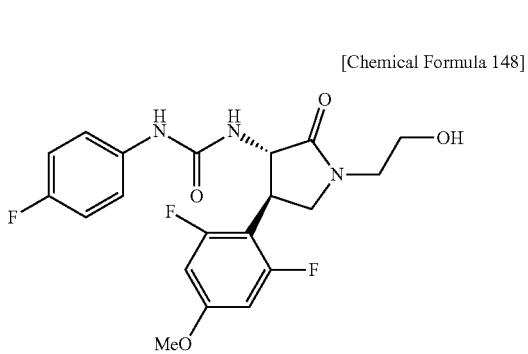 [SMILES: COc1cc(F)c([C@@H]2CN(CCO)C(=O)[C@H]2NC(=O)Nc2ccc(F)cc2)c(F)c1]

(−)-1-[(3S*,4R*)-4-(2,6-Difluoro-4-methoxyphenyl)-1-(2-hydroxyethyl)-2-oxopyrrolidin-3-yl]-3-(4-fluorophenyl)urea The same method as in Example 24-1 was performed using [(3S*,4R*)-4-(2,6-difluoro-4-methoxyphenyl)-1-(2-hydroxyethyl)-2-oxopyrrolidin-3-yl]carbamic acid benzyl ester in place of [(3S*,4R*)-4-(2,6-difluoro-4-methoxyphenyl)-1-methyl-2-oxopyrrolidin-3-yl]carbamic acid benzyl ester to obtain the title compound.

$^1$H-NMR (400 MHz, DMSO-d$_6$) δ 3.21-3.30 (1H, m), 3.36-3.45 (1H, m), 3.48-3.62 (4H, m), 3.71-3.78 (1H, m), 3.76 (3H, s), 4.66 (1H, dd, J=10.4, 8.6 Hz), 4.77 (1H, t, J=5.5 Hz), 6.51 (1H, d, J=8.6 Hz), 6.75 (2H, d, J=11.0 Hz), 6.99-7.06 (2H, m), 7.31-7.37 (2H, m), 8.68 (1H, s).

MS (ESI$^+$) m/z: 424 (MH$^+$).

[α]$_D^{27}$=−139 (c 0.11, EtOH)

Example 27-1

(+)-1-(4-Fluorophenyl)-3-[(3R*,4S*)-1-methoxy-4-(4-methoxyphenyl-2-oxopyrrolidin-3-yl]urea The same method as in Example 1-1 was performed using (3R*,4S*)-1-methoxy-4-(4-methoxyphenyl)-2-oxopyrrolidine-3-carboxylic acid in place of (−)-(3S*,4R*)-4-(4-methoxyphenyl)-2-oxopyrrolidine-3-carboxylic acid to obtain the title compound.

$^1$H-NMR (400 MHz, CDCl$_3$) δ 3.55 (1H, t, J=8.5 Hz), 3.74-3.82 (1H, m), 3.80 (3H, s), 3.89 (3H, s), 4.01 (1H, t, J=8.2 Hz), 4.10 (1H, dd, J=8.5, 8.2 Hz), 6.08 (1H, brs), 6.79 (2H, t, J=8.8 Hz), 6.89 (2H, d, J=9.1 Hz), 7.12 (2H, q, J=4.6 Hz), 7.20 (2H, d, J=9.1 Hz), 7.50 (1H, brs).

MS (ESI$^+$) m/z: 374 (MH$^+$).

[α]$_D^{27}$=+144 (c 0.12, EtOH)

Example 27-2

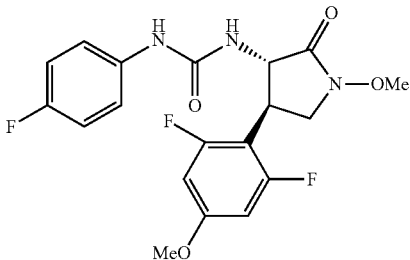

[Chemical Formula 150]

(−)-1-[(3S*,4R*)-4-(2,6-Difluoro-4-methoxyphenyl)-1-methoxy-2-oxopyrrolidin-3-yl]-3-(4-fluorophenyl)urea The same method as in Example 1-1 was performed using (3S*,4R*)-4-(2,6-difluoro-4-methoxyphenyl)-1-methoxy-2-oxopyrrolidine-3-carboxylic acid in place of (−)-(3S*,4R*)-4-(4-methoxyphenyl)-2-oxopyrrolidine-3-carboxylic acid to obtain the title compound.

$^1$H-NMR (400 MHz, DMSO-d$_6$) δ 3.54-3.61 (1H, m), 3.73 (3H, s), 3.76 (3H, s), 3.80-3.89 (2H, m), 4.46 (1H, t, J=8.9 Hz), 6.67 (1H, d, J=8.6 Hz), 6.77 (2H, d, J=8.6 Hz), 7.00-7.05 (2H, m), 7.32-7.36 (2H, m), 8.83 (1H, s).

MS (ESI$^+$) m/z: 410 (MH$^+$).

$[\alpha]_D^{25}$=−208 (c 0.20, EtOH)

Example 28-1

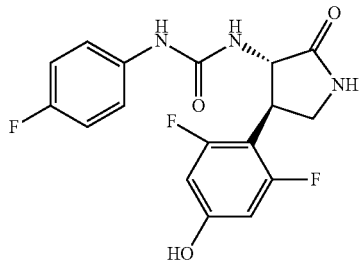

[Chemical Formula 151]

(−)-1-[(3S*,4R*)-4-(2,6-Difluoro-4-hydroxyphenyl)-2-oxopyrrolidin-3-yl]-3-(4-fluorophenyl)urea 10% Palladium on carbon (49 mg) was added to a solution of 1-[(3S*,4R*)-4-[4-(benzyloxy-2,6-difluorophenyl)-2-oxopyrrolidin-3-yl]-3-(4-fluorophenyl)urea (490 mg) in ethanol (10 mL) under an argon atmosphere to produce a reaction solution. The reaction solution was stirred at room temperature under a hydrogen atmosphere for 4 hours. The reaction solution was filtered over Celite, and the solvent was removed under reduced pressure. The residue was purified by silica gel column chromatography (hexane:ethyl acetate=4:1 followed by ethyl acetate), to obtain the title compound as a white solid (383 mg).

$^1$H-NMR (400 MHz, DMSO-d$_6$) δ 3.23-3.28 (1H, m), 3.41 (1H, t, J=9.2 Hz), 3.74 (1H, q, J=9.6 Hz), 4.52 (1H, dd, J=10.7, 8.3 Hz), 6.41 (2H, d, J=10.4 Hz), 6.45 (1H, d, J=7.9 Hz), 6.99-7.04 (2H, m), 7.31-7.35 (2H, m), 8.01 (1H, s), 8.66 (1H, s).

MS (ESI$^+$) m/z: 366 (MH$^+$).

$[\alpha]_D^{28}$=−151(c 0.1, EtOH)

Example 28-2

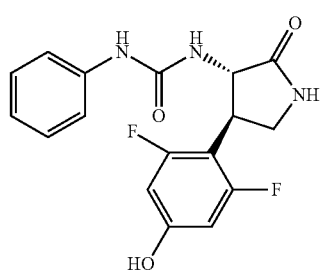

[Chemical Formula 152]

1-[(3S*,4R*)-4-(2,6-Difluoro-4-hydroxyphenyl)-2-oxopyrrolidin-3-yl]-3-phenylurea The same method as in Example 28-1 was performed using 1-[(3S*,4R*)-4-(4-(benzyloxy-2,6-difluorophenyl)-2-oxopyrrolidin-3-yl]-3-phenylurea in place of 1-[(3S*,4R*)-4-(4-benzyloxy-2,6-difluorophenyl)-2-oxopyrrolidin-3-yl]-3-(4-fluorophenyl)urea to obtain the title compound.

$^1$H NMR (400 MHz, DMSO-d$_6$) δ 3.25-3.30 (1H, m), 3.42 (1H, t, J=8.6 Hz), 3.74 (1H, q, J=9.6 Hz), 4.53 (1H, dd, J=11.0, 8.6 Hz), 6.41-6.47 (3H, m), 6.86 (1H, t, J=7.3 Hz), 7.18 (2H, t, J=7.9 Hz), 7.32 (2H, d, J=7.9 Hz), 8.03 (1H, s), 8.60 (1H, s), 10.35 (1H, brs).

MS (ESI$^+$) m/z: 348 (MH$^+$).

Example 28-3

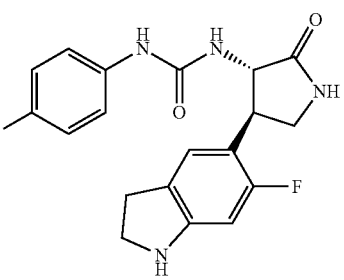

[Chemical Formula 153]

(−)-1-[(3S*,4R*)-4-(6-Fluoroindolin-5-yl)-2-oxopyrrolidin-3-yl]-3-(4-fluorophenyl)urea The same method as in Example 28-1 was performed using 1-[(3S*,4R*)-4-(1-benzyl-6-fluoroindolin-5-yl)-2-oxopyrrolidin-3-yl]-3-(4-fluorophenyl)urea in place of 1-[(3S*,4R*)-4-(4-benzyloxy-2,6-difluorophenyl)-2-oxopyrrolidin-3-yl]-3-(4-fluorophenyl)urea to obtain the title compound.

$^1$H-NMR (400 MHz, DMSO-d$_6$) δ 2.83 (2H, t, J=8.5 Hz), 3.11 (1H, t, J=9.7 Hz), 3.35-3.44 (3H, m), 3.53-3.61 (1H, m), 4.47 (1H, dd, J=11.5, 9.1 Hz), 5.68 (1H, br), 6.20 (1H, d, J=11.5 Hz), 6.36 (1H, d, J=8.5 Hz), 7.00-7.05 (2H, m), 7.11 (1H, d, J=7.9 Hz), 7.33-7.37 (2H, m), 7.87 (1H, s), 8.55 (1H, s).

MS (ESI$^+$) m/z: 373 (MH$^+$).

[α]$_D^{27}$=−202 (c 0.12, EtOH)

Example 28-4

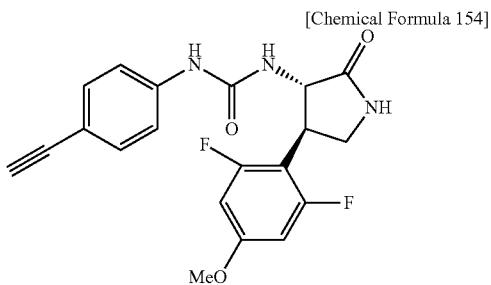 [SMILES: C#Cc1ccc(NC(=O)N[C@@H]2C(=O)NC[C@H]2c2c(F)cc(OC)cc2F)cc1]

[Chemical Formula 154]

(−)-1-[(3S*,4R*)-4-(2,6-Difluoro-4-methoxyphenyl)-2-oxopyrrolidin-3-yl]-3-(4-ethynylphenyl)urea Potassium carbonate (1 mg) was added to a solution of 1-[(3S*,4R*)-4-(2,6-difluoro-4-methoxyphenyl)-2-oxopyrrolidin-3-yl]-3-{4-[(trimethylsilyl)ethynyl]phenyl}urea (66 mg) in methanol (1.4 mL) under ice-cooling to produce a reaction solution. The reaction solution was stirred at room temperature for 8 hours. The reaction solution was concentrated under reduced pressure, and the residue was then purified by silica gel column chromatography (hexane:ethyl acetate=1:1, ethyl acetate, and ethyl acetate:methanol=4:1 in turn), to obtain the title compound as a colorless solid (44 mg).

$^1$H-NMR (400 MHz, DMSO-d$_6$) δ 3.27-3.32 (1H, m), 3.45 (1H, t, J=9.2 Hz), 3.75 (3H, s), 3.80 (1H, ddd, J=11.0, 9.2, 9.2 Hz), 3.98 (1H, s), 4.56 (1H, dd, J=11.0, 8.6 Hz), 6.57 (1H, d, J=8.6 Hz), 6.70-6.77 (2H, m), 7.28 (2H, d, J=8.6 Hz), 7.35 (2H, d, J=8.6 Hz), 8.07 (1H, s), 8.89 (1H, s).

MS (ESI$^+$) m/z: 386 (MH$^+$).

[α]$_D^{28}$=−147 (c 0.11, EtOH)

Example 28-5

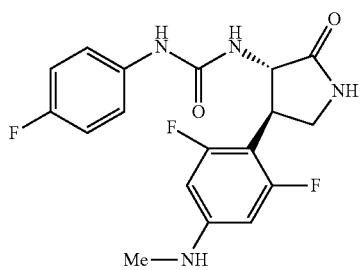

[Chemical Formula 155]

(−)-1-{(3S*,4R*)-4-[2,6-Difluoro-4-(methylamino)phenyl]-2-oxopyrrolidin-3-yl}-3-(4-fluorophenyl)urea Trifluoroacetic acid (1 mL) was added to (3,5-difluoro-4-{(3R*,4S*)-4-[3-(4-fluorophenyl)ureido]-5-oxopyrrolidin-3-yl}phenyl)(methyl)carbamic acid tert-butyl ester (80 mg) to produce a reaction solution. The reaction solution was stirred at 60° C. for 1 hour. The reaction solution was concentrated under reduced pressure, a saturated aqueous sodium hydrogen carbonate solution was added to the residue, and the mixture was extracted with ethyl acetate. The organic layer was washed with water and a brine successively, and dried over anhydrous sodium sulfate. The solvent was removed under reduced pressure, and the residue was then purified by silica gel column chromatography (ethyl acetate), to obtain the title compound as a colorless solid (30 mg).

$^1$H-NMR (400 MHz, DMSO-d$_6$) δ 2.63 (3H, d, J=4.9 Hz), 3.25 (1H, t, J=10.1 Hz), 3.37 (1H, t, J=8.9 Hz), 3.67 (1H, q, J=9.8 Hz), 4.52 (1H, dd, J=11.0, 8.6 Hz), 6.16 (2H, d, J=12.0 Hz), 6.21 (1H, d, J=4.9 Hz), 6.40 (1H, d, J=8.6 Hz), 6.99-7.04 (2H, m), 7.32-7.36 (2H, m), 7.98 (1H, s), 8.61 (1H, s).

MS (ESI$^+$) m/z: 379 (MH$^+$).

[α]$_D^{24}$=−54 (c 0.14, EtOH)

Example 28-6

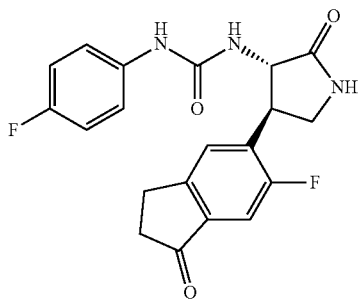

[Chemical Formula 156]

1-[(3S*,4R*)-4-(6-Fluoro-1-oxo-2,3-dihydro-1H-inden-5-yl)-2-oxopyrrolidin-3-yl]-3-(4-fluorophenyl)urea A Dess-Martin reagent (14 mg) was added to a solution of 1-[(3S*,4R*)-4-(6-fluoro-1-hydroxy-2,3-dihydro-1H-inden-5-yl)-2-oxopyrrolidin-3-yl]-3-(4-fluorophenyl)urea (13 mg) in a mixture of dichloromethane (0.66 mL) and acetonitrile (0.66 mL) under an argon atmosphere under cooling to produce a reaction solution. The reaction solution was stirred at room temperature for 3 hours. A saturated aqueous sodium hydrogen carbonate solution was added to the reaction solution, and the mixture was extracted with ethyl acetate. The organic layer was washed with a brine, and dried over anhydrous sodium sulfate. The solvent was removed under reduced pressure, and the residue was then purified by silica gel column chromatography (hexane:ethyl acetate=1:1, ethyl acetate, and ethyl acetate:methanol=9:1 in turn), to obtain the title compound as a colorless solid (11 mg).

¹H-NMR (400 MHz, DMSO-d₆) δ 2.64-2.67 (2H, m), 3.15 (2H, t, J=5.2 Hz), 3.27 (1H, t, J=8.6 Hz), 3.53 (1H, t, J=8.9 Hz), 3.89 (1H, q, J=9.8 Hz), 4.65 (1H, dd, J=11.6, 8.6 Hz), 6.53 (1H, d, J=8.6 Hz), 7.00-7.04 (2H, m), 7.32-7.37 (3H, m), 7.82 (1H, d, J=6.1 Hz), 8.04 (1H, s), 8.69 (1H, s).

MS (ESI⁺) m/z: 386 (MH⁺).

Example 29-1

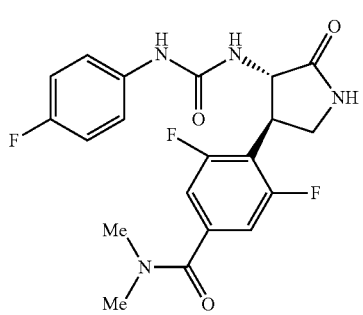

[Chemical Formula 157]

(−)-3,5-Difluoro-4-{(3R*,4S*)-4-[3-(4-fluorophenyl)ureido]-5-oxopyrrolidin-3-yl}-N,N-dimethylbenzamide Acetonitrile (3 mL), palladium(II) acetate (14 mg), (±)-2,2'-bis(diphenylphosphino)-1,1'-binaphthyl (rac-BINAP) (38 mg), hexacarbonyl molybdenum (Mo(CO)₆) (240 mg), cesium carbonate (236 mg), and dimethylamine (3 mL, 2.0 M tetrahydrofran solution) were added to a solution of 3,5-difluoro-4-{(3R*,4S*)-4-[3-(4-fluorophenyl)ureido]-5-oxopyrrolidin-3-yl}phenyl trifluoromethanesulfonate (300 mg) in toluene (6 mL) to produce a reaction solution. The reaction solution was stirred at 70° C. under an argon atmosphere for 3 hours. The reaction solution was filtered over Celite and washed with ethyl acetate. The solvent was removed under reduced pressure, and the residue was then purified by silica gel column chromatography (hexane:ethyl acetate=4:1, ethyl acetate, and ethyl acetate:methanol=9:1 in turn), to obtain the title compound as a white solid (192 mg).

¹H-NMR (400 MHz, DMSO-d₆) δ 2.88 (3H, s), 2.95 (3H, s), 3.35-3.39 (1H, m), 3.51 (1H, t, J=8.9 Hz), 3.94 (1H, q, J=9.6 Hz), 4.58 (1H, dd, J=10.7, 8.3 Hz), 6.50 (1H, d, J=7.9 Hz), 6.98-7.03 (2H, m), 7.17 (2H, d, J=9.2 Hz), 7.29-7.33 (2H, m), 8.11 (1H, s), 8.71 (1H, s).

MS (ESI⁺) m/z: 421 (MH⁺).

$[\alpha]_D^{28}$=−111(c 0.1, EtOH)

Example 29-2

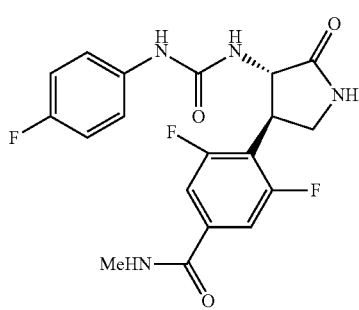

[Chemical Formula 158]

(−)-3,5-Difluoro-4-{(3R*,4S*)-4-[3-(4-fluorophenyl)ureido]-5-oxopyrrolidin-3-yl}-N-methylbenzamide The same method as in Example 29-1 was performed using methyl amine in place of dimethyl amine to obtain the title compound.

¹H-NMR (400 MHz, DMSO-d₆) δ 2.77 (3H, d, J=4.9 Hz), 3.34-3.40 (1H, m), 3.51 (1H, t, J=9.2 Hz), 3.93 (1H, q, J=9.6 Hz), 4.60 (1H, dd, J=10.4, 7.9 Hz), 6.53 (1H, d, J=7.9 Hz), 6.98-7.03 (2H, m), 7.29-7.32 (2H, m), 7.52 (2H, d, J=9.8 Hz), 8.13 (1H, s), 8.56-8.60 (1H, m), 8.74 (1H, s).

MS (ESI⁺) m/z: 407 (MH⁺).

$[\alpha]_D^{28}$=−167 (c 0.1, EtOH)

Example 30-1

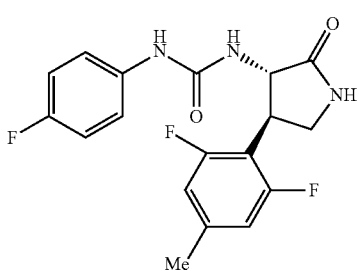

[Chemical Formula 159]

(−)-1-[(3S*,4R*)-4-(4-Cyano-2,6-difluorophenyl)-2-oxopyrrolidin-3-yl]-3-(4-fluorophenyl)urea Zinc cyanide (53 mg) and tetrakis(triphenylphosphine) palladium (18 mg) were added to a solution of 3,5-difluoro-4-[(3R*,4S*)-4-(3-(4-fluorophenyl) ureido)-5-oxopyrrolidin-3-yl]phenyl trifluoromethanesulfonate (150 mg) in N,N-dimethylformamide (3 mL) under an argon atmosphere to produce a reaction solution. The reaction solution was stirred at 80° C. for 5 hours. The reaction solution was filtered over Celite, the solvent was removed under reduced pressure, and the residue was purified by silica gel column chromatography (hexane:ethyl acetate=4:1 followed by ethyl acetate), to obtain the title compound as a white solid (100 mg).

¹H-NMR (400 MHz, DMSO-d₆) δ 3.33-3.38 (1H, m), 3.52 (1H, t, J=10.1 Hz), 3.95 (1H, q, J=9.8 Hz), 4.58 (1H, dd, J=10.4, 7.3 Hz), 6.51 (1H, d, J=7.9 Hz), 6.98-7.04 (2H, m), 7.27-7.32 (2H, m), 7.81 (2H, d, J=8.6 Hz), 8.18 (1H, s), 8.75 (1H, s).

MS (ESI⁺) m/z: 375 (MH⁺).

$[\alpha]_D^{28}$=−145 (c 0.1, EtOH)

Example 31-1

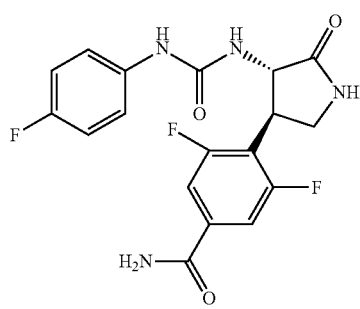

(−)-3,5-Difluoro-4-{(3R*,4S*)-4-[3-(4-fluorophenyl)ureido]-5-oxopyrrolidin-3-yl}benzamide A 2 mol/L sodium hydroxide aqueous solution (0.21 mL) was added to a solution of (−)-1-[(3S*,4R*)-4-(4-cyano-2,6-difluorophenyl)-2-oxopyrrolidin-3-yl]-3-(4-fluorophenyl) urea (160 mg) in methanol (4 mL) under an argon atmosphere to produce a reaction solution. The reaction solution was stirred under heating at room temperature for 1 hour. A 1 mol/L hydrochloric acid (1 mL) was added to the reaction solution to make the reaction solution acidic (pH: 1), and the mixture was extracted with ethyl acetate. The organic layer was washed with water and a brine, and dried over anhydrous sodium sulfate. The solvent was removed under reduced pressure, and the residue was then purified by silica gel column chromatography (hexane:ethyl acetate=4:1, ethyl acetate, and ethyl acetate:methanol=95:5 in turn), to obtain the title compound as a white solid (37 mg).

$^1$H-NMR (400 MHz, DMSO-d$_6$) δ 3.34-3.41 (1H, m), 3.52 (1H, t, J=9.2 Hz), 3.94 (1H, q, J=9.6 Hz), 4.62 (1H, dd, J=10.7, 8.3 Hz), 6.52 (1H, d, J=7.9 Hz), 6.99-7.05 (2H, m), 7.30-7.34 (2H, m), 7.58 (2H, d, J=9.8 Hz), 7.64 (1H, s), 8.10 (1H, s), 8.14 (1H, s), 8.74 (1H, s).

MS (ESI) m/z: 391 (M-H)$^-$.

HRESIMS (−): 391.10226 (calculated as C$_{18}$H$_{14}$F$_3$N$_4$O$_3$: 391.10180).

$[α]_D^{28}$=−130 (c 0.1, EtOH)

Example 32-1

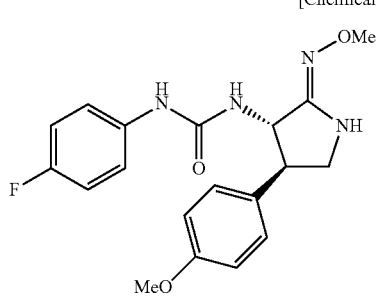

(−)-1-(4-Fluorophenyl)-3-[(3S*,4R*,Z)-2-(methoxyimino)-4-(4-methoxyphenyl)pyrrolidin-3-yl]urea 10% Palladium on carbon (22 mg) was added to a solution of [(3S*,4R*,Z)-2-(methoxyimino)-4-(4-methoxyphenyl)pyrrolidin-3-yl]carbamic acid benzyl ester (223 mg) in ethanol (12 mL) to produce a reaction solution. The reaction solution was stirred under a hydrogen atmosphere for 1 hour. The reaction solution was filtered over Celite, and the filtrate was removed under reduced pressure to obtain (3S*,4R*,Z)-3-amino-4-(4-methoxyphenyl)pyrrolidin-2-one O-methyloxime as a white solid. 4-Fluorophenyl isocyanate (68.3 µL) was added to a solution of the obtained (3S*,4R*,Z)-3-amino-4-(4-methoxyphenyl) pyrrolidin-2-one O-methyloxime (140 mg) in tetrahydrofuran (2 mL) to produce a reaction solution. The reaction solution was stirred at room temperature for 1 hour. The reaction solution was concentrated under reduced pressure, and the residue was then purified by silica gel column chromatography (ethyl acetate:methanol=10:1), to obtain the title compound as a white solid (156 mg).

$^1$H-NMR (400 MHz, DMSO-d$_6$) δ 3.13 (1H, t, J=9.1 Hz), 3.22-3.30 (1H, m), 3.48 (1H, t, J=8.2 Hz), 3.59 (3H, s), 3.70 (3H, s), 4.82 (1H, t, J=9.4 Hz), 6.40 (1H, d, J=9.7 Hz), 6.69 (1H, s), 6.86 (2H, d, J=8.5 Hz), 6.99-7.05 (2H, m), 7.26 (2H, d, J=8.5 Hz), 7.32-7.36 (2H, m), 8.45 (1H, s).

MS (ESI$^+$) m/z: 373 (MH$^+$).

$[α]_D^{28}$=−72 (c 0.31, DMSO)

The same method as in Example 32-1 was performed using a corresponding imino substance and isocyanate to obtain the following Examples 32-2 to 32-20.

The structures and spectral data thereof are shown in Tables 101 to 107.

TABLE 101

| Ex. No | Structure | Chemical name | P.D. |
| --- | --- | --- | --- |
| 32-2 | ![structure] | (−)-1-[(3S*,4R*,Z)-4-(2-fluoro-4-methoxyphenyl)-2-(methoxyimino)pyrrolidin-3-yl]-3-(4-fluorophenyl)urea | $^1$H-NMR (400 MHz, DMSO-d$_6$) δ 3.08-3.15 (1H, m), 3.40-3.49 (2H, m), 3.58 (3H, s), 3.71 (3H, s), 4.97 (1H, t, J = 9.2 Hz), 6.39 (1H, d, J = 9.2 Hz), 6.71-6.77 (3H, m), 6.97-7.03 (2H, m), 7.29-7.34 (2H, m), 7.38 (1H, dd, J = 8.6, 8.6 Hz), 8.48 (1H, s). MS (ESI$^+$) m/z: 391 (MH$^+$). $[α]_D^{29}$ = −50 (c 0.10, EtOH) |

TABLE 101-continued

| Ex. No | Structure | Chemical name | P.D. |
|---|---|---|---|
| 32-3 | 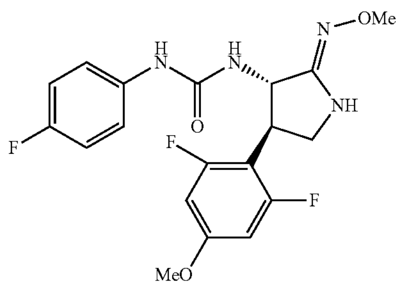 [SMILES: CO/N=C1\NC[C@@H](c2c(F)cc(OC)cc2F)[C@@H]1NC(=O)Nc1ccc(F)cc1] | (−)-1-[(3S*,4R*,Z)-4-(2,6-difluoro-4-methoxyphenyl)-2-(methoxyimino)pyrrolidin-3-yl]-3-(4-fluorophenyl)urea | $^1$H-NMR (400 MHz, DMSO-d$_6$) δ 3.26-3.46 (2H, m), 3.53-3.59 (1H, m), 3.60 (3H, s), 3.74 (3H, s), 5.08 (1H, t, J = 9.2 Hz), 6.43 (1H, d, J = 9.2 Hz), 6.71 (2H, d, J = 11.0 Hz), 6.80 (1H, s), 6.98-7.03 (2H, m), 7.29-7.33 (2H, m), 8.56 (1H, s). MS (ESI$^+$) m/z: 409 (MH$^+$). $[α]_D^{27}$ = −67 (c 0.10, EtOH) |
| 32-4 | 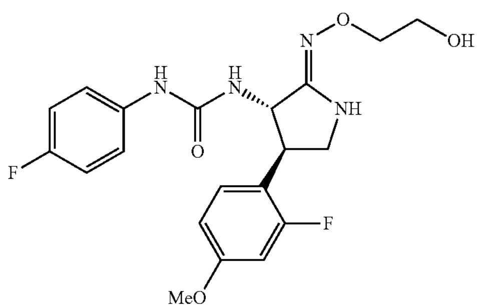 [SMILES: COc1ccc([C@@H]2CN/C(=N\OCCO)[C@H]2NC(=O)Nc2ccc(F)cc2)c(F)c1] | (−)-1-(4-fluorophenyl)-3-{(3S*,4R*,Z)-2-[(2-hydroxyethoxy)imino]-4-(4-methoxyphenyl)pyrrolidin-3-yl}urea | $^1$H-NMR (400 MHz, DMSO-d$_6$) δ 3.15 (1H, t, J = 9.1 Hz), 3.22-3.30 (1H, m), 3.48-3.58 (3H, m), 3.70 (3H, s), 3.80 (2H, t, J = 5.4 Hz), 4.45 (1H, t, J = 5.8 Hz), 4.82 (1H, t, J = 9.4 Hz), 6.39 (1H, d, J = 8.5 Hz), 6.69 (1H, s), 6.86 (2H, d, J = 9.1 Hz), 6.99-7.05 (2H, m), 7.27 (2H, d, J = 9.1 Hz), 7.31-7.36 (2H, m), 8.45 (1H, s). MS (ESI$^+$) m/z: 403 (MH$^+$). $[α]_D^{28}$ = −86 (c 0.36, EtOH) |

TABLE 102

| Ex. No | Structure | Chemical name | P.D. |
|---|---|---|---|
| 32-5 | 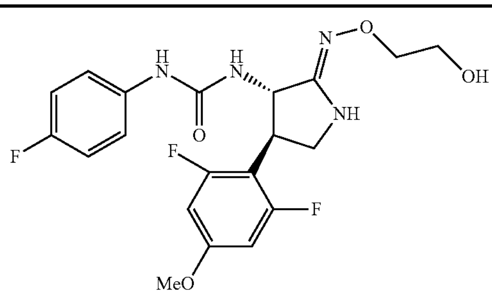 | (−)-1-{(3S*,4R*,Z)-4-(2,6-difluoro-4-methoxyphenyl)-2-[(2-hydroxyethoxy)imino]pyrrolidin-3-yl}-3-(4-fluorophenyl)urea | $^1$H-NMR (400 MHz, DMSO-d$_6$) δ 3.27-3.31 (1H, m), 3.45 (1H, t, J = 9.8 Hz), 3.50-3.62 (3H, m), 3.74 (3H, s), 3.80-3.82 (2H, m), 4.47 (1H, t, J = 5.5 Hz), 5.07 (1H, dd, J = 10.4, 9.2 Hz), 6.42 (1H, d, J = 9.2 Hz), 6.71 (2H, d, J = 11.0 Hz), 6.79 (1H, s), 6.97-7.04 (2H, m), 7.26-7.34 (2H, m), 8.56 (1H, s). MS (ESI$^+$) m/z: 439 (MH$^+$). $[α]_D^{27}$ = −105 (c 0.10, EtOH) |
| 32-6 | 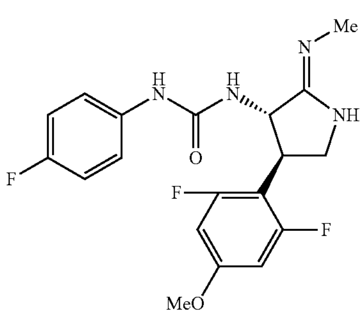 [SMILES: C/N=C1\NC[C@@H](c2c(F)cc(OC)cc2F)[C@@H]1NC(=O)Nc1ccc(F)cc1] | 1-[(3S*,4R*,Z)-4-(2,6-difluoro-4-methoxyphenyl)-2-(methylimino)pyrrolidin-3-yl]-3-(4-fluorophenyl)urea | $^1$H-NMR (400 MHz, DMSO-d$_6$) δ 2.68 (3H, d, J = 4.3 Hz), 3.35-3.51 (2H, m), 3.66-3.80 (4H, m), 5.04 (1H, t, J = 8.6 Hz), 5.96-6.03 (1H, m), 6.59 (1H, d, J = 9.8 Hz), 6.71 (2H, d, J = 10.4 Hz), 7.02 (2H, t, J = 9.2 Hz), 7.32-7.39 (2H, m), 8.53 (1H, s). MS (ESI$^+$) m/z: 393 (MH$^+$). $[α]_D^{28}$ = −205 (c 0.10, EtOH). |

TABLE 102-continued

| Ex. No | Structure | Chemical name | P.D. |
|---|---|---|---|
| 32-7 | 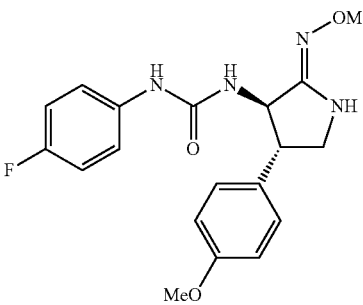 | (+)-1-(4-fluorophenyl)-3-[(3R*,4S*,Z)-2-(methoxyimino)-4-(4-methoxyphenyl)pyrrolidin-3-yl]urea | $^1$H-NMR (400 MHz, DMSO-d$_6$) δ 3.13 (1H, t, J = 9.1 Hz), 3.22-3.30 (1H, m), 3.48 (1H, t, J = 8.2 Hz), 3.59 (3H, s), 3.70 (3H, s), 4.82 (1H, t, J = 9.4 Hz), 6.40 (1H, d, J = 9.7 Hz), 6.69 (1H, s), 6.86 (2H, d, J = 8.5 Hz), 6.99-7.05 (2H, m), 7.26 (2H, d, J = 8.5 Hz), 7.32-7.36 (2H, m), 8.45 (1H, s). MS (ESI$^+$) m/z: 373 (MH$^+$). [α]$_D^{27}$ = +100 (c 0.15, EtOH) |

TABLE 103

| Ex. No | Structure | Chemical name | P.D. |
|---|---|---|---|
| 32-8 | 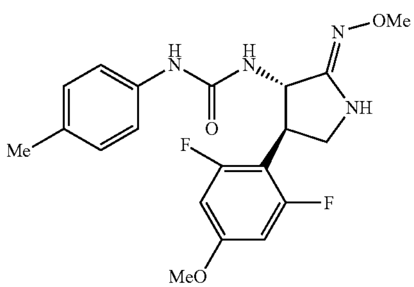 [SMILES: CO/N=C1\NC[C@@H](c2c(F)cc(OC)cc2F)[C@@H]1NC(=O)Nc1ccc(C#N)cc1] | (−)-1-[(3S*,4R*,Z)-4-(2,6-difluoro-4-methoxyphenyl)-2-(methoxyimino)pyrrolidin-3-yl]-3-(p-tolyl)urea | $^1$H-NMR (400 MHz, DMSO-d$_6$) δ 2.18 (3H, s), 3.25-3.31 (1H, m), 3.43 (1H, t, J = 9.2 Hz), 3.53 (1H, q, J = 9.2 Hz), 3.60 (3H, s), 3.74 (3H, s), 5.07 (1H, dd, J = 9.2, 8.6 Hz), 6.38 (1H, d, J = 8.6 Hz), 6.67-6.74 (2H, m), 6.79 (1H, s), 6.97 (2H, d, J = 8.6 Hz), 7.18 (2H, d, J = 8.6 Hz), 8.40 (1H, s). MS (ESI$^+$) m/z: 405 (MH$^+$). [α]$_D^{27}$ = −102 (c 0.11, EtOH) |
| 32-9 | 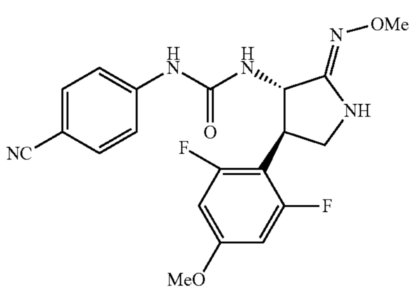 | (−)-1-(4-cyanophenyl)-3-[(3S*,4R*,Z)-4-(2,6-difluoro-4-methoxyphenyl)-2-(methoxyimino)pyrrolidin-3-yl]urea | $^1$H-NMR (400 MHz, DMSO-d$_6$) δ 3.25-3.34 (1H, m), 3.44 (1H, t, J = 9.2 Hz), 3.56-3.65 (1H, m), 3.60 (3H, s), 3.74 (3H, s), 5.08 (1H, dd, J = 10.4, 8.6 Hz), 6.68-6.76 (2H, m), 6.77-6.84 (2H, m), 7.49 (2H, d, J = 8.6 Hz), 7.62 (2H, d, J = 8.6 Hz), 9.18 (1H, s). MS (ESI$^+$) m/z: 416 (MH$^+$). [α]$_D^{28}$ = −69 (c 0.10, EtOH) |
| 32-10 | 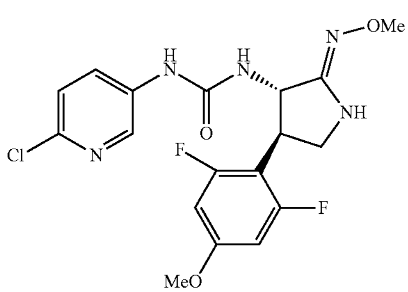 [SMILES: CO/N=C1\NC[C@@H](c2c(F)cc(OC)cc2F)[C@@H]1NC(=O)Nc1ccc(Cl)nc1] | (−)-1-(6-chloropyridin-3-yl)-3-[(3S*,4R*,Z)-4-(2,6-difluoro-4-methoxyphenyl)-2-(methoxyimino)pyrrolidin-3-yl]urea | $^1$H-NMR (400 MHz, DMSO-d$_6$) δ 3.25-3.35 (1H, m), 3.43 (1H, t, J = 8.6 Hz), 3.58-3.66 (1H, m), 3.60 (3H, s), 3.74 (3H, s), 5.08 (1H, dd, J = 10.4, 8.6 Hz), 6.68-6.80 (3H, m), 6.81 (1H, s), 7.31 (1H, d, J = 8.6 Hz), 7.85 (1H, dd, J = 8.6, 3.0 Hz), 8.32 (1H, d, J = 3.0 Hz), 8.94 (1H, s). MS (ESI$^+$) m/z: 426 (MH$^+$). [α]$_D^{26}$ = −66 (c 0.13, EtOH) |

TABLE 104

| Ex. No | Structure | Chemical name | P.D. |
|---|---|---|---|
| 32-11 | 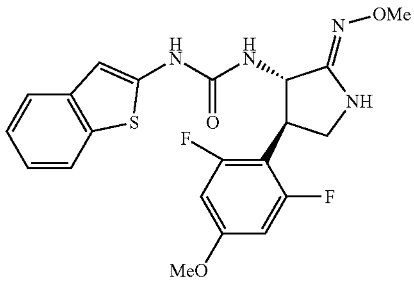 [SMILES: CO/N=C1\NC[C@@H](c2c(F)cc(OC)cc2F)[C@@H]1NC(=O)Nc1cc2ccccc2s1] | (−)-1-(benzo[b]thiophen-2-yl)-3-[(3S*,4R*,Z)-4-(2,6-difluoro-4-methoxyphenyl)-2-(methoxyimino)pyrrolidin-3-yl]urea | $^1$H-NMR (400 MHz, DMSO-d$_6$) δ 3.27-3.33 (1H, m), 3.60 (3H, s), 3.44 (1H, t, J = 9.2 Hz), 3.62-3.71 (1H, m), 3.74 (3H, s), 5.09 (1H, dd, J = 9.8, 9.2 Hz), 6.66 (1H, s), 6.70-6.76 (2H, m), 6.81-6.87 (2H, m), 7.08 (1H, td, J = 7.9, 1.2 Hz), 7.20 (1H, td, J = 7.9, 1.2 Hz), 7.51 (1H, d, J = 7.9 Hz), 7.69 (1H, d, J = 7.9 Hz), 9.93 (1H, s). MS (ESI$^+$) m/z: 447 (MH$^+$). $[α]_D^{28}$ = −78 (c 0.10, EtOH) |
| 32-12 | 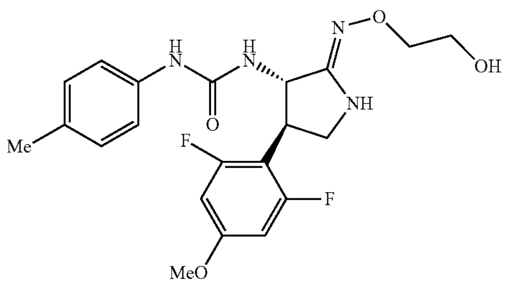 [SMILES: COc1cc(F)c([C@@H]2CN/C(=N\OCCO)[C@H]2NC(=O)Nc2ccc(C)cc2)c(F)c1] | (−)-1-{(3S*,4R*,Z)-4-(2,6-difluoro-4-methoxyphenyl)-2-[(2-hydroxyethoxy)imino]pyrrolidin-3-yl}-3-(p-tolyl)urea | $^1$H-NMR (400 MHz, DMSO-d$_6$) δ 2.18 (3H, s), 3.27-3.34 (1H, m), 3.45 (1H, t, J = 8.6 Hz), 3.50-3.60 (3H, m), 3.74 (3H, s), 3.79-3.82 (2H, m), 4.47 (1H, t, J = 6.1 Hz), 5.07 (1H, dd, J = 10.6, 8.6 Hz), 6.35 (1H, d, J = 8.6 Hz), 6.67-6.75 (2H, m), 6.78 (1H, s), 6.97 (2H, d, J = 8.6 Hz), 7.17 (2H, d, J = 8.6 Hz), 8.40 (1H, s). MS (ESI$^+$) m/z: 435 (MH$^+$). $[α]_D^{28}$ = −52 (c 0.17, EtOH) |
| 32-13 | 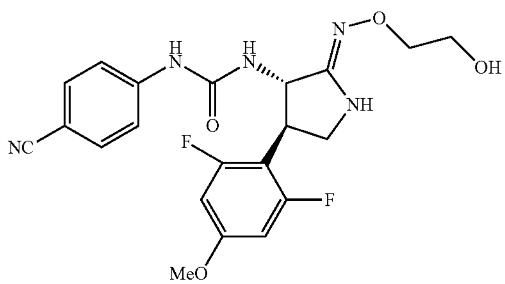 [SMILES: COc1cc(F)c([C@@H]2CN/C(=N\OCCO)[C@H]2NC(=O)Nc2ccc(C#N)cc2)c(F)c1] | (−)-1-(4-cyanophenyl)-3-{(3S*,4R*,Z)-4-(2,6-difluoro-4-methoxyphenyl)-2-[(2-hydroxyethoxy)imino]pyrrolidin-3-yl}urea | $^1$H-NMR (400 MHz, DMSO-d$_6$) δ 3.28-3.34 (1H, m), 3.46 (1H, t, J = 8.6 Hz), 3.51-3.67 (3H, m), 3.74 (3H, s), 3.79-3.82 (2H, m), 4.47 (1H, t, J = 5.5 Hz), 5.07 (1H, dd, J = 10.6, 8.6 Hz), 6.68-6.77 (3H, m), 6.82 (1H, s), 7.48 (2H, d, J = 9.2 Hz), 7.62 (2H, d, J = 9.2 Hz), 9.14 (1H, s). MS (ESI$^+$) m/z: 446 (MH$^+$). $[α]_D^{25}$ = −88 (c 0.10, EtOH) |

TABLE 105

| Ex. No | Structure | Chemical name | P.D. |
|---|---|---|---|
| 32-14 | 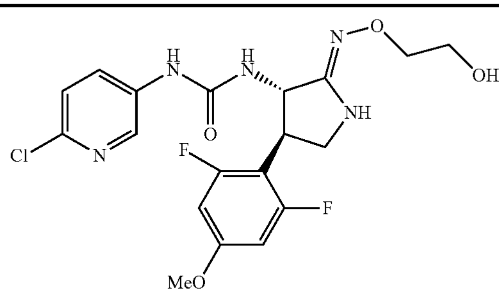 | (−)-1-(6-chloropyridin-3-yl)-3-{(3S*,4R*,Z)-4-(2,6-difluoro-4-methoxyphenyl)-2-[(2-hydroxyethoxy)imino]pyrrolidin-3-yl}urea | $^1$H-NMR (400 MHz, DMSO-d$_6$) δ 3.27-3.32 (1H, m), 3.46 (1H, t, J = 8.6 Hz), 3.52-3.67 (3H, m), 3.74 (3H, s), 3.81 (2H, t, J = 5.5 Hz) 4.45 (1H, t, J = 5.5 Hz), 5.07 (1H, dd, J = 10.4, 8.6 Hz), 6.68-6.76 (2H, m), 6.78-6.83 (2H, m), 7.31 (1H, d, J = 8.6 Hz), 7.84 (1H, dd, J = 8.6, 3.0 Hz), 8.32 (1H, d, J = 3.0 Hz), 9.00 (1H, s). MS (ESI$^+$) m/z: 456 (MH$^+$). $[α]_D^{22}$ = −71 (c 0.10, EtOH) |
| 32-15 | 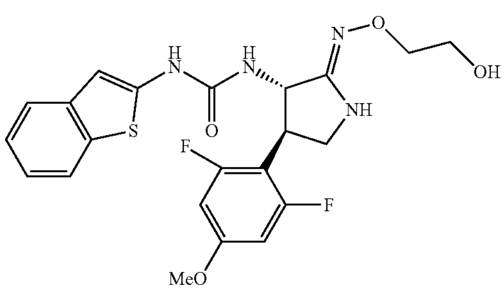 [SMILES: COc1cc(F)c([C@@H]2CN/C(=N\OCCO)[C@H]2NC(=O)Nc2cc3ccccc3s2)c(F)c1] | (−)-1-(benzo[b]thiophen-2-yl)-3-{(3S*,4R*,Z)-4-(2,6-difluoro-4-methoxyphenyl)-2-[(2-hydroxyethoxy)imino]pyrrolidin-3-yl}urea | $^1$H-NMR (400 MHz, DMSO-d$_6$) δ 3.27-3.35 (1H, m), 3.55 (1H, t, J = 9.8 Hz), 3.52-3.60 (2H, m), 3.67 (1H, q, J = 9.8 Hz), 3.74 (3H, s), 3.81 (2H, t, J = 4.9 Hz), 4.46 (1H, t, J = 5.5 Hz), 5.09 (1H, dd, J = 10.4, 9.2 Hz), 6.66 (1H, s), 6.70-6.77 (2H, m), 6.80 (1H, brd, J = 9.2 Hz), 6.821 (1H, s), 7.08 (1H, td, J = 7.9, 1.2 Hz), 7.20 (1H, td, J = 7.9, 1.2 Hz), 7.51 (1H, d, J = 7.9 Hz), 7.68 (1H, d, J = 7.9 Hz), 9.89 (1H, s). MS (ESI$^+$) m/z: 477 (MH$^+$). $[α]_D^{29}$ = −91 (c 0.12, EtOH) |

TABLE 105-continued

| Ex. No | Structure | Chemical name | P.D. |
|---|---|---|---|
| 32-16 | 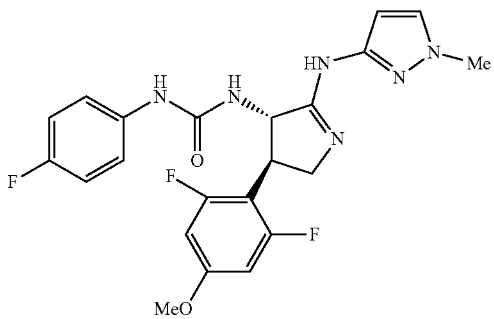 [SMILES: COc1cc(F)c([C@@H]2CN=C(Nc3ccn(C)n3)[C@H]2NC(=O)Nc2ccc(F)cc2)c(F)c1] | (−)-1-{(3R*,4S*)-3-(2,6-difluoro-4-methoxyphenyl)-5-[(1-methyl-1H-pyrazol-3-yl)amino]-3,4-dihydro-2H-pyrrol-4-yl}-3-(4-fluorophenyl)urea | $^1$H-NMR (400 MHz, DMSO-d$_6$) δ 3.50-3.73 (3H, m), 3.76 (3H, s), 3.76 (3H, s), 5.04 (1H, t, J = 8.9 Hz), 5.85 (1H, d, J = 2.4 Hz), 6.43 (1H, d, J = 7.9 Hz), 6.73 (2H, d, J = 11.0 Hz), 6.98-7.04 (2H, m), 7.30-7.36 (2H, m), 7.50 (1H, d, J = 2.4 Hz), 8.41 (1H, s), 8.72 (1H, s). MS (ESI$^+$) m/z: 459 (MH$^+$). [α]$_D^{24}$ = −30 (c 0.16, EtOH) |

TABLE 106

| Ex. No | Structure | Chemical name | P.D. |
|---|---|---|---|
| 32-17 | 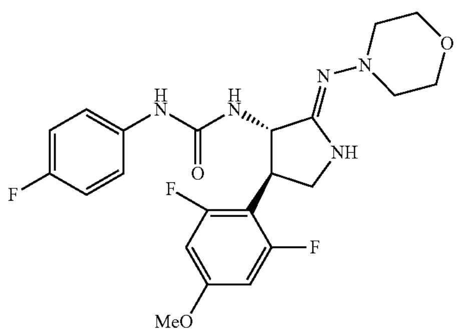 [SMILES: COc1cc(F)c([C@@H]2CN/C(=N\N3CCOCC3)[C@H]2NC(=O)Nc2ccc(F)cc2)c(F)c1] | (−)-1-[(3S*,4R*,Z)-4-(2,6-difluoro-4-methoxyphenyl)-2-(morpholinoimino)pyrrolidin-3-yl]-3-(4-fluorophenyl)urea | $^1$H-NMR (400 MHz, CDCl$_3$) δ 2.74-2.84 (4H, m), 3.57-3.83 (10H, m), 5.46 (1H, brs), 5.95 (1H, brs), 6.46 (2H, d, J = 11.0 Hz), 6.75-6.82 (2H, m), 7.06-7.12 (2H, m), 9.11 (1H, brs). MS (ESI$^+$) m/z: 464 (MH$^+$). [α]$_D^{24}$ = −31 (c 0.14, EtOH) |
| 32-18 | 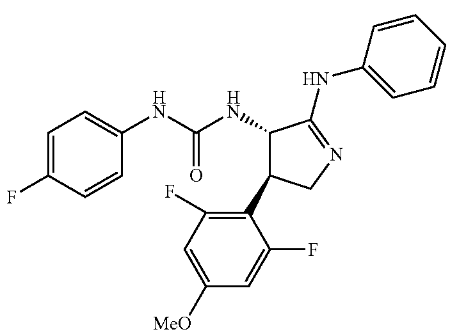 [SMILES: COc1cc(F)c([C@@H]2CN=C(Nc3ccccc3)[C@H]2NC(=O)Nc2ccc(F)cc2)c(F)c1] | 1-[(3R*,4S*)-3-(2,6-difluoro-4-methoxyphenyl)-5-(phenylamino)-3,4-dihydro-2H-pyrrol-4-yl]-3-(4-fluorophenyl)urea | $^1$H-NMR (400 MHz, DMSO-d$_6$) δ 3.52-3.63 (2H, m), 3.75 (3H, s), 3.99-4.08 (1H, m), 5.16 (1H, t, J = 8.9 Hz), 6.72 (2H, d, J = 11.0 Hz), 6.75 (1H, d, J = 6.4 Hz), 6.88 (1H, t, J = 7.9 Hz), 7.00-7.05 (2H, m), 7.22 (2H, t, J = 7.9 Hz), 7.36-7.40 (2H, m), 7.83 (2H, d, J = 7.9 Hz), 8.56 (1H, s), 8.60 (1H, s). MS (ESI$^+$) m/z: 455 (MH$^+$). |
| 32-19 | 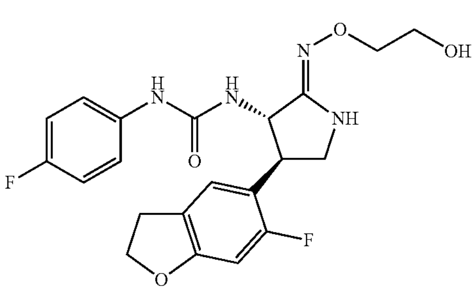 [SMILES: O=C(Nc1ccc(F)cc1)N[C@@H]1/C(=N/OCCO)NC[C@H]1c1cc2c(cc1F)OCC2] | (−)-1-((3S*,4R*,Z)-4-(6-fluoro-2,3-dihydrobenzofuran-5-yl)-2-[(2-hydroxyethoxy)imino]pyrrolidin-3-yl)-3-(4-fluorophenyl)urea | $^1$H-NMR (400 MHz, DMSO-d$_6$) δ 3.08-3.17 (3H, m), 3.42-3.49 (2H, m), 3.54-3.56 (2H, m), 3.79-3.81 (2H, m), 4.47 (1H, t, J = 5.2 Hz), 4.54 (2H, t, J = 8.6 Hz), 4.95 (1H, t, J = 8.9 Hz), 6.60-6.70 (3H, m), 7.02 (2H, t, J = 8.9 Hz), 7.30-7.36 (3H, m), 8.73 (1H, s). MS (ESI$^+$) m/z: 433 (MH$^+$). [α]$_D^{25}$ = −137 (c 0.14, EtOH) |

TABLE 107

| Ex. No | Structure | Chemical name | P.D. |
|---|---|---|---|
| 32-20 | 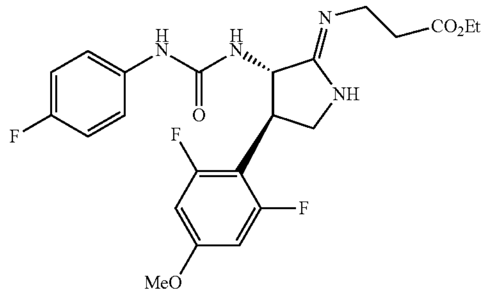 [SMILES: CCOC(=O)CC/N=C1\NC[C@@H](c2c(F)cc(OC)cc2F)[C@@H]1NC(=O)Nc1ccc(F)cc1] | 3-((Z)-{(3S,4R)-4-(2,6-difluoro-4-methoxyphenyl)-3-[3-(4-fluorophenyl)ureido]pyrrolidin-2-ylidene}amino)propanoic acid ethyl ester | $^1$H-NMR (DMSO-D$_6$) δ: 1.17 (3H, t, J = 7.3 Hz), 2.65 (2H, t, J = 7.3 Hz), 3.42-3.53 (2H, m), 3.57-3.66 (1H, m), 3.75 (3H, s), 3.86-3.93 (1H, m), 3.97-4.10 (3H, m), 5.18 (1H, t, J = 8.6 Hz), 6.70 (1H, d, J = 8.6 Hz), 6.77 (2H, d, J = 11.0 Hz), 7.04 (2H, t, J = 8.6 Hz), 7.33-7.37 (2H, m), 8.99 (1H, s). MS (ESI$^+$) m/z: 479 (MH$^+$). |

Example 33-1

[Chemical Formula 162]

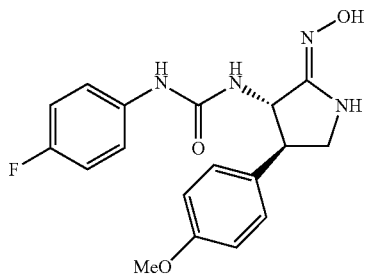

(−)-1-(4-Fluorophenyl)-3-[(3S*,4R*,Z)-2-(2-hydroxyimino)-4-(4-methoxyphenyl)pyrrolidin-3-yl]urea Water (1.35 mL) and trifluoroacetic acid (135 μL) were added to a solution of 1-((3S*,4R*,Z)-2-{[(tert-butyldimethylsilyl)oxy]imino}-4-(4-methoxyphenyl)pyrrolidin-3-yl)-3-(4-fluorophenyl)urea (290 mg) in 1,4-dioxane (1.5 mL) to produce a reaction solution. The reaction solution was stirred at room temperature for 30 minutes. After that, a saturated aqueous sodium hydrogen carbonate solution was added to the reaction solution under ice-cooling, and the mixture was extracted with ethyl acetate. The organic layer was washed with a brine, and dried over anhydrous sodium sulfate. The solvent was removed under reduced pressure, and the residue was washed with diisopropyl ether, to obtain the title compound as a white solid (212 mg).

$^1$H-NMR (400 MHz, DMSO-d$_6$) δ 3.19 (1H, t, J=9.1 Hz), 3.30 (1H, q, J=8.7 Hz), 3.55 (1H, t, J=8.2 Hz), 3.76 (3H, s), 4.80 (1H, t, J=9.4 Hz), 6.37 (1H, d, J=9.1 Hz), 6.43 (1H, s), 6.92 (2H, d, J=8.5 Hz), 7.04-7.10 (2H, m), 7.32 (2H, d, J=8.5 Hz), 7.36-7.40 (2H, m), 8.49 (1H, s), 8.89 (1H, s).

MS (ESI$^+$) m/z: 359 (MH$^+$).

$[α]_D^{29}$=−95 (c 0.30, EtOH)

Example 33-2

[Chemical Formula 163]

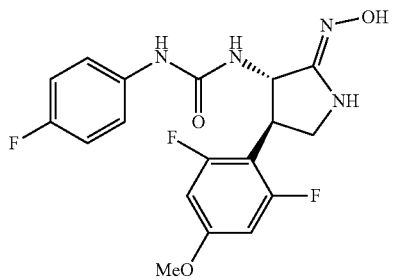

(−)-1-((3S*,4R*,Z)-4-(2,6-Difluoro-4-methoxyphenyl)-2-(hydroxyimino)pyrrolidin-3-yl)-3-(4-fluorophenyl)urea The same method as in Example 33-1 was performed using 1-((3S*,4R*,Z)-2-{[(tert-butyldimethylsilyl)oxy]imino}-4-(2,6-difluoro-4-methoxyphenyl)pyrrolidin-3-yl)-3-(4-fluorophenyl)urea in place of 1-((3S*,4R*,Z)-2-{[(tert-butyldimethylsilyl)oxy]imino}-4-(4-methoxyphenyl)pyrrolidin-3-yl)-3-(4-fluorophenyl)urea to obtain the title compound.

$^1$H-NMR (400 MHz, DMSO-d$_6$) δ 3.26-3.33 (1H, m), 3.42 (1H, t, J=8.6 Hz), 3.49-3.57 (1H, m), 3.75 (3H, s), 5.02 (1H, t, J=9.8 Hz), 6.33 (1H, d, J=8.6 Hz), 6.48 (1H, s), 6.72 (2H, d, J=10.4 Hz), 6.97-7.04 (2H, m), 7.26-7.32 (2H, m), 8.52 (1H, s), 8.90 (1H, s).

MS (ESI$^+$) m/z: 395 (MH$^+$).

[α]$_D^{26}$=−21 (c 0.10, EtOH)

Example 34-1

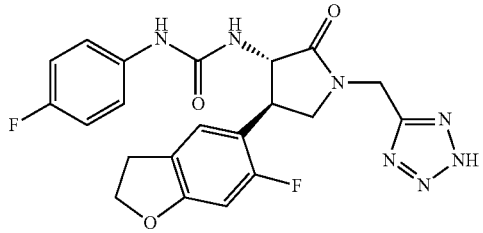

[Chemical Formula 164]

(−)-1-{(3S*,4R*)-1-[(2H-Tetrazol-5-yl)methyl]-4-(6-fluoro-2,3-dihydrobenzofuran-5-yl)-2-oxopyrrolidin-3-yl}-3-(4-fluorophenyl)urea Sodium azide (22 mg), triethylamine (47 μL), and acetic acid (19 μL) were added to a solution of 1-[(3S*,4R*)-1-(cyanomethyl)-4-(6-fluoro-2,3-dihydrobenzofuran-5-yl)-2-oxopyrrolidin-3-yl]-3-(4-fluorophenyl)urea (35 mg) in a mixture of toluene (850 μL) and N,N-dimethylformamide (500 μL) to produce a reaction solution. The reaction solution was stirred at 125° C. for 2 hours. The reaction solution was allowed to cool to room temperature, a 10% citric acid aqueous solution was added, and the mixture was extracted with ethyl acetate. The organic layer was washed with water and a brine successively, and dried over anhydrous sodium sulfate. The solvent was removed under reduced pressure, and the resulting crude product was washed with diethyl ether, to obtain the title compound as a pale brown solid (24 mg).

$^1$H-NMR (400 MHz, DMSO-d$_6$) δ 3.12 (2H, t, J=8.6 Hz), 3.31-3.35 (1H, m), 3.64 (1H, t, J=9.2 Hz), 3.71-3.78 (1H, m), 4.55 (2H, t, J=9.2 Hz), 4.70-4.76 (2H, m), 4.85-4.89 (1H, m), 6.51 (1H, d, J=9.2 Hz), 6.64 (1H, d, J=11.0 Hz), 7.01-7.06 (2H, m), 7.34-7.40 (3H, m), 8.67 (1H, s), 16.47 (1H, brs).

MS (ESI$^+$) m/z: 456(MH$^+$).

[α]$_D^{26}$=−120 (c 0.09, EtOH)

Next, results in support of availability of the compound of the present invention will be shown with reference to Test Examples.

Test Example 1

Measurement Test of Agonist Activity on Human FPRL1

(1-1) Construction of Human FPRL1 Expression Vector

Human FPRL (SEQ ID NO: 3) was amplified in a PCR reaction from cDNA derived from a monocytic leukemia cell line THP-1 (TIB-202, ATCC) as a template using a forward primer shown in SEQ ID NO: 1, a reverse primer shown in SEQ ID NO: 2, and KOD-plus-ver. 2 (KOD-211, TOYOBO CO., LTD.). The amplified PCR product and pCMV-script vector (212220, STRATAGENE) were digested with Hind III (1060A, Takara Bio Inc.) and XhoI (1094A, Takara Bio Inc.), and the resultant digest was ligated with Ligation high ver. 2 (LGK-201, TOYOBO CO., LTD.). The ligation product was transformed into DH5a (DNA-901, TOYOBO CO., LTD.), cultured on a 100 μg/mL kanamycin-containing LB medium, and purified with HiSpeed Plasmid Maxi Kit (12662, QIAGEN).

(1-2) Construction of Human Gα15 Expression Vector

Human Gα15 (SEQ ID NO: 6) was amplified in a PCR reaction from cDNA derived from a myeloid leukemia cell line HL-60 (CCL-240, ATCC) as a template using a forward primer shown in SEQ ID NO: 4, a reverse primer shown in SEQ ID NO: 5, and KOD-plus-ver. 2. The amplified PCR product and pCMV-script vector were digested with Hind III and XhoI, and the resultant digest was ligated with Ligation high ver. 2. The ligation product was transformed into DH5a, cultured on a 100 μg/mL kanamycin-containing LB medium, and purified with HiSpeed Plasmid Maxi Kit.

(2-1) Method for Culturing and Subculturing HEK293

HEK293 (JCRB9068, NIBIO) was cultured in an incubator at 5% $CO_2$ and 37° C. using DMEM (11885-092, GIBCO) containing 10% FBS and 1×Penicillin-Streptomycin (15140-122, GIBCO). Subculture was carried out as followings: The cells that reached 80 to 90% confluency were washed with PBS(−), separated using 0.25% Trypsin-EDTA (25200-072, GIBCO), centrifuged, re-suspended in a fresh medium, and then seeded in Collagen Type 1 Coated dish (4020-010, IWAKI) at a split ratio of 1:8 (cultured for 3 days).

(2-2) Introduction of Human FPRL1 and Gα15 Expression Vectors

HEK293 that reached 80 to 90% confluency was washed with PBS(−), separated using 0.25% Trypsin-EDTA, centrifuged, and re-suspended in a fresh medium excluding 1×Penicillin-Streptomycin. The cells were inoculated in a Collagen Type 1 coated 6-well plate (4810-010, IWAKI) to 5×10$^5$ cells/2.5 mL/well and cultured overnight. On the next day, human FPRL1 and Gα15 expression vectors were introduced using Lipofectamine 2000 transfection reagent (11668-019, Life technologies). First, the human FPRL1 and Gα15 expression vectors were diluted with Opti-MEM I Reduced Serum Medium (31985-070, GIBCO) to 2 μg/250 μL/well and Lipofectamine 2000 transfection reagent was diluted with Opti-MEM I Reduced Serum Medium to be 4 μL/250 μL/well. The vectors and reagent were softly diffused, and incubated at room temperature for 5 minutes. The vector solution was mixed with Lipofectamine 2000 transfection reagent in equal amounts. In order to form a composite of the vectors and Lipofectamine 2000 transfection reagent, the mixture was incubated at room temperature for 20 minutes, and added at 500 μL/well to the medium of inoculated cells. The treated cells were cultured for 24 hours, inoculated in Poly-D-Lysine coated 96-well plate (356640, BD Biosciences) at a cell density of 7×10$^4$ cells/100 μL/well, and cultured for another 24 hours. The resultant cells were used in a measurement test of calcium mobilization in the cells.

(3) Evaluation of Agonist Activity on Human FPRL1 (Test of Calcium Mobilization in Cell)

An appropriate amount of each test compound was first weighed, and dissolved to 10$^{-2}$ M by addition of dimethyl sulfoxide (DMSO). For calculation of an EC$_{50}$ value for agonist activity, each compound solution was serially diluted with DMSO by 10-fold increments to make eight solutions having a concentration of 10$^{-2}$ M to 10$^{-9}$ M. The formed compound solution having each concentration was diluted 100 times with an assay buffer that was contained in Fluo-4 NW Calcium Assay Kit (F36206, Life technologies), and dispensed in an amount of 100 μL into a 96-well plate with a V-bottom shape. The plate dispensed with compound solutions was set in Flexstation (Molecular Devices, LLC.) until measurement.

Subsequently, 10 mL of assay buffer and 100 μL of probenecid solution (dissolved by addition of 1 mL of assay buffer to a 250 mM stock) were sufficiently mixed and dissolved in Fluo-4 NW dye mix. The medium of cells inoculated on the previous day was removed, the dissolved Fluo-4 NW dye mix was added in an amount of 90 μL/well, and a reaction was caused in the dark at 37° C. for 45 minutes. The cells after the reaction and chips for addition of the compound were set in Flexstation, and variation in fluorescence intensity over time after addition of the compound was measured [amount of added compound=10 μL (final concentration: $10^{-5}$ M to $10^{-12}$ M), excitation wavelength: 485 nm, measured wavelength: 525 nm, 1.5 sec×54 read]. A value was calculated by subtracting a base value during addition of DMSO from the maximum value of relative fluorescence unit, and analyzed. All the measurement data were analyzed with Prism 4 that was a data analysis tool. As an $EC_{50}$ value, a molar concentration that resulted in 50% maximum activation was calculated. The $EC_{50}$ values of the resultant test compounds are shown in Tables I to V.

TABLE I

| COMPOUND TO BE TESTED | $EC_{50}$ (nM) |
|---|---|
| EXAMPLE 1-1 | 0.09 |
| EXAMPLE 1-2 | 0.09 |
| EXAMPLE 1-3 | 2.57 |
| EXAMPLE 1-5 | 2.88 |
| EXAMPLE 1-6 | 0.20 |
| EXAMPLE 1-7 | 0.22 |
| EXAMPLE 1-8 | 0.90 |
| EXAMPLE 1-9 | 0.45 |
| EXAMPLE 1-10 | 3.98 |

TABLE II

| COMPOUND TO BE TESTED | $EC_{50}$ (nM) |
|---|---|
| EXAMPLE 1-11 | 1.59 |
| EXAMPLE 1-12 | 0.06 |
| EXAMPLE 1-13 | 0.15 |
| EXAMPLE 1-14 | 4.12 |
| EXAMPLE 1-16 | 0.24 |
| EXAMPLE 1-18 | 0.36 |
| EXAMPLE 1-19 | 0.72 |
| EXAMPLE 1-20 | 1.75 |
| EXAMPLE 1-22 | 0.11 |
| EXAMPLE 1-23 | 0.78 |
| EXAMPLE 1-24 | 3.20 |
| EXAMPLE 1-26 | 1.91 |
| EXAMPLE 1-31 | 2.67 |
| EXAMPLE 1-32 | 4.54 |
| EXAMPLE 1-35 | 0.76 |
| EXAMPLE 1-39 | 3.51 |
| EXAMPLE 1-40 | 1.44 |
| EXAMPLE 1-41 | 0.73 |
| EXAMPLE 1-43 | 5.13 |
| EXAMPLE 1-53 | 0.18 |
| EXAMPLE 1-54 | 0.11 |
| EXAMPLE 1-55 | 1.02 |
| EXAMPLE 7-1 | 1.09 |
| EXAMPLE 7-2 | 0.45 |
| EXAMPLE 7-7 | 1.56 |
| EXAMPLE 7-8 | 0.95 |
| EXAMPLE 7-9 | 0.16 |
| EXAMPLE 8-1 | 0.29 |
| EXAMPLE 9-1 | 0.86 |
| EXAMPLE 12-1 | 0.13 |
| EXAMPLE 12-4 | 0.05 |
| EXAMPLE 14-1 | 0.32 |
| EXAMPLE 15-1A | 0.01 |
| EXAMPLE 15-1B | 1.99 |
| EXAMPLE 17-1 | 0.11 |
| EXAMPLE 18-1 | 2.36 |
| EXAMPLE 19-1 | 0.21 |

TABLE III

| COMPOUND TO BE TESTED | $EC_{50}$ (nM) |
|---|---|
| EXAMPLE 20-1 | 0.47 |
| EXAMPLE 21-1 | 0.04 |
| EXAMPLE 23-1 | 0.09 |
| EXAMPLE 24-1 | 0.09 |
| EXAMPLE 25-1 | 0.04 |
| EXAMPLE 26-1 | 0.07 |
| EXAMPLE 27-1 | 3.14 |
| EXAMPLE 31-1 | 1.94 |
| EXAMPLE 32-1 | 0.13 |
| EXAMPLE 32-2 | 0.03 |
| EXAMPLE 32-3 | 0.05 |
| EXAMPLE 32-4 | 0.17 |
| EXAMPLE 32-5 | 0.03 |
| EXAMPLE 32-6 | 0.37 |
| EXAMPLE 33-1 | 1.14 |

TABLE IV

| COMPOUND TO BE TESTED | $EC_{50}$ (nM) |
|---|---|
| EXAMPLE 1-57 | 0.16 |
| EXAMPLE 1-58 | 0.32 |
| EXAMPLE 1-62 | 1.05 |
| EXAMPLE 1-63 | 0.92 |
| EXAMPLE 1-68 | 0.08 |
| EXAMPLE 1-71 | 0.09 |
| EXAMPLE 1-72 | 0.05 |
| EXAMPLE 1-73 | 1.2 |
| EXAMPLE 1-74 | 1.8 |
| EXAMPLE 1-77 | 5.2 |
| EXAMPLE 1-80 | 0.69 |
| EXAMPLE 1-84 | 1.92 |
| EXAMPLE 1-85 | 3.5 |
| EXAMPLE 7-10 | 2.31 |
| EXAMPLE 7-12 | 3.9 |
| EXAMPLE 8-2 | 1.6 |
| EXAMPLE 12-11 | 4.57 |
| EXAMPLE 12-12 | 0.9 |
| EXAMPLE 12-13 | 1.12 |
| EXAMPLE 12-15 | 0.43 |
| EXAMPLE 16-2 | 0.49 |
| EXAMPLE 16-3 | 0.75 |
| EXAMPLE 17-2 | 0.07 |
| EXAMPLE 17-3 | 0.29 |
| EXAMPLE 22-2 | 0.38 |
| EXAMPLE 24-3 | 1.1 |
| EXAMPLE 24-4 | 0.81 |
| EXAMPLE 24-5 | 1.6 |
| EXAMPLE 24-6 | 0.4 |
| EXAMPLE 24-7 | 0.69 |
| EXAMPLE 24-8 | 0.39 |
| EXAMPLE 24-9 | 0.88 |
| EXAMPLE 24-10 | 1.0 |
| EXAMPLE 24-11 | 0.06 |

TABLE IV-continued

| COMPOUND TO BE TESTED | $EC_{50}$ (nM) |
|---|---|
| EXAMPLE 24-12 | 2.2 |
| EXAMPLE 24-13 | 0.11 |
| EXAMPLE 24-14 | 0.12 |
| EXAMPLE 24-15 | 0.03 |
| EXAMPLE 24-16 | 0.15 |

TABLE V

| COMPOUND TO BE TESTED | $EC_{50}$ (nM) |
|---|---|
| EXAMPLE 24-17 | 0.02 |
| EXAMPLE 24-18 | 0.03 |
| EXAMPLE 24-19 | 0.33 |
| EXAMPLE 24-20 | 0.15 |
| EXAMPLE 24-21 | 0.45 |
| EXAMPLE 24-22 | 1.32 |
| EXAMPLE 24-23 | 0.8 |
| EXAMPLE 24-24 | 0.46 |
| EXAMPLE 27-2 | 0.1 |
| EXAMPLE 28-4 | 1.64 |
| EXAMPLE 28-5 | 1.42 |
| EXAMPLE 32-8 | 0.44 |
| EXAMPLE 32-9 | 0.3 |
| EXAMPLE 32-10 | 0.53 |
| EXAMPLE 32-11 | 0.88 |
| EXAMPLE 32-12 | 0.27 |
| EXAMPLE 32-13 | 0.25 |
| EXAMPLE 32-14 | 0.82 |
| EXAMPLE 32-15 | 0.27 |
| EXAMPLE 32-16 | 0.54 |
| EXAMPLE 32-17 | 0.57 |
| EXAMPLE 32-18 | 0.54 |
| EXAMPLE 32-19 | 0.13 |
| EXAMPLE 32-20 | 2.86 |
| EXAMPLE 33-2 | 0.03 |

As seen from Tables I to V, the compounds (I) of the present invention or pharmacologically acceptable salts thereof show a superior FPRL1 agonist effect.

Test Example 2

Effect of Lipopolysaccharide Induction on Neutrophilic Infiltration in Mouse Lung A compound to be tested was orally administered to a mouse (BALB/c, male), and after 30 minutes, the mouse was placed in aplastic container. Lipopolysaccharide (0.3 mg/mL) dissolved in physiological saline was aerosolized with an ultrasonic wave nebulizer (NE-U17, OMRON Corporation), and exposed to the mouse for 10 minutes. After 5 hours, the anesthetized mouse was sacrificed by exsanguination. A cannula was inserted in the respiratory tract and bronchoalveolar lavage (BAL) with 1 mL of 0.85% NaCl liquid containing 0.4% sodium citrate was carried out. This operation was repeated 3 times, to obtain a BAL fluid. The BAL fluid was centrifuged at 4° C. and ×200 g for 5 minutes, and the pellet was suspended in a physiological saline containing 0.1% BSA. The number of white blood cells was counted using Turks solution with a microscope, and the total white blood cell count was calculated. The white blood cells were fixed on a glass slide using Cytospin 3 (Thermo BioAnalysis Japan K. K.). The cells were stained with Diff-Quik (SYSMEX INTERNATIONAL REAGENTS CO., LTD.), and the number thereof was counted with a microscope, and the neutrophil ratio was calculated. The neutrophil ratio was multiplied by the total white blood cell count to calculate the total neutrophil count. An effect of the compound to be tested represents a percentage (%) of suppression ratio relative to the neutrophil count in a control. The suppression ratios of the resultant test compounds are shown in Tables VI to VIII.

TABLE VI

| COMPOUND TO BE TESTED | SUPPRESSION RATIO | DOZE (mg/kg) |
|---|---|---|
| EXAMPLE 1-1 | 95.1 | 1 |
| EXAMPLE 1-2 | 99.2 | 1 |
| EXAMPLE 1-7 | 96.9 | 1 |
| EXAMPLE 1-9 | 98.5 | 3 |

TABLE VII

| COMPOUND TO BE TESTED | SUPPRESSION RATIO | DOZE (mg/kg) |
|---|---|---|
| EXAMPLE 1-12 | 96.8 | 1 |
| EXAMPLE 1-16 | 95.8 | 1 |
| EXAMPLE 1-18 | 98.3 | 1 |
| EXAMPLE 1-22 | 93.1 | 1 |
| EXAMPLE 1-23 | 98.9 | 3 |
| EXAMPLE 1-31 | 69.7 | 1 |
| EXAMPLE 1-53 | 78.9 | 1 |
| EXAMPLE 1-54 | 98.6 | 3 |
| EXAMPLE 1-55 | 83.7 | 3 |
| EXAMPLE 12-1 | 97.4 | 3 |
| EXAMPLE 25-1 | 99.1 | 3 |
| EXAMPLE 26-1 | 99.6 | 1 |
| EXAMPLE 32-1 | 99.0 | 3 |
| EXAMPLE 32-3 | 99.1 | 3 |
| EXAMPLE 32-5 | 99.8 | 1 |

TABLE VIII

| COMPOUND TO BE TESTED | SUPPRESSION RATIO (%) | DOZE (mg/kg) |
|---|---|---|
| EXAMPLE 1-68 | 85.6 | 3 |
| EXAMPLE 1-71 | 79.7 | 3 |
| EXAMPLE 1-72 | 93.3 | 3 |
| EXAMPLE 1-84 | 99.2 | 1 |
| EXAMPLE 7-2 | 87.7 | 1 |
| EXAMPLE 9-1 | 57.0 | 3 |
| EXAMPLE 32-12 | 96.8 | 1 |

As seen from Tables VI to VIII, the compounds (I) of the present invention or pharmacologically acceptable salts thereof had a superior action of suppressing neutrophil infiltration.

INDUSTRIAL APPLICABILITY

The compound of the present invention has a superior action of suppressing neutrophil infiltration due to a superior FPRL1 agonist effect, and therefore is useful as a therapeutic or prophylactic agent for inflammatory disease, chronic airway diseases, cancers, septicemia, allergic symptoms, HIV retrovirus infection, circulatory disorders, neuroinflammation, nervous disorders, pains, prion diseases, amyloidosis, immune disorders and the like.

Sequence Listing Free Text

<Sequence Listing 1>

SEQ ID NO: 1 is a sequence of a forward primer used for amplification of DNA of human FPRL1 (SEQ ID NO: 3), and is supplemented with a Hind III recognition site.

<Sequence Listing 2>

SEQ ID NO: 2 is a sequence of a reverse primer used for amplification of DNA of human FPRL1 (SEQ ID NO: 3), and is supplemented with an XhoI recognition site.

<Sequence Listing 3>

SEQ ID NO: 3 is an open reading frame (ORF) of human FPRL1, and is a DNA sequence of a site translated into an amino acid.

<Sequence Listing 4>

SEQ ID NO: 4 is a sequence of a forward primer used for amplification of DNA of human Gα15 (SEQ ID NO: 6), and is supplemented with a Hind III recognition site.

<Sequence Listing 5>

SEQ ID NO: 5 is a sequence of a reverse primer used for amplification of DNA of human Gα15 (SEQ ID NO: 6), and is supplemented with an XhoI recognition site.

<Sequence Listing 6>

SEQ ID NO: 6 is an open reading frame (ORF) of human Gα15, and is a DNA sequence of a site translated into an amino acid.

The invention claimed is:

1. A pharmaceutical composition comprising, as an active ingredient, a compound, or a pharmacologically acceptable salt thereof, wherein said compound is

- (−)-1-(4-fluorophenyl)-3-[(3S*,4R*)-4-(4-methoxyphenyl)-2-oxopyrrolidin-3-yl]urea,
- (−)-1-(4-chlorophenyl)-3-[(3S*,4R*)-4-(4-methoxyphenyl)-2-oxopyrrolidin-3-yl]urea,
- (−)-1-(3, 4-difluorophenyl)-3-[(3S*,4R*)-4-(4-methoxyphenyl)-2-oxopyrrolidin-3-yl]urea,
- (−)-1-(4-cyanophenyl)-3-[(3S*,4R*)-4-(4-methoxyphenyl)-2-oxopyrrolidin-3-yl]urea,
- (−)-1-(4-chlorophenyl)-3-[(3S*,4R*)-4-(4-methoxyphenyl)-1-methyl-2-oxopyrrolidin-3-yl]urea,
- (−)-1-(4-fluorophenyl)-3-[(3S*,4R*)-4-(4-methoxyphenyl)-1-methyl-2-oxopyrrolidin-3-yl]urea,
- (−)-1-[(3S*,4R*)-4-(3-fluoro-4-methoxyphenyl)-2-oxopyrrolidin-3-yl]-3-(4-fluorophenyl)urea,
- (−)-1-[(3S*,4R*)-4-(2-fluoro-4-methoxyphenyl)-2-oxopyrrolidin-3-yl]-3-(4-fluorophenyl)urea,
- 1-[(3S*,4R*)-4-(2-chloro-4-methoxyphenyl)-2-oxopyrrolidin-3-yl]-3-(4-fluorophenyl)urea,
- (−)-1-(4-fluorophenyl)-3-[(3S*,4R*)-4-(4-methoxy-2-methylphenyl)-2-oxopyrrolidin-3-yl]urea,
- (−)-1-[(3S*,4R*)-4-(2,6-difluoro-4-methoxyphenyl)-2-oxopyrrolidin-3-yl]-3-(4-fluorophenyl)urea,
- (−)-1-[(3S*,4R*)-4-(2,5-difluoro-4-methoxyphenyl)-2-oxopyrrolidin-3-yl]-3-(4-fluorophenyl)urea,
- (−)-1-[(3S*,4R*)-4-(3,5-difluoro-4-methoxyphenyl)-2-oxopyrrolidin-3-yl]-3-(4-fluorophenyl)urea,
- (−)-1-[(3S*,4R*)-4-(6-fluoro-2,3-dihydrobenzofuran-5-yl)-2-oxopyrrolidin-3-yl]-3-(4-fluorophenyl)urea,
- (−)-1-[(3S*,4R*)-4-(3-fluoro-5-methoxypyridin-2-yl)-2-oxopyrrolidin-3-yl]-3-(4-fluorophenyl)urea,
- (−)-1-(4-fluorophenyl)-3-[(3S*,4R*)-4-(5-methoxythiophen-2-yl)-2-oxopyrrolidin-3-yl]urea,
- (−)-1-(4-fluorophenyl)-3-[(3S*,4R*)-4-(4-methylthiophenyl)-2-oxopyrrolidin-3-yl]urea,
- (−)-1-(4-chlorophenyl)-3-[(3S*,4R*)-4-(2,6-difluoro-4-methoxyphenyl)-2-oxopyrrolidin-3-yl]urea,
- (−)-1-(4-cyanophenyl)-3-[(3S*,4R*)-4-(2,6-difluoro-4-methoxyphenyl)-2-oxopyrrolidin-3-yl]urea,
- (−)-1-[(3S*,4R*)-4-(2,6-difluoro-4-methoxyphenyl)-2-oxopyrrolidin-3-yl]-3-(4-methoxyphenyl)urea,
- (−)-1-(5-chlorothiazol-2-yl)-3-[(3S*,4R*)-4-(2,6-difluoro-4-methoxyphenyl)-2-oxopyrrolidin-3-yl]urea,
- (−)-1-(6-chloropyridin-3-yl)-3-[(3S*,4R*)-4-(2,6-difluoro-4-methoxyphenyl)-2-oxopyrrolidin-3-yl]urea,
- (−)-1-(5-chloropyridin-2-yl)-3-[(3S*,4R*)-4-(2,6-difluoro-4-methoxyphenyl)-2-oxopyrrolidin-3-yl]urea,
- (−)-1-(benzo[b]thiophen-2-yl)-3-[(3S*,4R*)-4-(2,6-difluoro-4-methoxyphenyl)-2-oxopyrrolidin-3-yl]urea,
- (−)-1-[(3S*,4R*)-4-(2,6-difluoro-4-methoxyphenyl)-2-oxopyrrolidin-3-yl]-3-(5-methylthiophen-2-yl)urea,
- (−)-1-(4-fluorophenyl)-3-[(3S*,4R*,5S*)-4-(4-methoxyphenyl)-5-methyl-2-oxopyrrolidin-3-yl]urea,
- (−)-1-(4-fluorophenyl)-3-[(3S*,4R*,5R*)-4-(4-methoxyphenyl)-5-methyl-2-oxopyrrolidin-3-yl]urea,
- (+)-1-(4-chlorophenyl)-3-[(3R*,4S*)-2-oxo-4-phenylpyrrolidin-3-yl]urea,
- (±)-trans-1-(4-chlorophenyl)-3-[4-(4-methoxyphenyl)-1-methyl-2-oxopyrrolidin-3-yl]urea,
- (±)-trans-1-(4-fluorophenyl)-3-[4-(4-methoxyphenyl)-2-oxopyrrolidin-3-yl]urea,
- (±)-trans-1-(4-chlorophenyl)-3-[4-(4-methoxyphenyl)-1-methyl-2-oxopyrrolidin-3-yl]urea,
- (−)-1-[(3S*,4R*)-4-(2,6-difluoro-4-methoxyphenyl)-2-oxopyrrolidin-3-yl]-3-[4-(trifluoromethoxy)phenyl]urea,
- (−)-1-[(3S*,4R*)-4-(2,6-difluoro-4-methoxyphenyl)-2-oxopyrrolidin-3-yl]-3-phenylurea,
- (−)-1-[(3S*,4R*)-4-(2,6-difluoro-4-methoxyphenyl)-2-oxopyrrolidin-3-yl]-3-(4-phenoxyphenyl)urea,
- (−)-1-[(3S*,4R*)-4-(2,6-difluoro-4-methoxyphenyl)-2-oxopyrrolidin-3-yl]-3-(3-fluorophenyl)urea,
- (−)-1-[(3S*,4R*)-4-(2,6-difluoro-4-methoxyphenyl)-2-oxopyrrolidin-3-yl]-3-(3,4-difluorophenyl)urea,
- (−)-1-(5-chlorothiophen-2-yl)-3-[(3S*,4R*)-4-(2,6-difluoro-4-methoxyphenyl)-2-oxopyrrolidin-3-yl]urea,
- (−)-1-[(3S*,4R*)-4-(2,6-difluoro-4-methoxyphenyl)-2-oxopyrrolidin-3-yl]-3-(p-tolyl)urea,
- (−)-1-[(3S*,4R*)-1-ethyl-4-(4-methoxyphenyl)-2-oxopyrrolidin-3-yl]-3-(4-fluorophenyl)urea,
- (−)-1-(4-fluorophenyl)-3-[(3S*,4R*)-1-(1-hydroxy-2-methylpropan-2-yl)-4-(4-methoxyphenyl)-2-oxopyrrolidin-3-yl]urea,
- (±)-trans-1-(4-chlorophenyl)-3-[1-(2-hydroxyethyl)-4-(4-methoxyphenyl)-2-oxopyrrolidin-3-yl]urea,
- (+)-trans-1-(4-chlorophenyl)-3-[1-(2-hydroxyethyl)-4-(4-methoxyphenyl)-2-oxopyrrolidin-3-yl]urea,
- (−)-trans-1-(4-chlorophenyl)-3-[1-(2-hydroxyethyl)-4-(4-methoxyphenyl)-2-oxopyrrolidin-3-yl]urea,
- (−)-2-{(3S*,4R*)-3-[3-(4-fluorophenyl)ureido]-4-(4-methoxyphenyl)-2-oxopyrrolidin-1-yl}-N-methylacetamide,
- (−)-2-{(3S*,4R*)-3-[3-(4-fluorophenyl)ureido]-4-(4-methoxyphenyl)-2-oxopyrrolidin-1-yl}propionic acid (isomer A),
- (−)-2-{(3S*,4R*)-3-[3-(4-fluorophenyl)ureido]-4-(4-methoxyphenyl)-2-oxopyrrolidin-1-yl}-N-methylpropionamide (isomer A),
- (−)-2-{(3S*,4R*)-3-[3-(4-fluorophenyl)ureido]-4-(4-methoxyphenyl)-2-oxopyrrolidin-1-yl}propionic acid (isomer B),
- (−)-2-{(3S*,4R*)-3-[3-(4-fluorophenyl)ureido]-4-(4-methoxyphenyl)-2-oxopyrrolidin-1-yl}-N-methylpropionamide (isomer B),
- (−)-2-{(3S*,4R*)-3-[3-(4-fluorophenyl)ureido]-4-(4-methoxyphenyl)-2-oxopyrrolidin-1-yl}-N,2-dimethylpropionamide,
- (−)-1-[(3S*,4R*)-4-(2,6-difluoro-4-methoxyphenyl)-1-methyl-2-oxopyrrolidin-3-yl]-3-(4-fluorophenyl)urea,
- (−)-1-[(3S*,4R*)-4-(2-fluoro-4-methoxyphenyl)-1-(2-hydroxyethyl)-2-oxopyrrolidin-3-yl]-3-(4-fluorophenyl)urea, (−)-1-[(3S*,4R*)-4-(2,6-difluoro-4-methoxyphenyl)-1-(2-hydroxyethyl)-2-oxopyrrolidin-3-yl]-3-(4-fluorophenyl)urea, (+)-1-(4-fluorophenyl)-3-[(3R*,4S*)-1-methoxy-4-(4-methoxyphenyl)-2-oxopyrrolidin-3-yl]urea, (−)-3,5-difluoro-4-{(3R*,4S*)-4-[3-(4-fluorophenyl)ureido]-5-oxopyrrolidin-3-yl}benzamide, (−)-1-(4-fluorophenyl)-3-[(3S*,4R*,Z)-2-(methoxyimino)-4-(4-methoxyphenyl)pyrrolidin-3-yl]urea, (−)-1-[(3S*,4R*,Z)-4-(2-fluoro-4-methoxyphenyl)-2-(methoxyimino)pyrrolidin-3-yl]-3-(4-fluorophenyl)urea, (−)-1-[(3S*,4R*,Z)-4-(2,6-difluoro-4-methoxyphenyl)-2-(methoxyimino)pyrrolidin-3-yl]-3-(4-fluorophenyl)urea, (−)-1-(4-fluorophenyl)-3-{(3S*,4R*,Z)-2-[(2-hydroxyethoxy)imino]-4-(4-methoxyphenyl)pyrrolidin-3-yl}urea, (−)-1-{(3S*,4R*,Z)-4-(2,6-difluoro-4-methoxyphenyl)-2-[(2-hydroxyethoxy)imino]pyrrolidin-3-yl}-3-(4-fluorophenyl)urea, (−)-1-[(3S*,4R*,Z)-4-(2,6-difluoro-4-methoxyphenyl)-2-(methylimino)pyrrolidin-3-yl]-3-(4-fluorophenyl)urea, (−)-1-(4-fluorophenyl)-3-[(3S*,4R*,Z)-2-(2-hydroxyimino)-4-(4-methoxyphenyl)pyrrolidin-3-yl]urea, (−)-1-[(3S*,4R*)-4-(2,6-difluoro-4-methoxyphenyl)-2-oxopyrrolidin-3-yl]-3-(3-hydroxy-4-methylphenyl)urea, (−)-1-[(3S*,4R*)-4-(2,6-difluoro-4-methoxyphenyl)-2-oxopyrrolidin-3-yl]-3-(4-fluoro-3-hydroxyphenyl)urea, (−)-1-(4-chloro-3-hydroxyphenyl)-3-[(3S*,4R*)-4-(2,6-difluoro-4-methoxyphenyl)-2-oxopyrrolidin-3-yl]urea, (−)-1-(4-cyanophenyl)-3-[(3S*,4R*)-4-(6-fluoro-2,3-dihydrobenzofuran-5-yl)-2-oxopyrrolidin-3-yl]urea, (−)-1-{(3S*,4R*,Z)-4-(2,6-difluoro-4-methoxyphenyl)-2-[(2-hydroxyethoxy)imino]pyrrolidin-3-yl}-3-(p-tolyl)urea, or (−)-1-[(3S*,4R*)-4-(2,6-difluoro-4-methoxyphenyl)-1-(2-hydroxyethyl)-2-oxopyrrolidin-3-yl]-3-phenylurea.

2. A pharmaceutical composition comprising, as an active ingredient, a compound, or a pharmacologically acceptable salt thereof, wherein said compound is

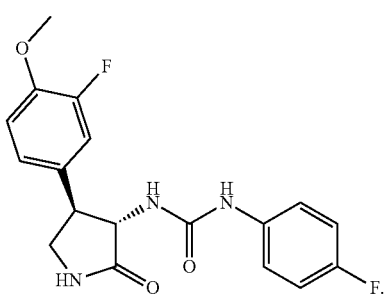 [SMILES: COc1ccc([C@@H]2CNC(=O)[C@H]2NC(=O)Nc2ccc(F)cc2)cc1F]

3. A pharmaceutical composition comprising, as an active ingredient, a compound, or a pharmacologically acceptable salt thereof, wherein said compound is

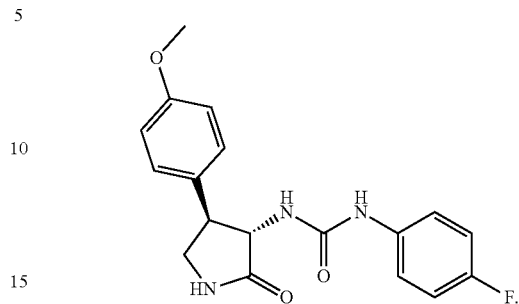

4. A pharmaceutical composition comprising, as an active ingredient, a compound, or a pharmacologically acceptable salt thereof, wherein said compound is

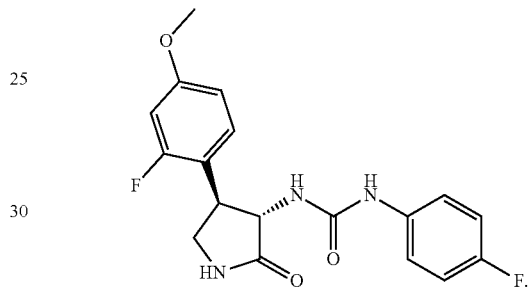

5. A pharmaceutical composition comprising, as an active ingredient, a compound, or a pharmacologically acceptable salt thereof, wherein said compound is

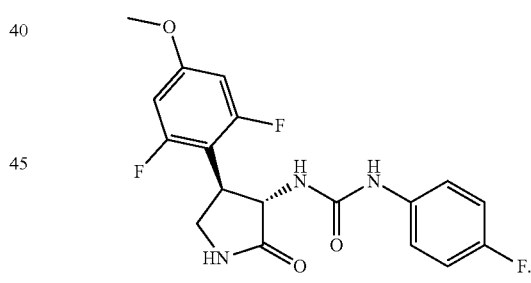

6. A pharmaceutical composition comprising, as an active ingredient, a compound, or a pharmacologically acceptable salt thereof, wherein said compound is

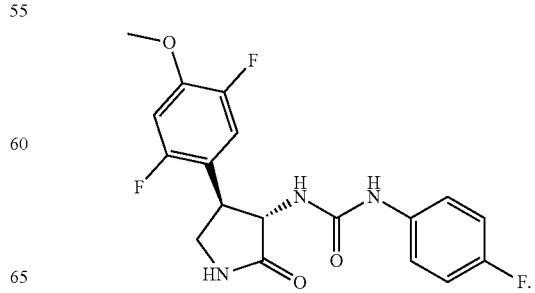

7. A pharmaceutical composition comprising, as an active ingredient, a compound, or a pharmacologically acceptable salt thereof, wherein said compound is

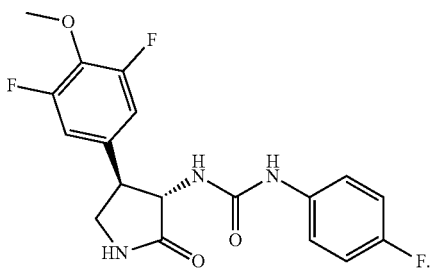 [SMILES: COc1c(F)cc([C@@H]2CNC(=O)[C@H]2NC(=O)Nc2ccc(F)cc2)cc1F]

8. A pharmaceutical composition comprising, as an active ingredient, a compound, or a pharmacologically acceptable salt thereof, wherein said compound is

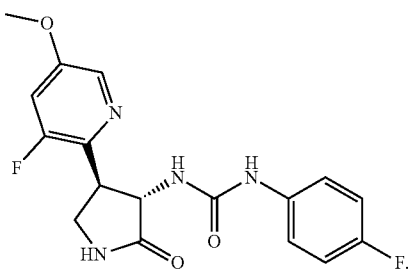 [SMILES: COc1cnc([C@@H]2CNC(=O)[C@H]2NC(=O)Nc2ccc(F)cc2)c(F)c1]

9. A pharmaceutical composition comprising, as an active ingredient, a compound, or a pharmacologically acceptable salt thereof, wherein said compound is

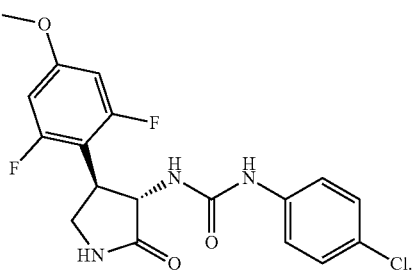 [SMILES: COc1cc(F)c([C@@H]2CNC(=O)[C@H]2NC(=O)Nc2ccc(Cl)cc2)c(F)c1]

10. A pharmaceutical composition comprising, as an active ingredient, a compound, or a pharmacologically acceptable salt thereof, wherein said compound is

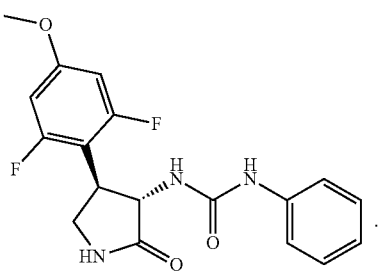 [SMILES: COc1cc(F)c([C@@H]2CNC(=O)[C@H]2NC(=O)Nc2ccccc2)c(F)c1]

11. A pharmaceutical composition comprising, as an active ingredient, a compound, or a pharmacologically acceptable salt thereof, wherein said compound is

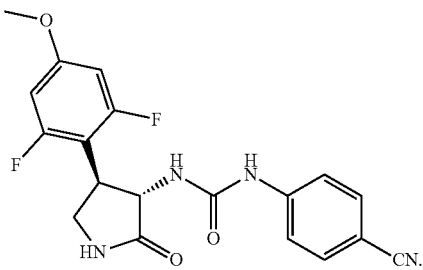 [SMILES: COc1cc(F)c([C@@H]2CNC(=O)[C@H]2NC(=O)Nc2ccc(C#N)cc2)c(F)c1]

12. A pharmaceutical composition comprising, as an active ingredient, a compound, or a pharmacologically acceptable salt thereof, wherein said compound is

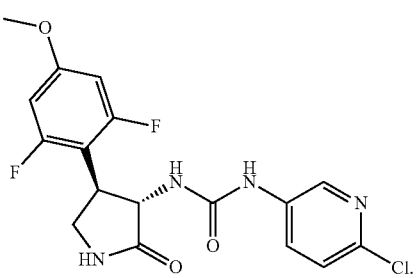 [SMILES: COc1cc(F)c([C@@H]2CNC(=O)[C@H]2NC(=O)Nc2ccc(Cl)nc2)c(F)c1]

13. A pharmaceutical composition comprising, as an active ingredient, a compound, or a pharmacologically acceptable salt thereof, wherein said compound is

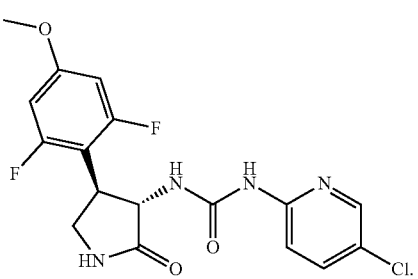 [SMILES: COc1cc(F)c([C@@H]2CNC(=O)[C@H]2NC(=O)Nc2ccc(Cl)cn2)c(F)c1]

* * * * *

```
                         SEQUENCE LISTING

<160> NUMBER OF SEQ ID NOS: 6

<210> SEQ ID NO 1
<211> LENGTH: 43
<212> TYPE: DNA
<213> ORGANISM: Artificial Sequence
<220> FEATURE:
<223> OTHER INFORMATION: Description of Artificial Sequence: Synthetic
      5' primer

<400> SEQUENCE: 1
cgaagcttca ccatggaaac caacttctcc actcctctga atg                          43

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Synthetic
      3' primer

<400> SEQUENCE: 2
cgctcgagtc atattgcctt tatttcaatg tcttcagg                                38

<210> SEQ ID NO 3
<211> LENGTH: 1056
<212> TYPE: DNA
<213> ORGANISM: Homo sapiens

<400> SEQUENCE: 3
atggaaacca acttctccac tcctctgaat gaatatgaag aagtgtccta tgagtctgct        60
ggctacactg ttctgcggat cctcccattg gtggtgcttg gggtcacctt tgtcctcggg       120
gtcctgggca tgggcttgt gatctgggtg gctggattcc ggatgacacg cacagtcacc       180
accatctgtt acctgaacct ggccctggct gacttttctt tcacggccac attaccattc      240
ctcattgtct ccatggccat gggagaaaaa tggccttttg gctggttcct gtgtaagtta      300
attcacatcg tggtggacat caacctcttt ggaagtgtct tcttgattgg tttcattgca      360
ctggaccgct gcatttgtgt cctgcatcca gtctgggccc agaaccaccg cactgtgagt      420
ctggccatga aggtgatcgt cggaccttgg attcttgctc tagtccttac cttgccagtt      480
ttcctctttt tgactacagt aactattcca atgggaaca catactgtac tttcaacttt      540
gcatcctggg gtggcacccc tgaggagagg ctgaaggtgg ccattaccat gctgacagcc      600
agagggatta tccggtttgt cattggcttt agcttgccga tgtccattgt tgccatctgc      660
tatgggctca ttgcagccaa gatccacaaa aagggcatga ttaaatccag ccgtcccta       720 cgggtcctca ctgctgtggt ggcttctttc ttcatctgtt ggtttccctt caactggttg      780
gcccttctgg gcaccgtctg gctcaagag atgttgttct atggcaagta caaaatcatt      840
```

| gacatcctgg ttaacccaac gagctccctg gccttcttca acagctgcct caaccccatg | 900 |
| ctttacgtct ttgtgggcca agacttccga gagagactga tccactccct gcccaccagt | 960 |
| ctggagaggg ccctgtctga ggactcagcc ccaactaatg cacggctgc caattctgct | 1020 |
| tcacctcctg cagagactga gttacaggca atgtga | 1056 |

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      5' primer

<400> SEQUENCE: 4

| cgaagcttca ccatggcccg ctcgctgac | 29 |

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

| cgctcgagtc acagcaggtt gatctcgtcc | 30 |

<210> SEQ ID NO 6
<211> LENGTH: 1125
<212> TYPE: DNA
<213> ORGANISM: Homo sapiens

<400> SEQUENCE: 6

| atggcccgct cgctgacctg gcgctgctgc ccctggtgcc tgacggagga tgagaaggcc | 60 |
| gccgccgggg tggaccagga gatcaacagg atcctcttgg agcagaagaa gcaggaccgc | 120 |
| ggggagctga agctgctgct tttgggccca ggcgagagcg ggaagagcac cttcatcaag | 180 |
| cagatgcgga tcatccacgg cgccggctac tcggaggagg agcgcaaggg cttccggccc | 240 |
| ctggtctacc agaacatctt cgtgtccatg cgggccatga tcgaggccat ggagcggctg | 300 |
| cagattccat tcagcaggcc cgagagcaag caccacgcta gcctggtcat gagccaggac | 360 |
| ccctataaag tgaccacgtt tgagaagcgc tacgctgcgg ccatgcagtg gctgtggagg | 420 |
| gatgccggca tccgggccta ctatgagcgt cggcgggaat tccacctgct cgattcagcc | 480 |
| gtgtactacc tgtcccacct ggagcgcatc accgaggagg gctacgtccc cacagctcag | 540 |
| gacgtgctcc gcagccgcat gcccaccact ggcatcaacg agtactgctt ctccgtgcag | 600 |
| aaaaccaacc tgcggatcgt ggacgtcggg ggccagaagt cagagcgtaa gaaatggatc | 660 |
| cattgtttcg agaacgtgat cgccctcatc tacctggcct cactgagtga atacgaccag | 720 |
| tgcctggagg agaacaacca ggagaaccgc atgaaggaga gctcgcatt gtttgggact | 780 |
| atcctggaac taccctggtt caaaagcaca tccgtcatcc tctttctcaa caaaaccgac | 840 |
| atcctggagg agaaaatccc cacctccacc ctggctacct atttcccag tttcagggc | 900 |
| cctaagcagg atgctgaggc agccaagagg ttcatcctgg acatgtacac gaggatgtac | 960 |
| accgggtgcg tggacggccc cgagggcagc aagaagggcg cacgatcccg acgcctcttc | 1020 |

```
agccactaca catgtgccac agacacacag aacatccgca aggtcttcaa ggacgtgcgg    1080
gactcggtgc tcgcccgcta cctggacgag atcaacctgc tgtga                   1125
```